(12) United States Patent
Wiltzius et al.

(10) Patent No.: US 10,501,775 B2
(45) Date of Patent: Dec. 10, 2019

(54) ANTIGEN BINDING MOLECULES AND METHODS OF USE THEREOF

(71) Applicant: KITE PHARMA, INC., Santa Monica, CA (US)

(72) Inventors: Jed Wiltzius, Woodland Hills, CA (US); Stuart Sievers, Van Nuys, CA (US); Arianne Perez Garcia, Woodland Hills, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 0 days.

(21) Appl. No.: 15/646,817

(22) Filed: Jul. 11, 2017

(65) Prior Publication Data

US 2018/0016620 A1    Jan. 18, 2018

Related U.S. Application Data

(60) Provisional application No. 62/361,420, filed on Jul. 12, 2016, provisional application No. 62/415,786, filed on Nov. 1, 2016.

(51) Int. Cl.
| | |
|---|---|
| *C07K 16/46* | (2006.01) |
| *A61K 47/68* | (2017.01) |
| *G01N 33/53* | (2006.01) |
| *C12Q 1/68* | (2018.01) |
| *C07K 1/14* | (2006.01) |
| *C07K 16/24* | (2006.01) |
| *C12N 15/70* | (2006.01) |
| *C07K 16/44* | (2006.01) |
| *A61K 39/00* | (2006.01) |
| *C12P 21/00* | (2006.01) |
| *A61K 35/00* | (2006.01) |
| *C07K 16/28* | (2006.01) |
| *A61K 38/00* | (2006.01) |

(52) U.S. Cl.
CPC ............... *C12Q 1/68* (2013.01); *C07K 1/14* (2013.01); *C07K 16/24* (2013.01); *C07K 16/44* (2013.01); *C07K 16/46* (2013.01); *C12N 15/70* (2013.01); *A61K 35/00* (2013.01); *A61K 38/00* (2013.01); *A61K 2039/505* (2013.01); *C07K 16/2809* (2013.01); *C07K 2317/24* (2013.01); *C07K 2317/31* (2013.01); *C07K 2317/34* (2013.01); *C07K 2317/626* (2013.01); *C07K 2317/73* (2013.01); *C07K 2317/75* (2013.01); *C07K 2317/76* (2013.01); *C12P 21/00* (2013.01); *Y02A 50/473* (2018.01)

(58) Field of Classification Search
CPC .... C07K 16/46; C07K 16/44; C07K 2317/73; C07K 2317/34; A61K 2039/505; A61K 47/6875; A61K 47/6887; A61K 47/643; G01N 33/53; G01N 33/577; G01N 33/582

See application file for complete search history.

(56) References Cited

U.S. PATENT DOCUMENTS

| | | | |
|---|---|---|---|
| 5,223,409 A | 6/1993 | Ladner | |
| 5,856,456 A * | 1/1999 | Whitlow .......... | C07K 14/70503 424/134.1 |
| 6,150,584 A * | 11/2000 | Kucherlapati ..... | C07K 16/1282 424/93.21 |
| 7,129,332 B2 * | 10/2006 | Pastan ................ | C07K 16/2863 530/387.3 |
| 7,666,424 B2 | 2/2010 | Cheung et al. | |
| 7,709,226 B2 | 5/2010 | Foote | |
| 7,935,340 B2 * | 5/2011 | Garcia-Martinez ......................... | C07K 16/248 424/133.1 |
| 2010/0310571 A1 * | 12/2010 | Cheung .............. | A61K 51/1078 424/141.1 |
| 2014/0065645 A1 | 3/2014 | Han et al. | |
| 2016/0096902 A1 | 4/2016 | Cooper et al. | |

FOREIGN PATENT DOCUMENTS

| | | |
|---|---|---|
| WO | 94/12520 A1 | 6/1994 |
| WO | 2015/057834 A1 | 4/2015 |
| WO | 2016/019300 A1 | 2/2016 |
| WO | 2016/033331 A1 | 3/2016 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Wu et al., J Mol Biol 294: 151-162 (Year: 1999).*
Rudikoff et al., Proc Nat Acad Sci 79: 1979-1983 (Year: 1982).*
Campbell et al (in Monoclonal Antibody Technology, Elsevier Science Publisher, New York, NY, p. 1-32 (Year: 1984).*
Whitlow, M., et al, An Improved Linker for Single-Chain FV with Reduced Aggregation and Enhanced Proteolytic Stability, Protein Engineering, 1993, pp. 989-995, vol. 6 No. 8.
Golub, et al., "Immunology—A Synthesis (2nd Edition)", Sinauer Assoc., Sunderland, Mass. (1991), table of contents only, 13 pages.
Stocks, "Intrabodies: production and promise" Drug Discovery Today, 2004, 9(22):960-66.
Bird et al., "Single-chain antigen-binding proteins", 1988, Science 242:423-26.
Huston et al., Protein engineering of antibody binding sites: recovery of specific activity in an anti-digoxin single-chain Fv analogue produced in *Escherichia coli* PNAS, Aug. 1, 1988, 85 (16) 5879-5883.
Holliger et al., "Diabodies: Small Bivalen and Bispecific Antibody Fagments" Proc Natl Acad Sci U.S.A., 1993, 90:6444-48 Biophysics.

(Continued)

*Primary Examiner* — Phuong Huynh
(74) *Attorney, Agent, or Firm* — Proskauer Rose LLP

(57) ABSTRACT

Isolated antigen binding molecules that specifically binds to a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) are provided. The antigen binding molecules can be used in the methods provided herein.

20 Claims, 63 Drawing Sheets

Specification includes a Sequence Listing.

(56) References Cited

OTHER PUBLICATIONS

Poljak et al., "Production and structure of diabodies" Structure, 1994, vol. 2, No. 12: 1121-23.
Perisic et al., "Crystal structure of a diabody, a bivalent antibody fragment" Structure, 1994, 2(12): 1217-26.
Korndorfer et al., "Crystallographic Analysis of an "Anticalin" With Tailored Specificity for Fluorescein Reveals High Structural Plasticity of the Lipocalin Loop Region" Proteins: Structure, Function, and Bioinformatics, 2003, 53(1):121-129 Wiley-Liss, Inc.
Roque et al., "Antibodies and Genetically Engineered Related Molecules: Production and Purification", Biotechnol. Prog. 20:639-654 (2004).
Kabat et al. "Sequences of Proteins of Immunological Interest", 1991, 5th Ed., NIH Publication 91-3242, Bethesda MD title page, publication page, and table of contents only, 10 pages.
Chothia et al., "Canonical structures for the hypervariable regions of immunoglobulins", J Mol Biol, 1987, 196: 901-917.
Al-Lazikani et al., "Standard conformations for the canonical structures of immunoglobulins" J Mol Biol, 1997, 273: 927-948.
Chothia et al., "Structural repertoire of the human VH segments" J Mol Biol, 1992, 227: 799-817.
Tramontano et al., "Framework residue 71 is a major determinant of the position and conformation of the second hypervariable region in the VH domains of immunoglobulins" J Mol Biol, 1990, 215(1): 175-82.
Bricogne, "Direct phase determination by entropy maximization and likelihood ranking: status report and perspectives", Acta Crystallogr D Biol Crystallogr, 1993, 49(Pt 1): 37-60.
Bricogne, "[23] Bayesian statistical viewpoint on structure determination: Basic concepts and examples", Meth Enzymol, 1997, 276A: 361-423.
Roversi et al., "Modeling prior distributions of atoms for macromolecular refinement and completion", Acta Crystallogr D Biol Crystallogr, 2000, 56 (Pt 10): 1316-1323.
Champe et al., "Monoclonal Antibodies That Block the Activity of Leukocyte Function-associated Antigen 1 Recognize Three Discrete Epitopes in the Inserted Domain of CD11a", J Biol Chem, 1995, 270(3): 1388-94.
Cunningham et al., "High-resolution epitope mapping of hGH-receptor interactions by alanine-scanning mutagenesis", Science 244(4908): 1081-85 (1989).
Goodwin et al.," Molecular and biological characterization of a ligand for CD27 defines a new family of cytokines with homology to tumor necrosis factor", Cell, 1993 73(3):447-56.
Bowman et al., "The cloning of CD70 and its identification as the ligand for CD27", Journal of immunology (Baltimore, Md. : 1950), 1994 152(4):1756-61.
Hartl et al., "Genetics: Principles and Analysis", 1997, Jones and Bartlett Publishers.
Dayhoff et al. A model of evolutionary change in proteins, in Dayhoff, M.O. Edition, Atlas of Protein Sequence and Structure, 1978, Natl. Biomed. Res. Found., Washington DC, 5(3), 345-352.
Henilkoff et al. "Amino acid substitution matrices from protein blocks", Proc Natl Acad Sci U S A., 89(22): 10915-10919, Nov. 15, 1992.
Bruggenmann et al. "Production of human antibody repertoires in transgenic mice", 1Curr. Opin. Biotechnol. 1997, 8:455-58.

Burton et al., "Human Antibodies from Combinatorial libraries", Advances in immunology, 1994, vol. 57, 191-280.
Winter, et al., "Making Antibodies by Phage Display Technology", Annual Review of Immunology, Publication Annual Review of Immunology, 1994, 12(1):433-455.
Huse, et al., "Generation of a Large Combinatorial Library of the Immunoglobulin Repertoire in Phage Lambda", Science, 1989, 246(4935):1275-1281.
Sastry et al. "Cloning of the immunological repertoire in Escherichia coli for generation of monoclonal catalytic antibodies: construction of a heavy chain variable region-specific cDNA library". Proceedings of the National Academy of Sciences of the United States of America. 1989, 86(15):5728-5732.
Kang et al., "Linkage of recognition and replication functions by assembling combinatorial antibody Fab libraries along phage surfaces", Proc Natl Acad Sci U S A., May 15, 1991, 88(10):4363-6.
Hoogenboom et al., "By-passing immunisation", Journal of Molecular Biology, 1992, 227(2):381-388.
Berzofsky, et al. "Antigen-Antibody interaction and Monoclonal Antibodies", Fundamental immunology, editor, William E. Paul.—7th ed., (2013), Ch 7, Lippincott Williams & Wilkins.
Schlebusch et al., "Production of a Single-Chain Fragment of the Murine Anti-Idiotypic Antibody ACA125 as Phage-Displayed and Soluble Antibody by Recombinant Phage Antibody Technique", 1997, Hybridoma 16:47-52.
Baines, et al., "Purification of Immunoglobulin G (IgG)", Methods in Molecular Biology, 1992, vol. 10: Immunochemical Protocols, 10:79-104 (The Humana Press).
Littman et al., "The isolation and sequence of the gene encoding T8: a molecule defining functional classes of T lymphocytes", Cell, 1985, 40(2):237-46.
Wyckoff et al., eds., Methods in Enzymology vol. 114—Diffraction Methods for Biological Macromolecules, Academic Press, Orlando, FL; title page, publication page, and table of contents only, 5 pages (1985).
Wyckoff et al., eds., Methods in Enzymology vol. 115. Diffraction Methods for Biological Macromolecules, Academic Press, Orlando, FL; title page, publication page, and table of contents only, 4 pages (1985).
Alting-Mees et al., "Monoclonal Antibody Expression Libraries: A Rapid Alternative to Hybridomas", (1990) Strategies in Molecular Biology 3:1-9.
Honegger et al. "Yet Another Numbering Scheme for Immunoglobulin Variable Domains: An Automatic Modeling and Analysis Tool" J. Mol. Biol., 2001, 309, 657-670.
Verber, et al., "The design of metabolically-stable peptide analogs,". Trends in Neurosciences, Sep. 1985, pp. 392-396.
Evans et al. "Design of nonpeptidal ligands for a peptide receptor: cholecystokinin antagonists" J. Med. Chem, 1987 30:1229-39.
Nicholson et al., Construction and Characterisation of a Functional CD19 Specific Single Chain Fv Fragment for Immunotherapy of B Lineage Leukaemia and Lymphoma Mol Immunol, 1997, vol. 34, No. 16-17:1157-65, Elsavier.
Seet et al., "Generation of mature T cells from human hematopoietic stem/progenitor cells in artificial thymic organoids", Nat Methods. May 2017; 14(5): 521-530.
Landegren, "Mechanism of T lymphocyte activation by OKT3 antibodies. A general model for T cell induction" Eur. J. Immunol., 1984, 14(4):325-28.

* cited by examiner

CDR Table (Kabat)

| Sequence | CDR1 | SEQ ID NO | CDR2 | SEQ ID NO | CDR3 | SEQ ID NO |
|---|---|---|---|---|---|---|
| 8_HC | NLAII | 492 | DIDGRGDIYCATWAK | 8 | DGDGSGWGDFNF | 9 |
| 16_HC | SYHMG | 493 | IIVSSGSAYYATWAK | 20 | NQYSGYGFSF | 21 |
| 8_LC | QASQSISTALA | 13 | RASTLAS | 14 | QQGWSTVNVDNV | 15 |
| 16_LC | QSSHSVYYGDWLA | 25 | RASNLAS | 26 | LGGYDDDGETA | 27 |

CDR Table (Chothia)

| Sequence | CDR1 | SEQ ID NO | CDR2 | SEQ ID NO | CDR3 | SEQ ID NO |
|---|---|---|---|---|---|---|
| 8_HC | GFTISNL | 7 | DIDGRGDIYCATWAK | 8 | DGDGSGWGDFNF | 9 |
| 16_HC | GSDISSY | 19 | IIVSSGSAYYATWAK | 20 | NQYSGYGFSF | 21 |
| 8_LC | QASQSISTALA | 13 | RASTLAS | 14 | QQGWSTVNVDNV | 15 |
| 16_LC | QSSHSVYYGDWLA | 25 | RASNLAS | 26 | LGGYDDDGETA | 27 |

CDR Table (IMGT)

| Sequence | CDR1 | SEQ ID NO | CDR2 | SEQ ID NO | CDR3 | SEQ ID NO |
|---|---|---|---|---|---|---|
| 8_HC | GFTISNLAII | 494 | DIDGRGDIYCATWAK | 8 | DGDGSGWGDFNF | 9 |
| 16_HC | GSDISSYHMG | 495 | IIVSSGSAYYATWAK | 20 | NQYSGYGFSF | 21 |
| 8_LC | QASQSISTALA | 13 | RASTLAS | 14 | QQGWSTVNVDNV | 15 |
| 16_LC | QSSHSVYYGDWLA | 25 | RASNLAS | 26 | LGGYDDDGETA | 27 |

Figure 6

| Clone 8 | | SEQ ID NO |
|---|---|---|
| VH DNA | ATGGAGACTGGGCTGCGCTGGCTTCTCCTGGTCGCTGTGCTCAAAGGTGTCCAGT GTCAGTCGGTGGAGGAGTCCGGGGGTCGCCTGGTCACGCCTGGGACACCCCTGA CACTCACCTGCACAGCCTCTGGATTCACCATCAGTAACCTTGCAATAATCTGGGTC CGCCAGGCTCCAGGGAAGGGGCTGGAATATATCGGAGACATTGATGGTCGTGGT GACATATACTGTGCGACCTGGGCGAAAGGCCGATTCACCATCTCCAAAACCTCGA CCACACTGGATCTGAGATTCACCAGCCCGACAACCGAGGACACGGCCACCTACTT CTGTGCCGTAGATGGTGATGGTAGTGGTTGGGGTGACTTTAACTTTGGGGCCCA GGCACCCTGGTCACCGTCTCCTCA | 4 |
| VH AA (CDRs underlined) | METGLRWLLLVAVLKGVQCQSVEESGGRLVTPGTPLTLTCTAS<u>GFTISNL</u>AIIWVRQA PGKGLEYIG<u>DIDGRGDIYCATWAK</u>GRFTISKTSTTLDLRFTSPTTEDTATYFCAV<u>DGDG SGWGDFNF</u>WGPGTLVTVSS | 5 |
| HC AA (CDRs underlined) | METGLRWLLLVAVLKGVQCQSVEESGGRLVTPGTPLTLTCTAS<u>GFTISNL</u>AIIWVRQA PGKGLEYIG<u>DIDGRGDIYCATWAK</u>GRFTISKTSTTLDLRFTSPTTEDTATYFCAV<u>DGDG SGWGDFNF</u>WGPGTLVTVSSGQPKAPSVFPLAPCCGDTPSSTVTLGCLVKGYLPEPVT VTWNSGTLTNGVRTFPSVRQSSGLYSLSSVVSVTSSSQPVTCNVAHPATNTKVDKTV APSTCSKPTCPPPELLGGPSVFIFPPKPKDTLMISRTPEVTCVVVDVSQDDPEVQFTW YINNEQVRTARPPLREQQFNSTIRVVSTLPIAHQDWLRGKEFKCKVHNKALPAPIEKTI SKARGQPLEPKVYTMGPPREELSSRSVSLTCMINGFYPSDISVEWEKNGKAEDNYKT TPAVLDSDGSYFLYSKLSVPTSEWQRGDVFTCSVMHEALHNHYTQKSISRSPGK | 6 |
| VL DNA | ATGGACACGAGGGCCCCCACTCAGCTGCTGGGGCTCCTGCTGCTCTGGCTCCCAG GTGCCAGATGTGCCTATGATATGACCCAGACTCCAGCCTCTGTGGAGGTAGCTGT GGGAGGCACAGTCAGCATCAAGTGCCAGGCCAGTCAGAGCATTAGCACTGCATT AGCCTGGTATCAGCAGAAACCAGGACAGCCTCCCAAGCTCCTGATCTACAGGGC ATCCACTCTGGCATCTGGGGTCTCATCGCGGTTCAAAGGCAGTGGATCTGGGACA CAGTTCACTCTCACCATCAGCGGCGTGGAGTGTGACGATGCTGCCACTTACTACT GTCAACAGGGTTGGAGTACTGTGAATGTTGATAATGTTTTCGGCGGAGGGACCG AGGTGGTGGTCAGA | 10 |
| VL AA (CDRs underlined) | MDTRAPTQLLGLLLLWLPGARCAYDMTQTPASVEVAVGGTVSIKC<u>QASQSISTALA</u> WYQQKPGQPPKLLIY<u>RASTLAS</u>GVSSRFKGSGSGTQFTLTISGVECDDAATYYC<u>QQG WSTVNVDNV</u>FGGGTEVVVR | 11 |
| LC AA (CDRs underlined) | MDTRAPTQLLGLLLLWLPGARCAYDMTQTPASVEVAVGGTVSIKC<u>QASQSISTALA</u> WYQQKPGQPPKLLIY<u>RASTLAS</u>GVSSRFKGSGSGTQFTLTISGVECDDAATYYC<u>QQG WSTVNVDNV</u>FGGGTEVVVRDPVAPTVLIFPPAADQVATGTVTIVCVANKYFPDVTV TWEVDGTTQTTGIENSKTPQNSADCTYNLSSTLTLTSTQYNSHKEYTCKVTQGTTSVV QSFNRGDC | 12 |

Figure 6 (Cont.)

| Clone 16 | | SEQ ID NO |
|---|---|---|
| VH DNA | ATGGAGACTGGGCTGCGCTGGCTTCTCCTGGTCGCTGTGCTCAAAGGTGTCCAGT GTCAGTCGCTGGAGGAGTCCGGGGGTCGCCTGGTCACGCCTGGGACACCCCTGA CACTCACCTGCACAGTCTCTGGATCCGACATCAGTAGCTACCACATGGGCTGGGT CCGCCAGGCTCCAGGGAAGGGGCTGGAATACATCGGAATCATTGTTAGTAGTGG TAGCGCATACTACGCGACCTGGGCAAAAGGCCGATTCACCATCTCCAGGACCTCG ACCACGGTGGATCTGAAAATCACCAGTCCGACAACCGAGGACTCGGCCACCTATT TCTGTGCCAGAAATCAATATAGTGGTTATGGCTTTAGCTTCTGGGGCCCAGGCAC CCTGGTCACCGTCTCCTCA | 16 |
| VH AA (CDRs underlined) | METGLRWLLLVAVLKGVQCQSLEESGGRLVTPGTPLTLTCTVS<u>GSDISSY</u>HMGWVR QAPGKGLEYIG<u>IIVSSGSAYYATWAK</u>GRFTISRTSTTVDLKITSPTTEDSATYFCAR<u>NQY SGYGFSF</u>WGPGTLVTVSS | 17 |
| HC AA (CDRs underlined) | METGLRWLLLVAVLKGVQCQSLEESGGRLVTPGTPLTLTCTVS<u>GSDISSY</u>HMGWVR QAPGKGLEYIG<u>IIVSSGSAYYATWAK</u>GRFTISRTSTTVDLKITSPTTEDSATYFCAR<u>NQY SGYGFSF</u>WGPGTLVTVSSGQPKAPSVFPLAPCCGDTPSSTVTLGCLVKGYLPEPVTVT WNSGTLTNGVRTFPSVRQSSGLYSLSSVVSVTSSSQPVTCNVAHPATNTKVDKTVAP STCSKPTCPPPELLGGPSVFIFPPKPKDTLMISRTPEVTCVVVDVSQDDPEVQFTWYIN NEQVRTARPPLREQQFNSTIRVVSTLPIAHQDWLRGKEFKCKVHNKALPAPIEKTISK ARGQPLEPKVYTMGPPREELSSRSVSLTCMINGFYPSDISVEWEKNGKAEDNYKTTP AVLDSDGSYFLYSKLSVPTSEWQRGDVFTCSVMHEALHNHYTQKSISRSPGK | 18 |
| VL DNA | ATGGACACGAGGGCCCCCACTCAGCTGCTGGGGCTCCTGCTGCTCTGGCTCCCAG GTGCCACATTTGCCGTCGTGCTGACCCAGACTCCATCCCCAGTGTCTACAGCTGTA GGAGGCACAGTCACCATCAATTGCCAGTCCAGTCACAGTGTTTATTATGGCGACT GGTTAGCCTGGTATCAGCAGAAACCAGGGCAGCCTCCTAAGCTCCTGATCTACAG GGCATCCAATCTGGCATCGGTGTCCCATCGCGGTTCAAAGGCAGTGGATCTGG GACACAGTTCACTCTCACCATCAGCGGCGTGCAGTGTGACGATGCTGCCACTTAC TACTGTCTAGGCGGTTATGATGATGATGGTGAGACTGCTTTCGGCGGAGGGACC GAGGTGGTGGTCAAA | 22 |
| VL AA (CDRs underlined) | MDTRAPTQLLGLLLLWLPGATFAVVLTQTPSPVSTAVGGTVTINC<u>QSSHSVYYGDWL AWYQQKPGQPPKLLIYRASNLAS</u>GVPSRFKGSGSGTQFTLTISGVQCDDAATYYC<u>LG GYDDDGETA</u>FGGGTEVVVK | 23 |
| LC AA (CDRs underlined) | MDTRAPTQLLGLLLLWLPGATFAVVLTQTPSPVSTAVGGTVTINC<u>QSSHSVYYGDWL AWYQQKPGQPPKLLIYRASNLAS</u>GVPSRFKGSGSGTQFTLTISGVQCDDAATYYC<u>LG GYDDDGETA</u>FGGGTEVVVKDPVAPTVLIFPPAADQVATGTVTIVCVANKYFPDVTVT WEVDGTTQTTGIENSKTPQNSADCTYNLSSTLTLTSTQYNSHKEYTCKVTQGTTSVV QSFNRGDC | 24 |

Figure 6 (Cont.)

Antibody Epitopes within Linker Sequence

| Linker Sequence | Clone 8 Epitope | Clone 16 Epitope |
|---|---|---|
| GSTSGSGKPGSGEGSTKG | GSGKPGSGEG | GKPGSGEG |
| SEQ ID NO: 1 | SEQ ID NO: 2 | SEQ ID NO: 3 |
|  | SGKPGSGE | KPGSG |
|  | SEQ ID NO: 499 | SEQ ID NO: 500 |

Figure 7

8-4 VH humanized sequences -- IMGT-LigM DB (Abysis) clustered at 90% (18 sequences)

```
>8_4_HC_humanized_866
VQLQESGGGVVQPGRSLRLSCAASGFTISNLAIIWVRQAPGKGLEWVADIDGRGDIYCATWAKGRFTISRDNST
LYLQMNSLRADDTAVYYCARDGDGSGWGDFNFWGQGTLVTVSS (SEQ ID NO: 28)
>8_4_HC_humanized_673
QSVVESGGVVVQPGGSLRLSCAASGFTISNLAIIWVRQAPGKGPEWVSDIDGRGDIYCATWAKGRFTISRDNSSL
YLQMNSLRTEDTAVYYCAKDGDGSGWGDFNFWGQGTMVTVSS (SEQ ID NO: 29)
>8_4_HC_humanized_631
QSVEESGGRLVTPGATVKISCKVSGFTISNLAIIWVQQAPGKGLEWMGDIDGRGDIYCATWAQGRVTITADSST
AYMELNGLRYADTAVYYCATDGDGSGWGDFNFWGQGTLVTVSS (SEQ ID NO: 30)
>8_4_HC_humanized_1002
QSLEESGGGVVQPGKSLRLSCTASGFTISNLAIIWVRQAPGKGLESVADIDGRGDIYCATWATGRFAISRDNSKLY
LHMDNLRAEDTAVYYCARDGDGSGWGDFNFWGQGTTVIVSS (SEQ ID NO: 31)
>8_4_HC_humanized_771
QSLEQSGGGLVQPGGSLRLSCAASGFTISNLAIIWVRQAPGKGLEWVSDIDGRGDIYCATWAKGRFTISKSKNTL
YLQMNSLRAEDTAVYYCAVDGDGSGWGDFNFWGQGTLVTVSS (SEQ ID NO: 32)
>8_4_HC_humanized_849
QSVEESGGDLVKPGGSLRLSCAASGFTISNLAIIWIRQAPGKGLEWLSDIDGRGDIYCATWAKGRFTISRDNASLN
LQMNSLRAEDTAVYYCAVDGDGSGWGDFNFWGQGTLVTVSS (SEQ ID NO: 33)
>8_4_HC_humanized_706
VLLLESGGGLAQPGGTLRLSCSASGFTISNLAIIWVRQAPGKGLEWVSDIDGRGDIYCATWARGRFIISRDNSTLY
LQMNSLRAEDTAVYYCAKDGDGSGWGDFNFWGQGILVTVSS (SEQ ID NO: 34)
>8_4_HC_humanized_703
VQLVESGGTLVQPGGSLRLSCSASGFTISNLAIIWVRQAPGKGLEYVSDIDGRGDIYCATWAKGRITISRDNSTLSL
QMSTLRTEDTAVYYCVRDGDGSGWGDFNFWGQGTLVTVSS (SEQ ID NO: 35)
>8_4_HC_humanized_278
VQLVQSGGGLVKPGGSLRLSCEASGFTISNLAIIWIRQAPGKGLEWVGDIDGRGDIYCATWAKGRFTISRDDSTL
YLQVNSLKTEDSAVYYCTTDGDGSGWGDFNFWGQGTLVTVSS (SEQ ID NO: 36)
>8_4_HC_humanized_800
QSVLESGPGLVKPSETLSLTCTVSGFTISNLAIIWIRQPPGKGLEWIGDIDGRGDIYCATWAKSRLTISTSKNQFSLR
LTSVTAADTAMYYCAVDGDGSGWGDFNFWGQGTLVSVSS (SEQ ID NO: 37)
>8_4_HC_humanized_809
VQLVESGGGLVQPGGSLRLSCAASGFTISNLAIIWVRQAPGKGLEWLSDIDGRGDIYCATWARGRFAISNARNSL
YLQMNSLRDEDTAVYFCARDGDGSGWGDFNFWGQGTLVTVSS (SEQ ID NO: 38)
```

Figure 8

>8_4_HC_humanized_273
VQLVQSGGGLVQPGGSLRLSCAASGFTISNLAIIWVRQASGKGLEWIGDIDGRGDIYCATWAKGRFTVSRSQNS
VFLQMNSLETEDTAVYYCARDGDGSGWGDFNFWGQGTLVTVSS (SEQ ID NO: 39)
>8_4_HC_humanized_716
QSVLESGGGWVQPGRSLRLSCSASGFTISNLAIIWVRQAPGKGLEWVSDIDGRGDIYCATWAKGRFTISRDNNS
LYLQMNSLRPEDTALYYCAKDGDGSGWGDFNFWGQGVLVTVSS (SEQ ID NO: 40)
>8_4_HC_humanized_202
VQLQESGEGLVQPGGSLRLSCAASGFTISNLAIIWVRQAPGKGLEYVSDIDGRGDIYCATWAKGRFTISRDNSTLY
LQMGSLRAEDMAVYYCAVDGDGSGWGDFNFWGQGTMVTVSS (SEQ ID NO: 41)
>8_4_HC_humanized_21
VQLVESGGGLVQPGGSLRLSCAASGFTISNLAIIWVRQAPGKGLEFVSDIDGRGDIYCATWAKDRFTISRDNSTVY
LQMDSLRTEDTAMYFCARDGDGSGWGDFNFWGQGTLVTVSS (SEQ ID NO: 42)
>8_4_HC_humanized_173
QSVEESGGRLVTPGGSLRLSCTATGFTISNLAIIWFRQAPGKGLEWVGDIDGRGDIYCATWAKGRFTISRDDNSL
YLQMNSLKTEDTAVYYCARDGDGSGWGDFNFWGQGTLVTVSS (SEQ ID NO: 43)
>8_4_HC_humanized_23
QSVLESGGDLVQPGGSLRLSCEASGFTISNLAIIWVRQAPGKGLEWVSDIDGRGDIYCATWAKGRFTISKSKHTLF
LQMHSLRVEDTAVYYCAKDGDGSGWGDFNFWGQGTTVTVSS (SEQ ID NO: 44)
>8_4_HC_humanized_879
QSVEESGGGLVQPGGSLRLSCTASGFTISNLAIIWVRQAPGKGLEWVSDIDGRGDIYCATWAKGRFTISRDSSTLY
LQMNNLRVEDTALYYCAHDGDGSGWGDFNFWGRGTQVTVSS (SEQ ID NO: 45)

Figure 8 (cont.)

*8-4 VL humanized sequences -- IMGT-LigM DB (Abysis) clustered at 90%*
*(39 sequences)*

>8_4_LC_humanized_866
DIQMTQSPSSLSASVGDRVTITCQASQSISTALAWYQQKPGKAPKRLIYRASTLASGVPSRFSGSGSGTEFTLTISS
LQPEDFATYYCQQGWSTVNVDNVFGQGTKVEIK (SEQ ID NO: 46)
>8_4_LC_humanized_340
DIQMTQSPFSLSASVGDRVTITCQASQSISTALAWYQQKPGKAPKLLIYRASTLASGVPSRFSGSGSGTDFTLTISS
LQPEDFATYFCQQGWSTVNVDNVFGGGTKLEIK (SEQ ID NO: 47)
>8_4_LC_humanized_322
DIQLTQSPSFLSASVGDTVSITCQASQSISTALAWYQQKPGKAPKHLIYRASTLASGVPSRFSGGGSGTDFTLTISSL
QPEDFATYYCQQGWSTVNVDNVFGGGTKVEIK (SEQ ID NO: 48)
>8_4_LC_humanized_305
DIQLTQSPSSLSASVGDRVTITCQASQSISTALAWFQQKPGKAPKSLIYRASTLASGVPSRFSGSGSGTDFTLTISSL
QPEDSATYYCQQGWSTVNVDNVFGGGTKVEIK (SEQ ID NO: 49)
>8_4_LC_humanized_303
DIQMTQSPSSLSASVGDRVTITCQASQSISTALAWYQQKPGKAPKLLIYRASTLASGVPSRFSGSGSGTDFTFTISS
LQPEDIATYYCQQGWSTVNVDNVFGPGTKVDIK (SEQ ID NO: 50)
>8_4_LC_humanized_291
DIQLTQSPSSLSASVGDRVTITCQASQSISTALAWYQQKPGKGPKLLIYRASTLASGVPSRFSGSGSGTDFSLTISSL
QPEDLATYYCQQGWSTVNVDNVFGGGTKVEIK (SEQ ID NO: 51)
>8_4_LC_humanized_217
DIVMTQSPDSLAVSLGERATINCQASQSISTALAWYQQKPGQPPKLLIYRASTLASGVPDRFSGSGSGTDFTLTISS
LQAEDVAVYYCQQGWSTVNVDNVFGQGTKVEIK (SEQ ID NO: 52)
>8_4_LC_humanized_197
AYDMTQTPATLSLSPGERATLSCQASQSISTALAWYQQKPGQAPRLLIYRASTLASGIPARFSGSGSGTDFTLTISS
LEPEDFAVYYCQQGWSTVNVDNVFGQGTEVVVR (SEQ ID NO: 53)
>8_4_LC_humanized_169
EIVLTQSPSFLSAFVGDRITITCQASQSISTALAWYQQKPGKAPKLLIYRASTLASGVPSRFSGSGSGTEFTLTISGLQ
PEDFASYYCQQGWSTVNVDNVFGGGTKLEIK (SEQ ID NO: 54)
>8_4_LC_humanized_17
DIQLTQSPSSLSAAVGDRVTIACQASQSISTALAWYQQKPGKAPKLLIYRASTLASGVPSRFSGSGSGTDFTLSISSL
QPGDFATYYCQQGWSTVNVDNVFGGGTKVQMK (SEQ ID NO: 55)
>8_4_LC_humanized_13
DIQMTQSPSSLSASVGDSVTITCQASQSISTALAWYQQKPGKAPKLLIYRASTLASGVPSRFSGSGSGTEFTLTING
LQPEDFATYYCQQGWSTVNVDNVFGGGTKLEIK (SEQ ID NO: 56)

Figure 8 (cont.)

>8_4_LC_humanized_791
AYELTQTPLSSPVTLGQPASISCQASQSISTALAWLHQRPGQPPRLLIYRASTLASGVPDRFSGSGAGTAFTLKISR
VEVEDVGIYYCQQGWSTVNVDNVFGQGTKVEIK (SEQ ID NO: 57)
>8_4_LC_humanized_673
AYDMTQTPASVEVSPGERATLSCQASQSISTALAWYQHKPGQAPRLLIYRASTLASGIPARFSGSGSGTEFTLTISS
VQSDDFAVYYCQQGWSTVNVDNVFGPGTKVDIK (SEQ ID NO: 58)
>8_4_LC_humanized_678
AYELTQSPSSLSASVGDRVTITCQASQSISTALAWFQQKPGKAPKLLIYRASTLASGVPSRFSGSGSGTDFTLTISSL
LPTDFATYFCQQGWSTVNVDNVFGQGTQVEVK (SEQ ID NO: 59)
>8_4_LC_humanized_631
AYDMTQTPASVEVSVGDRVTITCQASQSISTALAWYQQKPGKAPKLLIYRASTLASGVPSRFGGSGSGTDFTLTIS
SLQPEDFATYYCQQGWSTVNVDNVFGGGTKVEIK (SEQ ID NO: 60)
>8_4_LC_humanized_1002
AYELTQSPSSLSASVGDRVTITCQASQSISTALAWYQQKPGKAPKLLIYRASTLASGVSSRFSGSGSGTDFTLTISSL
QPEDFATYYCQQGWSTVNVDNVFGQGTKLEIK (SEQ ID NO: 61)
>8_4_LC_humanized_775
AYELTQTPLSSPVTLGQPASISCQASQSISTALAWLQQRPGQPPRLLIYRASTLASGVPDRFSGSGARTDFTLNISR
VEAEDAGVYYCQQGWSTVNVDNVFGQGTKLEIK (SEQ ID NO: 62)
>8_4_LC_humanized_771
AYELTQSPATLSLSPGERATLSCQASQSISTALAWYQQKPGQAPRLLIHRASTLASGIPARFSGSGSGTDFTLTISSL
EPEDFAVYYCQQGWSTVNVDNVFGGGTRVEIK (SEQ ID NO: 63)
>8_4_LC_humanized_188
DIQLTQSPSTLSASVGDRITITCQASQSISTALAWYQQKPGKAPKLLIYRASTLASGVPPRFSGSGSGTEFTLTISSLQ
PDDFATYYCQQGWSTVNVDNVFGQGTKVVVR (SEQ ID NO: 64)
>8_4_LC_humanized_717
ELVMTQSPSSLSASVGDRVTITCQASQSISTALAWYQQKPGKAPNLLIYRASTLASGIPSRFSGSGSGTYFTLTING
LQPEDFATYYCQQGWSTVNVDNVFGGGTKVDIK (SEQ ID NO: 65)
>8_4_LC_humanized_1048
SYELTQTPPSVSVSPGQTARITCQASQSISTALAWYQQKPGQAPKVLIYRASTLASGIPERFSGSSSGTTVTLTISGV
QAEDEADYYCQQGWSTVNVDNVFGGGTKLTVL (SEQ ID NO: 66)
>8_4_LC_humanized_849
AYELTQSPLSLSVTPGQPASISCQASQSISTALAWYLQKPGQPPQLLIYRASTLASGVPDRFSGSGSGTDFTLKISR
VEAEDVGVYYCQQGWSTVNVDNVFGQGTKVEIK (SEQ ID NO: 67)
>8_4_LC_humanized_1016
DIELTQSPSSLSASIGDRVSITCQASQSISTALAWYQQKPGKAPKLLIYRASTLASGVPSRFSGSGSGTDFTLTISSLQ
PEDFATFYCQQGWSTVNVDNVFGGGTRVEIK (SEQ ID NO: 68)

Figure 8 (cont.)

>8_4_LC_humanized_978
EIVLTQSPSSLSASVGDRVTITCQASQSISTALAWYQQKPGKAPKLLIYRASTLASGVPSRFSGSGSGTDFTLTISNL
QPEDFATYYCQQGWSTVNVDNVFGGGTKVEIK (SEQ ID NO: 69)
>8_4_LC_humanized_706
DIQMTQYPSSLSASVGDRVTIACQASQSISTALAWYQQKPGKPPKLLIYRASTLASGVPSRFSGSGSGTDFTLTISC
LQPEDVATYYCQQGWSTVNVDNVFGQGTRVEFK (SEQ ID NO: 70)
>8_4_LC_humanized_278
ELVLTQSPSSLSASVGDRVTITCQASQSISTALAWCQQKPGKSPTLLIYRASTLASGVPSRFSGSGSGTGFTLTISGL
QPEDFATYYCQQGWSTVNVDNVFGGGTKVEIR (SEQ ID NO: 71)
>8_4_LC_humanized_129
EIVMTQSPSSLSASVGDRVTITCQASQSISTALAWYQHKPGKAPRLLIYRASTLASGVPSRFSGSGSGTDFTLTISSL
QPDDFATYYCQQGWSTVNVDNVFGQGTKVEVK (SEQ ID NO: 72)
>8_4_LC_humanized_1133
AYDMTTQPPSVSVSPGQTASITCQASQSISTALAWYQQKPGQSPVLVIYRASTLASGIPERFSGSNSGNTATLTIS
GTQAMDEADYYCQQGWSTVNVDNVFGTGTEVVVR (SEQ ID NO: 73)
>8_4_LC_humanized_881
AYDMTQSPSSLSASVGDRVTITCQASQSISTALAWYQQKPGKAPNLLIYRASTLASGVPSRFSGSGSGTDFTLTISS
LQPEDFATYYCQQGWSTVNVDNVFGGGTKVQIK (SEQ ID NO: 74)
>8_4_LC_humanized_882
AYDMTQSPSSLSASVGDRVTITCQASQSISTALAWYQQKPGKAPKLLIYRASTLASGVPSRFSGSGFGTDFTFTISS
LQPEDSATYYCQQGWSTVNVDNVFGQGTKLEIK (SEQ ID NO: 75)
>8_4_LC_humanized_273
ELVMTQSPSSLSASVGDRVTITCQASQSISTALAWYQQKPGEAPKLLIYRASTLASGVPSRFSGSGSGTDFTLTISG
LQSEDFATYYCQQGWSTVNVDNVFGQGTKVEIK (SEQ ID NO: 76)
>8_4_LC_humanized_716
ELVMTQSPSSLSASEGDRVTITCQASQSISTALAWYQQKPGRAPKLLIHRASTLASGVPSRFSGSGSGTEFTLTISG
LQSEDFATYYCQQGWSTVNVDNVFGGGTTVDVK (SEQ ID NO: 77)
>8_4_LC_humanized_677
AYDMTQSPSFLSASVGDRVTITCQASQSISTALAWYQQKPGKAPKLLIYRASTLASGVPSRFSGSGSGTEFTLTISS
LQPEDFATYYCQQGWSTVNVDNVFGQGTRLEIK (SEQ ID NO: 78)
>8_4_LC_humanized_192
AYDMTQSPSSLSASVGDRVTITCQASQSISTALAWYQQKPGKAPKLLIYRASTLASGVPSRFSGSGSGTDFTLTISS
LQAEDFTTYYCQQGWSTVNVDNVFGQGTKVEFK (SEQ ID NO: 79)

Figure 8 (cont.)

>8_4_LC_humanized_802
AIRMTQSPSSFSASTGDRVTITCQASQSISTALAWYQQKPGKAPKLLIYRASTLASGVPSRFSGSGSGTDFTLTISCL
QSEDFATYYCQQGWSTVNVDNVFGGGTKVEIK (SEQ ID NO: 80)
>8_4_LC_humanized_54
AYGMTQSPDSLAVSLGERASINCQASQSISTALAWYQQKPGQPPKLLIYRASTLASGVPDRFSGGGSGTDFTLTIS
SLQAEDVAVYYCQQGWSTVNVDNVFGGGTKVEIK (SEQ ID NO: 81)
>8_4_LC_humanized_173
AIQMTQSPFSLSASVGDRVTITCQASQSISTALAWFQQKPGKAPKSLIYRASTLASGVSSKFSGSGSGTDFTLTISSL
QPEDFATYYCQQGWSTVNVDNVFGQGTRLVVR (SEQ ID NO: 82)
>8_4_LC_humanized_224
AYDMTQTPASVSLSPGERATLSCQASQSISTALAWYQQKPGQAPRLLIYRASTLASGIPDRFRGSGSATDFTLTIS
RLEPEDFAVYYCQQGWSTVNVDNVFGGGTEVVVR (SEQ ID NO: 83)
>8_4_LC_humanized_657
AYDMTQTPASVEVSVGDRVSITCQASQSISTALAWYQQKPGKAPKLLIYRASTLASGVPSRFSGSGSGTDFTLTIT
SLQPVDFATYYCQQGWSTVNVDNVFGPGTTVDAK (SEQ ID NO: 84)

Figure 8 (cont.)

*8-4 VH humanized sequences -- IMGT-LigM DB (Abysis) clustered at 95% (47 sequences)*

```
>cl|CABBABABA|10|117 >8_4_HC_humanized_866 >8_4_HC_humanized_340
>8_4_HC_humanized_336 >8_4_HC_humanized_332 >8_4_HC_humanized_322
VQLVESGGGVVQPGRSLRLSCAASGFTISNLAIIWVRQAPGKGLEWVADIDGRGDIYCATWAKGRFTISRDNSTL
YLQMNSLRAEDTAVYYCAVDGDGSGWGDFNFWGQGTLVTVSS (SEQ ID NO: 85)
>cl|KABBABABA|13|117 >8_4_HC_humanized_315 >8_4_HC_humanized_314
>8_4_HC_humanized_305 >8_4_HC_humanized_303 >8_4_HC_humanized_296
VQLVQSGGGVVQPGRSLRLSCAASGFTISNLAIIWVRQAPGKGLEWVADIDGRGDIYCATWAKGRFTISRDNST
LYLQMNSLRAEDTAVYYCAVDGDGSGWGDFNFWGQGTLVTVSS (SEQ ID NO: 86)
>cl|TABBABABA|8|117 >8_4_HC_humanized_217 >8_4_HC_humanized_197
>8_4_HC_humanized_678 >8_4_HC_humanized_978 >8_4_HC_humanized_635
VQLVESGGGLVKPGGSLRLSCAASGFTISNLAIIWVRQAPGKGLEWVSDIDGRGDIYCATWAKGRFTISRDNASL
YLQMNSLRAEDTAVYYCARDGDGSGWGDFNFWGQGTLVTVSS (SEQ ID NO: 87)
>cl|WABBABABA|7|117 >8_4_HC_humanized_169 >8_4_HC_humanized_122
>8_4_HC_humanized_676 >8_4_HC_humanized_893 >8_4_HC_humanized_57
VQLVESGGGLVQPGGSLRLSCAASGFTISNLAIIWVRQAPGKGLEWVSDIDGRGDIYCATWAKGRFTISRDNSTL
YLQMNSLRAEDTAVYYCAKDGDGSGWGDFNFWGQGTLVTVSS (SEQ ID NO: 88)
>cl|ZABBABABA|1|117 >8_4_HC_humanized_17
VQLVESGGGLVQPGGSLRLSCAASGFTISNLAIIWVRQAPGRGLVWVSDIDGRGDIYCATWAKGRFTISRDNAT
LYLQMNNLRAEDTAVYYCARDGDGSGWGDFNFWGQGTLVTVSS (SEQ ID NO: 89)
>cl|CEBBABABA|1|117 >8_4_HC_humanized_791
QSVLESGGGLVQPGGSLRLSCAASGFTISNLAIIWVRQAPGKGLEWVSDIDGRGDIYCATWARGRFTISRDNSTL
YLQMNSLRAEDTAIYYCAKDGDGSGWGDFNFWGRGTHVTVSS (SEQ ID NO: 90)
>cl|DEBBABABA|1|117 >8_4_HC_humanized_673
QSVVESGGVVVQPGGSLRLSCAASGFTISNLAIIWVRQAPGKGPEWVSDIDGRGDIYCATWAKGRFTISRDNSSL
YLQMNSLRTEDTAVYYCAKDGDGSGWGDFNFWGQGTMVTVSS (SEQ ID NO: 91)
>cl|GEBBABABA|1|117 >8_4_HC_humanized_631
QSVEESGGRLVTPGATVKISCKVSGFTISNLAIIWVQQAPGKGLEWMGDIDGRGDIYCATWAQGRVTITADSST
AYMELNGLRYADTAVYYCATDGDGSGWGDFNFWGQGTLVTVSS (SEQ ID NO: 92)
>cl|HEBBABABA|1|117 >8_4_HC_humanized_1002
QSLEESGGGVVQPGKSLRLSCTASGFTISNLAIIWVRQAPGKGLESVADIDGRGDIYCATWATGRFAISRDNSKLY
LHMDNLRAEDTAVYYCARDGDGSGWGDFNFWGQGTTVIVSS (SEQ ID NO: 93)
>cl|KEBBABABA|1|117 >8_4_HC_humanized_775
QSLEESGGGLVQPGGSLRLSCAASGFTISNLAIIWVRQASGKGLEWVSDIDGRGDIYCATWAKGRFTISRDNSTL
YLQMNSLRAEDTAVYSCAVDGDGSGWGDFNFWGQGTLVTVSS (SEQ ID NO: 94)
```

```
>cl|LEBBABABA|2|117 >8_4_HC_humanized_771 >8_4_HC_humanized_772
QSLEQSGGGLVQPGGSLRLSCAASGFTISNLAIIWVRQAPGKGLEWVSDIDGRGDIYCATWAKGRFTISKSKNTL
YLQMNSLRAEDTAVYYCAVDGDGSGWGDFNFWGQGTLVTVSS (SEQ ID NO: 95)
>cl|NEBBABABA|1|117 >8_4_HC_humanized_188
VQLVESGGGLVQPGGSLRLSCAASGFTISNLAIIWVRQAPGKGLEWASDIDGRGDIYCATWAKGRFTISRDSSTL
YLQMNSLRTDDTAVYYCAADGDGSGWGDFNFWGQGTLVTVSS (SEQ ID NO: 96)
>cl|PEBBABABA|9|117 >8_4_HC_humanized_186 >8_4_HC_humanized_292
>8_4_HC_humanized_283 >8_4_HC_humanized_204 >8_4_HC_humanized_201
VQLVESGGGVVQPGRSLRLSCAASGFTISNLAIIWVRQAPGKGLEWVADIDGRGDIYCATWAKGRFTISRDNSTL
YLQMNSLRAEDTAVYYCAKDGDGSGWGDFNFWGQGTLVTVSS (SEQ ID NO: 97)
>cl|QEBBABABA|1|117 >8_4_HC_humanized_717
QSVLESGGGWVQPGRSLRLSCAASGFTISNLAIIWVRQAPGKGLEWVADIDGRGDIYCATWAKGRFTISRDNAS
LYLEMKSLRAEDTAIYYCARDGDGSGWGDFNFWGQGVLVTVSS (SEQ ID NO: 98)
>cl|REBBABABA|2|117 >8_4_HC_humanized_1048 >8_4_HC_humanized_675
QSVEESGGGLVQPGGSLRLSCAASGFTISNLAIIWVRQAPGKGLEWVSDIDGRGDIYCATWAKGRFTISRDNASL
YLQMNSLRAEDTAVYYCARDGDGSGWGDFNFWGQGTLVTVSS (SEQ ID NO: 99)
>cl|SEBBABABA|1|117 >8_4_HC_humanized_849
QSVEESGGDLVKPGGSLRLSCAASGFTISNLAIIWIRQAPGKGLEWLSDIDGRGDIYCATWAKGRFTISRDNASLN
LQMNSLRAEDTAVYYCAVDGDGSGWGDFNFWGQGTLVTVSS (SEQ ID NO: 100)
>cl|TEBBABABA|3|117 >8_4_HC_humanized_1016 >8_4_HC_humanized_295
>8_4_HC_humanized_319
VQLVQSGGGLVKPGGSLRLSCAASGFTISNLAIIWVRQAPGKGLEWVADIDGRGDIYCATWAKGRFTISRDNSTL
YLQMNSLRAEDTAVYYCAVDGDGSGWGDFNFWGQGTLVTVSS (SEQ ID NO: 101)
>cl|XEBBABABA|2|117 >8_4_HC_humanized_868 >8_4_HC_humanized_55
QQLQESGGGLVQPGGSLRLSCSASGFTISNLAIIWVRQAPGKGLEYVSDIDGRGDIYCATWAKGRFTISRDNSTLY
LQMSSLRAEDTAVYYCVKDGDGSGWGDFNFWGQGTLVTVSS (SEQ ID NO: 102)
>cl|YEBBABABA|1|117 >8_4_HC_humanized_862
VRLVESGGGVVQPGRSLRLSCAASGFTISNLAIIWVRQAPGKGLEWVADIDGRGDIYCATWAKGRFTISRDNSTL
HLQMNSLRAEDTAVYYCAKDGDGSGWGDFNFWGKGTTVTVSS (SEQ ID NO: 103)
>cl|ZEBBABABA|1|117 >8_4_HC_humanized_715
VQLVESGGGLVQPGGSLRLSCAASGFTISNLAIIWVRQAPGKGLEWVSDIDGRGDIYCATWAKGRFTISRSKNTL
YLQMNSLRAEDTAVYYCARDGDGSGWGDFNFWGQGTTVTVSS (SEQ ID NO: 104)
>cl|BIBBABABA|1|117 >8_4_HC_humanized_706
VLLLESGGGLAQPGGTLRLSCSASGFTISNLAIIWVRQAPGKGLEWVSDIDGRGDIYCATWARGRFIISRDNSTLY
LQMNSLRAEDTAVYYCAKDGDGSGWGDFNFWGQGILVTVSS (SEQ ID NO: 105)
```

Figure 8 (cont.)

>cl|CIBBABABA|1|117 >8_4_HC_humanized_703
VQLVESGGTLVQPGGSLRLSCSASGFTISNLAIIWVRQAPGKGLEYVSDIDGRGDIYCATWAKGRITISRDNSTLSL
QMSTLRTEDTAVYYCVRDGDSGWGDFNFWGQGTLVTVSS (SEQ ID NO: 106)
>cl|FIBBABABA|1|117 >8_4_HC_humanized_341
VQLVQSGGSLVQPGRSLRLSCAASGFTISNLAIIWVRQAPGKGLEWVADIDGRGDIYCATWAKGRFTTSRDNST
LYLQMNSLRADDTAVYFCAVDGDSGWGDFNFWGQGTLVTVSS (SEQ ID NO: 107)
>cl|KIBBABABA|1|117 >8_4_HC_humanized_301
VQLVESGGDLVQPGESLRLSCAASGFTISNLAIIWVRQAPGKGLEWVSDIDGRGDIYCATWAKGRFTISRDNSTL
YLQMNSLRAEDTAVYYCARDGDSGWGDFNFWGQGTLVTVSS (SEQ ID NO: 108)
>cl|QIBBABABA|1|117 >8_4_HC_humanized_278
VQLVQSGGGLVKPGGSLRLSCEASGFTISNLAIIWIRQAPGKGLEWVGDIDGRGDIYCATWAKGRFTISRDDSTL
YLQVNSLKTEDSAVYYCTTDGDSGWGDFNFWGQGTLVTVSS (SEQ ID NO: 109)
>cl|TIBBABABA|1|117 >8_4_HC_humanized_129
MQLVESGGGLVQPGRSLRLSCVTSGFTISNLAIIWVRQVPGKGLEWVSDIDGRGDIYCATWAKGRFTISRDNTSL
YLQMNSLRPEDTAVYYCAKDGDSGWGDFNFWGQGTLVTVSS (SEQ ID NO: 110)
>cl|XIBBABABA|1|117 >8_4_HC_humanized_800
QSVLESGPGLVKPSETLSLTCTVSGFTISNLAIIWIRQPPGKGLEWIGDIDGRGDIYCATWAKSRLTISTSKNQFSLR
LTSVTAADTAMYYCAVDGDSGWGDFNFWGQGTLVSVSS (SEQ ID NO: 111)
>cl|YIBBABABA|7|117 >8_4_HC_humanized_1133 >8_4_HC_humanized_881
>8_4_HC_humanized_677 >8_4_HC_humanized_192 >8_4_HC_humanized_65
QSVEESGGGVVQPGRSLRLSCAASGFTISNLAIIWVRQAPGKGLEWVADIDGRGDIYCATWAKGRFTISRDNSTL
YLQMNSLRAEDTAVYYCARDGDSGWGDFNFWGQGTTVTVSS (SEQ ID NO: 112)
>cl|FOBBABABA|1|117 >8_4_HC_humanized_882
QSVEESGGGLVQPGGSLRLSCAASGFTISNLAIIWVRQPPGKGLEWVGDIDGRGDIYCATWAKGRFTISRSKSTV
YLQMNSLKTEDTAVYYCTADGDSGWGDFNFWGQGMLVTVSS (SEQ ID NO: 113)
>cl|GOBBABABA|1|117 >8_4_HC_humanized_660
QSVEESGGGLIQPGGSLRLSCAASGFTISNLAIIWVRQAPGKGLECVSDIDGRGDIYCATWAKGRFTISRDNSTLYL
QMTSLRAEDTAVYYCALDGDSGWGDFNFWGQGTLVTVSS (SEQ ID NO: 114)
>cl|HOBBABABA|2|117 >8_4_HC_humanized_1051 >8_4_HC_humanized_1050
VQLVESGGGLVKPGGSLRLSCAASGFTISNLAIIWVRQAPGKGLEWVGDIDGRGDIYCATWAKGRFTISRSKNTL
YLQMNSLKTEDTAVYYCTVDGDSGWGDFNFWGQGTLVTVSS (SEQ ID NO: 115)
>cl|MOBBABABA|1|117 >8_4_HC_humanized_809
VQLVESGGGLVQPGGSLRLSCAASGFTISNLAIIWVRQAPGKGLEWLSDIDGRGDIYCATWARGRFAISNARNSL
YLQMNSLRDEDTAVYFCARDGDSGWGDFNFWGQGTLVTVSS (SEQ ID NO: 116)

Figure 8 (cont.)

>cl|VOBBABABA|1|117 >8_4_HC_humanized_273
VQLVQSGGGLVQPGGSLRLSCAASGFTISNLAIIWVRQASGKGLEWIGDIDGRGDIYCATWAKGRFTVSRSQNS
VFLQMNSLETEDTAVYYCARDGDGSGWGDFNFWGQGTLVTVSS (SEQ ID NO: 117)
>cl|WOBBABABA|1|117 >8_4_HC_humanized_716
QSVLESGGGWVQPGRSLRLSCSASGFTISNLAIIWVRQAPGKGLEWVSDIDGRGDIYCATWAKGRFTISRDNNS
LYLQMNSLRPEDTALYYCAKDGDGSGWGDFNFWGQGVLVTVSS (SEQ ID NO: 118)
>cl|ZOBBABABA|1|117 >8_4_HC_humanized_202
VQLQESGEGLVQPGGSLRLSCAASGFTISNLAIIWVRQAPGKGLEYVSDIDGRGDIYCATWAKGRFTISRDNSTLY
LQMGSLRAEDMAVYYCAVDGDGSGWGDFNFWGQGTMVTVSS (SEQ ID NO: 119)
>cl|GUBBABABA|1|117 >8_4_HC_humanized_54
VQLVESGGGLVQPGGSLRLSCATSGFTISNLAIIWVRQPPGKGLEWVSDIDGRGDIYCATWAKGRFTISRENATL
YLQMNSLRAEDTAVYYCAVDGDGSGWGDFNFWGQGTLVTVSS (SEQ ID NO: 120)
>cl|HUBBABABA|1|117 >8_4_HC_humanized_21
VQLVESGGGLVQPGGSLRLSCAASGFTISNLAIIWVRQAPGKGLEFVSDIDGRGDIYCATWAKDRFTISRDNSTVY
LQMDSLRTEDTAMYFCARDGDGSGWGDFNFWGQGTLVTVSS (SEQ ID NO: 121)
>cl|KUBBABABA|1|117 >8_4_HC_humanized_788
QSVLESGGGLVQPGGSLRLSCAASGFTISNLAIIWVRQAPGKGLEWVSDIDGRGDIYCATWAKGRFTISRDNSTL
FLQISSLRAEDTAVYYCAKDGDGSGWGDFNFWGPGTLVTVSS (SEQ ID NO: 122)
>cl|MUBBABABA|1|117 >8_4_HC_humanized_762
VKLLESGGGLVQPGGSLRLSCAASGFTISNLAIIWVRQAPGKGLEWVADIDGRGDIYCATWAKGRFTISRDNSTL
YLQMNSLGAEDTAVYYCARDGDGSGWGDFNFWGQGTLVTVSS (SEQ ID NO: 123)
>cl|PUBBABABA|1|117 >8_4_HC_humanized_173
QSVEESGGRLVTPGGSLRLSCTATGFTISNLAIIWFRQAPGKGLEWVGDIDGRGDIYCATWAKGRFTISRDDNSL
YLQMNSLKTEDTAVYYCARDGDGSGWGDFNFWGQGTLVTVSS (SEQ ID NO: 124)
>cl|RUBBABABA|1|117 >8_4_HC_humanized_224
QSVEESGGGLVKPGGSLRLSCAASGFTISNLAIIWVRQAPGKGLEWVGDIDGRGDIYCATWAKGRFTISRSKNTL
YLQMNSLKTEDTAVYYCATDGDGSGWGDFNFWGQGTLVTVSS (SEQ ID NO: 125)
>cl|VUBBABABA|1|117 >8_4_HC_humanized_672
QSVVESGGGLIQPGGSLRLSCAASGFTISNLAIIWVRQAPGKGLEWVSDIDGRGDIYCATWAKGRFTISRDNSTL
YLQMNSLRAEDTAVYYCALDGDGSGWGDFNFWGQGTLVTVSS (SEQ ID NO: 126)
>cl|XUBBABABA|1|117 >8_4_HC_humanized_267
QSVEQSGGGLVQPGESLRLSCAGSGFTISNLAIIWVRQAPGKGLEWVADIDGRGDIYCATWAKGRFTISRDNAS
LFLQMNSLRVEDTAVYYCARDGDGSGWGDFNFWGQGTLVTVSS (SEQ ID NO: 127)

Figure 8 (cont.)

>cl|YUBBABABA|1|117 >8_4_HC_humanized_23
QSVLESGGDLVQPGGSLRLSCEASGFTISNLAIIWVRQAPGKGLEWVSDIDGRGDIYCATWAKGRFTISKSKHTLF
LQMHSLRVEDTAVYYCAKDGDGSGWGDFNFWGQGTTVTVSS (SEQ ID NO: 128)
>cl|ZUBBABABA|1|117 >8_4_HC_humanized_657
QSVEESGGRLVTPGGSLRLSCAASGFTISNLAIIWVRQAPGKGLEWVSDIDGRGDIYCATWAKGRFTISRDNSSLY
LQMNSLRTEDSALYYCAIDGDGSGWGDFNFWGQGSLVTVSS (SEQ ID NO: 129)
>cl|BACBABABA|1|117 >8_4_HC_humanized_879
QSVEESGGGLVQPGGSLRLSCTASGFTISNLAIIWVRQAPGKGLEWVSDIDGRGDIYCATWAKGRFTISRDSSTLY
LQMNNLRVEDTALYYCAHDGDGSGWGDFNFWGRGTQVTVSS (SEQ ID NO: 130)

Figure 8 (cont.)

*8-4 LC humanized sequences -- IMGT-LigM DB (Abysis) clustered at 95%*
*(99 sequences)*

>cl|CACBABABA|1|110 >8_4_LC_humanized_866
DIQMTQSPSSLSASVGDRVTITCQASQSISTALAWYQQKPGKAPKRLIYRASTLASGVPSRFSGSGSGTEFTLTISS
LQPEDFATYYCQQGWSTVNVDNVFGQGTKVEIK (SEQ ID NO: 131)
>cl|DACBABABA|1|110 >8_4_LC_humanized_340
DIQMTQSPFSLSASVGDRVTITCQASQSISTALAWYQQKPGKAPKLLIYRASTLASGVPSRFSGSGSGTDFTLTISS
LQPEDFATYFCQQGWSTVNVDNVFGGGTKLEIK (SEQ ID NO: 132)
>cl|FACBABABA|1|110 >8_4_LC_humanized_336
DIQLTQSPSSLSASVGDRVTITCQASQSISTALAWYQQKPGKAPKLLIYRASTLASGVPSRFSGSGSGTDFTLTISSL
QPEDFATYYCQQGWSTVNVDNVFGQGTKLEIK (SEQ ID NO: 133)
>cl|GACBABABA|1|110 >8_4_LC_humanized_332
DIQMTQSPSSLSASVGDRVTITCQASQSISTALAWYQQKPGKAPKLLVYRASTLASGVPSRFSGSGSGTDFTLTISS
LQPEDFATYYCQQGWSTVNVDNVFGQGTKVEIK (SEQ ID NO: 134)
>cl|HACBABABA|1|110 >8_4_LC_humanized_322
DIQLTQSPSFLSASVGDTVSITCQASQSISTALAWYQQKPGKAPKHLIYRASTLASGVPSRFSGGGSGTDFTLTISSL
QPEDFATYYCQQGWSTVNVDNVFGGGTKVEIK (SEQ ID NO: 135)
>cl|KACBABABA|1|110 >8_4_LC_humanized_315
DIQLTQSPSSLSASVGDRVTITCQASQSISTALAWYQQKPGKAPKLLIYRASTLASGVPSRFSGSGSGTGFTLTISSL
QPEDFATYYCQQGWSTVNVDNVFGGGTKVEIK (SEQ ID NO: 136)
>cl|LACBABABA|1|110 >8_4_LC_humanized_314
DIQMTQSPSSLSASVGDRVTITCQASQSISTALAWYQQKPGKAPNLLIYRASTLASGVPSRFSGSGSGTDFTLTISS
LQPEDFATYYCQQGWSTVNVDNVFGQGTKVEIK (SEQ ID NO: 137)
>cl|MACBABABA|1|110 >8_4_LC_humanized_305
DIQLTQSPSSLSASVGDRVTITCQASQSISTALAWFQQKPGKAPKSLIYRASTLASGVPSRFSGSGSGTDFTLTISSL
QPEDSATYYCQQGWSTVNVDNVFGGGTKVEIK (SEQ ID NO: 138)
>cl|NACBABABA|1|110 >8_4_LC_humanized_303
DIQMTQSPSSLSASVGDRVTITCQASQSISTALAWYQQKPGKAPKLLIYRASTLASGVPSRFSGSGSGTDFTFTISS
LQPEDIATYYCQQGWSTVNVDNVFGPGTKVDIK (SEQ ID NO: 139)
>cl|PACBABABA|1|110 >8_4_LC_humanized_296
DIQMTQSPSSLSASVGDRVTITCQASQSISTALAWYQQKPGKAPKLLIYRASTLASGVPSTFSGSGSGTDFTLTISS
LQPEDFATYYCQQGWSTVNVDNVFGQGTKVEIK (SEQ ID NO: 140)
>cl|QACBABABA|1|110 >8_4_LC_humanized_294
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGGGTKVEIK (SEQ ID NO: 141)

Figure 8 (cont.)

>cl|RACBABABA|1|110 >8_4_LC_humanized_291
DIQLTQSPSSLSASVGDRVTITCQASQSISTALAWYQQKPGKGPKLLIYRASTLASGVPSRFSGSGSGTDFSLTISSL
QPEDLATYYCQQGWSTVNVDNVFGGGTKVEIK (SEQ ID NO: 142)
>cl|SACBABABA|1|110 >8_4_LC_humanized_284
DIQMTQSPSSLSASVGDRVTITCQASQSISTALAWYQQKPGKAPKSLIYRASTLASGVPSKFSGSGSGTEFTLTISSL
QPDDFATYYCQQGWSTVNVDNVFGQGTRLEIK (SEQ ID NO: 143)
>cl|TACBABABA|1|110 >8_4_LC_humanized_217
DIVMTQSPDSLAVSLGERATINCQASQSISTALAWYQQKPGQPPKLLIYRASTLASGVPDRFSGSGSGTDFTLTISS
LQAEDVAVYYCQQGWSTVNVDNVFGQGTKVEIK (SEQ ID NO: 144)
>cl|VACBABABA|1|110 >8_4_LC_humanized_197
AYDMTQTPATLSLSPGERATLSCQASQSISTALAWYQQKPGQAPRLLIYRASTLASGIPARFSGSGSGTDFTLTISS
LEPEDFAVYYCQQGWSTVNVDNVFGQGTEVVVR (SEQ ID NO: 145)
>cl|WACBABABA|1|110 >8_4_LC_humanized_169
EIVLTQSPSFLSAFVGDRITITCQASQSISTALAWYQQKPGKAPKLLIYRASTLASGVPSRFSGSGSGTEFTLTISGLQ
PEDFASYYCQQGWSTVNVDNVFGGGTKLEIK (SEQ ID NO: 146)
>cl|XACBABABA|1|110 >8_4_LC_humanized_122
DVVMTQSPASLSASVGDRVTIICQASQSISTALAWYQQKPGKAPKLLIYRASTLASGVPSRFSGSGSRTDFTFTISS
LQPEDIATYYCQQGWSTVNVDNVFGPGTKVDIK (SEQ ID NO: 147)
>cl|YACBABABA|1|110 >8_4_LC_humanized_44
DIQMTQSPSSLSASVGDRVTITCQASQSISTALAWYQQKPGKAPKRLIYRASTLASGVPSRFSGSGSGTEFTLTISS
LQPEDFATYYCQQGWSTVNVDNVFGQGTKVEIK (SEQ ID NO: 148)
>cl|ZACBABABA|1|110 >8_4_LC_humanized_17
DIQLTQSPSSLSAAVGDRVTIACQASQSISTALAWYQQKPGKAPKLLIYRASTLASGVPSRFSGSGSGTDFTLSISSL
QPGDFATYYCQQGWSTVNVDNVFGGGTKVQMK (SEQ ID NO: 149)
>cl|BECBABABA|1|110 >8_4_LC_humanized_13
DIQMTQSPSSLSASVGDSVTITCQASQSISTALAWYQQKPGKAPKLLIYRASTLASGVPSRFSGSGSGTEFTLTING
LQPEDFATYYCQQGWSTVNVDNVFGGGTKLEIK (SEQ ID NO: 150)
>cl|CECBABABA|1|110 >8_4_LC_humanized_791
AYELTQTPLSSPVTLGQPASISCQASQSISTALAWLHQRPGQPPRLLIYRASTLASGVPDRFSGSGAGTAFTLKISR
VEVEDVGIYYCQQGWSTVNVDNVFGQGTKVEIK (SEQ ID NO: 151)
>cl|DECBABABA|1|110 >8_4_LC_humanized_673
AYDMTQTPASVEVSPGERATLSCQASQSISTALAWYQHKPGQAPRLLIYRASTLASGIPARFSGSGSGTEFTLTISS
VQSDDFAVYYCQQGWSTVNVDNVFGPGTKVDIK (SEQ ID NO: 152)

Figure 8 (cont.)

\>cl|FECBABABA|1|110 >8_4_LC_humanized_678
AYELTQSPSSLSASVGDRVTITCQASQSISTALAWFQQKPGKAPKLLIYRASTLASGVPSRFSGSGSGTDFTLTISSL
LPTDFATYFCQQGWSTVNVDNVFGQGTQVEVK (SEQ ID NO: 153)
\>cl|GECBABABA|1|110 >8_4_LC_humanized_631
AYDMTQTPASVEVSVGDRVTITCQASQSISTALAWYQQKPGKAPKLLIYRASTLASGVPSRFGGSGSGTDFTLTIS
SLQPEDFATYYCQQGWSTVNVDNVFGGGTKVEIK (SEQ ID NO: 154)
\>cl|HECBABABA|1|110 >8_4_LC_humanized_1002
AYELTQSPSSLSASVGDRVTITCQASQSISTALAWYQQKPGKAPKLLIYRASTLASGVSSRFSGSGSGTDFTLTISSL
QPEDFATYYCQQGWSTVNVDNVFGQGTKLEIK (SEQ ID NO: 155)
\>cl|KECBABABA|1|110 >8_4_LC_humanized_775
AYELTQTPLSSPVTLGQPASISCQASQSISTALAWLQQRPGQPPRLLIYRASTLASGVPDRFSGSGARTDFTLNISR
VEAEDAGVYYCQQGWSTVNVDNVFGQGTKLEIK (SEQ ID NO: 156)
\>cl|LECBABABA|2|110 >8_4_LC_humanized_771 >8_4_LC_humanized_772
AYELTQSPATLSLSPGERATLSCQASQSISTALAWYQQKPGQAPRLLIHRASTLASGIPARFSGSGSGTDFTLTISSL
EPEDFAVYYCQQGWSTVNVDNVFGGGTRVEIK (SEQ ID NO: 157)
\>cl|MECBABABA|1|110 >8_4_LC_humanized_676
AYDMTQSPATLSLSPGERATLSCQASQSISTALAWYQQKPGQAPRLLIYRASTLASGIPARFSGSGSGTDFTLTISS
LEPEDFAVYYCQQGWSTVNVDNVFGGGTKVEIK (SEQ ID NO: 158)
\>cl|NECBABABA|1|110 >8_4_LC_humanized_188
DIQLTQSPSTLSASVGDRITITCQASQSISTALAWYQQKPGKAPKLLIYRASTLASGVPPRFSGSGSGTEFTLTISSLQ
PDDFATYYCQQGWSTVNVDNVFGQGTKVVVR (SEQ ID NO: 159)
\>cl|PECBABABA|1|110 >8_4_LC_humanized_186
DIQLTQSPSTLSASVGDRVTITCQASQSISTALAWYQQKPGKAPKLLIYRASTLASGVPSRFSGSGSGTEFTLTISSL
QPDDFATYYCQQGWSTVNVDNVFGQGTKVVVR (SEQ ID NO: 160)
\>cl|QECBABABA|1|110 >8_4_LC_humanized_717
ELVMTQSPSSLSASVGDRVTITCQASQSISTALAWYQQKPGKAPNLLIYRASTLASGIPSRFSGSGSGTYFTLTING
LQPEDFATYYCQQGWSTVNVDNVFGGGTKVDIK (SEQ ID NO: 161)
\>cl|RECBABABA|1|110 >8_4_LC_humanized_1048
SYELTQPPSVSVSPGQTARITCQASQSISTALAWYQQKPGQAPKVLIYRASTLASGIPERFSGSSSGTTVTLTISGV
QAEDEADYYCQQGWSTVNVDNVFGGGTKLTVL (SEQ ID NO: 162)
\>cl|SECBABABA|1|110 >8_4_LC_humanized_849
AYELTQSPLSLSVTPGQPASISCQASQSISTALAWYLQKPGQPPQLLIYRASTLASGVPDRFSGSGSGTDFTLKISR
VEAEDVGVYYCQQGWSTVNVDNVFGQGTKVEIK (SEQ ID NO: 163)

Figure 8 (cont.)

\>cl|TECBABABA|1|110 >8_4_LC_humanized_1016
DIELTQSPSSLSASIGDRVSITCQASQSISTALAWYQQKPGKAPKLLIYRASTLASGVPSRFSGSGSGTDFTLTISSLQ
PEDFATFYCQQGWSTVNVDNVFGGGTRVEIK (SEQ ID NO: 164)
\>cl|VECBABABA|1|110 >8_4_LC_humanized_978
EIVLTQSPSSLSASVGDRVTITCQASQSISTALAWYQQKPGKAPKLLIYRASTLASGVPSRFSGSGSGTDFTLTISNL
QPEDFATYYCQQGWSTVNVDNVFGGGTKVEIK (SEQ ID NO: 165)
\>cl|WECBABABA|1|110 >8_4_LC_humanized_893
DIEMTQSPSSLSASVGDRVTITCQASQSISTALAWYQQKPGKAPKRLIQRASTLASGVPSRFSGSGSGTEFTLTISS
LQPEDFATYHCQQGWSTVNVDNVFGGGTKVEIK (SEQ ID NO: 166)
\>cl|XECBABABA|1|110 >8_4_LC_humanized_868
DIVMTQSPDSLAVSLGERATINCQASQSISTALAWYQQKPGQPPKLLIYRASTLASGVPDRFSGSGSGTDFTLTISS
LQAEDVAVYYCQQGWSTVNVDNVFGQGTKLEIK (SEQ ID NO: 167)
\>cl|YECBABABA|1|110 >8_4_LC_humanized_862
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGQGTKVEIK (SEQ ID NO: 168)
\>cl|ZECBABABA|1|110 >8_4_LC_humanized_715
DIQMTQSPSSLSASVGDRVTITCQASQSISTALAWYQQKPGKAPKFLIYRASTLASGVPSRFSGSGSGTDFTLTISS
LQPEDFATYYCQQGWSTVNVDNVFGQGTKVEIK (SEQ ID NO: 169)
\>cl|BICBABABA|1|110 >8_4_LC_humanized_706
DIQMTQYPSSLSASVGDRVTIACQASQSISTALAWYQQKPGKPPKLLIYRASTLASGVPSRFSGSGSGTDFTLTISC
LQPEDVATYYCQQGWSTVNVDNVFGQGTRVEFK (SEQ ID NO: 170)
\>cl|CICBABABA|1|110 >8_4_LC_humanized_703
DIVMTQSPDSLAVSLGERATINCQASQSISTALAWYQQKAGQPPKLLIYRASTLASGVPDRFSGSGSGTDFTLTIS
SLQAEDVAVYYCQQGWSTVNVDNVFGGGTKVEIK (SEQ ID NO: 171)
\>cl|DICBABABA|1|110 >8_4_LC_humanized_635
DIQMTQSPSSLSASVGDRVTITCQASQSISTALAWYQQKPGKVPKLLIYRASTLASGVPSRFSGSGSGTDFTLTISS
LQPEDVATYYCQQGWSTVNVDNVFGQGTKLEIK (SEQ ID NO: 172)
\>cl|FICBABABA|1|110 >8_4_LC_humanized_341
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGGGTKLEIK (SEQ ID NO: 173)
\>cl|GICBABABA|1|110 >8_4_LC_humanized_328
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGRGTKVEIK (SEQ ID NO: 174)

Figure 8 (cont.)

\>cl|HICBABABA|1|110 >8_4_LC_humanized_324
DIQMTQSPSSLSASVGDRVTITCQASQSISTALAWYQQKPGNAPKSLIYRASTLASGVPSKFSGSGSGTDFTLTISS
LQPEDFATYYCQQGWSTVNVDNVFGGGTKVEIK (SEQ ID NO: 175)
\>cl|KICBABABA|1|110 >8_4_LC_humanized_301
DIQMTQSPDSLAVSLGERATINCQASQSISTALAWYQQKPGQPPKLLIYRASTLASGVPDRFSGSGSGTDFTLTIS
SLQAEDVAVYYCQQGWSTVNVDNVFGQGTKLEIK (SEQ ID NO: 176)
\>cl|LICBABABA|1|110 >8_4_LC_humanized_295
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGQGTRLEIK (SEQ ID NO: 177)
\>cl|MICBABABA|1|110 >8_4_LC_humanized_292
DIQMTQSPSSLSASVGDRVTITCQASQSISTALAWYQQKPGKAPNLLIYRASTLASGVPSRFSGSVSGTDFTLTISS
LQPEDFATYYCQQGWSTVNVDNVFGGGTKVEIK (SEQ ID NO: 178)
\>cl|NICBABABA|1|110 >8_4_LC_humanized_283
DIQLTQSPSSVSASVGDRVTITCQASQSISTALAWYQQKPGKAPKLLIYRASTLASGVPSRFSGSGSGTDFTLTISSL
QPEDFATYYCQQGWSTVNVDNVFGQGTRLEIK (SEQ ID NO: 179)
\>cl|PICBABABA|1|110 >8_4_LC_humanized_282
DIQMTQSPSSVSASVGDRVTITCQASQSISTALAWYQQKLGKAPKLLIYRASTLASGVPSRFSGSGSGTDFTLTISS
LQPEDFATYYCQQGWSTVNVDNVFGGGTKVEIK (SEQ ID NO: 180)
\>cl|QICBABABA|1|110 >8_4_LC_humanized_278
ELVLTQSPSSLSASVGDRVTITCQASQSISTALAWCQQKPGKSPTLLIYRASTLASGVPSRFSGSGSGTGFTLTISGL
QPEDFATYYCQQGWSTVNVDNVFGGGTKVEIR (SEQ ID NO: 181)
\>cl|RICBABABA|1|110 >8_4_LC_humanized_204
DIQLTQSPSSLSASVGDRVTITCQASQSISTALAWYQQKPGKAPKLLIYRASTLASGVPSRFSGSGSGTDFTLTISSL
QPEDFATYYCQQGWSTVNVDNVFGQGTKVEIK (SEQ ID NO: 182)
\>cl|SICBABABA|1|110 >8_4_LC_humanized_201
DIRVTQSPSSLSASVGDRVTITCQASQSISTALAWYQQKPGKAPKLLIYRASTLASGVPSRFSGSGSGTDFTFTISSL
QPEDIATYYCQQGWSTVNVDNVFGGGTKVDIK (SEQ ID NO: 183)
\>cl|TICBABABA|1|110 >8_4_LC_humanized_129
EIVMTQSPSSLSASVGDRVTITCQASQSISTALAWYQHKPGKAPRLLIYRASTLASGVPSRFSGSGSGTDFTLTISSL
QPDDFATYYCQQGWSTVNVDNVFGQGTKVEVK (SEQ ID NO: 184)
\>cl|VICBABABA|1|110 >8_4_LC_humanized_108
DVVMTQSPSSVSASVGDRVTITCQASQSISTALAWYQQKPGKAPKLLIYRASTLASGVPSRFSGSGSGTDFTLTIT
SLQPEDFATYYCQQGWSTVNVDNVFGGGTKVEIK (SEQ ID NO: 185)

Figure 8 (cont.)

\>cl|WICBABABA|1|110 >8_4_LC_humanized_57
DIQMTQSPSSLSASVGDRVTITCQASQSISTALAWYQQKPGKAPKRLIYRASTLASGVPSRFSGSGSGTEFTLTISS
LQPEDFATYYCQQGWSTVNVDNVFGQGTRLEIK (SEQ ID NO: 186)
\>cl|XICBABABA|1|110 >8_4_LC_humanized_800
AYELTQTPPSLSVTPGQPASISCQASQSISTALAWYLQKPGQPPQLLIYRASTLASGVPDRFSGSGSGTDFTLKISR
VEAEDVGVYYCQQGWSTVNVDNVFGQGTKVEIK (SEQ ID NO: 187)
\>cl|YICBABABA|1|110 >8_4_LC_humanized_1133
AYDMTTQPPSVSVSPGQTASITCQASQSISTALAWYQQKPGQSPVLVIYRASTLASGIPERFSGSNSGNTATLTIS
GTQAMDEADYYCQQGWSTVNVDNVFGTGTEVVVR (SEQ ID NO: 188)
\>cl|ZICBABABA|1|110 >8_4_LC_humanized_621
AYELTQSPSSLSASVGDRVTITCQASQSISTALAWYQQKPGKAPKLLIYRASTLASGVPSRFSGSGSGTDFTLTISSL
QPEDFATYYCQQGWSTVNVDNVFGQGTKVEIK (SEQ ID NO: 189)
\>cl|COCBABABA|1|110 >8_4_LC_humanized_881
AYDMTQSPSSLSASVGDRVTITCQASQSISTALAWYQQKPGKAPNLLIYRASTLASGVPSRFSGSGSGTDFTLTISS
LQPEDFATYYCQQGWSTVNVDNVFGGGTKVQIK (SEQ ID NO: 190)
\>cl|DOCBABABA|1|110 >8_4_LC_humanized_55
AYDMTQTPASVEVSPGERATLSCQASQSISTALAWYQQKPGQAPRLLIYRASTLASGIPARFSGSGSGTEFTLTISS
LQSEDFAVYYCQQGWSTVNVDNVFGQGTEVVVR (SEQ ID NO: 191)
\>cl|FOCBABABA|1|110 >8_4_LC_humanized_882
AYDMTQSPSSLSASVGDRVTITCQASQSISTALAWYQQKPGKAPKLLIYRASTLASGVPSRFSGSGFGTDFTFTISS
LQPEDSATYYCQQGWSTVNVDNVFGQGTKLEIK (SEQ ID NO: 192)
\>cl|GOCBABABA|1|110 >8_4_LC_humanized_660
AYVMTQSPATLSLSPGERATLSCQASQSISTALAWYQQRPGQAPRLLIYRASTLASGIPARFSGSGSGTDFTLTISS
LEPEDFAVYYCQQGWSTVNVDNVFGGGTKVEIK (SEQ ID NO: 193)
\>cl|HOCBABABA|1|110 >8_4_LC_humanized_1051
SYELTQTPPSVSVSPGQTARITCQASQSISTALAWYQQKPGQAPVLVIYRASTLASGIPERFSGSSSGTTVTLTISGV
QAEDEADYYCQQGWSTVNVDNVFGTGTKVTVL (SEQ ID NO: 194)
\>cl|KOCBABABA|1|110 >8_4_LC_humanized_1050
SYELTQTPPSVSVSPGQTARITCQASQSISTALAWYQQKPGQAPVLVIYRASTLASGIPERFSGSSSGTTVTLTISGV
QAEDEADYYCQQGWSTVNVDNVFGTGTKVTVL (SEQ ID NO: 195)
\>cl|LOCBABABA|1|110 >8_4_LC_humanized_860
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGGGTKVEIK (SEQ ID NO: 196)

Figure 8 (cont.)

>cl|MOCBABABA|1|110 >8_4_LC_humanized_809
DIQMTQSPSSVSASVRDRVTITCQASQSISTALAWYQQKPGKAPKLLIYRASTLASGVPSRFSGSGSGTDFTLTISS
LQPEDFATYYCQQGWSTVNVDNVFGPGTKVDIK (SEQ ID NO: 197)
>cl|NOCBABABA|1|110 >8_4_LC_humanized_346
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGQGTKVEIK (SEQ ID NO: 198)
>cl|POCBABABA|1|110 >8_4_LC_humanized_345
DIQMTQSPSSLSASVGDRVTITCQASQSISTALAWYQQKPGKAPKLLIYRASTLASGVPSRFSGSGSGTDFTFTISS
LQPDDFATYYCQQGWSTVNVDNVFGGGTKVEIK (SEQ ID NO: 199)
>cl|QOCBABABA|1|110 >8_4_LC_humanized_334
DIQMTQSPSFVSASVGDRVTITCQASQSISTALAWYQQKPGKAPKLLIYRASTLASGVPSRFSGSGSGTDFTLTISS
LQPEDFATYYCQQGWSTVNVDNVFGGGTKVEIK (SEQ ID NO: 200)
>cl|ROCBABABA|1|110 >8_4_LC_humanized_319
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGQGTKVEIK (SEQ ID NO: 201)
>cl|SOCBABABA|1|110 >8_4_LC_humanized_308
DIQMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGGGTKVEIK (SEQ ID NO: 202)
>cl|TOCBABABA|1|110 >8_4_LC_humanized_281
DIQLTQSPSSVSASVGDRVTITCQASQSISTALAWYQQKPGKAPKLLIYRASTLASGVPSRFSGSGSGTDFTLTISSL
QPEDFATYYCQQGWSTVNVDNVFGGGTKVDIK (SEQ ID NO: 203)
>cl|VOCBABABA|1|110 >8_4_LC_humanized_273
ELVMTQSPSSLSASVGDRVTITCQASQSISTALAWYQQKPGEAPKLLIYRASTLASGVPSRFSGSGSGTDFTLTISG
LQSEDFATYYCQQGWSTVNVDNVFGQGTKVEIK (SEQ ID NO: 204)
>cl|WOCBABABA|1|110 >8_4_LC_humanized_716
ELVMTQSPSSLSASEGDRVTITCQASQSISTALAWYQQKPGRAPKLLIHRASTLASGVPSRFSGSGSGTEFTLTISG
LQSEDFATYYCQQGWSTVNVDNVFGGGTTVDVK (SEQ ID NO: 205)
>cl|XOCBABABA|1|110 >8_4_LC_humanized_677
AYDMTQSPSFLSASVGDRVTITCQASQSISTALAWYQQKPGKAPKLLIYRASTLASGVPSRFSGSGSGTEFTLTISS
LQPEDFATYYCQQGWSTVNVDNVFGQGTRLEIK (SEQ ID NO: 206)
>cl|YOCBABABA|1|110 >8_4_LC_humanized_192
AYDMTQSPSSLSASVGDRVTITCQASQSISTALAWYQQKPGKAPKLLIYRASTLASGVPSRFSGSGSGTDFTLTISS
LQAEDFTTYYCQQGWSTVNVDNVFGQGTKVEFK (SEQ ID NO: 207)

Figure 8 (cont.)

>cl|ZOCBABABA|1|110 >8_4_LC_humanized_202
DIRMTQSPSSLSASVGDRVTITCQASQSISTALAWYQQKPGKVPKLLIYRASTLASGVPSRFSGSGSGTDFTLTISSL
QPEDVATYYCQQGWSTVNVDNVFGPGTKVVVR (SEQ ID NO: 208)
>cl|BUCBABABA|1|110 >8_4_LC_humanized_802
AIRMTQSPSSFSASTGDRVTITCQASQSISTALAWYQQKPGKAPKLLIYRASTLASGVPSRFSGSGSGTDFTLTISCL
QSEDFATYYCQQGWSTVNVDNVFGGGTKVEIK (SEQ ID NO: 209)
>cl|CUCBABABA|1|110 >8_4_LC_humanized_347
DIQMTQSPSSLSASVGDRVSITCQASQSISTALAWYQQKPGKAPKRLIYRASTLASGVPSRFSGSGSGTEFTLTISS
LQPDDFATYYCQQGWSTVNVDNVFGGGTKVEIK (SEQ ID NO: 210)
>cl|DUCBABABA|1|110 >8_4_LC_humanized_339
DIQLTQSPSSLSASVGDRVTITCQASQSISTALAWYQQKPGKAPKLLIYRASTLASGVPSRFSGSGSGTEFTLTISSL
QPDDFATYYCQQGWSTVNVDNVFGGGTKVEIK (SEQ ID NO: 211)
>cl|FUCBABABA|1|110 >8_4_LC_humanized_168
DIVMTQSPSTLSASVGDRVTITCQASQSISTALAWYQQKPGKAPKLLIYRASTLASGVPSRFSGSGSGTEFTLTISG
LQPEDFATYYCQQGWSTVNVDNVFGGGTKLEIK (SEQ ID NO: 212)
>cl|GUCBABABA|1|110 >8_4_LC_humanized_54
AYGMTQSPDSLAVSLGERASINCQASQSISTALAWYQQKPGQPPKLLIYRASTLASGVPDRFSGGGSGTDFTLTIS
SLQAEDVAVYYCQQGWSTVNVDNVFGGGTKVEIK (SEQ ID NO: 213)
>cl|HUCBABABA|1|110 >8_4_LC_humanized_21
DIQMTQSPSSLSASVGDRVTITCQASQSISTALAWYQQKPGKAPKVLIYRASTLASGVPSRFSGSGSGTDFTLTISS
LQPEDFATYYCQQGWSTVNVDNVFGPGTKVEVR (SEQ ID NO: 214)
>cl|KUCBABABA|1|110 >8_4_LC_humanized_788
AYELTQTPLSSPVTLGQPASISCQASQSISTALAWLQQRPGQPPRLLIYRASTLASGVPDRFSGSGAGTDFTLKISR
VEAEDVGIYYCQQGWSTVNVDNVFGQGTKVEIK (SEQ ID NO: 215)
>cl|LUCBABABA|1|110 >8_4_LC_humanized_675
AYDMTQSPSSLSASVGDRVTITCQASQSISTALAWYQQKPGKAPKLLIYRASTLASGVPSRFSGSGSGTEFTLTITS
LQPEDFATYYCQQGWSTVNVDNVFGPGTKLEIK (SEQ ID NO: 216)
>cl|MUCBABABA|1|110 >8_4_LC_humanized_762
AYELTQSPDSLAVSLGERATINCQASQSISTALAWYQQKPGQPPKLLIYRASTLASGVPDRFSGSGSGTDFTLTISS
LQAEDVAVYYCQQGWSTVNVDNVFGGGTKVEIK (SEQ ID NO: 217)

Figure 8 (cont.)

\>cl|NUCBABABA|1|110 >8_4_LC_humanized_818
AYDMTQTPSSVSASVGDRVTITCQASQSISTALAWYQQKPGKAPKLLIYRASTLASGVPSRFSGSGSGTDFTLTISS
LQPEDFATYYCQQGWSTVNVDNVFGQGTKVEIK (SEQ ID NO: 218)
\>cl|PUCBABABA|1|110 >8_4_LC_humanized_173
AIQMTQSPFSLSASVGDRVTITCQASQSISTALAWFQQKPGKAPKSLIYRASTLASGVSSKFSGSGSGTDFTLTISSL
QPEDFATYYCQQGWSTVNVDNVFGQGTRLVVR (SEQ ID NO: 219)
\>cl|QUCBABABA|1|110 >8_4_LC_humanized_65
DIQMTQSPSTLSASVGDRVTITCQASQSISTALAWYQQKPGKAPKLLIYRASTLASGVPSRFSGSGSGTEFTLTISSL
QPDDFATYYCQQGWSTVNVDNVFGQGTKVEIK (SEQ ID NO: 220)
\>cl|RUCBABABA|1|110 >8_4_LC_humanized_224
AYDMTQTPASVSLSPGERATLSCQASQSISTALAWYQQKPGQAPRLLIYRASTLASGIPDRFRGSGSATDFTLTIS
RLEPEDFAVYYCQQGWSTVNVDNVFGGGTEVVVR (SEQ ID NO: 221)
\>cl|SUCBABABA|1|110 >8_4_LC_humanized_230
AYDMTQTPASVSASVGDRVTITCQASQSISTALAWYQQKPGKAPKVLIYRASTLASGVPSRFSGSGSGTDFTLTIS
TLQPEDFATYYCQQGWSTVNVDNVFGQGTKLEIK (SEQ ID NO: 222)
\>cl|TUCBABABA|1|110 >8_4_LC_humanized_880
AYDMTQSPSSLSASVGDRVNITCQASQSISTALAWYQQKPGKAPKLLIYRASTLASGVPSRFSGSGSGTDFTLTISS
LQPEDFATYYCQQGWSTVNVDNVFGPGTKVDIK (SEQ ID NO: 223)
\>cl|VUCBABABA|1|110 >8_4_LC_humanized_672
AYDMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGQGTKLEIK (SEQ ID NO: 224)
\>cl|WUCBABABA|1|110 >8_4_LC_humanized_299
DIQMTQSPSSVSASVGDRVTITCQASQSISTALAWYQQKPGKAPKLLIYRASTLASGVPSRFSGSGSGTEFTLTISS
LQPDDFATYYCQQGWSTVNVDNVFGGGTKVEIK (SEQ ID NO: 225)
\>cl|XUCBABABA|1|110 >8_4_LC_humanized_267
AYDMTQSPSTLAASVGDRVTITCQASQSISTALAWYQQKPGKAPKLLIYRASTLASGVPSRFSGSGSGTEFTLTISS
LQPDDFATYYCQQGWSTVNVDNVFGQGTKVEVK (SEQ ID NO: 226)
\>cl|YUCBABABA|1|110 >8_4_LC_humanized_23
AYELTQSPSSLSASVGDRVTITCQASQSISTALAWYQQKPGKAPKLLIYRASTLASGVPSRFSGSGSGTDFTLTISSL
QPEDFATYYCQQGWSTVNVDNVFGPGTKVDIK (SEQ ID NO: 227)
\>cl|ZUCBABABA|1|110 >8_4_LC_humanized_657
AYDMTQTPASVEVSVGDRVSITCQASQSISTALAWYQQKPGKAPKLLIYRASTLASGVPSRFSGSGSGTDFTLTIT
SLQPVDFATYYCQQGWSTVNVDNVFGPGTTVDAK (SEQ ID NO: 228)
\>cl|BADBABABA|1|110 >8_4_LC_humanized_879
AYDMTQSPSSLSASVGDRVTITCQASQSISTALAWYQQKPGKAPKLLIYRASTLASGVPSRFSGSGSGTDFTLTISS
LQPEDFATYFCQQGWSTVNVDNVFGGGTKVEIK (SEQ ID NO: 229)

Figure 8 (cont.)

*8-4 VH humanized sequences -- germline database clustered at 90%*
*(2 sequences)*

>cl|CABBABABA|15|117 >8_4_HC_humanized_356 >8_4_HC_humanized_340
>8_4_HC_humanized_335 >8_4_HC_humanized_303 >8_4_HC_humanized_287
VQLVESGGGVVQPGGSLRLSCAASGFTISNLAIIWVRQAPGKGLEWVSDIDGRGDIYCATWAKGRFTISRDNSSL
YLQMNSLRAEDTAVYYCARDGDGSGWGDFNFWGPGTLVTVSS (SEQ ID NO: 230)
>cl|LABBABABA|85|117 >8_4_HC_humanized_2049 >8_4_HC_humanized_2033
>8_4_HC_humanized_1360 >8_4_HC_humanized_1344 >8_4_HC_humanized_777
VQLVESGGGLVQPGGSLRLSCAASGFTISNLAIIWVRQAPGKGLEWVSDIDGRGDIYCATWAKGRFTISRDNSTL
YLQMNSLRAEDTAVYYCARDGDGSGWGDFNFWGPGTLVTVSS (SEQ ID NO: 231)

*8-4 VL humanized sequences -- germline database clustered at 90%*
*(5 sequences)*

>cl|CACBABABA|76|110 >8_4_LC_humanized_356 >8_4_LC_humanized_340
>8_4_LC_humanized_335 >8_4_LC_humanized_303 >8_4_LC_humanized_287
AYDMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGGGTEVVVR (SEQ ID NO: 232)
>cl|LACBABABA|2|110 >8_4_LC_humanized_2049 >8_4_LC_humanized_2033
AYDMTQSPDSLAVSLGERATINCQASQSISTALAWYQQKPGQPPKLLIYRASTLASGVPDRFSGSGSGTDFTLTIS
SLQAEDVAVYYCQQGWSTVNVDNVFGGGTEVVVR (SEQ ID NO: 233)
>cl|NACBABABA|2|110 >8_4_LC_humanized_1360 >8_4_LC_humanized_1344
AYDMTQTPLSLSVTPGQPASISCQASQSISTALAWYLQKPGQPPQLLIYRASTLASGVPDRFSGSGSGTDFTLKIS
RVEAEDVGVYYCQQGWSTVNVDNVFGGGTEVVVR (SEQ ID NO: 234)
>cl|CECBABABA|5|110 >8_4_LC_humanized_2207 >8_4_LC_humanized_2206
>8_4_LC_humanized_2197 >8_4_LC_humanized_2208 >8_4_LC_humanized_2192
AYDMTQSPAFLSVTPGEKVTITCQASQSISTALAWYQQKPDQAPKLLIKRASTLASGVPSRFSGSGSGTDFTFTISS
LEAEDAATYYCQQGWSTVNVDNVFGGGTEVVVR (SEQ ID NO: 235)
>cl|DICBABABA|15|110 >8_4_LC_humanized_2263 >8_4_LC_humanized_2262
>8_4_LC_humanized_2258 >8_4_LC_humanized_2257 >8_4_LC_humanized_2256
AYDMTQSPASLAVSPGQRATITCQASQSISTALAWYQQKPGQPPKLLIYRASTLASGVPARFSGSGSGTDFTLTI
NPVEANDTANYYCQQGWSTVNVDNVFGGGTEVVVR (SEQ ID NO: 236)

Figure 8 (cont.)

*8-4 VH humanized sequences -- germline database clustered at 95%*
*(7 sequences)*

>cl|CABBABABA|2|117 >8_4_HC_humanized_356 >8_4_HC_humanized_303
VQLVESRGVLVQPGGSLRLSCAASGFTISNLAIIWVRQAPGKGLEWVSDIDGRGDIYCATWAKGRFTISRDNSTL
HLQMNSLRAEDTAVYYCKKDGDGSGWGDFNFWGPGTLVTVSS (SEQ ID NO: 237)
>cl|DABBABABA|17|117 >8_4_HC_humanized_340 >8_4_HC_humanized_335
>8_4_HC_humanized_287 >8_4_HC_humanized_282 >8_4_HC_humanized_2207
VQLVESGGGLVQPGGSLRLSCAASGFTISNLAIIWVRQAPGKGLEWVSDIDGRGDIYCATWAKGRFTISRDNASL
YLQMNSLRAEDTAVYYCARDGDGSGWGDFNFWGPGTLVTVSS (SEQ ID NO: 238)
>cl|LABBABABA|37|117 >8_4_HC_humanized_2049 >8_4_HC_humanized_2033
>8_4_HC_humanized_1360 >8_4_HC_humanized_1344 >8_4_HC_humanized_777
VQLVESGGGLVQPGGSLRLSCAASGFTISNLAIIWVRQAPGKGLEWVGDIDGRGDIYCATWAKGRFTISRSKNTL
YLQMNSLKTEDTAVYYCTRDGDGSGWGDFNFWGPGTLVTVSS (SEQ ID NO: 239)
>cl|DEBBABABA|22|117 >8_4_HC_humanized_2206 >8_4_HC_humanized_988
>8_4_HC_humanized_987 >8_4_HC_humanized_935 >8_4_HC_humanized_934
VQLVESGGGLVQPGGSLRLSCAASGFTISNLAIIWVRQAPGKGLEWVSDIDGRGDIYCATWAKGRFTISRDNSTL
YLQMNSLRAEDTAVYYCARDGDGSGWGDFNFWGPGTLVTVSS (SEQ ID NO: 240)
>cl|FEBBABABA|16|117 >8_4_HC_humanized_2197 >8_4_HC_humanized_978
>8_4_HC_humanized_925 >8_4_HC_humanized_660 >8_4_HC_humanized_395
VQLLESGGGLVQPGGSLRLSCAASGFTISNLAIIWVRQAPGKGLEWVSDIDGRGDIYCATWAKGRFTISRDNSTL
YLQMNSLRAEDTAVYYCAKDGDGSGWGDFNFWGPGTLVTVSS (SEQ ID NO: 241)
>cl|HIBBABABA|3|117 >8_4_HC_humanized_2257 >8_4_HC_humanized_349
>8_4_HC_humanized_296
VQLVESGGGLVQPGRSLRLSCTASGFTISNLAIIWFRQAPGKGLEWVGDIDGRGDIYCATWAKGRFTISRSKSIAY
LQMNSLKTEDTAVYYCTRDGDGSGWGDFNFWGPGTLVTVSS (SEQ ID NO: 242)
>cl|LIBBABABA|3|117 >8_4_HC_humanized_2254 >8_4_HC_humanized_346
>8_4_HC_humanized_293
VQLVESGGVVVQPGGSLRLSCAASGFTISNLAIIWVRQAPGKGLEWVSDIDGRGDIYCATWAKGRFTISRDNSSL
YLQMNSLRTEDTALYYCAKDGDGSGWGDFNFWGPGTLVTVSS (SEQ ID NO: 243)

Figure 8 (cont.)

*8-4 VL humanized sequences -- germline database clustered at 95%*
*(12 sequences)*

>cl|CACBABABA|1|110 >8_4_LC_humanized_356
AYDMTQSPSSVSASVGDRVTITCQASQSISTALAWYQQKPGKAPKLLIYRASTLASGVPSRFSGSGSGTDFTLTISS
LQPEDFATYYCQQGWSTVNVDNVFGGGTEVVVR (SEQ ID NO: 244)
>cl|LACBABABA|2|110 >8_4_LC_humanized_2049 >8_4_LC_humanized_2033
AYDMTQSPDSLAVSLGERATINCQASQSISTALAWYQQKPGQPPKLLIYRASTLASGVPDRFSGSGSGTDFTLTIS
SLQAEDVAVYYCQQGWSTVNVDNVFGGGTEVVVR (SEQ ID NO: 245)
>cl|NACBABABA|2|110 >8_4_LC_humanized_1360 >8_4_LC_humanized_1344
AYDMTQTPLSLSVTPGQPASISCQASQSISTALAWYLQKPGQPPQLLIYRASTLASGVPDRFSGSGSGTDFTLKIS
RVEAEDVGVYYCQQGWSTVNVDNVFGGGTEVVVR (SEQ ID NO: 246)
>cl|QACBABABA|1|110 >8_4_LC_humanized_777
AYDMTQSPSSLSASVGDRVTITCQASQSISTALAWYQQKPGKAPKLLIYRASTLASGVPSRFSGSGSGTDFTFTISS
LQPEDIATYYCQQGWSTVNVDNVFGGGTEVVVR (SEQ ID NO: 247)
>cl|VACBABABA|1|110 >8_4_LC_humanized_565
AYDMTQSPSSLSASVGDRVTITCQASQSISTALAWYQQKPGKAPKRLIYRASTLASGVPSRFSGSGSGTEFTLTISS
LQPEDFATYYCQQGWSTVNVDNVFGGGTEVVVR (SEQ ID NO: 248)
>cl|XACBABABA|2|110 >8_4_LC_humanized_247 >8_4_LC_humanized_231
AYDMTQSPSFLSASVGDRVTITCQASQSISTALAWYQQKPGKAPKLLIYRASTLASGVPSRFSGSGSGTEFTLTISS
LQPEDFATYYCQQGWSTVNVDNVFGGGTEVVVR (SEQ ID NO: 249)
>cl|ZACBABABA|2|110 >8_4_LC_humanized_141 >8_4_LC_humanized_125
AYDMTQSPSSFSASTGDRVTITCQASQSISTALAWYQQKPGKAPKLLIYRASTLASGVPSRFSGSGSGTDFTLTISC
LQSEDFATYYCQQGWSTVNVDNVFGGGTEVVVR (SEQ ID NO: 250)
>cl|CECBABABA|1|110 >8_4_LC_humanized_2207
AYDMTQSPAFLSVTPGEKVTITCQASQSISTALAWYQQKPDQAPKLLIKRASTLASGVPSRFSGSGSGTDFTFTISS
LEAEDAATYYCQQGWSTVNVDNVFGGGTEVVVR (SEQ ID NO: 251)
>cl|GECBABABA|1|110 >8_4_LC_humanized_988
AYDMTQSPSSLSASVGDRVTITCQASQSISTALAWYQQKPGKAPKLLIYRASTLASGVPSRFSGSGSGTDFTLTISS
LQPEDFATYYCQQGWSTVNVDNVFGGGTEVVVR (SEQ ID NO: 252)
>cl|PECBABABA|1|110 >8_4_LC_humanized_670
AYDMTQSPSSLSASVGDRVTITCQASQSISTALAWYQQKPGKVPKLLIYRASTLASGVPSRFSGSGSGTDFTLTISS
LQPEDVATYYCQQGWSTVNVDNVFGGGTEVVVR (SEQ ID NO: 253)
>cl|ZECBABABA|1|110 >8_4_LC_humanized_34
AYDMTQSPSTLSASVGDRVTITCQASQSISTALAWYQQKPGKAPKLLIYRASTLASGVPSRFSGSGSGTEFTLTISS
LQPDDFATYYCQQGWSTVNVDNVFGGGTEVVVR (SEQ ID NO: 254)
>cl|DICBABABA|15|110 >8_4_LC_humanized_2263 >8_4_LC_humanized_2262
>8_4_LC_humanized_2258 >8_4_LC_humanized_2257 >8_4_LC_humanized_2256
AYDMTQSPASLAVSPGQRATITCQASQSISTALAWYQQKPGQPPKLLIYRASTLASGVPARFSGSGSGTDFTLTI
NPVEANDTANYYCQQGWSTVNVDNVFGGGTEVVVR (SEQ ID NO: 255)

Figure 8 (cont.)

*16-6 VH humanized sequences -- IMGT-LigM DB (Abysis) clustered at 90% (41 sequences)*

>cl|CABBABABA|1|115 >16_6_HC_humanized_586
VQLQESGGGVVQPGTSLRLSCVVSGSDISSYHMGWVRQAPGKGLEWLAIIVSSGSAYYATWAKGRFTVSRSKST
LFLKMNSLRADDTAVYYCARNQYSGYGFSFWGQGTLVTVSS (SEQ ID NO: 256)
>cl|DABBABABA|2|115 >16_6_HC_humanized_411 >16_6_HC_humanized_213
LQLQESGPRLVKPSETLSLTCTVSGSDISSYHMGWIRQPPGKGLEWIGIIVSSGSAYYATWAKSRLTISTSKNQFSL
RLSSVTAADSAVYYCARNQYSGYGFSFWGQGTLVTVSS (SEQ ID NO: 257)
>cl|FABBABABA|1|115 >16_6_HC_humanized_372
VQLVESGGGLVQPGGSLRLSCAASGSDISSYHMGWVRQAPGKGLEAVAIIVSSGSAYYATWAKGRFTISRDSSTL
FLQLNSLRVEDSGIYYCAKNQYSGYGFSFWGQGTLVTVSS (SEQ ID NO: 258)
>cl|GABBABABA|7|115 >16_6_HC_humanized_1996 >16_6_HC_humanized_230
>16_6_HC_humanized_2056 >16_6_HC_humanized_672 >16_6_HC_humanized_657
QSLEESGGRLVTPGGSLRLSCAASGSDISSYHMGWVRQAPGKGLEWVSIIVSSGSAYYATWAKGRFTISRDNSTL
YLQMNSLRAEDTAVYYCARNQYSGYGFSFWGQGTLVTVSS (SEQ ID NO: 259)
>cl|HABBABABA|2|115 >16_6_HC_humanized_1907 >16_6_HC_humanized_716
QSLLESGGGWVQPGRSLRLSCSASGSDISSYHMGWVRQAPGKGLEWVGIIVSSGSAYYATWAKGRFTISRDNN
SLYLQMNSLRPEDTALYYCAKNQYSGYGFSFWGQGVLVTVSS (SEQ ID NO: 260)
>cl|LABBABABA|3|115 >16_6_HC_humanized_1945 >16_6_HC_humanized_1451
>16_6_HC_humanized_65
QSLEESGGGLVKPGESLRLSCAASGSDISSYHMGWVRQAPGKGLEWVGIIVSSGSAYYATWAKGRFTISRDDST
VYLEMNSLKTEDTAVYYCATNQYSGYGFSFWGQGTLVTVSS (SEQ ID NO: 261)
>cl|NABBABABA|1|115 >16_6_HC_humanized_1004
QSLLESGPRLVKPSETLSLTCSVSGSDISSYHMGWVRQPPGQGLEWIGIIVSSGSAYYATWARSRVSISTSQNQVS
LKLTSVTAADTAVYYCARNQYSGYGFSFWGQGILVTVSS (SEQ ID NO: 262)
>cl|PABBABABA|13|115 >16_6_HC_humanized_1971 >16_6_HC_humanized_305
>16_6_HC_humanized_1877 >16_6_HC_humanized_860 >16_6_HC_humanized_283
VQLVESGGGVVQPGRSLRLSCAASGSDISSYHMGWVRQAPGKGLEWVAIIVSSGSAYYATWAKGRFTISRDNS
TLYLQMNSLRAEDTAVYYCAKNQYSGYGFSFWGQGTLVTVSS (SEQ ID NO: 263)

Figure 8 (cont.)

>cl|QABBABABA|22|115 >16_6_HC_humanized_802 >16_6_HC_humanized_587
>16_6_HC_humanized_1012 >16_6_HC_humanized_988 >16_6_HC_humanized_129
VQLVESGGGLVQPGGSLRLSCAASGSDISSYHMGWVRQAPGKGLEWVSIIVSSGSAYYATWAKGRFTISRDNST
LYLQMNSLRAEDTAVYYCARNQYSGYGFSFWGQGTLVTVSS (SEQ ID NO: 264)
>cl|RABBABABA|1|115 >16_6_HC_humanized_609
VQLVESGGGLVQPGGSLRLSCTTSGSDISSYHMGWVRQVPGKGLEWVSIIVSSGSAYYATWAKGRFTISRDNST
SYLQMTSLTPEDTAVYYCAKNQYSGYGFSFWGQGTVVSVSS (SEQ ID NO: 265)
>cl|YABBABABA|4|115 >16_6_HC_humanized_910 >16_6_HC_humanized_218
>16_6_HC_humanized_912 >16_6_HC_humanized_917
VQLQESGPGLVKPSQTLSLTCTVSGSDISSYHMGWIRQPPGKGLEWIGIIVSSGSAYYATWAKSRVTISTSKNQLS
LKLTSVTAADTAVYYCARNQYSGYGFSFWGQGTTVTVSS (SEQ ID NO: 266)
>cl|GEBBABABA|1|115 >16_6_HC_humanized_136
VQLQQSGPGLVKTSETLPLTCTVSGSDISSYHMGWIRQPPGKGLEYIGIIVSSGSAYYATWAKNRVTISTSKNQFS
LKLSSVTAADTALYYCARNQYSGYGFSFWGQGTLVTVSS (SEQ ID NO: 267)
>cl|KEBBABABA|1|115 >16_6_HC_humanized_109
VQLVESGPGLVKPSQTLSLTCTVSGSDISSYHMGWIRQPPGKGLEYIGIIVSSGSAYYATWAKSRLTMSVDTSNY
QLKLSSVTAADTAVYYCARNQYSGYGFSFWGQGTTVTVSS (SEQ ID NO: 268)
>cl|LEBBABABA|1|115 >16_6_HC_humanized_103
VQLQQSGPGLVKPSGTLSLTCDVSGSDISSYHMGWVRQPPGKGLEWIGIIVSSGSAYYATWAKSRVTISKSKNQF
SLRLTSVTAADTAVYYCARNQYSGYGFSFWGQGTLVTVSS (SEQ ID NO: 269)
>cl|NEBBABABA|6|115 >16_6_HC_humanized_902 >16_6_HC_humanized_1982
>16_6_HC_humanized_734 >16_6_HC_humanized_920 >16_6_HC_humanized_149
VQLVESGPGLVKPSQTLSLTCTVSGSDISSYHMGWIRQPPGKGLEWIGIIVSSGSAYYATWAKSRVTISTSKNQFS
LKLSSVTAADTAVYYCARNQYSGYGFSFWGQGTLVTVSS (SEQ ID NO: 270)
>cl|PEBBABABA|1|115 >16_6_HC_humanized_851
VQLVQSGGGVVQPGGSLRVSCAASGSDISSYHMGWVRQAPGKGLEWMAIIVSSGSAYYATWAKGRFTISRDN
STVSLQMSSLRAEDTAVYYCAKNQYSGYGFSFWGRGTLVTVSS (SEQ ID NO: 271)
>cl|SEBBABABA|1|115 >16_6_HC_humanized_926
VQLVESGPGLVKPSQTLSLTCTVSGSDISSYHMGWIRQHSGKTLEWIGIIVSSGSAYYATWAESRVTISADTSKISL
KLSSVTAADTAVYYCARNQYSGYGFSFWGQGTTVTVSS (SEQ ID NO: 272)

Figure 8 (cont.)

>cl|VEBBABABA|1|115 >16_6_HC_humanized_904
VQLVESGPGLVKPSQTLSLTCNVSGSDISSYHMGWIRQSPGKGLEWIGIIVSSGSAYYATWARSRVTISADTSKVS
LELSPMTAADTAVYYCARNQYSGYGFSFWGQGTTVTVSS (SEQ ID NO: 273)

>cl|WEBBABABA|1|115 >16_6_HC_humanized_903
VQLQESGPGLVKPSQTLSLTCTVSGSDISSYHMGWIRQPPGTGLEWIGIIVSSGSAYYATWAKSRVTISGDTSKFS
LMLRSVTAADTAVYYCARNQYSGYGFSFWGQGTMVTVSS (SEQ ID NO: 274)

>cl|YEBBABABA|1|115 >16_6_HC_humanized_946
VQLVESGGGLIKPGGSLRLSCEVPGSDISSYHMGWVRQGPGRGLEWVGIIVSSGSAYYATWARGRFTISRSKSTV
YLEMNALKTEDTGIYYCVTNQYSGYGFSFWGQGTMVTVSS (SEQ ID NO: 275)

>cl|ZEBBABABA|1|115 >16_6_HC_humanized_882
QSLEESGGGLVQPGGSLRLSCAASGSDISSYHMGWVRQPPGKGLEWVGIIVSSGSAYYATWAKGRFTISRSKST
VYLQMNSLKTEDTAVYYCTANQYSGYGFSFWGQGMLVTVSS (SEQ ID NO: 276)

>cl|CIBBABABA|1|115 >16_6_HC_humanized_2041
QSLVQSGTEVRKPGASVKVSCKASGSDISSYHMGWVRQAPGQGLEWMGIIVSSGSAYYATWAQGRVTMSDT
STTVYMELSSLTSEDTAIYYCARNQYSGYGFSFWGPGTLVTVSS (SEQ ID NO: 277)

>cl|KIBBABABA|1|115 >16_6_HC_humanized_1944
QSLEESGGRLVTPGTPLTLTCTVSGSDISSYHMGWVRQPPGKGLEWIGIIVSSGSAYYATWAKNRVTISTSKNQF
SLRLNSVTAADTAVYYCARNQYSGYGFSFWGQGTLVTVSS (SEQ ID NO: 278)

>cl|LIBBABABA|4|115 >16_6_HC_humanized_1895 >16_6_HC_humanized_1992
>16_6_HC_humanized_1995 >16_6_HC_humanized_1949
QSLEESGGRLVTPGTPLTLTCTVSGSDISSYHMGWVRQAPGKGLVWVSIIVSSGSAYYATWAKGRFTISRDNATL
YLQMNSLRAEDTAVYYCARNQYSGYGFSFWGPGTLVTVSS (SEQ ID NO: 279)

>cl|SIBBABABA|2|115 >16_6_HC_humanized_993 >16_6_HC_humanized_994
VQLVESGGGLIQPGRPLRLSCSGSGSDISSYHMGWVRQAPGKGLEWVGIIVSSGSAYYATWAKGRFTISRDDSV
VHLQMNSLRSEDTAVYYCTRNQYSGYGFSFWGQGTMVTVSS (SEQ ID NO: 280)

>cl|TIBBABABA|2|115 >16_6_HC_humanized_956 >16_6_HC_humanized_965
VQLQESGPGLVKPSQTLSLTCTVSGSDISSYHMGWIRQHPGKGLEWIGIIVSSGSAYYATWAESRLTISADTSNIQ
LRLSSVTAADTAVYFCARNQYSGYGFSFWGQGTTVTVSS (SEQ ID NO: 281)

>cl|WIBBABABA|1|115 >16_6_HC_humanized_278
VQLVQSGGGLVKPGGSLRLSCEASGSDISSYHMGWIRQAPGKGLEWVGIIVSSGSAYYATWAKGRFTISRDDST
LYLQVNSLKTEDSAVYYCTTNQYSGYGFSFWGQGTLVTVSS (SEQ ID NO: 282)

Figure 8 (cont.)

\>cl|GOBBABABA|1|115 >16_6_HC_humanized_1894
QSLEESGGRLVTPGTPLTLTCTVSGSDISSYHMGWVRQAPGKGLEWVSIIVSSGSAYYATWAKGRFTISRDNASL
YLQMNSLRAEDTAVYYCARNQYSGYGFSFFSDYWLVTVSS (SEQ ID NO: 283)
\>cl|MOBBABABA|3|115 >16_6_HC_humanized_1917 >16_6_HC_humanized_677
\>16_6_HC_humanized_267
QSLEESGGGVVQPGRSLRLSCAASGSDISSYHMGWVRQAPGKGLEWVAIIVSSGSAYYATWAKRRFTISRDNST
LYLQMNSLRAEDTAVYYCARNQYSGYGFSFWGQGTLVTVSS (SEQ ID NO: 284)
\>cl|POBBABABA|1|115 >16_6_HC_humanized_2038
QSLEESGGRLVTPGTPLTLTCTVSGSDISSYHMGWVRQAPGKGLEWVAIIVSSGSAYYATWAKGRFTISRDNASL
YLQMNSLRAEDTAVYYCARNQYSGYGFSFPTSGYYYMDVS (SEQ ID NO: 285)
\>cl|QOBBABABA|1|115 >16_6_HC_humanized_23
QSLLESGGDLVQPGGSLRLSCEASGSDISSYHMGWVRQAPGKGLEWVSIIVSSGSAYYATWAKGRFTISRDKSTL
FLQMHSLRVEDTAVYYCAKNQYSGYGFSFWGQGTTVTVSS (SEQ ID NO: 286)
\>cl|VOBBABABA|1|115 >16_6_HC_humanized_1013
VQLVQSGGGVVQPGRSLRLSCEVSGSDISSYHMGWVRQAPGKGLEWVAIIVSSGSAYYATWAKGRFTISRSNN
TLYLQMNSLTAEDTALYFCARNQYSGYGFSFWGKGTTVTVSS (SEQ ID NO: 287)
\>cl|YOBBABABA|1|115 >16_6_HC_humanized_113
LQLQESGPGLVKPSQTLSLTCSVSGSDISSYHMGWIRQHPGKGLEWIGIIVSSGSAYYATWAKSRITISTSKNQFSL
KLTSVTAADTALYYCARNQYSGYGFSFWGRGTLVTVSS (SEQ ID NO: 288)
\>cl|HUBBABABA|1|115 >16_6_HC_humanized_12
VQLVQSGGGVVQPGGSLRLSCAASGSDISSYHMGWVRQAPGKGLEWVAIIVSSGSAYYATWAQGRVTISRDN
STVHLQITSLKSEDTAVYYCAKNQYSGYGFSFWGQGTLVTVSS (SEQ ID NO: 289)
\>cl|LUBBABABA|1|115 >16_6_HC_humanized_273
VQLVQSGGGLVQPGGSLRLSCAASGSDISSYHMGWVRQASGKGLEWIGIIVSSGSAYYATWAKGRFTVSRSQN
SVFLQMNSLETEDTAVYYCARNQYSGYGFSFWGQGTLVTVSS (SEQ ID NO: 290)
\>cl|NUBBABABA|1|115 >16_6_HC_humanized_879
QSLEESGGGLVQPGGSLRLSCTASGSDISSYHMGWVRQAPGKGLEWVSIIVSSGSAYYATWAKGRFTISRDSSTL
YLQMNNLRVEDTALYYCAHNQYSGYGFSFWGRGTQVTVSS (SEQ ID NO: 291)
\>cl|TUBBABABA|1|115 >16_6_HC_humanized_1934
QSLEESGGRLVTPGTPLTLTCTVSGSDISSYHMGWVRQAPGKGLEWVSIIVSSGSAYYATWAKGRFTISRDNASL
YLQMNSLRAEDTAVYYCARNQYSGYGFSFGIFDYWVTVSS (SEQ ID NO: 292)

Figure 8 (cont.)

>cl|VUBBABABA|1|115 >16_6_HC_humanized_200
VQLQESGPGLVKPSETLSLTCSVSGSDISSYHMGWIRQPAGKGLEWIGIIVSSGSAYYATWARSRVTMSMSKNH
FSLKLRSVTAADTAVYFCARNQYSGYGFSFWGQGTLVTVSS (SEQ ID NO: 293)
>cl|WUBBABABA|1|115 >16_6_HC_humanized_1977
QSLEESGGRLVTPGTPLTLTCTVSGSDISSYHMGWVRQAPGKGLEWVAIIVSSGSAYYATWAKGRFTISRSKNTL
YLQMNSLRAEDTAVYYCARNQYSGYGFSFTCPYFDYWVSS (SEQ ID NO: 294)
>cl|XUBBABABA|1|115 >16_6_HC_humanized_2027
QSLEESGGRLVTPGTPLTLTCTVSGSDISSYHMGWVRQAPGKGLEWVAIIVSSGSAYYATWAEGRFTISRDNSTL
YLQMYSLRTEDTAVYYCARNQYSGYGFSFYYYGMGVWVSS (SEQ ID NO: 295)
>cl|YUBBABABA|1|115 >16_6_HC_humanized_1958
VHLVESGGGVVQPGRSLRLSCAASGSDISSYHMGWVRQAPGKGLEWVAIIVSSGSAYYATWAEGRFTISRDNS
KLYLQMNSLRAEDSATYYCARNQYSGYGFSFFGPPYYYYYMS (SEQ ID NO: 296)
>cl|BACBABABA|1|115 >16_6_HC_humanized_1905
QSLEESGGRLVTPGTPLTLTCTVSGSDISSYHMGWVRQAPGKGLEWVSIIVSSGSAYYATWAKGRFTISRDNSTL
YLQMNSLRAEDTALYYCARNQYSGYGFSFVRGGYFYHMDS (SEQ ID NO: 297)

Figure 8 (cont.)

*16-6 VL humanized sequences -- IMGT-LigM DB (Abysis) clustered at 90% (21 sequences)*

>cl|CACBABABA|1|110 >16_6_LC_humanized_586
IVLTQTPSSLSASVGDRITITCQSSHSVYYGDWLAWYQQKPGKAPKLLIYRASNLASGVPSRFSGSRSGTDFTFTIS
SLRPEDIATYYCLGGYDDDGETAFGGGTKVEIK (SEQ ID NO: 298)
>cl|DACBABABA|27|110 >16_6_LC_humanized_411 >16_6_LC_humanized_1004
>16_6_LC_humanized_587 >16_6_LC_humanized_305 >16_6_LC_humanized_988
IVLTQSPSSLSASVGDRVTITCQSSHSVYYGDWLAWYQQKPGKAPKLLIYRASNLASGVPSRFSGSGSGTDFTLTIS
SLQPEDFATYYCLGGYDDDGETAFGGGTKVEIK (SEQ ID NO: 299)
>cl|FACBABABA|15|110 >16_6_LC_humanized_372 >16_6_LC_humanized_1877
>16_6_LC_humanized_1012 >16_6_LC_humanized_860 >16_6_LC_humanized_283
IQLTQSPSSLSASVGDRVTITCQSSHSVYYGDWLAWYQQKPGKAPKLLIYRASNLASGVPSRFSGSGSGTEFTLTIS
SLQPDDFATYYCLGGYDDDGETAFGQGTKVEIK (SEQ ID NO: 300)
>cl|GACBABABA|1|110 >16_6_LC_humanized_1996
VVLTQTPSPVSTAVGGTVTLSCQSSHSVYYGDWLAWYQQKPGQAPRLLIYRASNLASGIPDRFSGSGSGTDFTLT
ISRLEPEDFAVYYCLGGYDDDGETAKGPGTEVVVK (SEQ ID NO: 301)
>cl|HACBABABA|2|110 >16_6_LC_humanized_1907 >16_6_LC_humanized_716
LVMTQSPSSLSASEGDRVTITCQSSHSVYYGDWLAWYQQKPGRAPKLLIHRASNLASGVPSRFSGSGSGTEFTLT
ISGLQSEDFATYYCLGGYDDDGETAFGGGTTVDVK (SEQ ID NO: 302)
>cl|LACBABABA|2|110 >16_6_LC_humanized_1945 >16_6_LC_humanized_1451
VELTQPPSVSAAPGQKVTISCQSSHSVYYGDWLAWYQQLPGTAPKLLIYRASNLASGIPDRFSGSKSGTSATLGI
TGLQTGDEADYYCLGGYDDDGETAFGGGTRLTVL (SEQ ID NO: 303)
>cl|PACBABABA|10|110 >16_6_LC_humanized_1971 >16_6_LC_humanized_2041
>16_6_LC_humanized_2038 >16_6_LC_humanized_2008 >16_6_LC_humanized_1992
VVLTQTPSPVSTAVGGTVTITCQSSHSVYYGDWLAWYQQKPGKAPKLLIYRASNLASGVPSRFSGSGSGTDFTLT
ISSLQPEDFATYYCLGGYDDDGETAFGGGTEVVVK (SEQ ID NO: 304)
>cl|QACBABABA|5|110 >16_6_LC_humanized_802 >16_6_LC_humanized_609
>16_6_LC_humanized_851 >16_6_LC_humanized_908 >16_6_LC_humanized_108
VVMTQSPSSLSASVGDRVTITCQSSHSVYYGDWLAWYQQKPGKAPKLLIYRASNLASGVPSRFSGSGSGTDFTLT
ISSLQPEDFATYYCLGGYDDDGETAFGGGTKVEIK (SEQ ID NO: 305)
>cl|CECBABABA|7|110 >16_6_LC_humanized_253 >16_6_LC_humanized_103
>16_6_LC_humanized_882 >16_6_LC_humanized_1982 >16_6_LC_humanized_734
IVLTQSPSSLSASVGDRVTITCQSSHSVYYGDWLAWYQQKPGKAPKLLIYRASNLASGVPSRFSGSGSGTEFTLTIS
SLQPEDSATYYCLGGYDDDGETAFGQGTKVEIK (SEQ ID NO: 306)

Figure 8 (cont.)

>cl|KECBABABA|2|110 >16_6_LC_humanized_109 >16_6_LC_humanized_334
IQLTQSPSFVSASVGDRITITCQSSHSVYYGDWLAWYQQKPGKAPKLLIYRASNLASGVPSRFSGSRSGTDFTLTIS
SLQPEDFATYYCLGGYDDDGETAFGQGTKVEIK (SEQ ID NO: 307)
>cl|RECBABABA|2|110 >16_6_LC_humanized_17 >16_6_LC_humanized_21
IQLTQSPSSLSAAVGDRVTIACQSSHSVYYGDWLAWYQQKPGKAPKLLIYRASNLASGVPSRFSGSGSGTDFTLSI
SSLQPEDFATYYCLGGYDDDGETAFGGGTKVQMK (SEQ ID NO: 308)
>cl|DICBABABA|1|110 >16_6_LC_humanized_202
IRMTQSPSSLSASVGDRVTITCQSSHSVYYGDWLAWYQQKPGKVPKLLIYRASNLASGVPSRFSGSGSGTDFTLTI
SSLQPEDVATYYCLGGYDDDGETAFGPGTKVVVK (SEQ ID NO: 309)
>cl|FICBABABA|14|110 >16_6_LC_humanized_192 >16_6_LC_humanized_956
>16_6_LC_humanized_230 >16_6_LC_humanized_880 >16_6_LC_humanized_2056
VVLTQSPSSLSASVGDRVTITCQSSHSVYYGDWLAWYQQKPGKAPKLLIYRASNLASGVPSRFSGSGSGTDFTLTI
SSLQPEDFATYYCLGGYDDDGETAFGQGTKVEIK (SEQ ID NO: 310)
>cl|NICBABABA|2|110 >16_6_LC_humanized_1938 >16_6_LC_humanized_762
VELTQSPDSLAVSLGERATINCQSSHSVYYGDWLAWYQQKPGQPPKLLIYRASNLASGVPDRFSGSGSGTDFTLT
ISSLQAEDVAVYYCLGGYDDDGETAFGGGTKVEIK (SEQ ID NO: 311)
>cl|WICBABABA|1|110 >16_6_LC_humanized_278
LVLTQSPSSLSASVGDRVTITCQSSHSVYYGDWLAWCQQKPGKSPTLLIYRASNLASGVPSRFSGSGSGTGFTLTI
SGLQPEDFATYYCLGGYDDDGETAFGGGTKVEIR (SEQ ID NO: 312)
>cl|YICBABABA|1|110 >16_6_LC_humanized_169
IVLTQSPSFLSAFVGDRITITCQSSHSVYYGDWLAWYQQKPGKAPKLLIYRASNLASGVPSRFSGSGSGTEFTLTIS
GLQPEDFASYYCLGGYDDDGETAFGGGTKLEIK (SEQ ID NO: 313)
>cl|GOCBABABA|1|110 >16_6_LC_humanized_1894
VVLTQTPSPVSTAVGDRVTITCQSSHSVYYGDWLAWYRQKPGKVPKLLIYRASNLASGVPSRFSGSGSGTDFTLTI
SSLQPEDVATYYGLGGYDDDGETAFGGGTEVVVK (SEQ ID NO: 314)
>cl|LOCBABABA|1|110 >16_6_LC_humanized_657
VVLTQTPSPVSTSVGDRVSITCQSSHSVYYGDWLAWYQQKPGKAPKLLIYRASNLASGVPSRFSGSGSGTDFTLTI
TSLQPVDFATYYCLGGYDDDGETAFGPGTTVDAK (SEQ ID NO: 315)
>cl|YOCBABABA|1|110 >16_6_LC_humanized_113
IVLTQSPSSVSASVGDRVTITCQSSHSVYYGDWLAWYQLKPGKAPKLLINRASNLASGVPSRFSGSGSGTDFTLTI
SGLQPEDFATYYCLGGYDDDGETAFGPGTTVDIK (SEQ ID NO: 316)
>cl|MUCBABABA|3|110 >16_6_LC_humanized_2032 >16_6_LC_humanized_200
>16_6_LC_humanized_1905
VVLTQTPSPVSTAVGGTGTINCQSSHSVYYGDWLAWYQQKPGQPPKLLIYRASNLASGVPDRFSGSGSGTDFTL
TISSLQAEDVAVYYCLGGYDDDGETAFGGGTKVVVK (SEQ ID NO: 317)
>cl|RUCBABABA|1|110 >16_6_LC_humanized_1995
VVLTQTPSPVSTAVGGTVTINCQSSHSVYYGDWLAWYQQKPGQPXKLLIYRASNLASGVPDRFSGSGSGTDFTL
TISSLQAEDVAVYYCLGGYDDDGETAFGQGTEVVVK (SEQ ID NO: 318)

Figure 8 (cont.)

16-6 VH humanized sequences -- IMGT-LigM DB (Abysis) clustered at 95%
(81 sequences)

>cl|CABBABABA|1|115 >16_6_HC_humanized_586
VQLQESGGGVVQPGTSLRLSCVVSGSDISSYHMGWVRQAPGKGLEWLAIIVSSGSAYYATWAKGRFTVSRSKST
LFLKMNSLRADDTAVYYCARNQYSGYGFSFWGQGTLVTVSS (SEQ ID NO: 319)
>cl|DABBABABA|1|115 >16_6_HC_humanized_411
LQLQESGPRLVKPSETLSLTCTVSGSDISSYHMGWIRQSPGKGLEWIGIIVSSGSAYYATWAKSRLTMSTSKNQFS
LRLSSVTAADSAVYYCARNQYSGYGFSFWGQGTLVTVSS (SEQ ID NO: 320)
>cl|FABBABABA|1|115 >16_6_HC_humanized_372
VQLVESGGGLVQPGGSLRLSCAASGSDISSYHMGWVRQAPGKGLEAVAIIVSSGSAYYATWAKGRFTISRDSSTL
FLQLNSLRVEDSGIYYCAKNQYSGYGFSFWGQGTLVTVSS (SEQ ID NO: 321)
>cl|GABBABABA|1|115 >16_6_HC_humanized_1996
QSLEESGGRLVTPGGSLRLSCAASGSDISSYHMGWVRQAPGKGLEWVGIIVSSGSAYYATWAKGRFTISRDNST
LYLQMNSLRVEDTARYYCARNQYSGYGFSFWGQGTLVTVSS (SEQ ID NO: 322)
>cl|HABBABABA|2|115 >16_6_HC_humanized_1907 >16_6_HC_humanized_716
QSLLESGGGWVQPGRSLRLSCSASGSDISSYHMGWVRQAPGKGLEWVGIIVSSGSAYYATWAKGRFTISRDNN
SLYLQMNSLRPEDTALYYCAKNQYSGYGFSFWGQGVLVTVSS (SEQ ID NO: 323)
>cl|LABBABABA|2|115 >16_6_HC_humanized_1945 >16_6_HC_humanized_1451
QSLEESGGGLVKPGESLRLSCAASGSDISSYHMGWVRQAPGKGLEWVGIIVSSGSAYYATWAKGRFTISRDDST
VYLEMNSLKTEDTAVYYCATNQYSGYGFSFWGQGTLVTVSS (SEQ ID NO: 324)
>cl|NABBABABA|1|115 >16_6_HC_humanized_1004
QSLLESGPRLVKPSETLSLTCSVSGSDISSYHMGWVRQPPGQGLEWIGIIVSSGSAYYATWARSRVSISTSQNQVS
LKLTSVTAADTAVYYCARNQYSGYGFSFWGQGILVTVSS (SEQ ID NO: 325)
>cl|PABBABABA|1|115 >16_6_HC_humanized_1971
VQLVESGGGVVQPGRSLRLSCAASGSDISSYHMGWVRQAPGKGLEWLAIIVSSGSAYYATWAKGRFTISRDNSS
LYLQLSSLRNEDTAVYYCAKNQYSGYGFSFWGPGTLVTVSS (SEQ ID NO: 326)
>cl|QABBABABA|2|115 >16_6_HC_humanized_802 >16_6_HC_humanized_988
VQLVESGGGLIQPGGSLRLSCAASGSDISSYHMGWVRQAPGKGLEWVSIIVSSGSAYYATWAKGRFTISRDNAS
LYLQMNSLRAEDTAVYYCARNQYSGYGFSFWGQGTLVTVSS (SEQ ID NO: 327)
>cl|RABBABABA|1|115 >16_6_HC_humanized_609
VQLVESGGGLVQPGGSLRLSCTTSGSDISSYHMGWVRQVPGKGLEWVSIIVSSGSAYYATWAKGRFTISRDNST
SYLQMTSLPEDTAVYYCAKNQYSGYGFSFWGQGTVVSVSS (SEQ ID NO: 328)
>cl|SABBABABA|1|115 >16_6_HC_humanized_587
VQLVESGGGLVKPGGSLRLSCVVSGSDISSYHMGWVRQAPGKGLEWLSIIVSSGSAYYATWAKGRFTISRDNAS
LFLQMNSLRADDTALYFCARNQYSGYGFSFWGQGTLVTVSS (SEQ ID NO: 329)

Figure 8 (cont.)

>cl|TABBABABA|6|115 >16_6_HC_humanized_305 >16_6_HC_humanized_283
>16_6_HC_humanized_334 >16_6_HC_humanized_281 >16_6_HC_humanized_339
VQLVESGGGVVQPGRSLRLSCAASGSDISSYHMGWVRQAPGKGLEWVAIIVSSGSAYYATWAKGRFTISRDNS
TLYLQMNSLRAEDTAVYYCAKNQYSGYGFSFWGQGTLVTVSS (SEQ ID NO: 330)
>cl|VABBABABA|4|115 >16_6_HC_humanized_1877 >16_6_HC_humanized_860
>16_6_HC_humanized_204 >16_6_HC_humanized_818
VQLVESGGGVVQPGRSLRLSCAASGSDISSYHMGWVRQAPGKGLEWVAIIVSSGSAYYATWAKGRFTISRDNS
TLYLQMNSLRAEDTAVYYCARNQYSGYGFSFWGQGTLVTVSS (SEQ ID NO: 331)
>cl|WABBABABA|1|115 >16_6_HC_humanized_1012
VQLQEWGGGVVQPGRSLRLSCAASGSDISSYHMGWVRQAPGKGLEWVAIIVSSGSAYYATWAKGRFTISRDN
STLYLQMNSLRAEDTAVYYCARNQYSGYGFSFWGQGTLVTVSS (SEQ ID NO: 332)
>cl|YABBABABA|1|115 >16_6_HC_humanized_910
VQLQESGPGLVKPSQTLSLTCTVSGSDISSYHMGWIRQPPGKGLEWIGIIVSSGSAYYATWAQSRVLISTSKSQLS
LKLTSVTAADTAVYYCARNQYSGYGFSFWGQGTTVTVSS (SEQ ID NO: 333)
>cl|CEBBABABA|1|115 >16_6_HC_humanized_253
VQLVESGGGLVQPGRSLRLSCATSGSDISSYHMGWVRQAPGKGLEWVGIIVSSGSAYYATWAKGRFTISRDNAS
LYLQMSSLRAEDTALYYCAKNQYSGYGFSFWGQGTLVTVSS (SEQ ID NO: 334)
>cl|DEBBABABA|1|115 >16_6_HC_humanized_218
VQLQESGPGLVKPSETLSLTCTVSGSDISSYHMGWIRQPPGKGLEWIGIIVSSGSAYYATWAKSRVTISTSKNQFS
LKLSSVTAADTAVYYCARNQYSGYGFSFWGQGTTVTVSS (SEQ ID NO: 335)
>cl|FEBBABABA|1|115 >16_6_HC_humanized_213
LQLQESGPGLVKPSETLSLTCTVSGSDISSYHMGWIRQPPGKGLEWIGIIVSSGSAYYATWAKSRVTISTSKNQFSL
KLSSVTAADTAVYYCASNQYSGYGFSFWGQGTLVTVSS (SEQ ID NO: 336)
>cl|GEBBABABA|1|115 >16_6_HC_humanized_136
VQLQQSGPGLVKTSETLPLTCTVSGSDISSYHMGWIRQPPGKGLEYIGIIVSSGSAYYATWAKNRVTISTSKNQFS
LKLSSVTAADTALYYCARNQYSGYGFSFWGQGTLVTVSS (SEQ ID NO: 337)
>cl|HEBBABABA|1|115 >16_6_HC_humanized_129
MQLVESGGGLVQPGRSLRLSCVTSGSDISSYHMGWVRQVPGKGLEWVGIIVSSGSAYYATWAKGRFTISRDNT
SLYLQMNSLRPEDTAVYYCAKNQYSGYGFSFWGQGTLVTVSS (SEQ ID NO: 338)
>cl|KEBBABABA|1|115 >16_6_HC_humanized_109
VQLVESGPGLVKPSQTLSLTCTVSGSDISSYHMGWIRQPPGKGLEYIGIIVSSGSAYYATWAKSRLTMSVDTSNY
QLKLSSVTAADTAVYYCARNQYSGYGFSFWGQGTTVTVSS (SEQ ID NO: 339)

Figure 8 (cont.)

\>cl|LEBBABABA|1|115 >16_6_HC_humanized_103
VQLQQSGPGLVKPSGTLSLTCDVSGSDISSYHMGWVRQPPGKGLEWIGIIVSSGSAYYATWAKSRVTISKSKNQF
SLRLTSVTAADTAVYYCARNQYSGYGFSFWGQGTLVTVSS (SEQ ID NO: 340)
\>cl|MEBBABABA|1|115 >16_6_HC_humanized_954
VQLVESGGGVVQPGRSLRLSCAASGSDISSYHMGWVRQAPGKGLEWVAIIVSSGSAYYATWAKGRFTISRDNS
TLYLQMNSLRAEDTAVYYCAKNQYSGYGFSFWGQGTTVTVSS (SEQ ID NO: 341)
\>cl|NEBBABABA|1|115 >16_6_HC_humanized_902
VQLVESGPGLVKPSQTLSLTCTVSGSDISSYHMGWLRQPPGRGLEWIGIIVSSGSAYYATWAKSRVTLSTSKNQF
SLKLNSVTAADTAVYYCARNQYSGYGFSFWGQGTLVTVSS (SEQ ID NO: 342)
\>cl|PEBBABABA|1|115 >16_6_HC_humanized_851
VQLVQSGGGVVQPGGSLRVSCAASGSDISSYHMGWVRQAPGKGLEWMAIIVSSGSAYYATWAKGRFTISRDN
STVSLQMSSLRAEDTAVYYCAKNQYSGYGFSFWGRGTLVTVSS (SEQ ID NO: 343)
\>cl|REBBABABA|1|115 >16_6_HC_humanized_17
VQLVESGGGLVQPGGSLRLSCAASGSDISSYHMGWVRQAPGRGLVWVSIIVSSGSAYYATWAKGRFTISRDNA
TLYLQMNNLRAEDTAVYYCARNQYSGYGFSFWGQGTLVTVSS (SEQ ID NO: 344)
\>cl|SEBBABABA|1|115 >16_6_HC_humanized_926
VQLVESGPGLVKPSQTLSLTCTVSGSDISSYHMGWIRQHSGKTLEWIGIIVSSGSAYYATWAESRVTISADTSKISL
KLSSVTAADTAVYYCARNQYSGYGFSFWGQGTTVTVSS (SEQ ID NO: 345)
\>cl|TEBBABABA|1|115 >16_6_HC_humanized_908
VQLVESGGGLVEPGGSLRLSCAASGSDISSYHMGWIRQAPGKGLEWLSIIVSSGSAYYATWAKGRFTISRDNASL
YLQMNSLRAEDTAVYYCVRNQYSGYGFSFWGQGTMVTVSS (SEQ ID NO: 346)
\>cl|VEBBABABA|1|115 >16_6_HC_humanized_904
VQLVESGPGLVKPSQTLSLTCNVSGSDISSYHMGWIRQSPGKGLEWIGIIVSSGSAYYATWARSRVTISADTSKVS
LELSPMTAADTAVYYCARNQYSGYGFSFWGQGTTVTVSS (SEQ ID NO: 347)
\>cl|WEBBABABA|1|115 >16_6_HC_humanized_903
VQLQESGPGLVKPSQTLSLTCTVSGSDISSYHMGWIRQPPGTGLEWIGIIVSSGSAYYATWAKSRVTISGDTSKFS
LMLRSVTAADTAVYYCARNQYSGYGFSFWGQGTMVTVSS (SEQ ID NO: 348)
\>cl|XEBBABABA|1|115 >16_6_HC_humanized_108
VQLVESGGGLVKPGGSLRLSCAASGSDISSYHMGWIRQAPGKGLEWVSIIVSSGSAYYATWAKGRFTISRDNASL
FLQMNSLRAEDTAVYYCAKNQYSGYGFSFWGQGTLITVSS (SEQ ID NO: 349)
\>cl|YEBBABABA|1|115 >16_6_HC_humanized_946
VQLVESGGGLIKPGGSLRLSCEVPGSDISSYHMGWVRQGPGRGLEWVGIIVSSGSAYYATWARGRFTISRSKSTV
YLEMNALKTEDTGIYYCVTNQYSGYGFSFWGQGTMVTVSS (SEQ ID NO: 350)

Figure 8 (cont.)

>cl|ZEBBABABA|1|115 >16_6_HC_humanized_882
QSLEESGGGLVQPGGSLRLSCAASGSDISSYHMGWVRQPPGKGLEWVGIIVSSGSAYYATWAKGRFTISRSKST
VYLQMNSLKTEDTAVYYCTANQYSGYGFSFWGQGMLVTVSS (SEQ ID NO: 351)
>cl|BIBBABABA|1|115 >16_6_HC_humanized_186
VQLVESGGGVVQPGRSLRLSCAASGSDISSYHMGWVRQAPGKGLESVAIIVSSGSAYYATWAKGRFTISRDNST
LYLQMNSLRAEDTAVYYCARNQYSGYGFSFWGQGTLVTVSS (SEQ ID NO: 352)
>cl|CIBBABABA|1|115 >16_6_HC_humanized_2041
QSLVQSGTEVRKPGASVKVSCKASGSDISSYHMGWVRQAPGQGLEWMGIIVSSGSAYYATWAQGRVTMSDT
STTVYMELSSLTSEDTAIYYCARNQYSGYGFSFWGPGTLVTVSS (SEQ ID NO: 353)
>cl|DIBBABABA|1|115 >16_6_HC_humanized_202
VQLQESGEGLVQPGGSLRLSCAASGSDISSYHMGWVRQAPGKGLEYVSIIVSSGSAYYATWAKGRFTISRDNSTL
YLQMGSLRAEDMAVYYCARNQYSGYGFSFWGQGTMVTVSS (SEQ ID NO: 354)
>cl|FIBBABABA|2|115 >16_6_HC_humanized_192 >16_6_HC_humanized_880
QHLEESGGGVVQPGRSLRLSCAASGSDISSYHMGWVRQAPGKGLEWVAIIVSSGSAYYATWAKGRFTISRDNS
TLYLQMNSLRAEDTAVYYCARNQYSGYGFSFWGQGTTVTVSS (SEQ ID NO: 355)
>cl|GIBBABABA|2|115 >16_6_HC_humanized_1982 >16_6_HC_humanized_734
QSLLESGPGLVKPSQTLSLTCTVSGSDISSYHMGWIRQPPGKGLEWIGIIVSSGSAYYATWAKSRVTMSTSKNHF
SLRLSSVTAADTAVYYCARNQYSGYGFSFWGQGTLVTVSS (SEQ ID NO: 356)
>cl|KIBBABABA|1|115 >16_6_HC_humanized_1944
QSLEESGGRLVTPGTPLTLTCTVSGSDISSYHMGWVRQPPGKGLEWIGIIVSSGSAYYATWAKNRVTISTSKNQF
SLRLNSVTAADTAVYYCARNQYSGYGFSFWGQGTLVTVSS (SEQ ID NO: 357)
>cl|LIBBABABA|1|115 >16_6_HC_humanized_1895
QSLEESGGRLVTPGTPLTLTCTVSGSDISSYHMGWVRQAPGKGLVWVSIIVSSGSAYYATWAKGRFTISRDNATL
YLQMNSLRAEDTAVYYCARNQYSGYGFSFWGKGTTVTVSS (SEQ ID NO: 358)
>cl|MIBBABABA|1|115 >16_6_HC_humanized_65
QSLEESGGGLVQPGRSLRLSCAASGSDISSYHMGWVRQAPGKGLEWVGIIVSSGSAYYATWAKGRFTISRDNAS
LYLQMNSLRAEDTALYYCAKNQYSGYGFSFWGQGTLVTVSS (SEQ ID NO: 359)
>cl|NIBBABABA|2|115 >16_6_HC_humanized_1938 >16_6_HC_humanized_762
VKLLESGGGLVQPGGSLRLSCAASGSDISSYHMGWVRQAPGKGLEWVAIIVSSGSAYYATWAKGRFTISRDNST
LYLQMNSLGAEDTAVYYCARNQYSGYGFSFWGQGTLVTVSS (SEQ ID NO: 360)
>cl|QIBBABABA|2|115 >16_6_HC_humanized_2031 >16_6_HC_humanized_621
VQLVESGGGLVKPGGSLRLSCAASGSDISSYHMGWVRQAPGKGLEWVSIIVSSGSAYYATWAKGRFTISRDNST
LYLQMNNLRAEDTAVYYCARNQYSGYGFSFWGQGTLVTVLS (SEQ ID NO: 361)

Figure 8 (cont.)

\>cl|SIBBABABA|1|115 >16_6_HC_humanized_993
VQLVESGGGLIQPGRPLRLSCSGSGSDISSYHMGWVRQAPGKGLEWVGIIVSSGSAYYATWAKGRFTISRDDSV
VHLQMNSLKSEDTAVYYCTRNQYSGYGFSFWGQGTTVTVSS (SEQ ID NO: 362)
\>cl|TIBBABABA|1|115 >16_6_HC_humanized_956
VQLQESGPGLVKPSQTLSLTCTVSGSDISSYHMGWFRQHPGKGLEWIGIIVSSGSAYYATWAESRLTISEDTSNIQ
LRLTSVTAADTAVYFCARNQYSGYGFSFWGQGTTVTVSS (SEQ ID NO: 363)
\>cl|VIBBABABA|1|115 >16_6_HC_humanized_920
VQLVESGPGLVKPSQTLSLTCTVSGSDISSYHMGWIRQFPGKGLEWIGIIVSSGSAYYATWAKSRFTISTSKNQFSL
KVDSVTAADTAVYYCARNQYSGYGFSFWGQGTTVTVSS (SEQ ID NO: 364)
\>cl|WIBBABABA|1|115 >16_6_HC_humanized_278
VQLVQSGGGLVKPGGSLRLSCEASGSDISSYHMGWIRQAPGKGLEWVGIIVSSGSAYYATWAKGRFTISRDDST
LYLQVNSLKTEDSAVYYCTTNQYSGYGFSFWGQGTLVTVSS (SEQ ID NO: 365)
\>cl|YIBBABABA|2|115 >16_6_HC_humanized_169 >16_6_HC_humanized_168
VQLVESGGGLVQPGGSLRLSCAASGSDISSYHMGWVRQAPGKGLEWVSIIVSSGSAYYATWAKGRFTISRDNST
LYLQMDSLRAEDTAIYYCAKNQYSGYGFSFWGQGTLVTVSS (SEQ ID NO: 366)
\>cl|ZIBBABABA|1|115 >16_6_HC_humanized_994
VQLVESGGGLIQPGRSLRLSCSGSGSDISSYHMGWVRQAPGKGLEWVGIIVSSGSAYYATWAKGRFTISRDDSV
VYLQMNSLRSEDTAVYYCTRNQYSGYGFSFWGQGTMVTVSS (SEQ ID NO: 367)
\>cl|BOBBABABA|2|115 >16_6_HC_humanized_975 >16_6_HC_humanized_978
VQLVESGGGVVRPGGSLRLSCAASGSDISSYHMGWVRQAPGKGLEWVGIIVSSGSAYYATWAKGRFTISRDNA
SLYLEMNSLRAEDTALYFCARNQYSGYGFSFWGQGTMVTVSS (SEQ ID NO: 368)
\>cl|DOBBABABA|1|115 >16_6_HC_humanized_230
QSLEESGGGLVQPGGSLRLSCAASGSDISSYHMGWVRQAPGKGLEWVSIIVSSGSAYYATWAKGRFTISRDNST
LYLQMNSLRAEDTAVYYCAKNQYSGYGFSFWGQGTTVTVSS (SEQ ID NO: 369)
\>cl|GOBBABABA|1|115 >16_6_HC_humanized_1894
QSLEESGGRLVTPGTPLTLTCTVSGSDISSYHMGWVRQAPGKGLEWVSIIVSSGSAYYATWAKGRFTISRDNASL
YLQMNSLRAEDTAVYYCARNQYSGYGFSFFSDYWLVTVSS (SEQ ID NO: 370)
\>cl|HOBBABABA|2|115 >16_6_HC_humanized_2056 >16_6_HC_humanized_672
QSLVESGGGLIQPGGSLRLSCAASGSDISSYHMGWVRQAPGKGLEWVSIIVSSGSAYYATWAKGRFTISRDNSTL
YLQMNSLRAEDTAVYYCARNQYSGYGFSFWGQGTLVTVSS (SEQ ID NO: 371)
\>cl|LOBBABABA|1|115 >16_6_HC_humanized_657
QSLEESGGRLVTPGGSLRLSCAASGSDISSYHMGWVRQAPGKGLEWVSIIVSSGSAYYATWAKGRFTISRDNSSL
YLQMNSLRTEDSALYYCALNQYSGYGFSFWGQGSLVTVSS (SEQ ID NO: 372)

Figure 8 (cont.)

>cl|MOBBABABA|2|115 >16_6_HC_humanized_1917 >16_6_HC_humanized_677
QSLEESGGGVVQPGRSLRLSCAASGSDISSYHMGWVRQAPGKGLEWVAIIVSSGSAYYATWAKRRFTISRDNST
LYLQMNSLRAEDTAVYYCARNQYSGYGFSFWGQGTLVTVSS (SEQ ID NO: 373)
>cl|POBBABABA|1|115 >16_6_HC_humanized_2038
QSLEESGGRLVTPGTPLTLTCTVSGSDISSYHMGWVRQAPGKGLEWVAIIVSSGSAYYATWAKGRFTISRDNASL
YLQMNSLRAEDTAVYYCARNQYSGYGFSFPTSGYYYMDVS (SEQ ID NO: 374)
>cl|QOBBABABA|1|115 >16_6_HC_humanized_23
QSLLESGGDLVQPGGSLRLSCEASGSDISSYHMGWVRQAPGKGLEWVSIIVSSGSAYYATWAKGRFTISRDKSTL
FLQMHSLRVEDTAVYYCAKNQYSGYGFSFWGQGTTVTVSS (SEQ ID NO: 375)
>cl|ROBBABABA|1|115 >16_6_HC_humanized_21
VQLVESGGGLVQPGGSLRLSCAASGSDISSYHMGWVRQAPGKGLEFVSIIVSSGSAYYATWAKDRFTISRDNSTV
YLQMDSLRTEDTAMYFCARNQYSGYGFSFWGQGTLVTVSS (SEQ ID NO: 376)
>cl|SOBBABABA|1|115 >16_6_HC_humanized_469
VQLVESGGGLVQPGGSLRLSCAASGSDISSYHMGWVRQAPGKGLEWVAIIVSSGSAYYATWAKGRFTISRDNTS
LFLHMSSLRGEDTAIYYCARNQYSGYGFSFWGQGTLVTVSS (SEQ ID NO: 377)
>cl|TOBBABABA|1|115 >16_6_HC_humanized_2008
QSLEESGGRLVTPGTSLRLSCAVSGSDISSYHMGWVRQAPGKGLEWVSIIVSSGSAYYATWAKGRFTISRDNSTV
YLQMNSLRAEDTAVFYCARNQYSGYGFSFWGQGTLVTVSS (SEQ ID NO: 378)
>cl|VOBBABABA|1|115 >16_6_HC_humanized_1013
VQLVQSGGGVVQPGRSLRLSCEVSGSDISSYHMGWVRQAPGKGLEWVAIIVSSGSAYYATWAKGRFTISRSNN
TLYLQMNSLTAEDTALYFCARNQYSGYGFSFWGKGTTVTVSS (SEQ ID NO: 379)
>cl|XOBBABABA|1|115 >16_6_HC_humanized_149
VQLVQSGPGLVKPSRTLSLTCTVSGSDISSYHMGWIRQPPGKGLEWIGIIVSSGSAYYATWAQNRLTISTSKNQFS
LKLASVTAADTAVYFCARNQYSGYGFSFWGQGTLVTVSS (SEQ ID NO: 380)
>cl|YOBBABABA|1|115 >16_6_HC_humanized_113
LQLQESGPGLVKPSQTLSLTCSVSGSDISSYHMGWIRQHPGKGLEWIGIIVSSGSAYYATWAKSRITISTSKNQFSL
KLTSVTAADTALYYCARNQYSGYGFSFWGRGTLVTVSS (SEQ ID NO: 381)
>cl|BUBBABABA|1|115 >16_6_HC_humanized_965
VQLQESGPGLVKPSQTLSLTCTVSGSDISSYHMGWIRQHPGKGLEWIGIIVSSGSAYYATWAKSRVTISADTSKIS
LKLSSVTAADTAVYYCARNQYSGYGFSFWGQGTTVTVSS (SEQ ID NO: 382)
>cl|CUBBABABA|1|115 >16_6_HC_humanized_912
VQLQESGPGLVKPSQTLSLTCTVSGSDISSYHMGWIRQPPGKGLEWIGIIVSSGSAYYATWAKSRVLISTSKNQVS
LKLSSVTAADTAVYYCARNQYSGYGFSFWGQGTTVTVSS (SEQ ID NO: 383)

Figure 8 (cont.)

>cl|HUBBABABA|1|115 >16_6_HC_humanized_12
VQLVQSGGGVVQPGGSLRLSCAASGSDISSYHMGWVRQAPGKGLEWVAIIVSSGSAYYATWAQGRVTISRDN
STVHLQITSLKSEDTAVYYCAKNQYSGYGFSFWGQGTLVTVSS (SEQ ID NO: 384)
>cl|KUBBABABA|1|115 >16_6_HC_humanized_924
VQLVESGPGLVKPSQTLSLTCTVSGSDISSYHMGWFRQPPGKGLEWIGIIVSSGSAYYATWAKSRVTISTSKNQV
SLKLSPVTGADTAVYFCARNQYSGYGFSFWGQGTLVTVSS (SEQ ID NO: 385)
>cl|LUBBABABA|1|115 >16_6_HC_humanized_273
VQLVQSGGGLVQPGGSLRLSCAASGSDISSYHMGWVRQASGKGLEWIGIIVSSGSAYYATWAKGRFTVSRSQN
SVFLQMNSLETEDTAVYYCARNQYSGYGFSFWGQGTLVTVSS (SEQ ID NO: 386)
>cl|MUBBABABA|1|115 >16_6_HC_humanized_2032
QSLEESGGRLVTPGGSLRLSCAGSGSDISSYHMGWVRQAPGKGLEWVSIIVSSGSAYYATWAEGRFTISRDNATL
YLQMNSLRVEDTAVYYCATNQYSGYGFSFWGQGTLVTVSS (SEQ ID NO: 387)
>cl|NUBBABABA|1|115 >16_6_HC_humanized_879
QSLEESGGGLVQPGGSLRLSCTASGSDISSYHMGWVRQAPGKGLEWVSIIVSSGSAYYATWAKGRFTISRDSSTL
YLQMNNLRVEDTALYYCAHNQYSGYGFSFWGRGTQVTVSS (SEQ ID NO: 388)
>cl|PUBBABABA|1|115 >16_6_HC_humanized_267
QSLEQSGGGLVQPGESLRLSCAGSGSDISSYHMGWVRQAPGKGLEWVAIIVSSGSAYYATWAKGRFTISRDNAS
LFLQMNSLRVEDTAVYYCARNQYSGYGFSFWGQGTLVTVSS (SEQ ID NO: 389)
>cl|QUBBABABA|1|115 >16_6_HC_humanized_1992
QSLEESGGRLVTPGTPLTLTCTVSGSDISSYHMGWVRQAPGKGLVWVSIIVSSGSAYYATWAKGRFTISRDNATL
YLQMNSLRVEDTAVYYCARNQYSGYGFSFWGPGTLVTVSS (SEQ ID NO: 390)
>cl|RUBBABABA|1|115 >16_6_HC_humanized_1995
QSLEESGGRLVTPGTPLTLTCTVSGSDISSYHMGWVRQAPGKGLEWVSIIVSSGSAYYATWAKGRFTISRDNSTL
YLQMNSLRAEDTAVYYCAKNQYSGYGFSFWGPGTLVTVSS (SEQ ID NO: 391)
>cl|SUBBABABA|1|115 >16_6_HC_humanized_917
VQLQESGPGLVKPSQTLSLTCTVSGSDISSYHMGWIRQPPGKGLEWIGIIVSSGSAYYATWARSRITISETSKNLSL
KLTSVTAADTAVYYCARNQYSGYGFSFWGQGTTVTVSS (SEQ ID NO: 392)
>cl|TUBBABABA|1|115 >16_6_HC_humanized_1934
QSLEESGGRLVTPGTPLTLTCTVSGSDISSYHMGWVRQAPGKGLEWVSIIVSSGSAYYATWAKGRFTISRDNASL
YLQMNSLRAEDTAVYYCARNQYSGYGFSFGIFDYWVTVSS (SEQ ID NO: 393)
>cl|VUBBABABA|1|115 >16_6_HC_humanized_200
VQLQESGPGLVKPSETLSLTCSVSGSDISSYHMGWIRQPAGKGLEWIGIIVSSGSAYYATWARSRVTMSMSKNH
FSLKLRSVTAADTAVYFCARNQYSGYGFSFWGQGTLVTVSS (SEQ ID NO: 394)

Figure 8 (cont.)

>cl|WUBBABABA|1|115 >16_6_HC_humanized_1977
QSLEESGGRLVTPGTPLTLTCTVSGSDISSYHMGWVRQAPGKGLEWVAIIVSSGSAYYATWAKGRFTISRSKNTL
YLQMNSLRAEDTAVYYCARNQYSGYGFSFTCPYFDYWVSS (SEQ ID NO: 395)
>cl|XUBBABABA|1|115 >16_6_HC_humanized_2027
QSLEESGGRLVTPGTPLTLTCTVSGSDISSYHMGWVRQAPGKGLEWVAIIVSSGSAYYATWAEGRFTISRDNSTL
YLQMYSLRTEDTAVYYCARNQYSGYGFSFYYYGMGVWVSS (SEQ ID NO: 396)
>cl|YUBBABABA|1|115 >16_6_HC_humanized_1958
VHLVESGGGVVQPGRSLRLSCAASGSDISSYHMGWVRQAPGKGLEWVAIIVSSGSAYYATWAEGRFTISRDNS
KLYLQMNSLRAEDSATYYCARNQYSGYGFSFFGPPYYYYMS (SEQ ID NO: 397)
>cl|ZUBBABABA|1|115 >16_6_HC_humanized_1949
QSLEESGGRLVTPGTPLTLTCTVSGSDISSYHMGWVRQAPGKGLEYVSIIVSSGSAYYATWAKGRFTISRDNSTLY
LQMSSLRAEDTAVYYCVKNQYSGYGFSFWGPGTLVTVSS (SEQ ID NO: 398)
>cl|BACBABABA|1|115 >16_6_HC_humanized_1905
QSLEESGGRLVTPGTPLTLTCTVSGSDISSYHMGWVRQAPGKGLEWVSIIVSSGSAYYATWAKGRFTISRDNSTL
YLQMNSLRAEDTALYYCARNQYSGYGFSFVRGGYFYHMDS (SEQ ID NO: 399)

Figure 8 (cont.)

*16-6 VL humanized sequences -- IMGT-LigM DB (Abysis) clustered at 95%*
*(64 sequences)*

>cl|CACBABABA|1|110 >16_6_LC_humanized_586
IVLTQTPSSLSASVGDRITITCQSSHSVYYGDWLAWYQQKPGKAPKLLIYRASNLASGVPSRFSGSRSGTDFTFTIS
SLRPEDIATYYCLGGYDDDGETAFGGGTKVEIK (SEQ ID NO: 400)
>cl|DACBABABA|1|110 >16_6_LC_humanized_411
IVLTQSPSSLSASVGDRVTITCQSSHSVYYGDWLAWYQQKPGKAPNLLIYRASNLASGVPSRFSGSGSATDFTLTI
SSLQPEDFATYYCLGGYDDDGETAFGGGTRVEIK (SEQ ID NO: 401)
>cl|FACBABABA|1|110 >16_6_LC_humanized_372
IQLTQSPSTLSASVGDRVTITCQSSHSVYYGDWLAWYQQKAGKAPTLLIYRASNLASGVPSRFSGSGSGTEFTLTIS
SLQPDDFATYYCLGGYDDDGETAFGQGTKVDIK (SEQ ID NO: 402)
>cl|GACBABABA|1|110 >16_6_LC_humanized_1996
VVLTQTPSPVSTAVGGTVTLSCQSSHSVYYGDWLAWYQQKPGQAPRLLIYRASNLASGIPDRFSGSGSGTDFTLT
ISRLEPEDFAVYYCLGGYDDDGETAKGPGTEVVVK (SEQ ID NO: 403)
>cl|HACBABABA|2|110 >16_6_LC_humanized_1907 >16_6_LC_humanized_716
LVMTQSPSSLSASEGDRVTITCQSSHSVYYGDWLAWYQQKPGRAPKLLIHRASNLASGVPSRFSGSGSGTEFTLT
ISGLQSEDFATYYCLGGYDDDGETAFGGGTTVDVK (SEQ ID NO: 404)
>cl|LACBABABA|2|110 >16_6_LC_humanized_1945 >16_6_LC_humanized_1451
VELTQPPSPVSAAPGQKVTISCQSSHSVYYGDWLAWYQQLPGTAPKLLIYRASNLASGIPDRFSGSKSGTSATLGI
TGLQTGDEADYYCLGGYDDDGETAFGGGTRLTVL (SEQ ID NO: 405)
>cl|NACBABABA|2|110 >16_6_LC_humanized_1004 >16_6_LC_humanized_283
IQLTQSPSSVSASVGDRVTITCQSSHSVYYGDWLAWYQQKPGKAPKLLIYRASNLASGVPSRFSGSGSGTDFALTI
SSLQPEDFATYYCLGGYDDDGETAFGQGTRLEIK (SEQ ID NO: 406)
>cl|PACBABABA|1|110 >16_6_LC_humanized_1971
VVLTQTPSPVSTAVGGTVTITCQSSHSVYYGDWLAWYQQKSGKAPKLLIYRASNLASGVPSRFSGSGSGTDFTLTI
SSLQPEDFATYYCLGGYDDDGETAFGGGTEVVVK (SEQ ID NO: 407)
>cl|QACBABABA|1|110 >16_6_LC_humanized_802
IRMTQSPSSFSASTGDRVTITCQSSHSVYYGDWLAWYQQKPGKAPKLLIYRASNLASGVPSRFSGSGSGTDFTLTI
SCLQSEDFATYYCLGGYDDDGETAFGGGTKVEIK (SEQ ID NO: 408)
>cl|RACBABABA|1|110 >16_6_LC_humanized_609
IRLTQSPSFLSASVGDRVTITCQSSHSVYYGDWLAWYQQKPGKAPKLLIYRASNLASGVPSRFSGSGSGTDFTLTIS
TLQPEDFATYYCLGGYDDDGETAFGQGTKLEIK (SEQ ID NO: 409)

Figure 8 (cont.)

>cl|SACBABABA|1|110 >16_6_LC_humanized_587
VVMTQSPSSLSASVGDRVTITCQSSHSVYYGDWLAWFQQKPGKAPNLLIYRASNLASGVPSRFSGSGSGTEFTLT
ISSLQPEDFATYYCLGGYDDDGETAFGQGTKVEIK (SEQ ID NO: 410)
>cl|TACBABABA|1|110 >16_6_LC_humanized_305
IQLTQSPSSLSASVGDRVTITCQSSHSVYYGDWLAWFQQKPGKAPKSLIYRASNLASGVPSRFSGSGSGTDFTLTI
SSLQPEDSATYYCLGGYDDDGETAFGGGTKVEIK (SEQ ID NO: 411)
>cl|VACBABABA|12|110 >16_6_LC_humanized_1877 >16_6_LC_humanized_860
>16_6_LC_humanized_213 >16_6_LC_humanized_902 >16_6_LC_humanized_334
IQLTQSPSSLSASVGDRVTITCQSSHSVYYGDWLAWYQQKPGKAPKLLIYRASNLASGVPSRFSGSGSGTDFTLTI
SSLQPEDFATYYCLGGYDDDGETAFGGGTKVEIK (SEQ ID NO: 412)
>cl|WACBABABA|2|110 >16_6_LC_humanized_1012 >16_6_LC_humanized_65
IQLTQSPSTLSASVGDRVTITCQSSHSVYYGDWLAWYQQKPGKAPKLLIYRASNLASGVPSRFSGSGSGTEFTLTIS
SLQPDDFATYYCLGGYDDDGETAFGQGTKLEIK (SEQ ID NO: 413)
>cl|XACBABABA|6|110 >16_6_LC_humanized_988 >16_6_LC_humanized_910
>16_6_LC_humanized_956 >16_6_LC_humanized_2056 >16_6_LC_humanized_672
IVLTQSPSSLSASVGDRVTITCQSSHSVYYGDWLAWYQQKPGKAPKLLIYRASNLASGVPSRFSGSGSGTDFTLTIS
SLQPEDFATYYCLGGYDDDGETAFGQGTRLEIK (SEQ ID NO: 414)
>cl|CECBABABA|1|110 >16_6_LC_humanized_253
IVLTQSPSAMSASVGDRVTITCQSSHSVYYGDWLAWFQQKPGKAPKLLIYRASNLASGVPSRFSGSGSGTEFTLTI
SSLQPEDSATYYCLGGYDDDGETAFGQGTKVDIK (SEQ ID NO: 415)
>cl|DECBABABA|1|110 >16_6_LC_humanized_218
IVMTQSPSSLSASVGDRVTITCQSSHSVYYGDWLAWYQQKPGKVPKLLIYRASNLASGVPSRFSGSGSGTDFTLTI
SSLQPEDVATYYCLGGYDDDGETAFGPGTKVEIK (SEQ ID NO: 416)
>cl|GECBABABA|1|110 >16_6_LC_humanized_136
VVMTQSPSTLSASVGDRVTITCQSSHSVYYGDWLAWYQQKPGKAPKVLIYRASNLASGVPSRFSGSGSGTEFTL
TISSLQPDDFASYYCLGGYDDDGETAFGPGTKVDIK (SEQ ID NO: 417)
>cl|HECBABABA|1|110 >16_6_LC_humanized_129
IVMTQSPSSLSASVGDRVTITCQSSHSVYYGDWLAWYQHKPGKAPRLLIYRASNLASGVPSRFSGSGSGTDFTLTI
SSLQPDDFATYYCLGGYDDDGETAFGQGTKVEVK (SEQ ID NO: 418)
>cl|KECBABABA|1|110 >16_6_LC_humanized_109
IQLTQSPSSVSASVGDTITITCQSSHSVYYGDWLAWYQQKPGKAPKLLIYRASNLASGVPSRFSGSRSGTDFTLTIS
SLQPEDFATYYCLGGYDDDGETAFGQGTKVEIK (SEQ ID NO: 419)

Figure 8 (cont.)

\>cl|LECBABABA|1|110 >16_6_LC_humanized_103
IVLTQSPSTLSASVGDRVTITCQSSHSVYYGDWLAWYQQKPGQAPKLLIYRASNLASGVPSRFSGSGSGTEFTLSI
NSLQPDDSATYFCLGGYDDDGETAFGQGTKVEIK (SEQ ID NO: 420)
\>cl|MECBABABA|1|110 >16_6_LC_humanized_954
IVLTQSPSTLSASVGDRVTITCQSSHSVYYGDWLAWYQQKPGKAPKLLIYRASNLASGVPSRFSGSGSGTEFTLTIS
SLQPDDFATYYCLGGYDDDGETAFGQGTKAEIK (SEQ ID NO: 421)
\>cl|PECBABABA|3|110 >16_6_LC_humanized_851 >16_6_LC_humanized_908
\>16_6_LC_humanized_912
VVMTQSPSSLSASVGDRVTITCQSSHSVYYGDWLAWYQQKPGKAPKLLIYRASNLASGVPSRFSGSGSGTDFTLT
ISSLQPEDFATYYCLGGYDDDGETAFGGGTKVEIK (SEQ ID NO: 422)
\>cl|RECBABABA|1|110 >16_6_LC_humanized_17
IQLTQSPSSLSAAVGDRVTIACQSSHSVYYGDWLAWYQQKPGKAPKLLIYRASNLASGVPSRFSGSGSGTDFTLSI
SSLQPGDFATYYCLGGYDDDGETAFGGGTKVQMK (SEQ ID NO: 423)
\>cl|XECBABABA|2|110 >16_6_LC_humanized_108 >16_6_LC_humanized_946
IVLTQSPSSVSASVGDRVTITCQSSHSVYYGDWLAWYQQKPGKAPKLLIYRASNLASGVPSRFSGSGSGTDFTLTI
SSLQPEDFATYYCLGGYDDDGETAFGGGTKVEIK (SEQ ID NO: 424)
\>cl|ZECBABABA|1|110 >16_6_LC_humanized_882
VVLTQSPSSLSASVGDRVTITCQSSHSVYYGDWLAWYQQKPGKAPKLLIYRASNLASGVPSRFSGSGFGTDFTFTI
SSLQPEDSATYYCLGGYDDDGETAFGQGTKLEIK (SEQ ID NO: 425)
\>cl|BICBABABA|1|110 >16_6_LC_humanized_186
IQLTQSPSTLSASVGDRVTITCQSSHSVYYGDWLAWYQQKPGKAPKLLIYRASNLASGVPSRFSGSGSGTEFTLTIS
SLQPDDFATYYCLGGYDDDGETAFGQGTKVVVK (SEQ ID NO: 426)
\>cl|CICBABABA|1|110 >16_6_LC_humanized_2041
VVLTQTPSPVSTAVGGTVTITCQSSHSVYYGDWLAWYQQKPGKAPKLLIYRASNLASGVPSRFSGSGSGTDFTLT
ISCLQSEDFATYYCLGGYDDDGETAFGGGTEVVVK (SEQ ID NO: 427)
\>cl|DICBABABA|1|110 >16_6_LC_humanized_202
IRMTQSPSSLSASVGDRVTITCQSSHSVYYGDWLAWYQQKPGKVPKLLIYRASNLASGVPSRFSGSGSGTDFTLTI
SSLQPEDVATYYCLGGYDDDGETAFGPGTKVVVK (SEQ ID NO: 428)
\>cl|FICBABABA|1|110 >16_6_LC_humanized_192
VVMTQSPSSLSASVGDRVTITCQSSHSVYYGDWLAWYQQKPGKAPKLLIYRASNLASGVPSRFSGSGSGTDFTLT
ISSLQAEDFTTYYCLGGYDDDGETAFGQGTKVEFK (SEQ ID NO: 429)
\>cl|GICBABABA|2|110 >16_6_LC_humanized_1982 >16_6_LC_humanized_734
VELTQSPSSVSASVGDRVTITCQSSHSVYYGDWLAWYQQKPGKAPKLLIYRASNLASGVPSRFSGSGSGTDFSLTI
SSLQPEDSATYYCLGGYDDDGETAFGQGTKVEIK (SEQ ID NO: 430)

Figure 8 (cont.)

>cl|KICBABABA|2|110 >16_6_LC_humanized_1944 >16_6_LC_humanized_1895
IELTQSPSTLSASVGDRVIISCQSSHSVYYGDWLAWYQQKPGKAPKLLIYRASNLASGVPSRFSGSGSGTEFSLTIN
SLQPDDFATYYCLGGYDDDGETAFGPGTKVDIK (SEQ ID NO: 431)
>cl|NICBABABA|2|110 >16_6_LC_humanized_1938 >16_6_LC_humanized_762
VELTQSPDSLAVSLGERATINCQSSHSVYYGDWLAWYQQKPGQPPKLLIYRASNLASGVPDRFSGSGSGTDFTLT
ISSLQAEDVAVYYCLGGYDDDGETAFGGGTKVEIK (SEQ ID NO: 432)
>cl|QICBABABA|2|110 >16_6_LC_humanized_2031 >16_6_LC_humanized_621
VELTQSPSSLSASVGDRVTITCQSSHSVYYGDWLAWYQQKPGKAPKLLIYRASNLASGVPSRFSGSGSGTDFTLTI
SSLQPEDFATYYCLGGYDDDGETAFGQGTKVEIK (SEQ ID NO: 433)
>cl|SICBABABA|4|110 >16_6_LC_humanized_993 >16_6_LC_humanized_880
>16_6_LC_humanized_23 >16_6_LC_humanized_917
VVLTQSPSSLSASVGDRVTITCQSSHSVYYGDWLAWYQQKPGKAPKLLIYRASNLASGVPSRFSGSGSGTDFTLTI
SSLQPEDFATYYCLGGYDDDGETAFGPGTKVDIK (SEQ ID NO: 434)
>cl|VICBABABA|1|110 >16_6_LC_humanized_920
IVMTQSPSSLSASVGDRVTITCQSSHSVYYGDWLAWYQQKPGKAPKLLIYRASNLASGVPSRFSGSGSGTDFTLTI
SSLQPEDIATYYCLGGYDDDGETAFGQGTKVEIK (SEQ ID NO: 435)
>cl|WICBABABA|1|110 >16_6_LC_humanized_278
LVLTQSPSSLSASVGDRVTITCQSSHSVYYGDWLAWCQQKPGKSPTLLIYRASNLASGVPSRFSGSGSGTGFTLTI
SGLQPEDFATYYCLGGYDDDGETAFGGGTKVEIR (SEQ ID NO: 436)
>cl|YICBABABA|1|110 >16_6_LC_humanized_169
IVLTQSPSFLSAFVGDRITITCQSSHSVYYGDWLAWYQQKPGKAPKLLIYRASNLASGVPSRFSGSGSGTEFTLTIS
GLQPEDFASYYCLGGYDDDGETAFGGGTKLEIK (SEQ ID NO: 437)
>cl|ZICBABABA|1|110 >16_6_LC_humanized_994
IVLTQSPSSLSASVGDRVTITCQSSHSVYYGDWLAWYQQKPGKVPKLLIYRASNLASGVPSRFSGSGSGTDFTLTIS
SLQPEDVATYYCLGGYDDDGETAFGQGTKVEIK (SEQ ID NO: 438)
>cl|BOCBABABA|1|110 >16_6_LC_humanized_975
IVLTQSPSTQSASVGDRVTITCQSSHSVYYGDWLAWYQQKPGKAPKLLIYRASNLASGVPSRFSGSGSGTEFTLTI
SSLQPDDFATYYCLGGYDDDGETAFGQGTKLEIK (SEQ ID NO: 439)
>cl|DOCBABABA|1|110 >16_6_LC_humanized_230
VVLTQTPSPVSASVGDRVTITCQSSHSVYYGDWLAWYQQKPGKAPKVLIYRASNLASGVPSRFSGSGSGTDFTLT
ISTLQPEDFATYYCLGGYDDDGETAFGQGTKLEIK (SEQ ID NO: 440)
>cl|GOCBABABA|1|110 >16_6_LC_humanized_1894
VVLTQTPSPVSTAVGDRVTITCQSSHSVYYGDWLAWYRQKPGKVPKLLIYRASNLASGVPSRFSGSGSGTDFTLTI
SSLQPEDVATYYGLGGYDDDGETAFGGGTEVVVK (SEQ ID NO: 441)

Figure 8 (cont.)

>cl|LOCBABABA|1|110 >16_6_LC_humanized_657
VVLTQTPSPVSTSVGDRVSITCQSSHSVYYGDWLAWYQQKPGKAPKLLIYRASNLASGVPSRFSGSGSGTDFTLTI
TSLQPVDFATYYCLGGYDDDGETAFGPGTTVDAK (SEQ ID NO: 442)
>cl|MOCBABABA|2|110 >16_6_LC_humanized_1917 >16_6_LC_humanized_677
VVLTQSPSFLSASVGDRVTITCQSSHSVYYGDWLAWYQQKPGKAPKLLIYRASNLASGVPSRFSGSGSGTEFTLTI
SSLQ
PEDFATYYCLGGYDDDGETAFGQGTRLEIK (SEQ ID NO: 443)
>cl|POCBABABA|1|110 >16_6_LC_humanized_2038
VVLTQTPSPVSTAVGGRVTITCQSSHSVYYGDWLAWYQQKPGKAPKLLIYRASNLASGVPSRFSGSGSGTEFTLTI
SSLQDKPFATYYCLGGYDDDGETAFGGGTEVVVK (SEQ ID NO: 444)
>cl|ROCBABABA|1|110 >16_6_LC_humanized_21
IQMTQSPSSLSASVGDRVTITCQSSHSVYYGDWLAWYQQKPGKAPKVLIYRASNLASGVPSRFSGSGSGTDFTLT
ISSLQPEDFATYYCLGGYDDDGETAFGPGTKVEVK (SEQ ID NO: 445)
>cl|SOCBABABA|1|110 >16_6_LC_humanized_469
IVLTQSPSLLSASIGDRVTIPCQSSHSVYYGDWLAWYQQKPGKAPKLLIYRASNLASGVPSRFSGSGSGTEFTLTISS
LQPEDFATYYCLGGYDDDGETAFGGGTKVDIK (SEQ ID NO: 446)
>cl|TOCBABABA|1|110 >16_6_LC_humanized_2008
VVLTQTPSPVSTAVGGRVTITCQSSHSVYYGDWLAWYQQKPGKAPKLLIYRASNLASGVPSRFSGSGSGTDFTLT
IGSLQPEDFAAYFCLGGYDDDGETAFGGGTKVEIK (SEQ ID NO: 447)
>cl|WOCBABABA|1|110 >16_6_LC_humanized_168
IVMTQSPSTLSASVGDRVTITCQSSHSVYYGDWLAWYQQKPGKAPKLLIYRASNLASGVPSRFSGSGSGTEFTLTI
SGLQPEDFATYYCLGGYDDDGETAFGGGTKLEIK (SEQ ID NO: 448)
>cl|XOCBABABA|1|110 >16_6_LC_humanized_149
IVLTQSPSSLSASVGDRVTITCQSSHSVYYGDWLAWYQQKPGKAPKRLIYRASNLASGVPSRFSGSGSGTEFTLTIS
GLQPEDIATYYCLGGYDDDGETAFGQGTKVEIK (SEQ ID NO: 449)
>cl|YOCBABABA|1|110 >16_6_LC_humanized_113
IVLTQSPSSVSASVGDRVTITCQSSHSVYYGDWLAWYQLKPGKAPKLLINRASNLASGVPSRFSGSGSGTDFTLTI
SGLQPEDFATYYCLGGYDDDGETAFGPGTTVDIK (SEQ ID NO: 450)
>cl|ZOCBABABA|4|110 >16_6_LC_humanized_978 >16_6_LC_humanized_965
>16_6_LC_humanized_924 >16_6_LC_humanized_879
IVLTQSPSSLSASVGDRVTITCQSSHSVYYGDWLAWYQQKPGKAPKLLIYRASNLASGVPSRFSGSGSGTDFTLTIS
SLQPEDFATYYCLGGYDDDGETAFGGGTKVEIK (SEQ ID NO: 451)

Figure 8 (cont.)

\>cl|GUCBABABA|1|110 >16_6_LC_humanized_818
VVLTQTPSSVSASVGDRVTITCQSSHSVYYGDWLAWYQQKPGKAPKLLIYRASNLASGVPSRFSGSGSGTDFTLTI
SSLQPEDFATYYCLGGYDDDGETAFGQGTKVEIK (SEQ ID NO: 452)
\>cl|HUCBABABA|1|110 >16_6_LC_humanized_12
VVMTQSPSTVSASVGDRVTLTCQSSHSVYYGDWLAWYQQKPGQPPKLLIYRASNLASGVPDRFSGSGSGTDFT
LTISSLQADDFATYYCLGGYDDDGETAFGQGTKVEIK (SEQ ID NO: 453)
\>cl|LUCBABABA|1|110 >16_6_LC_humanized_273
LVMTQSPSSLSASVGDRVTITCQSSHSVYYGDWLAWYQQKPGEAPKLLIYRASNLASGVPSRFSGSGSGTDFTLT
ISGLQSEDFATYYCLGGYDDDGETAFGQGTKVEIK (SEQ ID NO: 454)
\>cl|MUCBABABA|1|110 >16_6_LC_humanized_2032
VVLTQTPSPVSTAVGGTGPINCQSSHSVYYGDWLAWYQQKPGQPPKLLIYRASNLASGVPDRFSGSGSGTDFTL
TISSLQAEDVAVYYCLGGYDDDGETAFGGGTKLEIK (SEQ ID NO: 455)
\>cl|PUCBABABA|1|110 >16_6_LC_humanized_267
VVLTQSPSTLAASVGDRVTITCQSSHSVYYGDWLAWYQQKPGKAPKLLIYRASNLASGVPSRFSGSGSGTEFTLTI
SSLQPDDFATYYCLGGYDDDGETAFGQGTKVEVK (SEQ ID NO: 456)
\>cl|QUCBABABA|1|110 >16_6_LC_humanized_1992
VVLTQTPSPVSTAVGDRVTITCQSSHSVYYGDWLAWYQQKPGKAPKLLIYRASNLASGVPSRFSGSGSGTDFTLT
ISSLQPEDFATYYCLGGYDDDGETAFGGGTEVVVK (SEQ ID NO: 457)
\>cl|RUCBABABA|1|110 >16_6_LC_humanized_1995
VVLTQTPSPVSTAVGGTVTINCQSSHSVYYGDWLAWYQQKPGQPXKLLIYRASNLASGVPDRFSGSGSGTDFTL
TISSLQAEDVAVYYCLGGYDDDGETAFGQGTEVVVK (SEQ ID NO: 458)
\>cl|TUCBABABA|2|110 >16_6_LC_humanized_1934 >16_6_LC_humanized_1977
VVLTQTPSPVSTAVGGTVTITCQSSHSVYYGDWLAWYQQKPGKAPKLLIYRASNLASGVPSRFSGSGSGTDFTFT
ISSLQPEDIATYYCLGGYDDDGETAFGGGTEVVVK (SEQ ID NO: 459)
\>cl|VUCBABABA|1|110 >16_6_LC_humanized_200
VVLTQTPSPVSTAVGERATINCQSSHSVYYGDWLAWYQQKPGQPPKLLIYRASNLASGVPDRFSGTGSGTDFTL
TISSLQAEDVAVYYCLGGYDDDGETAFGGGTKVVVK (SEQ ID NO: 460)
\>cl|XUCBABABA|1|110 >16_6_LC_humanized_2027
VVLTQTPSPVSTAVGGTVTITCQSSHSVYYGDWLAWYQQKPGKAPKRLIYRASNLASGVPSRFSGSGSGTEFTLT
ISSLQPEDFATYYXLGGYDDDGETAFGGGTEVVVK (SEQ ID NO: 461)
\>cl|YUCBABABA|2|110 >16_6_LC_humanized_1958 >16_6_LC_humanized_1949
VVLTQTPSPVSTAVGGTVTIPCQSSHSVYYGDWLAWYQQKPGKAPKLLIYRASNLASGVPSRFSGSGSGTEFTLTI
SSLQPDDFATYYCLGGYDDDGETAFGGGTEVVVK (SEQ ID NO: 462)
\>cl|BADBABABA|1|110 >16_6_LC_humanized_1905
VVLTQTPSPVSTAVGGTVTINCQSSHSVYYGDWLAWYQQKPGQPPKLLIYRASNLASGVPDRFSGSGSGTDFTL
TISSLQAEDVAVYYCLGGYDDDGETAFGGGTEVVVK (SEQ ID NO: 463)

Figure 8 (cont.)

*16-6 VH humanized sequences -- germline database clustered at 90%*
*(3 sequences)*

>cl|CABBABABA|43|115 >16_6_HC_humanized_775 >16_6_HC_humanized_722
>16_6_HC_humanized_563 >16_6_HC_humanized_139 >16_6_HC_humanized_988
VQLVESGGGLVQPGGSLRLSCAASGSDISSYHMGWVRQAPGKGLEWVSIIVSSGSAYYATWAKGRFTISRDNST
LYLQMNSLRAEDTAVYYCARNQYSGYGFSFWGPGTLVTVSS (SEQ ID NO: 464)
>cl|DABBABABA|39|115 >16_6_HC_humanized_724 >16_6_HC_humanized_565
>16_6_HC_humanized_141 >16_6_HC_humanized_990 >16_6_HC_humanized_985
VQLVESGGGLVQPGGSLRLSCAASGSDISSYHMGWVRQAPGKGLEWVGIIVSSGSAYYATWAKGRFTISRSKNT
LYLQMNSLKTEDTAVYYCTRNQYSGYGFSFWGPGTLVTVSS (SEQ ID NO: 465)
>cl|REBBABABA|18|115 >16_6_HC_humanized_365 >16_6_HC_humanized_364
>16_6_HC_humanized_363 >16_6_HC_humanized_360 >16_6_HC_humanized_359
VQLQESGPGLVKPSETLSLTCTVSGSDISSYHMGWIRQPPGKGLEWIGIIVSSGSAYYATWAKSRVTISTSKNQFS
LKLSSVTAADTAVYYCARNQYSGYGFSFWGPGTLVTVSS (SEQ ID NO: 466)

*16-6 VL humanized sequences -- germline database clustered at 90%*
*(1 sequences)*

>cl|CACBABABA|100|110 >16_6_LC_humanized_775 >16_6_LC_humanized_724
>16_6_LC_humanized_722 >16_6_LC_humanized_565 >16_6_LC_humanized_563
VVLTQSPSSLSASVGDRVTITCQSSHSVYYGDWLAWYQQKPGKAPKLLIYRASNLASGVPSRFSGSGSGTDFTLTI
SSLQPEDFATYYCLGGYDDDGETAFGGGTEVVVK (SEQ ID NO: 467)

Figure 8 (cont.)

16-6 VH humanized sequences -- germline database clustered at 95% (10 sequences)

>cl|CABBABABA|13|115 >16_6_HC_humanized_775 >16_6_HC_humanized_722
>16_6_HC_humanized_563 >16_6_HC_humanized_139 >16_6_HC_humanized_987
VQLVESGGGLVQPGGSLRLSCAASGSDISSYHMGWVRQAPGKGLEYVSIIVSSGSAYYATWAKGRFTISRDNSTL
YLQMGSLRAEDMAVYYCARNQYSGYGFSFWGPGTLVTVSS (SEQ ID NO: 468)
>cl|DABBABABA|12|115 >16_6_HC_humanized_724 >16_6_HC_humanized_565
>16_6_HC_humanized_141 >16_6_HC_humanized_989 >16_6_HC_humanized_936
VQLVESGGGLVQPGGSLRLSCAASGSDISSYHMGWVRQAPGKGLEWVGIIVSSGSAYYATWAKGRFTISRSKNS
LYLQMNSLKTEDTAVYYCARNQYSGYGFSFWGPGTLVTVSS (SEQ ID NO: 469)
>cl|MABBABABA|9|115 >16_6_HC_humanized_990 >16_6_HC_humanized_937
>16_6_HC_humanized_672 >16_6_HC_humanized_407 >16_6_HC_humanized_248
VQLVESGGGLVQPGGSLKLSCAASGSDISSYHMGWVRQASGKGLEWVGIIVSSGSAYYATWAKGRFTISRSKNT
AYLQMNSLKTEDTAVYYCTRNQYSGYGFSFWGPGTLVTVSS (SEQ ID NO: 470)
>cl|NABBABABA|27|115 >16_6_HC_humanized_988 >16_6_HC_humanized_935
>16_6_HC_humanized_670 >16_6_HC_humanized_405 >16_6_HC_humanized_246
VQLVESGGGLVQPGGSLRLSCAASGSDISSYHMGWVRQAPGKGLEWVSIIVSSGSAYYATWAKGRFTISRDNST
LYLQMNSLRAEDTAVYYCARNQYSGYGFSFWGPGTLVTVSS (SEQ ID NO: 471)
>cl|PABBABABA|9|115 >16_6_HC_humanized_985 >16_6_HC_humanized_932
>16_6_HC_humanized_667 >16_6_HC_humanized_402 >16_6_HC_humanized_243
VQLVESGGGLVQPGRSLRLSCTASGSDISSYHMGWFRQAPGKGLEWVGIIVSSGSAYYATWAKGRFTISRSKSIA
YLQMNSLKTEDTAVYYCTRNQYSGYGFSFWGPGTLVTVSS (SEQ ID NO: 472)
>cl|QABBABABA|9|115 >16_6_HC_humanized_973 >16_6_HC_humanized_920
>16_6_HC_humanized_655 >16_6_HC_humanized_390 >16_6_HC_humanized_231
VQLVESGGGLVKPGGSLRLSCAASGSDISSYHMGWVRQAPGKGLEWVGIIVSSGSAYYATWAKGRFTISRSKNT
LYLQMNSLKTEDTAVYYCTTNQYSGYGFSFWGPGTLVTVSS (SEQ ID NO: 473)
>cl|REBBABABA|12|115 >16_6_HC_humanized_365 >16_6_HC_humanized_364
>16_6_HC_humanized_363 >16_6_HC_humanized_360 >16_6_HC_humanized_312
VQLQESGPGLVKPSETLSLTCTVSGSDISSYHMGWIRQPPGKGLEWIGIIVSSGSAYYATWAKSRVTISTSKNQFS
LKLSSVTAADTAVYYCARNQYSGYGFSFWGPGTLVTVSS (SEQ ID NO: 474)
>cl|WEBBABABA|3|115 >16_6_HC_humanized_359 >16_6_HC_humanized_306
>16_6_HC_humanized_41
LQLQESGSGLVKPSQTLSLTCAVSGSDISSYHMGWIRQPPGKGLEWIGIIVSSGSAYYATWAKSRVTISRSKNQFS
LKLSSVTAADTAVYYCARNQYSGYGFSFWGPGTLVTVSS (SEQ ID NO: 475)

Figure 8 (cont.)

>cl|XEBBABABA|3|115 >16_6_HC_humanized_357 >16_6_HC_humanized_304
>16_6_HC_humanized_39
VQLQESGPGLVKPPGTLSLTCAVSGSDISSYHMGWVRQPPGKGLEWIGIIVSSGSAYYATWAKSRVTISKSKNQF
SLKLSSVTAADTAVYYCCARNQYSGYGFSFWGPGTLVTVSS (SEQ ID NO: 476)
>cl|CIBBABABA|3|115 >16_6_HC_humanized_343 >16_6_HC_humanized_290
>16_6_HC_humanized_25
VQLVESGGGVVQPGRSLRLSCAASGSDISSYHMGWVRQAPGKGLEWVAIIVSSGSAYYATWAKGRFTISRDNS
TLYLQMNSLRAEDTAVYYCARNQYSGYGFSFWGPGTLVTVSS (SEQ ID NO: 477)

*16-6 VL humanized sequences -- germline database clustered at 95% (7 sequences)*

>cl|CACBABABA|3|110 >16_6_LC_humanized_775 >16_6_LC_humanized_724
>16_6_LC_humanized_722
VVLTQSPSSLSASVGDRVTITCQSSHSVYYGDWLAWYQQKPGKAPKLLIYRASNLASGVPSRFSGSGSGTDFTFTI
SSLQPEDIATYYCLGGYDDDGETAFGGGTEVVVK (SEQ ID NO: 478)
>cl|GACBABABA|2|110 >16_6_LC_humanized_565 >16_6_LC_humanized_563
VVLTQSPSSLSASVGDRVTITCQSSHSVYYGDWLAWYQQKPGKAPKRLIYRASNLASGVPSRFSGSGSGTEFTLTI
SSLQPEDFATYYCLGGYDDDGETAFGGGTEVVVK (SEQ ID NO: 479)
>cl|KACBABABA|2|110 >16_6_LC_humanized_141 >16_6_LC_humanized_139
VVLTQSPSSFSASTGDRVTITCQSSHSVYYGDWLAWYQQKPGKAPKLLIYRASNLASGVPSRFSGSGSGTDFTLTI
SCLQSEDFATYYCLGGYDDDGETAFGGGTEVVVK (SEQ ID NO: 480)
>cl|MACBABABA|62|110 >16_6_LC_humanized_990 >16_6_LC_humanized_988
>16_6_LC_humanized_985 >16_6_LC_humanized_973 >16_6_LC_humanized_937
VVLTQSPSSVSASVGDRVTITCQSSHSVYYGDWLAWYQQKPGKAPKLLIYRASNLASGVPSRFSGSGSGTDFTLTI
SSLQPEDFATYYCLGGYDDDGETAFGGGTEVVVK (SEQ ID NO: 481)
>cl|WACBABABA|6|110 >16_6_LC_humanized_672 >16_6_LC_humanized_670
>16_6_LC_humanized_667 >16_6_LC_humanized_655 >16_6_LC_humanized_671
VVLTQSPSSLSASVGDRVTITCQSSHSVYYGDWLAWYQQKPGKVPKLLIYRASNLASGVPSRFSGSGSGTDFTLTI
SSLQPEDVATYYCLGGYDDDGETAFGGGTEVVVK (SEQ ID NO: 482)
>cl|GECBABABA|6|110 >16_6_LC_humanized_248 >16_6_LC_humanized_246
>16_6_LC_humanized_243 >16_6_LC_humanized_231 >16_6_LC_humanized_247
VVLTQSPSFLSASVGDRVTITCQSSHSVYYGDWLAWYQQKPGKAPKLLIYRASNLASGVPSRFSGSGSGTEFTLTI
SSLQPEDFATYYCLGGYDDDGETAFGGGTEVVVK (SEQ ID NO: 483)
>cl|YICBABABA|19|110 >16_6_LC_humanized_47 >16_6_LC_humanized_46
>16_6_LC_humanized_45 >16_6_LC_humanized_42 >16_6_LC_humanized_41
VVLTQSPSTLSASVGDRVTITCQSSHSVYYGDWLAWYQQKPGKAPKLLIYRASNLASGVPSRFSGSGSGTEFTLTI
SSLQPDDFATYYCLGGYDDDGETAFGGGTEVVVK (SEQ ID NO: 484)

SEQUENCE LISTING

```
<160> NUMBER OF SEQ ID NOS: 500

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker fragment sequence

<400> SEQUENCE: 1

Gly Ser Thr Ser Gly Ser Gly Lys Pro Gly Ser Gly Glu Gly Ser Thr
1               5                   10                  15

Lys Gly

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker fragment sequence; Clone 8 epitope

<400> SEQUENCE: 2

Gly Ser Gly Lys Pro Gly Ser Gly Glu Gly
1               5                   10

<210> SEQ ID NO 3
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: Linker fragment sequence; Clone 16 epitope

<400> SEQUENCE: 3

Gly Lys Pro Gly Ser Gly Glu Gly
1               5

<210> SEQ ID NO 4
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Clone 8 VH DNA

<400> SEQUENCE: 4
atggagactg ggctgcgctg gcttctcctg gtcgctgtgc tcaaaggtgt ccagtgtcag      60
tcggtggagg agtccggggg tcgcctggtc acgcctggga caccctgac actcacctgc     120 acagcctctg gattcaccat cagtaacctt gcaataatct gggtccgcca ggctccaggg     180
aaggggctgg aatatatcgg agacattgat ggtcgtggtg acatatactg tgcgacctgg     240
gcgaaaggcc gattcaccat ctccaaaacc tcgaccacac tggatctgag attcaccagc     300
ccgacaaccg aggacacggc cacctacttc tgtgccgtag atggtgatgg tagtggttgg     360
ggtgacttta actttggggg cccaggcacc ctggtcaccg tctcctca                 408

<210> SEQ ID NO 5
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 8 VH AA

<400> SEQUENCE: 5

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Thr Ile Ser
        35                  40                  45

Asn Leu Ala Ile Ile Trp Val Arg Gln Ala Pro Gly Lys Gly Leu Glu
    50                  55                  60

Tyr Ile Gly Asp Ile Asp Gly Arg Gly Asp Ile Tyr Cys Ala Thr Trp
65                  70                  75                  80

Ala Lys Gly Arg Phe Thr Ile Ser Lys Thr Ser Thr Thr Leu Asp Leu
                85                  90                  95

Arg Phe Thr Ser Pro Thr Thr Glu Asp Thr Ala Thr Tyr Phe Cys Ala
            100                 105                 110

Val Asp Gly Asp Gly Ser Gly Trp Gly Asp Phe Asn Phe Trp Gly Pro
        115                 120                 125

Gly Thr Leu Val Thr Val Ser Ser
    130                 135
```

```
<210> SEQ ID NO 6
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 8 HC AA

<400> SEQUENCE: 6

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Thr Ile Ser
        35                  40                  45

Asn Leu Ala Ile Ile Trp Val Arg Gln Ala Pro Gly Lys Gly Leu Glu
    50                  55                  60

Tyr Ile Gly Asp Ile Asp Gly Arg Gly Asp Ile Tyr Cys Ala Thr Trp
65                  70                  75                  80

Ala Lys Gly Arg Phe Thr Ile Ser Lys Thr Ser Thr Thr Leu Asp Leu
                85                  90                  95

Arg Phe Thr Ser Pro Thr Thr Glu Asp Thr Ala Thr Tyr Phe Cys Ala
            100                 105                 110

Val Asp Gly Asp Gly Ser Gly Trp Gly Asp Phe Asn Phe Trp Gly Pro
            115                 120                 125

Gly Thr Leu Val Thr Val Ser Ser Gly Gln Pro Lys Ala Pro Ser Val
130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
            195                 200                 205

Ser Ser Ser Gln Pro Val Thr Cys Asn Val Ala His Pro Ala Thr Asn
210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
            275                 280                 285

Trp Tyr Ile Asn Asn Glu Gln Val Arg Thr Ala Arg Pro Pro Leu Arg
290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
```

```
            355                 360                 365
Glu Leu Ser Ser Arg Ser Val Ser Leu Thr Cys Met Ile Asn Gly Phe
    370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Ser Lys Leu Ser Val Pro Thr Ser Glu Trp Gln Arg Gly
            420                 425                 430

Asp Val Phe Thr Cys Ser Val Met His Glu Ala Leu His Asn His Tyr
                435                 440                 445

Thr Gln Lys Ser Ile Ser Arg Ser Pro Gly Lys
            450                 455

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 VH CDR1 AA

<400> SEQUENCE: 7

Gly Phe Thr Ile Ser Asn Leu
1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 VH CDR2 AA

<400> SEQUENCE: 8

Asp Ile Asp Gly Arg Gly Asp Ile Tyr Cys Ala Thr Trp Ala Lys
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 VH CDR3 AA

<400> SEQUENCE: 9

Asp Gly Asp Gly Ser Gly Trp Gly Asp Phe Asn Phe
1               5                   10

<210> SEQ ID NO 10
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Clone 8 VL DNA
```

-continued

<400> SEQUENCE: 10

```
atggacacga gggcccccac tcagctgctg gggctcctgc tgctctggct cccaggtgcc      60
agatgtgcct atgatatgac ccagactcca gcctctgtgg aggtagctgt gggaggcaca     120
gtcagcatca agtgccaggc cagtcagagc attagcactg cattagcctg gtatcagcag     180
aaaccaggac agcctcccaa gctcctgatc tacagggcat ccactctggc atctggggtc     240
tcatcgcggt tcaaaggcag tggatctggg acacagttca ctctcaccat cagcggcgtg     300
gagtgtgacg atgctgccac ttactactgt caacagggtt ggagtactgt gaatgttgat     360
aatgttttcg gcggagggac cgaggtggtg gtcaga                              396
```

<210> SEQ ID NO 11
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 8 VL AA

<400> SEQUENCE: 11

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Ser Ile Lys Cys Gln Ala Ser
        35                  40                  45

Gln Ser Ile Ser Thr Ala Leu Ala Trp Tyr Gln Gln Lys Pro Gly Gln
    50                  55                  60

Pro Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Gln Phe Thr Leu Thr
                85                  90                  95

Ile Ser Gly Val Glu Cys Asp Asp Ala Ala Thr Tyr Tyr Cys Gln Gln
            100                 105                 110

Gly Trp Ser Thr Val Asn Val Asp Asn Val Phe Gly Gly Gly Thr Glu
        115                 120                 125

Val Val Val Arg
    130
```

<210> SEQ ID NO 12
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 8 LC AA

<400> SEQUENCE: 12

```
Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Ser Ile Lys Cys Gln Ala Ser
        35                  40                  45

Gln Ser Ile Ser Thr Ala Leu Ala Trp Tyr Gln Gln Lys Pro Gly Gln
```

```
                50                  55                  60
Pro Pro Lys Leu Leu Ile Tyr Arg Ala Ser Thr Leu Ala Ser Gly Val
 65                  70                  75                  80

Ser Ser Arg Phe Lys Gly Ser Gly Ser Gly Thr Gln Phe Thr Leu Thr
                 85                  90                  95

Ile Ser Gly Val Glu Cys Asp Asp Ala Thr Tyr Tyr Cys Gln Gln
                100                 105                 110

Gly Trp Ser Thr Val Asn Val Asp Asn Val Phe Gly Gly Thr Glu
                115                 120                 125

Val Val Val Arg Asp Pro Val Ala Pro Thr Val Leu Ile Phe Pro Pro
                130                 135                 140

Ala Ala Asp Gln Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
                165                 170                 175

Thr Gln Thr Thr Gly Ile Glu Asn Ser Lys Thr Pro Gln Asn Ser Ala
                180                 185                 190

Asp Cys Thr Tyr Asn Leu Ser Ser Thr Leu Thr Leu Thr Ser Thr Gln
                195                 200                 205

Tyr Asn Ser His Lys Glu Tyr Thr Cys Lys Val Thr Gln Gly Thr Thr
                210                 215                 220

Ser Val Val Gln Ser Phe Asn Arg Gly Asp Cys
225                 230                 235
```

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 VL CDR1 AA

<400> SEQUENCE: 13

```
Gln Ala Ser Gln Ser Ile Ser Thr Ala Leu Ala
 1               5                  10
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 VL CDR2 AA

<400> SEQUENCE: 14

```
Arg Ala Ser Thr Leu Ala Ser
 1               5
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 VL CDR3 AA

<400> SEQUENCE: 15

Gln Gln Gly Trp Ser Thr Val Asn Val Asp Asn Val
1               5                   10

<210> SEQ ID NO 16
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Clone 16 VH DNA

<400> SEQUENCE: 16
atggagactg ggctgcgctg gcttctcctg gtcgctgtgc tcaaaggtgt ccagtgtcag    60
tcgctggagg agtccggggg tcgcctggtc acgcctggga caccoctgac actcacctgc   120 acagtctctg gatccgacat cagtagctac cacatgggct gggtccgcca ggctccaggg   180
aaggggctgg aatacatcgg aatcattgtt agtagtggta gcgcatacta cgcgacctgg   240
gcaaaaggcc gattcaccat ctccaggacc tcgaccacgg tggatctgaa aatcaccagt   300
ccgacaaccg aggactcggc cacctatttc tgtgccagaa atcaatatag tggttatggc   360
tttagcttct ggggcccagg caccctggtc accgtctcct ca                      402

<210> SEQ ID NO 17
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 16 VH AA

<400> SEQUENCE: 17

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ser Asp Ile Ser
        35                  40                  45

Ser Tyr His Met Gly Trp Val Arg Gln Ala Pro Gly Lys Gly Leu Glu
    50                  55                  60

Tyr Ile Gly Ile Ile Val Ser Ser Gly Ser Ala Tyr Tyr Ala Thr Trp
65                  70                  75                  80

Ala Lys Gly Arg Phe Thr Ile Ser Arg Thr Ser Thr Thr Val Asp Leu
                85                  90                  95

Lys Ile Thr Ser Pro Thr Thr Glu Asp Ser Ala Thr Tyr Phe Cys Ala
            100                 105                 110

Arg Asn Gln Tyr Ser Gly Tyr Gly Phe Ser Phe Trp Gly Pro Gly Thr
        115                 120                 125

Leu Val Thr Val Ser Ser
    130

<210> SEQ ID NO 18
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: Clone 16 HC AA

<400> SEQUENCE: 18

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ser Asp Ile Ser
        35                  40                  45

Ser Tyr His Met Gly Trp Val Arg Gln Ala Pro Gly Lys Gly Leu Glu
    50                  55                  60

Tyr Ile Gly Ile Ile Val Ser Ser Gly Ser Ala Tyr Tyr Ala Thr Trp
65                  70                  75                  80

Ala Lys Gly Arg Phe Thr Ile Ser Arg Thr Ser Thr Thr Val Asp Leu
                85                  90                  95

Lys Ile Thr Ser Pro Thr Thr Glu Asp Ser Ala Thr Tyr Phe Cys Ala
            100                 105                 110

Arg Asn Gln Tyr Ser Gly Tyr Gly Phe Ser Phe Trp Gly Pro Gly Thr
        115                 120                 125

Leu Val Thr Val Ser Ser Gly Gln Pro Lys Ala Pro Ser Val Phe Pro
    130                 135                 140

Leu Ala Pro Cys Cys Gly Asp Thr Pro Ser Ser Thr Val Thr Leu Gly
145                 150                 155                 160

Cys Leu Val Lys Gly Tyr Leu Pro Glu Pro Val Thr Val Thr Trp Asn
                165                 170                 175

Ser Gly Thr Leu Thr Asn Gly Val Arg Thr Phe Pro Ser Val Arg Gln
            180                 185                 190

Ser Ser Gly Leu Tyr Ser Leu Ser Ser Val Val Ser Val Thr Ser Ser
        195                 200                 205

Ser Gln Pro Val Thr Cys Asn Val Ala His Pro Ala Thr Asn Thr Lys
    210                 215                 220

Val Asp Lys Thr Val Ala Pro Ser Thr Cys Ser Lys Pro Thr Cys Pro
225                 230                 235                 240

Pro Pro Glu Leu Leu Gly Gly Pro Ser Val Phe Ile Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Asp Asp Pro Glu Val Gln Phe Thr Trp Tyr
        275                 280                 285

Ile Asn Asn Glu Gln Val Arg Thr Ala Arg Pro Pro Leu Arg Glu Gln
    290                 295                 300

Gln Phe Asn Ser Thr Ile Arg Val Val Ser Thr Leu Pro Ile Ala His
305                 310                 315                 320

Gln Asp Trp Leu Arg Gly Lys Glu Phe Lys Cys Lys Val His Asn Lys
                325                 330                 335

Ala Leu Pro Ala Pro Ile Glu Lys Thr Ile Ser Lys Ala Arg Gly Gln
            340                 345                 350

Pro Leu Glu Pro Lys Val Tyr Thr Met Gly Pro Pro Arg Glu Glu Leu
        355                 360                 365

Ser Ser Arg Ser Val Ser Leu Thr Cys Met Ile Asn Gly Phe Tyr Pro
    370                 375                 380

Ser Asp Ile Ser Val Glu Trp Glu Lys Asn Gly Lys Ala Glu Asp Asn
385                 390                 395                 400
```

```
Tyr Lys Thr Thr Pro Ala Val Leu Asp Ser Asp Gly Ser Tyr Phe Leu
            405                 410                 415

Tyr Ser Lys Leu Ser Val Pro Thr Ser Glu Trp Gln Arg Gly Asp Val
            420                 425                 430

Phe Thr Cys Ser Val Met His Glu Ala Leu His Asn His Tyr Thr Gln
        435                 440                 445

Lys Ser Ile Ser Arg Ser Pro Gly Lys
    450                 455

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 VH CDR1 AA

<400> SEQUENCE: 19

Gly Ser Asp Ile Ser Ser Tyr
1               5

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 VH CDR2 AA

<400> SEQUENCE: 20

Ile Ile Val Ser Ser Gly Ser Ala Tyr Tyr Ala Thr Trp Ala Lys
1               5                   10                  15

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 VH CDR3 AA

<400> SEQUENCE: 21

Asn Gln Tyr Ser Gly Tyr Gly Phe Ser Phe
1               5                   10

<210> SEQ ID NO 22
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Clone 16 VL DNA

<400> SEQUENCE: 22
atggacacga gggcccccac tcagctgctg gggctcctgc tgctctggct cccaggtgcc      60
acatttgccg tcgtgctgac ccagactcca tccccagtgt ctacagctgt aggaggcaca    120
gtcaccatca attgccagtc cagtcacagt gtttattatg cgactggtt agcctggtat     180
```

```
cagcagaaac cagggcagcc tcctaagctc ctgatctaca gggcatccaa tctggcatct    240
ggtgtcccat cgcggttcaa aggcagtgga tctgggacac agttcactct caccatcagc    300
ggcgtgcagt gtgacgatgc tgccacttac tactgtctag gcggttatga tgatgatggt    360
gagactgctt cggcggagg gaccgaggtg gtggtcaaa                            399
```

<210> SEQ ID NO 23
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 16 VL AA

<400> SEQUENCE: 23

Met Asp Thr Arg Ala Pro Thr Gln Leu Leu Gly Leu Leu Leu Leu Trp
1               5                   10                  15

Leu Pro Gly Ala Thr Phe Ala Val Val Leu Thr Gln Thr Pro Ser Pro
            20                  25                  30

Val Ser Thr Ala Val Gly Gly Thr Val Thr Ile Asn Cys Gln Ser Ser
        35                  40                  45

His Ser Val Tyr Tyr Gly Asp Trp Leu Ala Trp Tyr Gln Gln Lys Pro
    50                  55                  60

Gly Gln Pro Pro Lys Leu Leu Ile Tyr Arg Ala Ser Asn Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Leu Gly Gly Tyr Asp Asp Asp Gly Glu Thr Ala Phe Gly Gly Gly Thr
        115                 120                 125

Glu Val Val Val Lys
    130

<210> SEQ ID NO 24
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 16 LC AA

<400> SEQUENCE: 24

Met Asp Thr Arg Ala Pro Thr Gln Leu Leu Gly Leu Leu Leu Leu Trp
1               5                   10                  15

Leu Pro Gly Ala Thr Phe Ala Val Val Leu Thr Gln Thr Pro Ser Pro
            20                  25                  30

Val Ser Thr Ala Val Gly Gly Thr Val Thr Ile Asn Cys Gln Ser Ser
        35                  40                  45

His Ser Val Tyr Tyr Gly Asp Trp Leu Ala Trp Tyr Gln Gln Lys Pro
    50                  55                  60

Gly Gln Pro Pro Lys Leu Leu Ile Tyr Arg Ala Ser Asn Leu Ala Ser
65                  70                  75                  80

Gly Val Pro Ser Arg Phe Lys Gly Ser Gly Ser Gly Thr Gln Phe Thr
                85                  90                  95

```
Leu Thr Ile Ser Gly Val Gln Cys Asp Asp Ala Ala Thr Tyr Tyr Cys
            100                 105                 110

Leu Gly Gly Tyr Asp Asp Asp Gly Glu Thr Ala Phe Gly Gly Gly Thr
            115                 120                 125

Glu Val Val Lys Asp Pro Val Ala Pro Thr Val Leu Ile Phe Pro
130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
            210                 215                 220

Thr Ser Val Val Gln Ser Phe Asn Arg Gly Asp Cys
225                 230                 235

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 VL CDR1 AA

<400> SEQUENCE: 25

Gln Ser Ser His Ser Val Tyr Tyr Gly Asp Trp Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 VL CDR2 AA

<400> SEQUENCE: 26

Arg Ala Ser Asn Leu Ala Ser
1               5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 VL CDR3 AA

<400> SEQUENCE: 27

Leu Gly Gly Tyr Asp Asp Asp Gly Glu Thr Ala
1               5                   10

<210> SEQ ID NO 28
<211> LENGTH: 117
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 866

<400> SEQUENCE: 28

Val Gln Leu Gln Glu Ser Gly Gly Val Val Gln Pro Arg Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ala
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Asp Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 29
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 673

<400> SEQUENCE: 29

Gln Ser Val Val Glu Ser Gly Gly Val Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Pro Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Ser Leu Tyr Leu Gln Met Asn
65                  70                  75                  80

Ser Leu Arg Thr Glu Asp Thr Ala Val Tyr Tyr Cys Ala Lys Asp Gly
                85                  90                  95

Asp Gly Ser Gly Trp Gly Asp Phe Asn Phe Trp Gly Gln Gly Thr Met
            100                 105                 110

Val Thr Val Ser Ser
        115

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: 8 4 HC humanized 631

<400> SEQUENCE: 30

Gln Ser Val Glu Glu Ser Gly Gly Arg Leu Val Thr Pro Gly Ala Thr
1               5                   10                  15

Val Lys Ile Ser Cys Lys Val Ser Gly Phe Thr Ile Ser Asn Leu Ala
            20                  25                  30

Ile Ile Trp Val Gln Gln Ala Pro Gly Lys Gly Leu Glu Trp Met Gly
        35                  40                  45

Asp Ile Asp Gly Arg Gly Asp Ile Tyr Cys Ala Thr Trp Ala Gln Gly
    50                  55                  60

Arg Val Thr Ile Thr Ala Asp Ser Ser Thr Ala Tyr Met Glu Leu Asn
65                  70                  75                  80

Gly Leu Arg Tyr Ala Asp Thr Ala Val Tyr Tyr Cys Ala Thr Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 1002

<400> SEQUENCE: 31

Gln Ser Leu Glu Glu Ser Gly Gly Gly Val Val Gln Pro Gly Lys Ser
1               5                   10                  15

Leu Arg Leu Ser Cys Thr Ala Ser Gly Phe Thr Ile Ser Asn Leu Ala
            20                  25                  30

Ile Ile Trp Val Arg Gln Ala Pro Gly Lys Gly Leu Glu Ser Val Ala
        35                  40                  45

Asp Ile Asp Gly Arg Gly Asp Ile Tyr Cys Ala Thr Trp Ala Thr Gly
    50                  55                  60

Arg Phe Ala Ile Ser Arg Asp Asn Ser Lys Leu Tyr Leu His Met Asp
65                  70                  75                  80

Asn Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Thr
            100                 105                 110

Val Ile Val Ser Ser
        115

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 771

<400> SEQUENCE: 32
```

```
Gln Ser Leu Glu Gln Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Lys Ser Lys Asn Thr Leu Tyr Leu Gln Met Asn
65                  70                  75                  80

Ser Leu Arg Ala Glu Asp Thr Ala Val Tyr Tyr Cys Ala Val Asp Gly
                85                  90                  95

Asp Gly Ser Gly Trp Gly Asp Phe Asn Phe Trp Gly Gln Gly Thr Leu
            100                 105                 110

Val Thr Val Ser Ser
            115

<210> SEQ ID NO 33
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 849

<400> SEQUENCE: 33

Gln Ser Val Glu Glu Ser Gly Gly Asp Leu Val Lys Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Ile Arg Gln Ala Pro Gly Lys Gly Leu Glu Trp Leu Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ala Ser Leu Asn Leu Gln Met Asn
65                  70                  75                  80

Ser Leu Arg Ala Glu Asp Thr Ala Val Tyr Tyr Cys Ala Val Asp Gly
                85                  90                  95

Asp Gly Ser Gly Trp Gly Asp Phe Asn Phe Trp Gly Gln Gly Thr Leu
            100                 105                 110

Val Thr Val Ser Ser
            115

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 706

<400> SEQUENCE: 34

Val Leu Leu Leu Glu Ser Gly Gly Gly Leu Ala Gln Pro Gly Gly Thr
1               5                   10                  15

Leu Arg Leu Ser Cys Ser Ala Ser Gly Phe Thr Ile Ser Asn Leu Ala
            20                  25                  30
```

-continued

```
Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Arg Gly
     50                  55                  60

Arg Phe Ile Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Lys Asp Gly
                 85                  90                  95

Asp Gly Ser Gly Trp Gly Asp Phe Asn Phe Trp Gly Gln Gly Ile Leu
             100                 105                 110

Val Thr Val Ser Ser
        115

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 703

<400> SEQUENCE: 35

Val Gln Leu Val Glu Ser Gly Gly Thr Leu Val Gln Pro Gly Gly Ser
1               5                   10                  15

Leu Arg Leu Ser Cys Ser Ala Ser Gly Phe Thr Ile Ser Asn Leu Ala
             20                  25                  30

Ile Ile Trp Val Arg Gln Ala Pro Gly Lys Gly Leu Glu Tyr Val Ser
        35                  40                  45

Asp Ile Asp Gly Arg Gly Asp Ile Tyr Cys Ala Thr Trp Ala Lys Gly
     50                  55                  60

Arg Ile Thr Ile Ser Arg Asp Asn Ser Thr Leu Ser Leu Gln Met Ser
 65                  70                  75                  80

Thr Leu Arg Thr Glu Asp Thr Ala Val Tyr Tyr Cys Val Arg Asp Gly
                 85                  90                  95

Asp Gly Ser Gly Trp Gly Asp Phe Asn Phe Trp Gly Gln Gly Thr Leu
             100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 278

<400> SEQUENCE: 36

Val Gln Leu Val Gln Ser Gly Gly Gly Leu Val Lys Pro Gly Gly Ser
1               5                   10                  15

Leu Arg Leu Ser Cys Glu Ala Ser Gly Phe Thr Ile Ser Asn Leu Ala
             20                  25                  30

Ile Ile Trp Ile Arg Gln Ala Pro Gly Lys Gly Leu Glu Trp Val Gly
        35                  40                  45

Asp Ile Asp Gly Arg Gly Asp Ile Tyr Cys Ala Thr Trp Ala Lys Gly
```

```
                50                   55                  60
Arg Phe Thr Ile Ser Arg Asp Asp Ser Thr Leu Tyr Leu Gln Val Asn
 65                  70                  75                  80

Ser Leu Lys Thr Glu Asp Ser Ala Val Tyr Tyr Cys Thr Thr Asp Gly
                 85                  90                  95

Asp Gly Ser Gly Trp Gly Asp Phe Asn Phe Trp Gly Gln Gly Thr Leu
                100                 105                 110

Val Thr Val Ser Ser
            115

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 800

<400> SEQUENCE: 37

Gln Ser Val Leu Glu Ser Gly Pro Gly Leu Val Lys Pro Ser Glu Thr
 1               5                  10                  15

Leu Ser Leu Thr Cys Thr Val Ser Gly Phe Thr Ile Ser Asn Leu Ala
                20                  25                  30

Ile Ile Trp Ile Arg Gln Pro Pro Gly Lys Gly Leu Glu Trp Ile Gly
             35                  40                  45

Asp Ile Asp Gly Arg Gly Asp Ile Tyr Cys Ala Thr Trp Ala Lys Ser
 50                  55                  60

Arg Leu Thr Ile Ser Thr Ser Lys Asn Gln Phe Ser Leu Arg Leu Thr
 65                  70                  75                  80

Ser Val Thr Ala Ala Asp Thr Ala Met Tyr Tyr Cys Ala Val Asp Gly
                 85                  90                  95

Asp Gly Ser Gly Trp Gly Asp Phe Asn Phe Trp Gly Gln Gly Thr Leu
                100                 105                 110

Val Ser Val Ser Ser
            115

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 809

<400> SEQUENCE: 38

Val Gln Leu Val Glu Ser Gly Gly Gly Leu Val Gln Pro Gly Gly Ser
 1               5                  10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Leu Glu Trp Leu Ser
             35                  40                  45

Asp Ile Asp Gly Arg Gly Asp Ile Tyr Cys Ala Thr Trp Ala Arg Gly
 50                  55                  60

Arg Phe Ala Ile Ser Asn Ala Arg Asn Ser Leu Tyr Leu Gln Met Asn
 65                  70                  75                  80
```

```
Ser Leu Arg Asp Glu Asp Thr Ala Val Tyr Phe Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 273

<400> SEQUENCE: 39

Val Gln Leu Val Gln Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Ser Gly Lys Gly Leu Glu Trp Ile Gly
        35                  40                  45

Asp Ile Asp Gly Arg Gly Asp Ile Tyr Cys Ala Thr Trp Ala Lys Gly
    50                  55                  60

Arg Phe Thr Val Ser Arg Ser Gln Asn Ser Val Phe Leu Gln Met Asn
65                  70                  75                  80

Ser Leu Glu Thr Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 716

<400> SEQUENCE: 40

Gln Ser Val Leu Glu Ser Gly Gly Gly Trp Val Gln Pro Gly Arg Ser
1               5                   10                  15

Leu Arg Leu Ser Cys Ser Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Leu Tyr Leu Gln Met Asn
65                  70                  75                  80

Ser Leu Arg Pro Glu Asp Thr Ala Leu Tyr Tyr Cys Ala Lys Asp Gly
                85                  90                  95

Asp Gly Ser Gly Trp Gly Asp Phe Asn Phe Trp Gly Gln Gly Val Leu
            100                 105                 110
```

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 202

<400> SEQUENCE: 41

Val Gln Leu Gln Glu Ser Gly Glu Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Tyr Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Gly
65                  70                  75                  80

Ser Leu Arg Ala Glu Asp Met Ala Val Tyr Tyr Cys Ala Val Asp Gly
                85                  90                  95

Asp Gly Ser Gly Trp Gly Asp Phe Asn Phe Trp Gly Gln Gly Thr Met
            100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 21

<400> SEQUENCE: 42

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Phe Val Ser
        35                  40                  45

Asp Ile Asp Gly Arg Gly Asp Ile Tyr Cys Ala Thr Trp Ala Lys Asp
    50                  55                  60

Arg Phe Thr Ile Ser Arg Asp Asn Ser Thr Val Tyr Leu Gln Met Asp
65                  70                  75                  80

Ser Leu Arg Thr Glu Asp Thr Ala Met Tyr Phe Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

```
<210> SEQ ID NO 43
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 173

<400> SEQUENCE: 43

Gln Ser Val Glu Glu Ser Gly Gly Arg Leu Val Thr Pro Gly Gly Ser
1               5                   10                  15

Leu Arg Leu Ser Cys Thr Ala Thr Gly Phe Thr Ile Ser Asn Leu Ala
            20                  25                  30

Ile Ile Trp Phe Arg Gln Ala Pro Gly Lys Gly Leu Glu Trp Val Gly
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asp Asn Ser Leu Tyr Leu Gln Met Asn
65                  70                  75                  80

Ser Leu Lys Thr Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 44
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 HC humanized 23

<400> SEQUENCE: 44

Gln Ser Val Leu Glu Ser Gly Gly Asp Leu Val Gln Pro Gly Gly Ser
1               5                   10                  15

Leu Arg Leu Ser Cys Glu Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Lys Ser Lys His Thr Leu Phe Leu Gln Met His
65                  70                  75                  80

Ser Leu Arg Val Glu Asp Thr Ala Val Tyr Tyr Cys Ala Lys Asp Gly
                85                  90                  95

Asp Gly Ser Gly Trp Gly Asp Phe Asn Phe Trp Gly Gln Gly Thr Thr
            100                 105                 110

Val Thr Val Ser Ser
        115

<210> SEQ ID NO 45
<211> LENGTH: 117
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: 8 4 HC humanized 879

<400> SEQUENCE: 45

Gln Ser Val Glu Glu Ser Gly Gly Leu Val Gln Pro Gly Gly Ser
1               5                   10                  15

Leu Arg Leu Ser Cys Thr Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
50                  55                  60

Arg Phe Thr Ile Ser Arg Asp Ser Ser Thr Leu Tyr Leu Gln Met Asn
65                  70                  75                  80

Asn Leu Arg Val Glu Asp Thr Ala Leu Tyr Tyr Cys Ala His Asp Gly
                85                  90                  95

Asp Gly Ser Gly Trp Gly Asp Phe Asn Phe Trp Gly Arg Gly Thr Gln
                100                 105                 110

Val Thr Val Ser Ser
            115

<210> SEQ ID NO 46
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 866

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Arg Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
                100                 105                 110

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 340

<400> SEQUENCE: 47

Asp Ile Gln Met Thr Gln Ser Pro Phe Ser Leu Ser Ala Ser Val Gly

```
                1               5                  10                  15
Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Trp Ser Thr Val Asn
                85                  90                  95

Val Asp Asn Val Phe Gly Gly Gly Thr Lys Leu Glu Ile Lys
                100                 105                 110
```

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 322

<400> SEQUENCE: 48

```
Asp Ile Gln Leu Thr Gln Ser Pro Ser Phe Leu Ser Ala Ser Val Gly
1               5                   10                  15

Asp Thr Val Ser Ile Thr Cys Gln Ala Ser Gln Ser Ile Ser Thr Ala
                20                  25                  30

Leu Ala Trp Tyr Gln Gln Lys Pro Gly Lys Ala Pro Lys His Leu Ile
        35                  40                  45

Tyr Arg Ala Ser Thr Leu Ala Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
                100                 105                 110
```

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 305

<400> SEQUENCE: 49

```
Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Phe Gln Gln Lys Pro Gly Lys Ala Pro Lys Ser Leu Ile
        35                  40                  45

Tyr Arg Ala Ser Thr Leu Ala Ser Gly Val Pro Ser Arg Phe Ser Gly
    50                  55                  60
```

-continued

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Gly Trp Ser Thr Val Asn
            85                  90                  95

Val Asp Asn Val Phe Gly Gly Gly Thr Lys Val Glu Ile Lys
        100                 105                 110

<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 303

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Trp Ser Thr Val Asn
            85                  90                  95

Val Asp Asn Val Phe Gly Pro Gly Thr Lys Val Asp Ile Lys
        100                 105                 110

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 291

<400> SEQUENCE: 51

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Gly Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Leu Ala Thr Tyr Tyr Cys Gln Gln Gly Trp Ser Thr Val Asn
            85                  90                  95

Val Asp Asn Val Phe Gly Gly Gly Thr Lys Val Glu Ile Lys
        100                 105                 110

<210> SEQ ID NO 52

-continued

```
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 217

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 197

<400> SEQUENCE: 53

Ala Tyr Asp Met Thr Gln Thr Pro Ala Thr Leu Ser Leu Ser Pro Gly
1               5                   10                  15

Glu Arg Ala Thr Leu Ser Cys Gln Ala Ser Gln Ser Ile Ser Thr Ala
            20                  25                  30

Leu Ala Trp Tyr Gln Gln Lys Pro Gly Gln Ala Pro Arg Leu Leu Ile
        35                  40                  45

Tyr Arg Ala Ser Thr Leu Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Trp Ser Thr Val Asn
                85                  90                  95

Val Asp Asn Val Phe Gly Gln Gly Thr Glu Val Val Val Arg
            100                 105                 110

<210> SEQ ID NO 54
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 169

<400> SEQUENCE: 54
```

```
Glu Ile Val Leu Thr Gln Ser Pro Ser Phe Leu Ser Ala Phe Val Gly
1               5                   10                  15

Asp Arg Ile Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Gly Leu Gln Pro
65                  70                  75                  80

Glu Asp Phe Ala Ser Tyr Tyr Cys Gln Gln Gly Trp Ser Thr Val Asn
                85                  90                  95

Val Asp Asn Val Phe Gly Gly Gly Thr Lys Leu Glu Ile Lys
                100                 105                 110

<210> SEQ ID NO 55
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 17

<400> SEQUENCE: 55

Asp Ile Gln Leu Thr Gln Ser Pro Ser Ser Leu Ser Ala Ala Val Gly
1               5                   10                  15

Asp Arg Val Thr Ile Ala Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Ser Ile Ser Ser Leu Gln Pro
65                  70                  75                  80

Gly Asp Phe Ala Thr Tyr Tyr Cys Gln Gln Gly Trp Ser Thr Val Asn
                85                  90                  95

Val Asp Asn Val Phe Gly Gly Gly Thr Lys Val Gln Met Lys
                100                 105                 110

<210> SEQ ID NO 56
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 13

<400> SEQUENCE: 56

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60
```

```
Ser Gly Ser Gly Thr Glu Phe Thr Leu Thr Ile Asn Gly Leu Gln Pro
 65                  70                  75                  80

Glu Asp Phe Ala Thr Tyr Tyr Cys Gln Gln Gly Trp Ser Thr Val Asn
                 85                  90                  95

Val Asp Asn Val Phe Gly Gly Gly Thr Lys Leu Glu Ile Lys
            100                 105                 110

<210> SEQ ID NO 57
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 791

<400> SEQUENCE: 57

Ala Tyr Glu Leu Thr Gln Thr Pro Leu Ser Ser Pro Val Thr Leu Gly
  1               5                  10                  15

Gln Pro Ala Ser Ile Ser Cys Gln Ala Ser Gln Ser Ile Ser Thr Ala
                 20                  25                  30

Leu Ala Trp Leu His Gln Arg Pro Gly Gln Pro Pro Arg Leu Leu Ile
             35                  40                  45

Tyr Arg Ala Ser Thr Leu Ala Ser Gly Val Pro Asp Arg Phe Ser Gly
 50                  55                  60

Ser Gly Ala Gly Thr Ala Phe Thr Leu Lys Ile Ser Arg Val Glu Val
 65                  70                  75                  80

Glu Asp Val Gly Ile Tyr Tyr Cys Gln Gln Gly Trp Ser Thr Val Asn
                 85                  90                  95

Val Asp Asn Val Phe Gly Gln Gly Thr Lys Val Glu Ile Lys
            100                 105                 110

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 673

<400> SEQUENCE: 58

Ala Tyr Asp Met Thr Gln Thr Pro Ala Ser Val Glu Val Ser Pro Gly
  1               5                  10                  15

Glu Arg Ala Thr Leu Ser Cys Gln Ala Ser Gln Ser Ile Ser Thr Ala
                 20                  25                  30

Leu Ala Trp Tyr Gln His Lys Pro Gly Gln Ala Pro Arg Leu Leu Ile
             35                  40                  45

Tyr Arg Ala Ser Thr Leu Ala Ser Gly Ile Pro Ala Arg Phe Ser Gly
 50                  55                  60

Ser Gly Ser Gly Thr Glu Phe Thr Leu Thr Ile Ser Ser Val Gln Ser
 65                  70                  75                  80

Asp Asp Phe Ala Val Tyr Tyr Cys Gln Gln Gly Trp Ser Thr Val Asn
                 85                  90                  95

Val Asp Asn Val Phe Gly Pro Gly Thr Lys Val Asp Ile Lys
            100                 105                 110
```

<210> SEQ ID NO 59
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 678

<400> SEQUENCE: 59

Ala Tyr Glu Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Phe Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Leu Pro
65                  70                  75                  80

Thr Asp Phe Ala Thr Tyr Phe Cys Gln Gln Gly Trp Ser Thr Val Asn
                85                  90                  95

Val Asp Asn Val Phe Gly Gln Gly Thr Gln Val Glu Val Lys
            100                 105                 110

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 631

<400> SEQUENCE: 60

Ala Tyr Asp Met Thr Gln Thr Pro Ala Ser Val Glu Val Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Gly Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 61
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 1002

<400> SEQUENCE: 61

Ala Tyr Glu Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Ser Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110

<210> SEQ ID NO 62
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 775

<400> SEQUENCE: 62

Ala Tyr Glu Leu Thr Gln Thr Pro Leu Ser Ser Pro Val Thr Leu Gly
1               5                   10                  15

Gln Pro Ala Ser Ile Ser Cys Gln Ala Ser Gln Ser Ile Ser Thr Ala
            20                  25                  30

Leu Ala Trp Leu Gln Gln Arg Pro Gly Gln Pro Pro Arg Leu Leu Ile
            35                  40                  45

Tyr Arg Ala Ser Thr Leu Ala Ser Gly Val Pro Asp Arg Phe Ser Gly
50                  55                  60

Ser Gly Ala Arg Thr Asp Phe Thr Leu Asn Ile Ser Arg Val Glu Ala
65                  70                  75                  80

Glu Asp Ala Gly Val Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110

<210> SEQ ID NO 63
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 771

<400> SEQUENCE: 63

Ala Tyr Glu Leu Thr Gln Ser Pro Ala Thr Leu Ser Leu Ser Pro Gly
1               5                   10                  15

Glu Arg Ala Thr Leu Ser Cys Gln Ala Ser Gln Ser Ile Ser Thr Ala
            20                  25                  30

Leu Ala Trp Tyr Gln Gln Lys Pro Gly Gln Ala Pro Arg Leu Leu Ile
            35                  40                  45

His Arg Ala Ser Thr Leu Ala Ser Gly Ile Pro Ala Arg Phe Ser Gly

```
                50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Gly Trp Ser Thr Val Asn
                    85                  90                  95

Val Asp Asn Val Phe Gly Gly Gly Thr Arg Val Glu Ile Lys
                100                 105                 110

<210> SEQ ID NO 64
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 188

<400> SEQUENCE: 64

Asp Ile Gln Leu Thr Gln Ser Pro Ser Thr Leu Ser Ala Ser Val Gly
 1               5                  10                  15

Asp Arg Ile Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
             35                  40                  45

Tyr Arg Ala Ser Thr Leu Ala Ser Gly Val Pro Pro Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Gly Trp Ser Thr Val Asn
                    85                  90                  95

Val Asp Asn Val Phe Gly Gln Gly Thr Lys Val Val Val Arg
                100                 105                 110

<210> SEQ ID NO 65
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 717

<400> SEQUENCE: 65

Glu Leu Val Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Asn Leu Leu Ile
             35                  40                  45

Tyr Arg Ala Ser Thr Leu Ala Ser Gly Ile Pro Ser Arg Phe Ser Gly
         50                  55                  60

Ser Gly Ser Gly Thr Tyr Phe Thr Leu Thr Ile Asn Gly Leu Gln Pro
 65                  70                  75                  80

Glu Asp Phe Ala Thr Tyr Tyr Cys Gln Gln Gly Trp Ser Thr Val Asn
                    85                  90                  95

Val Asp Asn Val Phe Gly Gly Gly Thr Lys Val Asp Ile Lys
                100                 105                 110
```

<210> SEQ ID NO 66
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 1048

<400> SEQUENCE: 66

Ser Tyr Glu Leu Thr Gln Thr Pro Pro Ser Val Ser Val Ser Pro Gly
1               5                   10                  15

Gln Thr Ala Arg Ile Thr Cys Gln Ala Ser Gln Ser Ile Ser Thr Ala
            20                  25                  30

Leu Ala Trp Tyr Gln Gln Lys Pro Gly Gln Ala Pro Lys Val Leu Ile
        35                  40                  45

Tyr Arg Ala Ser Thr Leu Ala Ser Gly Ile Pro Glu Arg Phe Ser Gly
    50                  55                  60

Ser Ser Ser Gly Thr Thr Val Thr Leu Thr Ile Ser Gly Val Gln Ala
65                  70                  75                  80

Glu Asp Glu Ala Asp Tyr Tyr Cys Gln Gln Gly Trp Ser Thr Val Asn
                85                  90                  95

Val Asp Asn Val Phe Gly Gly Gly Thr Lys Leu Thr Val Leu
            100                 105                 110

<210> SEQ ID NO 67
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 849

<400> SEQUENCE: 67

Ala Tyr Glu Leu Thr Gln Ser Pro Leu Ser Leu Ser Val Thr Pro Gly
1               5                   10                  15

Gln Pro Ala Ser Ile Ser Cys Gln Ala Ser Gln Ser Ile Ser Thr Ala
            20                  25                  30

Leu Ala Trp Tyr Leu Gln Lys Pro Gly Gln Pro Pro Gln Leu Leu Ile
        35                  40                  45

Tyr Arg Ala Ser Thr Leu Ala Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 68
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 1016

<400> SEQUENCE: 68

Asp Ile Glu Leu Thr Gln Ser Pro Ser Leu Ser Ala Ser Ile Gly
1               5                   10                  15

Asp Arg Val Ser Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Phe Tyr Cys Gln Gln Gly Trp Ser Thr Val Asn
                85                  90                  95

Val Asp Asn Val Phe Gly Gly Gly Thr Arg Val Glu Ile Lys
            100                 105                 110

<210> SEQ ID NO 69
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 978

<400> SEQUENCE: 69

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 70
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 706

<400> SEQUENCE: 70

Asp Ile Gln Met Thr Gln Tyr Pro Ser Ser Leu Ser Ala Ser Val Gly
1               5                   10                  15

Asp Arg Val Thr Ile Ala Cys Gln Ala Ser Gln Ser Ile Ser Thr Ala
            20                  25                  30

Leu Ala Trp Tyr Gln Gln Lys Pro Gly Lys Pro Pro Lys Leu Leu Ile
        35                  40                  45

```
Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Cys Leu Gln Pro
65                  70                  75                  80

Glu Asp Val Ala Thr Tyr Tyr Cys Gln Gln Gly Trp Ser Thr Val Asn
                85                  90                  95

Val Asp Asn Val Phe Gly Gln Gly Thr Arg Val Glu Phe Lys
                100                 105                 110

<210> SEQ ID NO 71
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 278

<400> SEQUENCE: 71

Glu Leu Val Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Cys Gln Gln Lys Pro Gly Lys Ser Pro Thr Leu Leu Ile
            35                  40                  45

Tyr Arg Ala Ser Thr Leu Ala Ser Gly Val Pro Ser Arg Phe Ser Gly
    50                  55                  60

Ser Gly Ser Gly Thr Gly Phe Thr Leu Thr Ile Ser Gly Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Arg
                100                 105                 110

<210> SEQ ID NO 72
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 129

<400> SEQUENCE: 72

Glu Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Tyr Gln His Lys Pro Gly Lys Ala Pro Arg Leu Leu Ile
            35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Val Lys
                100                 105                 110
```

<210> SEQ ID NO 73
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 1133

<400> SEQUENCE: 73

Ala Tyr Asp Met Thr Gln Pro Pro Ser Val Ser Val Ser Pro Gly
1               5                   10                  15

Gln Thr Ala Ser Ile Thr Cys Gln Ala Ser Gln Ser Ile Ser Thr Ala
            20                  25                  30

Leu Ala Trp Tyr Gln Gln Lys Pro Gly Gln Ser Pro Val Leu Val Ile
        35                  40                  45

Tyr Arg Ala Ser Thr Leu Ala Ser Gly Ile Pro Glu Arg Phe Ser Gly
50                  55                  60

Ser Asn Ser Gly Asn Thr Ala Thr Leu Thr Ile Ser Gly Thr Gln Ala
65                  70                  75                  80

Met Asp Glu Ala Asp Tyr Tyr Cys Gln Gln Gly Trp Ser Thr Val Asn
                85                  90                  95

Val Asp Asn Val Phe Gly Thr Gly Thr Glu Val Val Val Arg
            100                 105                 110

<210> SEQ ID NO 74
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 881

<400> SEQUENCE: 74

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Asn Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Gln Ile Lys
            100                 105                 110

<210> SEQ ID NO 75
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 882

<400> SEQUENCE: 75

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Phe Gly Thr Asp Phe Thr Phe Thr Ile Ser Ser Leu Gln Pro
65                  70                  75                  80

Glu Asp Ser Ala Thr Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110

<210> SEQ ID NO 76
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 273

<400> SEQUENCE: 76

Glu Leu Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Glu Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Gly Leu Gln Ser
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 77
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 716

<400> SEQUENCE: 77

Glu Leu Val Met Thr Gln Ser Pro Ser Ser Leu Ser Ala Ser Glu Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Arg Ala Pro Lys Leu Leu Ile
        35                  40                  45

```
His Arg Ala Ser Thr Leu Ala Ser Gly Val Pro Ser Arg Phe Ser Gly
        50                  55                  60

Ser Gly Ser Gly Thr Glu Phe Thr Leu Thr Ile Ser Gly Leu Gln Ser
 65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Thr Val Asp Val Lys
            100                 105                 110

<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 677

<400> SEQUENCE: 78

Ala Tyr Asp Met Thr Gln Ser Pro Ser Phe Leu Ser Ala Ser Val Gly
 1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Arg Leu Glu Ile Lys
            100                 105                 110

<210> SEQ ID NO 79
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 192

<400> SEQUENCE: 79

Ala Tyr Asp Met Thr Gln Ser Pro Ser Ser Leu Ser Ala Ser Val Gly
 1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Ala
 65                  70                  75                  80

Glu Asp Phe Thr Thr Tyr Tyr Cys Gln Gln Gly Trp Ser Thr Val Asn
                85                  90                  95

Val Asp Asn Val Phe Gly Gln Gly Thr Lys Val Glu Phe Lys
```

-continued

```
                100                 105                 110

<210> SEQ ID NO 80
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 802

<400> SEQUENCE: 80

Ala Ile Arg Met Thr Gln Ser Pro Ser Ser Phe Ser Ala Ser Thr Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
                100                 105                 110

<210> SEQ ID NO 81
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 54

<400> SEQUENCE: 81

Ala Tyr Gly Met Thr Gln Ser Pro Asp Ser Leu Ala Val Ser Leu Gly
1               5                   10                  15

Glu Arg Ala Ser Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
    50                  55                  60

Gly Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gly Gly Thr Lys Val Glu Ile Lys
                100                 105                 110

<210> SEQ ID NO 82
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: 8 4 LC humanized 173

<400> SEQUENCE: 82

Ala Ile Gln Met Thr Gln Ser Pro Phe Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Phe Gln Gln Lys Pro Gly Lys Ala Pro Lys Ser Leu Ile
        35                  40                  45

Tyr Arg Ala Ser Thr Leu Ala Ser Gly Val Ser Ser Lys Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
            85                  90                  95

Val Asp Asn Val Phe Gly Gln Gly Thr Arg Leu Val Val Arg
            100                 105                 110

<210> SEQ ID NO 83
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 224

<400> SEQUENCE: 83

Ala Tyr Asp Met Thr Gln Thr Pro Ala Ser Val Ser Leu Ser Pro Gly
1               5                   10                  15

Glu Arg Ala Thr Leu Ser Cys Gln Ala Ser Gln Ser Ile Ser Thr Ala
            20                  25                  30

Leu Ala Trp Tyr Gln Gln Lys Pro Gly Gln Ala Pro Arg Leu Leu Ile
        35                  40                  45

Tyr Arg Ala Ser Thr Leu Ala Ser Gly Ile Pro Asp Arg Phe Arg Gly
50                  55                  60

Ser Gly Ser Ala Thr Asp Phe Thr Leu Thr Ile Ser Arg Leu Glu Pro
65                  70                  75                  80

Glu Asp Phe Ala Val Tyr Tyr Cys Gln Gln Gly Trp Ser Thr Val Asn
            85                  90                  95

Val Asp Asn Val Phe Gly Gly Gly Thr Glu Val Val Val Arg
            100                 105                 110

<210> SEQ ID NO 84
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8 4 LC humanized 657

<400> SEQUENCE: 84

Ala Tyr Asp Met Thr Gln Thr Pro Ala Ser Val Glu Val Ser Val Gly
1               5                   10                  15

Asp Arg Val Ser Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile

```
            35                  40                  45
Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Val Asp Phe Ala Thr Tyr Tyr Cys Gln Gln Gly Trp Ser Thr Val Asn
                 85                  90                  95

Val Asp Asn Val Phe Gly Pro Gly Thr Thr Val Asp Ala Lys
            100                 105                 110

<210> SEQ ID NO 85
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CABBABABA_10_117; 8 4 HC humanized 866; 8 4
      HC humanized 340; 8 4 HC humanized 336; 8 4 HC humanized 332; 8 4
      HC humanized 322

<400> SEQUENCE: 85

Val Gln Leu Val Glu Ser Gly Gly Gly Val Val Gln Pro Gly Arg Ser
 1               5                  10                  15

Leu Arg Leu Ser Cys Ala Ala Ser Gly Phe Thr Ile Ser Asn Leu Ala
             20                  25                  30

Ile Ile Trp Val Arg Gln Ala Pro Gly Lys Gly Leu Glu Trp Val Ala
         35                  40                  45

Asp Ile Asp Gly Arg Gly Asp Ile Tyr Cys Ala Thr Trp Ala Lys Gly
 50                  55                  60

Arg Phe Thr Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Val Asp Gly
                 85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 86
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KABBABABA_13_117; 8 4 HC humanized 315; 8 4
      HC humanized 314; 8 4 HC humanized 305; 8 4 HC humanized 303; 8 4
      HC humanized 296

<400> SEQUENCE: 86

Val Gln Leu Val Gln Ser Gly Gly Gly Val Val Gln Pro Gly Arg Ser
 1               5                  10                  15

Leu Arg Leu Ser Cys Ala Ala Ser Gly Phe Thr Ile Ser Asn Leu Ala
             20                  25                  30

Ile Ile Trp Val Arg Gln Ala Pro Gly Lys Gly Leu Glu Trp Val Ala
         35                  40                  45

Asp Ile Asp Gly Arg Gly Asp Ile Tyr Cys Ala Thr Trp Ala Lys Gly
 50                  55                  60
```

-continued

```
Arg Phe Thr Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Val Asp Gly
                 85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 87
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TABBABABA_8_117; 8 4 HC humanized 217; 8 4
      HC humanized 197; 8 4 HC humanized 678; 8 4 HC humanized 978; 8 4
      HC humanized 635

<400> SEQUENCE: 87

Val Gln Leu Val Glu Ser Gly Gly Gly Leu Val Lys Pro Gly Gly Ser
 1               5                  10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Leu Glu Trp Val Ser
            35                  40                  45

Asp Ile Asp Gly Arg Gly Asp Ile Tyr Cys Ala Thr Trp Ala Lys Gly
 50                  55                  60

Arg Phe Thr Ile Ser Arg Asp Asn Ala Ser Leu Tyr Leu Gln Met Asn
 65                  70                  75                  80

Ser Leu Arg Ala Glu Asp Thr Ala Val Tyr Tyr Cys Ala Arg Asp Gly
                 85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 88
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WABBABABA_7_117; 8 4 HC humanized 169; 8 4
      HC humanized 122; 8 4 HC humanized 676; 8 4 HC humanized 893; 8 4
      HC humanized 57

<400> SEQUENCE: 88

Val Gln Leu Val Glu Ser Gly Gly Gly Leu Val Gln Pro Gly Gly Ser
 1               5                  10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Leu Glu Trp Val Ser
            35                  40                  45

Asp Ile Asp Gly Arg Gly Asp Ile Tyr Cys Ala Thr Trp Ala Lys Gly
 50                  55                  60
```

```
Arg Phe Thr Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Lys Asp Gly
                 85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 89
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZABBABABA_1_117; 8 4 HC humanized 17

<400> SEQUENCE: 89

Val Gln Leu Val Glu Ser Gly Gly Gly Leu Val Gln Pro Gly Gly Ser
 1               5                  10                  15

Leu Arg Leu Ser Cys Ala Ala Ser Gly Phe Thr Ile Ser Asn Leu Ala
             20                  25                  30

Ile Ile Trp Val Arg Gln Ala Pro Gly Arg Gly Leu Val Trp Val Ser
         35                  40                  45

Asp Ile Asp Gly Arg Gly Asp Ile Tyr Cys Ala Thr Trp Ala Lys Gly
     50                  55                  60

Arg Phe Thr Ile Ser Arg Asp Asn Ala Thr Leu Tyr Leu Gln Met Asn
 65                  70                  75                  80

Asn Leu Arg Ala Glu Asp Thr Ala Val Tyr Tyr Cys Ala Arg Asp Gly
                 85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 90
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CEBBABABA_1_117; 8 4 HC humanized 791

<400> SEQUENCE: 90

Gln Ser Val Leu Glu Ser Gly Gly Gly Leu Val Gln Pro Gly Gly Ser
 1               5                  10                  15

Leu Arg Leu Ser Cys Ala Ala Ser Gly Phe Thr Ile Ser Asn Leu Ala
             20                  25                  30

Ile Ile Trp Val Arg Gln Ala Pro Gly Lys Gly Leu Glu Trp Val Ser
         35                  40                  45

Asp Ile Asp Gly Arg Gly Asp Ile Tyr Cys Ala Thr Trp Ala Arg Gly
     50                  55                  60

Arg Phe Thr Ile Ser Arg Asp Asn Ser Thr Leu Tyr Leu Gln Met Asn
 65                  70                  75                  80

Ser Leu Arg Ala Glu Asp Thr Ala Ile Tyr Tyr Cys Ala Lys Asp Gly
                 85                  90                  95
```

```
Asp Gly Ser Gly Trp Gly Asp Phe Asn Phe Trp Gly Arg Gly Thr His
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DEBBABABA_1_117; 8 4 HC humanized 673

<400> SEQUENCE: 91

Gln Ser Val Val Glu Ser Gly Gly Val Val Gln Pro Gly Gly Ser
1               5                   10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Pro Glu Trp Val Ser
            35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Ser Leu Tyr Leu Gln Met Asn
65                  70                  75                  80

Ser Leu Arg Thr Glu Asp Thr Ala Val Tyr Tyr Cys Ala Lys Asp Gly
                85                  90                  95

Asp Gly Ser Gly Trp Gly Asp Phe Asn Phe Trp Gly Gln Gly Thr Met
            100                 105                 110

Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GEBBABABA_1_117; 8 4 HC humanized 631

<400> SEQUENCE: 92

Gln Ser Val Glu Glu Ser Gly Gly Arg Leu Val Thr Pro Gly Ala Thr
1               5                   10                  15

Val Lys Ile Ser Cys Lys Val Ser Gly Phe Thr Ile Ser Asn Leu Ala
                20                  25                  30

Ile Ile Trp Val Gln Gln Ala Pro Gly Lys Gly Leu Glu Trp Met Gly
            35                  40                  45

Asp Ile Asp Gly Arg Gly Asp Ile Tyr Cys Ala Thr Trp Ala Gln Gly
    50                  55                  60

Arg Val Thr Ile Thr Ala Asp Ser Ser Thr Ala Tyr Met Glu Leu Asn
65                  70                  75                  80

Gly Leu Arg Tyr Ala Asp Thr Ala Val Tyr Tyr Cys Ala Thr Asp Gly
                85                  90                  95

Asp Gly Ser Gly Trp Gly Asp Phe Asn Phe Trp Gly Gln Gly Thr Leu
            100                 105                 110

Val Thr Val Ser Ser
```

<210> SEQ ID NO 93
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_HEBBABABA_1_117; 8 4 HC humanized 1002

<400> SEQUENCE: 93

Gln Ser Leu Glu Glu Ser Gly Gly Val Val Gln Pro Gly Lys Ser
1               5                   10                  15

Leu Arg Leu Ser Cys Thr Ala Ser Gly Phe Thr Ile Ser Asn Leu Ala
            20                  25                  30

Ile Ile Trp Val Arg Gln Ala Pro Gly Lys Gly Leu Glu Ser Val Ala
        35                  40                  45

Asp Ile Asp Gly Arg Gly Asp Ile Tyr Cys Ala Thr Trp Ala Thr Gly
    50                  55                  60

Arg Phe Ala Ile Ser Arg Asp Asn Ser Lys Leu Tyr Leu His Met Asp
65                  70                  75                  80

Asn Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Thr
            100                 105                 110

Val Ile Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_KEBBABABA_1_117; 8 4 HC humanized 775

<400> SEQUENCE: 94

Gln Ser Leu Glu Glu Ser Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Ser Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Ser Cys Ala Val Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 95
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LEBBABABA_2_117; 8 4 HC humanized 771; 8 4
      HC humanized 772

<400> SEQUENCE: 95
```

Gln Ser Leu Glu Gln Ser Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Lys Ser Lys Asn Thr Leu Tyr Leu Gln Met Asn
65                  70                  75                  80

Ser Leu Arg Ala Glu Asp Thr Ala Val Tyr Tyr Cys Ala Val Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

```
<210> SEQ ID NO 96
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NEBBABABA_1_117; 8 4 HC humanized 188

<400> SEQUENCE: 96
```

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Ala Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Ser Ser Thr Leu Tyr Leu Gln Met Asn
65                  70                  75                  80

Ser Leu Arg Thr Asp Asp Thr Ala Val Tyr Tyr Cys Ala Ala Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

```
<210> SEQ ID NO 97
<211> LENGTH: 117
<212> TYPE: PRT
<213> ORGANISM: Artificial Sequence
<220> FEATURE:
<223> OTHER INFORMATION: Description of Artificial Sequence: Synthetic
```

-continued polypeptide
<220> FEATURE:
<223> OTHER INFORMATION: cl_PEBBABABA_9_117; 8 4 HC humanized 186; 8 4
      HC humanized 292; 8 4 HC humanized 283; 8 4 HC humanized 204; 8 4
      HC humanized 201

<400> SEQUENCE: 97

Val Gln Leu Val Glu Ser Gly Gly Gly Val Gln Pro Gly Arg Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ala
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Lys Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 98
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QEBBABABA_1_117; 8 4 HC humanized 717

<400> SEQUENCE: 98

Gln Ser Val Leu Glu Ser Gly Gly Gly Trp Val Gln Pro Gly Arg Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ala
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ala Ser Leu Tyr Leu Glu Met Lys
65                  70                  75                  80

Ser Leu Arg Ala Glu Asp Thr Ala Ile Tyr Tyr Cys Ala Arg Asp Gly
                85                  90                  95

Asp Gly Ser Gly Trp Gly Asp Phe Asn Phe Trp Gly Gln Gly Val Leu
            100                 105                 110

Val Thr Val Ser Ser
        115

<210> SEQ ID NO 99
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_REBBABABA_2_117; 8 4 HC humanized 1048; 8 4

HC humanized 675

<400> SEQUENCE: 99

Gln Ser Val Glu Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 100
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SEBBABABA_1_117; 8 4 HC humanized 849

<400> SEQUENCE: 100

Gln Ser Val Glu Glu Ser Gly Gly Asp Leu Val Lys Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Ile Arg Gln Ala Pro Gly Lys Gly Leu Glu Trp Leu Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ala Ser Leu Asn Leu Gln Met Asn
65                  70                  75                  80

Ser Leu Arg Ala Glu Asp Thr Ala Val Tyr Tyr Cys Ala Val Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 101
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TEBBABABA_3_117; 8 4 HC humanized 1016; 8 4
      HC humanized 295; 8 4 HC humanized 319

<400> SEQUENCE: 101

```
Val Gln Leu Val Gln Ser Gly Gly Gly Leu Val Lys Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ala
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Val Asp Gly
                85                  90                  95

Asp Gly Ser Gly Trp Gly Asp Phe Asn Phe Trp Gly Gln Gly Thr Leu
                100                 105                 110

Val Thr Val Ser Ser
            115
```

<210> SEQ ID NO 102
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XEBBABABA_2_117; 8 4 HC humanized 868; 8 4
      HC humanized 55

<400> SEQUENCE: 102

```
Gln Gln Leu Gln Glu Ser Gly Gly Gly Leu Val Gln Pro Gly Gly Ser
1               5                   10                  15

Leu Arg Leu Ser Cys Ser Ala Ser Gly Phe Thr Ile Ser Asn Leu Ala
            20                  25                  30

Ile Ile Trp Val Arg Gln Ala Pro Gly Lys Gly Leu Glu Tyr Val Ser
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asn Ser Thr Leu Tyr Leu Gln Met Ser
65                  70                  75                  80

Ser Leu Arg Ala Glu Asp Thr Ala Val Tyr Tyr Cys Val Lys Asp Gly
                85                  90                  95

Asp Gly Ser Gly Trp Gly Asp Phe Asn Phe Trp Gly Gln Gly Thr Leu
                100                 105                 110

Val Thr Val Ser Ser
            115
```

<210> SEQ ID NO 103
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YEBBABABA_1_117; 8 4 HC humanized 862

<400> SEQUENCE: 103

```
Val Arg Leu Val Glu Ser Gly Gly Gly Val Val Gln Pro Gly Arg Ser
1               5                   10                  15

Leu Arg Leu Ser Cys Ala Ala Ser Gly Phe Thr Ile Ser Asn Leu Ala
```

```
                    20                  25                  30

Ile Ile Trp Val Arg Gln Ala Pro Gly Lys Gly Leu Glu Trp Val Ala
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asn Ser Thr Leu His Leu Gln Met Asn
65                  70                  75                  80

Ser Leu Arg Ala Glu Asp Thr Ala Val Tyr Tyr Cys Ala Lys Asp Gly
                85                  90                  95

Asp Gly Ser Gly Trp Gly Asp Phe Asn Phe Trp Gly Lys Gly Thr Thr
            100                 105                 110

Val Thr Val Ser Ser
        115

<210> SEQ ID NO 104
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZEBBABABA_1_117; 8 4 HC humanized 715

<400> SEQUENCE: 104

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
            35                  40                  45

Asp Ile Asp Gly Arg Gly Asp Ile Tyr Cys Ala Thr Trp Ala Lys Gly
        50                  55                  60

Arg Phe Thr Ile Ser Arg Ser Lys Asn Thr Leu Tyr Leu Gln Met Asn
65                  70                  75                  80

Ser Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Thr
            100                 105                 110

Val Thr Val Ser Ser
        115

<210> SEQ ID NO 105
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BIBBABABA_1_117; 8 4 HC humanized 706

<400> SEQUENCE: 105

Val Leu Leu Leu Glu Ser Gly Gly Gly Leu Ala Gln Pro Gly Gly Thr
1               5                   10                  15

Leu Arg Leu Ser Cys Ser Ala Ser Gly Phe Thr Ile Ser Asn Leu Ala
            20                  25                  30

Ile Ile Trp Val Arg Gln Ala Pro Gly Lys Gly Leu Glu Trp Val Ser
            35                  40                  45
```

```
Asp Ile Asp Gly Arg Gly Asp Ile Tyr Cys Ala Thr Trp Ala Arg Gly
        50                  55                  60

Arg Phe Ile Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Lys Asp Gly
                 85                  90                  95

Asp Gly Ser Gly Trp Gly Asp Phe Asn Phe Trp Gly Gln Gly Ile Leu
                100                 105                 110

Val Thr Val Ser Ser
            115

<210> SEQ ID NO 106
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CIBBABABA_1_117; 8 4 HC humanized 703

<400> SEQUENCE: 106

Val Gln Leu Val Glu Ser Gly Gly Thr Leu Val Gln Pro Gly Gly Ser
 1               5                  10                  15

Leu Arg Leu Ser Cys Ser Ala Ser Gly Phe Thr Ile Ser Asn Leu Ala
                20                  25                  30

Ile Ile Trp Val Arg Gln Ala Pro Gly Lys Gly Leu Glu Tyr Val Ser
            35                  40                  45

Asp Ile Asp Gly Arg Gly Asp Ile Tyr Cys Ala Thr Trp Ala Lys Gly
        50                  55                  60

Arg Ile Thr Ile Ser Arg Asp Asn Ser Thr Leu Ser Leu Gln Met Ser
 65                  70                  75                  80

Thr Leu Arg Thr Glu Asp Thr Ala Val Tyr Tyr Cys Val Arg Asp Gly
                 85                  90                  95

Asp Gly Ser Gly Trp Gly Asp Phe Asn Phe Trp Gly Gln Gly Thr Leu
                100                 105                 110

Val Thr Val Ser Ser
            115

<210> SEQ ID NO 107
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FIBBABABA_1_117; 8 4 HC humanized 341

<400> SEQUENCE: 107

Val Gln Leu Val Gln Ser Gly Gly Ser Leu Val Gln Pro Gly Arg Ser
 1               5                  10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Leu Glu Trp Val Ala
            35                  40                  45

Asp Ile Asp Gly Arg Gly Asp Ile Tyr Cys Ala Thr Trp Ala Lys Gly
        50                  55                  60

Arg Phe Thr Thr Ser Arg Asp Asn Ser Thr Leu Tyr Leu Gln Met Asn
 65                  70                  75                  80
```

```
Ser Leu Arg Ala Asp Asp Thr Ala Val Tyr Phe Cys Ala Val Asp Gly
                85                  90                  95

Asp Gly Ser Gly Trp Gly Asp Phe Asn Phe Trp Gly Gln Gly Thr Leu
            100                 105                 110

Val Thr Val Ser Ser
            115

<210> SEQ ID NO 108
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KIBBABABA_1_117; 8 4 HC humanized 301

<400> SEQUENCE: 108

Val Gln Leu Val Glu Ser Gly Gly Asp Leu Val Gln Pro Gly Glu Ser
1               5                   10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Leu Glu Trp Val Ser
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
            115

<210> SEQ ID NO 109
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QIBBABABA_1_117; 8 4 HC humanized 278

<400> SEQUENCE: 109

Val Gln Leu Val Gln Ser Gly Gly Gly Leu Val Lys Pro Gly Gly Ser
1               5                   10                  15

Leu Arg Leu Ser Cys Glu Ala Ser Gly Phe Thr Ile Ser Asn Leu Ala
                20                  25                  30

Ile Ile Trp Ile Arg Gln Ala Pro Gly Lys Gly Leu Glu Trp Val Gly
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asp Ser Thr Leu Tyr Leu Gln Val Asn
65                  70                  75                  80

Ser Leu Lys Thr Glu Asp Ser Ala Val Tyr Tyr Cys Thr Thr Asp Gly
                85                  90                  95

Asp Gly Ser Gly Trp Gly Asp Phe Asn Phe Trp Gly Gln Gly Thr Leu
```

Val Thr Val Ser Ser
        115

<210> SEQ ID NO 110
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TIBBABABA_1_117; 8 4 HC humanized 129

<400> SEQUENCE: 110

Met Gln Leu Val Glu Ser Gly Gly Gly Leu Val Gln Pro Gly Arg Ser
1               5                   10                  15

Leu Arg Leu Ser Cys Val Thr Ser Gly Phe Thr Ile Ser Asn Leu Ala
            20                  25                  30

Ile Ile Trp Val Arg Gln Val Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Thr Ser Leu Tyr Leu Gln Met Asn
65                  70                  75                  80

Ser Leu Arg Pro Glu Asp Thr Ala Val Tyr Tyr Cys Ala Lys Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 111
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XIBBABABA_1_117; 8 4 HC humanized 800

<400> SEQUENCE: 111

Gln Ser Val Leu Glu Ser Gly Pro Gly Leu Val Lys Pro Ser Glu Thr
1               5                   10                  15

Leu Ser Leu Thr Cys Thr Val Ser Gly Phe Thr Ile Ser Asn Leu Ala
            20                  25                  30

Ile Ile Trp Ile Arg Gln Pro Pro Gly Lys Gly Leu Glu Trp Ile Gly
        35                  40                  45

Asp Ile Asp Gly Arg Gly Asp Ile Tyr Cys Ala Thr Trp Ala Lys Ser
    50                  55                  60

Arg Leu Thr Ile Ser Thr Ser Lys Asn Gln Phe Ser Leu Arg Leu Thr
65                  70                  75                  80

Ser Val Thr Ala Ala Asp Thr Ala Met Tyr Tyr Cys Ala Val Asp Gly
                85                  90                  95

Asp Gly Ser Gly Trp Gly Asp Phe Asn Phe Trp Gly Gln Gly Thr Leu
            100                 105                 110

Val Ser Val Ser Ser
        115

```
<210> SEQ ID NO 112
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YIBBABABA_7_117; 8 4 HC humanized 1133; 8 4
      HC humanized 881; 8 4 HC humanized 677; 8 4 HC humanized 192; 8 4
      HC humanized 65

<400> SEQUENCE: 112

Gln Ser Val Glu Glu Ser Gly Gly Val Val Gln Pro Gly Arg Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ala
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Thr
            100                 105                 110

Val Thr Val Ser Ser
        115

<210> SEQ ID NO 113
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FOBBABABA_1_117; 8 4 HC humanized 882

<400> SEQUENCE: 113

Gln Ser Val Glu Glu Ser Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Pro Pro Gly Lys Gly Leu Glu Trp Val Gly
        35                  40                  45

Asp Ile Asp Gly Arg Gly Asp Ile Tyr Cys Ala Thr Trp Ala Lys Gly
    50                  55                  60

Arg Phe Thr Ile Ser Arg Ser Lys Ser Thr Val Tyr Leu Gln Met Asn
65                  70                  75                  80

Ser Leu Lys Thr Glu Asp Thr Ala Val Tyr Tyr Cys Thr Ala Asp Gly
                85                  90                  95

Asp Gly Ser Gly Trp Gly Asp Phe Asn Phe Trp Gly Gln Gly Met Leu
            100                 105                 110

Val Thr Val Ser Ser
        115

<210> SEQ ID NO 114
<211> LENGTH: 117
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GOBBABABA_1_117; 8 4 HC humanized 660

<400> SEQUENCE: 114

Gln Ser Val Glu Glu Ser Gly Gly Leu Ile Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Cys Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Thr
65              70                  75                  80

Ser Leu Arg Ala Glu Asp Thr Ala Val Tyr Tyr Cys Ala Leu Asp Gly
                85                  90                  95

Asp Gly Ser Gly Trp Gly Asp Phe Asn Phe Trp Gly Gln Gly Thr Leu
                100                 105                 110

Val Thr Val Ser Ser
        115

<210> SEQ ID NO 115
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HOBBABABA_2_117; 8 4 HC humanized 1051; 8 4
      HC humanized 1050

<400> SEQUENCE: 115

Val Gln Leu Val Glu Ser Gly Gly Gly Leu Val Lys Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Gly
        35                  40                  45

Asp Ile Asp Gly Arg Gly Asp Ile Tyr Cys Ala Thr Trp Ala Lys Gly
    50                  55                  60

Arg Phe Thr Ile Ser Arg Ser Lys Asn Thr Leu Tyr Leu Gln Met Asn
65              70                  75                  80

Ser Leu Lys Thr Glu Asp Thr Ala Val Tyr Tyr Cys Thr Val Asp Gly
                85                  90                  95

Asp Gly Ser Gly Trp Gly Asp Phe Asn Phe Trp Gly Gln Gly Thr Leu
                100                 105                 110

Val Thr Val Ser Ser
        115

<210> SEQ ID NO 116
<211> LENGTH: 117
<212> TYPE: PRT
<213> ORGANISM: Artificial Sequence
<220> FEATURE:
<223> OTHER INFORMATION: Description of Artificial Sequence: Synthetic
```

```
                                    polypeptide
<220> FEATURE:
<223> OTHER INFORMATION: cl_MOBBABABA_1_117; 8 4 HC humanized 809

<400> SEQUENCE: 116

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Leu Ser
        35                  40                  45

Asp Ile Asp Gly Arg Gly Asp Ile Tyr Cys Ala Thr Trp Ala Arg Gly
    50                  55                  60

Arg Phe Ala Ile Ser Asn Ala Arg Asn Ser Leu Tyr Leu Gln Met Asn
65                  70                  75                  80

Ser Leu Arg Asp Glu Asp Thr Ala Val Tyr Phe Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 117
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VOBBABABA_1_117; 8 4 HC humanized 273

<400> SEQUENCE: 117

Val Gln Leu Val Gln Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Ser Gly Lys Gly Leu Glu Trp Ile Gly
        35                  40                  45

Asp Ile Asp Gly Arg Gly Asp Ile Tyr Cys Ala Thr Trp Ala Lys Gly
    50                  55                  60

Arg Phe Thr Val Ser Arg Ser Gln Asn Ser Val Phe Leu Gln Met Asn
65                  70                  75                  80

Ser Leu Glu Thr Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 118
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WOBBABABA_1_117; 8 4 HC humanized 716

<400> SEQUENCE: 118
```

```
Gln Ser Val Leu Glu Ser Gly Gly Trp Val Gln Pro Gly Arg Ser
1               5                   10                  15

Leu Arg Leu Ser Cys Ser Ala Ser Gly Phe Thr Ile Ser Asn Leu Ala
                20                  25                  30

Ile Ile Trp Val Arg Gln Ala Pro Gly Lys Gly Leu Glu Trp Val Ser
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asn Asn Ser Leu Tyr Leu Gln Met Asn
65                  70                  75                  80

Ser Leu Arg Pro Glu Asp Thr Ala Leu Tyr Tyr Cys Ala Lys Asp Gly
                85                  90                  95

Asp Gly Ser Gly Trp Gly Asp Phe Asn Phe Trp Gly Gln Gly Val Leu
            100                 105                 110

Val Thr Val Ser Ser
        115

<210> SEQ ID NO 119
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZOBBABABA_1_117; 8 4 HC humanized 202

<400> SEQUENCE: 119

Val Gln Leu Gln Glu Ser Gly Glu Gly Leu Val Gln Pro Gly Gly Ser
1               5                   10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Leu Glu Tyr Val Ser
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asn Ser Thr Leu Tyr Leu Gln Met Gly
65                  70                  75                  80

Ser Leu Arg Ala Glu Asp Met Ala Val Tyr Tyr Cys Ala Val Asp Gly
                85                  90                  95

Asp Gly Ser Gly Trp Gly Asp Phe Asn Phe Trp Gly Gln Gly Thr Met
            100                 105                 110

Val Thr Val Ser Ser
        115

<210> SEQ ID NO 120
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GUBBABABA_1_117; 8 4 HC humanized 54

<400> SEQUENCE: 120

Val Gln Leu Val Glu Ser Gly Gly Gly Leu Val Gln Pro Gly Gly Ser
1               5                   10                  15

Leu Arg Leu Ser Cys Ala Thr Ser Gly Phe Thr Ile Ser Asn Leu Ala
```

```
                  20                  25                  30

Ile Ile Trp Val Arg Gln Pro Pro Gly Lys Gly Leu Glu Trp Val Ser
         35                  40                  45

Asp Ile Asp Gly Arg Gly Asp Ile Tyr Cys Ala Thr Trp Ala Lys Gly
     50                  55                  60

Arg Phe Thr Ile Ser Arg Glu Asn Ala Thr Leu Tyr Leu Gln Met Asn
 65                  70                  75                  80

Ser Leu Arg Ala Glu Asp Thr Ala Val Tyr Tyr Cys Ala Val Asp Gly
                 85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 121
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HUBBABABA_1_117; 8 4 HC humanized 21

<400> SEQUENCE: 121

Val Gln Leu Val Glu Ser Gly Gly Gly Leu Val Gln Pro Gly Gly Ser
 1               5                  10                  15

Leu Arg Leu Ser Cys Ala Ala Ser Gly Phe Thr Ile Ser Asn Leu Ala
             20                  25                  30

Ile Ile Trp Val Arg Gln Ala Pro Gly Lys Gly Leu Glu Phe Val Ser
         35                  40                  45

Asp Ile Asp Gly Arg Gly Asp Ile Tyr Cys Ala Thr Trp Ala Lys Asp
     50                  55                  60

Arg Phe Thr Ile Ser Arg Asp Asn Ser Thr Val Tyr Leu Gln Met Asp
 65                  70                  75                  80

Ser Leu Arg Thr Glu Asp Thr Ala Met Tyr Phe Cys Ala Arg Asp Gly
                 85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 122
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KUBBABABA_1_117; 8 4 HC humanized 788

<400> SEQUENCE: 122

Gln Ser Val Leu Glu Ser Gly Gly Gly Leu Val Gln Pro Gly Gly Ser
 1               5                  10                  15

Leu Arg Leu Ser Cys Ala Ala Ser Gly Phe Thr Ile Ser Asn Leu Ala
             20                  25                  30

Ile Ile Trp Val Arg Gln Ala Pro Gly Lys Gly Leu Glu Trp Val Ser
         35                  40                  45
```

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Phe Leu Gln Ile Ser
65                  70                  75                  80

Ser Leu Arg Ala Glu Asp Thr Ala Val Tyr Tyr Cys Ala Lys Asp Gly
                85                  90                  95

Asp Gly Ser Gly Trp Gly Asp Phe Asn Phe Trp Gly Pro Gly Thr Leu
            100                 105                 110

Val Thr Val Ser Ser
            115

<210> SEQ ID NO 123
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MUBBABABA_1_117; 8 4 HC humanized 762

<400> SEQUENCE: 123

Val Lys Leu Leu Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ala
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Gly Ala Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
            115

<210> SEQ ID NO 124
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PUBBABABA_1_117; 8 4 HC humanized 173

<400> SEQUENCE: 124

Gln Ser Val Glu Glu Ser Gly Gly Arg Leu Val Thr Pro Gly Gly Ser
1               5                   10                  15

Leu Arg Leu Ser Cys Thr Ala Thr Gly Phe Thr Ile Ser Asn Leu Ala
            20                  25                  30

Ile Ile Trp Phe Arg Gln Ala Pro Gly Lys Gly Leu Glu Trp Val Gly
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asp Asn Ser Leu Tyr Leu Gln Met Asn
65                  70                  75                  80

```
Ser Leu Lys Thr Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 125
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RUBBABABA_1_117; 8 4 HC humanized 224

<400> SEQUENCE: 125

Gln Ser Val Glu Glu Ser Gly Gly Gly Leu Val Lys Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Gly
        35                  40                  45

Asp Ile Asp Gly Arg Gly Asp Ile Tyr Cys Ala Thr Trp Ala Lys Gly
    50                  55                  60

Arg Phe Thr Ile Ser Arg Ser Lys Asn Thr Leu Tyr Leu Gln Met Asn
65                  70                  75                  80

Ser Leu Lys Thr Glu Asp Thr Ala Val Tyr Tyr Cys Ala Thr Asp Gly
                85                  90                  95

Asp Gly Ser Gly Trp Gly Asp Phe Asn Phe Trp Gly Gln Gly Thr Leu
            100                 105                 110

Val Thr Val Ser Ser
        115

<210> SEQ ID NO 126
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VUBBABABA_1_117; 8 4 HC humanized 672

<400> SEQUENCE: 126

Gln Ser Val Val Glu Ser Gly Gly Gly Leu Ile Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Leu Asp Gly
                85                  90                  95

Asp Gly Ser Gly Trp Gly Asp Phe Asn Phe Trp Gly Gln Gly Thr Leu
```

Val Thr Val Ser Ser
        115

<210> SEQ ID NO 127
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XUBBABABA_1_117; 8 4 HC humanized 267

<400> SEQUENCE: 127

Gln Ser Val Glu Gln Ser Gly Gly Leu Val Gln Pro Gly Glu Ser
1               5                   10                  15

Leu Arg Leu Ser Cys Ala Gly Ser Gly Phe Thr Ile Ser Asn Leu Ala
                20                  25                  30

Ile Ile Trp Val Arg Gln Ala Pro Gly Lys Gly Leu Glu Trp Val Ala
            35                  40                  45

Asp Ile Asp Gly Arg Gly Asp Ile Tyr Cys Ala Thr Trp Ala Lys Gly
        50                  55                  60

Arg Phe Thr Ile Ser Arg Asp Asn Ala Ser Leu Phe Leu Gln Met Asn
65                  70                  75                  80

Ser Leu Arg Val Glu Asp Thr Ala Val Tyr Tyr Cys Ala Arg Asp Gly
                85                  90                  95

Asp Gly Ser Gly Trp Gly Asp Phe Asn Phe Trp Gly Gln Gly Thr Leu
                100                 105                 110

Val Thr Val Ser Ser
        115

<210> SEQ ID NO 128
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YUBBABABA_1_117; 8 4 HC humanized 23

<400> SEQUENCE: 128

Gln Ser Val Leu Glu Ser Gly Gly Asp Leu Val Gln Pro Gly Gly Ser
1               5                   10                  15

Leu Arg Leu Ser Cys Glu Ala Ser Gly Phe Thr Ile Ser Asn Leu Ala
                20                  25                  30

Ile Ile Trp Val Arg Gln Ala Pro Gly Lys Gly Leu Glu Trp Val Ser
            35                  40                  45

Asp Ile Asp Gly Arg Gly Asp Ile Tyr Cys Ala Thr Trp Ala Lys Gly
        50                  55                  60

Arg Phe Thr Ile Ser Lys Ser Lys His Thr Leu Phe Leu Gln Met His
65                  70                  75                  80

Ser Leu Arg Val Glu Asp Thr Ala Val Tyr Tyr Cys Ala Lys Asp Gly
                85                  90                  95

Asp Gly Ser Gly Trp Gly Asp Phe Asn Phe Trp Gly Gln Gly Thr Thr
                100                 105                 110

Val Thr Val Ser Ser
        115

<210> SEQ ID NO 129
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_ZUBBABABA_1_117; 8 4 HC humanized 657

<400> SEQUENCE: 129

Gln Ser Val Glu Glu Ser Gly Gly Arg Leu Val Thr Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Ser Leu Tyr Leu Gln Met Asn
65                  70                  75                  80

Ser Leu Arg Thr Glu Asp Ser Ala Leu Tyr Tyr Cys Ala Ile Asp Gly
                85                  90                  95

Asp Gly Ser Gly Trp Gly Asp Phe Asn Phe Trp Gly Gln Gly Ser Leu
            100                 105                 110

Val Thr Val Ser Ser
        115

<210> SEQ ID NO 130
<211> LENGTH: 117
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_BACBABABA_1_117; 8 4 HC humanized 879

<400> SEQUENCE: 130

Gln Ser Val Glu Glu Ser Gly Gly Gly Leu Val Gln Pro Gly Gly Ser
1               5                   10                  15

Leu Arg Leu Ser Cys Thr Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Ser Ser Thr Leu Tyr Leu Gln Met Asn
65                  70                  75                  80

Asn Leu Arg Val Glu Asp Thr Ala Leu Tyr Tyr Cys Ala His Asp Gly
                85                  90                  95

Asp Gly Ser Gly Trp Gly Asp Phe Asn Phe Trp Gly Arg Gly Thr Gln
            100                 105                 110

Val Thr Val Ser Ser
        115

<210> SEQ ID NO 131
<211> LENGTH: 110
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: cl_CACBABABA_1_110; 8 4 LC humanized 866

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Arg Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 132
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DACBABABA_1_110; 8 4 LC humanized 340

<400> SEQUENCE: 132

Asp Ile Gln Met Thr Gln Ser Pro Phe Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Trp Ser Thr Val Asn
                85                  90                  95

Val Asp Asn Val Phe Gly Gly Gly Thr Lys Leu Glu Ile Lys
            100                 105                 110

<210> SEQ ID NO 133
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FACBABABA_1_110; 8 4 LC humanized 336

<400> SEQUENCE: 133

Asp Ile Gln Leu Thr Gln Ser Pro Ser Ser Leu Ser Ala Ser Val Gly
1               5                   10                  15
```

```
Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110

<210> SEQ ID NO 134
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GACBABABA_1_110; 8 4 LC humanized 332

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Val
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 135
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HACBABABA_1_110; 8 4 LC humanized 322

<400> SEQUENCE: 135

Asp Ile Gln Leu Thr Gln Ser Pro Ser Phe Leu Ser Ala Ser Val Gly
1               5                   10                  15

Asp Thr Val Ser Ile Thr Cys Gln Ala Ser Gln Ser Ile Ser Thr Ala
            20                  25                  30

Leu Ala Trp Tyr Gln Gln Lys Pro Gly Lys Ala Pro Lys His Leu Ile
        35                  40                  45

Tyr Arg Ala Ser Thr Leu Ala Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 136
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KACBABABA_1_110; 8 4 LC humanized 315

<400> SEQUENCE: 136

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 137
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LACBABABA_1_110; 8 4 LC humanized 314

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Asn Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 138
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MACBABABA_1_110; 8 4 LC humanized 305

<400> SEQUENCE: 138

```
Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Phe Gln Gln Lys Pro Gly Lys Ala Pro Lys Ser Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110
```

<210> SEQ ID NO 139
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NACBABABA_1_110; 8 4 LC humanized 303

<400> SEQUENCE: 139

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Trp Ser Thr Val Asn
                85                  90                  95

Val Asp Asn Val Phe Gly Pro Gly Thr Lys Val Asp Ile Lys
            100                 105                 110
```

<210> SEQ ID NO 140
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PACBABABA_1_110; 8 4 LC humanized 296

<400> SEQUENCE: 140

```
Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Thr Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 141
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QACBABABA_1_110; 8 4 LC humanized 294

<400> SEQUENCE: 141

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 142
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RACBABABA_1_110; 8 4 LC humanized 291

<400> SEQUENCE: 142

Asp Ile Gln Leu Thr Gln Ser Pro Ser Ser Leu Ser Ala Ser Val Gly
 1               5                  10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Gly Pro Lys Leu Leu Ile
        35                  40                  45

Tyr Arg Ala Ser Thr Leu Ala Ser Gly Val Pro Ser Arg Phe Ser Gly
 50                  55                  60

Ser Gly Ser Gly Thr Asp Phe Ser Leu Thr Ile Ser Ser Leu Gln Pro
```

```
                 65                  70                  75                  80
Glu Asp Leu Ala Thr Tyr Tyr Cys Gln Gln Gly Trp Ser Thr Val Asn
                 85                  90                  95

Val Asp Asn Val Phe Gly Gly Gly Thr Lys Val Glu Ile Lys
                100                 105                 110

<210> SEQ ID NO 143
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SACBABABA_1_110; 8 4 LC humanized 284

<400> SEQUENCE: 143

Asp Ile Gln Met Thr Gln Ser Pro Ser Ser Leu Ser Ala Ser Val Gly
1               5                  10                  15

Asp Arg Val Thr Ile Thr Cys Gln Ala Ser Gln Ser Ile Ser Thr Ala
                 20                  25                  30

Leu Ala Trp Tyr Gln Gln Lys Pro Gly Lys Ala Pro Lys Ser Leu Ile
             35                  40                  45

Tyr Arg Ala Ser Thr Leu Ala Ser Gly Val Pro Ser Lys Phe Ser Gly
 50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
                 85                  90                  95

Val Asp Asn Val Phe Gly Gln Gly Thr Arg Leu Glu Ile Lys
                100                 105                 110

<210> SEQ ID NO 144
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TACBABABA_1_110; 8 4 LC humanized 217

<400> SEQUENCE: 144

Asp Ile Val Met Thr Gln Ser Pro Asp Ser Leu Ala Val Ser Leu Gly
1               5                  10                  15

Glu Arg Ala Thr Ile Asn Cys Gln Ala Ser Gln Ser Ile Ser Thr Ala
                 20                  25                  30

Leu Ala Trp Tyr Gln Gln Lys Pro Gly Gln Pro Pro Lys Leu Leu Ile
             35                  40                  45

Tyr Arg Ala Ser Thr Leu Ala Ser Gly Val Pro Asp Arg Phe Ser Gly
 50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                 85                  90                  95

Val Asp Asn Val Phe Gly Gln Gly Thr Lys Val Glu Ile Lys
                100                 105                 110

<210> SEQ ID NO 145
<211> LENGTH: 110
```

-continued

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VACBABABA_1_110; 8 4 LC humanized 197

<400> SEQUENCE: 145

Ala Tyr Asp Met Thr Gln Thr Pro Ala Thr Leu Ser Leu Ser Pro Gly
1               5                   10                  15

Glu Arg Ala Thr Leu Ser Cys Gln Ala Ser Gln Ser Ile Ser Thr Ala
            20                  25                  30

Leu Ala Trp Tyr Gln Gln Lys Pro Gly Gln Ala Pro Arg Leu Leu Ile
        35                  40                  45

Tyr Arg Ala Ser Thr Leu Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Trp Ser Thr Val Asn
                85                  90                  95

Val Asp Asn Val Phe Gly Gln Gly Thr Glu Val Val Arg
            100                 105                 110

<210> SEQ ID NO 146
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WACBABABA_1_110; 8 4 LC humanized 169

<400> SEQUENCE: 146

Glu Ile Val Leu Thr Gln Ser Pro Ser Phe Leu Ser Ala Phe Val Gly
1               5                   10                  15

Asp Arg Ile Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Gly Leu Gln Pro
65                  70                  75                  80

Glu Asp Phe Ala Ser Tyr Tyr Cys Gln Gln Gly Trp Ser Thr Val Asn
                85                  90                  95

Val Asp Asn Val Phe Gly Gly Gly Thr Lys Leu Glu Ile Lys
            100                 105                 110

<210> SEQ ID NO 147
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XACBABABA_1_110; 8 4 LC humanized 122

<400> SEQUENCE: 147

Asp Val Val Met Thr Gln Ser Pro Ala Ser Leu Ser Ala Ser Val Gly
```

```
                1               5                  10                  15
Asp Arg Val Thr Ile Ile Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Arg Thr Asp Phe Thr Phe Thr Ile Ser Ser Leu Gln Pro
65                  70                  75                  80

Glu Asp Ile Ala Thr Tyr Tyr Cys Gln Gln Gly Trp Ser Thr Val Asn
                85                  90                  95

Val Asp Asn Val Phe Gly Pro Gly Thr Lys Val Asp Ile Lys
                100                 105                 110

<210> SEQ ID NO 148
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YACBABABA_1_110; 8 4 LC humanized 44

<400> SEQUENCE: 148

Asp Ile Gln Met Thr Gln Ser Pro Ser Ser Leu Ser Ala Ser Val Gly
1               5                  10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Arg Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
                100                 105                 110

<210> SEQ ID NO 149
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZACBABABA_1_110; 8 4 LC humanized 17

<400> SEQUENCE: 149

Asp Ile Gln Leu Thr Gln Ser Pro Ser Ser Leu Ser Ala Ala Val Gly
1               5                  10                  15

Asp Arg Val Thr Ile Ala Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60
```

```
Ser Gly Ser Gly Thr Asp Phe Thr Leu Ser Ile Ser Ser Leu Gln Pro
 65                  70                  75                  80

Gly Asp Phe Ala Thr Tyr Tyr Cys Gln Gln Gly Trp Ser Thr Val Asn
                 85                  90                  95

Val Asp Asn Val Phe Gly Gly Gly Thr Lys Val Gln Met Lys
            100                 105                 110

<210> SEQ ID NO 150
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_BECBABABA_1_110; 8 4 LC humanized 13

<400> SEQUENCE: 150

Asp Ile Gln Met Thr Gln Ser Pro Ser Ser Leu Ser Ala Ser Val Gly
 1               5                  10                  15

Asp Ser Val Thr Ile Thr Cys Gln Ala Ser Gln Ser Ile Ser Thr Ala
             20                  25                  30

Leu Ala Trp Tyr Gln Gln Lys Pro Gly Lys Ala Pro Lys Leu Leu Ile
             35                  40                  45

Tyr Arg Ala Ser Thr Leu Ala Ser Gly Val Pro Ser Arg Phe Ser Gly
 50                  55                  60

Ser Gly Ser Gly Thr Glu Phe Thr Leu Thr Ile Asn Gly Leu Gln Pro
 65                  70                  75                  80

Glu Asp Phe Ala Thr Tyr Tyr Cys Gln Gln Gly Trp Ser Thr Val Asn
                 85                  90                  95

Val Asp Asn Val Phe Gly Gly Gly Thr Lys Leu Glu Ile Lys
            100                 105                 110

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_CECBABABA_1_110; 8 4 LC humanized 791

<400> SEQUENCE: 151

Ala Tyr Glu Leu Thr Gln Thr Pro Leu Ser Ser Pro Val Thr Leu Gly
 1               5                  10                  15

Gln Pro Ala Ser Ile Ser Cys Gln Ala Ser Gln Ser Ile Ser Thr Ala
             20                  25                  30

Leu Ala Trp Leu His Gln Arg Pro Gly Gln Pro Pro Arg Leu Leu Ile
             35                  40                  45

Tyr Arg Ala Ser Thr Leu Ala Ser Gly Val Pro Asp Arg Phe Ser Gly
 50                  55                  60

Ser Gly Ala Gly Thr Ala Phe Thr Leu Lys Ile Ser Arg Val Glu Val
 65                  70                  75                  80

Glu Asp Val Gly Ile Tyr Tyr Cys Gln Gln Gly Trp Ser Thr Val Asn
                 85                  90                  95

Val Asp Asn Val Phe Gly Gln Gly Thr Lys Val Glu Ile Lys
            100                 105                 110

<210> SEQ ID NO 152
```

-continued

```
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DECBABABA_1_110; 8 4 LC humanized 673

<400> SEQUENCE: 152
```

Ala Tyr Asp Met Thr Gln Thr Pro Ala Ser Val Glu Val Ser Pro Gly
1               5                   10                  15

Glu Arg Ala Thr Leu Ser Cys Gln Ala Ser Gln Ser Ile Ser Thr Ala
            20                  25                  30

Leu Ala Trp Tyr Gln His Lys Pro Gly Gln Ala Pro Arg Leu Leu Ile
        35                  40                  45

Tyr Arg Ala Ser Thr Leu Ala Ser Gly Ile Pro Ala Arg Phe Ser Gly
50                  55                  60

Ser Gly Ser Gly Thr Glu Phe Thr Leu Thr Ile Ser Ser Val Gln Ser
65                  70                  75                  80

Asp Asp Phe Ala Val Tyr Tyr Cys Gln Gln Gly Trp Ser Thr Val Asn
                85                  90                  95

Val Asp Asn Val Phe Gly Pro Gly Thr Lys Val Asp Ile Lys
            100                 105                 110

```
<210> SEQ ID NO 153
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FECBABABA_1_110; 8 4 LC humanized 678

<400> SEQUENCE: 153
```

Ala Tyr Glu Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Phe Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Leu Pro
65                  70                  75                  80

Thr Asp Phe Ala Thr Tyr Phe Cys Gln Gln Gly Trp Ser Thr Val Asn
                85                  90                  95

Val Asp Asn Val Phe Gly Gln Gly Thr Gln Val Glu Val Lys
            100                 105                 110

```
<210> SEQ ID NO 154
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GECBABABA_1_110; 8 4 LC humanized 631

<400> SEQUENCE: 154
```

```
Ala Tyr Asp Met Thr Gln Thr Pro Ala Ser Val Glu Val Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Gly Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110
```

<210> SEQ ID NO 155
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HECBABABA_1_110; 8 4 LC humanized 1002

<400> SEQUENCE: 155

```
Ala Tyr Glu Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Ser Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110
```

<210> SEQ ID NO 156
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KECBABABA_1_110; 8 4 LC humanized 775

<400> SEQUENCE: 156

```
Ala Tyr Glu Leu Thr Gln Thr Pro Leu Ser Ser Pro Val Thr Leu Gly
1               5                   10                  15

Gln Pro Ala Ser Ile Ser Cys Gln Ala Ser Gln Ser Ile Ser Thr Ala
            20                  25                  30

Leu Ala Trp Leu Gln Gln Arg Pro Gly Gln Pro Pro Arg Leu Leu Ile
        35                  40                  45

Tyr Arg Ala Ser Thr Leu Ala Ser Gly Val Pro Asp Arg Phe Ser Gly
50                  55                  60
```

Ser Gly Ala Arg Thr Asp Phe Thr Leu Asn Ile Ser Arg Val Glu Ala
65                  70                  75                  80

Glu Asp Ala Gly Val Tyr Tyr Cys Gln Gln Gly Trp Ser Thr Val Asn
                85                  90                  95

Val Asp Val Phe Gly Gln Gly Thr Lys Leu Glu Ile Lys
            100                 105                 110

<210> SEQ ID NO 157
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LECBABABA_2_110; 8 4 LC humanized 771; 8 4
      LC humanized 772

<400> SEQUENCE: 157

Ala Tyr Glu Leu Thr Gln Ser Pro Ala Thr Leu Ser Leu Ser Pro Gly
1               5                   10                  15

Glu Arg Ala Thr Leu Ser Cys Gln Ala Ser Gln Ser Ile Ser Thr Ala
                20                  25                  30

Leu Ala Trp Tyr Gln Gln Lys Pro Gly Gln Ala Pro Arg Leu Leu Ile
            35                  40                  45

His Arg Ala Ser Thr Leu Ala Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Trp Ser Thr Val Asn
                85                  90                  95

Val Asp Asn Val Phe Gly Gly Gly Thr Arg Val Glu Ile Lys
            100                 105                 110

<210> SEQ ID NO 158
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MECBABABA_1_110; 8 4 LC humanized 676

<400> SEQUENCE: 158

Ala Tyr Asp Met Thr Gln Ser Pro Ala Thr Leu Ser Leu Ser Pro Gly
1               5                   10                  15

Glu Arg Ala Thr Leu Ser Cys Gln Ala Ser Gln Ser Ile Ser Thr Ala
                20                  25                  30

Leu Ala Trp Tyr Gln Gln Lys Pro Gly Gln Ala Pro Arg Leu Leu Ile
            35                  40                  45

Tyr Arg Ala Ser Thr Leu Ala Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 159
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_NECBABABA_1_110; 8 4 LC humanized 188

<400> SEQUENCE: 159

Asp Ile Gln Leu Thr Gln Ser Pro Ser Thr Leu Ser Ala Ser Val Gly
1               5                   10                  15

Asp Arg Ile Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Pro Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
                85                  90                  95

Val Asp Asn Val Phe Gly Gln Gly Thr Lys Val Val Val Arg
            100                 105                 110

<210> SEQ ID NO 160
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_PECBABABA_1_110; 8 4 LC humanized 186

<400> SEQUENCE: 160

Asp Ile Gln Leu Thr Gln Ser Pro Ser Thr Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
                85                  90                  95

Val Asp Asn Val Phe Gly Gln Gly Thr Lys Val Val Val Arg
            100                 105                 110

<210> SEQ ID NO 161
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_QECBABABA_1_110; 8 4 LC humanized 717

<400> SEQUENCE: 161

Glu Leu Val Met Thr Gln Ser Pro Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Asn Leu Leu Ile
        35                  40                  45

Tyr Arg Ala Ser Thr Leu Ala Ser Gly Ile Pro Ser Arg Phe Ser Gly
50                  55                  60

Ser Gly Ser Gly Thr Tyr Phe Thr Leu Thr Ile Asn Gly Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Asp Ile Lys
            100                 105                 110

<210> SEQ ID NO 162
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RECBABABA_1_110; 8 4 LC humanized 1048

<400> SEQUENCE: 162

Ser Tyr Glu Leu Thr Gln Thr Pro Pro Ser Val Ser Val Ser Pro Gly
1               5                   10                  15

Gln Thr Ala Arg Ile Thr Cys Gln Ala Ser Gln Ser Ile Ser Thr Ala
            20                  25                  30

Leu Ala Trp Tyr Gln Gln Lys Pro Gly Gln Ala Pro Lys Val Leu Ile
        35                  40                  45

Tyr Arg Ala Ser Thr Leu Ala Ser Gly Ile Pro Glu Arg Phe Ser Gly
50                  55                  60

Ser Ser Ser Gly Thr Thr Val Thr Leu Thr Ile Ser Gly Val Gln Ala
65                  70                  75                  80

Glu Asp Glu Ala Asp Tyr Tyr Cys Gln Gln Gly Trp Ser Thr Val Asn
                85                  90                  95

Val Asp Asn Val Phe Gly Gly Gly Thr Lys Leu Thr Val Leu
            100                 105                 110

<210> SEQ ID NO 163
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SECBABABA_1_110; 8 4 LC humanized 849

<400> SEQUENCE: 163

Ala Tyr Glu Leu Thr Gln Ser Pro Leu Ser Leu Ser Val Thr Pro Gly
1               5                   10                  15

Gln Pro Ala Ser Ile Ser Cys Gln Ala Ser Gln Ser Ile Ser Thr Ala
            20                  25                  30

Leu Ala Trp Tyr Leu Gln Lys Pro Gly Gln Pro Pro Gln Leu Leu Ile
        35                  40                  45

Tyr Arg Ala Ser Thr Leu Ala Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 164
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TECBABABA_1_110; 8 4 LC humanized 1016

<400> SEQUENCE: 164

Asp Ile Glu Leu Thr Gln Ser Pro Ser Ser Leu Ser Ala Ser Ile Gly
1               5                   10                  15

Asp Arg Val Ser Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Phe Tyr Cys Gln Gln Gly Trp Ser Thr Val Asn
                85                  90                  95

Val Asp Asn Val Phe Gly Gly Gly Thr Arg Val Glu Ile Lys
            100                 105                 110

<210> SEQ ID NO 165
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VECBABABA_1_110; 8 4 LC humanized 978

<400> SEQUENCE: 165

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 166
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_WECBABABA_1_110; 8 4 LC humanized 893

<400> SEQUENCE: 166

Asp Ile Glu Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Arg Leu Ile
        35                  40                  45

Gln Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr His Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 167
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_XECBABABA_1_110; 8 4 LC humanized 868

<400> SEQUENCE: 167

Asp Ile Val Met Thr Gln Ser Pro Asp Ser Leu Ala Val Ser Leu Gly
1               5                   10                  15

Glu Arg Ala Thr Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110

<210> SEQ ID NO 168
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_YECBABABA_1_110; 8 4 LC humanized 862

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 169
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZECBABABA_1_110; 8 4 LC humanized 715

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Phe Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 170
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BICBABABA_1_110; 8 4 LC humanized 706

<400> SEQUENCE: 170

Asp Ile Gln Met Thr Gln Tyr Pro Ser Ser Leu Ser Ala Ser Val Gly
1               5                   10                  15

Asp Arg Val Thr Ile Ala Cys Gln Ala Ser Gln Ser Ile Ser Thr Ala
            20                  25                  30

Leu Ala Trp Tyr Gln Gln Lys Pro Gly Lys Pro Pro Lys Leu Leu Ile
        35                  40                  45

```
Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Cys Leu Gln Pro
65                  70                  75                  80

Glu Asp Val Ala Thr Tyr Tyr Cys Gln Gln Gly Trp Ser Thr Val Asn
                85                  90                  95

Val Asp Asn Val Phe Gly Gln Gly Thr Arg Val Glu Phe Lys
            100                 105                 110

<210> SEQ ID NO 171
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CICBABABA_1_110; 8 4 LC humanized 703

<400> SEQUENCE: 171

Asp Ile Val Met Thr Gln Ser Pro Asp Ser Leu Ala Val Ser Leu Gly
1               5                   10                  15

Glu Arg Ala Thr Ile Asn Cys Gln Ala Ser Gln Ser Ile Ser Thr Ala
                20                  25                  30

Leu Ala Trp Tyr Gln Gln Lys Ala Gly Gln Pro Pro Lys Leu Leu Ile
            35                  40                  45

Tyr Arg Ala Ser Thr Leu Ala Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 172
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DICBABABA_1_110; 8 4 LC humanized 635

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Val Pro Lys Leu Leu Ile
            35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Trp Ser Thr Val Asn
                85                  90                  95

Val Asp Asn Val Phe Gly Gln Gly Thr Lys Leu Glu Ile Lys
```

<210> SEQ ID NO 173
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_FICBABABA_1_110; 8 4 LC humanized 341

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Leu Glu Ile Lys
            100                 105                 110

<210> SEQ ID NO 174
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_GICBABABA_1_110; 8 4 LC humanized 328

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Arg Gly Thr Lys Val Glu Ile Lys
            100                 105                 110

<210> SEQ ID NO 175
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<223> OTHER INFORMATION: cl_HICBABABA_1_110; 8 4 LC humanized 324

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Asn Ala Pro Lys Ser Leu Ile
        35                  40                  45

Tyr Arg Ala Ser Thr Leu Ala Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 176
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KICBABABA_1_110; 8 4 LC humanized 301

<400> SEQUENCE: 176

Asp Ile Gln Met Thr Gln Ser Pro Asp Ser Leu Ala Val Ser Leu Gly
1               5                   10                  15

Glu Arg Ala Thr Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110

<210> SEQ ID NO 177
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LICBABABA_1_110; 8 4 LC humanized 295

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile

```
                35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                 85                  90                  95

Val Asp Asn Val Phe Gly Gln Gly Thr Arg Leu Glu Ile Lys
                100                 105                 110

<210> SEQ ID NO 178
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MICBABABA_1_110; 8 4 LC humanized 292

<400> SEQUENCE: 178

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Asn Leu Leu Ile
                35                  40                  45

Tyr Arg Ala Ser Thr Leu Ala Ser Gly Val Pro Ser Arg Phe Ser Gly
 50                  55                  60

Ser Val Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                 85                  90                  95

Val Asp Asn Val Phe Gly Gly Gly Thr Lys Val Glu Ile Lys
                100                 105                 110

<210> SEQ ID NO 179
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NICBABABA_1_110; 8 4 LC humanized 283

<400> SEQUENCE: 179

Asp Ile Gln Leu Thr Gln Ser Pro Ser Val Ser Ala Ser Val Gly
 1               5                  10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
                35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                 85                  90                  95
```

```
Val Asp Asn Val Phe Gly Gln Gly Thr Arg Leu Glu Ile Lys
            100                 105                 110
```

<210> SEQ ID NO 180
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PICBABABA_1_110; 8 4 LC humanized 282

<400> SEQUENCE: 180

```
Asp Ile Gln Met Thr Gln Ser Pro Ser Ser Val Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Leu Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110
```

<210> SEQ ID NO 181
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QICBABABA_1_110; 8 4 LC humanized 278

<400> SEQUENCE: 181

```
Glu Leu Val Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Cys Gln Gln Lys Pro Gly Lys Ser Pro Thr Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Gly Phe Thr Leu Thr Ile Ser Gly Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Arg
            100                 105                 110
```

<210> SEQ ID NO 182
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<223> OTHER INFORMATION: cl_RICBABABA_1_110; 8 4 LC humanized 204

<400> SEQUENCE: 182

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 183
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SICBABABA_1_110; 8 4 LC humanized 201

<400> SEQUENCE: 183

Asp Ile Arg Val Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Trp Ser Thr Val Asn
                85                  90                  95

Val Asp Asn Val Phe Gly Gly Gly Thr Lys Val Asp Ile Lys
            100                 105                 110

<210> SEQ ID NO 184
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TICBABABA_1_110; 8 4 LC humanized 129

<400> SEQUENCE: 184

Glu Ile Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30
```

```
Leu Ala Trp Tyr Gln His Lys Pro Gly Lys Ala Pro Arg Leu Leu Ile
        35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Val Lys
                100                 105                 110
```

<210> SEQ ID NO 185
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VICBABABA_1_110; 8 4 LC humanized 108

<400> SEQUENCE: 185

```
Asp Val Val Met Thr Gln Ser Pro Ser Ser Val Ser Ala Ser Val Gly
 1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
                100                 105                 110
```

<210> SEQ ID NO 186
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WICBABABA_1_110; 8 4 LC humanized 57

<400> SEQUENCE: 186

```
Asp Ile Gln Met Thr Gln Ser Pro Ser Ser Leu Ser Ala Ser Val Gly
 1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Arg Leu Ile
        35                  40                  45

Tyr Arg Ala Ser Thr Leu Ala Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                85                  90                  95
```

```
Val Asp Asn Val Phe Gly Gln Gly Thr Arg Leu Glu Ile Lys
            100                 105                 110

<210> SEQ ID NO 187
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XICBABABA_1_110; 8 4 LC humanized 800

<400> SEQUENCE: 187

Ala Tyr Glu Leu Thr Gln Thr Pro Pro Ser Leu Ser Val Thr Pro Gly
1               5                   10                  15

Gln Pro Ala Ser Ile Ser Cys Gln Ala Ser Gln Ser Ile Ser Thr Ala
            20                  25                  30

Leu Ala Trp Tyr Leu Gln Lys Pro Gly Gln Pro Pro Gln Leu Leu Ile
        35                  40                  45

Tyr Arg Ala Ser Thr Leu Ala Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 188
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YICBABABA_1_110; 8 4 LC humanized 1133

<400> SEQUENCE: 188

Ala Tyr Asp Met Thr Thr Gln Pro Pro Ser Val Ser Val Ser Pro Gly
1               5                   10                  15

Gln Thr Ala Ser Ile Thr Cys Gln Ala Ser Gln Ser Ile Ser Thr Ala
            20                  25                  30

Leu Ala Trp Tyr Gln Gln Lys Pro Gly Gln Ser Pro Val Leu Val Ile
        35                  40                  45

Tyr Arg Ala Ser Thr Leu Ala Ser Gly Ile Pro Glu Arg Phe Ser Gly
    50                  55                  60

Ser Asn Ser Gly Asn Thr Ala Thr Leu Thr Ile Ser Gly Thr Gln Ala
65                  70                  75                  80

Met Asp Glu Ala Asp Tyr Tyr Cys Gln Gln Gly Trp Ser Thr Val Asn
                85                  90                  95

Val Asp Asn Val Phe Gly Thr Gly Thr Glu Val Val Val Arg
            100                 105                 110

<210> SEQ ID NO 189
<211> LENGTH: 110
<212> TYPE: PRT
<213> ORGANISM: Artificial Sequence
<220> FEATURE:
<223> OTHER INFORMATION: Description of Artificial Sequence: Synthetic
```

```
                       polypeptide
<220> FEATURE:
<223> OTHER INFORMATION: cl_ZICBABABA_1_110; 8 4 LC humanized 621

<400> SEQUENCE: 189

Ala Tyr Glu Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 190
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_COCBABABA_1_110; 8 4 LC humanized 881

<400> SEQUENCE: 190

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Asn Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Gln Ile Lys
            100                 105                 110

<210> SEQ ID NO 191
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DOCBABABA_1_110; 8 4 LC humanized 55

<400> SEQUENCE: 191

Ala Tyr Asp Met Thr Gln Thr Pro Ala Ser Val Glu Val Ser Pro Gly
1               5                   10                  15

Glu Arg Ala Thr Leu Ser Cys Gln Ala Ser Gln Ser Ile Ser Thr Ala
            20                  25                  30
```

```
Leu Ala Trp Tyr Gln Gln Lys Pro Gly Gln Ala Pro Arg Leu Leu Ile
         35                  40                  45

Tyr Arg Ala Ser Thr Leu Ala Ser Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Gly Trp Ser Thr Val Asn
                 85                  90                  95

Val Asp Asn Val Phe Gly Gln Gly Thr Glu Val Val Val Arg
                100                 105                 110

<210> SEQ ID NO 192
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FOCBABABA_1_110; 8 4 LC humanized 882

<400> SEQUENCE: 192

Ala Tyr Asp Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Thr Ala
             20                  25                  30

Leu Ala Trp Tyr Gln Gln Lys Pro Gly Lys Ala Pro Lys Leu Leu Ile
         35                  40                  45

Tyr Arg Ala Ser Thr Leu Ala Ser Gly Val Pro Ser Arg Phe Ser Gly
     50                  55                  60

Ser Gly Phe Gly Thr Asp Phe Thr Phe Thr Ile Ser Ser Leu Gln Pro
 65                  70                  75                  80

Glu Asp Ser Ala Thr Tyr Tyr Cys Gln Gln Gly Trp Ser Thr Val Asn
                 85                  90                  95

Val Asp Asn Val Phe Gly Gln Gly Thr Lys Leu Glu Ile Lys
                100                 105                 110

<210> SEQ ID NO 193
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GOCBABABA_1_110; 8 4 LC humanized 660

<400> SEQUENCE: 193

Ala Tyr Val Met Thr Gln Ser Pro Ala Thr Leu Ser Leu Ser Pro Gly
 1               5                  10                  15

Glu Arg Ala Thr Leu Ser Cys Gln Ala Ser Gln Ser Ile Ser Thr Ala
             20                  25                  30

Leu Ala Trp Tyr Gln Gln Arg Pro Gly Gln Ala Pro Arg Leu Leu Ile
         35                  40                  45

Tyr Arg Ala Ser Thr Leu Ala Ser Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Gly Trp Ser Thr Val Asn
```

```
                    85                  90                  95

Val Asp Asn Val Phe Gly Gly Gly Thr Lys Val Glu Ile Lys
                100                 105                 110

<210> SEQ ID NO 194
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_HOCBABABA_1_110; 8 4 LC humanized 1051

<400> SEQUENCE: 194

Ser Tyr Glu Leu Thr Gln Thr Pro Pro Ser Val Ser Val Ser Pro Gly
1               5                   10                  15

Gln Thr Ala Arg Ile Thr Cys Gln Ala Ser Gln Ser Ile Ser Thr Ala
            20                  25                  30

Leu Ala Trp Tyr Gln Gln Lys Pro Gly Gln Ala Pro Val Leu Val Ile
        35                  40                  45

Tyr Arg Ala Ser Thr Leu Ala Ser Gly Ile Pro Glu Arg Phe Ser Gly
    50                  55                  60

Ser Ser Ser Gly Thr Thr Val Thr Leu Thr Ile Ser Gly Val Gln Ala
65                  70                  75                  80

Glu Asp Glu Ala Asp Tyr Tyr Cys Gln Gln Gly Trp Ser Thr Val Asn
                85                  90                  95

Val Asp Asn Val Phe Gly Thr Gly Thr Lys Val Thr Val Leu
                100                 105                 110

<210> SEQ ID NO 195
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_KOCBABABA_1_110; 8 4 LC humanized 1050

<400> SEQUENCE: 195

Ser Tyr Glu Leu Thr Gln Thr Pro Pro Ser Val Ser Val Ser Pro Gly
1               5                   10                  15

Gln Thr Ala Arg Ile Thr Cys Gln Ala Ser Gln Ser Ile Ser Thr Ala
            20                  25                  30

Leu Ala Trp Tyr Gln Gln Lys Pro Gly Gln Ala Pro Val Leu Val Ile
        35                  40                  45

Tyr Arg Ala Ser Thr Leu Ala Ser Gly Ile Pro Glu Arg Phe Ser Gly
    50                  55                  60

Ser Ser Ser Gly Thr Thr Val Thr Leu Thr Ile Ser Gly Val Gln Ala
65                  70                  75                  80

Glu Asp Glu Ala Asp Tyr Tyr Cys Gln Gln Gly Trp Ser Thr Val Asn
                85                  90                  95

Val Asp Asn Val Phe Gly Thr Gly Thr Lys Val Thr Val Leu
                100                 105                 110

<210> SEQ ID NO 196
<211> LENGTH: 110
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: cl_LOCBABABA_1_110; 8 4 LC humanized 860

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 197
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MOCBABABA_1_110; 8 4 LC humanized 809

<400> SEQUENCE: 197

Asp Ile Gln Met Thr Gln Ser Pro Ser Ser Val Ser Ala Ser Val Arg
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Pro Gly Thr Lys Val Asp Ile Lys
            100                 105                 110

<210> SEQ ID NO 198
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NOCBABABA_1_110; 8 4 LC humanized 346

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala

```
                  20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
                100                 105                 110

<210> SEQ ID NO 199
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_POCBABABA_1_110; 8 4 LC humanized 345

<400> SEQUENCE: 199

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Asp Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
                100                 105                 110

<210> SEQ ID NO 200
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QOCBABABA_1_110; 8 4 LC humanized 334

<400> SEQUENCE: 200

Asp Ile Gln Met Thr Gln Ser Pro Ser Phe Val Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 201
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ROCBABABA_1_110; 8 4 LC humanized 319

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 202
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SOCBABABA_1_110; 8 4 LC humanized 308

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 203
<211> LENGTH: 110
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: cl_TOCBABABA_1_110; 8 4 LC humanized 281

<400> SEQUENCE: 203

Asp Ile Gln Leu Thr Gln Ser Pro Ser Ser Val Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Asp Ile Lys
            100                 105                 110

<210> SEQ ID NO 204
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VOCBABABA_1_110; 8 4 LC humanized 273

<400> SEQUENCE: 204

Glu Leu Val Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Glu Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Gly Leu Gln Ser
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

<210> SEQ ID NO 205
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WOCBABABA_1_110; 8 4 LC humanized 716

<400> SEQUENCE: 205

Glu Leu Val Met Thr Gln Ser Pro Ser Ser Leu Ser Ala Ser Glu Gly
1               5                   10                  15
```

```
Asp Arg Val Thr Ile Thr Cys Gln Ala Ser Gln Ser Ile Ser Thr Ala
            20                  25                  30

Leu Ala Trp Tyr Gln Gln Lys Pro Gly Arg Ala Pro Lys Leu Leu Ile
        35                  40                  45

His Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Gly Leu Gln Ser
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Thr Val Asp Val Lys
            100                 105                 110

<210> SEQ ID NO 206
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XOCBABABA_1_110; 8 4 LC humanized 677

<400> SEQUENCE: 206

Ala Tyr Asp Met Thr Gln Ser Pro Ser Phe Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Arg Leu Glu Ile Lys
            100                 105                 110

<210> SEQ ID NO 207
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YOCBABABA_1_110; 8 4 LC humanized 192

<400> SEQUENCE: 207

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80
```

Glu Asp Phe Thr Thr Tyr Tyr Cys Gln Gln Gly Trp Ser Thr Val Asn
                85                  90                  95

Val Asp Asn Val Phe Gly Gln Gly Thr Lys Val Glu Phe Lys
            100                 105                 110

<210> SEQ ID NO 208
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZOCBABABA_1_110; 8 4 LC humanized 202

<400> SEQUENCE: 208

Asp Ile Arg Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Val Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Trp Ser Thr Val Asn
                85                  90                  95

Val Asp Asn Val Phe Gly Pro Gly Thr Lys Val Val Val Arg
            100                 105                 110

<210> SEQ ID NO 209
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BUCBABABA_1_110; 8 4 LC humanized 802

<400> SEQUENCE: 209

Ala Ile Arg Met Thr Gln Ser Pro Ser Ser Phe Ser Ala Ser Thr Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 210
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CUCBABABA_1_110; 8 4 LC humanized 347

<400> SEQUENCE: 210

Asp Ile Gln Met Thr Gln Ser Pro Ser Ser Leu Ser Ala Ser Val Gly
1               5                   10                  15

Asp Arg Val Ser Ile Thr Cys Gln Ala Ser Gln Ser Ile Ser Thr Ala
            20                  25                  30

Leu Ala Trp Tyr Gln Gln Lys Pro Gly Lys Ala Pro Lys Arg Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 211
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DUCBABABA_1_110; 8 4 LC humanized 339

<400> SEQUENCE: 211

Asp Ile Gln Leu Thr Gln Ser Pro Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 212
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FUCBABABA_1_110; 8 4 LC humanized 168

<400> SEQUENCE: 212

Asp Ile Val Met Thr Gln Ser Pro Ser Thr Leu Ser Ala Ser Val Gly
1               5                   10                  15

```
Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Gly Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Lys Leu Glu Ile Lys
            100                 105                 110

<210> SEQ ID NO 213
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GUCBABABA_1_110; 8 4 LC humanized 54

<400> SEQUENCE: 213

Ala Tyr Gly Met Thr Gln Ser Pro Asp Ser Leu Ala Val Ser Leu Gly
1               5                   10                  15

Glu Arg Ala Ser Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
50                  55                  60

Gly Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

<210> SEQ ID NO 214
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HUCBABABA_1_110; 8 4 LC humanized 21

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Val Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Gly Trp Ser Thr Val Asn
                    85                  90                  95

Val Asp Asn Val Phe Gly Pro Gly Thr Lys Val Glu Val Arg
                100                 105                 110

<210> SEQ ID NO 215
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KUCBABABA_1_110; 8 4 LC humanized 788

<400> SEQUENCE: 215

Ala Tyr Glu Leu Thr Gln Thr Pro Leu Ser Ser Pro Val Thr Leu Gly
1               5                   10                  15

Gln Pro Ala Ser Ile Ser Cys Gln Ala Ser Gln Ser Ile Ser Thr Ala
                20                  25                  30

Leu Ala Trp Leu Gln Gln Arg Pro Gly Gln Pro Pro Arg Leu Leu Ile
            35                  40                  45

Tyr Arg Ala Ser Thr Leu Ala Ser Gly Val Pro Asp Arg Phe Ser Gly
        50                  55                  60

Ser Gly Ala Gly Thr Asp Phe Thr Leu Lys Ile Ser Arg Val Glu Ala
65                  70                  75                  80

Glu Asp Val Gly Ile Tyr Tyr Cys Gln Gln Gly Trp Ser Thr Val Asn
                    85                  90                  95

Val Asp Asn Val Phe Gly Gln Gly Thr Lys Val Glu Ile Lys
                100                 105                 110

<210> SEQ ID NO 216
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LUCBABABA_1_110; 8 4 LC humanized 675

<400> SEQUENCE: 216

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Glu Phe Thr Leu Thr Ile Ser Leu Gln Pro
65                  70                  75                  80

Glu Asp Phe Ala Thr Tyr Tyr Cys Gln Gln Gly Trp Ser Thr Val Asn
                    85                  90                  95

Val Asp Asn Val Phe Gly Pro Gly Thr Lys Leu Glu Ile Lys
                100                 105                 110

<210> SEQ ID NO 217
<211> LENGTH: 110
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MUCBABABA_1_110; 8 4 LC humanized 762

<400> SEQUENCE: 217
```

Ala Tyr Glu Leu Thr Gln Ser Pro Asp Ser Leu Ala Val Ser Leu Gly
1               5                   10                  15

Glu Arg Ala Thr Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110

```
<210> SEQ ID NO 218
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NUCBABABA_1_110; 8 4 LC humanized 818

<400> SEQUENCE: 218
```

Ala Tyr Asp Met Thr Gln Thr Pro Ser Ser Val Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Val Glu Ile Lys
            100                 105                 110

```
<210> SEQ ID NO 219
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PUCBABABA_1_110; 8 4 LC humanized 173

<400> SEQUENCE: 219
```

Ala Ile Gln Met Thr Gln Ser Pro Phe Ser Leu Ser Ala Ser Val Gly

```
                1               5                  10                 15
Asp Arg Val Thr Ile Thr Cys Gln Ala Ser Gln Ser Ile Ser Thr Ala
                20                 25                 30

Leu Ala Trp Phe Gln Gln Lys Pro Gly Lys Ala Pro Lys Ser Leu Ile
            35                 40                 45

Tyr Arg Ala Ser Thr Leu Ala Ser Gly Val Ser Ser Lys Phe Ser Gly
        50                 55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Gly Trp Ser Thr Val Asn
                85                 90                 95

Val Asp Asn Val Phe Gly Gln Gly Thr Arg Leu Val Val Arg
                100                105                110

<210> SEQ ID NO 220
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QUCBABABA_1_110; 8 4 LC humanized 65

<400> SEQUENCE: 220

Asp Ile Gln Met Thr Gln Ser Pro Ser Thr Leu Ser Ala Ser Val Gly
1               5                  10                 15

Asp Arg Val Thr Ile Thr Cys Gln Ala Ser Gln Ser Ile Ser Thr Ala
                20                 25                 30

Leu Ala Trp Tyr Gln Gln Lys Pro Gly Lys Ala Pro Lys Leu Leu Ile
            35                 40                 45

Tyr Arg Ala Ser Thr Leu Ala Ser Gly Val Pro Ser Arg Phe Ser Gly
        50                 55                 60

Ser Gly Ser Gly Thr Glu Phe Thr Leu Thr Ile Ser Ser Leu Gln Pro
65                  70                 75                 80

Asp Asp Phe Ala Thr Tyr Tyr Cys Gln Gln Gly Trp Ser Thr Val Asn
                85                 90                 95

Val Asp Asn Val Phe Gly Gln Gly Thr Lys Val Glu Ile Lys
                100                105                110

<210> SEQ ID NO 221
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RUCBABABA_1_110; 8 4 LC humanized 224

<400> SEQUENCE: 221

Ala Tyr Asp Met Thr Gln Thr Pro Ala Ser Val Ser Leu Ser Pro Gly
1               5                  10                 15

Glu Arg Ala Thr Leu Ser Cys Gln Ala Ser Gln Ser Ile Ser Thr Ala
                20                 25                 30

Leu Ala Trp Tyr Gln Gln Lys Pro Gly Gln Ala Pro Arg Leu Leu Ile
            35                 40                 45

Tyr Arg Ala Ser Thr Leu Ala Ser Gly Ile Pro Asp Arg Phe Arg Gly
        50                 55                 60
```

Ser Gly Ser Ala Thr Asp Phe Thr Leu Thr Ile Ser Arg Leu Glu Pro
65                  70                  75                  80

Glu Asp Phe Ala Val Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 222
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SUCBABABA_1_110; 8 4 LC humanized 230

<400> SEQUENCE: 222

Ala Tyr Asp Met Thr Gln Thr Pro Ala Ser Val Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Val Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110

<210> SEQ ID NO 223
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TUCBABABA_1_110; 8 4 LC humanized 880

<400> SEQUENCE: 223

Ala Tyr Asp Met Thr Gln Ser Pro Ser Ser Leu Ser Ala Ser Val Gly
1               5                   10                  15

Asp Arg Val Asn Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Pro Gly Thr Lys Val Asp Ile Lys
            100                 105                 110

<210> SEQ ID NO 224

<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: cl_VUCBABABA_1_110; 8 4 LC humanized 672

<400> SEQUENCE: 224

```
Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gln Gly Thr Lys Leu Glu Ile Lys
            100                 105                 110
```

<210> SEQ ID NO 225
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: cl_WUCBABABA_1_110; 8 4 LC humanized 299

<400> SEQUENCE: 225

```
Asp Ile Gln Met Thr Gln Ser Pro Ser Ser Val Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
                85                  90                  95

Val Asp Asn Val Phe Gly Gly Gly Thr Lys Val Glu Ile Lys
            100                 105                 110
```

<210> SEQ ID NO 226
<211> LENGTH: 110
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: cl_XUCBABABA_1_110; 8 4 LC humanized 267

<400> SEQUENCE: 226

-continued

Ala Tyr Asp Met Thr Gln Ser Pro Ser Thr Leu Ala Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Trp Ser Thr Val Asn
            85                  90                  95

Val Asp Asn Val Phe Gly Gln Gly Thr Lys Val Glu Val Lys
            100                 105                 110

<210> SEQ ID NO 227
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YUCBABABA_1_110; 8 4 LC humanized 23

<400> SEQUENCE: 227

Ala Tyr Glu Leu Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
            85                  90                  95

Val Asp Asn Val Phe Gly Pro Gly Thr Lys Val Asp Ile Lys
            100                 105                 110

<210> SEQ ID NO 228
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZUCBABABA_1_110; 8 4 LC humanized 657

<400> SEQUENCE: 228

Ala Tyr Asp Met Thr Gln Thr Pro Ala Ser Val Glu Val Ser Val Gly
1               5                   10                  15

Asp Arg Val Ser Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

```
Ser Gly Ser Gly Thr Asp Phe Thr Leu Thr Ile Thr Ser Leu Gln Pro
 65                  70                  75                  80

Val Asp Phe Ala Thr Tyr Tyr Cys Gln Gln Gly Trp Ser Thr Val Asn
                 85                  90                  95

Val Asp Asn Val Phe Gly Pro Gly Thr Thr Val Asp Ala Lys
            100                 105                 110

<210> SEQ ID NO 229
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BADBABABA_1_110; 8 4 LC humanized 879

<400> SEQUENCE: 229

Ala Tyr Asp Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Thr Ala
                 20                  25                  30

Leu Ala Trp Tyr Gln Gln Lys Pro Gly Lys Ala Pro Lys Leu Leu Ile
             35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Trp Ser Thr Val Asn
                 85                  90                  95

Val Asp Asn Val Phe Gly Gly Gly Thr Lys Val Glu Ile Lys
            100                 105                 110

<210> SEQ ID NO 230
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CABBABABA_15_117; 8 4 HC humanized 356; 8 4
      HC humanized 340; 8 4 HC humanized 335; 8 4 HC humanized 303; 8 4
      HC humanized 287

<400> SEQUENCE: 230

Val Gln Leu Val Glu Ser Gly Gly Gly Val Val Gln Pro Gly Gly Ser
 1               5                  10                  15

Leu Arg Leu Ser Cys Ala Ala Ser Gly Phe Thr Ile Ser Asn Leu Ala
                 20                  25                  30

Ile Ile Trp Val Arg Gln Ala Pro Gly Lys Gly Leu Glu Trp Val Ser
             35                  40                  45

Asp Ile Asp Gly Arg Gly Asp Ile Tyr Cys Ala Thr Trp Ala Lys Gly
 50                  55                  60

Arg Phe Thr Ile Ser Arg Asp Asn Ser Ser Leu Tyr Leu Gln Met Asn
 65                  70                  75                  80

Ser Leu Arg Ala Glu Asp Thr Ala Val Tyr Tyr Cys Ala Arg Asp Gly
                 85                  90                  95

Asp Gly Ser Gly Trp Gly Asp Phe Asn Phe Trp Gly Pro Gly Thr Leu
            100                 105                 110
```

Val Thr Val Ser Ser
        115

<210> SEQ ID NO 231
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LABBABABA_85_117; 8 4 HC humanized 2049; 8 4
      HC humanized 2033; 8 4 HC humanized 1360; 8 4 HC humanized 1344;
      8 4 HC humanized 777

<400> SEQUENCE: 231

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Pro Gly Thr Leu
            100                 105                 110

Val Thr Val Ser Ser
        115

<210> SEQ ID NO 232
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CACBABABA_76_110; 8 4 LC humanized 356; 8 4
      LC humanized 340; 8 4 LC humanized 335; 8 4 LC humanized 303; 8 4
      LC humanized 287

<400> SEQUENCE: 232

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

```
<210> SEQ ID NO 233
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LACBABABA_2_110; 8 4 LC humanized 2049; 8 4
      LC humanized 2033

<400> SEQUENCE: 233

Ala Tyr Asp Met Thr Gln Ser Pro Asp Ser Leu Ala Val Ser Leu Gly
1               5                   10                  15

Glu Arg Ala Thr Ile Asn Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 234
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NACBABABA_2_110; 8 4 LC humanized 1360; 8 4
      LC humanized 1344

<400> SEQUENCE: 234

Ala Tyr Asp Met Thr Gln Thr Pro Leu Ser Leu Ser Val Thr Pro Gly
1               5                   10                  15

Gln Pro Ala Ser Ile Ser Cys Gln Ala Ser Gln Ser Ile Ser Thr Ala
            20                  25                  30

Leu Ala Trp Tyr Leu Gln Lys Pro Gly Gln Pro Pro Gln Leu Leu Ile
        35                  40                  45

Tyr Arg Ala Ser Thr Leu Ala Ser Gly Val Pro Asp Arg Phe Ser Gly
50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 235
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<223> OTHER INFORMATION: cl_CECBABABA_5_110; 8 4 LC humanized 2207; 8 4
      LC humanized 2206; 8 4 LC humanized 2197; 8 4 LC humanized 2208;
      8 4 LC humanized 2192

<400> SEQUENCE: 235

Ala Tyr Asp Met Thr Gln Ser Pro Ala Phe Leu Ser Val Thr Pro Gly
1               5                   10                  15

Glu Lys Val Thr Ile Thr Cys Gln Ala Ser Gln Ser Ile Ser Thr Ala
            20                  25                  30

Leu Ala Trp Tyr Gln Gln Lys Pro Asp Gln Ala Pro Lys Leu Leu Ile
        35                  40                  45

Lys Arg Ala Ser Thr Leu Ala Ser Gly Val Pro Ser Arg Phe Ser Gly
 50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 236
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DICBABABA_15_110; 8 4 LC humanized 2263; 8 4
      LC humanized 2262; 8 4 LC humanized 2258; 8 4 LC humanized 2257;
      8 4 LC humanized 2256

<400> SEQUENCE: 236

Ala Tyr Asp Met Thr Gln Ser Pro Ala Ser Leu Ala Val Ser Pro Gly
1               5                   10                  15

Gln Arg Ala Thr Ile Thr Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ala Arg Phe Ser Gly
 50                  55                  60

Ser Gly Ser Gly Thr Asp Phe Thr Leu Thr Ile Asn Pro Val Glu Ala
65                  70                  75                  80

Asn Asp Thr Ala Asn Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 237
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CABBABABA_2_117; 8 4 HC humanized 356; 8 4
      HC humanized 303

<400> SEQUENCE: 237

Val Gln Leu Val Glu Ser Arg Gly Val Leu Val Gln Pro Gly Gly Ser
1               5                   10                  15
```

```
Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu His Leu Gln Met Asn
65                  70                  75                  80

Ser Leu Arg Ala Glu Asp Thr Ala Val Tyr Tyr Cys Lys Lys Asp Gly
                85                  90                  95

Asp Gly Ser Gly Trp Gly Asp Phe Asn Phe Trp Gly Pro Gly Thr Leu
            100                 105                 110

Val Thr Val Ser Ser
            115

<210> SEQ ID NO 238
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DABBABABA_17_117; 8 4 HC humanized 340; 8 4
      HC humanized 335; 8 4 HC humanized 287; 8 4 HC humanized 282; 8 4
      HC humanized 2207

<400> SEQUENCE: 238

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Pro Gly Thr Leu
            100                 105                 110

Val Thr Val Ser Ser
            115

<210> SEQ ID NO 239
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LABBABABA_37_117; 8 4 HC humanized 2049; 8 4
      HC humanized 2033; 8 4 HC humanized 1360; 8 4 HC humanized 1344;
      8 4 HC humanized 777

<400> SEQUENCE: 239

Val Gln Leu Val Glu Ser Gly Gly Gly Leu Val Gln Pro Gly Gly Ser
1               5                   10                  15
```

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Gly
        35                  40                  45

Asp Ile Asp Gly Arg Gly Asp Ile Tyr Cys Ala Thr Trp Ala Lys Gly
    50                  55                  60

Arg Phe Thr Ile Ser Arg Ser Lys Asn Thr Leu Tyr Leu Gln Met Asn
65                  70                  75                  80

Ser Leu Lys Thr Glu Asp Thr Ala Val Tyr Tyr Cys Thr Arg Asp Gly
                85                  90                  95

Asp Gly Ser Gly Trp Gly Asp Phe Asn Phe Trp Gly Pro Gly Thr Leu
            100                 105                 110

Val Thr Val Ser Ser
        115

<210> SEQ ID NO 240
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DEBBABABA_22_117; 8 4 HC humanized 2206; 8 4
      HC humanized 988; 8 4 HC humanized 987; 8 4 HC humanized 935; 8 4
      HC humanized 934

<400> SEQUENCE: 240

Val Gln Leu Val Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala
            20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asp Gly
                85                  90                  95

Asp Gly Ser Gly Trp Gly Asp Phe Asn Phe Trp Gly Pro Gly Thr Leu
            100                 105                 110

Val Thr Val Ser Ser
        115

<210> SEQ ID NO 241
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FEBBABABA_16_117; 8 4 HC humanized 2197; 8 4
      HC humanized 978; 8 4 HC humanized 925; 8 4 HC humanized 660; 8 4
      HC humanized 395

<400> SEQUENCE: 241

Val Gln Leu Leu Glu Ser Gly Gly Gly Leu Val Gln Pro Gly Gly Ser
1               5                   10                  15

Leu Arg Leu Ser Cys Ala Ala Ser Gly Phe Thr Ile Ser Asn Leu Ala

```
                20                  25                  30

Ile Ile Trp Val Arg Gln Ala Pro Gly Lys Gly Leu Glu Trp Val Ser
        35                  40                  45

Asp Ile Asp Gly Arg Gly Asp Ile Tyr Cys Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Lys Asp Gly
                85                  90                  95

Asp Gly Ser Gly Trp Gly Asp Phe Asn Phe Trp Gly Pro Gly Thr Leu
            100                 105                 110

Val Thr Val Ser Ser
        115

<210> SEQ ID NO 242
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HIBBABABA_3_117; 8 4 HC humanized 2257; 8 4
      HC humanized 349; 8 4 HC humanized 296

<400> SEQUENCE: 242

Val Gln Leu Val Glu Ser Gly Gly Gly Leu Val Gln Pro Gly Arg Ser
1               5                   10                  15

Leu Arg Leu Ser Cys Thr Ala Ser Gly Phe Thr Ile Ser Asn Leu Ala
                20                  25                  30

Ile Ile Trp Phe Arg Gln Ala Pro Gly Lys Gly Leu Glu Trp Val Gly
        35                  40                  45

Asp Ile Asp Gly Arg Gly Asp Ile Tyr Cys Ala Thr Trp Ala Lys Gly
    50                  55                  60

Arg Phe Thr Ile Ser Arg Ser Lys Ser Ile Ala Tyr Leu Gln Met Asn
65                  70                  75                  80

Ser Leu Lys Thr Glu Asp Thr Ala Val Tyr Tyr Cys Thr Arg Asp Gly
                85                  90                  95

Asp Gly Ser Gly Trp Gly Asp Phe Asn Phe Trp Gly Pro Gly Thr Leu
            100                 105                 110

Val Thr Val Ser Ser
        115

<210> SEQ ID NO 243
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LIBBABABA_3_117; 8 4 HC humanized 2254; 8 4
      HC humanized 346; 8 4 HC humanized 293

<400> SEQUENCE: 243

Val Gln Leu Val Glu Ser Gly Gly Val Val Val Gln Pro Gly Gly Ser
1               5                   10                  15

Leu Arg Leu Ser Cys Ala Ala Ser Gly Phe Thr Ile Ser Asn Leu Ala
                20                  25                  30

Ile Ile Trp Val Arg Gln Ala Pro Gly Lys Gly Leu Glu Trp Val Ser
```

```
            35                  40                  45
Asp Ile Asp Gly Arg Gly Asp Ile Tyr Cys Ala Thr Trp Ala Lys Gly
 50                  55                  60

Arg Phe Thr Ile Ser Arg Asp Asn Ser Ser Leu Tyr Leu Gln Met Asn
65                  70                  75                  80

Ser Leu Arg Thr Glu Asp Thr Ala Leu Tyr Tyr Cys Ala Lys Asp Gly
                85                  90                  95

Asp Gly Ser Gly Trp Gly Asp Phe Asn Phe Trp Gly Pro Gly Thr Leu
                100                 105                 110

Val Thr Val Ser Ser
        115

<210> SEQ ID NO 244
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CACBABABA_1_110; 8 4 LC humanized 356

<400> SEQUENCE: 244

Ala Tyr Asp Met Thr Gln Ser Pro Ser Ser Val Ser Ala Ser Val Gly
1               5                   10                  15

Asp Arg Val Thr Ile Thr Cys Gln Ala Ser Gln Ser Ile Ser Thr Ala
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Glu Val Val Val Arg
                100                 105                 110

<210> SEQ ID NO 245
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LACBABABA_2_110; 8 4 LC humanized 2049; 8 4
      LC humanized 2033

<400> SEQUENCE: 245

Ala Tyr Asp Met Thr Gln Ser Pro Asp Ser Leu Ala Val Ser Leu Gly
1               5                   10                  15

Glu Arg Ala Thr Ile Asn Cys Gln Ala Ser Gln Ser Ile Ser Thr Ala
                20                  25                  30

Leu Ala Trp Tyr Gln Gln Lys Pro Gly Gln Pro Pro Lys Leu Leu Ile
            35                  40                  45

Tyr Arg Ala Ser Thr Leu Ala Ser Gly Val Pro Asp Arg Phe Ser Gly
 50                  55                  60

Ser Gly Ser Gly Thr Asp Phe Thr Leu Thr Ile Ser Ser Leu Gln Ala
65                  70                  75                  80
```

Glu Asp Val Ala Val Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 246
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NACBABABA_2_110; 8 4 LC humanized 1360; 8 4
      LC humanized 1344

<400> SEQUENCE: 246

Ala Tyr Asp Met Thr Gln Thr Pro Leu Ser Leu Ser Val Thr Pro Gly
1               5                   10                  15

Gln Pro Ala Ser Ile Ser Cys Gln Ala Ser Gln Ser Ile Ser Thr Ala
            20                  25                  30

Leu Ala Trp Tyr Leu Gln Lys Pro Gly Gln Pro Pro Gln Leu Leu Ile
        35                  40                  45

Tyr Arg Ala Ser Thr Leu Ala Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 247
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QACBABABA_1_110; 8 4 LC humanized 777

<400> SEQUENCE: 247

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 248
<211> LENGTH: 110

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VACBABABA_1_110; 8 4 LC humanized 565

<400> SEQUENCE: 248

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Arg Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 249
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XACBABABA_2_110; 8 4 LC humanized 247; 8 4
      LC humanized 231

<400> SEQUENCE: 249

Ala Tyr Asp Met Thr Gln Ser Pro Ser Phe Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 250
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZACBABABA_2_110; 8 4 LC humanized 141; 8 4
      LC humanized 125

<400> SEQUENCE: 250
```

```
Ala Tyr Asp Met Thr Gln Ser Pro Ser Ser Phe Ser Ala Ser Thr Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Gly Trp Ser Thr Val Asn
                85                  90                  95

Val Asp Asn Val Phe Gly Gly Gly Thr Glu Val Val Val Arg
                100                 105                 110

<210> SEQ ID NO 251
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CECBABABA_1_110; 8 4 LC humanized 2207

<400> SEQUENCE: 251

Ala Tyr Asp Met Thr Gln Ser Pro Ala Phe Leu Ser Val Thr Pro Gly
1               5                   10                  15

Glu Lys Val Thr Ile Thr Cys Gln Ala Ser Gln Ser Ile Ser Thr Ala
            20                  25                  30

Leu Ala Trp Tyr Gln Gln Lys Pro Asp Gln Ala Pro Lys Leu Leu Ile
        35                  40                  45

Lys Arg Ala Ser Thr Leu Ala Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Trp Ser Thr Val Asn
                85                  90                  95

Val Asp Asn Val Phe Gly Gly Gly Thr Glu Val Val Val Arg
                100                 105                 110

<210> SEQ ID NO 252
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GECBABABA_1_110; 8 4 LC humanized 988

<400> SEQUENCE: 252

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Ala
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
```

```
                    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Ser Thr Val Asn
                     85                  90                  95

Val Asp Asn Val Phe Gly Gly Gly Thr Glu Val Val Val Arg
                100                 105                 110

<210> SEQ ID NO 253
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PECBABABA_1_110; 8 4 LC humanized 670

<400> SEQUENCE: 253

Ala Tyr Asp Met Thr Gln Ser Pro Ser Ser Leu Ser Ala Ser Val Gly
 1                   5                  10                  15

Asp Arg Val Thr Ile Thr Cys Gln Ala Ser Gln Ser Ile Ser Thr Ala
                    20                  25                  30

Leu Ala Trp Tyr Gln Gln Lys Pro Gly Lys Val Pro Lys Leu Leu Ile
                35                  40                  45

Tyr Arg Ala Ser Thr Leu Ala Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Gly Trp Ser Thr Val Asn
                     85                  90                  95

Val Asp Asn Val Phe Gly Gly Gly Thr Glu Val Val Val Arg
                100                 105                 110

<210> SEQ ID NO 254
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZECBABABA_1_110; 8 4 LC humanized 34

<400> SEQUENCE: 254

Ala Tyr Asp Met Thr Gln Ser Pro Ser Thr Leu Ser Ala Ser Val Gly
 1                   5                  10                  15

Asp Arg Val Thr Ile Thr Cys Gln Ala Ser Gln Ser Ile Ser Thr Ala
                    20                  25                  30

Leu Ala Trp Tyr Gln Gln Lys Pro Gly Lys Ala Pro Lys Leu Leu Ile
                35                  40                  45

Tyr Arg Ala Ser Thr Leu Ala Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Gly Trp Ser Thr Val Asn
                     85                  90                  95

Val Asp Asn Val Phe Gly Gly Gly Thr Glu Val Val Val Arg
                100                 105                 110
```

<210> SEQ ID NO 255
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_DICBABABA_15_110; 8 4 LC humanized 2263; 8 4 LC humanized 2262; 8 4 LC humanized 2258; 8 4 LC humanized 2257; 8 4 LC humanized 2256

<400> SEQUENCE: 255

Ala Tyr Asp Met Thr Gln Ser Pro Ala Ser Leu Ala Val Ser Pro Gly
1               5                   10                  15

Gln Arg Ala Thr Ile Thr Cys Gln Ala Ser Gln Ser Ile Ser Thr Ala
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ala Arg Phe Ser Gly
    50                  55                  60

Ser Gly Ser Gly Thr Asp Phe Thr Leu Thr Ile Asn Pro Val Glu Ala
65                  70                  75                  80

Asn Asp Thr Ala Asn Tyr Tyr Cys Gln Gln Gly Trp Ser Thr Val Asn
                85                  90                  95

Val Asp Asn Val Phe Gly Gly Gly Thr Glu Val Val Val Arg
            100                 105                 110

<210> SEQ ID NO 256
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_CABBABABA_1_115; 16 6 HC humanized 586

<400> SEQUENCE: 256

Val Gln Leu Gln Glu Ser Gly Gly Gly Val Val Gln Pro Gly Thr Ser
1               5                   10                  15

Leu Arg Leu Ser Cys Val Val Ser Gly Ser Asp Ile Ser Ser Tyr His
            20                  25                  30

Met Gly Trp Val Arg Gln Ala Pro Gly Lys Gly Leu Glu Trp Leu Ala
        35                  40                  45

Ile Ile Val Ser Ser Gly Ser Ala Tyr Tyr Ala Thr Trp Ala Lys Gly
    50                  55                  60

Arg Phe Thr Val Ser Arg Ser Lys Ser Thr Leu Phe Leu Lys Met Asn
65                  70                  75                  80

Ser Leu Arg Ala Asp Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 257
<211> LENGTH: 115
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: cl_DABBABABA_2_115; 16 6 HC humanized 411; 16 6
      HC humanized 213

<400> SEQUENCE: 257

Leu Gln Leu Gln Glu Ser Gly Pro Arg Leu Val Lys Pro Ser Glu Thr
1               5                   10                  15

Leu Ser Leu Thr Cys Thr Val Ser Gly Ser Asp Ile Ser Ser Tyr His
            20                  25                  30

Met Gly Trp Ile Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Leu Thr Ile Ser Thr Ser Lys Asn Gln Phe Ser Leu Arg Leu Ser
65                  70                  75                  80

Ser Val Thr Ala Ala Asp Ser Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 258
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FABBABABA_1_115; 16 6 HC humanized 372

<400> SEQUENCE: 258

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Ala Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Ser Ser Thr Leu Phe Leu Gln Leu Asn
65                  70                  75                  80

Ser Leu Arg Val Glu Asp Ser Gly Ile Tyr Tyr Cys Ala Lys Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 259
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GABBABABA_7_115; 16 6 HC humanized 1996; 16

6 HC humanized 230; 16 6 HC humanized 2056; 16 6 HC humanized 672;
16 6 HC humanized 657

<400> SEQUENCE: 259

Gln Ser Leu Glu Glu Ser Gly Gly Arg Leu Val Thr Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 260
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HABBABABA_2_115; 16 6 HC humanized 1907; 16
      6 HC humanized 716

<400> SEQUENCE: 260

Gln Ser Leu Leu Glu Ser Gly Gly Gly Trp Val Gln Pro Gly Arg Ser
1               5                   10                  15

Leu Arg Leu Ser Cys Ser Ala Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Asn Ser Leu Tyr Leu Gln Met Asn
65                  70                  75                  80

Ser Leu Arg Pro Glu Asp Thr Ala Leu Tyr Tyr Cys Ala Lys Asn Gln
                85                  90                  95

Tyr Ser Gly Tyr Gly Phe Ser Phe Trp Gly Gln Gly Val Leu Val Thr
            100                 105                 110

Val Ser Ser
        115

<210> SEQ ID NO 261
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LABBABABA_3_115; 16 6 HC humanized 1945; 16
      6 HC humanized 1451; 16 6 HC humanized 65

-continued

<400> SEQUENCE: 261

```
Gln Ser Leu Glu Glu Ser Gly Gly Leu Val Lys Pro Glu Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asp Ser Thr Val Tyr Leu Glu Met Asn
65                  70                  75                  80

Ser Leu Lys Thr Glu Asp Thr Ala Val Tyr Tyr Cys Ala Thr Asn Gln
                85                  90                  95

Tyr Ser Gly Tyr Gly Phe Ser Phe Trp Gly Gln Gly Thr Leu Val Thr
            100                 105                 110

Val Ser Ser
        115
```

<210> SEQ ID NO 262
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NABBABABA_1_115; 16 6 HC humanized 1004

<400> SEQUENCE: 262

```
Gln Ser Leu Leu Glu Ser Gly Pro Arg Leu Val Lys Pro Ser Glu Thr
1               5                   10                  15

Leu Ser Leu Thr Cys Ser Val Ser Gly Ser Asp Ile Ser Ser Tyr His
            20                  25                  30

Met Gly Trp Val Arg Gln Pro Pro Gly Gln Gly Leu Glu Trp Ile Gly
        35                  40                  45

Ile Ile Val Ser Ser Gly Ser Ala Tyr Tyr Ala Thr Trp Ala Arg Ser
50                  55                  60

Arg Val Ser Ile Ser Thr Ser Gln Asn Gln Val Ser Leu Lys Leu Thr
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Ile Leu Val Thr
            100                 105                 110

Val Ser Ser
        115
```

<210> SEQ ID NO 263
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PABBABABA_13_115; 16 6 HC humanized 1971; 16
      6 HC humanized 305; 16 6 HC humanized 1877; 16 6 HC humanized 860;
      16 6 HC humanized 283

<400> SEQUENCE: 263

Val Gln Leu Val Glu Ser Gly Gly Gly Val Val Gln Pro Gly Arg Ser

```
                1               5                  10                 15
Leu Arg Leu Ser Cys Ala Ala Ser Gly Ser Asp Ile Ser Ser Tyr His
                20                 25                 30

Met Gly Trp Val Arg Gln Ala Pro Gly Lys Gly Leu Glu Trp Val Ala
            35                 40                 45

Ile Ile Val Ser Ser Gly Ser Ala Tyr Tyr Ala Thr Trp Ala Lys Gly
        50                 55                 60

Arg Phe Thr Ile Ser Arg Asp Asn Ser Thr Leu Tyr Leu Gln Met Asn
65                  70                 75                  80

Ser Leu Arg Ala Glu Asp Thr Ala Val Tyr Tyr Cys Ala Lys Asn Gln
                85                 90                 95

Tyr Ser Gly Tyr Gly Phe Ser Phe Trp Gly Gln Gly Thr Leu Val Thr
                100                105                110

Val Ser Ser
        115

<210> SEQ ID NO 264
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QABBABABA_22_115; 16 6 HC humanized 802; 16
      6 HC humanized 587; 16 6 HC humanized 1012; 16 6 HC humanized 988;
      16 6 HC humanized 129

<400> SEQUENCE: 264

Val Gln Leu Val Glu Ser Gly Gly Gly Leu Val Gln Pro Gly Gly Ser
1               5                  10                 15

Leu Arg Leu Ser Cys Ala Ala Ser Gly Ser Asp Ile Ser Ser Tyr His
                20                 25                 30

Met Gly Trp Val Arg Gln Ala Pro Gly Lys Gly Leu Glu Trp Val Ser
            35                 40                 45

Ile Ile Val Ser Ser Gly Ser Ala Tyr Tyr Ala Thr Trp Ala Lys Gly
        50                 55                 60

Arg Phe Thr Ile Ser Arg Asp Asn Ser Thr Leu Tyr Leu Gln Met Asn
65                  70                 75                  80

Ser Leu Arg Ala Glu Asp Thr Ala Val Tyr Tyr Cys Ala Arg Asn Gln
                85                 90                 95

Tyr Ser Gly Tyr Gly Phe Ser Phe Trp Gly Gln Gly Thr Leu Val Thr
                100                105                110

Val Ser Ser
        115

<210> SEQ ID NO 265
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RABBABABA_1_115; 16 6 HC humanized 609

<400> SEQUENCE: 265

Val Gln Leu Val Glu Ser Gly Gly Gly Leu Val Gln Pro Gly Gly Ser
1               5                  10                 15

Leu Arg Leu Ser Cys Thr Thr Ser Gly Ser Asp Ile Ser Ser Tyr His
```

```
                    20                  25                  30

Met Gly Trp Val Arg Gln Val Pro Gly Lys Gly Leu Glu Trp Val Ser
            35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Ser Tyr Leu Gln Met Thr
65                  70                  75                  80

Ser Leu Thr Pro Glu Asp Thr Ala Val Tyr Tyr Cys Ala Lys Asn Gln
                85                  90                  95

Tyr Ser Gly Tyr Gly Phe Ser Phe Trp Gly Gln Gly Thr Val Val Ser
                100                 105                 110

Val Ser Ser
        115

<210> SEQ ID NO 266
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YABBABABA_4_115; 16 6 HC humanized 910; 16 6
      HC humanized 218; 16 6 HC humanized 912; 16 6 HC humanized 917

<400> SEQUENCE: 266

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
                20                  25                  30

Met Gly Trp Ile Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Lys Ser
    50                  55                  60

Arg Val Thr Ile Ser Thr Ser Lys Asn Gln Leu Ser Leu Lys Leu Thr
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
                100                 105                 110

Val Ser Ser
        115

<210> SEQ ID NO 267
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GEBBABABA_1_115; 16 6 HC humanized 136

<400> SEQUENCE: 267

Val Gln Leu Gln Gln Ser Gly Pro Gly Leu Val Lys Pro Ser Glu Thr
1               5                   10                  15

Leu Pro Leu Thr Cys Thr Val Ser Gly Ser Asp Ile Ser Ser Tyr His
                20                  25                  30

Met Gly Trp Ile Arg Gln Pro Pro Gly Lys Gly Leu Glu Trp Ile Gly
            35                  40                  45
```

```
Ile Ile Val Ser Ser Gly Ser Ala Tyr Tyr Ala Thr Trp Ala Lys Asn
 50                  55                  60

Arg Val Thr Ile Ser Thr Ser Lys Asn Gln Phe Ser Leu Lys Leu Ser
 65                  70                  75                  80

Ser Val Thr Ala Ala Asp Thr Ala Leu Tyr Tyr Cys Ala Arg Asn Gln
                 85                  90                  95

Tyr Ser Gly Tyr Gly Phe Ser Phe Trp Gly Gln Gly Thr Leu Val Thr
                100                 105                 110

Val Ser Ser
        115

<210> SEQ ID NO 268
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KEBBABABA_1_115; 16 6 HC humanized 109

<400> SEQUENCE: 268

Val Gln Leu Val Glu Ser Gly Pro Gly Leu Val Lys Pro Ser Gln Thr
 1               5                  10                  15

Leu Ser Leu Thr Cys Thr Val Ser Gly Ser Asp Ile Ser Ser Tyr His
                20                  25                  30

Met Gly Trp Ile Arg Gln Pro Pro Gly Lys Gly Leu Glu Tyr Ile Gly
            35                  40                  45

Ile Ile Val Ser Ser Gly Ser Ala Tyr Tyr Ala Thr Trp Ala Lys Ser
 50                  55                  60

Arg Leu Thr Met Ser Val Asp Thr Ser Asn Tyr Gln Leu Lys Leu Ser
 65                  70                  75                  80

Ser Val Thr Ala Ala Asp Thr Ala Val Tyr Tyr Cys Ala Arg Asn Gln
                 85                  90                  95

Tyr Ser Gly Tyr Gly Phe Ser Phe Trp Gly Gln Gly Thr Thr Val Thr
                100                 105                 110

Val Ser Ser
        115

<210> SEQ ID NO 269
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LEBBABABA_1_115; 16 6 HC humanized 103

<400> SEQUENCE: 269

Val Gln Leu Gln Gln Ser Gly Pro Gly Leu Val Lys Pro Ser Gly Thr
 1               5                  10                  15

Leu Ser Leu Thr Cys Asp Val Ser Gly Ser Asp Ile Ser Ser Tyr His
                20                  25                  30

Met Gly Trp Val Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Lys Ser
 50                  55                  60

Arg Val Thr Ile Ser Lys Ser Lys Asn Gln Phe Ser Leu Arg Leu Thr
```

```
                65                  70                  75                  80
Ser Val Thr Ala Ala Asp Thr Ala Val Tyr Tyr Cys Ala Arg Asn Gln
                    85                  90                  95

Tyr Ser Gly Tyr Gly Phe Ser Phe Trp Gly Gln Gly Thr Leu Val Thr
                    100                 105                 110

Val Ser Ser
        115

<210> SEQ ID NO 270
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NEBBABABA_6_115; 16 6 HC humanized 902; 16 6
      HC humanized 1982; 16 6 HC humanized 734; 16 6 HC humanized 920;
      16 6 HC humanized 149

<400> SEQUENCE: 270

Val Gln Leu Val Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
                20                  25                  30

Met Gly Trp Ile Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Lys Ser
        50                  55                  60

Arg Val Thr Ile Ser Thr Ser Lys Asn Gln Phe Ser Leu Lys Leu Ser
65                  70                  75                  80

Ser Val Thr Ala Ala Asp Thr Ala Val Tyr Tyr Cys Ala Arg Asn Gln
                    85                  90                  95

Tyr Ser Gly Tyr Gly Phe Ser Phe Trp Gly Gln Gly Thr Leu Val Thr
                    100                 105                 110

Val Ser Ser
        115

<210> SEQ ID NO 271
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PEBBABABA_1_115; 16 6 HC humanized 851

<400> SEQUENCE: 271

Val Gln Leu Val Gln Ser Gly Gly Gly Val Val Gln Pro Gly Gly Ser
1               5                   10                  15

Leu Arg Val Ser Cys Ala Ala Ser Gly Ser Asp Ile Ser Ser Tyr His
                20                  25                  30

Met Gly Trp Val Arg Gln Ala Pro Gly Lys Gly Leu Glu Trp Met Ala
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ser Thr Val Ser Leu Gln Met Ser
65                  70                  75                  80

Ser Leu Arg Ala Glu Asp Thr Ala Val Tyr Tyr Cys Ala Lys Asn Gln
```

```
                    85                  90                  95

Tyr Ser Gly Tyr Gly Phe Ser Phe Trp Gly Arg Gly Thr Leu Val Thr
                    100                 105                 110

Val Ser Ser
        115

<210> SEQ ID NO 272
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SEBBABABA_1_115; 16 6 HC humanized 926

<400> SEQUENCE: 272

Val Gln Leu Val Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
                20                  25                  30

Met Gly Trp Ile Arg Gln His Ser Gly Lys Thr Leu Glu Trp Ile Gly
        35                  40                  45

Ile Ile Val Ser Ser Gly Ser Ala Tyr Tyr Ala Thr Trp Ala Glu Ser
    50                  55                  60

Arg Val Thr Ile Ser Ala Asp Thr Ser Lys Ile Ser Leu Lys Leu Ser
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
                100                 105                 110

Val Ser Ser
        115

<210> SEQ ID NO 273
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VEBBABABA_1_115; 16 6 HC humanized 904

<400> SEQUENCE: 273

Val Gln Leu Val Glu Ser Gly Pro Gly Leu Val Lys Pro Ser Gln Thr
1               5                   10                  15

Leu Ser Leu Thr Cys Asn Val Ser Gly Ser Asp Ile Ser Ser Tyr His
                20                  25                  30

Met Gly Trp Ile Arg Gln Ser Pro Gly Lys Gly Leu Glu Trp Ile Gly
        35                  40                  45

Ile Ile Val Ser Ser Gly Ser Ala Tyr Tyr Ala Thr Trp Ala Arg Ser
    50                  55                  60

Arg Val Thr Ile Ser Ala Asp Thr Ser Lys Val Ser Leu Glu Leu Ser
65                  70                  75                  80

Pro Met Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
                100                 105                 110
```

Val Ser Ser
        115

<210> SEQ ID NO 274
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_WEBBABABA_1_115; 16 6 HC humanized 903

<400> SEQUENCE: 274

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln Pro Pro Gly Thr Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Val Thr Ile Ser Gly Asp Thr Ser Lys Phe Ser Leu Met Leu Arg
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 275
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_YEBBABABA_1_115; 16 6 HC humanized 946

<400> SEQUENCE: 275

Val Gln Leu Val Glu Ser Gly Gly Gly Leu Ile Lys Pro Gly Gly Ser
1               5                   10                  15

Leu Arg Leu Ser Cys Glu Val Pro Gly Ser Asp Ile Ser Ser Tyr His
            20                  25                  30

Met Gly Trp Val Arg Gln Gly Pro Gly Arg Gly Leu Glu Trp Val Gly
        35                  40                  45

Ile Ile Val Ser Ser Gly Ser Ala Tyr Tyr Ala Thr Trp Ala Arg Gly
    50                  55                  60

Arg Phe Thr Ile Ser Arg Ser Lys Ser Thr Val Tyr Leu Glu Met Asn
65                  70                  75                  80

Ala Leu Lys Thr Glu Asp Thr Gly Ile Tyr Tyr Cys Val Thr Asn Gln
                85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 276

```
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZEBBABABA_1_115; 16 6 HC humanized 882

<400> SEQUENCE: 276
```

Gln Ser Leu Glu Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Pro Pro Gly Lys Gly Leu Glu Trp Val Gly
        35                  40                  45

Ile Ile Val Ser Ser Gly Ser Ala Tyr Tyr Ala Thr Trp Ala Lys Gly
50                  55                  60

Arg Phe Thr Ile Ser Arg Ser Lys Ser Thr Val Tyr Leu Gln Met Asn
65                  70                  75                  80

Ser Leu Lys Thr Glu Asp Thr Ala Val Tyr Tyr Cys Thr Ala Asn Gln
                85                  90                  95

Tyr Ser Gly Tyr Gly Phe Ser Phe Trp Gly Gln Gly Met Leu Val Thr
            100                 105                 110

Val Ser Ser
        115

```
<210> SEQ ID NO 277
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CIBBABABA_1_115; 16 6 HC humanized 2041

<400> SEQUENCE: 277
```

Gln Ser Leu Val Gln Ser Gly Thr Glu Val Arg Lys Pro Gly Ala Ser
1               5                   10                  15

Val Lys Val Ser Cys Lys Ala Ser Gly Ser Asp Ile Ser Ser Tyr His
            20                  25                  30

Met Gly Trp Val Arg Gln Ala Pro Gly Gln Gly Leu Glu Trp Met Gly
        35                  40                  45

Ile Ile Val Ser Ser Gly Ser Ala Tyr Tyr Ala Thr Trp Ala Gln Gly
50                  55                  60

Arg Val Thr Met Ser Asp Thr Ser Thr Val Tyr Met Glu Leu Ser
65                  70                  75                  80

Ser Leu Thr Ser Glu Asp Thr Ala Ile Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

```
<210> SEQ ID NO 278
<211> LENGTH: 115
<212> TYPE: PRT
<213> ORGANISM: Artificial Sequence
<220> FEATURE:
<223> OTHER INFORMATION: Description of Artificial Sequence: Synthetic
```

```
    polypeptide
<220> FEATURE:
<223> OTHER INFORMATION: cl_KIBBABABA_1_115; 16 6 HC humanized 1944

<400> SEQUENCE: 278

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Asn
50                  55                  60

Arg Val Thr Ile Ser Thr Ser Lys Asn Gln Phe Ser Leu Arg Leu Asn
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 279
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LIBBABABA_4_115; 16 6 HC humanized 1895; 16
      6 HC humanized 1992; 16 6 HC humanized 1995; 16 6 HC humanized
      1949

<400> SEQUENCE: 279

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Val Trp Val Ser
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ala Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 280
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SIBBABABA_2_115; 16 6 HC humanized 993; 16 6
```

HC humanized 994

<400> SEQUENCE: 280

Val Gln Leu Val Glu Ser Gly Gly Gly Leu Ile Gln Pro Gly Arg Pro
1               5                   10                  15

Leu Arg Leu Ser Cys Ser Gly Gly Ser Asp Ile Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asp Ser Val Val His Leu Gln Met Asn
65                  70                  75                  80

Ser Leu Arg Ser Glu Asp Thr Ala Val Tyr Tyr Cys Thr Arg Asn Gln
                85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 281
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TIBBABABA_2_115; 16 6 HC humanized 956; 16 6
      HC humanized 965

<400> SEQUENCE: 281

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln His Pro Gly Lys Gly Leu Glu Trp Ile Gly
        35                  40                  45

Ile Ile Val Ser Ser Gly Ser Ala Tyr Tyr Ala Thr Trp Ala Glu Ser
    50                  55                  60

Arg Leu Thr Ile Ser Ala Asp Thr Ser Asn Ile Gln Leu Arg Leu Ser
65                  70                  75                  80

Ser Val Thr Ala Ala Asp Thr Ala Val Tyr Phe Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 282
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WIBBABABA_1_115; 16 6 HC humanized 278

<400> SEQUENCE: 282

```
Val Gln Leu Val Gln Ser Gly Gly Gly Leu Val Lys Pro Gly Gly Ser
1               5                   10                  15

Leu Arg Leu Ser Cys Glu Ala Ser Gly Ser Asp Ile Ser Ser Tyr His
                20                  25                  30

Met Gly Trp Ile Arg Gln Ala Pro Gly Lys Gly Leu Glu Trp Val Gly
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asp Ser Thr Leu Tyr Leu Gln Val Asn
65                  70                  75                  80

Ser Leu Lys Thr Glu Asp Ser Ala Val Tyr Tyr Cys Thr Thr Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 283
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GOBBABABA_1_115; 16 6 HC humanized 1894

<400> SEQUENCE: 283

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
                20                  25                  30

Met Gly Trp Val Arg Gln Ala Pro Gly Lys Gly Leu Glu Trp Val Ser
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Phe Ser Asp Tyr Trp Leu Val Thr
            100                 105                 110

Val Ser Ser
        115

<210> SEQ ID NO 284
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MOBBABABA_3_115; 16 6 HC humanized 1917; 16
      6 HC humanized 677; 16 6 HC humanized 267

<400> SEQUENCE: 284

Gln Ser Leu Glu Glu Ser Gly Gly Gly Val Val Gln Pro Gly Arg Ser
1               5                   10                  15

Leu Arg Leu Ser Cys Ala Ala Ser Gly Ser Asp Ile Ser Ser Tyr His
```

```
                20                  25                  30

Met Gly Trp Val Arg Gln Ala Pro Gly Lys Gly Leu Glu Trp Val Ala
            35                  40                  45

Ile Ile Val Ser Ser Gly Ser Ala Tyr Tyr Ala Thr Trp Ala Lys Arg
        50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 285
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_POBBABABA_1_115; 16 6 HC humanized 2038

<400> SEQUENCE: 285

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ala
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Pro Thr Gly Tyr Tyr Tyr Met
            100                 105                 110

Asp Val Ser
        115

<210> SEQ ID NO 286
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c1_QOBBABABA_1_115; 16 6 HC humanized 23

<400> SEQUENCE: 286

Gln Ser Leu Leu Glu Ser Gly Gly Asp Leu Val Gln Pro Gly Gly Ser
1               5                   10                  15

Leu Arg Leu Ser Cys Glu Ala Ser Gly Ser Asp Ile Ser Ser Tyr His
            20                  25                  30

Met Gly Trp Val Arg Gln Ala Pro Gly Lys Gly Leu Glu Trp Val Ser
            35                  40                  45
```

Ile Ile Val Ser Ser Gly Ser Ala Tyr Tyr Ala Thr Trp Ala Lys Gly
50                      55                      60

Arg Phe Thr Ile Ser Arg Asp Lys Ser Thr Leu Phe Leu Gln Met His
65                      70                      75                      80

Ser Leu Arg Val Glu Asp Thr Ala Val Tyr Tyr Cys Ala Lys Asn Gln
                85                      90                      95

Tyr Ser Gly Tyr Gly Phe Ser Phe Trp Gly Gln Gly Thr Thr Val Thr
                100                     105                     110

Val Ser Ser
        115

<210> SEQ ID NO 287
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VOBBABABA_1_115; 16 6 HC humanized 1013

<400> SEQUENCE: 287

Val Gln Leu Val Gln Ser Gly Gly Gly Val Val Gln Pro Gly Arg Ser
1               5                       10                      15

Leu Arg Leu Ser Cys Glu Val Ser Gly Ser Asp Ile Ser Ser Tyr His
                20                      25                      30

Met Gly Trp Val Arg Gln Ala Pro Gly Lys Gly Leu Glu Trp Val Ala
                35                      40                      45

Ile Ile Val Ser Ser Gly Ser Ala Tyr Tyr Ala Thr Trp Ala Lys Gly
50                      55                      60

Arg Phe Thr Ile Ser Arg Ser Asn Asn Thr Leu Tyr Leu Gln Met Asn
65                      70                      75                      80

Ser Leu Thr Ala Glu Asp Thr Ala Leu Tyr Phe Cys Ala Arg Asn Gln
                85                      90                      95

Tyr Ser Gly Tyr Gly Phe Ser Phe Trp Gly Lys Gly Thr Thr Val Thr
                100                     105                     110

Val Ser Ser
        115

<210> SEQ ID NO 288
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YOBBABABA_1_115; 16 6 HC humanized 113

<400> SEQUENCE: 288

Leu Gln Leu Gln Glu Ser Gly Pro Gly Leu Val Lys Pro Ser Gln Thr
1               5                       10                      15

Leu Ser Leu Thr Cys Ser Val Ser Gly Ser Asp Ile Ser Ser Tyr His
                20                      25                      30

Met Gly Trp Ile Arg Gln His Pro Gly Lys Gly Leu Trp Ile Gly
                35                      40                      45

Ile Ile Val Ser Ser Gly Ser Ala Tyr Tyr Ala Thr Trp Ala Lys Ser
50                      55                      60

Arg Ile Thr Ile Ser Thr Ser Lys Asn Gln Phe Ser Leu Lys Leu Thr
65                      70                      75                      80

Ser Val Thr Ala Ala Asp Thr Ala Leu Tyr Tyr Cys Ala Arg Asn Gln
            85                  90                  95

Tyr Ser Gly Tyr Gly Phe Ser Phe Trp Gly Arg Gly Thr Leu Val Thr
            100                 105                 110

Val Ser Ser
        115

<210> SEQ ID NO 289
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HUBBABABA_1_115; 16 6 HC humanized 12

<400> SEQUENCE: 289

Val Gln Leu Val Gln Ser Gly Gly Gly Val Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Gln Gly
    50                  55                  60

Arg Val Thr Ile Ser Arg Asp Asn Ser Thr Val His Leu Gln Ile Thr
65                  70                  75                  80

Ser Leu Lys Ser Glu Asp Thr Ala Val Tyr Tyr Cys Ala Lys Asn Gln
            85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 290
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LUBBABABA_1_115; 16 6 HC humanized 273

<400> SEQUENCE: 290

Val Gln Leu Val Gln Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Ser Gly Lys Gly Leu Glu Trp Ile Gly
        35                  40                  45

Ile Ile Val Ser Ser Gly Ser Ala Tyr Tyr Ala Thr Trp Ala Lys Gly
    50                  55                  60

Arg Phe Thr Val Ser Arg Ser Gln Asn Ser Val Phe Leu Gln Met Asn
65                  70                  75                  80

Ser Leu Glu Thr Glu Asp Thr Ala Val Tyr Tyr Cys Ala Arg Asn Gln
            85                  90                  95

Tyr Ser Gly Tyr Gly Phe Ser Phe Trp Gly Gln Gly Thr Leu Val Thr

Val Ser Ser
        115

<210> SEQ ID NO 291
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NUBBABABA_1_115; 16 6 HC humanized 879

<400> SEQUENCE: 291

Gln Ser Leu Glu Glu Ser Gly Gly Gly Leu Val Gln Pro Gly Gly Ser
1               5                   10                  15

Leu Arg Leu Ser Cys Thr Ala Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Ser Ser Thr Leu Tyr Leu Gln Met Asn
65                  70                  75                  80

Asn Leu Arg Val Glu Asp Thr Ala Leu Tyr Tyr Cys Ala His Asn Gln
                85                  90                  95

Tyr Ser Gly Tyr Gly Phe Ser Phe Trp Gly Arg Gly Thr Gln Val Thr
            100                 105                 110

Val Ser Ser
        115

<210> SEQ ID NO 292
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TUBBABABA_1_115; 16 6 HC humanized 1934

<400> SEQUENCE: 292

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Gly Ile Phe Asp Tyr Trp Val Thr
            100                 105                 110

Val Ser Ser
        115

<210> SEQ ID NO 293
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: cl_VUBBABABA_1_115; 16 6 HC humanized 200

<400> SEQUENCE: 293

```
Val Gln Leu Gln Glu Ser Gly Pro Gly Leu Val Lys Pro Ser Glu Thr
1               5                   10                  15

Leu Ser Leu Thr Cys Ser Val Ser Gly Ser Asp Ile Ser Ser Tyr His
            20                  25                  30

Met Gly Trp Ile Arg Gln Pro Ala Gly Lys Gly Leu Glu Trp Ile Gly
        35                  40                  45

Ile Ile Val Ser Ser Gly Ser Ala Tyr Tyr Ala Thr Trp Ala Arg Ser
    50                  55                  60

Arg Val Thr Met Ser Met Ser Lys Asn His Phe Ser Leu Lys Leu Arg
65                  70                  75                  80

Ser Val Thr Ala Ala Asp Thr Ala Val Tyr Phe Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115
```

<210> SEQ ID NO 294
<211> LENGTH: 115
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: cl_WUBBABABA_1_115; 16 6 HC humanized 1977

<400> SEQUENCE: 294

```
Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Ser Lys Asn Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Thr Cys Pro Tyr Phe Asp Tyr Trp
            100                 105                 110

Val Ser Ser
        115
```

<210> SEQ ID NO 295
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: cl_XUBBABABA_1_115; 16 6 HC humanized 2027

<400> SEQUENCE: 295

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Glu Gly
50                  55                  60

Arg Phe Thr Ile Ser Arg Asp Asn Ser Thr Leu Tyr Leu Gln Met Tyr
65                  70                  75                  80

Ser Leu Arg Thr Glu Asp Thr Ala Val Tyr Tyr Cys Ala Arg Asn Gln
                85                  90                  95

Tyr Ser Gly Tyr Gly Phe Ser Phe Tyr Tyr Tyr Gly Met Gly Val Trp
            100                 105                 110

Val Ser Ser
        115

<210> SEQ ID NO 296
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YUBBABABA_1_115; 16 6 HC humanized 1958

<400> SEQUENCE: 296

Val His Leu Val Glu Ser Gly Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Glu Gly
50                  55                  60

Arg Phe Thr Ile Ser Arg Asp Asn Ser Lys Leu Tyr Leu Gln Met Asn
65                  70                  75                  80

Ser Leu Arg Ala Glu Asp Ser Ala Thr Tyr Tyr Cys Ala Arg Asn Gln
                85                  90                  95

Tyr Ser Gly Tyr Gly Phe Ser Phe Phe Gly Pro Tyr Tyr Tyr
            100                 105                 110

Tyr Met Ser
        115

<210> SEQ ID NO 297
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BACBABABA_1_115; 16 6 HC humanized 1905
```

<400> SEQUENCE: 297

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
                20                  25                  30

Met Gly Trp Val Arg Gln Ala Pro Gly Lys Gly Leu Glu Trp Val Ser
            35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Leu Tyr Tyr Cys Ala Arg Asn Gln
                85                  90                  95

Tyr Ser Gly Tyr Gly Phe Ser Phe Val Arg Gly Gly Tyr Phe Tyr His
                100                 105                 110

Met Asp Ser
        115

<210> SEQ ID NO 298
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CACBABABA_1_110; 16 6 LC humanized 586

<400> SEQUENCE: 298

Ile Val Leu Thr Gln Thr Pro Ser Ser Leu Ser Ala Ser Val Gly Asp
1               5                   10                  15

Arg Ile Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
    50                  55                  60

Gly Ser Arg Ser Gly Thr Asp Phe Thr Phe Thr Ile Ser Ser Leu Arg
65                  70                  75                  80

Pro Glu Asp Ile Ala Thr Tyr Tyr Cys Leu Gly Gly Tyr Asp Asp Asp
                85                  90                  95

Gly Glu Thr Ala Phe Gly Gly Gly Thr Lys Val Glu Ile Lys
                100                 105                 110

<210> SEQ ID NO 299
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DACBABABA_27_110; 16 6 LC humanized 411; 16
      6 LC humanized 1004; 16 6 LC humanized 587; 16 6 LC humanized 305;
      16 6 LC humanized 988

<400> SEQUENCE: 299

Ile Val Leu Thr Gln Ser Pro Ser Ser Leu Ser Ala Ser Val Gly Asp
1               5                   10                  15

```
Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Lys Val Glu Ile Lys
            100                 105                 110

<210> SEQ ID NO 300
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FACBABABA_15_110; 16 6 LC humanized 372; 16
      6 LC humanized 1877; 16 6 LC humanized 1012; 16 6 LC humanized
      860; 16 6 LC humanized 283

<400> SEQUENCE: 300

Ile Gln Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
            100                 105                 110

<210> SEQ ID NO 301
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GACBABABA_1_110; 16 6 LC humanized 1996

<400> SEQUENCE: 301

Val Val Leu Thr Gln Thr Pro Ser Pro Val Ser Thr Ala Val Gly Gly
1               5                   10                  15

Thr Val Thr Leu Ser Cys Gln Ser Ser His Ser Val Tyr Tyr Gly Asp
            20                  25                  30

Trp Leu Ala Trp Tyr Gln Gln Lys Pro Gly Gln Ala Pro Arg Leu Leu
        35                  40                  45

Ile Tyr Arg Ala Ser Asn Leu Ala Ser Gly Ile Pro Asp Arg Phe Ser
    50                  55                  60
```

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Leu Gly Gly Tyr Asp Asp Asp
                85                  90                  95

Gly Glu Thr Ala Lys Gly Pro Gly Thr Glu Val Val Val Lys
            100                 105                 110

<210> SEQ ID NO 302
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HACBABABA_2_110; 16 6 LC humanized 1907; 16
      6 LC humanized 716

<400> SEQUENCE: 302

Leu Val Met Thr Gln Ser Pro Ser Ser Leu Ser Ala Ser Glu Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Arg Ala Pro Lys Leu Leu
            35                  40                  45

Ile His Arg Ala Ser Asn Leu Ala Ser Gly Val Pro Ser Arg Phe Ser
        50                  55                  60

Gly Ser Gly Ser Gly Thr Glu Phe Thr Leu Thr Ile Ser Gly Leu Gln
65                  70                  75                  80

Ser Glu Asp Phe Ala Thr Tyr Tyr Cys Leu Gly Gly Tyr Asp Asp Asp
                85                  90                  95

Gly Glu Thr Ala Phe Gly Gly Gly Thr Thr Val Asp Val Lys
            100                 105                 110

<210> SEQ ID NO 303
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LACBABABA_2_110; 16 6 LC humanized 1945; 16
      6 LC humanized 1451

<400> SEQUENCE: 303

Val Glu Leu Thr Gln Pro Pro Ser Pro Val Ser Ala Ala Pro Gly Gln
1               5                   10                  15

Lys Val Thr Ile Ser Cys Gln Ser Ser His Ser Val Tyr Tyr Gly Asp
                20                  25                  30

Trp Leu Ala Trp Tyr Gln Gln Leu Pro Gly Thr Ala Pro Lys Leu Leu
            35                  40                  45

Ile Tyr Arg Ala Ser Asn Leu Ala Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Leu Gly Gly Tyr Asp Asp Asp
                85                  90                  95

Gly Glu Thr Ala Phe Gly Gly Gly Thr Arg Leu Thr Val Leu
            100                 105                 110
```

```
<210> SEQ ID NO 304
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PACBABABA_10_110; 16 6 LC humanized 1971; 16
      6 LC humanized 2041; 16 6 LC humanized 2038; 16 6 LC humanized
      2008; 16 6 LC humanized 1992

<400> SEQUENCE: 304

Val Val Leu Thr Gln Thr Pro Ser Pro Val Ser Thr Ala Val Gly Gly
1               5                   10                  15

Thr Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
                100                 105                 110

<210> SEQ ID NO 305
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QACBABABA_5_110; 16 6 LC humanized 802; 16 6
      LC humanized 609; 16 6 LC humanized 851; 16 6 LC humanized 908; 16
      6 LC humanized 108

<400> SEQUENCE: 305

Val Val Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Lys Val Glu Ile Lys
                100                 105                 110

<210> SEQ ID NO 306
<211> LENGTH: 110
<212> TYPE: PRT
<213> ORGANISM: Artificial Sequence
<220> FEATURE:
<223> OTHER INFORMATION: Description of Artificial Sequence: Synthetic
```

-continued

```
                                      polypeptide
<220> FEATURE:
<223> OTHER INFORMATION: cl_CECBABABA_7_110; 16 6 LC humanized 253; 16 6
      LC humanized 103; 16 6 LC humanized 882; 16 6 LC humanized 1982;
      16 6 LC humanized 734

<400> SEQUENCE: 306

Ile Val Leu Thr Gln Ser Pro Ser Ser Leu Ser Ala Ser Val Gly Asp
1               5                   10                  15

Arg Val Thr Ile Thr Cys Gln Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Ser Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
            100                 105                 110

<210> SEQ ID NO 307
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KECBABABA_2_110; 16 6 LC humanized 109; 16 6
      LC humanized 334

<400> SEQUENCE: 307

Ile Gln Leu Thr Gln Ser Pro Ser Phe Val Ser Ala Ser Val Gly Asp
1               5                   10                  15

Arg Ile Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
            100                 105                 110

<210> SEQ ID NO 308
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RECBABABA_2_110; 16 6 LC humanized 17; 16 6
      LC humanized 21

<400> SEQUENCE: 308

Ile Gln Leu Thr Gln Ser Pro Ser Ser Leu Ser Ala Ala Val Gly Asp
```

```
                1               5                   10                  15
            Arg Val Thr Ile Ala Cys Gln Ser Ser His Ser Val Tyr Tyr Gly Asp
                        20                  25                  30

Trp Leu Ala Trp Tyr Gln Gln Lys Pro Gly Lys Ala Pro Lys Leu Leu
                        35                  40                  45

Ile Tyr Arg Ala Ser Asn Leu Ala Ser Gly Val Pro Ser Arg Phe Ser
                        50                  55                  60

Gly Ser Gly Ser Gly Thr Asp Phe Thr Leu Ser Ile Ser Ser Leu Gln
             65                 70                  75                  80

Pro Glu Asp Phe Ala Thr Tyr Tyr Cys Leu Gly Gly Tyr Asp Asp Asp
                        85                  90                  95

Gly Glu Thr Ala Phe Gly Gly Gly Thr Lys Val Gln Met Lys
                        100                 105                 110

<210> SEQ ID NO 309
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DICBABABA_1_110; 16 6 LC humanized 202

<400> SEQUENCE: 309

Ile Arg Met Thr Gln Ser Pro Ser Ser Leu Ser Ala Ser Val Gly Asp
            1               5                   10                  15

Arg Val Thr Ile Thr Cys Gln Ser Ser His Ser Val Tyr Tyr Gly Asp
                        20                  25                  30

Trp Leu Ala Trp Tyr Gln Gln Lys Pro Gly Lys Val Pro Lys Leu Leu
                        35                  40                  45

Ile Tyr Arg Ala Ser Asn Leu Ala Ser Gly Val Pro Ser Arg Phe Ser
                        50                  55                  60

Gly Ser Gly Ser Gly Thr Asp Phe Thr Leu Thr Ile Ser Ser Leu Gln
             65                 70                  75                  80

Pro Glu Asp Val Ala Thr Tyr Tyr Cys Leu Gly Gly Tyr Asp Asp Asp
                        85                  90                  95

Gly Glu Thr Ala Phe Gly Pro Gly Thr Lys Val Val Val Lys
                        100                 105                 110

<210> SEQ ID NO 310
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FICBABABA_14_110; 16 6 LC humanized 192; 16
      6 LC humanized 956; 16 6 LC humanized 230; 16 6 LC humanized 880;
      16 6 LC humanized 2056

<400> SEQUENCE: 310

Val Val Leu Thr Gln Ser Pro Ser Ser Leu Ser Ala Ser Val Gly Asp
            1               5                   10                  15

Arg Val Thr Ile Thr Cys Gln Ser Ser His Ser Val Tyr Tyr Gly Asp
                        20                  25                  30

Trp Leu Ala Trp Tyr Gln Gln Lys Pro Gly Lys Ala Pro Lys Leu Leu
                        35                  40                  45

Ile Tyr Arg Ala Ser Asn Leu Ala Ser Gly Val Pro Ser Arg Phe Ser
```

```
                    50                  55                  60
Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Leu Gly Gly Tyr Asp Asp Asp
                     85                  90                  95

Gly Glu Thr Ala Phe Gly Gln Gly Thr Lys Val Glu Ile Lys
                100                 105                 110

<210> SEQ ID NO 311
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NICBABABA_2_110; 16 6 LC humanized 1938; 16
      6 LC humanized 762

<400> SEQUENCE: 311

Val Glu Leu Thr Gln Ser Pro Asp Ser Leu Ala Val Ser Leu Gly Glu
 1               5                  10                  15

Arg Ala Thr Ile Asn Cys Gln Ser Ser His Ser Val Tyr Gly Asp
                 20                  25                  30

Trp Leu Ala Trp Tyr Gln Gln Lys Pro Gly Gln Pro Lys Leu Leu
             35                  40                  45

Ile Tyr Arg Ala Ser Asn Leu Ala Ser Gly Val Pro Asp Arg Phe Ser
 50                  55                  60

Gly Ser Gly Ser Gly Thr Asp Phe Thr Leu Thr Ile Ser Ser Leu Gln
 65                  70                  75                  80

Ala Glu Asp Val Ala Val Tyr Tyr Cys Leu Gly Gly Tyr Asp Asp
                     85                  90                  95

Gly Glu Thr Ala Phe Gly Gly Gly Thr Lys Val Glu Ile Lys
                100                 105                 110

<210> SEQ ID NO 312
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WICBABABA_1_110; 16 6 LC humanized 278

<400> SEQUENCE: 312

Leu Val Leu Thr Gln Ser Pro Ser Ser Leu Ser Ala Ser Val Gly Asp
 1               5                  10                  15

Arg Val Thr Ile Thr Cys Gln Ser Ser His Ser Val Tyr Gly Asp
                 20                  25                  30

Trp Leu Ala Trp Cys Gln Gln Lys Pro Gly Lys Ser Pro Thr Leu Leu
             35                  40                  45

Ile Tyr Arg Ala Ser Asn Leu Ala Ser Gly Val Pro Ser Arg Phe Ser
 50                  55                  60

Gly Ser Gly Ser Gly Thr Gly Phe Thr Leu Thr Ile Ser Gly Leu Gln
 65                  70                  75                  80

Pro Glu Asp Phe Ala Thr Tyr Tyr Cys Leu Gly Gly Tyr Asp Asp
                     85                  90                  95

Gly Glu Thr Ala Phe Gly Gly Gly Thr Lys Val Glu Ile Arg
                100                 105                 110
```

<210> SEQ ID NO 313
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YICBABABA_1_110; 16 6 LC humanized 169

<400> SEQUENCE: 313

Ile Val Leu Thr Gln Ser Pro Ser Phe Leu Ser Ala Phe Val Gly Asp
1               5                   10                  15

Arg Ile Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Gly Leu Gln
65                  70                  75                  80

Pro Glu Asp Phe Ala Ser Tyr Tyr Cys Leu Gly Gly Tyr Asp Asp Asp
                85                  90                  95

Gly Glu Thr Ala Phe Gly Gly Gly Thr Lys Leu Glu Ile Lys
            100                 105                 110

<210> SEQ ID NO 314
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GOCBABABA_1_110; 16 6 LC humanized 1894

<400> SEQUENCE: 314

Val Val Leu Thr Gln Thr Pro Ser Pro Val Ser Thr Ala Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Arg Gln Lys Pro Gly Lys Val Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Gly Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 315
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LOCBABABA_1_110; 16 6 LC humanized 657

<400> SEQUENCE: 315

Val Val Leu Thr Gln Thr Pro Ser Pro Val Ser Thr Val Gly Asp
1               5                   10                  15

Arg Val Ser Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
50                  55                  60

Gly Ser Gly Ser Gly Thr Asp Phe Thr Leu Thr Ile Thr Ser Leu Gln
65                  70                  75                  80

Pro Val Asp Phe Ala Thr Tyr Tyr Cys Leu Gly Gly Tyr Asp Asp Asp
                85                  90                  95

Gly Glu Thr Ala Phe Gly Pro Gly Thr Thr Val Asp Ala Lys
            100                 105                 110

<210> SEQ ID NO 316
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YOCBABABA_1_110; 16 6 LC humanized 113

<400> SEQUENCE: 316

Ile Val Leu Thr Gln Ser Pro Ser Ser Val Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Leu Lys Pro Gly Lys Ala Pro Lys Leu Leu
        35                  40                  45

Ile Asn Arg Ala Ser Asn Leu Ala Ser Gly Val Pro Ser Arg Phe Ser
50                  55                  60

Gly Ser Gly Ser Gly Thr Asp Phe Thr Leu Thr Ile Ser Gly Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Pro Gly Thr Thr Val Asp Ile Lys
            100                 105                 110

<210> SEQ ID NO 317
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MUCBABABA_3_110; 16 6 LC humanized 2032; 16
      6 LC humanized 200; 16 6 LC humanized 1905

<400> SEQUENCE: 317

Val Val Leu Thr Gln Thr Pro Ser Pro Val Ser Thr Ala Val Gly Gly
1               5                   10                  15

Thr Gly Thr Ile Asn Cys Gln Ser Ser His Ser Val Tyr Tyr Gly Asp
            20                  25                  30

Trp Leu Ala Trp Tyr Gln Gln Lys Pro Gly Gln Pro Pro Lys Leu Leu

```
                35                  40                  45

Ile Tyr Arg Ala Ser Asn Leu Ala Ser Gly Val Pro Asp Arg Phe Ser
         50                  55                  60

Gly Ser Gly Ser Gly Thr Asp Phe Thr Leu Thr Ile Ser Ser Leu Gln
 65                  70                  75                  80

Ala Glu Asp Val Ala Val Tyr Tyr Cys Leu Gly Gly Tyr Asp Asp Asp
                 85                  90                  95

Gly Glu Thr Ala Phe Gly Gly Gly Thr Lys Val Val Val Lys
            100                 105                 110

<210> SEQ ID NO 318
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RUCBABABA_1_110; 16 6 LC humanized 1995
<220> FEATURE:
<221> NAME/KEY: MOD_RES
<222> LOCATION: (45)..(45)
<223> OTHER INFORMATION: Any amino acid

<400> SEQUENCE: 318

Val Val Leu Thr Gln Thr Pro Ser Pro Val Ser Thr Ala Val Gly Gly
 1               5                  10                  15

Thr Val Thr Ile Asn Cys Gln Ser Ser His Ser Val Tyr Tyr Gly Asp
                20                  25                  30

Trp Leu Ala Trp Tyr Gln Gln Lys Pro Gly Gln Pro Xaa Lys Leu Leu
            35                  40                  45

Ile Tyr Arg Ala Ser Asn Leu Ala Ser Gly Val Pro Asp Arg Phe Ser
         50                  55                  60

Gly Ser Gly Ser Gly Thr Asp Phe Thr Leu Thr Ile Ser Ser Leu Gln
 65                  70                  75                  80

Ala Glu Asp Val Ala Val Tyr Tyr Cys Leu Gly Gly Tyr Asp Asp Asp
                 85                  90                  95

Gly Glu Thr Ala Phe Gly Gln Gly Thr Glu Val Val Val Lys
            100                 105                 110

<210> SEQ ID NO 319
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CABBABABA_1_115; 16 6 HC humanized 586

<400> SEQUENCE: 319

Val Gln Leu Gln Glu Ser Gly Gly Val Val Gln Pro Gly Thr Ser
 1               5                  10                  15

Leu Arg Leu Ser Cys Val Val Ser Gly Ser Asp Ile Ser Ser Tyr His
                20                  25                  30

Met Gly Trp Val Arg Gln Ala Pro Gly Lys Gly Leu Glu Trp Leu Ala
            35                  40                  45

Ile Ile Val Ser Ser Gly Ser Ala Tyr Tyr Ala Thr Trp Ala Lys Gly
         50                  55                  60

Arg Phe Thr Val Ser Arg Ser Lys Ser Thr Leu Phe Leu Lys Met Asn
 65                  70                  75                  80
```

Ser Leu Arg Ala Asp Asp Thr Ala Val Tyr Tyr Cys Ala Arg Asn Gln
            85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 320
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DABBABABA_1_115; 16 6 HC humanized 411

<400> SEQUENCE: 320

Leu Gln Leu Gln Glu Ser Gly Pro Arg Leu Val Lys Pro Ser Glu Thr
1               5                   10                  15

Leu Ser Leu Thr Cys Thr Val Ser Gly Ser Asp Ile Ser Ser Tyr His
            20                  25                  30

Met Gly Trp Ile Arg Gln Ser Pro Gly Lys Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Leu Thr Met Ser Thr Ser Lys Asn Gln Phe Ser Leu Arg Leu Ser
65                  70                  75                  80

Ser Val Thr Ala Ala Asp Ser Ala Val Tyr Tyr Cys Ala Arg Asn Gln
            85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 321
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FABBABABA_1_115; 16 6 HC humanized 372

<400> SEQUENCE: 321

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Ala Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Ser Ser Thr Leu Phe Leu Gln Leu Asn
65                  70                  75                  80

Ser Leu Arg Val Glu Asp Ser Gly Ile Tyr Tyr Cys Ala Lys Asn Gln
            85                  90                  95

Tyr Ser Gly Tyr Gly Phe Ser Phe Trp Gly Gln Gly Thr Leu Val Thr

Val Ser Ser
      115

<210> SEQ ID NO 322
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GABBABABA_1_115; 16 6 HC humanized 1996

<400> SEQUENCE: 322

Gln Ser Leu Glu Glu Ser Gly Gly Arg Leu Val Thr Pro Gly Gly Ser
1               5                   10                  15

Leu Arg Leu Ser Cys Ala Ala Ser Gly Ser Asp Ile Ser Ser Tyr His
                20                  25                  30

Met Gly Trp Val Arg Gln Ala Pro Gly Lys Gly Leu Glu Trp Val Gly
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ser Thr Leu Tyr Leu Gln Met Asn
65                  70                  75                  80

Ser Leu Arg Val Glu Asp Thr Ala Arg Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
      115

<210> SEQ ID NO 323
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HABBABABA_2_115; 16 6 HC humanized 1907; 16
      6 HC humanized 716

<400> SEQUENCE: 323

Gln Ser Leu Leu Glu Ser Gly Gly Gly Trp Val Gln Pro Gly Arg Ser
1               5                   10                  15

Leu Arg Leu Ser Cys Ser Ala Ser Gly Ser Asp Ile Ser Ser Tyr His
                20                  25                  30

Met Gly Trp Val Arg Gln Ala Pro Gly Lys Gly Leu Glu Trp Val Gly
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Asn Ser Leu Tyr Leu Gln Met Asn
65                  70                  75                  80

Ser Leu Arg Pro Glu Asp Thr Ala Leu Tyr Tyr Cys Ala Lys Asn Gln
                85                  90                  95

Tyr Ser Gly Tyr Gly Phe Ser Phe Trp Gly Gln Gly Val Leu Val Thr
            100                 105                 110

Val Ser Ser
      115

<210> SEQ ID NO 324
<211> LENGTH: 115
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_LABBABABA_2_115; 16 6 HC humanized 1945; 16
    6 HC humanized 1451

<400> SEQUENCE: 324

Gln Ser Leu Glu Glu Ser Gly Gly Gly Leu Val Lys Pro Gly Glu Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asp Ser Thr Val Tyr Leu Glu Met Asn
65                  70                  75                  80

Ser Leu Lys Thr Glu Asp Thr Ala Val Tyr Tyr Cys Ala Thr Asn Gln
            85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 325
<211> LENGTH: 115
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: cl_NABBABABA_1_115; 16 6 HC humanized 1004

<400> SEQUENCE: 325

Gln Ser Leu Leu Glu Ser Gly Pro Arg Leu Val Lys Pro Ser Glu Thr
1               5                   10                  15

Leu Ser Leu Thr Cys Ser Val Ser Gly Ser Asp Ile Ser Ser Tyr His
            20                  25                  30

Met Gly Trp Val Arg Gln Pro Pro Gly Gln Gly Leu Glu Trp Ile Gly
        35                  40                  45

Ile Ile Val Ser Ser Gly Ser Ala Tyr Tyr Ala Thr Trp Ala Arg Ser
    50                  55                  60

Arg Val Ser Ile Ser Thr Ser Gln Asn Gln Val Ser Leu Lys Leu Thr
65                  70                  75                  80

Ser Val Thr Ala Ala Asp Thr Ala Val Tyr Tyr Cys Ala Arg Asn Gln
            85                  90                  95

Tyr Ser Gly Tyr Gly Phe Ser Phe Trp Gly Gln Gly Ile Leu Val Thr
            100                 105                 110

Val Ser Ser
        115

<210> SEQ ID NO 326
<211> LENGTH: 115

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PABBABABA_1_115; 16 6 HC humanized 1971

<400> SEQUENCE: 326

Val Gln Leu Val Glu Ser Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Leu Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Ser Leu Tyr Leu Gln Leu Ser
65                  70                  75                  80

Ser Leu Arg Asn Glu Asp Thr Ala Val Tyr Tyr Cys Ala Lys Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 327
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QABBABABA_2_115; 16 6 HC humanized 802; 16 6
      HC humanized 988

<400> SEQUENCE: 327

Val Gln Leu Val Glu Ser Gly Gly Leu Ile Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 328
<211> LENGTH: 115
<212> TYPE: PRT
<213> ORGANISM: Artificial Sequence
<220> FEATURE:
<223> OTHER INFORMATION: Description of Artificial Sequence: Synthetic
```

-continued

```
                         polypeptide
<220> FEATURE:
<223> OTHER INFORMATION: cl_RABBABABA_1_115; 16 6 HC humanized 609

<400> SEQUENCE: 328

Val Gln Leu Val Glu Ser Gly Gly Gly Leu Val Gln Pro Gly Ser
1               5                   10                  15

Leu Arg Leu Ser Cys Thr Thr Ser Gly Ser Asp Ile Ser Ser Tyr His
                20                  25                  30

Met Gly Trp Val Arg Gln Val Pro Gly Lys Gly Leu Glu Trp Val Ser
            35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ser Thr Ser Tyr Leu Gln Met Thr
65                  70                  75                  80

Ser Leu Thr Pro Glu Asp Thr Ala Val Tyr Tyr Cys Ala Lys Asn Gln
                85                  90                  95

Tyr Ser Gly Tyr Gly Phe Ser Phe Trp Gly Gln Gly Thr Val Val Ser
                100                 105                 110

Val Ser Ser
        115

<210> SEQ ID NO 329
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SABBABABA_1_115; 16 6 HC humanized 587

<400> SEQUENCE: 329

Val Gln Leu Val Glu Ser Gly Gly Gly Leu Val Lys Pro Gly Ser
1               5                   10                  15

Leu Arg Leu Ser Cys Val Val Ser Gly Ser Asp Ile Ser Ser Tyr His
                20                  25                  30

Met Gly Trp Val Arg Gln Ala Pro Gly Lys Gly Leu Glu Trp Leu Ser
            35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ala Ser Leu Phe Leu Gln Met Asn
65                  70                  75                  80

Ser Leu Arg Ala Asp Asp Thr Ala Leu Tyr Phe Cys Ala Arg Asn Gln
                85                  90                  95

Tyr Ser Gly Tyr Gly Phe Ser Phe Trp Gly Gln Gly Thr Leu Val Thr
                100                 105                 110

Val Ser Ser
        115

<210> SEQ ID NO 330
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TABBABABA_6_115; 16 6 HC humanized 305; 16 6
      HC humanized 283; 16 6 HC humanized 334; 16 6 HC humanized 281; 16
      6 HC humanized 339
```

<400> SEQUENCE: 330

Val Gln Leu Val Glu Ser Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Lys Asn Gln
                85                  90                  95

Tyr Ser Gly Tyr Gly Phe Ser Phe Trp Gly Gln Gly Thr Leu Val Thr
                100                 105                 110

Val Ser Ser
        115

<210> SEQ ID NO 331
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VABBABABA_4_115; 16 6 HC humanized 1877; 16
      6 HC humanized 860; 16 6 HC humanized 204; 16 6 HC humanized 818

<400> SEQUENCE: 331

Val Gln Leu Val Glu Ser Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
                100                 105                 110

Val Ser Ser
        115

<210> SEQ ID NO 332
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WABBABABA_1_115; 16 6 HC humanized 1012

<400> SEQUENCE: 332

Val Gln Leu Gln Glu Trp Gly Gly Gly Val Val Gln Pro Gly Arg Ser

```
                1               5                   10                  15
Leu Arg Leu Ser Cys Ala Ala Ser Gly Ser Asp Ile Ser Ser Tyr His
                20                  25                  30

Met Gly Trp Val Arg Gln Ala Pro Gly Lys Gly Leu Glu Trp Val Ala
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
                100                 105                 110

Val Ser Ser
        115

<210> SEQ ID NO 333
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YABBABABA_1_115; 16 6 HC humanized 910

<400> SEQUENCE: 333

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
                20                  25                  30

Met Gly Trp Ile Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Gln Ser
        50                  55                  60

Arg Val Leu Ile Ser Thr Ser Lys Ser Gln Leu Ser Leu Lys Leu Thr
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
                100                 105                 110

Val Ser Ser
        115

<210> SEQ ID NO 334
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CEBBABABA_1_115; 16 6 HC humanized 253

<400> SEQUENCE: 334

Val Gln Leu Val Glu Ser Gly Gly Gly Leu Val Gln Pro Gly Arg Ser
1               5                   10                  15

Leu Arg Leu Ser Cys Ala Thr Ser Gly Ser Asp Ile Ser Ser Tyr His
                20                  25                  30
```

-continued

Met Gly Trp Val Arg Gln Ala Pro Gly Lys Gly Leu Glu Trp Val Gly
            35                  40                  45

Ile Ile Val Ser Ser Gly Ser Ala Tyr Tyr Ala Thr Trp Ala Lys Gly
 50                  55                  60

Arg Phe Thr Ile Ser Arg Asp Asn Ala Ser Leu Tyr Leu Gln Met Ser
 65                  70                  75                  80

Ser Leu Arg Ala Glu Asp Thr Ala Leu Tyr Tyr Cys Ala Lys Asn Gln
                 85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 335
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DEBBABABA_1_115; 16 6 HC humanized 218

<400> SEQUENCE: 335

Val Gln Leu Gln Glu Ser Gly Pro Gly Leu Val Lys Pro Ser Glu Thr
 1               5                  10                  15

Leu Ser Leu Thr Cys Thr Val Ser Gly Ser Asp Ile Ser Ser Tyr His
             20                  25                  30

Met Gly Trp Ile Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Lys Ser
 50                  55                  60

Arg Val Thr Ile Ser Thr Ser Lys Asn Gln Phe Ser Leu Lys Leu Ser
 65                  70                  75                  80

Ser Val Thr Ala Ala Asp Thr Ala Val Tyr Tyr Cys Ala Arg Asn Gln
                 85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 336
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FEBBABABA_1_115; 16 6 HC humanized 213

<400> SEQUENCE: 336

Leu Gln Leu Gln Glu Ser Gly Pro Gly Leu Val Lys Pro Ser Glu Thr
 1               5                  10                  15

Leu Ser Leu Thr Cys Thr Val Ser Gly Ser Asp Ile Ser Ser Tyr His
             20                  25                  30

Met Gly Trp Ile Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Lys Ser
 50                  55                  60

```
Arg Val Thr Ile Ser Thr Ser Lys Asn Gln Phe Ser Leu Lys Leu Ser
65                  70                  75                  80

Ser Val Thr Ala Ala Asp Thr Ala Val Tyr Tyr Cys Ala Ser Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 337
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GEBBABABA_1_115; 16 6 HC humanized 136

<400> SEQUENCE: 337

Val Gln Leu Gln Gln Ser Gly Pro Gly Leu Val Lys Thr Ser Glu Thr
1               5                   10                  15

Leu Pro Leu Thr Cys Thr Val Ser Gly Ser Asp Ile Ser Ser Tyr His
                20                  25                  30

Met Gly Trp Ile Arg Gln Pro Pro Gly Lys Gly Leu Glu Tyr Ile Gly
            35                  40                  45

Ile Ile Val Ser Ser Gly Ser Ala Tyr Tyr Ala Thr Trp Ala Lys Asn
        50                  55                  60

Arg Val Thr Ile Ser Thr Ser Lys Asn Gln Phe Ser Leu Lys Leu Ser
65                  70                  75                  80

Ser Val Thr Ala Ala Asp Thr Ala Leu Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 338
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HEBBABABA_1_115; 16 6 HC humanized 129

<400> SEQUENCE: 338

Met Gln Leu Val Glu Ser Gly Gly Gly Leu Val Gln Pro Gly Arg Ser
1               5                   10                  15

Leu Arg Leu Ser Cys Val Thr Ser Gly Ser Asp Ile Ser Ser Tyr His
                20                  25                  30

Met Gly Trp Val Arg Gln Val Pro Gly Lys Gly Leu Glu Trp Val Gly
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Thr Ser Leu Tyr Leu Gln Met Asn
65                  70                  75                  80

Ser Leu Arg Pro Glu Asp Thr Ala Val Tyr Tyr Cys Ala Lys Asn Gln
```

```
                85                  90                  95
Tyr Ser Gly Tyr Gly Phe Ser Phe Trp Gly Gln Gly Thr Leu Val Thr
            100                 105                 110

Val Ser Ser
        115

<210> SEQ ID NO 339
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KEBBABABA_1_115; 16 6 HC humanized 109

<400> SEQUENCE: 339

Val Gln Leu Val Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln Pro Pro Gly Lys Gly Leu Glu Tyr Ile Gly
        35                  40                  45

Ile Ile Val Ser Ser Gly Ser Ala Tyr Tyr Ala Thr Trp Ala Lys Ser
    50                  55                  60

Arg Leu Thr Met Ser Val Asp Thr Ser Asn Tyr Gln Leu Lys Leu Ser
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 340
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LEBBABABA_1_115; 16 6 HC humanized 103

<400> SEQUENCE: 340

Val Gln Leu Gln Gln Ser Gly Pro Gly Leu Val Lys Pro Ser Gly Thr
1               5                   10                  15

Leu Ser Leu Thr Cys Asp Val Ser Gly Ser Asp Ile Ser Ser Tyr His
            20                  25                  30

Met Gly Trp Val Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Val Thr Ile Ser Lys Ser Lys Asn Gln Phe Ser Leu Arg Leu Thr
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110
```

-continued

Val Ser Ser
        115

<210> SEQ ID NO 341
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MEBBABABA_1_115; 16 6 HC humanized 954

<400> SEQUENCE: 341

Val Gln Leu Val Glu Ser Gly Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Lys Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 342
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NEBBABABA_1_115; 16 6 HC humanized 902

<400> SEQUENCE: 342

Val Gln Leu Val Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Leu Arg Gln Pro Pro Gly Arg Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Val Thr Leu Ser Thr Ser Lys Asn Gln Phe Ser Leu Lys Leu Asn
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 343

-continued

```
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PEBBABABA_1_115; 16 6 HC humanized 851

<400> SEQUENCE: 343
```

Val Gln Leu Val Gln Ser Gly Gly Val Val Gln Pro Gly Gly Ser
1               5                   10                  15

Leu Arg Val Ser Cys Ala Ala Ser Gly Ser Asp Ile Ser Ser Tyr His
            20                  25                  30

Met Gly Trp Val Arg Gln Ala Pro Gly Lys Gly Leu Glu Trp Met Ala
        35                  40                  45

Ile Ile Val Ser Ser Gly Ser Ala Tyr Tyr Ala Thr Trp Ala Lys Gly
 50                  55                  60

Arg Phe Thr Ile Ser Arg Asp Asn Ser Thr Val Ser Leu Gln Met Ser
65                  70                  75                  80

Ser Leu Arg Ala Glu Asp Thr Ala Val Tyr Tyr Cys Ala Lys Asn Gln
                85                  90                  95

Tyr Ser Gly Tyr Gly Phe Ser Phe Trp Gly Arg Gly Thr Leu Val Thr
            100                 105                 110

Val Ser Ser
        115

```
<210> SEQ ID NO 344
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_REBBABABA_1_115; 16 6 HC humanized 17

<400> SEQUENCE: 344
```

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Arg Gly Leu Val Trp Val Ser
        35                  40                  45

Ile Ile Val Ser Ser Gly Ser Ala Tyr Tyr Ala Thr Trp Ala Lys Gly
 50                  55                  60

Arg Phe Thr Ile Ser Arg Asp Asn Ala Thr Leu Tyr Leu Gln Met Asn
65                  70                  75                  80

Asn Leu Arg Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

```
<210> SEQ ID NO 345
<211> LENGTH: 115
<212> TYPE: PRT
<213> ORGANISM: Artificial Sequence
<220> FEATURE:
<223> OTHER INFORMATION: Description of Artificial Sequence: Synthetic
```

```
                               polypeptide
<220> FEATURE:
<223> OTHER INFORMATION: cl_SEBBABABA_1_115; 16 6 HC humanized 926

<400> SEQUENCE: 345

Val Gln Leu Val Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln His Ser Gly Lys Thr Leu Glu Trp Ile Gly
        35                  40                  45

Ile Ile Val Ser Ser Gly Ser Ala Tyr Tyr Ala Thr Trp Ala Glu Ser
50                  55                  60

Arg Val Thr Ile Ser Ala Asp Thr Ser Lys Ile Ser Leu Lys Leu Ser
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 346
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TEBBABABA_1_115; 16 6 HC humanized 908

<400> SEQUENCE: 346

Val Gln Leu Val Glu Ser Gly Gly Gly Leu Val Glu Pro Gly Gly Ser
1               5                   10                  15

Leu Arg Leu Ser Cys Ala Ala Ser Gly Ser Asp Ile Ser Ser Tyr His
            20                  25                  30

Met Gly Trp Ile Arg Gln Ala Pro Gly Lys Gly Leu Glu Trp Leu Ser
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Val Arg Asn Gln
                85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 347
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VEBBABABA_1_115; 16 6 HC humanized 904

<400> SEQUENCE: 347
```

```
Val Gln Leu Val Glu Ser Gly Pro Gly Leu Val Lys Pro Ser Gln Thr
1               5                   10                  15

Leu Ser Leu Thr Cys Asn Val Ser Gly Ser Asp Ile Ser Ser Tyr His
            20                  25                  30

Met Gly Trp Ile Arg Gln Ser Pro Gly Lys Gly Leu Glu Trp Ile Gly
            35                  40                  45

Ile Ile Val Ser Ser Gly Ser Ala Tyr Tyr Ala Thr Trp Ala Arg Ser
50                  55                  60

Arg Val Thr Ile Ser Ala Asp Thr Ser Lys Val Ser Leu Glu Leu Ser
65              70                  75                  80

Pro Met Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 348
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WEBBABABA_1_115; 16 6 HC humanized 903

<400> SEQUENCE: 348

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln Pro Pro Gly Thr Gly Leu Glu Trp Ile Gly
            35                  40                  45

Ile Ile Val Ser Ser Gly Ser Ala Tyr Tyr Ala Thr Trp Ala Lys Ser
50                  55                  60

Arg Val Thr Ile Ser Gly Asp Thr Ser Lys Phe Ser Leu Met Leu Arg
65              70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 349
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XEBBABABA_1_115; 16 6 HC humanized 108

<400> SEQUENCE: 349

Val Gln Leu Val Glu Ser Gly Gly Gly Leu Val Lys Pro Gly Gly Ser
1               5                   10                  15

Leu Arg Leu Ser Cys Ala Ala Ser Gly Ser Asp Ile Ser Ser Tyr His
```

```
                    20                  25                  30

Met Gly Trp Ile Arg Gln Ala Pro Gly Lys Gly Leu Glu Trp Val Ser
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ala Ser Leu Phe Leu Gln Met Asn
65                  70                  75                  80

Ser Leu Arg Ala Glu Asp Thr Ala Val Tyr Tyr Cys Ala Lys Asn Gln
                85                  90                  95

Tyr Ser Gly Tyr Gly Phe Ser Phe Trp Gly Gln Gly Thr Leu Ile Thr
            100                 105                 110

Val Ser Ser
        115

<210> SEQ ID NO 350
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YEBBABABA_1_115; 16 6 HC humanized 946

<400> SEQUENCE: 350

Val Gln Leu Val Glu Ser Gly Gly Gly Leu Ile Lys Pro Gly Gly Ser
1               5                   10                  15

Leu Arg Leu Ser Cys Glu Val Pro Gly Ser Asp Ile Ser Ser Tyr His
            20                  25                  30

Met Gly Trp Val Arg Gln Gly Pro Gly Arg Gly Leu Glu Trp Val Gly
            35                  40                  45

Ile Ile Val Ser Ser Gly Ser Ala Tyr Tyr Ala Thr Trp Ala Arg Gly
        50                  55                  60

Arg Phe Thr Ile Ser Arg Ser Lys Ser Thr Val Tyr Leu Glu Met Asn
65                  70                  75                  80

Ala Leu Lys Thr Glu Asp Thr Gly Ile Tyr Tyr Cys Val Thr Asn Gln
                85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 351
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZEBBABABA_1_115; 16 6 HC humanized 882

<400> SEQUENCE: 351

Gln Ser Leu Glu Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Pro Pro Gly Lys Gly Leu Glu Trp Val Gly
            35                  40                  45
```

```
Ile Ile Val Ser Ser Gly Ser Ala Tyr Tyr Ala Thr Trp Ala Lys Gly
    50                  55                  60

Arg Phe Thr Ile Ser Arg Ser Lys Ser Thr Val Tyr Leu Gln Met Asn
 65                  70                  75                  80

Ser Leu Lys Thr Glu Asp Thr Ala Val Tyr Tyr Cys Thr Ala Asn Gln
                 85                  90                  95

Tyr Ser Gly Tyr Gly Phe Ser Phe Trp Gly Gln Gly Met Leu Val Thr
            100                 105                 110

Val Ser Ser
        115

<210> SEQ ID NO 352
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BIBBABABA_1_115; 16 6 HC humanized 186

<400> SEQUENCE: 352

Val Gln Leu Val Glu Ser Gly Gly Gly Val Val Gln Pro Gly Arg Ser
 1               5                  10                  15

Leu Arg Leu Ser Cys Ala Ala Ser Gly Ser Asp Ile Ser Ser Tyr His
             20                  25                  30

Met Gly Trp Val Arg Gln Ala Pro Gly Lys Gly Leu Glu Ser Val Ala
         35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Arg Asn Gln
                 85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 353
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CIBBABABA_1_115; 16 6 HC humanized 2041

<400> SEQUENCE: 353

Gln Ser Leu Val Gln Ser Gly Thr Glu Val Arg Lys Pro Gly Ala Ser
 1               5                  10                  15

Val Lys Val Ser Cys Lys Ala Ser Gly Ser Asp Ile Ser Ser Tyr His
             20                  25                  30

Met Gly Trp Val Arg Gln Ala Pro Gly Gln Gly Leu Glu Trp Met Gly
         35                  40                  45

Ile Ile Val Ser Ser Gly Ser Ala Tyr Tyr Ala Thr Trp Ala Gln Gly
    50                  55                  60

Arg Val Thr Met Ser Asp Thr Ser Thr Thr Val Tyr Met Glu Leu Ser
 65                  70                  75                  80
```

Ser Leu Thr Ser Glu Asp Thr Ala Ile Tyr Tyr Cys Ala Arg Asn Gln
            85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 354
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DIBBABABA_1_115; 16 6 HC humanized 202

<400> SEQUENCE: 354

Val Gln Leu Gln Glu Ser Gly Glu Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Tyr Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Gly
65                  70                  75                  80

Ser Leu Arg Ala Glu Asp Met Ala Val Tyr Tyr Cys Ala Arg Asn Gln
            85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 355
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FIBBABABA_2_115; 16 6 HC humanized 192; 16 6
      HC humanized 880

<400> SEQUENCE: 355

Gln His Leu Glu Glu Ser Gly Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
            85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 356
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GIBBABABA_2_115; 16 6 HC humanized 1982; 16
      6 HC humanized 734

<400> SEQUENCE: 356

Gln Ser Leu Leu Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Val Thr Met Ser Thr Ser Lys Asn His Phe Ser Leu Arg Leu Ser
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 357
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KIBBABABA_1_115; 16 6 HC humanized 1944

<400> SEQUENCE: 357

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Asn
    50                  55                  60

Arg Val Thr Ile Ser Thr Ser Lys Asn Gln Phe Ser Leu Arg Leu Asn
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser

<210> SEQ ID NO 358
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_LIBBABABA_1_115; 16 6 HC humanized 1895

<400> SEQUENCE: 358

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Val Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ala Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Lys Gly Thr Thr Val Thr
            100                 105                 110

Val Ser Ser
        115

<210> SEQ ID NO 359
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_MIBBABABA_1_115; 16 6 HC humanized 65

<400> SEQUENCE: 359

Gln Ser Leu Glu Glu Ser Gly Gly Gly Leu Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Leu Tyr Tyr Cys Ala Lys Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 360
<211> LENGTH: 115

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NIBBABABA_2_115; 16 6 HC humanized 1938; 16
      6 HC humanized 762

<400> SEQUENCE: 360
```

Val Lys Leu Leu Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ser Thr Leu Tyr Leu Gln Met Asn
65                  70                  75                  80

Ser Leu Gly Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

```
<210> SEQ ID NO 361
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QIBBABABA_2_115; 16 6 HC humanized 2031; 16
      6 HC humanized 621

<400> SEQUENCE: 361
```

Val Gln Leu Val Glu Ser Gly Gly Gly Leu Val Lys Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ser Thr Leu Tyr Leu Gln Met Asn
65                  70                  75                  80

Asn Leu Arg Ala Glu Asp Thr Ala Val Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Leu Ser
        115

```
<210> SEQ ID NO 362
<211> LENGTH: 115
<212> TYPE: PRT
<213> ORGANISM: Artificial Sequence
<220> FEATURE:
```

-continued

<223> OTHER INFORMATION: Description of Artificial Sequence: Synthetic
     polypeptide
<220> FEATURE:
<223> OTHER INFORMATION: cl_SIBBABABA_1_115; 16 6 HC humanized 993

<400> SEQUENCE: 362

Val Gln Leu Val Glu Ser Gly Gly Leu Ile Gln Pro Gly Arg Pro
1               5                   10                  15

Leu Arg Leu Ser Cys Ser Gly Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asp Ser Val Val His Leu Gln Met Asn
65                  70                  75                  80

Ser Leu Lys Ser Glu Asp Thr Ala Val Tyr Tyr Cys Thr Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 363
<211> LENGTH: 115
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: cl_TIBBABABA_1_115; 16 6 HC humanized 956

<400> SEQUENCE: 363

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Phe Arg Gln His Pro Gly Lys Gly Leu Glu Trp Ile Gly
        35                  40                  45

Ile Ile Val Ser Ser Gly Ser Ala Tyr Tyr Ala Thr Trp Ala Glu Ser
    50                  55                  60

Arg Leu Thr Ile Ser Glu Asp Thr Ser Asn Ile Gln Leu Arg Leu Thr
65                  70                  75                  80

Ser Val Thr Ala Ala Asp Thr Ala Val Tyr Phe Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 364
<211> LENGTH: 115
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: cl_VIBBABABA_1_115; 16 6 HC humanized 920

<400> SEQUENCE: 364

Val Gln Leu Val Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln Phe Pro Gly Lys Gly Leu Glu Trp Ile Gly
        35                  40                  45

Ile Ile Val Ser Ser Gly Ser Ala Tyr Tyr Ala Thr Trp Ala Lys Ser
50                  55                  60

Arg Phe Thr Ile Ser Thr Ser Lys Asn Gln Phe Ser Leu Lys Val Asp
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 365
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WIBBABABA_1_115; 16 6 HC humanized 278

<400> SEQUENCE: 365

Val Gln Leu Val Gln Ser Gly Gly Gly Leu Val Lys Pro Gly Gly Ser
1               5                   10                  15

Leu Arg Leu Ser Cys Glu Ala Ser Gly Ser Asp Ile Ser Ser Tyr His
            20                  25                  30

Met Gly Trp Ile Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asp Ser Thr Leu Tyr Leu Gln Val Asn
65                  70                  75                  80

Ser Leu Lys Thr Glu Asp Ser Ala Val Tyr Tyr Cys Thr Thr Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 366
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YIBBABABA_2_115; 16 6 HC humanized 169; 16 6
      HC humanized 168

<400> SEQUENCE: 366

Val Gln Leu Val Glu Ser Gly Gly Gly Leu Val Gln Pro Gly Gly Ser
1               5                   10                  15

```
Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asp
65                  70                  75                  80

Ser Leu Arg Ala Glu Asp Thr Ala Ile Tyr Tyr Cys Ala Lys Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 367
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZIBBABABA_1_115; 16 6 HC humanized 994

<400> SEQUENCE: 367

Val Gln Leu Val Glu Ser Gly Gly Gly Leu Ile Gln Pro Gly Arg Ser
1               5                   10                  15

Leu Arg Leu Ser Cys Ser Gly Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asp Ser Val Val Tyr Leu Gln Met Asn
65                  70                  75                  80

Ser Leu Arg Ser Glu Asp Thr Ala Val Tyr Tyr Cys Thr Arg Asn Gln
                85                  90                  95

Tyr Ser Gly Tyr Gly Phe Ser Phe Trp Gly Gln Gly Thr Met Val Thr
            100                 105                 110

Val Ser Ser
        115

<210> SEQ ID NO 368
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BOBBABABA_2_115; 16 6 HC humanized 975; 16 6
      HC humanized 978

<400> SEQUENCE: 368

Val Gln Leu Val Glu Ser Gly Gly Gly Val Val Arg Pro Gly Gly Ser
1               5                   10                  15

Leu Arg Leu Ser Cys Ala Ala Ser Gly Ser Asp Ile Ser Ser Tyr His
            20                  25                  30
```

```
Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
 50                  55                  60

Arg Phe Thr Ile Ser Arg Asp Asn Ala Ser Leu Tyr Leu Glu Met Asn
 65                  70                  75                  80

Ser Leu Arg Ala Glu Asp Thr Ala Leu Tyr Phe Cys Ala Arg Asn Gln
                85                  90                  95

Tyr Ser Gly Tyr Gly Phe Ser Phe Trp Gly Gln Gly Thr Met Val Thr
               100                 105                 110

Val Ser Ser
       115

<210> SEQ ID NO 369
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DOBBABABA_1_115; 16 6 HC humanized 230

<400> SEQUENCE: 369

Gln Ser Leu Glu Glu Ser Gly Gly Gly Leu Val Gln Pro Gly Gly Ser
 1               5                  10                  15

Leu Arg Leu Ser Cys Ala Ala Ser Gly Ser Asp Ile Ser Ser Tyr His
                20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
 50                  55                  60

Arg Phe Thr Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Lys Asn Gln
                85                  90                  95

Tyr Ser Gly Tyr Gly Phe Ser Phe Trp Gly Gln Gly Thr Thr Val Thr
               100                 105                 110

Val Ser Ser
       115

<210> SEQ ID NO 370
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GOBBABABA_1_115; 16 6 HC humanized 1894

<400> SEQUENCE: 370

Gln Ser Leu Glu Glu Ser Gly Gly Arg Leu Val Thr Pro Gly Thr Pro
 1               5                  10                  15

Leu Thr Leu Thr Cys Thr Val Ser Gly Ser Asp Ile Ser Ser Tyr His
                20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
 50                  55                  60
```

```
Arg Phe Thr Ile Ser Arg Asp Asn Ala Ser Leu Tyr Leu Gln Met Asn
 65                  70                  75                  80

Ser Leu Arg Ala Glu Asp Thr Ala Val Tyr Tyr Cys Ala Arg Asn Gln
                 85                  90                  95

Tyr Ser Gly Tyr Gly Phe Ser Phe Phe Ser Asp Tyr Trp Leu Val Thr
                100                 105                 110

Val Ser Ser
        115

<210> SEQ ID NO 371
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HOBBABABA_2_115; 16 6 HC humanized 2056; 16
      6 HC humanized 672

<400> SEQUENCE: 371

Gln Ser Leu Val Glu Ser Gly Gly Gly Leu Ile Gln Pro Gly Gly Ser
1               5                   10                  15

Leu Arg Leu Ser Cys Ala Ala Ser Gly Ser Asp Ile Ser Ser Tyr His
                20                  25                  30

Met Gly Trp Val Arg Gln Ala Pro Gly Lys Gly Leu Glu Trp Val Ser
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ser Thr Leu Tyr Leu Gln Met Asn
 65                  70                  75                  80

Ser Leu Arg Ala Glu Asp Thr Ala Val Tyr Tyr Cys Ala Arg Asn Gln
                 85                  90                  95

Tyr Ser Gly Tyr Gly Phe Ser Phe Trp Gly Gln Gly Thr Leu Val Thr
                100                 105                 110

Val Ser Ser
        115

<210> SEQ ID NO 372
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LOBBABABA_1_115; 16 6 HC humanized 657

<400> SEQUENCE: 372

Gln Ser Leu Glu Glu Ser Gly Gly Arg Leu Val Thr Pro Gly Gly Ser
1               5                   10                  15

Leu Arg Leu Ser Cys Ala Ala Ser Gly Ser Asp Ile Ser Ser Tyr His
                20                  25                  30

Met Gly Trp Val Arg Gln Ala Pro Gly Lys Gly Leu Glu Trp Val Ser
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ser Ser Leu Tyr Leu Gln Met Asn
 65                  70                  75                  80
```

```
Ser Leu Arg Thr Glu Asp Ser Ala Leu Tyr Tyr Cys Ala Leu Asn Gln
            85                  90                  95

Tyr Ser Gly Tyr Gly Phe Ser Phe Trp Gly Gln Gly Ser Leu Val Thr
            100                 105                 110

Val Ser Ser
        115

<210> SEQ ID NO 373
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MOBBABABA_2_115; 16 6 HC humanized 1917; 16
      6 HC humanized 677

<400> SEQUENCE: 373

Gln Ser Leu Glu Glu Ser Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
            35                  40                  45

Ile Ile Val Ser Ser Gly Ser Ala Tyr Tyr Ala Thr Trp Ala Lys Arg
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
            85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 374
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_POBBABABA_1_115; 16 6 HC humanized 2038

<400> SEQUENCE: 374

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ala
            35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asn Gln
            85                  90                  95

Tyr Ser Gly Tyr Gly Phe Ser Phe Pro Thr Ser Gly Tyr Tyr Tyr Met
```

Asp Val Ser
        115

<210> SEQ ID NO 375
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QOBBABABA_1_115; 16 6 HC humanized 23

<400> SEQUENCE: 375

Gln Ser Leu Leu Glu Ser Gly Gly Asp Leu Val Gln Pro Gly Gly Ser
1               5                   10                  15

Leu Arg Leu Ser Cys Glu Ala Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Lys Ser Thr Leu Phe Leu Gln Met His
65                  70                  75                  80

Ser Leu Arg Val Glu Asp Thr Ala Val Tyr Tyr Cys Ala Lys Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 376
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ROBBABABA_1_115; 16 6 HC humanized 21

<400> SEQUENCE: 376

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Phe Val Ser
        35                  40                  45

Ile Ile Val Ser Ser Gly Ser Ala Tyr Tyr Ala Thr Trp Ala Lys Asp
50                  55                  60

Arg Phe Thr Ile Ser Arg Asp Asn Ser Thr Val Tyr Leu Gln Met Asp
65                  70                  75                  80

Ser Leu Arg Thr Glu Asp Thr Ala Met Tyr Phe Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

```
<210> SEQ ID NO 377
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SOBBABABA_1_115; 16 6 HC humanized 469

<400> SEQUENCE: 377

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Thr Ser Leu Phe Leu His Met Ser
65                  70                  75                  80

Ser Leu Arg Gly Glu Asp Thr Ala Ile Tyr Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 378
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TOBBABABA_1_115; 16 6 HC humanized 2008

<400> SEQUENCE: 378

Gln Ser Leu Glu Glu Ser Gly Gly Arg Leu Val Thr Pro Gly Thr Ser
1               5                   10                  15

Leu Arg Leu Ser Cys Ala Val Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Val Tyr Leu Gln Met Asn
65                  70                  75                  80

Ser Leu Arg Ala Glu Asp Thr Ala Val Phe Tyr Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 379
<211> LENGTH: 115
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: cl_VOBBABABA_1_115; 16 6 HC humanized 1013

<400> SEQUENCE: 379

Val Gln Leu Val Gln Ser Gly Gly Gly Val Gln Pro Gly Arg Ser
1               5                   10                  15

Leu Arg Leu Ser Cys Glu Val Ser Gly Ser Asp Ile Ser Tyr His
                20                  25                  30

Met Gly Trp Val Arg Gln Ala Pro Gly Lys Gly Leu Glu Trp Val Ala
            35                  40                  45

Ile Ile Val Ser Ser Gly Ser Ala Tyr Tyr Ala Thr Trp Ala Lys Gly
        50                  55                  60

Arg Phe Thr Ile Ser Arg Ser Asn Asn Thr Leu Tyr Leu Gln Met Asn
65              70                  75                  80

Ser Leu Thr Ala Glu Asp Thr Ala Leu Tyr Phe Cys Ala Arg Asn Gln
                85                  90                  95

Tyr Ser Gly Tyr Gly Phe Ser Phe Trp Gly Lys Gly Thr Thr Val Thr
                100                 105                 110

Val Ser Ser
        115

<210> SEQ ID NO 380
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XOBBABABA_1_115; 16 6 HC humanized 149

<400> SEQUENCE: 380

Val Gln Leu Val Gln Ser Gly Pro Gly Leu Val Lys Pro Ser Arg Thr
1               5                   10                  15

Leu Ser Leu Thr Cys Thr Val Ser Gly Ser Asp Ile Ser Tyr His
                20                  25                  30

Met Gly Trp Ile Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Gln Asn
        50                  55                  60

Arg Leu Thr Ile Ser Thr Ser Lys Asn Gln Phe Ser Leu Lys Leu Ala
65              70                  75                  80

Ser Val Thr Ala Ala Asp Thr Ala Val Tyr Phe Cys Ala Arg Asn Gln
                85                  90                  95

Tyr Ser Gly Tyr Gly Phe Ser Phe Trp Gly Gln Gly Thr Leu Val Thr
                100                 105                 110

Val Ser Ser
        115

<210> SEQ ID NO 381
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YOBBABABA_1_115; 16 6 HC humanized 113
```

<400> SEQUENCE: 381

Leu Gln Leu Gln Glu Ser Gly Pro Gly Leu Val Lys Pro Ser Gln Thr
1               5                   10                  15

Leu Ser Leu Thr Cys Ser Val Ser Gly Ser Asp Ile Ser Ser Tyr His
            20                  25                  30

Met Gly Trp Ile Arg Gln His Pro Gly Lys Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Ile Thr Ile Ser Thr Ser Lys Asn Gln Phe Ser Leu Lys Leu Thr
65                  70                  75                  80

Ser Val Thr Ala Ala Asp Thr Ala Leu Tyr Tyr Cys Ala Arg Asn Gln
                85                  90                  95

Tyr Ser Gly Tyr Gly Phe Ser Phe Trp Gly Arg Gly Thr Leu Val Thr
            100                 105                 110

Val Ser Ser
        115

<210> SEQ ID NO 382
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BUBBABABA_1_115; 16 6 HC humanized 965

<400> SEQUENCE: 382

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln His Pro Gly Lys Gly Leu Glu Trp Ile Gly
        35                  40                  45

Ile Ile Val Ser Ser Gly Ser Ala Tyr Tyr Ala Thr Trp Ala Lys Ser
    50                  55                  60

Arg Val Thr Ile Ser Ala Asp Thr Ser Lys Ile Ser Leu Lys Leu Ser
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 383
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CUBBABABA_1_115; 16 6 HC humanized 912

<400> SEQUENCE: 383

Val Gln Leu Gln Glu Ser Gly Pro Gly Leu Val Lys Pro Ser Gln Thr
1               5                   10                  15

```
Leu Ser Leu Thr Cys Thr Val Ser Gly Ser Asp Ile Ser Ser Tyr His
            20                  25                  30

Met Gly Trp Ile Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Ser
50                  55                  60

Arg Val Leu Ile Ser Thr Ser Lys Asn Gln Val Ser Leu Lys Leu Ser
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 384
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HUBBABABA_1_115; 16 6 HC humanized 12

<400> SEQUENCE: 384

Val Gln Leu Val Gln Ser Gly Gly Gly Val Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Gln Gly
50                  55                  60

Arg Val Thr Ile Ser Arg Asp Asn Ser Thr Val His Leu Gln Ile Thr
65                  70                  75                  80

Ser Leu Lys Ser Glu Asp Thr Ala Val Tyr Tyr Cys Ala Lys Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 385
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KUBBABABA_1_115; 16 6 HC humanized 924

<400> SEQUENCE: 385

Val Gln Leu Val Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Phe Arg Gln Pro Pro Gly Lys Gly Leu Glu Trp Ile Gly
```

```
            35                  40                  45
Ile Ile Val Ser Ser Gly Ser Ala Tyr Tyr Ala Thr Trp Ala Lys Ser
 50                  55                  60

Arg Val Thr Ile Ser Thr Ser Lys Asn Gln Val Ser Leu Lys Leu Ser
 65                  70                  75                  80

Pro Val Thr Gly Ala Asp Thr Ala Val Tyr Phe Cys Ala Arg Asn Gln
                 85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 386
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LUBBABABA_1_115; 16 6 HC humanized 273

<400> SEQUENCE: 386

Val Gln Leu Val Gln Ser Gly Gly Gly Leu Val Gln Pro Gly Gly Ser
 1               5                  10                  15

Leu Arg Leu Ser Cys Ala Ala Ser Gly Ser Asp Ile Ser Ser Tyr His
                20                  25                  30

Met Gly Trp Val Arg Gln Ala Ser Gly Lys Gly Leu Glu Trp Ile Gly
            35                  40                  45

Ile Ile Val Ser Ser Gly Ser Ala Tyr Tyr Ala Thr Trp Ala Lys Gly
 50                  55                  60

Arg Phe Thr Val Ser Arg Ser Gln Asn Ser Val Phe Leu Gln Met Asn
 65                  70                  75                  80

Ser Leu Glu Thr Glu Asp Thr Ala Val Tyr Tyr Cys Ala Arg Asn Gln
                 85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 387
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MUBBABABA_1_115; 16 6 HC humanized 2032

<400> SEQUENCE: 387

Gln Ser Leu Glu Glu Ser Gly Gly Arg Leu Val Thr Pro Gly Gly Ser
 1               5                  10                  15

Leu Arg Leu Ser Cys Ala Gly Ser Gly Ser Asp Ile Ser Ser Tyr His
                20                  25                  30

Met Gly Trp Val Arg Gln Ala Pro Gly Lys Gly Leu Glu Trp Val Ser
            35                  40                  45

Ile Ile Val Ser Ser Gly Ser Ala Tyr Tyr Ala Thr Trp Ala Glu Gly
 50                  55                  60
```

```
Arg Phe Thr Ile Ser Arg Asp Asn Ala Thr Leu Tyr Leu Gln Met Asn
 65                  70                  75                  80

Ser Leu Arg Val Glu Asp Thr Ala Val Tyr Tyr Cys Ala Thr Asn Gln
                 85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 388
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NUBBABABA_1_115; 16 6 HC humanized 879

<400> SEQUENCE: 388

Gln Ser Leu Glu Glu Ser Gly Gly Gly Leu Val Gln Pro Gly Gly Ser
  1               5                  10                  15

Leu Arg Leu Ser Cys Thr Ala Gly Ser Asp Ile Ser Ser Tyr His
                 20                  25                  30

Met Gly Trp Val Arg Gln Ala Pro Gly Lys Gly Leu Glu Trp Val Ser
             35                  40                  45

Ile Ile Val Ser Ser Gly Ser Ala Tyr Tyr Ala Thr Trp Ala Lys Gly
 50                  55                  60

Arg Phe Thr Ile Ser Arg Asp Ser Ser Thr Leu Tyr Leu Gln Met Asn
 65                  70                  75                  80

Asn Leu Arg Val Glu Asp Thr Ala Leu Tyr Tyr Cys Ala His Asn Gln
                 85                  90                  95

Tyr Ser Gly Tyr Gly Phe Ser Phe Trp Gly Arg Gly Thr Gln Val Thr
            100                 105                 110

Val Ser Ser
        115

<210> SEQ ID NO 389
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PUBBABABA_1_115; 16 6 HC humanized 267

<400> SEQUENCE: 389

Gln Ser Leu Glu Gln Ser Gly Gly Gly Leu Val Gln Pro Gly Glu Ser
  1               5                  10                  15

Leu Arg Leu Ser Cys Ala Gly Ser Gly Ser Asp Ile Ser Ser Tyr His
                 20                  25                  30

Met Gly Trp Val Arg Gln Ala Pro Gly Lys Gly Leu Glu Trp Val Ala
             35                  40                  45

Ile Ile Val Ser Ser Gly Ser Ala Tyr Tyr Ala Thr Trp Ala Lys Gly
 50                  55                  60

Arg Phe Thr Ile Ser Arg Asp Asn Ala Ser Leu Phe Leu Gln Met Asn
 65                  70                  75                  80

Ser Leu Arg Val Glu Asp Thr Ala Val Tyr Tyr Cys Ala Arg Asn Gln
                 85                  90                  95
```

```
Tyr Ser Gly Tyr Gly Phe Ser Phe Trp Gly Gln Gly Thr Leu Val Thr
            100                 105                 110

Val Ser Ser
        115

<210> SEQ ID NO 390
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QUBBABABA_1_115; 16 6 HC humanized 1992

<400> SEQUENCE: 390

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Val Trp Val Ser
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ala Thr Leu Tyr Leu Gln Met Asn
65                  70                  75                  80

Ser Leu Arg Val Glu Asp Thr Ala Val Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 391
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RUBBABABA_1_115; 16 6 HC humanized 1995

<400> SEQUENCE: 391

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Lys Asn Gln
                85                  90                  95

Tyr Ser Gly Tyr Gly Phe Ser Phe Trp Gly Pro Gly Thr Leu Val Thr
            100                 105                 110

Val Ser Ser
```

115

<210> SEQ ID NO 392
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SUBBABABA_1_115; 16 6 HC humanized 917

<400> SEQUENCE: 392

Val Gln Leu Gln Glu Ser Gly Pro Gly Leu Val Lys Pro Ser Gln Thr
1               5                   10                  15

Leu Ser Leu Thr Cys Thr Val Ser Gly Ser Asp Ile Ser Ser Tyr His
            20                  25                  30

Met Gly Trp Ile Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Arg Ser
    50                  55                  60

Arg Ile Thr Ile Ser Glu Thr Ser Lys Asn Leu Ser Leu Lys Leu Thr
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Gln Gly Thr Thr Val Thr
            100                 105                 110

Val Ser Ser
        115

<210> SEQ ID NO 393
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TUBBABABA_1_115; 16 6 HC humanized 1934

<400> SEQUENCE: 393

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ala Ser Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Gly Ile Phe Asp Tyr Trp Val Thr
            100                 105                 110

Val Ser Ser
        115

<210> SEQ ID NO 394
<211> LENGTH: 115

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VUBBABABA_1_115; 16 6 HC humanized 200

<400> SEQUENCE: 394

Val Gln Leu Gln Glu Ser Gly Pro Gly Leu Val Lys Pro Ser Glu Thr
1               5                   10                  15

Leu Ser Leu Thr Cys Ser Val Ser Gly Ser Asp Ile Ser Ser Tyr His
                20                  25                  30

Met Gly Trp Ile Arg Gln Pro Ala Gly Lys Gly Leu Glu Trp Ile Gly
            35                  40                  45

Ile Ile Val Ser Ser Gly Ser Ala Tyr Tyr Ala Thr Trp Ala Arg Ser
50                  55                  60

Arg Val Thr Met Ser Met Ser Lys Asn His Phe Ser Leu Lys Leu Arg
65                  70                  75                  80

Ser Val Thr Ala Ala Asp Thr Ala Val Tyr Phe Cys Ala Arg Asn Gln
                85                  90                  95

Tyr Ser Gly Tyr Gly Phe Ser Phe Trp Gly Gln Gly Thr Leu Val Thr
            100                 105                 110

Val Ser Ser
        115

<210> SEQ ID NO 395
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WUBBABABA_1_115; 16 6 HC humanized 1977

<400> SEQUENCE: 395

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
                20                  25                  30

Met Gly Trp Val Arg Gln Ala Pro Gly Lys Gly Leu Glu Trp Val Ala
            35                  40                  45

Ile Ile Val Ser Ser Gly Ser Ala Tyr Tyr Ala Thr Trp Ala Lys Gly
50                  55                  60

Arg Phe Thr Ile Ser Arg Ser Lys Asn Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Thr Cys Pro Tyr Phe Asp Tyr Trp
            100                 105                 110

Val Ser Ser
        115

<210> SEQ ID NO 396
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: cl_XUBBABABA_1_115; 16 6 HC humanized 2027

<400> SEQUENCE: 396

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Glu Gly
    50                  55                  60

Arg Phe Thr Ile Ser Arg Asp Asn Ser Thr Leu Tyr Leu Gln Met Tyr
65                  70                  75                  80

Ser Leu Arg Thr Glu Asp Thr Ala Val Tyr Tyr Cys Ala Arg Asn Gln
                85                  90                  95

Tyr Ser Gly Tyr Gly Phe Ser Phe Tyr Tyr Tyr Gly Met Gly Val Trp
            100                 105                 110

Val Ser Ser
        115

<210> SEQ ID NO 397
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YUBBABABA_1_115; 16 6 HC humanized 1958

<400> SEQUENCE: 397

Val His Leu Val Glu Ser Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Glu Gly
    50                  55                  60

Arg Phe Thr Ile Ser Arg Asp Asn Ser Lys Leu Tyr Leu Gln Met Asn
65                  70                  75                  80

Ser Leu Arg Ala Glu Asp Ser Ala Thr Tyr Tyr Cys Ala Arg Asn Gln
                85                  90                  95

Tyr Ser Gly Tyr Gly Phe Ser Phe Phe Gly Pro Pro Tyr Tyr Tyr Tyr
            100                 105                 110

Tyr Met Ser
        115

<210> SEQ ID NO 398
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZUBBABABA_1_115; 16 6 HC humanized 1949

<400> SEQUENCE: 398
```

-continued

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Tyr Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Ser
65                  70                  75                  80

Ser Leu Arg Ala Glu Asp Thr Ala Val Tyr Tyr Cys Val Lys Asn Gln
                85                  90                  95

Tyr Ser Gly Tyr Gly Phe Ser Phe Trp Gly Pro Gly Thr Leu Val Thr
                100                 105                 110

Val Ser Ser
        115

<210> SEQ ID NO 399
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BACBABABA_1_115; 16 6 HC humanized 1905

<400> SEQUENCE: 399

Gln Ser Leu Glu Glu Ser Gly Gly Arg Leu Val Thr Pro Gly Thr Pro
1               5                   10                  15

Leu Thr Leu Thr Cys Thr Val Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Leu Tyr Tyr Cys Ala Arg Asn Gln
                85                  90                  95

Tyr Ser Gly Tyr Gly Phe Ser Phe Val Arg Gly Gly Tyr Phe Tyr His
                100                 105                 110

Met Asp Ser
        115

<210> SEQ ID NO 400
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CACBABABA_1_110; 16 6 LC humanized 586

<400> SEQUENCE: 400

Ile Val Leu Thr Gln Thr Pro Ser Ser Leu Ser Ala Ser Val Gly Asp
1               5                   10                  15

Arg Ile Thr Ile Thr Cys Gln Ser Ser His Ser Val Tyr Tyr Gly Asp
            20                  25                  30

-continued

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
 50                  55                  60

Gly Ser Arg Ser Gly Thr Asp Phe Thr Phe Thr Ile Ser Ser Leu Arg
 65                  70                  75                  80

Pro Glu Asp Ile Ala Thr Tyr Tyr Cys Leu Gly Gly Tyr Asp Asp Asp
                 85                  90                  95

Gly Glu Thr Ala Phe Gly Gly Gly Thr Lys Val Glu Ile Lys
                100                 105                 110

<210> SEQ ID NO 401
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DACBABABA_1_110; 16 6 LC humanized 411

<400> SEQUENCE: 401

Ile Val Leu Thr Gln Ser Pro Ser Ser Leu Ser Ala Ser Val Gly Asp
 1               5                  10                  15

Arg Val Thr Ile Thr Cys Gln Ser Ser His Ser Val Tyr Tyr Gly Asp
                 20                  25                  30

Trp Leu Ala Trp Tyr Gln Gln Lys Pro Gly Lys Ala Pro Asn Leu Leu
            35                  40                  45

Ile Tyr Arg Ala Ser Asn Leu Ala Ser Gly Val Pro Ser Arg Phe Ser
 50                  55                  60

Gly Ser Gly Ser Ala Thr Asp Phe Thr Leu Thr Ile Ser Ser Leu Gln
 65                  70                  75                  80

Pro Glu Asp Phe Ala Thr Tyr Tyr Cys Leu Gly Gly Tyr Asp Asp Asp
                 85                  90                  95

Gly Glu Thr Ala Phe Gly Gly Gly Thr Arg Val Glu Ile Lys
                100                 105                 110

<210> SEQ ID NO 402
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FACBABABA_1_110; 16 6 LC humanized 372

<400> SEQUENCE: 402

Ile Gln Leu Thr Gln Ser Pro Ser Thr Leu Ser Ala Ser Val Gly Asp
 1               5                  10                  15

Arg Val Thr Ile Thr Cys Gln Ser Ser His Ser Val Tyr Tyr Gly Asp
                 20                  25                  30

Trp Leu Ala Trp Tyr Gln Gln Lys Ala Gly Lys Ala Pro Thr Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Asp Asp Phe Ala Thr Tyr Tyr Cys Leu Gly Gly Tyr Asp Asp Asp

```
                    85                  90                  95

Gly Glu Thr Ala Phe Gly Gln Gly Thr Lys Val Asp Ile Lys
                100                 105                 110

<210> SEQ ID NO 403
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GACBABABA_1_110; 16 6 LC humanized 1996

<400> SEQUENCE: 403

Val Val Leu Thr Gln Thr Pro Ser Pro Val Ser Thr Ala Val Gly Gly
1               5                   10                  15

Thr Val Thr Leu Ser Cys Gln Ser Ser His Ser Val Tyr Tyr Gly Asp
                20                  25                  30

Trp Leu Ala Trp Tyr Gln Gln Lys Pro Gly Gln Ala Pro Arg Leu Leu
            35                  40                  45

Ile Tyr Arg Ala Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Leu Gly Gly Tyr Asp Asp Asp
                85                  90                  95

Gly Glu Thr Ala Lys Gly Pro Gly Thr Glu Val Val Val Lys
                100                 105                 110

<210> SEQ ID NO 404
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HACBABABA_2_110; 16 6 LC humanized 1907; 16
      6 LC humanized 716

<400> SEQUENCE: 404

Leu Val Met Thr Gln Ser Pro Ser Ser Leu Ser Ala Ser Glu Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Arg Ala Pro Lys Leu Leu
            35                  40                  45

Ile His Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Gly Leu Gln
65                  70                  75                  80

Ser Glu Asp Phe Ala Thr Tyr Tyr Cys Leu Gly Gly Tyr Asp Asp Asp
                85                  90                  95

Gly Glu Thr Ala Phe Gly Gly Gly Thr Thr Val Asp Val Lys
                100                 105                 110

<210> SEQ ID NO 405
<211> LENGTH: 110
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: cl_LACBABABA_2_110; 16 6 LC humanized 1945; 16
      6 LC humanized 1451

<400> SEQUENCE: 405

Val Glu Leu Thr Gln Pro Pro Ser Pro Val Ser Ala Ala Pro Gly Gln
1               5                   10                  15

Lys Val Thr Ile Ser Cys Gln Ser Ser His Ser Val Tyr Tyr Gly Asp
            20                  25                  30

Trp Leu Ala Trp Tyr Gln Gln Leu Pro Gly Thr Ala Pro Lys Leu Leu
        35                  40                  45

Ile Tyr Arg Ala Ser Asn Leu Ala Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Leu Gly Tyr Asp Asp Asp
                85                  90                  95

Gly Glu Thr Ala Phe Gly Gly Gly Thr Arg Leu Thr Val Leu
                100                 105                 110

<210> SEQ ID NO 406
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NACBABABA_2_110; 16 6 LC humanized 1004; 16
      6 LC humanized 283

<400> SEQUENCE: 406

Ile Gln Leu Thr Gln Ser Pro Ser Ser Val Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Ala Leu Thr Ile Ser Ser Leu Gln
65                  70                  75                  80

Pro Glu Asp Phe Ala Thr Tyr Tyr Cys Leu Gly Tyr Asp Asp Asp
                85                  90                  95

Gly Glu Thr Ala Phe Gly Gln Gly Thr Arg Leu Glu Ile Lys
                100                 105                 110

<210> SEQ ID NO 407
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PACBABABA_1_110; 16 6 LC humanized 1971

<400> SEQUENCE: 407

Val Val Leu Thr Gln Thr Pro Ser Pro Val Ser Thr Ala Val Gly Gly
```

```
                1               5                      10                      15
Thr Val Thr Ile Thr Cys Gln Ser Ser His Ser Val Tyr Tyr Gly Asp
            20                      25                      30

Trp Leu Ala Trp Tyr Gln Gln Lys Ser Gly Lys Ala Pro Lys Leu Leu
            35                      40                      45

Ile Tyr Arg Ala Ser Asn Leu Ala Ser Gly Val Pro Ser Arg Phe Ser
    50                      55                      60

Gly Ser Gly Ser Gly Thr Asp Phe Thr Leu Thr Ile Ser Ser Leu Gln
65                      70                      75                      80

Pro Glu Asp Phe Ala Thr Tyr Tyr Cys Leu Gly Gly Tyr Asp Asp Asp
                85                      90                      95

Gly Glu Thr Ala Phe Gly Gly Gly Thr Glu Val Val Val Lys
                100                     105                     110
```

<210> SEQ ID NO 408
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QACBABABA_1_110; 16 6 LC humanized 802

<400> SEQUENCE: 408

```
Ile Arg Met Thr Gln Ser Pro Ser Ser Phe Ser Ala Ser Thr Gly Asp
1               5                      10                      15

Arg Val Thr Ile Thr Cys Gln Ser Ser His Ser Val Tyr Tyr Gly Asp
            20                      25                      30

Trp Leu Ala Trp Tyr Gln Gln Lys Pro Gly Lys Ala Pro Lys Leu Leu
            35                      40                      45

Ile Tyr Arg Ala Ser Asn Leu Ala Ser Gly Val Pro Ser Arg Phe Ser
    50                      55                      60

Gly Ser Gly Ser Gly Thr Asp Phe Thr Leu Thr Ile Ser Cys Leu Gln
65                      70                      75                      80

Ser Glu Asp Phe Ala Thr Tyr Tyr Cys Leu Gly Gly Tyr Asp Asp Asp
                85                      90                      95

Gly Glu Thr Ala Phe Gly Gly Gly Thr Lys Val Glu Ile Lys
                100                     105                     110
```

<210> SEQ ID NO 409
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RACBABABA_1_110; 16 6 LC humanized 609

<400> SEQUENCE: 409

```
Ile Arg Leu Thr Gln Ser Pro Ser Phe Leu Ser Ala Ser Val Gly Asp
1               5                      10                      15

Arg Val Thr Ile Thr Cys Gln Ser Ser His Ser Val Tyr Tyr Gly Asp
            20                      25                      30

Trp Leu Ala Trp Tyr Gln Gln Lys Pro Gly Lys Ala Pro Lys Leu Leu
            35                      40                      45

Ile Tyr Arg Ala Ser Asn Leu Ala Ser Gly Val Pro Ser Arg Phe Ser
    50                      55                      60
```

Gly Ser Gly Ser Gly Thr Asp Phe Thr Leu Thr Ile Ser Thr Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gln Gly Thr Lys Leu Glu Ile Lys
            100                 105                 110

<210> SEQ ID NO 410
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SACBABABA_1_110; 16 6 LC humanized 587

<400> SEQUENCE: 410

Val Val Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Phe Gln Gln Lys Pro Gly Lys Ala Pro Asn Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
            100                 105                 110

<210> SEQ ID NO 411
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TACBABABA_1_110; 16 6 LC humanized 305

<400> SEQUENCE: 411

Ile Gln Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Phe Gln Gln Lys Pro Gly Lys Ala Pro Lys Ser Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ser Ala Thr Tyr Tyr Cys Leu Gly Gly Tyr Asp Asp Asp
                85                  90                  95

Gly Glu Thr Ala Phe Gly Gly Gly Thr Lys Val Glu Ile Lys
            100                 105                 110

<210> SEQ ID NO 412

<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_VACBABABA_12_110; 16 6 LC humanized 1877; 16 6 LC humanized 860; 16 6 LC humanized 213; 16 6 LC humanized 902; 16 6 LC humanized 334

<400> SEQUENCE: 412

```
Ile Gln Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Lys Val Glu Ile Lys
            100                 105                 110
```

<210> SEQ ID NO 413
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_WACBABABA_2_110; 16 6 LC humanized 1012; 16 6 LC humanized 65

<400> SEQUENCE: 413

```
Ile Gln Leu Thr Gln Ser Pro Ser Thr Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Gly Tyr Asp Asp Asp
                85                  90                  95

Gly Glu Thr Ala Phe Gly Gln Gly Thr Lys Leu Glu Ile Lys
            100                 105                 110
```

<210> SEQ ID NO 414
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: cl_XACBABABA_6_110; 16 6 LC humanized 988; 16 6

LC humanized 910; 16 6 LC humanized 956; 16 6 LC humanized 2056;
16 6 LC humanized 672

<400> SEQUENCE: 414

```
Ile Val Leu Thr Gln Ser Pro Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gln Gly Thr Arg Leu Glu Ile Lys
                100                 105                 110
```

<210> SEQ ID NO 415
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CECBABABA_1_110; 16 6 LC humanized 253

<400> SEQUENCE: 415

```
Ile Val Leu Thr Gln Ser Pro Ser Ala Met Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Phe Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Ser Ala Thr Tyr Tyr Cys Leu Gly Gly Tyr Asp Asp Asp
                85                  90                  95

Gly Glu Thr Ala Phe Gly Gln Gly Thr Lys Val Asp Ile Lys
                100                 105                 110
```

<210> SEQ ID NO 416
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DECBABABA_1_110; 16 6 LC humanized 218

<400> SEQUENCE: 416

```
Ile Val Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30
```

```
Trp Leu Ala Trp Tyr Gln Gln Lys Pro Gly Lys Val Pro Lys Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Val Ala Thr Tyr Tyr Cys Leu Gly Gly Tyr Asp Asp Asp
                 85                  90                  95

Gly Glu Thr Ala Phe Gly Pro Gly Thr Lys Val Glu Ile Lys
                100                 105                 110
```

<210> SEQ ID NO 417
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GECBABABA_1_110; 16 6 LC humanized 136

<400> SEQUENCE: 417

```
Val Val Met Thr Gln Ser Pro Ser Thr Leu Ser Ala Ser Val Gly Asp
 1               5                  10                  15

Arg Val Thr Ile Thr Cys Gln Ser Ser His Ser Val Tyr Tyr Gly Asp
                 20                  25                  30

Trp Leu Ala Trp Tyr Gln Gln Lys Pro Gly Lys Ala Pro Lys Val Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Asp Asp Phe Ala Ser Tyr Tyr Cys Leu Gly Gly Tyr Asp Asp Asp
                 85                  90                  95

Gly Glu Thr Ala Phe Gly Pro Gly Thr Lys Val Asp Ile Lys
                100                 105                 110
```

<210> SEQ ID NO 418
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HECBABABA_1_110; 16 6 LC humanized 129

<400> SEQUENCE: 418

```
Ile Val Met Thr Gln Ser Pro Ser Ser Leu Ser Ala Ser Val Gly Asp
 1               5                  10                  15

Arg Val Thr Ile Thr Cys Gln Ser Ser His Ser Val Tyr Tyr Gly Asp
                 20                  25                  30

Trp Leu Ala Trp Tyr Gln His Lys Pro Gly Lys Ala Pro Arg Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Asp Asp Phe Ala Thr Tyr Tyr Cys Leu Gly Gly Tyr Asp Asp Asp
                 85                  90                  95
```

```
Gly Glu Thr Ala Phe Gly Gln Gly Thr Lys Val Glu Val Lys
            100                 105                 110

<210> SEQ ID NO 419
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KECBABABA_1_110; 16 6 LC humanized 109

<400> SEQUENCE: 419

Ile Gln Leu Thr Gln Ser Pro Ser Val Ser Ala Ser Val Gly Asp
1               5                   10                  15

Thr Ile Thr Ile Thr Cys Gln Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Leu Gly Tyr Asp Asp
                85                  90                  95

Gly Glu Thr Ala Phe Gly Gln Gly Thr Lys Val Glu Ile Lys
            100                 105                 110

<210> SEQ ID NO 420
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LECBABABA_1_110; 16 6 LC humanized 103

<400> SEQUENCE: 420

Ile Val Leu Thr Gln Ser Pro Ser Thr Leu Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Gln Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Glu Phe Thr Leu Ser Ile Asn Ser Leu Gln
65                  70                  75                  80

Pro Asp Asp Ser Ala Thr Tyr Phe Cys Leu Gly Tyr Asp Asp
                85                  90                  95

Gly Glu Thr Ala Phe Gly Gln Gly Thr Lys Val Glu Ile Lys
            100                 105                 110

<210> SEQ ID NO 421
<211> LENGTH: 110
<212> TYPE: PRT
<213> ORGANISM: Artificial Sequence
<220> FEATURE:
<223> OTHER INFORMATION: Description of Artificial Sequence: Synthetic
```

```
    polypeptide
<220> FEATURE:
<223> OTHER INFORMATION: cl_MECBABABA_1_110; 16 6 LC humanized 954

<400> SEQUENCE: 421

Ile Val Leu Thr Gln Ser Pro Ser Thr Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Gly Tyr Asp Asp Asp
                85                  90                  95

Gly Glu Thr Ala Phe Gly Gln Gly Thr Lys Ala Glu Ile Lys
            100                 105                 110

<210> SEQ ID NO 422
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PECBABABA_3_110; 16 6 LC humanized 851; 16 6
      LC humanized 908; 16 6 LC humanized 912

<400> SEQUENCE: 422

Val Val Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Lys Val Glu Ile Lys
            100                 105                 110

<210> SEQ ID NO 423
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RECBABABA_1_110; 16 6 LC humanized 17

<400> SEQUENCE: 423

Ile Gln Leu Thr Gln Ser Pro Ser Ser Leu Ser Ala Ala Val Gly Asp
1               5                   10                  15

Arg Val Thr Ile Ala Cys Gln Ser Ser His Ser Val Tyr Tyr Gly Asp
```

```
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Asp Phe Thr Leu Ser Ile Ser Ser Leu Gln
 65                  70                  75                  80

Pro Gly Asp Phe Ala Thr Tyr Tyr Cys Leu Gly Gly Tyr Asp Asp Asp
                85                  90                  95

Gly Glu Thr Ala Phe Gly Gly Gly Thr Lys Val Gln Met Lys
                100                 105                 110

<210> SEQ ID NO 424
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XECBABABA_2_110; 16 6 LC humanized 108; 16 6
      LC humanized 946

<400> SEQUENCE: 424

Ile Val Leu Thr Gln Ser Pro Ser Ser Val Ala Ser Val Gly Asp
 1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Lys Val Glu Ile Lys
                100                 105                 110

<210> SEQ ID NO 425
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZECBABABA_1_110; 16 6 LC humanized 882

<400> SEQUENCE: 425

Val Val Leu Thr Gln Ser Pro Ser Ser Leu Ser Ala Ser Val Gly Asp
 1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
 50                  55                  60

Gly Ser Gly Phe Gly Thr Asp Phe Thr Phe Thr Ile Ser Ser Leu Gln
 65                  70                  75                  80
```

```
Pro Glu Asp Ser Ala Thr Tyr Tyr Cys Leu Gly Gly Tyr Asp Asp Asp
            85                  90                  95

Gly Glu Thr Ala Phe Gly Gln Gly Thr Lys Leu Glu Ile Lys
            100                 105                 110

<210> SEQ ID NO 426
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BICBABABA_1_110; 16 6 LC humanized 186

<400> SEQUENCE: 426

Ile Gln Leu Thr Gln Ser Pro Ser Thr Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Gly Tyr Asp Asp Asp
            85                  90                  95

Gly Glu Thr Ala Phe Gly Gln Gly Thr Lys Val Val Val Lys
            100                 105                 110

<210> SEQ ID NO 427
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CICBABABA_1_110; 16 6 LC humanized 2041

<400> SEQUENCE: 427

Val Val Leu Thr Gln Thr Pro Ser Pro Val Ser Thr Ala Val Gly Gly
1               5                   10                  15

Thr Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Cys Leu Gln
65                  70                  75                  80

Ser Glu Asp Phe Ala Thr Tyr Tyr Cys Leu Gly Gly Tyr Asp Asp Asp
            85                  90                  95

Gly Glu Thr Ala Phe Gly Gly Gly Thr Glu Val Val Val Lys
            100                 105                 110

<210> SEQ ID NO 428
<211> LENGTH: 110
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DICBABABA_1_110; 16 6 LC humanized 202

<400> SEQUENCE: 428

```
Ile Arg Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Val Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Gly Tyr Asp Asp Asp
                85                  90                  95

Gly Glu Thr Ala Phe Gly Pro Gly Thr Lys Val Val Val Lys
            100                 105                 110
```

<210> SEQ ID NO 429
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_FICBABABA_1_110; 16 6 LC humanized 192

<400> SEQUENCE: 429

```
Val Val Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Ala Glu Asp Phe Thr Thr Tyr Tyr Cys Leu Gly Gly Tyr Asp Asp Asp
                85                  90                  95

Gly Glu Thr Ala Phe Gly Gln Gly Thr Lys Val Glu Phe Lys
            100                 105                 110
```

<210> SEQ ID NO 430
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GICBABABA_2_110; 16 6 LC humanized 1982; 16
      6 LC humanized 734

<400> SEQUENCE: 430

Val Glu Leu Thr Gln Ser Pro Ser Ser Val Ser Ala Ser Val Gly Asp

```
                1               5                   10                  15
Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Asp Phe Ser Leu Thr Ile Ser Ser Leu Gln
65                  70                  75                  80

Pro Glu Asp Ser Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
                100                 105                 110

<210> SEQ ID NO 431
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KICBABABA_2_110; 16 6 LC humanized 1944; 16
      6 LC humanized 1895

<400> SEQUENCE: 431

Ile Glu Leu Thr Gln Ser Pro Ser Thr Leu Ser Ala Ser Val Gly Asp
1               5                   10                  15

Arg Val Ile Ile Ser Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Glu Phe Ser Leu Thr Ile Asn Ser Leu Gln
65                  70                  75                  80

Pro Asp Asp Phe Ala Thr Tyr Tyr Cys Leu Gly Gly Tyr Asp Asp Asp
                85                  90                  95

Gly Glu Thr Ala Phe Gly Pro Gly Thr Lys Val Asp Ile Lys
                100                 105                 110

<210> SEQ ID NO 432
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NICBABABA_2_110; 16 6 LC humanized 1938; 16
      6 LC humanized 762

<400> SEQUENCE: 432

Val Glu Leu Thr Gln Ser Pro Asp Ser Leu Ala Val Ser Leu Gly Glu
1               5                   10                  15

Arg Ala Thr Ile Asn Cys Gln Ser Ser His Ser Val Tyr Tyr Gly Asp
                20                  25                  30

Trp Leu Ala Trp Tyr Gln Gln Lys Pro Gly Gln Pro Pro Lys Leu Leu
            35                  40                  45

Ile Tyr Arg Ala Ser Asn Leu Ala Ser Gly Val Pro Asp Arg Phe Ser
```

```
                  50                  55                  60

Gly Ser Gly Ser Gly Thr Asp Phe Thr Leu Thr Ile Ser Ser Leu Gln
 65                  70                  75                  80

Ala Glu Asp Val Ala Val Tyr Tyr Cys Leu Gly Gly Tyr Asp Asp Asp
                 85                  90                  95

Gly Glu Thr Ala Phe Gly Gly Gly Thr Lys Val Glu Ile Lys
                100                 105                 110

<210> SEQ ID NO 433
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QICBABABA_2_110; 16 6 LC humanized 2031; 16
      6 LC humanized 621

<400> SEQUENCE: 433

Val Glu Leu Thr Gln Ser Pro Ser Ser Leu Ser Ala Ser Val Gly Asp
  1               5                  10                  15

Arg Val Thr Ile Thr Cys Gln Ser Ser His Ser Val Tyr Tyr Gly Asp
                 20                  25                  30

Trp Leu Ala Trp Tyr Gln Gln Lys Pro Gly Lys Ala Pro Lys Leu Leu
             35                  40                  45

Ile Tyr Arg Ala Ser Asn Leu Ala Ser Gly Val Pro Ser Arg Phe Ser
         50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Leu Gly Gly Tyr Asp Asp Asp
                 85                  90                  95

Gly Glu Thr Ala Phe Gly Gln Gly Thr Lys Val Glu Ile Lys
                100                 105                 110

<210> SEQ ID NO 434
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SICBABABA_4_110; 16 6 LC humanized 993; 16 6
      LC humanized 880; 16 6 LC humanized 23; 16 6 LC humanized 917

<400> SEQUENCE: 434

Val Val Leu Thr Gln Ser Pro Ser Ser Leu Ser Ala Ser Val Gly Asp
  1               5                  10                  15

Arg Val Thr Ile Thr Cys Gln Ser Ser His Ser Val Tyr Tyr Gly Asp
                 20                  25                  30

Trp Leu Ala Trp Tyr Gln Gln Lys Pro Gly Lys Ala Pro Lys Leu Leu
             35                  40                  45

Ile Tyr Arg Ala Ser Asn Leu Ala Ser Gly Val Pro Ser Arg Phe Ser
         50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Leu Gly Gly Tyr Asp Asp Asp
                 85                  90                  95

Gly Glu Thr Ala Phe Gly Pro Gly Thr Lys Val Asp Ile Lys
```

-continued

```
                100                 105                 110
```

<210> SEQ ID NO 435
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VICBABABA_1_110; 16 6 LC humanized 920

<400> SEQUENCE: 435

```
Ile Val Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Ile Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
            100                 105                 110
```

<210> SEQ ID NO 436
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WICBABABA_1_110; 16 6 LC humanized 278

<400> SEQUENCE: 436

```
Leu Val Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Cys Gln Gln Lys Pro Gly Lys Ser Pro Thr Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Gly Phe Thr Leu Thr Ile Ser Gly Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Lys Val Glu Ile Arg
            100                 105                 110
```

<210> SEQ ID NO 437
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: cl_YICBABABA_1_110; 16 6 LC humanized 169

<400> SEQUENCE: 437

Ile Val Leu Thr Gln Ser Pro Ser Phe Leu Ser Ala Phe Val Gly Asp
1               5                   10                  15

Arg Ile Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Gly Leu Gln
65                  70                  75                  80

Pro Glu Asp Phe Ala Ser Tyr Tyr Cys Leu Gly Gly Tyr Asp Asp Asp
                85                  90                  95

Gly Glu Thr Ala Phe Gly Gly Gly Thr Lys Leu Glu Ile Lys
            100                 105                 110

<210> SEQ ID NO 438
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ZICBABABA_1_110; 16 6 LC humanized 994

<400> SEQUENCE: 438

Ile Val Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Val Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
            100                 105                 110

<210> SEQ ID NO 439
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BOCBABABA_1_110; 16 6 LC humanized 975

<400> SEQUENCE: 439

Ile Val Leu Thr Gln Ser Pro Ser Thr Gln Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu

```
            35                  40                  45
Ile Tyr Arg Ala Ser Asn Leu Ala Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Asp Asp Phe Ala Thr Tyr Tyr Cys Leu Gly Gly Tyr Asp Asp Asp
                 85                  90                  95

Gly Glu Thr Ala Phe Gly Gln Gly Thr Lys Leu Glu Ile Lys
            100                 105                 110

<210> SEQ ID NO 440
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DOCBABABA_1_110; 16 6 LC humanized 230

<400> SEQUENCE: 440

Val Val Leu Thr Gln Thr Pro Ser Pro Val Ser Ala Ser Val Gly Asp
 1               5                  10                  15

Arg Val Thr Ile Thr Cys Gln Ser Ser His Ser Val Tyr Tyr Gly Asp
                 20                  25                  30

Trp Leu Ala Trp Tyr Gln Gln Lys Pro Gly Lys Ala Pro Lys Val Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Asp Phe Thr Leu Thr Ile Ser Thr Leu Gln
 65                  70                  75                  80

Pro Glu Asp Phe Ala Thr Tyr Tyr Cys Leu Gly Gly Tyr Asp Asp Asp
                 85                  90                  95

Gly Glu Thr Ala Phe Gly Gln Gly Thr Lys Leu Glu Ile Lys
            100                 105                 110

<210> SEQ ID NO 441
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GOCBABABA_1_110; 16 6 LC humanized 1894

<400> SEQUENCE: 441

Val Val Leu Thr Gln Thr Pro Ser Pro Val Ser Thr Ala Val Gly Asp
 1               5                  10                  15

Arg Val Thr Ile Thr Cys Gln Ser Ser His Ser Val Tyr Tyr Gly Asp
                 20                  25                  30

Trp Leu Ala Trp Tyr Arg Gln Lys Pro Gly Lys Val Pro Lys Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Asp Phe Thr Leu Thr Ile Ser Ser Leu Gln
 65                  70                  75                  80

Pro Glu Asp Val Ala Thr Tyr Tyr Gly Leu Gly Gly Tyr Asp Asp Asp
                 85                  90                  95
```

```
Gly Glu Thr Ala Phe Gly Gly Gly Thr Glu Val Val Val Lys
                100             105             110
```

<210> SEQ ID NO 442
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LOCBABABA_1_110; 16 6 LC humanized 657

<400> SEQUENCE: 442

```
Val Val Leu Thr Gln Thr Pro Ser Pro Val Ser Ser Val Gly Asp
1               5                   10                  15

Arg Val Ser Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Asp Phe Thr Leu Thr Ile Thr Ser Leu Gln
65                  70                  75                  80

Pro Val Asp Phe Ala Thr Tyr Tyr Cys Leu Gly Gly Tyr Asp Asp Asp
                85                  90                  95

Gly Glu Thr Ala Phe Gly Pro Gly Thr Thr Val Asp Ala Lys
                100             105             110
```

<210> SEQ ID NO 443
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MOCBABABA_2_110; 16 6 LC humanized 1917; 16
      6 LC humanized 677

<400> SEQUENCE: 443

```
Val Val Leu Thr Gln Ser Pro Ser Phe Leu Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gln Gly Thr Arg Leu Glu Ile Lys
                100             105             110
```

<210> SEQ ID NO 444
<211> LENGTH: 110
<212> TYPE: PRT
<213> ORGANISM: Artificial Sequence
<220> FEATURE:
<223> OTHER INFORMATION: Description of Artificial Sequence: Synthetic

```
    polypeptide
<220> FEATURE:
<223> OTHER INFORMATION: cl_POCBABABA_1_110; 16 6 LC humanized 2038

<400> SEQUENCE: 444

Val Val Leu Thr Gln Thr Pro Ser Pro Val Ser Thr Ala Val Gly Gly
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Asp Lys Pro Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 445
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_ROCBABABA_1_110; 16 6 LC humanized 21

<400> SEQUENCE: 445

Ile Gln Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Val Leu
        35                  40                  45

Ile Tyr Arg Ala Ser Asn Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Pro Gly Thr Lys Val Glu Val Lys
            100                 105                 110

<210> SEQ ID NO 446
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_SOCBABABA_1_110; 16 6 LC humanized 469

<400> SEQUENCE: 446

Ile Val Leu Thr Gln Ser Pro Ser Leu Leu Ser Ala Ser Ile Gly Asp
1               5                   10                  15

Arg Val Thr Ile Pro Cys Gln Ser Ser His Ser Val Tyr Tyr Gly Asp
            20                  25                  30
```

```
Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Leu Gly Gly Tyr Asp Asp Asp
                 85                  90                  95

Gly Glu Thr Ala Phe Gly Gly Gly Thr Lys Val Asp Ile Lys
            100                 105                 110

<210> SEQ ID NO 447
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TOCBABABA_1_110; 16 6 LC humanized 2008

<400> SEQUENCE: 447

Val Val Leu Thr Gln Thr Pro Ser Pro Val Ser Thr Ala Val Gly Gly
 1               5                  10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
 50                  55                  60

Gly Ser Gly Ser Gly Thr Asp Phe Thr Leu Thr Ile Gly Ser Leu Gln
 65                  70                  75                  80

Pro Glu Asp Phe Ala Ala Tyr Phe Cys Leu Gly Gly Tyr Asp Asp Asp
                 85                  90                  95

Gly Glu Thr Ala Phe Gly Gly Gly Thr Lys Val Glu Ile Lys
            100                 105                 110

<210> SEQ ID NO 448
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WOCBABABA_1_110; 16 6 LC humanized 168

<400> SEQUENCE: 448

Ile Val Met Thr Gln Ser Pro Ser Thr Leu Ser Ala Ser Val Gly Asp
 1               5                  10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
 50                  55                  60

Gly Ser Gly Ser Gly Thr Glu Phe Thr Leu Thr Ile Ser Gly Leu Gln
 65                  70                  75                  80

Pro Glu Asp Phe Ala Thr Tyr Tyr Cys Leu Gly Gly Tyr Asp Asp Asp
```

```
                85                  90                  95

Gly Glu Thr Ala Phe Gly Gly Gly Thr Lys Leu Glu Ile Lys
            100                 105                 110

<210> SEQ ID NO 449
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XOCBABABA_1_110; 16 6 LC humanized 149

<400> SEQUENCE: 449

Ile Val Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Arg Leu
            35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Gly Leu Gln
65                  70                  75                  80

Pro Glu Asp Ile Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
            100                 105                 110

<210> SEQ ID NO 450
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YOCBABABA_1_110; 16 6 LC humanized 113

<400> SEQUENCE: 450

Ile Val Leu Thr Gln Ser Pro Ser Val Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Leu Lys Pro Gly Lys Ala Pro Lys Leu Leu
            35                  40                  45

Ile Asn Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Gly Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Pro Gly Thr Thr Val Asp Ile Lys
            100                 105                 110

<210> SEQ ID NO 451
<211> LENGTH: 110
<212> TYPE: PRT
<213> ORGANISM: Artificial Sequence
<220> FEATURE:
```

-continued

<223> OTHER INFORMATION: Description of Artificial Sequence: Synthetic
      polypeptide
<220> FEATURE:
<223> OTHER INFORMATION: cl_ZOCBABABA_4_110; 16 6 LC humanized 978; 16 6
      LC humanized 965; 16 6 LC humanized 924; 16 6 LC humanized 879

<400> SEQUENCE: 451

Ile Val Leu Thr Gln Ser Pro Ser Ser Leu Ser Ala Ser Val Gly Asp
1               5                   10                  15

Arg Val Thr Ile Thr Cys Gln Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp
                85                  90                  95

Gly Glu Thr Ala Phe Gly Gly Gly Thr Lys Val Glu Ile Lys
                100                 105                 110

<210> SEQ ID NO 452
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GUCBABABA_1_110; 16 6 LC humanized 818

<400> SEQUENCE: 452

Val Val Leu Thr Gln Thr Pro Ser Ser Val Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp
                85                  90                  95

Gly Glu Thr Ala Phe Gly Gln Gly Thr Lys Val Glu Ile Lys
                100                 105                 110

<210> SEQ ID NO 453
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_HUCBABABA_1_110; 16 6 LC humanized 12

<400> SEQUENCE: 453

Val Val Met Thr Gln Ser Pro Thr Val Ser Ala Ser Val Gly Asp
1               5                   10                  15

```
Arg Val Thr Leu Thr Cys Gln Ser Ser His Ser Val Tyr Tyr Gly Asp
                20                  25                  30

Trp Leu Ala Trp Tyr Gln Gln Lys Pro Gly Gln Pro Pro Lys Leu Leu
            35                  40                  45

Ile Tyr Arg Ala Ser Asn Leu Ala Ser Gly Val Pro Asp Arg Phe Ser
    50                  55                  60

Gly Ser Gly Ser Gly Thr Asp Phe Thr Leu Thr Ile Ser Ser Leu Gln
65                  70                  75                  80

Ala Asp Asp Phe Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
                100                 105                 110

<210> SEQ ID NO 454
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_LUCBABABA_1_110; 16 6 LC humanized 273

<400> SEQUENCE: 454

Leu Val Met Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Glu Ala Pro Lys Leu Leu
            35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Gly Leu Gln
65                  70                  75                  80

Ser Glu Asp Phe Ala Thr Tyr Tyr Cys Leu Gly Gly Tyr Asp Asp Asp
                85                  90                  95

Gly Glu Thr Ala Phe Gly Gln Gly Thr Lys Val Glu Ile Lys
                100                 105                 110

<210> SEQ ID NO 455
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MUCBABABA_1_110; 16 6 LC humanized 2032

<400> SEQUENCE: 455

Val Val Leu Thr Gln Thr Pro Ser Pro Val Ser Thr Ala Val Gly Gly
1               5                   10                  15

Thr Gly Pro Ile Asn Cys Gln Ser Ser His Ser Val Tyr Tyr Gly Asp
                20                  25                  30

Trp Leu Ala Trp Tyr Gln Gln Lys Pro Gly Gln Pro Pro Lys Leu Leu
            35                  40                  45

Ile Tyr Arg Ala Ser Asn Leu Ala Ser Gly Val Pro Asp Arg Phe Ser
    50                  55                  60

Gly Ser Gly Ser Gly Thr Asp Phe Thr Leu Thr Ile Ser Ser Leu Gln
65                  70                  75                  80
```

Ala Glu Asp Val Ala Val Tyr Tyr Cys Leu Gly Gly Tyr Asp Asp Asp
            85                  90                  95

Gly Glu Thr Ala Phe Gly Gly Gly Thr Lys Leu Glu Ile Lys
            100                 105                 110

<210> SEQ ID NO 456
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PUCBABABA_1_110; 16 6 LC humanized 267

<400> SEQUENCE: 456

Val Val Leu Thr Gln Ser Pro Ser Thr Leu Ala Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Gly Tyr Asp Asp Asp
                85                  90                  95

Gly Glu Thr Ala Phe Gly Gln Gly Thr Lys Val Glu Val Lys
            100                 105                 110

<210> SEQ ID NO 457
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QUCBABABA_1_110; 16 6 LC humanized 1992

<400> SEQUENCE: 457

Val Val Leu Thr Gln Thr Pro Ser Pro Val Ser Thr Ala Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 458
<211> LENGTH: 110
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_RUCBABABA_1_110; 16 6 LC humanized 1995
<220> FEATURE:
<221> NAME/KEY: MOD_RES
<222> LOCATION: (45)..(45)
<223> OTHER INFORMATION: Any amino acid

<400> SEQUENCE: 458

Val Val Leu Thr Gln Thr Pro Ser Pro Val Ser Thr Ala Val Gly Gly
1               5                   10                  15

Thr Val Thr Ile Asn Cys Gln Ser Ser His Ser Val Tyr Tyr Gly Asp
            20                  25                  30

Trp Leu Ala Trp Tyr Gln Gln Lys Pro Gly Gln Pro Xaa Lys Leu Leu
        35                  40                  45

Ile Tyr Arg Ala Ser Asn Leu Ala Ser Gly Val Pro Asp Arg Phe Ser
    50                  55                  60

Gly Ser Gly Ser Gly Thr Asp Phe Thr Leu Thr Ile Ser Ser Leu Gln
65                  70                  75                  80

Ala Glu Asp Val Ala Val Tyr Tyr Cys Leu Gly Tyr Asp Asp
                85                  90                  95

Gly Glu Thr Ala Phe Gly Gln Gly Thr Glu Val Val Val Lys
                100                 105                 110

<210> SEQ ID NO 459
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_TUCBABABA_2_110; 16 6 LC humanized 1934; 16
      6 LC humanized 1977

<400> SEQUENCE: 459

Val Val Leu Thr Gln Thr Pro Ser Pro Val Ser Thr Ala Val Gly Gly
1               5                   10                  15

Thr Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Leu Gly Tyr Asp Asp
                85                  90                  95

Gly Glu Thr Ala Phe Gly Gly Gly Thr Glu Val Val Val Lys
                100                 105                 110

<210> SEQ ID NO 460
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_VUCBABABA_1_110; 16 6 LC humanized 200
```

<400> SEQUENCE: 460

Val Val Leu Thr Gln Thr Pro Ser Pro Val Ser Thr Ala Val Gly Glu
1               5                   10                  15

Arg Ala Thr Ile Asn Cys Gln Ser Ser His Ser Val Tyr Tyr Gly Asp
            20                  25                  30

Trp Leu Ala Trp Tyr Gln Gln Lys Pro Gly Gln Pro Pro Lys Leu Leu
        35                  40                  45

Ile Tyr Arg Ala Ser Asn Leu Ala Ser Gly Val Pro Asp Arg Phe Ser
50                  55                  60

Gly Thr Gly Ser Gly Thr Asp Phe Thr Leu Thr Ile Ser Ser Leu Gln
65                  70                  75                  80

Ala Glu Asp Val Ala Val Tyr Tyr Cys Leu Gly Gly Tyr Asp Asp Asp
                85                  90                  95

Gly Glu Thr Ala Phe Gly Gly Gly Thr Lys Val Val Val Lys
            100                 105                 110

<210> SEQ ID NO 461
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XUCBABABA_1_110; 16 6 LC humanized 2027
<220> FEATURE:
<221> NAME/KEY: MOD_RES
<222> LOCATION: (89)..(89)
<223> OTHER INFORMATION: Any amino acid

<400> SEQUENCE: 461

Val Val Leu Thr Gln Thr Pro Ser Pro Val Ser Thr Ala Val Gly Gly
1               5                   10                  15

Thr Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Arg Leu
        35                  40                  45

Ile Tyr Arg Ala Ser Asn Leu Ala Ser Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Xaa Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 462
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YUCBABABA_2_110; 16 6 LC humanized 1958; 16
      6 LC humanized 1949

<400> SEQUENCE: 462

Val Val Leu Thr Gln Thr Pro Ser Pro Val Ser Thr Ala Val Gly Gly
1               5                   10                  15

```
Thr Val Thr Ile Pro Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 463
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_BADBABABA_1_110; 16 6 LC humanized 1905

<400> SEQUENCE: 463

Val Val Leu Thr Gln Thr Pro Ser Pro Val Ser Thr Ala Val Gly Gly
1               5                   10                  15

Thr Val Thr Ile Asn Cys Gln Ser Ser His Ser Val Tyr Tyr Gly Asp
            20                  25                  30

Trp Leu Ala Trp Tyr Gln Gln Lys Pro Gly Gln Pro Pro Lys Leu Leu
            35                  40                  45

Ile Tyr Arg Ala Ser Asn Leu Ala Ser Gly Val Pro Asp Arg Phe Ser
    50                  55                  60

Gly Ser Gly Ser Gly Thr Asp Phe Thr Leu Thr Ile Ser Ser Leu Gln
65                  70                  75                  80

Ala Glu Asp Val Ala Val Tyr Tyr Cys Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 464
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CABBABABA_43_115; 16 6 HC humanized 775; 16
      6 HC humanized 722; 16 6 HC humanized 563; 16 6 HC humanized 139;
      16 6 HC humanized 988

<400> SEQUENCE: 464

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ser
            35                  40                  45

Ile Ile Val Ser Ser Gly Ser Ala Tyr Tyr Ala Thr Trp Ala Lys Gly
    50                  55                  60
```

```
Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 465
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DABBABABA_39_115; 16 6 HC humanized 724; 16
      6 HC humanized 565; 16 6 HC humanized 141; 16 6 HC humanized 990;
      16 6 HC humanized 985

<400> SEQUENCE: 465

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
                20                  25                  30

Met Gly Trp Val Arg Gln Ala Pro Gly Lys Gly Leu Glu Trp Val Gly
            35                  40                  45

Ile Ile Val Ser Ser Gly Ser Ala Tyr Tyr Ala Thr Trp Ala Lys Gly
50                  55                  60

Arg Phe Thr Ile Ser Arg Ser Lys Asn Thr Leu Tyr Leu Gln Met Asn
65                  70                  75                  80

Ser Leu Lys Thr Glu Asp Thr Ala Val Tyr Tyr Cys Thr Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 466
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_REBBABABA_18_115; 16 6 HC humanized 365; 16
      6 HC humanized 364; 16 6 HC humanized 363; 16 6 HC humanized 360;
      16 6 HC humanized 359

<400> SEQUENCE: 466

Val Gln Leu Gln Glu Ser Gly Pro Gly Leu Val Lys Pro Ser Glu Thr
1               5                   10                  15

Leu Ser Leu Thr Cys Thr Val Ser Gly Ser Asp Ile Ser Ser Tyr His
                20                  25                  30

Met Gly Trp Ile Arg Gln Pro Pro Gly Lys Gly Leu Glu Trp Ile Gly
            35                  40                  45

Ile Ile Val Ser Ser Gly Ser Ala Tyr Tyr Ala Thr Trp Ala Lys Ser
50                  55                  60

Arg Val Thr Ile Ser Thr Ser Lys Asn Gln Phe Ser Leu Lys Leu Ser
```

```
                65                  70                  75                  80
Ser Val Thr Ala Ala Asp Thr Ala Val Tyr Tyr Cys Ala Arg Asn Gln
                    85                  90                  95

Tyr Ser Gly Tyr Gly Phe Ser Phe Trp Gly Pro Gly Thr Leu Val Thr
                100                 105                 110

Val Ser Ser
        115

<210> SEQ ID NO 467
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CACBABABA_100_110; 16 6 LC humanized 775; 16
      6 LC humanized 724; 16 6 LC humanized 722; 16 6 LC humanized 565;
      16 6 LC humanized 563

<400> SEQUENCE: 467

Val Val Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
                100                 105                 110

<210> SEQ ID NO 468
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CABBABABA_13_115; 16 6 HC humanized 775; 16
      6 HC humanized 722; 16 6 HC humanized 563; 16 6 HC humanized 139;
      16 6 HC humanized 987

<400> SEQUENCE: 468

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
                20                  25                  30

Met Gly Trp Val Arg Gln Ala Pro Gly Lys Gly Leu Glu Tyr Val Ser
            35                  40                  45

Ile Ile Val Ser Ser Gly Ser Ala Tyr Tyr Ala Thr Trp Ala Lys Gly
        50                  55                  60

Arg Phe Thr Ile Ser Arg Asp Asn Ser Thr Leu Tyr Leu Gln Met Gly
65                  70                  75                  80

Ser Leu Arg Ala Glu Asp Met Ala Val Tyr Tyr Cys Ala Arg Asn Gln
                85                  90                  95
```

```
Tyr Ser Gly Tyr Gly Phe Ser Phe Trp Gly Pro Gly Thr Leu Val Thr
            100                 105                 110

Val Ser Ser
        115

<210> SEQ ID NO 469
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_DABBABABA_12_115; 16 6 HC humanized 724; 16
      6 HC humanized 565; 16 6 HC humanized 141; 16 6 HC humanized 989;
      16 6 HC humanized 936

<400> SEQUENCE: 469

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Ser Lys Asn Ser Leu Tyr Leu Gln Met Asn
65                  70                  75                  80

Ser Leu Lys Thr Glu Asp Thr Ala Val Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 470
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MABBABABA_9_115; 16 6 HC humanized 990; 16 6
      HC humanized 937; 16 6 HC humanized 672; 16 6 HC humanized 407; 16
      6 HC humanized 248

<400> SEQUENCE: 470

Val Gln Leu Val Glu Ser Gly Gly Gly Leu Val Gln Pro Gly Gly Ser
1               5                   10                  15

Leu Lys Leu Ser Cys Ala Ala Ser Gly Ser Asp Ile Ser Ser Tyr His
            20                  25                  30

Met Gly Trp Val Arg Gln Ala Ser Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Ser Lys Asn Thr Ala Tyr Leu Gln Met Asn
65                  70                  75                  80

Ser Leu Lys Thr Glu Asp Thr Ala Val Tyr Tyr Cys Thr Arg Asn Gln
                85                  90                  95
```

```
Tyr Ser Gly Tyr Gly Phe Ser Phe Trp Gly Pro Gly Thr Leu Val Thr
            100                 105                 110

Val Ser Ser
        115

<210> SEQ ID NO 471
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_NABBABABA_27_115; 16 6 HC humanized 988; 16
      6 HC humanized 935; 16 6 HC humanized 670; 16 6 HC humanized 405;
      16 6 HC humanized 246

<400> SEQUENCE: 471

Val Gln Leu Val Glu Ser Gly Gly Gly Leu Val Gln Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ser
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 472
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_PABBABABA_9_115; 16 6 HC humanized 985; 16 6
      HC humanized 932; 16 6 HC humanized 667; 16 6 HC humanized 402; 16
      6 HC humanized 243

<400> SEQUENCE: 472

Val Gln Leu Val Glu Ser Gly Gly Gly Leu Val Gln Pro Gly Arg Ser
1               5                   10                  15

Leu Arg Leu Ser Cys Thr Ala Ser Gly Ser Asp Ile Ser Ser Tyr His
            20                  25                  30

Met Gly Trp Phe Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
    50                  55                  60

Arg Phe Thr Ile Ser Arg Ser Lys Ser Ile Ala Tyr Leu Gln Met Asn
65                  70                  75                  80

Ser Leu Lys Thr Glu Asp Thr Ala Val Tyr Tyr Cys Thr Arg Asn Gln
                85                  90                  95

Tyr Ser Gly Tyr Gly Phe Ser Phe Trp Gly Pro Gly Thr Leu Val Thr
```

```
              100                 105                 110

Val Ser Ser
        115
```

<210> SEQ ID NO 473
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_QABBABABA_9_115; 16 6 HC humanized 973; 16 6
      HC humanized 920; 16 6 HC humanized 655; 16 6 HC humanized 390; 16
      6 HC humanized 231

<400> SEQUENCE: 473

```
Val Gln Leu Val Glu Ser Gly Gly Gly Leu Val Lys Pro Gly Gly Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Gly
        35                  40                  45

Ile Ile Val Ser Ser Gly Ser Ala Tyr Tyr Ala Thr Trp Ala Lys Gly
50                  55                  60

Arg Phe Thr Ile Ser Arg Ser Lys Asn Thr Leu Tyr Leu Gln Met Asn
65                  70                  75                  80

Ser Leu Lys Thr Glu Asp Thr Ala Val Tyr Tyr Cys Thr Thr Asn Gln
            85                  90                  95

Tyr Ser Gly Tyr Gly Phe Ser Phe Trp Gly Pro Gly Thr Leu Val Thr
            100                 105                 110

Val Ser Ser
        115
```

<210> SEQ ID NO 474
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_REBBABABA_12_115; 16 6 HC humanized 365; 16
      6 HC humanized 364; 16 6 HC humanized 363; 16 6 HC humanized 360;
      16 6 HC humanized 312

<400> SEQUENCE: 474

```
Val Gln Leu Gln Glu Ser Gly Pro Gly Leu Val Lys Pro Ser Glu Thr
1               5                   10                  15

Leu Ser Leu Thr Cys Thr Val Ser Gly Ser Asp Ile Ser Ser Tyr His
            20                  25                  30

Met Gly Trp Ile Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Ser
50                  55                  60

Arg Val Thr Ile Ser Thr Ser Lys Asn Gln Phe Ser Leu Lys Leu Ser
65                  70                  75                  80

Ser Val Thr Ala Ala Asp Thr Ala Val Tyr Tyr Cys Ala Arg Asn Gln
            85                  90                  95

Tyr Ser Gly Tyr Gly Phe Ser Phe Trp Gly Pro Gly Thr Leu Val Thr
            100                 105                 110
```

Val Ser Ser
    115

<210> SEQ ID NO 475
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WEBBABABA_3_115; 16 6 HC humanized 359; 16 6
      HC humanized 306; 16 6 HC humanized 41

<400> SEQUENCE: 475

Leu Gln Leu Gln Glu Ser Gly Ser Gly Leu Val Lys Pro Ser Gln Thr
1               5                   10                  15

Leu Ser Leu Thr Cys Ala Val Ser Gly Ser Asp Ile Ser Ser Tyr His
            20                  25                  30

Met Gly Trp Ile Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Ser
50                  55                  60

Arg Val Thr Ile Ser Arg Ser Lys Asn Gln Phe Ser Leu Lys Leu Ser
65                  70                  75                  80

Ser Val Thr Ala Ala Asp Thr Ala Val Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
    115

<210> SEQ ID NO 476
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_XEBBABABA_3_115; 16 6 HC humanized 357; 16 6
      HC humanized 304; 16 6 HC humanized 39

<400> SEQUENCE: 476

Val Gln Leu Gln Glu Ser Gly Pro Gly Leu Val Lys Pro Pro Gly Thr
1               5                   10                  15

Leu Ser Leu Thr Cys Ala Val Ser Gly Ser Asp Ile Ser Ser Tyr His
            20                  25                  30

Met Gly Trp Val Arg Gln Pro Pro Gly Lys Gly Leu Glu Trp Ile Gly
        35                  40                  45

Ile Ile Val Ser Ser Gly Ser Ala Tyr Tyr Ala Thr Trp Ala Lys Ser
50                  55                  60

Arg Val Thr Ile Ser Lys Ser Lys Asn Gln Phe Ser Leu Lys Leu Ser
65                  70                  75                  80

Ser Val Thr Ala Ala Asp Thr Ala Val Tyr Cys Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
    115

<210> SEQ ID NO 477
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CIBBABABA_3_115; 16 6 HC humanized 343; 16 6
      HC humanized 290; 16 6 HC humanized 25

<400> SEQUENCE: 477

Val Gln Leu Val Glu Ser Gly Gly Gly Val Val Gln Pro Gly Arg Ser
1               5                   10                  15

Leu Arg Leu Ser Cys Ala Ala Ser Gly Ser Asp Ile Ser Ser Tyr His
            20                  25                  30

Met Gly Trp Val Arg Gln Ala Pro Gly Lys Gly Leu Glu Trp Val Ala
        35                  40                  45

Ile Ile Val Ser Ser Gly Ser Ala Tyr Tyr Ala Thr Trp Ala Lys Gly
    50                  55                  60

Arg Phe Thr Ile Ser Arg Asp Asn Ser Thr Leu Tyr Leu Gln Met Asn
65                  70                  75                  80

Ser Leu Arg Ala Glu Asp Thr Ala Val Tyr Tyr Cys Ala Arg Asn Gln
                85                  90                  95

Tyr Ser Gly Tyr Gly Phe Ser Phe Trp Gly Pro Gly Thr Leu Val Thr
            100                 105                 110

Val Ser Ser
        115

<210> SEQ ID NO 478
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_CACBABABA_3_110; 16 6 LC humanized 775; 16 6
      LC humanized 724; 16 6 LC humanized 722

<400> SEQUENCE: 478

Val Val Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 479
<211> LENGTH: 110
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: cl_GACBABABA_2_110; 16 6 LC humanized 565; 16 6
      LC humanized 563

<400> SEQUENCE: 479

Val Val Leu Thr Gln Ser Pro Ser Ser Leu Ser Ala Ser Val Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Arg Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 480
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_KACBABABA_2_110; 16 6 LC humanized 141; 16 6
      LC humanized 139

<400> SEQUENCE: 480

Val Val Leu Thr Gln Ser Pro Ser Ser Phe Ser Ala Ser Thr Gly Asp
1               5                   10                  15

Arg Val Thr Ile Thr Cys Gln Ser Ser His Ser Val Tyr Tyr Gly Asp
            20                  25                  30

Trp Leu Ala Trp Tyr Gln Gln Lys Pro Gly Lys Ala Pro Lys Leu Leu
        35                  40                  45

Ile Tyr Arg Ala Ser Asn Leu Ala Ser Gly Val Pro Ser Arg Phe Ser
    50                  55                  60

Gly Ser Gly Ser Gly Thr Asp Phe Thr Leu Thr Ile Ser Cys Leu Gln
65                  70                  75                  80

Ser Glu Asp Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
            100                 105                 110

<210> SEQ ID NO 481
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_MACBABABA_62_110; 16 6 LC humanized 990; 16
      6 LC humanized 988; 16 6 LC humanized 985; 16 6 LC humanized 973;
      16 6 LC humanized 937

<400> SEQUENCE: 481
```

-continued

Val Val Leu Thr Gln Ser Pro Ser Val Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gly Gly Tyr Asp Asp Asp
                85                  90                  95

Gly Glu Thr Ala Phe Gly Gly Gly Thr Glu Val Val Val Lys
                100                 105                 110

<210> SEQ ID NO 482
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_WACBABABA_6_110; 16 6 LC humanized 672; 16 6
      LC humanized 670; 16 6 LC humanized 667; 16 6 LC humanized 655;
      16 6 LC humanized 671

<400> SEQUENCE: 482

Val Val Leu Thr Gln Ser Pro Ser Leu Ser Ala Ser Val Gly Asp
1               5                   10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Val Pro Lys Leu Leu
            35                  40                  45

Ile Tyr Arg Ala Ser Asn Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Gly Tyr Asp Asp Asp
                85                  90                  95

Gly Glu Thr Ala Phe Gly Gly Gly Thr Glu Val Val Val Lys
                100                 105                 110

<210> SEQ ID NO 483
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_GECBABABA_6_110; 16 6 LC humanized 248; 16 6
      LC humanized 246; 16 6 LC humanized 243; 16 6 LC humanized 231; 16
      6 LC humanized 247

<400> SEQUENCE: 483

Val Val Leu Thr Gln Ser Pro Ser Phe Leu Ser Ala Ser Val Gly Asp
1               5                   10                  15

Arg Val Thr Ile Thr Cys Gln Ser Ser His Ser Val Tyr Tyr Gly Asp
                20                  25                  30

```
Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Leu Gly Gly Tyr Asp Asp Asp
                 85                  90                  95

Gly Glu Thr Ala Phe Gly Gly Gly Thr Glu Val Val Val Lys
                100                 105                 110

<210> SEQ ID NO 484
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cl_YICBABABA_19_110; 16 6 LC humanized 47; 16 6
      LC humanized 46; 16 6 LC humanized 45; 16 6 LC humanized 42; 16 6
      LC humanized 41

<400> SEQUENCE: 484

Val Val Leu Thr Gln Ser Pro Ser Thr Leu Ser Ala Ser Val Gly Asp
 1               5                  10                  15

Arg Val Thr Ile Thr Cys Gln Ser Ser His Ser Val Tyr Tyr Gly Asp
                20                  25                  30

Trp Leu Ala Trp Tyr Gln Gln Lys Pro Gly Lys Ala Pro Lys Leu Leu
            35                  40                  45

Ile Tyr Arg Ala Ser Asn Leu Ala Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Asp Asp Phe Ala Thr Tyr Tyr Cys Leu Gly Gly Tyr Asp Asp Asp
                 85                  90                  95

Gly Glu Thr Ala Phe Gly Gly Gly Thr Glu Val Val Val Lys
                100                 105                 110

<210> SEQ ID NO 485
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 485

Gly Ser Thr Ser Gly Ser Gly Lys Pro Gly Ser Gly Glu Gly Ser Thr
 1               5                  10                  15

<210> SEQ ID NO 486
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 486
```

```
Gly Ser Thr Ser Gly Ser Gly Lys Pro Gly Ser Gly Glu Gly
1               5                   10
```

<210> SEQ ID NO 487
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 487

```
Gly Ser Thr Ser Gly Ser Gly Lys Pro Gly Ser Gly
1               5                   10
```

<210> SEQ ID NO 488
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 488

```
Gly Ser Thr Ser Gly Ser Gly Lys Pro Gly
1               5                   10
```

<210> SEQ ID NO 489
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 489

```
Gly Ser Gly Lys Pro Gly Ser Gly Glu Gly Ser Thr Lys Gly
1               5                   10
```

<210> SEQ ID NO 490
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 490

```
Gly Lys Pro Gly Ser Gly Glu Gly Ser Thr Lys Gly
1               5                   10
```

<210> SEQ ID NO 491
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

```
<400> SEQUENCE: 491

Pro Gly Ser Gly Glu Gly Ser Thr Lys Gly
1               5                   10

<210> SEQ ID NO 492
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 HC CDR1 (Kabat)

<400> SEQUENCE: 492

Asn Leu Ala Ile Ile
1               5

<210> SEQ ID NO 493
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 HC CDR1 (Kabat)

<400> SEQUENCE: 493

Ser Tyr His Met Gly
1               5

<210> SEQ ID NO 494
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 HC CDR1 (IMGT)

<400> SEQUENCE: 494

Gly Phe Thr Ile Ser Asn Leu Ala Ile Ile
1               5                   10

<210> SEQ ID NO 495
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 HC CDR1 (IMGT)

<400> SEQUENCE: 495

Gly Ser Asp Ile Ser Ser Tyr His Met Gly
1               5                   10

<210> SEQ ID NO 496
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope
```

```
<400> SEQUENCE: 496

Gly Ser Thr Ser Gly Ser Gly Lys Pro Gly Ser Gly Glu
1               5                   10

<210> SEQ ID NO 497
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 497

Ser Gly Lys Pro Gly Ser Gly Glu Gly Ser Thr Lys Gly
1               5                   10

<210> SEQ ID NO 498
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 and Clone 16 epitope

<400> SEQUENCE: 498

Lys Pro Gly Ser Gly Glu Gly Ser Thr Lys Gly
1               5                   10

<210> SEQ ID NO 499
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 8 epitope

<400> SEQUENCE: 499

Ser Gly Lys Pro Gly Ser Gly Glu
1               5

<210> SEQ ID NO 500
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Clone 16 epitope

<400> SEQUENCE: 500

Lys Pro Gly Ser Gly
1               5
```

ANTIGEN BINDING MOLECULES AND METHODS OF USE THEREOF

CROSS REFERENCE TO RELATED APPLICATIONS

This application claims priority to U.S. Provisional Patent Application Ser. Nos. 62/361,420 filed on Jul. 12, 2016 and 62/415,786 and Nov. 1, 2016; the entirety of each of which is hereby incorporated by reference.

SEQUENCE LISTING

The instant application contains a Sequence Listing, which has been submitted electronically in ASCII format and is hereby incorporated by reference in its entirety. Said ASCII copy, created on Jul. 10, 2017 is named K1033_03_SL.txt and is 571,539 bytes in size.

FIELD OF THE INVENTION

This disclosure relates to antigen binding molecules, such as antibodies, which specifically bind to the sequence GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules, polynucleotides encoding such antigen binding molecules, as well as humanized forms of the antigen binding molecules; methods of using the antigen binding molecules are also disclosed.

BACKGROUND OF THE INVENTION

Antigen binding molecules, including antibodies, are used in immunotherapy and solid phase-based applications such as biosensors, affinity chromatography, and immunoassays. These antibodies and antigen binding molecules gain their utility by virtue of their ability to specifically bind their targets.

Linker sequences, which are often peptide-based when employed in biotechnological and biotherapeutic applications, can serve a range of scientifically-relevant applications. For example, a linker can be used as simply a spacer moiety in order to impart a desired structural and/or functional property to a larger molecule. In another example, a linker can impart little or no structural or functional properties to a larger molecule, but can be used simply as a distinguishing feature (e.g., a "marker" or "biomarker" or "tag"), uniquely identifying a larger molecule. In still another example, a linker can be used to impart a recognizable feature that can serve as a binding site for an antibody directed against a larger molecule comprising the linker sequence.

When a linker sequence is used as a distinguishing, detectable or identifiable feature of a larger molecule, an antibody that specifically binds the linker sequence, to the exclusion of other sequences present in the larger molecule, the antibody can serve as a detection agent. Such antibodies can be labeled with a moiety that is detectable under certain conditions. Additional applications for such an antibody include purification and isolation of a molecule comprising the linker, characterization of a molecule in a particular setting, enrichment of the concentration of a population of molecules comprising and/or presenting the linker, and therapeutic applications as well.

In 1993, Whitlow et al. disclosed a synthetic linker peptide comprising the amino acid sequence GSTSGSGKPGSGEGSTKG (SEQ ID NO: 1) (Whitlow et al., (1993) *Prot. Eng.* 6(8):989-95). The disclosed peptide was studied as a component of an scFv, and was designed to remove a proteolytic site identified in a previous linker peptide. Whitlow et al. concluded that this newly-designed synthetic linker peptide was more stable to proteolysis in vitro when compared to the prior linker peptide upon which its sequence was based, and also showed less aggregation compared to the same prior linker. Whitlow et al. did not disclose any antigen binding molecules directed to their second generation linker peptide.

Disclosed herein are antigen binding molecules, including antibodies, that specifically bind the sequence GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules. Humanized forms of the antigen binding molecules are also provided. Applications and uses thereof are also disclosed.

SUMMARY OF THE INVENTION

An isolated antigen binding molecule that specifically binds to a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499), and KPGSG (SEQ ID NO: 500) is provided. In various embodiments, the antigen binding molecule is selected from the group consisting of an antibody, an scFv, a Fab, a Fab', a Fv, a F(ab')$_2$, a dAb, a non-human antibody (e.g., rabbit) a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody, an IgG2 antibody having at least one mutation in the hinge region, an IgG3 antibody, an IgG1 antibody having at least one mutation in the hinge region, an IgG4 antibody, an IgG4 antibody having at least one mutation in the hinge region, an antibody comprising at least one non-naturally occurring amino acid, and any combination thereof. In a specific embodiment, the antigen binding molecule comprises an antibody.

In various embodiments, the antigen binding molecule comprises a heavy chain (HC) and in some embodiments, the HC comprises a heavy chain variable region (VH) sequence selected from the group consisting of SEQ ID NOs: 5 and 17. In other embodiments, the variable region (VH) comprises one or more of (a) a CDR1, (b) a CDR2, and (c) a CDR3. In some embodiments, the antigen binding molecule comprises a heavy chain CDR1 selected from the group consisting of SEQ ID NOs: 7 and 19; in other embodiments, the antigen binding molecule comprises a heavy chain CDR2 selected from the group consisting of SEQ ID NOs: 8 and 20, and still other embodiments, the antigen binding molecule comprises a heavy chain CDR3 selected from the group consisting of SEQ ID NOs: 9 and 21. In a various embodiments, an antigen binding molecule comprises a heavy chain CDR1, a heavy chain CDR2, and a heavy chain CDR3, each CDR comprising an amino acid sequence shown in FIGS. 6 and 8, and in further embodiments, an antigen binding molecule comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule provided herein, e.g., in the attached Sequence Listing and in FIGS. 6 and 8.

In various embodiments, the antigen binding molecule comprises a light chain (LC) and in some embodiments, the LC comprises a light chain variable region (VL) sequence selected from the group consisting of SEQ ID NOs: 11 and 23. In other embodiments, the variable region (VL) comprises one or more of (a) a CDR1, (b) a CDR2, and (c) a CDR3. In some embodiments, the antigen binding molecule comprises a light chain CDR1 selected from the group consisting of SEQ ID NOs: 13 and 25; in other embodiments, the antigen binding molecule comprises a light chain CDR2 selected from the group consisting of SEQ ID NOs: 14 and 26, and still other embodiments, the antigen binding molecule comprises a light chain CDR3 selected from the group consisting of SEQ ID NOs: 15 and 27. In a various embodiments, an antigen binding molecule comprises a light chain CDR1, a light chain CDR2, and a light chain CDR3, each CDR comprising an amino acid sequence shown in FIGS. 6 and 8, and in further embodiments, an antigen binding molecule comprises a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VL of an antigen binding molecule provided herein, e.g., in the attached Sequence Listing and in FIGS. 6 and 8.

In a specific embodiment, the antigen binding molecule comprises: (a) a VH comprising the amino acid sequence of SEQ ID NO: 5; and (b) a VL comprising the amino acid sequence of SEQ ID NO: 11. In a further specific embodiment, the antigen binding molecule comprises: (a) a VH CDR1 region comprising the amino acid sequence of SEQ ID NO: 7; (b) a VH CDR2 region comprising the amino acid sequence of SEQ ID NO: 8; (c) a VH CDR3 region comprising the amino acid sequence of SEQ ID NO: 9; (d) a VL CDR1 region comprising the amino acid sequence of SEQ ID NO: 13; (e) a VL CDR2 region comprising the amino acid sequence of SEQ ID NO: 14; and (f) a VL CDR3 region comprising the amino acid sequence of SEQ ID NO: 15.

In a specific embodiment, the antigen binding molecule comprises: (a) a VH comprising the amino acid sequence of SEQ ID NO: 17; and (b) a VL comprising the amino acid sequence of SEQ ID NO: 23. In a further specific embodiment, the antigen binding molecule comprises: (a) a VH CDR1 region comprising the amino acid sequence of SEQ ID NO: 19; (b) a VH CDR2 region comprising the amino acid sequence of SEQ ID NO: 20; (c) a VH CDR3 region comprising the amino acid sequence of SEQ ID NO: 21; (d) a VL CDR1 region comprising the amino acid sequence of SEQ ID NO: 25; (e) a VL CDR2 region comprising the amino acid sequence of SEQ ID NO: 26; and (f) a VL CDR3 region comprising the amino acid sequence of SEQ ID NO: 27.

In some embodiments, an antigen binding molecule provided herein further comprises a detectable label, which can be selected from the group consisting of a fluorescent label, a photochromic compound, a proteinaceous fluorescent label, a magnetic label, a radiolabel, and a hapten. In a specific embodiment, the detectable label comprises a fluorescent label and is selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry.

Also provided are compositions comprising the antigen binding molecules, polynucleotides encoding the heavy chain of the antigen binding molecules and polynucleotides encoding the light chain of an antigen binding molecules. Vectors comprising the polynucleotides and cells comprising such vectors form additional aspects of the disclosure. In various embodiments, a cell can be selected from the group consisting of a CHO cell, a Sp2/0 cell, a rabbit cell other mammalian cells, yeast cells, or bacterial cells, such as an *E. coli* cell. Methods of making an antigen binding molecule disclosed herein, which can comprise incubating the cell under suitable conditions, are also provided.

In another aspect, a method of administering a dose of a medicament to a subject, the dose comprising a preselected number of cells presenting a therapeutic molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided. In an embodiment, the method comprises (a) providing a sample of known volume comprising a population comprising a known number of cells, the population known or suspected to be expressing a therapeutic molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500); (b) providing an aliquot of the sample comprising a population of cells presenting a molecule comprising the selected amino acid sequence; (c) providing an antigen binding molecule that specifically binds the selected amino acid sequence and comprises a detectable label; (d) contacting the aliquot of (b) with the antigen binding molecule of (c) under conditions that permit the formation of a binding complex comprising a cell present in the sample and the antigen binding molecule; (e) determining the fraction of cells present in a binding complex of (d) in the aliquot; (f) determining the concentration of cells presenting a molecule comprising the selected amino acid sequence in the sample, based on the fraction of cells determined in (e); (g) determining the volume of the sample that comprises the selected number of cells; and (h) administering the volume of the sample determined in (g) to the subject.

In some embodiments, (a) the therapeutic molecule is a CAR; and (b) the cell is an immune cell selected from the group consisting of CD8+ T cells, CD4+ T cells, tumor infiltrating lymphocytes (TILs), NK cells, TCR-expressing cells, dendritic cells, and NK-T cells. In specific embodiments, the CAR comprises a molecule, or a fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof. In some embodiments, the immune cell is a T cell, which can be disposed in vitro or in vivo, and can be in one of blood, extracted tissue, tissue grown ex vivo, and cell culture media. A T cell can be an autologous T cell or an allogenic T cell. In some embodiments, the dose comprises $0.5 \times 10^6$ cells per kilogram of the subject, $1.0 \times 10^6$ cells per kilogram of the subject, $2.0 \times 10^6$ cells per kilogram of the subject, $3.0 \times 10^6$ cells per kilogram of the subject, $4.0 \times 10^6$ cells per kilogram of the subject, or $5.0 \times 10^6$ cells per kilogram of the subject. In a specific embodiment, the dose comprises $1.0 \times 10^6$ cells per kg. In other embodiments, the detectable label is selected from the group consisting of a fluorescent label, a photochromic compound, a proteinaceous fluorescent label, a magnetic label, a radiolabel, and a hapten. When the detectable label is a fluorescent label, the fluorescent label can be selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. In yet further embodiments, the antigen binding molecule is a humanized antigen binding molecule.

In another aspect, a method of activating an immune cell expressing a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided. In an embodiment, the method comprises (a) providing a sample comprising an immune cell known or suspected to be expressing a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500); and (b) contacting an antigen binding molecule with the sample, under conditions that permit the formation of a binding complex comprising the antigen binding molecule and two molecules comprising the selected amino acid sequence, wherein the molecules comprising the selected amino acid sequences are disposed on two different immune cells.

In some embodiments, the immune cell selected from the group consisting of CD8+ T cells, CD4+ T cells, tumor infiltrating lymphocytes (TILs), NK cells, TCR-expressing cells, dendritic cells, and NK-T cells. In specific embodiments, the molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is a CAR. In further embodiments, the CAR comprises a molecule, or a fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof. In some embodiments, the immune cell is a T cell, which can be disposed in vitro or in vivo, and can be in one of blood, extracted tissue, tissue grown ex vivo, and cell culture media. A T cell can be an autologous T cell or an allogenic T cell. In yet further embodiments, the antigen binding molecule is a humanized antigen binding molecule.

In another aspect, a method of determining a number of cells presenting a molecule in a sample wherein the molecule comprises an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided. In an embodiment, the method comprises (a) providing a sample comprising cells known or suspected to be presenting a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500); (b) contacting the sample of (a) with an antigen binding molecule that specifically binds the selected amino acid sequence and comprises a detectable label, under conditions that permit the formation of a binding complex comprising a cell present in the sample and the antigen binding molecule; and (c) determining the number of cells present in a binding complex of (b) in the sample.

In some embodiments, the molecule comprising an amino acid sequence selected from the group consisting of GSTSGSGKPGSGEGSTKG (SEQ ID NO: 1), GSGKPGSGEG (SEQ ID NO: 2) and GKPGSGEG (SEQ ID NO: 3), SGKPGSGE (SEQ ID NO: 499) and KPGSG (SEQ ID NO: 500) is a CAR. In specific embodiments, the CAR comprises a molecule, or a fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, WIC class 1 molecule, MHC class 2 molecule, a TNF receptor protein, an immunoglobulin protein, a cytokine receptor, an integrin, activating NK cell receptors, a Toll-like receptor, and combinations thereof. In other embodiments, the cells are immune cells selected from the group consisting of CD8+ T cells, CD4+ T cells, tumor infiltrating lymphocytes (TILs), NK cells, TCR-expressing cells, dendritic cells, and NK-T cells. In some embodiments, the cells are T cells, which can be disposed in vitro or in vivo, and can be in one of blood, extracted tissue, tissue grown ex vivo, and cell culture media. T cells can be autologous T cells or allogenic T cells. In yet further embodiments, the antigen binding molecule is a humanized antigen binding molecule.

In another aspect, a method of isolating a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided. The molecule can comprise the selected amino acid at the N-terminus, C-terminus, between domains, in loops, or anywhere in the molecule that may or may not disrupt the structure. In an embodiment, the method comprises (a) providing a sample known or suspected to comprise a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500); (b) providing an antigen binding molecule that specifically binds the selected amino acid sequence, optionally comprising a detectable label; (c) contacting the sample with the antigen binding molecule, under conditions that permit the formation of a binding complex comprising a molecule comprising the selected amino acid sequence and the antigen binding molecule; and (d) separating any molecules not part of a binding complex from formed binding complexes; and (e) separating a formed binding complex into: (1) a molecule comprising the selected amino acid sequence, and (2) an antigen binding molecule.

In some embodiments, the molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is a CAR. In specific embodiments, the CAR comprises a molecule, or a fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336

(NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof. In other embodiments, the antigen binding molecule is disposed on a surface selected from the group consisting of an agarose bead, a magnetic bead, a plastic welled plate, a glass welled plate, a ceramic welled plate and a cell culture bag. In other embodiments, the detectable label is selected from the group consisting of a fluorescent label, a photochromic compound, a proteinaceous fluorescent label, a magnetic label, a radiolabel, and a hapten. When the detectable label is a fluorescent label, the fluorescent label can be selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, Tru-Red, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. In yet further embodiments, the antigen binding molecule is a humanized antigen binding molecule.

In a further aspect, a method of determining the presence or absence of a molecule comprising an amino acid sequence selected from the group consisting of GSTSGS-GKPGSGEGSTKG (SEQ ID NO: 1), GSGKPGSGEG (SEQ ID NO: 2), GKPGSGEG (SEQ ID NO: 3), SGK-PGSGE (SEQ ID NO: 499) and KPGSG (SEQ ID NO: 500) is provided. In embodiments, the method comprises (a) providing a sample known or suspected to comprise a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500); (b) providing an antigen binding molecule that specifically binds the selected amino acid sequence, the antigen binding protein further comprising a detectable label; (c) contacting the sample with the antigen binding molecule under conditions that permit the formation of a binding complex; (d) separating any molecules not part of a binding complex from formed binding complexes; and (e) detecting the presence or absence of a binding complex.

In embodiments, the molecule comprising an amino acid sequence selected from the group consisting of GSTSGS-GKPGSGEGSTKG (SEQ ID NO: 1), GSGKPGSGEG (SEQ ID NO: 2), GKPGSGEG (SEQ ID NO: 3), SGK-PGSGE (SEQ ID NO: 499) and KPGSG (SEQ ID NO: 500) is a CAR. In further embodiments, the CAR comprises a molecule, or a fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof. In other embodiments, the antigen binding molecule is disposed on a surface selected from the group consisting of an agarose bead, a magnetic bead, a plastic welled plate, a glass welled plate, a ceramic welled plate and a cell culture bag. In other embodiments, the detectable label is selected from the group consisting of a fluorescent label, a photochromic compound, a proteinaceous fluorescent label, a magnetic label, a radiolabel, and a hapten. When the detectable label is a fluorescent label, the fluorescent label can be selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, Tru-Red, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. In yet further embodiments, the antigen binding molecule is a humanized antigen binding molecule.

Also provided is a method of increasing the concentration of cells presenting a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500). In some embodiments, the method comprises (a) providing a sample comprising cells known or suspected to comprise a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500); (b) providing an antigen binding molecule that specifically binds the selected amino acid sequence and optionally comprises a detectable label; (c) contacting the sample with the antigen binding molecule under conditions that permit the formation of a binding complex comprising molecule comprising the selected amino acid sequence and the antigen binding molecule; (d) removing any components not part of a binding complex; and (e) repeating steps (a)-(d) a desired number of times.

In embodiments, (a) the molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is a CAR; and (b) the cells are immune cells selected from the group consisting of CD8+ T cells, CD4+ T cells, tumor infiltrating lymphocytes (TILs), NK cells, TCR-expressing cells, dendritic cells, and NK-T cells. In further embodiments, the CAR comprises a molecule, or a fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MEW class 1 molecule, MHC class 2 molecule, a TNF receptor protein, an immunoglobulin protein, a cytokine receptor, an integrin, activating NK cell receptors, a Toll-like receptor, and combinations thereof. In some embodiments, the cells are T cells, which can be disposed in vitro or in vivo, and can be in one of blood, extracted tissue, tissue grown ex vivo, and cell culture media. T cells can be autologous T cells or allogenic T cells. In yet further embodiments, the antigen binding molecule is a humanized antigen binding molecule.

In still a further aspect, a method of depleting a population of cells (e.g., immune cells) presenting a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided. In embodiments, the method comprises (a) providing a population of immune cells to be depleted, wherein the immune cells are known or suspected to be expressing a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500); and (b) contacting the immune cells with an antigen binding molecule that specifically binds to (a) the molecule comprising the selected amino acid sequence, and (b) an activating molecule presented on the surface of that immune cell that does not comprise the selected amino acid sequence, under conditions that permit the formation of a ternary binding complex comprising the molecule comprising the molecule comprising the selected amino acid sequence, the activating molecule and the antigen binding molecule.

In specific embodiments, the molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is a CAR. In further embodiments, the CAR comprises a molecule, or a fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MEW class 2 molecule, a TNF receptor protein, an immunoglobulin protein, a cytokine receptor, an integrin, activating NK cell receptors, a Toll-like receptor, and combinations thereof. In some embodiments, the immune cell is a T cell, which can be disposed in vitro or in vivo, and can be in one of blood, extracted tissue, tissue grown ex vivo, and cell culture media. A T cell can be an autologous T cell or an allogenic T cell. In yet further embodiments, the antigen binding molecule is a humanized antigen binding molecule.

In one aspect, the present invention provides a method of monitoring distribution in vivo of a population of cells presenting a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500). In some embodiments, the population of cells are CAR cells. In some embodiments, the present invention provides a method of monitoring distribution in vivo of a population of cells presenting a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) comprising providing an antigen binding molecule; and performing a positron emission tomography (PET) scan. In some embodiments, providing the antigen binding molecule stimulates or depletes the CAR T-cells in vivo.

BRIEF DESCRIPTION OF THE FIGURES

FIG. 6 is a series of tables showing the CDR1, 2 and 3 regions of the heavy chain (HC) and light chain (LC) of antibodies secreted by Clones 8 and 16; heavy and light chain CDRs are shown for each antibody using the Kabat (SEQ ID NOS 492, 8, 9, 493, 20, 21, 13-15, and 25-27, respectively, in order of appearance), Chothia (SEQ ID NOS 7-9, 19-21, 13-15, and 25-27, respectively, in order of appearance) and IMGT (SEQ ID NOS 494, 8, 9, 495, 20, 21, 13-15, and 25-27, respectively, in order of appearance) numbering systems.

FIG. 7 is a table showing the 18 mer sequence GSTSGSGKPGSGEGSTKG (SEQ ID NO: 1) as well as the epitopes on this sequence where the antibodies of clone 8 bind (GSGKPGSGEG; SEQ ID NO: 2 and SGKPGSGE; SEQ ID NO: 499) and where the antibodies of clone 16 bind (GKPGSGEG; SEQ ID NO: 3 and KPGSG; SEQ ID NO: 500).

FIG. 8 is a series of tables showing humanized forms of the antigen binding molecules provided herein.

As shown in FIG. 14A, as the diabody concentration is increased, a larger median fluorescent intensity is seen in the average of three replicates of CAR constructs containing the specific peptide. When a control CAR or Mock-transduced cells are incubated with the diabody, there is not a significant increase in the amount of cytotoxic dye fluorescence. In FIG. 14B, the percentage of CAR+ T-cells is measured as a function of increasing diabody concentration.

DETAILED DESCRIPTION OF THE INVENTION

Figure 1A:
FIG. 1A is a ribbon diagram and FIG. 1B is a space-filling diagram of an scFv sequence comprising the linker sequence of SEQ ID NO: 1; the linker is shown in gray.
Figure 1B:
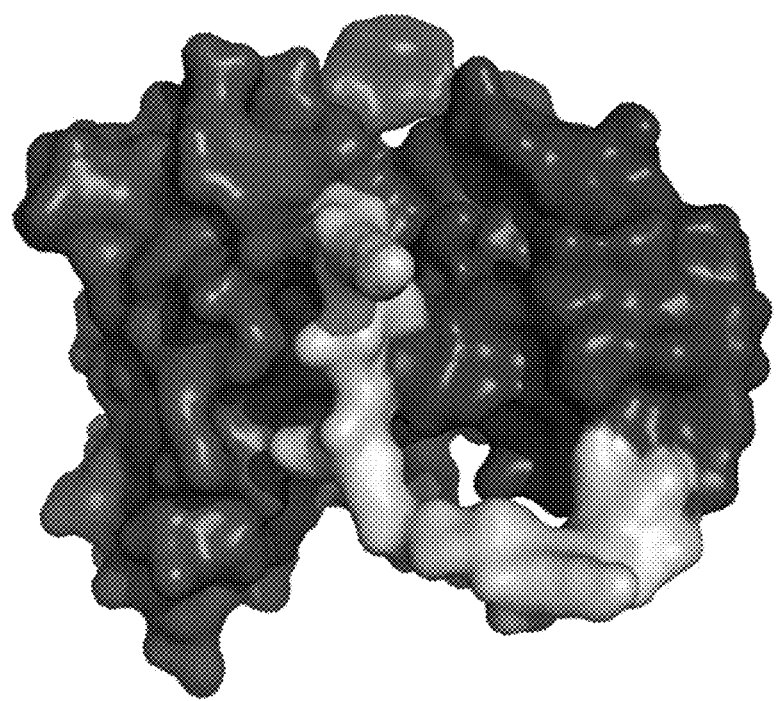

The present disclosure relates to antigen binding molecules, including antibodies, which specifically bind a moiety comprising the sequence GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), as well as humanized forms of the antigen binding molecules, molecules comprising SEQ ID NOs: 1, 2, 3, 499 and/or 500, cells presenting such molecules, polynucleotides encoding the molecules, and vectors comprising the polynucleotides; in vitro cells comprising the polynucleotides and vectors are also disclosed.

Methods of using the disclosed antigen binding molecules are provided. The antigen binding molecules, polynucleotides, vectors, in vitro cells and methods described herein can be used in a range of applications, e.g., as reagents to detect the presence of molecules comprising GSTSGSGK-PGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), and cells presenting such molecules, quantifying the amount of a molecule comprising SEQ ID NOs: 1, 2, 3, 499 and/or 500, molecules and cells presenting such molecules, screening for molecules comprising SEQ ID NOs: 1, 2, 3, 499 and/or 500, and cells presenting such molecules, purifying molecules comprising SEQ ID NOs: 1, 2, 3, 499 and/or 500, and cells presenting such molecules, and biomarker studies focused on molecules comprising SEQ ID NOs: 1, 2, 3, 499 and/or 500, and cells presenting such molecules. Therapeutic uses are also provided, for example applications in which the biological activity of a molecule comprising SEQ ID NOs: 1, 2, 3, 499 and/or 500, and cells presenting such molecules, is modulated (enhanced or repressed), as well as dose ranging studies related to therapeutics comprising SEQ ID NOs: 1, 2, 3, 499 and/or 500, and cells presenting such molecules.

The antigen binding molecules (antibodies) disclosed herein were generated from hybridomas generated using B-cells of rabbit origin, but can be readily humanized using standard methods known to those of skill in the art, as well as those described herein. Representative humanized forms of the disclosed antigen binding molecules are provided herein.

I. Definitions

In order that the present disclosure may be more readily understood, certain terms are first defined. As used in this application, except as otherwise expressly provided herein, each of the following terms shall have the meaning set forth below. Additional definitions are set forth throughout the application. The headings provided herein are not limitations of the various aspects of the disclosure, which aspects can be understood by reference to the specification as a whole.

It is understood that wherever aspects are described herein with the language "comprising," otherwise analogous aspects described in terms of "consisting of" and/or "consisting essentially of" are also provided.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, *The Concise Dictionary of Biomedicine and Molecular Biology*, 2$^{nd}$ ed., (2001), CRC Press; *The Dictionary of Cell & Molecular Biology*, 5$^{th}$ ed., (2013), Academic Press; and *The Oxford Dictionary Of Biochemistry And Molecular Biology*, Cammack et al. eds., 2$^{nd}$ ed, (2006), Oxford University Press, provide those of skill in the art with a general dictionary for many of the terms used in this disclosure.

As used herein, the twenty conventional (e.g., naturally occurring) amino acids and their abbreviations follow conventional usage. See, e.g., *Immunology—A Synthesis* (2nd Edition), Golub and Green, eds., Sinauer Assoc., Sunderland, Mass. (1991), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the present invention. Examples of unconventional amino acids include: 4-hydroxyproline, gamma-carboxyglutamate, epsilon-N,N,N-trimethyllysine, e-N-acetyllysine, O-phosphoserine, N-acetylserine, N-formylmethionine, 3-methylhistidine, 5-hydroxylysine, sigma-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein, the term the terms "a" and "an" are used per standard convention and mean one or more, unless context dictates otherwise.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. Alternatively, "about" or "comprising essentially of" can mean a range of up to 10% (i.e., ±10%). For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

As used herein, the term "and/or" is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as 'A, B, and/or C" is intended to encompass each of the following aspects: A, B, and C; A, B, or C; A or C; A or B; B or C; A and C; A and B; B and C; A (alone); B (alone); and C (alone).

As used herein, the term the use of the alternative (e.g., "or") should be understood to mean either one, both, or any combination thereof of the alternatives.

As used herein, the term "allogeneic" refers to any material derived from one individual which is then introduced to another individual of the same species, e.g., allogeneic T cell transplantation.

As used herein, the term "antibody" (Ab) includes, without limitation, a glycoprotein immunoglobulin which binds specifically to an antigen. In general, an antibody can comprise at least two heavy (HC) chains and two light (LC) chains interconnected by disulfide bonds, or an antigen binding molecule thereof. Each HC chain comprises a heavy chain variable region (abbreviated herein as VH) and a heavy chain constant region. The heavy chain constant region comprises three constant domains, CH1, CH2 and CH3. Each LC chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component of the classical complement system (C1q).

The term "antibody" also encompasses an intact immunoglobulin or an antigen binding portion thereof that competes with the intact antibody for specific binding, unless otherwise specified. Antigen binding portions can be produced by recombinant DNA techniques or by enzymatic or chemical cleavage of intact antibodies. Antigen binding portions include, inter alia, Fab, Fab', F(ab')$_2$, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

The term "antibody" includes, both naturally occurring and non-naturally occurring (recombinantly-produced) antibodies, human and non-human antibodies, monospecific antibodies, multispecific antibodies (including bispecific antibodies), immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies (see, e.g., Stocks, (2004) *Drug Discovery Today* 9(22):960-66), antibody fusions (which term encompasses antibody-drug conjugates) and which are sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments thereof. In certain embodiments, antibodies described herein refer to polyclonal antibody populations.

A non-human antibody can be humanized using recombinant methods to reduce its immunogenicity in humans, as disclosed herein with respect to antibodies that specifically bind GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules. Examples of humanized antibodies are provided herein. Where not expressly stated, and unless the context indicates otherwise, the term "antibody" also includes an antigen-binding fragment of an antigen binding molecule of any of the aforementioned immunoglobulins, and includes a monovalent and a divalent fragment or portion, and a single chain antibody (i.e., a scFv).

In various embodiments, an antibody specifically binds GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules. In some embodiments, the antibody specifically binds to a CAR (or component thereof) comprising SEQ ID NOs: 1, 2, 3, 499 and/or 500, molecules comprising this sequence, and cells presenting such molecules; cells presenting SEQ ID NOs: 1, 2, 3, 499 and/or 500 can, but need not be, an immune cell, such as a T cell.

As used herein, the term "antigen" means any molecule that provokes an immune response or is capable of being bound by an antibody or other antigen binding molecule. The immune response can involve either antibody production, or the activation of specific immunologically-competent cells, or both. Those of skill in the art will readily understand that any macromolecule, including virtually all proteins or peptides (including SEQ ID NOs: 1, 2, 3, 499 and/or 500), molecules comprising this sequence and cells presenting such molecules), can serve as an antigen. Generally, an antigen can be endogenously expressed, i.e. expressed by genomic DNA, or it can be recombinantly expressed, or it can be chemically synthesized. In one particular embodiment, an antigen comprises all or a portion of GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences, which is optionally conjugated to an adjuvant such as keyhole limpet hemocyanin (KLH).

As used herein, the term "antigen binding molecule" means a protein comprising a portion that binds to an antigen or target protein and, optionally, a scaffold or framework portion that allows the antigen binding portion to adopt a conformation that promotes binding of the antigen binding molecule to the antigen. Examples of the representative types of antigen binding molecules include a scFv, a human, mouse or rabbit antibody; a humanized antibody; a chimeric antibody; a recombinant antibody; a single chain antibody; a diabody; a triabody; a tetrabody; a Fab fragment; a F(ab')2 fragment; an IgD antibody; an IgE antibody; an IgM antibody; an IgG1 antibody; an IgG2 anti-body; an IgG3 antibody; or an IgG4 antibody, and fragments thereof.

An antigen binding molecule can comprise, for example, an alternative protein scaffold or artificial scaffold with grafted complementarity determining regions (CDRs) or CDR derivatives. Such scaffolds include, but are not limited to, antibody-derived scaffolds comprising mutations introduced to, for example, stabilize the three-dimensional structure of the antigen binding molecule as well as wholly synthetic scaffolds comprising, for example, a biocompatible polymer. See, e.g., Korndorfer et al., 2003, *Proteins: Structure, Function, and Bioinformatics,* 53(1):121-129 (2003); Roque et al., *Biotechnol. Prog.* 20:639-654 (2004). In addition, peptide antibody mimetics ("PAMs") can be used, as well as scaffolds based on antibody mimetics utilizing various components (e.g., fibronectin) as a scaffold. An antigen binding molecule can have, for example, the structure of a naturally occurring immunoglobulin.

An antigen binding molecule can have one or more binding sites. If there is more than one binding site, the binding sites can be identical to one another or they can be different. For example, a naturally occurring human immunoglobulin typically has two identical binding sites, while a "bispecific" or "bifunctional" antibody has two different binding sites, and is capable of specifically binding two different antigens (e.g., SEQ ID NOs: 1, 2, 3, 499 and/or 500 and a cell surface activator molecule).

In various embodiments, an antigen binding molecule is an antibody or fragment thereof, including one or more of the complementarity determining regions (CDRs) disclosed herein and shown in FIGS. 6 and 8, which specifically bind GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising SEQ ID NOs: 1, 2, 3, 499 and/or 500, and cells presenting such molecules. In further embodiments, the antigen binding molecule binds to a CAR comprising the SEQ ID NOs: 1, 2, 3, 499 and/or 500, and can be expressed on an immune cell, such as a T cell.

The term "autologous" refers to any material derived from the same individual to which it is later to be re-introduced. For example, the engineered autologous cell therapy (eACT™) methods described herein involve collection of lymphocytes from a patient, which are then engineered to express a construct, e.g., a CAR construct, and then administered back to the same patient.

As used herein, the term "binding affinity" means the strength of the sum total of non-covalent interactions between a single binding site of a molecule (e.g., an antigen binding molecule such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by standard techniques known to one of ordinary skill in the art, such as BIAcore® or KinExA or surface plasmon resonance.

As used herein, the term "complementarity determining region" or "CDR" means an amino acid sequence that contributes to antigen binding specificity and affinity. Framework regions can aid in maintaining the proper confirmation of the CDRs to promote binding between the antigen binding molecule and an antigen. There are three CDRs in each of the variable regions of the heavy chain and the light chain, which are designated CDR1, CDR2 and CDR3, for each of the variable regions. The exact boundaries of CDRs have been defined differently according to different systems.

A number of definitions of the CDRs are commonly in use: Kabat numbering, Chothia numbering, AbM numbering, or contact numbering. The AbM definition is a compromise between the Kabat and Chothia systems, and is used by Oxford Molecular's AbM antibody modelling software.

The system described by Kabat (Kabat et al., Sequences of Proteins of Immunological Interest (National Institutes of Health, Bethesda, Md. (1987) and (1991)) provides a residue numbering system applicable to any variable region of an antibody, and also provides precise residue boundaries defining the three CDRs.

Chothia and coworkers (Chothia and Lesk, (1987) J. Mol. Biol., 196:901-917; and Chothia et al., (1989) Nature, 342: 877-883) found that certain sub-portions within Kabat CDRs adopt nearly identical peptide backbone conformations, despite having great diversity at the level of amino acid sequence. Chothia CDRs have boundaries that overlap with Kabat CDRs. Other boundaries defining CDRs overlapping with the Kabat CDRs have been described by Padlan et al. ((1995) FASEB J., 9:133-139) and MacCallum et al. ((1996) J. Mol. Biol., 262(5):732-745). Still other CDR boundary definitions may not strictly follow one of the described systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although exemplary embodiments use Chothia defined CDRs.

Table A defines CDRs using each numbering system. The contact definition is based on an analysis of the available complex crystal structures.

TABLE A

| Loop | Kabat | AbM | Chothia | Contact |
| --- | --- | --- | --- | --- |
| L1 | L24 - - - L34 | L24 - - - L34 | L24 - - - L34 | L30 - - - L36 |
| L2 | L50 - - - L56 | L50 - - - L56 | L50 - - - L56 | L46 - - - L55 |
| L3 | L89 - - - L97 | L89 - - - L97 | L89 - - - L97 | L89 - - - L96 |
| H1 | H31 - - - H35B | H26 - - - H35B | H26 - - - H32 . . . 34 | H30 - - - H35B |
| H1 | H31 - - - H35 | H26 - - - H35 | H26 - - - H32 | H30 - - - H35 |
| H2 | H50 - - - H65 | H50 - - - H58 | H52 - - - H56 | H47 - - - H58 |
| H3 | H95 - - - H102 | H95 - - - H102 | H95 - - - H102 | H93 - - - H101 |

The term "Kabat numbering" and like terms are recognized in the art and refer to a system of numbering amino acid residues in the heavy and light chain variable regions of an antibody, or an antigen binding molecule thereof. In certain aspects, the CDRs of an antibody can be determined according to the Kabat numbering system (see, e.g., Kabat et al. in Sequences of Proteins of Immunological Interest, 5th Ed., NIH Publication 91-3242, Bethesda Md. 1991). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein can be described according to the Kabat numbering scheme although they can readily be construed in other numbering systems using Table A.

In certain aspects, the CDRs of an antibody can be determined according to the Chothia numbering scheme, which refers to the location of immunoglobulin structural loops (see, e.g., Chothia C & Lesk A M, (1987), *J Mol Biol* 196: 901-917; Al-Lazikani B et al., (1997) *J Mol Biol* 273: 927-948; Chothia C et al., (1992) *J Mol Biol* 227: 799-817; Tramontano A et al., (1990) *J Mol Biol* 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). See Table A. In a specific embodiment, the CDRs of the antibodies described herein have been determined according to the Chothia numbering scheme, as shown in FIGS. 6 and 8.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen binding molecule provided herein (or fragment thereof) can be replaced with an amino acid residue with a similar side chain.

Conservative amino acid substitutions, which are encompassed by the present disclosure, can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:
  hydrophobic: norleucine, Met, Ala, Val, Leu, Ile;
    neutral hydrophilic: Cys, Ser, Thr, Asn, Gln;
      acidic: Asp, Glu;
        basic: His, Lys, Arg;
  residues that influence chain orientation: Gly, Pro; and
    aromatic: Trp, Tyr, Phe.

Non-conservative substitutions can involve the exchange of a member of one of these classes for a member from another class. Such substituted residues can be introduced, for example, into regions of a human antibody that are homologous with non-human antibodies, or into the non-homologous regions of the molecule. Exemplary conservative amino acid substitutions are set forth in Table B below.

TABLE B

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "cross competes" means the situation in which the interaction between an antigen and a first antigen binding molecule or binding fragment thereof blocks, limits, inhibits, or otherwise reduces the ability of a reference antigen binding molecule or binding fragment thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross competes with a reference antigen binding molecule binds the same or an overlapping epitope as the reference antigen binding molecule. In other embodiments, the antigen binding molecule that cross competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., (1983) *Method Enzymol* 9:242-53); solid phase direct biotin-avidin EIA (Kirkland et al., (1986) *J Immunol* 137:3614-19); solid phase direct labeled assay, solid phase direct labeled sandwich assay (Harlow and Lane, 1988, *Antibodies, A Laboratory Manual*, Cold Spring Harbor Press); solid phase direct label RIA using $I^{125}$ label (Morel et al., (1988) *Molec*

Immunol 25:7-15); solid phase direct biotin-avidin EIA (Cheung et al., (1990) *Virology* 176:546-52); and direct labeled RIA (Moldenhauer et al., (1990) *Scand J Immunol* 32:77-82).

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding molecule (a derivative) can have a greater circulating half-life than an antigen binding molecule that is not chemically modified. In some embodiments, a derivative antigen binding molecule is covalently modified to include one or more water soluble polymer attachments, including, but not limited to, polyethylene glycol, polyoxyethylene glycol, or polypropylene glycol.

As used herein, the term "diabody" or dAB means bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., (1993) *Proc Natl Acad Sci U.S.A.* 90:6444-48, Poljak et al., (1994) *Structure* 2: 1121-23, and Perisic et al., (1994) *Structure* 2(12): 1217-26). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giege et al., (1994) *Acta Crystallogr D Biol Crystallogr* 50 (Pt 4): 339-350; McPherson, (1990) *Eur J Biochem* 189: 1-23; Chayen, (1997) *Structure* 5: 1269-1274; McPherson, (1976) *J Biol Chem* 251: 6300-6303). Antibody:antigen crystals can be studied using well known X-ray diffraction techniques and may be refined using computer software such as X-PLOR (Yale University, 1992, distributed by Molecular Simulations, Inc.; see, e.g., *Meth Enzymol* (1985) Vols 114 & 115, eds Wyckoff et al.), and BUSTER (Bricogne, (1993) *Acta Crystallogr D Biol Crystallogr* 49 (Pt 1): 37-60; Bricogne, (1997) *Meth Enzymol* 276A: 361-423, ed. Carter; Roversi et al., (2000) *Acta Crystallogr D Biol Crystallogr* 56 (Pt 10): 1316-1323). Mutagenesis mapping studies can be accomplished using any method known to one of skill in the art. See, e.g., Champe et al., (1995) *J Biol Chem* 270: 1388-94 and Cunningham & Wells, (1989) *Science* 244: 1081-85 for a description of mutagenesis techniques, including alanine and arginine scanning mutagenesis techniques.

As used herein, the term "Fab fragment" means is a monovalent fragment having the VL, VH, CL and CH domains; a "F(ab')$_2$ fragment" is a bivalent fragment having two Fab fragments linked by a disulfide bridge at the hinge region; a "Fv fragment" has the VH and VL domains of a single arm of an antibody; and a "dAb fragment" has a VH domain, a VL domain, or an antigen-binding fragment of a VH or VL domain.

As used herein, the terms "immunospecifically binds," "immunospecifically recognizes," "specifically binds," and "specifically recognizes" are analogous terms and are used interchangeably in the context of antigen binding molecules, and means that a given molecule preferentially binds to an antigen (e.g., epitope or immune complex) as such binding is understood by one skilled in the art. For example, an antigen binding molecule that specifically binds to an antigen may bind to other peptides or polypeptides, but with a comparatively lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

In another embodiment, molecules that specifically bind to an antigen (e.g., GSTSGSGKPGSGEGSTKG (SEQ ID NO: 1) and subsequences thereof, particularly GSGKPGS-GEG (SEQ ID NO: 2), GKPGSGEG (SEQ ID NO: 3), SGKPGSGE (SEQ ID NO: 499), and/or KPGSG (SEQ ID NO: 500)), molecules comprising this sequence and cells presenting such molecules) bind with a dissociation constant ($K_d$) of about $1 \times 10^{-7}$ M. In some embodiments, the antigen binding molecule specifically binds an antigen (e.g., SEQ ID NOs: 1, 2, 3, 499 and/or 500, molecules comprising this sequence and cells presenting such molecules) with "high affinity" when the $K_d$ is about $1 \times 10^{-9}$ M to about $5 \times 10^{-9}$ M. In some embodiments, the antigen binding molecule specifically binds an antigen (e.g., SEQ ID NOs: 1, 2, 3, 499 and/or 500, molecules comprising this sequence and cells presenting such molecules) with "very high affinity" when the $K_d$ is $1 \times 10^{-10}$ M to about $5 \times 10^{-10}$ M.

In still another embodiment, molecules that specifically bind to an antigen (e.g., SEQ ID NOs: 1, 2, 3, 499 and/or 500, molecules comprising these sequences and cells presenting such molecules) do not cross react with other proteins under similar binding conditions. In another specific embodiment, molecules that specifically bind to an antigen (e.g., SEQ ID NOs: 1, 2, 3, 499 and/or 500, molecules comprising these sequences and cells presenting such molecules) do not cross react with other proteins that do not comprise SEQ ID NOs: 1, 2, 3, 499 and/or 500, molecules comprising these sequences and cells presenting such molecules. In a specific embodiment, provided herein is an antibody or fragment thereof that binds to SEQ ID NOs: 1, 2, 3, 499 and/or 500, molecules comprising these sequences and cells presenting such molecules, with higher affinity than to another unrelated antigen. In certain embodiments, provided herein is an antigen binding molecule (e.g., an antibody) or fragment thereof that binds to SEQ ID NOs: 1, 2, 3, 499 and/or 500, molecules comprising these sequences and cells presenting such molecules as molecules comprising this sequence and cells presenting such molecules, with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an antigen binding molecule, antibody or antigen binding fragment thereof that specifically binds SEQ ID NOs: 1, 2, 3, 499 and/or 500, molecules comprising these sequences and cells presenting such molecules, described herein compared to an unrelated protein which does not comprise SEQ ID NOs: 1, 2, 3, 499 and/or 500, is less than 10%, 15%, or 20% of the binding of the antibody to linker fragment protein as measured by, e.g., a radioimmunoassay.

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

As used herein, the term "immunoglobulin" means an immune molecule from any of the commonly known isotypes, including but not limited to IgA, secretory IgA, IgG and IgM. IgG subclasses are also well known to those in the art and include but are not limited to human IgG1, IgG2, IgG3 and IgG4. Many of the molecules described herein are immunoglobulins. As used herein, "isotype" means the antibody class or subclass (e.g., IgM or IgG1) that is encoded by the heavy chain constant region genes.

An immunoglobulin is a tetrameric molecule, normally composed of two identical pairs of polypeptide chains, each pair having one "light" (about 25 kDa) and one "heavy" chain (about 50-70 kDa). The amino-terminal portion of each chain includes a variable region of about 100 to 130 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, or IgE, respectively. Within light and heavy chains, the variable and constant regions are joined by a "J" region of about 12 or more amino acids, with the heavy chain also including a "D" region of about 10 more amino acids. See generally, Berzofsky & Berkower, in *Fundamental Immunology* (Paul, (ed), Lippincott Williams & Wilkins (2012); which chapter and volume is incorporated by reference in its entirety for all purposes). The variable regions of each light/heavy chain pair form the antibody binding site such that an intact immunoglobulin has two primary binding sites.

Naturally occurring immunoglobulin chains exhibit the same general structure of relatively conserved framework regions (FR) joined by three hypervariable regions, also called complementarity determining regions or "CDRs." From N-terminus to C-terminus, both light and heavy chains comprise the domains FR1, CDR1, FR2, CDR2, FR3, CDR3 and FR4. The assignment of amino acids to each domain can be done in accordance with the definitions of Kabat (see, e.g., Kabat et al. in *Sequences of Proteins of immunological Interest*, 5th Ed., NIH Publication 91-3242, Bethesda Md. (1991)) or Chothia (Chothia, used herein, (see, e.g., Chothia & Lesk (1987), *J. Mol. Biol.* 196:901-917; Chothia et al., 1989, *Nature* 342:878-883 or Honegger & Pluckthun (2001), *J Mol Biol* 309:657-670). The Kabat, Chothia and Abm (Oxford Molecular) numbering systems are described more fully herein.

As used herein, the term "in vitro cell" refers to any cell that is cultured ex vivo. An in vitro cell can include a human cell such as a T cell or dendritic cell, or it can include CHO, sP2/0, rabbit and other non-human cells.

As used herein, the term "light chain" when used in reference to an antibody can refer to any distinct type, e.g., kappa (κ) or lambda (λ) based on the amino acid sequence of the constant domains. Light chain amino acid sequences are known in the art. In specific embodiments, the light chain is a human light chain.

The term "neutralizing" refers to an antigen binding molecule, scFv, antibody, or a fragment thereof, that binds to a ligand (e.g., a moiety comprising SEQ ID NOs: 1, 2, 3, 499 and/or 500) and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "patient" means any human who is being treated for an abnormal physiological condition, such as cancer or has been formally diagnosed with a disorder, those without formally recognized disorders, those receiving medical attention, those at risk of developing the disorders, etc. The terms "subject" and "patient" are used interchangeably herein and include both human and non-human animal subjects.

As used herein, the terms "peptide," "polypeptide," and "protein" are used interchangeably herein, and mean a compound comprised of amino acid residues covalently linked by peptide bonds. A polypeptide, protein or peptide must contain at least two amino acids, but no limitation is placed on the maximum number of amino acids that can comprise a protein's or peptide's amino acid sequence. As used herein, the term refers to both short chains, which also commonly are referred to as peptides, oligopeptides and oligomers, and to longer chains, which generally are referred to as proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The term "polypeptide" includes natural peptides, recombinant peptides, synthetic peptides, or a combination thereof.

In some aspects, the polypeptides and/or proteins have deletions from, additions to, and/or substitutions of one or more amino acids of antigen binding molecule. Useful polypeptide fragments may include immunologically functional fragments of antigen binding molecules, including not limited to one or more CDR regions, variable domains of a heavy and/or light chain, a portion of other portions of an antibody chain, and the like. Moieties that can be substituted for one or more amino acids of an antigen binding molecule include, e.g., D or L forms of amino acids, an amino acid different from the amino acid normally found in the same position of an antigen binding molecule (relative to those sequences provided in FIGS. 6 and 8, and their recited SEQ ID NOs), deletions, non-naturally occurring amino acids, and chemical analogs of amino acids.

Peptide analogs are commonly used in the pharmaceutical industry as non-peptide drugs with properties analogous to those of the template peptide and form an aspect of the instant disclosure. These types of non-peptide compound are termed "peptide mimetics" or "peptidomimetics." See, e.g., Fauchere, (1986) *Adv. Drug Res.* (Testa, ed.) 15:29-69; Veber & Freidinger, (1985) *TINS*, p. 392; and Evans et al., (1987) *J. Med. Chem*, 30:1229-39, which are incorporated herein by reference for any purpose.

Polypeptides, peptides, proteins and analogous molecules comprising SEQ ID NOs: 1, 2, 3, 499 and/or 500, molecules comprising these sequences and cells presenting such molecules, are specifically encompassed by the terms.

As used herein, the term "percent identity" means the percent of identical residues between the amino acids or nucleotides in the compared molecules. For these calculations, gaps in alignments (if any) must be addressed by a particular mathematical model or computer program (i.e., an "algorithm"). Methods that can be used to calculate the identity of the aligned nucleic acids or polypeptides include those described in *Computational Molecular Biology*, (Lesk, ed.), (1988) New York: Oxford University Press; *Biocomputing Informatics and Genome Projects*, (Smith, ed.), 1993, New York: Academic Press; *Computer Analysis of Sequence Data, Part I*, (Griffin and Griffin, eds.), 1994, New Jersey: Humana Press; von Heinje, (1987) *Sequence Analysis in Molecular Biology*, New York: Academic Press; *Sequence Analysis Primer*, (Gribskov and Devereux, eds.), 1991, New York: M. Stockton Press; and Carillo et al., (1988) *J. Applied Math.* 48:1073.

In calculating percent identity, the sequences being compared are aligned in a way that gives the largest match between the sequences. The computer program used to determine percent identity can be, e.g., MOE (Chemical Computing Group) or DNASTAR (University of Wisconsin, Madison, Wis.). The computer algorithm GAP can be used to align the two polypeptides or polynucleotides for which the percent sequence identity is to be determined. The sequences are aligned for optimal matching of their respective amino acid or nucleotide (the "matched span," as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, e.g., Dayhoff et al., (1978) *Atlas of Protein Sequence and Structure* 5:345-352 for the PAM 250 comparison matrix; Henikoff et al., (1992) *Proc. Natl. Acad. Sci. U.S.A.* 89: 10915-10919 for the BLOSUM 62 comparison matrix) is also used by the algorithm.

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if desired to result in an alignment that spans at least 50 contiguous amino acids of the target polypeptide.

As used herein, the terms "single-chain antibody" and "single chain fragment variable (scFv)" are used interchangeably and mean an antigen binding molecule in which a VL and a VH region are joined via a linker to form a continuous protein chain wherein the linker is long enough to allow the protein chain to fold back on itself and form a monovalent antigen binding site (see, e.g., Bird et al., (1988) *Science* 242:423-26 and Huston et al., (1988) *Proc. Natl. Acad. Sci. U.S.A.* 85:5879-83 (1988). FMC63 (Nicholson et al., (1997) *Mol. Immunol.* 34:(16-17) 1157-65) is a specific example of a scFv, and is specific for CD19.

A "therapeutically effective amount," "effective dose," "effective amount," or "therapeutically effective dosage" of a therapeutic agent, (e.g., a moiety comprising SEQ ID NOs: 1, 2, 3, 499 and/or 500, molecules comprising these sequences and cells presenting such molecules), is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Hartl and Jones (1997) *Genetics: Principles and Analysis*, 4$^{th}$ ed, Jones & Bartlett). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

As used herein, the terms "variable region" or "variable domain" are used interchangeably and mean a portion of an antibody, generally, a portion of a light or heavy chain, typically the amino-terminal end of the antibody, and comprising about 100-130 amino acids in the heavy chain and about 90 to 115 amino acids in the light chain, which differ extensively in sequence among antibodies and are used in the binding and specificity of a particular antibody for a particular antigen. The variability in sequence is concentrated in those regions called complementarity determining regions (CDRs) while the more highly conserved regions in the variable domain are called framework regions (FR). The CDRs of the light and heavy chains are primarily responsible for the interaction and specificity of the antibody with antigen.

In certain embodiments, the variable region of an antigen binding molecule is a human variable region. In further embodiments, the variable region comprises rodent, human or murine CDRs and human framework regions (FRs). In further embodiments, the variable region is a primate (e.g., a non-human primate) variable region. In yet further embodiments, the variable region is a rabbit variable region. In other embodiments, the variable region comprises human CDRs and non-human (e.g., rabbit, murine, rat or non-human primate) framework regions (FRs). In other embodiments, the variable region comprises non-human (e.g., rabbit, murine, rat or non-human primate) CDRs and human framework regions (FRs).

The terms "VH," "VH domain" and "VH chain" are used interchangeably and mean the heavy chain variable region of an antigen binding molecule, antibody or an antigen binding fragment thereof.

The terms "VL," "VL domain" and "VL chain" are used interchangeably and mean the light chain variable region of an antigen binding molecule, antibody or an antigen binding fragment thereof.

Various aspects of the invention are described in further detail in the following subsections.

II. Antigen Binding Molecules and Polynucleotides Encoding the Same

The present disclosure is directed to antigen binding molecules, including antibodies, that specifically bind GST-SGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules, and/or antigen binding molecules which cross compete with one or more antigen binding molecules described herein (i.e., one or more of those described in FIGS. 6 and 8 and/or disclosed in the appended Sequence Listing). Polynucleotides encoding the antigen binding molecules are also provided, and form an aspect of the instant disclosure.

An antibody or antigen binding molecule encoded of the present invention can be single chained or double chained. In some embodiments, the antibody or antigen binding molecule is single chained. In certain embodiments, the antigen binding molecule is selected from the group consisting of an scFv, a Fab, a Fab', a Fv, a F(ab')$_2$, a dAb, and any combination thereof. In one particular embodiment, the antibody or antigen binding molecule comprises an scFv.

In certain embodiments, an antigen binding molecule such as an antibody comprises a single chain, wherein the heavy chain variable region and the light chain variable region are connected by a linker (an scFv). In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises between about 8 amino acids and about 18 amino acids (e.g., 10 amino acids).

In some embodiments, the antigen binding molecules of the present invention specifically bind to GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules. In certain embodiments, an antigen binding molecule of the present disclosure specifically binds SEQ ID NOs: 1, 2, 3, 499 and/or 500, as well as molecules comprising these sequences and cells presenting such molecules, with a $K_D$ of less than $1\times10^{-6}$ M, less than $1\times10^{-7}$ M, less than $1\times10^{-8}$ M, or less than $1\times10^{-9}$ M. In one particular embodiment, an antigen binding molecule specifically binds to SEQ ID NOs: 1, 2, 3, 499 and/or 500, as well as molecules comprising these sequences and cells presenting such molecules, with a $K_D$ of less than $1\times10^{-7}$ M. In another embodiment, an antigen binding molecule specifically binds SEQ ID NOs: 1, 2, 3, 499 and/or 500, as well as molecules comprising these sequences and cells presenting such molecules, with a $K_D$ of less than $1\times10^{-8}$ M. In some embodiments, an antigen binding molecule binds the scFv FMC63, as well as molecules comprising this sequence and cells presenting such molecules, with a $K_D$ of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-7}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. $K_D$ can be calculated using standard methodologies, as described herein.

In specific embodiments, an antigen binding molecule of the instant disclosure is an antibody identified herein as Clone 8 or Clone 16 and each comprises the following heavy and light chain amino acid, coding, variable, and CDR sequences, as provided and labeled:

```
Clone 8 VH DNA Coding Sequence
                                              (SEQ ID NO: 4)
ATGGAGACTGGGCTGCGCTGGCTTCTCCTGGTCGCTGTGCTCAAAGGTGTCCAG

TGTCAGTCGGTGGAGGAGTCCGGGGGTCGCCTGGTCACGCCTGGGACACCCCTG

ACACTCACCTGCACAGCCTCTGGATTCACCATCAGTAACCTTGCAATAATCTGG

GTCCGCCAGGCTCCAGGGAAGGGGCTGGAATATATCGGAGACATTGATGGTCG

TGGTGACATATACTGTGCGACCTGGGCGAAAGGCCGATTCACCATCTCCAAAAC

CTCGACCACACTGGATCTGAGATTCACCAGCCCGACAACCGAGGACACGGCCA

CCTACTTCTGTGCCGTAGATGGTGATGGTAGTGGTTGGGGTGACTTTAACTTTTG

GGGCCCAGGCACCCTGGTCACCGTCTCCTCA

Clone 8 VH AA (CDRs underlined)
                                              (SEQ ID NO: 5)
METGLRWLLLVAVLKGVQCQSVEESGGRLVTPGTPLTLTCTAS<u>GFTISNLA</u>IIWVR QAPGKGLEYIG<u>DIDGRGDIYCATWAK</u>GRFTISKTSTTLDLRFTSPTTEDTATYFCAV <u>DGDGSGWGDFNF</u>WGPGTLVTVSS
```

-continued

Clone 8 HC AA (CDRs underlined)
(SEQ ID NO: 6)
METGLRWLLLVAVLKGVQCQSVEESGGRLVTPGTPLTLTCTAS<u>GFTISNL</u>AIIWVR QAPGKGLEYIG<u>DIDGRDIYCATWAK</u>GRFTISKTSTTLDLRFTSPTTEDTATYFCAV <u>DGDGSGWGDFNF</u>WGPGTLVTVSSGQPKAPSVFPLAPCCGDTPSSTVTLGCLVKGY

LPEPVTVTWNSGTLTNGVRTFPSVRQSSGLYSLSSVVSVTSSSQPVTCNVAHPATNT

KVDKTVAPSTCSKPTCPPPELLGGPSVFIFPPKPKDTLMISRTPEVTCVVVDVSQDDP

EVQFTWYINNEQVRTARPPLREQQFNSTIRVVSTLPIAHQDWLRGKEFKCKVHNKA

LPAPIEKTISKARGQPLEPKVYTMGPPREELSSRSVSLTCMINGFYPSDISVEWEKNG

KAEDNYKTTPAVLDSDGSYFLYSKLSVPTSEWQRGDVFTCSVMHEALHNHYTQKS

ISRSPGK

Clone 8 VH CDR1 AA
(SEQ ID NO: 7)
GFTISNL

Clone 8 VH CDR2 AA
(SEQ ID NO: 8)
DIDGRGDIYCATWAK

Clone 8 VH CDR3 AA
(SEQ ID NO: 9)
DGDGSGWGDFNF

Clone 8 VL DNA Coding Sequence
(SEQ ID NO: 10)
ATGGACACGAGGGCCCCCACTCAGCTGCTGGGGCTCCTGCTGCTCTGGCTCCCA

GGTGCCAGATGTGCCTATGATATGACCCAGACTCCAGCCTCTGTGGAGGTAGCT

GTGGGAGGCACAGTCAGCATCAAGTGCCAGGCCAGTCAGAGCATTAGCACTGC

ATTAGCCTGGTATCAGCAGAAACCAGGACAGCCTCCCAAGCTCCTGATCTACAG

GGCATCCACTCTGGCATCTGGGGTCTCATCGCGGTTCAAAGGCAGTGGATCTGG

GACACAGTTCACTCTCACCATCAGCGGCGTGGAGTGTGACGATGCTGCCACTTA

CTACTGTCAACAGGGTTGGAGTACTGTGAATGTTGATAATGTTTTCGGCGGAGG

GACCGAGGTGGTGGTCAGA

Clone 8 VL AA (CDRs underlined)
(SEQ ID NO: 11)
MDTRAPTQLLGLLLLWLPGARCAYDMTQTPASVEVAVGGTVSIKC<u>QASQSISTALA</u>

WYQQKPGQPPKLLIY<u>RASTLAS</u>GVSSRFKGSGSGTQFTLTISGVECDDAATYYC<u>QQ</u>

<u>GWSTVNVDNV</u>FGGGTEVVVR

Clone 8 LC AA (CDRs underlined)
(SEQ ID NO: 12)
MDTRAPTQLLGLLLLWLPGARCAYDMTQTPASVEVAVGGTVSIKC<u>QASQSISTALA</u>

WYQQKPGQPPKLLIY<u>RASTLAS</u>GVSSRFKGSGSGTQFTLTISGVECDDAATYYC<u>QQ</u>

<u>GWSTVNVDNV</u>FGGGTEVVVRDPVAPTVLIFPPAADQVATGTVTIVCVANKYFPDV

TVTWEVDGTTQTTGIENSKTPQNSADCTYNLSSTLTLTSTQYNSHKEYTCKVTQGT

TSVVQSFNRGDC

Clone 8 VL CDR1 AA
(SEQ ID NO: 13)
QASQSISTALA

Clone 8 VL CDR2 AA
(SEQ ID NO: 14)
RASTLAS

Clone 8 VL CDR3 AA
(SEQ ID NO: 15)
QQGWSTVNVDNV

Clone 16 VH DNA Coding Sequence
(SEQ ID NO: 16)
ATGGAGACTGGGCTGCGCTGGCTTCTCCTGGTCGCTGTGCTCAAAGGTGTCCAG

TGTCAGTCGCTGGAGGAGTCCGGGGGTCGCCTGGTCACGCCTGGGACACCCCTG

ACACTCACCTGCACAGTCTCTGGATCCGACATCAGTAGCTACCACATGGGCTGG

GTCCGCCAGGCTCCAGGGAAGGGGCTGGAATACATCGGAATCATTGTTAGTAG

TGGTAGCGCATACTACGCGACCTGGGCAAAAGGCCGATTCACCATCTCCAGGA

CCTCGACCACGGTGGATCTGAAAATCACCAGTCCGACAACCGAGGACTCGGCC

ACCTATTTCTGTGCCAGAAATCAATATAGTGGTTATGGCTTTAGCTTCTGGGGCC

CAGGCACCCTGGTCACCGTCTCCTCA

Clone 16 VH AA (CDRs underlined)
(SEQ ID NO: 17)
METGLRWLLLVAVLKGVQCQSLEESGGRLVTPGTPLTLTCTVS<u>GSDISSY</u>HMGWV RQAPGKGLEYIG<u>IIVSSGSAYYATWAK</u>GRFTISRTSTTVDLKITSPTTEDSATYFCAR <u>NQYSGYGFSF</u>WGPGTLVTVSS Clone 16 HC AA (CDRs underlined)
(SEQ ID NO: 18)
METGLRWLLLVAVLKGVQCQSLEESGGRLVTPGTPLTLTCTVS<u>GSDISSY</u>HMGWV RQAPGKGLEYIG<u>IIVSSGSAYYATWAK</u>GRFTISRTSTTVDLKITSPTTEDSATYFCAR <u>NQYSGYGFSF</u>WGPGTLVTVSSGQPKAPSVFPLAPCCGDTPSSTVTLGCLVKGYLPEP

VTVTWNSGTLTNGVRTFPSVRQSSGLYSLSSVVSVTSSSQPVTCNVAHPATNTKVD

KTVAPSTCSKPTCPPPELLGGPSVFIFPPKPKDTLMISRTPEVTCVVVDVSQDDPEVQ

FTWYINNEQVRTARPPLREQQFNSTIRVVSTLPIAHQDWLRGKEFKCKVHNKALPA

PIEKTISKARGQPLEPKVYTMGPPREELSSRSVSLTCMINGFYPSDISVEWEKNGKAE

DNYKTTPAVLDSDGSYFLYSKLSVPTSEWQRGDVFTCSVMHEALHNHYTQKSISRS

PGK

Clone 16 VH CDR1 AA
(SEQ ID NO: 19)
GSDISSY

Clone 16 VH CDR2 AA
(SEQ ID NO: 20)
IIVSSGSAYYATWAK

Clone 16 VH CDR3 AA
(SEQ ID NO: 21)
NQYSGYGFSF

Clone 16 VL DNA Coding Sequence
(SEQ ID NO: 22)
ATGGACACGAGGGCCCCCACTCAGCTGCTGGGGCTCCTGCTGCTCTGGCTCCCA

GGTGCCACATTTGCCGTCGTGCTGACCCAGACTCCATCCCCAGTGTCTACAGCT

GTAGGAGGCACAGTCACCATCAATTGCCAGTCCAGTCACAGTGTTTATTATGGC

GACTGGTTAGCCTGGTATCAGCAGAAACCAGGGCAGCCTCCTAAGCTCCTGATC

TACAGGGCATCCAATCTGGCATCTGGTGTCCCATCGCGGTTCAAAGGCAGTGGA

TCTGGGACACAGTTCACTCTCACCATCAGCGGCGTGCAGTGTGACGATGCTGCC

ACTTACTACTGTCTAGGCGGTTATGATGATGATGGTGAGACTGCTTTCGGCGGA

GGGACCGAGGTGGTGGTCAAA

-continued

Clone 16 VL AA (CDRs underlined)
(SEQ ID NO: 23)
MDTRAPTQLLGLLLLWLPGATFAVVLTQTPSPVSTAVGGTVTINCQSSHSVYYGD

WLAWYQQKPGQPPKWYRASNLASGVPSRFKGSGSGTQFTLTISGVQCDDAATYY

CLGGYDDDGETAFGGGTEVVVK

Clone 16 LC AA (CDRs underlined)
(SEQ ID NO: 24)
MDTRAPTQLLGLLLLWLPGATFAVVLTQTPSPVSTAVGGTVTINCQSSHSVYYGD

WLAWYQQKPGQPPKWYRASNLASGVPSRFKGSGSGTQFTLTISGVQCDDAATYY

CLGGYDDDGETAFGGGTEVVVKDPVAPTVLIFPPAADQVATGTVTIVCVANKYFP

DVTVTWEVDGTTQTTGIENSKTPQNSADCTYNLSSTLTLTSTQYNSHKEYTCKVTQ

GTTSVVQSFNRGDC

Clone 16 VL CDR1 AA
(SEQ ID NO: 25)
QSSHSVYYGDWLA

Clone 16 VL CDR2 AA
(SEQ ID NO: 26)
RASNLAS

Clone 16 VL CDR3 AA
(SEQ ID NO: 27)
LGGYDDDGETA

In one embodiment, the antigen binding molecules of the present disclosure are antibodies and antigen binding fragments thereof. In one embodiment, the antibodies of the present disclosure comprise at least one CDR set forth in FIGS. 6 and 8. In another aspect, the present disclosure provides hybridomas capable of producing the antibodies disclosed herein and methods of producing antibodies from hybridomas, as described herein and as known in the art.

Humanized antibodies are described herein and may be prepared by known techniques. In one embodiment, a humanized monoclonal antibody comprises the variable domain of a murine or rabbit antibody (or all or part of the antigen binding site thereof) and a constant domain derived from a human antibody. Alternatively, a humanized antibody fragment may comprise an antigen binding site of a murine or rabbit monoclonal antibody and a variable domain fragment (lacking the antigen binding site) derived from a human antibody. Procedures for the production of engineered monoclonal antibodies include those described in Riechmann et al., (1988) *Nature* 332:323, Liu et al., (1987) *Proc. Nat. Acad. Sci. USA* 84:3439, Larrick et al., (1989) *Bio/Technology* 7:934, and Winter et al., (1993) *TIPS* 14:139. In one embodiment, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557; Padlan et al., (1995) *FASEB J.* 9:133-39; Tamura et al., (2000) *J. Immunol.* 164:1432-41; Zhang et al., (2005) *Mol. Immunol.* 42(12): 1445-1451; Hwang et al., *Methods.* (2005) 36(1):35-42; Dall'Acqua et al., (2005) *Methods* 36(1):43-60; and Clark, (2000) *Immunology Today* 21(8):397-402.

An antigen binding molecule of the present invention can also be a fully human monoclonal antibody. Fully human monoclonal antibodies can be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., (1997) *Curr. Opin. Biotechnol.* 8:455-58).

Examples of techniques for production and use of transgenic animals for the production of human or partially human antibodies are described in U.S. Pat. Nos. 5,814,318, 5,569,825, and 5,545,806; Davis et al., *Antibody Engineering: Methods and Protocols*, (Lo, ed) Humana Press, NJ, 191-200 (2003); Kellermann et al., (2002) *Curr Opin Biotechnol.* 13:593-97; Russel et al., (2000) *Infect Immun.* 68:1820-26; Gallo et al., (2000) *Eur J. Immun.* 30:534-40; Davis et al., (1999) *Cancer Metastasis Rev.* 18:421-25; Green, (1999) *J Immunol Methods* 231:11-23; Jakobovits, (1998) *Advanced Drug Delivery Reviews* 31:33-42; Green et al., (1998) *J Exp Med.* 188:483-95; Jakobovits, (1998) *Exp. Opin. Invest. Drugs.* 7:607-14; Tsuda et al., (1997) *Genomics*, 42:413-21; Mendez et al., (1997) *Nat. Genet.* 15:146-56; Jakobovits, (1994) *Curr Biol.* 4:761-63; Arbones et al., (1994) *Immunity* 1:247-60; Green et al., (1994) *Nat. Genet.* 7:13-21; Jakobovits et al., (1993) *Nature* 362:255-58; Jakobovits et al., (1993) *Proc Natl Acad Sci USA* 90:2551-55; Chen et al., (1993) *Intl Immunol* 5:647-656; Choi et al., (1993) *Nature Genetics* 4:117-23; Fishwild et al., (1996) *Nature Biotechnology* 14:845-51; Lonberg et al., (1994) *Nature* 368: 856-59; Lonberg, (1994) *Handbook of Experimental Pharmacology* 113: 49-101; Neuberger, (1996)

Nature Biotech 14:826; Taylor et al., (1992) Nucleic Acids Research 20:6287-95; Taylor et al., (1994) Intl Immunol 6:579-91; Tomizuka et al., (1997) Nature Genetics 16:133-43; Tomizuka et al., (2000) Proc Nat Acad Sci USA 97:722-27; Tuaillon et al., (1993) Proc Nat Acad Sci USA 90:3720-24; Tuaillon et al., (1994) J Immunol 152:2912-20; Lonberg et al., (1994) Nature 368:856; Taylor et al., (1994) Intl Immunol 6:579; U.S. Pat. No. 5,877,397; Bruggemann et al., (1997) Curr. Opin. Biotechnol. 8:455-58; Jakobovits et al., (1995) Ann. N.Y. Acad. Sci. 764:525-35.

An additional method for obtaining antigen binding molecules of the invention is by the use of phage display, which is well-established for this purpose. See, e.g., Winter et al., (1994) Ann. Rev. Immunol. 12:433-55; Burton et al., (1994) Adv. Immunol 57:191-280. Human or murine immunoglobulin variable region gene combinatorial libraries can be created in phage vectors that can be screened to select Ig fragments (Fab, Fv, sFv, or multimers thereof) that bind the scFv FMC63, as well as molecules comprising this sequence and cells presenting such molecules. See, e.g., U.S. Pat. No. 5,223,409; Huse et al., (1989) Science 246:1275-81; Sastry et al., (1989) Proc. Natl. Acad. Sci. USA 86:5728-32; Alting-Mees et al., (1990) Strategies in Molecular Biology 3:1-9; Kang et al., (1991) Proc. Natl. Acad. Sci. USA 88:4363-66; Hoogenboom et al., (1992) J. Mol. Biol. 227:381-388; Schlebusch et al., (1997) Hybridoma 16:47-52 and references cited therein. For example, a library containing a plurality of polynucleotide sequences encoding Ig variable region fragments can be inserted into the genome of a filamentous bacteriophage, such as M13 or lambda phage (λImmunoZap™ (H) and λImmunoZap™ (L) vectors (Stratagene, La Jolla, Calif.) can also be used in this approach) or a variant thereof, in frame with the sequence encoding a phage coat protein.

Briefly, mRNA is isolated from a B-cell population, and used to create heavy and light chain immunoglobulin cDNA expression libraries in the λImmunoZap™ (H) and λImmunoZap™ (L) and similar vectors. These vectors can be screened individually or co-expressed to form Fab fragments or antibodies. Positive plaques can subsequently be converted to a non-lytic plasmid that allows high level expression of monoclonal antibody fragments from E. coli.

In one embodiment, in a hybridoma the variable regions of a gene expressing a monoclonal antibody of interest are amplified using nucleotide primers. These primers can be synthesized by one of ordinary skill in the art, or can be purchased from commercial sources, which also sell primers for mouse and human variable regions including, among others, primers for $V_H$, $V_L$, $C_H$ and $C_L$ regions). These primers can be used to amplify heavy or light chain variable regions, which can then be inserted into vectors. These vectors can then be introduced into E. coli, yeast, or mammalian-based systems for expression. Large amounts of a single-chain protein containing a fusion of the VH and VL domains can be produced using these methods.

Once cells producing the antigen binding molecules provided herein have been obtained using any of the above-described immunization and other techniques, the specific antibody genes can be cloned by isolating and amplifying DNA or mRNA therefrom according to standard procedures as described herein. The antibodies produced therefrom can be sequenced and the CDRs identified and the DNA coding for the CDRs can be manipulated as described previously to generate other antibodies according to the invention.

It will be understood by those of skill in the art that some proteins, such as antibodies, can undergo a variety of post-translational modifications. The type and extent of these modifications often depends on the host cell line used to express the protein as well as the culture conditions. Such modifications can include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in, e.g., Harris, (1995) J Chromatog 705:129-34).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, e.g., Baines and Thorpe, (1992) in Methods in Molecular Biology, 10:79-104 (The Humana Press). Monoclonal antibodies can be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, and an anti-idiotype antibody.

Although the disclosed antigen binding molecules were produced in a rabbit system, human, partially human, or humanized antibodies may be suitable for many applications, particularly those involving administration of the antibody to a human subject, other types of antigen binding molecules will be suitable for certain applications. Such antibodies can be prepared as described herein and form an aspect of the instant disclosure.

The instant disclosure provides antigen binding molecules that specifically bind to GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules. Antigen binding molecules that cross compete with the antigen binding molecules disclosed herein form another aspect of the instant disclosure.

In certain embodiments, the antigen binding molecule cross competes with a reference antibody comprising an amino acid sequence selected from the group consisting of SEQ ID NOs: 5, 11, 17 and 23. In certain embodiments, the antigen binding molecule cross competes with a reference antibody, wherein the reference antibody comprises a VH CDR1 comprising an amino acid sequence of SEQ ID NOs: 13 or 19. In certain embodiments, the antigen binding molecule cross competes with a reference antibody, wherein the reference antibody comprises a VH CDR2 comprising an amino acid sequence of SEQ ID NOs: 14 or 20. In certain embodiments, the antigen binding molecule cross competes with a reference antibody, wherein the reference antibody comprises a VH CDR3 comprising an amino acid sequence of SEQ ID NOs: 15 or 21.

In other embodiments, the antigen binding molecule cross competes with a reference antibody, wherein the reference antibody comprises a VL CDR1 comprising an amino acid sequence of SEQ ID NO: 13 or 25. In certain embodiments, the antigen binding molecule cross competes with a reference antibody, wherein the reference antibody comprises a VL CDR2 comprising an amino acid sequence of SEQ ID NO: 14 or 26. In certain embodiments, the antigen binding molecule cross competes with a reference antibody, wherein the reference antibody comprises a VL CDR3 comprising an amino acid sequence of SEQ ID NO: 15 or 27.

In some embodiments, the antibody or antigen binding molecule that specifically binds SEQ ID NOs: 1, 2, 3, 499 and/or 500 binds the same or an overlapping epitope as a reference antibody disclosed herein (e.g., those comprising sequences presented in FIGS. 6 and 8). In certain embodiments, the antibody or antigen binding molecule binds the same or an overlapping epitope as a reference antibody.

IIa. Clone 8

In some embodiments, an antigen binding molecule or antibody that specifically binds to GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR1 comprising, consisting of, or consisting essentially of the amino acid sequence GFTISNL (SEQ ID NO: 7).

In some embodiments, an antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR2 comprising, consisting of, or consisting essentially of the amino acid sequence DIDGRGDIYCATWAK (SEQ ID NO: 8).

In some embodiments, an antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR3 comprising, consisting of, or consisting essentially of the amino acid sequence DGDGSGWGDFNF (SEQ ID NO: 9).

In some embodiments, an antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain VH comprising: (a) a VH CDR1 comprising, consisting of, or consisting essentially of the amino acid sequence GFTISNL (SEQ ID NO: 7); and/or (b) a VH CDR2 comprising, consisting of, or consisting essentially of the amino acid sequence DIDGRGDIYCATWAK (SEQ ID NO: 8); and/or (c) a VH CDR3 comprising, consisting of, or consisting essentially of the amino acid sequence DGDGSGWGDFNF (SEQ ID NO: 9).

In some embodiments, the antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 6 and 8.

In some embodiments, the antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain variable region sequence comprising an amino acid sequence of FIGS. 6 and 8 (e.g., (SEQ ID NO: 5)).

In some embodiments, the antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises the VH framework regions (FRs) described herein. In specific embodiments, the antibody or antigen binding molecule comprises the VH FRs as set forth in, or derivable from, the sequences presented in FIGS. 6 and 8 (e.g., one, two, three, or four of the FRs in one sequence of FIG. 6 or 8).

In some embodiments, the antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain sequence disclosed herein (e.g., SEQ ID NO: 6 in FIG. 6). In one embodiment, the antibody or antigen binding molecule comprises a heavy chain variable region comprising the amino acid sequence of SEQ ID NO: 5.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:5.

In some embodiments, an antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR1 comprising, consisting of, or consisting essentially of the amino acid sequence QASQSISTALA (SEQ ID NO: 13).

In some embodiments, an antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR2 comprising, consisting of, or consisting essentially of the amino acid sequence RASTLAS (SEQ ID NO: 14).

In some embodiments, an antigen binding molecule or antibody that specifically binds to the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR3 comprising, consisting of, or consisting essentially of the amino acid sequence QQGWSTVNVDNV (SEQ ID NO: 15).

In some embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a light chain VL comprising: (a) a VL CDR1 comprising, consisting of, or consisting essentially of the amino acid sequence QASQSISTALA (SEQ ID NO: 13); and/or (b) a VL CDR2 comprising, consisting of, or consisting essentially of the amino acid sequence RASTLAS (SEQ ID NO: 14); and/or (c) a VL CDR3 comprising, consisting of, or consisting essentially of the amino acid sequence QQGWSTVNVDNV (SEQ ID NO: 15).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIGS. 6 and 8.

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a light chain variable region sequence comprising an amino acid sequence of FIG. 6 or FIG. 8 (e.g., SEQ ID NO: 11).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises the VL framework regions (FRs) described herein. In specific embodiments, the antibody or antigen binding molecule comprises the VL FRs as set forth in, or derivable from, the sequences presented in FIGS. 6 and 8 (e.g., one, two, three, or four of the FRs in one sequence of FIG. 6 or 8).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a light chain sequence disclosed herein (e.g., SEQ ID NO: 12 in FIG. 6, or in FIG. 8). In one embodiment, the antibody or antigen binding molecule comprises a light chain variable region comprising the amino acid sequence of SEQ ID NO: 11.

In various embodiments, the light chain variable region is 80%, 85%, 90%, 91%, 92%, 93%, 94%, 95%, 96%, 97%, 98% or 99% identical to the light chain variable region sequence of SEQ ID NO: 11.

In some embodiments, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises: (a) a VH CDR1 region comprising the amino acid sequence of SEQ ID NO: 7; (b) a VH CDR2 region comprising the amino acid sequence of SEQ ID NO: 8; (c) a VH CDR3 region comprising the amino acid sequence of SEQ ID NO: 9; (d) a VL CDR1 region comprising the amino acid sequence of SEQ ID NO: 13; (e) a VL CDR2 region comprising the amino acid sequence of SEQ ID NO: 14; and (f) a VL CDR3 region comprising the amino acid sequence of SEQ ID NO: 15.

In one embodiment, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 6 and 8.

In some embodiments, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain variable region sequence disclosed herein (e.g., in FIGS. 6 and 8) and a light chain variable region sequence disclosed herein (e.g., in FIGS. 6 and 8).

In one embodiment, the antibody or antigen binding molecule comprises: (a) a heavy chain variable region comprising the amino acid sequence of SEQ ID NO: 5; and (b) a light chain variable region comprising the amino acid sequence of SEQ ID NO: 11. Nucleotide sequences encoding the heavy chain variable region and the light chain variable region are provided in FIG. 6.

In some embodiments, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain sequence disclosed herein (e.g., in FIGS. 6 and 8) and a light chain sequence disclosed herein (e.g., in FIGS. 6 and 8).

In one embodiment, the antibody or antigen binding molecule comprises: (a) a heavy chain comprising the amino acid sequence of SEQ ID NO: 6; and (b) a light chain comprising the amino acid sequence of SEQ ID NO: 12.

In one embodiment, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 6; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 12.

IIb. Clone 16

In some embodiments, an antigen binding molecule or antibody that specifically binds to GSTSGSGKPGSGEG-STKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR1 comprising, consisting of, or consisting essentially of the amino acid sequence GSDISSY (SEQ ID NO: 19).

In some embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR2 comprising, consisting of, or consisting essentially of the amino acid sequence IIVSSGSAYYATWAK (SEQ ID NO: 20).

In some embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR3 comprising, consisting of, or consisting essentially of the amino acid sequence NQYSGYGFSF (SEQ ID NO: 21).

In some embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain VH comprising: (a) a VH CDR1 comprising, consisting of, or consisting essentially of the amino acid sequence GSDISSY (SEQ ID NO: 19); and/or (b) a VH CDR2 comprising, consisting of, or consisting essentially of the amino acid sequence IIVSSGSAYYATWAK (SEQ ID NO: 20); and/or (c) a VH CDR3 comprising, consisting of, or consisting essentially of the amino acid sequence NQYS-GYGFSF (SEQ ID NO: 21).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 6 and 8.

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain variable region sequence comprising an amino acid sequence of FIG. 6 or 8 (e.g., SEQ ID NO: 17).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises the VH framework regions (FRs) described herein. In specific embodiments, the antibody or antigen binding molecule comprises the VH FRs as set forth in, or derivable from, the sequences presented in FIG. 6 (e.g., one, two, three, or four of the FRs in one sequence of FIG. 6 or 8 (e.g., SEQ ID NO: 17).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain sequence disclosed herein (e.g., SEQ ID NO: 18 in FIG. 6). In one embodiment, the antibody or antigen binding molecule comprises a heavy chain variable region comprising the amino acid sequence of SEQ ID NO: 17.

In various embodiments, the heavy chain variable region is 80%, 85%, 90%, 91%, 92%, 93%, 94%, 95%, 96%, 97%, 98% or 99% identical to the heavy chain variable region sequence of SEQ ID NO: 17.

In some embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR1 comprising, consisting of, or consisting essentially of the amino acid sequence QSSHSVYYGDWLA (SEQ ID NO: 25).

In some embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR2 comprising, consisting of, or consisting essentially of the amino acid sequence RASNLAS (SEQ ID NO: 26).

In some embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR3 comprising, consisting of, or consisting essentially of the amino acid sequence LGGYDDDGETA (SEQ ID NO: 27).

In embodiments, an antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a light chain VL comprising: (a) a VL CDR1 comprising, consisting of, or consisting essentially of the amino acid sequence QSSHSVYYGDWLA (SEQ ID NO: 25); and/or (b) a VL CDR2 comprising, consisting of, or consisting essentially of the amino acid sequence RASTLAS (SEQ ID NO: 26); and/or (c) a VL CDR3 comprising, consisting of, or consisting essentially of the amino acid sequence LGGYDDDGETA (SEQ ID NO: 27).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a VL CDR1, a VL CDR2, and VL CDR3, wherein the VL CDR1, VL CDR2, and VL CDR3 comprise the amino acid sequence of the VL CDR1, VL CDR2, and VL CDR3 sequences presented in FIG. 6 or 8.

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a light chain variable region sequence comprising an amino acid sequence of FIG. 6 or FIG. 8 (e.g., SEQ ID NO: 23).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises the VL framework regions (FRs) described herein. In specific embodiments, the antibody or antigen binding molecule comprises the VL FRs as set forth in, or derivable from, the sequences presented in FIGS. 6 and 8 (e.g., one, two, three, or four of the FRs in one sequence of FIG. 6 or FIG. 8).

In some embodiments, the antigen binding molecule or antibody that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a light chain sequence disclosed herein (e.g., SEQ ID NO: 24 in FIG. 6, or in FIG. 8). In one embodiment, the antibody or antigen binding molecule comprises a light chain variable region comprising the amino acid sequence of SEQ ID NO: 23.

In various embodiments, the light chain variable region is 80%, 85%, 90%, 91%, 92%, 93%, 94%, 95%, 96%, 97%, 98% or 99% identical to the light chain variable region sequence of SEQ ID NO: 23.

In some embodiments, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises: (a) a VH CDR1 region comprising the amino acid sequence of SEQ ID NO: 19; (b) a VH CDR2 region comprising the amino acid sequence of SEQ ID NO: 20; (c) a VH CDR3 region comprising the amino acid sequence of SEQ ID NO: 21; (d) a VL CDR1 region comprising the amino acid sequence of SEQ ID NO: 25; (e) a VL CDR2 region comprising the amino acid sequence of SEQ ID NO: 26; and (f) a VL CDR3 region comprising the amino acid sequence of SEQ ID NO: 27.

In one embodiment, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules (SEQ ID NO: 1), molecules comprising this sequence and cells presenting this sequence, comprises: (a) a VH CDR1 region; (b) a VH CDR2 region; (c) a VH CDR3 region; (d) a VL CDR1 region; (e) a VL CDR2 region; and (f) a VL CDR3 region, wherein the VH and VL CDRs are shown in FIGS. 6 and 8.

In some embodiments, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain variable region sequence disclosed herein (e.g., in FIGS. 6 and 8) and a light chain variable region sequence disclosed herein (e.g., in FIGS. 6 and 8).

In one embodiment, the antibody or antigen binding molecule comprises: (a) a heavy chain variable region comprising the amino acid sequence of SEQ ID NO: 17; and (b) a light chain variable region comprising the amino acid sequence of SEQ ID NO: 23. Nucleotide sequences encoding the heavy chain variable region and the light chain variable region are provided in FIG. 6.

In some embodiments, the antibody or antigen binding molecule that specifically binds to the GSTSGSGKPGS-GEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising this sequence and cells presenting such molecules, comprises a heavy chain sequence disclosed herein (e.g., in FIGS. 6 and 8) and a light chain sequence disclosed herein (e.g., in FIGS. 6 and 8).

In one embodiment, the antibody or antigen binding molecule comprises: (a) a heavy chain comprising the amino acid sequence of SEQ ID NO: 18; and (b) a light chain comprising the amino acid sequence of SEQ ID NO: 24.

In one embodiment, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 18; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 24.

III Polynucleotides Encoding Antibodies and Antigen Binding Molecules

The present invention is also directed to polynucleotides encoding antibodies and antigen binding molecules that specifically bind to GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules.

In some embodiments, a polynucleotide of the present invention encodes an antigen binding molecule, wherein the antigen binding molecule comprises a heavy chain variable region amino acid sequence that is at least about 75%, at least about 85%, at least about 85%, at least about 90%, at least about 95%, at least about 96%, at least about 97%, at least about 98%, at least about 99%, or 100% identical to a heavy chain variable region amino acid sequence selected from the group consisting of SEQ ID NOs: 5 and 17.

In some embodiments, a polynucleotide of the present invention encodes antigen binding molecule, wherein the antigen binding molecule comprises a light chain variable amino acid sequence that is at least about 75%, at least about 85%, at least about 85%, at least about 90%, at least about 95%, at least about 96%, at least about 97%, at least about 98%, at least about 99%, or 100% identical to a light chain variable region amino acid sequence selected from the group consisting of SEQ ID NOs: 11 and 23.

In certain embodiments, the polynucleotide comprises a heavy chain coding sequence selected from the group consisting of SEQ ID NOs: 4 and 16. In another embodiment, the polynucleotide comprises a light chain coding sequence selected from the group consisting of SEQ ID NOs: 10 and 22.

As will be appreciated by those of skill in the art, variations of the disclosed polynucleotide sequences are possible due to the degeneracy of the genetic code. Such variants of the disclosed polynucleotide sequences thus form an aspect of the instant disclosure.

IV. Vectors, Cells, and Pharmaceutical Compositions

In certain aspects, provided herein are vectors comprising a polynucleotide of the present invention. In some embodiments, the present invention is directed to a vector or a set of vectors comprising a polynucleotide encoding an antibody or antigen binding molecule that specifically binds to GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) and molecules comprising these sequences and cells presenting such molecules, as described herein.

Any vector known in the art can be suitable for expressing the antibodies and antigen binding molecules of the present invention. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In other aspects, provided herein are cells comprising a polynucleotide or a vector of the present invention. In some embodiments, the present invention is directed to cells, in vitro cells, comprising a polynucleotide encoding an antigen binding molecule, as described herein. In some embodiments, the present invention is directed to cells, e.g., in vitro cells, comprising a polynucleotide encoding an antibody or an antigen binding molecule thereof that specifically binds to GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules, as disclosed herein.

Any cell can be used as a host cell for the polynucleotides and vectors encoding all or a fragment of the antibodies and antigen binding molecules of the present invention. In some embodiments, a host cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobacteriaceae such as *Escherichia*, e.g., *E. coli*; Bacilli such as *B. subtilis* and *B. licheniformis*; *Pseudomonas* such as *P. aeruginosa*; and *Streptomyces*. In some embodiments, a host cell is a mammalian cell, such as a human cell. In some embodiments, a host cell is a CHO cell and in other embodiments, a host cell is a sP2/0 or other murine cell. A host cell of the present invention can be obtained through any source known in the art.

Other aspects of the present invention are directed to compositions comprising a polynucleotide described herein, a vector described herein, an antibody an antigen binding molecule described herein, and/or an in vitro cell described herein. In some embodiments, the composition comprises a pharmaceutically acceptable carrier, diluent, solubilizer, emulsifier, preservative and/or adjuvant. In some embodiments, the composition comprises an excipient.

In one embodiment, the composition comprises a polynucleotide encoding an antibody or antigen binding molecule that specifically binds to that specifically binds to GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499), and/or KPGSG (SEQ ID NO: 500), and molecules comprising these sequences and cells presenting such molecules. In another embodiment, the composition comprises an antigen binding molecule that specifically binds to SEQ ID NOs: 1, 2, 3, 499 and/or 500, and molecules comprising these sequences and cells presenting such molecules. In another embodiment, the composition comprises an in vitro cell comprising a polynucleotide encoding an antibody or an antigen binding molecule thereof encoded by a polynucleotide disclosed herein.

In some embodiments, the composition comprises more than one different antibody or antigen binding molecule that specifically binds to GSTSGSGKPGSGEGSTKG (SEQ ID NO: 1) and subsequences thereof, particularly GSGKPGS-GEG (SEQ ID NO: 2), GKPGSGEG (SEQ ID NO: 3), SGKPGSGE (SEQ ID NO: 499), and/or KPGSG (SEQ ID NO: 500), and molecules comprising these sequences and cells presenting such molecules. In some embodiments, the composition includes more than one antibody or antigen binding molecule that specifically binds to SEQ ID NOs: 1, 2, 3, 499 and/or 500, and molecules comprising these sequences and cells presenting such molecules, wherein the antibodies or antigen binding molecules bind more than one epitope. In some embodiments, the antibodies or antigen binding molecules will not compete with one another for binding to that epitope. In some embodiments, two or more of the antibodies or antigen binding molecules provided herein are combined together in a pharmaceutical composition. Preferably such a composition will be suitable for administration to a subject, including a human.

V. Exemplary Methods

The following section describes various exemplary methods of using the disclosed antigen binding molecules herein. Any of the antigen binding molecules, and fragments thereof, disclosed herein (including those provided by the Figures and the attached Sequence Listing) can be employed in the disclosed methods.

In some of the disclosed methods T cells can be employed. Such T cells can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

In various embodiments, the antigen binding molecule specifically binds to a molecule comprising the amino acid sequence GSTSGSGKPGSGEGSTKG (SEQ ID NO: 1) or a subsequence comprising the amino acid sequence GSGK-PGSGEG (SEQ ID NO: 2) or SGKPGSGE (SEQ ID NO: 499), molecules comprising these sequences and cells presenting such sequences. In further embodiments, the antigen binding molecule comprises one or more of (a) a light chain CDR1, (b) a light chain CDR2, (c) a light chain CDR3, (d) a heavy chain CDR1, (e) a heavy chain CDR2, and (f) a heavy chain CDR3. In additional embodiments, the antigen binding molecule comprises a heavy chain CDR3 of SEQ ID NO: 9 or 21, or a light chain CDR3 of SEQ ID NO: 15 or 27, or both the heavy and light chains. In other embodiments, the antigen binding molecule comprises a heavy chain CDR1 comprising the amino acid sequence SEQ ID NO: 7 or 19, a heavy chain CDR2 comprising the amino acid sequence SEQ ID NO: 8 or 20, or a light chain CDR1 comprising the amino acid sequence SEQ ID NO: 13 or 25, or a light chain CDR2 comprising the amino acid sequence SEQ ID NO: 14 or 26. In various embodiments, the antigen binding molecule comprises a heavy chain CDR1, a heavy chain CDR2, a heavy chain CDR3, a light chain CDR1, a light chain CDR2, and a light chain CDR3, each CDR comprising an amino acid sequence shown in FIG. 6.

In various embodiments, an antigen binding molecule comprises a heavy chain (HC), and the HC can comprise a heavy chain variable region (VH) sequence comprising SEQ ID NO: 5. In various embodiments, the heavy chain comprises a heavy chain CDR1, a heavy chain CDR2, and a heavy chain CDR3, each CDR comprising an amino acid sequence shown in FIGS. 6 and 8. Moreover, in some embodiments, an antigen binding molecule can be employed which comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule of claim disclosed herein (e.g., an antigen binding molecule comprising a variable region (VH) sequence comprising SEQ ID NO: 5).

In various embodiments, an antigen binding molecule comprises a light chain (LC), and the LC can comprise a light chain variable region (VL) sequence comprising SEQ ID NO: 11. In various embodiments, the light chain comprises a light chain CDR1, a light chain CDR2, and a light chain CDR3, each CDR comprising an amino acid sequence shown in FIGS. 6 and 8. Moreover, in some embodiments, an antigen binding molecule can be employed which comprises a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule of claim disclosed herein (e.g., an antigen binding molecules comprising a variable region (VL) sequence comprising SEQ ID NO: 11).

In various embodiments, the antigen binding molecule can specifically bind to a molecule comprising the amino acid sequence GSTSGSGKPGSGEGSTKG (SEQ ID NO: 1) or a subsequence comprising the amino acid sequence GKPGSGEG (SEQ ID NO: 3) or KPGSG (SEQ ID NO: 500). In further embodiments of the disclosed methods, the antigen binding molecule comprises one or more of (a) a light chain CDR1, (b) a light chain CDR2, (c) a light chain CDR3, (d) a heavy chain CDR1, (e) a heavy chain CDR2, and (f) a heavy chain CDR3. In additional embodiments of the disclosed methods, the antigen binding molecule comprises a heavy chain CDR3 of SEQ ID NO: 21, or a light chain CDR3 of SEQ ID NO: 27, or both the heavy and light chains. In other embodiments of the disclosed methods, the antigen binding molecule comprises a heavy chain CDR1 comprising the amino acid sequence SEQ ID NO: 19 or a heavy chain CDR2 comprising the amino acid sequence SEQ ID NO: 20 or a light chain CDR1 comprising the amino acid sequence SEQ ID NO: 25 or a light chain CDR2 comprising the amino acid sequence SEQ ID NO: 26.

In various embodiments, the antigen binding molecule comprises a heavy chain CDR1, a heavy chain CDR2, a heavy chain CDR3, a light chain CDR1, a light chain CDR2, and a light chain CDR3, each CDR comprising an amino acid sequence shown in FIGS. 6 and 8.

In various embodiments of the disclosed methods, an antigen binding molecule comprises a heavy chain (HC), and the HC can comprise a heavy chain variable region (VH)

sequence comprising SEQ ID NO: 17. Referring to the Figures, in various embodiments of the disclosed methods the heavy chain comprises a heavy chain CDR1, a heavy chain CDR2, and a heavy chain CDR3, each CDR comprising an amino acid sequence shown in FIG. 6. Moreover, in embodiments of the disclosed methods, an antigen binding molecule can be employed which comprises a VH amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule of claim disclosed herein (e.g., an antigen binding molecule comprising a variable region (VH) sequence comprising SEQ ID NO: 17).

In various embodiments of the disclosed methods, an antigen binding molecule comprises a light chain (LC), and the LC can comprise a light chain variable region (LH) sequence comprising SEQ ID NO: 23. Referring to the Figures, in various embodiments of the disclosed methods the light chain comprises a light chain CDR1, a light chain CDR2, and a light chain CDR3, each CDR comprising an amino acid sequence shown in FIGS. 6 and 8. Moreover, in embodiments of the disclosed methods, an antigen binding molecule can be employed which comprises a VL amino acid sequence that is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule of claim disclosed herein (e.g., an antigen binding molecule comprising a variable region (VL) sequence comprising SEQ ID NO: 23).

In specific embodiments of the disclosed methods, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27.

In specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

In view of the above description of antigen binding molecules that can be employed in the disclosed methods, representative methods will now be discussed in more detail.

Va. Method of Administering a Dose of a Medicament to a Subject

In one aspect, a method of administering a dose of a medicament to a subject, the dose comprising a preselected number of cells presenting a therapeutic molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided.

In specific embodiments, the dose comprises $0.5 \times 10^6$ cells per kilogram of the subject, $1.0 \times 10^6$ cells per kilogram of the subject, $2.0 \times 10^6$ cells per kilogram of the subject, $3.0 \times 10^6$ cells per kilogram of the subject, $4.0 \times 10^6$ cells per kilogram of the subject, or $5.0 \times 10^6$ cells per kilogram of the subject, although the method can be employed using any dose. $1.0 \times 10^6$ cells per kilogram of the subject is a preferred dose.

Consistent with the definition provided herein, in various embodiments, a subject is a human or non-human subject. When the subject is a human, the subject can be, e.g., any human who is being treated for an abnormal physiological condition, such as cancer or has been formally diagnosed with a disorder, those without formally recognized disorders, those receiving medical attention, those at risk of developing the disorders, those being studied for the presence or absence of a disorder, etc.

Initially, a sample comprising a population comprising a known number of cells, the population known or suspected to be expressing a therapeutic molecule comprising an amino acid sequence selected from the group consisting of GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), is provided.

In one embodiment, the selected amino acid sequence comprises GSTSGSGKPGSGEGSTKG (SEQ ID NO: 1); in another embodiment, the selected amino acid sequence comprises GSGKPGSGEG (SEQ ID NO: 2); in another embodiment, the selected amino acid sequence comprises GKPGSGEG (SEQ ID NO: 3); in another embodiment, the selected amino acid sequence comprises SGKPGSGE (SEQ ID NO: 499); and in a another embodiment, the selected amino acid sequence comprises KPGSG (SEQ ID NO: 500).

Consistent with the definition provided herein, in various embodiments, a subject is a human or non-human subject. When the subject is a human, the subject can be, e.g., any human who is being treated for an abnormal physiological condition, such as cancer or has been formally diagnosed with a disorder, those without formally recognized disorders, those receiving medical attention, those at risk of developing the disorders, those being studied for the presence or absence of a disorder, etc.

Initially, a sample of known volume comprising a population comprising a known number of cells, which cells are known or suspected to be presenting a molecule comprising the selected amino acid sequence (i.e., SEQ ID NO:s 1, 2, 3, 499 or 500) is provided. The number of cells can be determined using any known method. In preferred embodiments the population is determined by counting the cells in the sample using an automated apparatus, such as a cell sorter (e.g., a FACS), however traditional non-automated cell counting methods can also be employed.

The cells of the method can comprise any type of cell, with immune cells (e.g., B lymphocytes, monocytes, dendritic cells, Langerhans cells, keratinocytes, endothelial cells, astrocytes, fibroblasts, and oligodendrocytes) being preferred. T cells (including T cytotoxic, T helper and Treg cells) are especially preferred. In specific embodiments, the cells are T cells, which can be obtained as described herein and by methods known in the art. Any type of cell can be employed in the method, and the cell can be a human or non-human cell (including both prokaryotic and eukaryotic cells). Exemplary cells include, but are not limited to immune cells such as T cells, tumor infiltrating lymphocytes (TILs), NK cells, TCR-expressing cells, dendritic cells, and NK-T cells. A T cell can be autologous, allogeneic, or heterologous, or it can be an in vivo T cell or an in vitro T cell, and can be a CD4+ T cell or a CD8+ T cell. In additional embodiments, the cells are T cells presenting a CAR. Moreover, the cells can be disposed in, or isolated from, any environment capable of maintaining the cells in a viable form, such as blood, tissue or any other sample obtained from a subject, cell culture media, tissue grown ex vivo, etc. Gradient purification, cell culture selection and/or cell sorting can be useful in obtaining cells.

The therapeutic molecule expressed by the cell can comprise any molecule known or suspected to provide a therapeutic benefit to a subject to which is it administered. Thus, a therapeutic molecule can be a peptide or polypeptide of any structure or design. Preferably the portion of the therapeutic molecule comprising the selected amino acid sequence (i.e., SEQ ID NO: 1, 2, 3, 499 or 500) is expressed or disposed, at least in part, extracellularly, i.e., to a degree that it can be recognized by an extracellular interaction partner such as the antigen binding molecules of the instant disclosure.

In specific embodiments, the therapeutic molecule is a CAR. When the therapeutic molecule is a CAR it can comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

Continuing, an aliquot of the sample comprising a population of cells presenting a molecule comprising the selected amino acid sequence is provided. The aliquot can be obtained using any convenient means, such as by a cell sorter, by a simply pipetting of material out of the sample, etc.

Further, an antigen binding molecule that specifically binds the selected amino acid sequence and comprises a detectable label is provided. The antigen binding molecule is preferably an antigen binding molecule disclosed herein, e.g., in the Figures, Sequence Listing or the instant disclosure. Any detectable label can be employed in the method, and suitable labels can be selected using a desired set of criteria. Examples of types of detectable labels include a fluorescent dye, which can be selected from the group consisting of an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. Other types of detectable labels include optical dyes, which are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I), photochromic compounds, magnetic labels (e.g., DYNABEADS), etc. Strategies for the labeling of proteins are known in the art and can be employed in the disclosed method.

The label can be associated with the antigen binding molecule at any position in the molecule, although it is preferable to associate the label with the molecule at a position (or positions, if multiple labels are employed) at a point such that the binding properties of the molecule are not modified, unless such modified binding activity is desired. Any antigen binding molecule that specifically binds the selected amino acid sequence (i.e., SEQ ID NO: 1, 2, 3, 499 or 500) can be employed. Examples of suitable antigen binding molecules and components thereof are provided herein, e.g., in the attached Sequence Listing and in FIGS. 6 and 8. In specific embodiments of the disclosed method, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27. In other specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

Continuing, the aliquot of the sample is contacted with the antigen binding molecule under conditions that permit the formation of a binding complex comprising a cell present in the sample and the antigen binding molecule. Thus, the result of this step of the method is the formation of a binding complex in which the antigen binding molecule, with which a detectable label is associated, is bound to the cell expressing the therapeutic molecule, which comprises the selected amino acid sequence (i.e., SEQ ID NO: 1, 2, 3, 499 or 500). Thus, the binding complex itself is detectable. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

The fraction of cells present in a binding complex of in the aliquot is determined. This calculation can be performed by comparing the number of cells bearing the detectable label to those that do not, and can be represented as percentage. The number of cells in binding complexes can be determined. The specific method employed to determine the number of cells present in a binding complex will be dependent on the nature of the label selected. For example, FACS can be employed when a fluorescent label is selected; when an isotope label is selected mass spectrometry, NMR or other technique can be employed; magnetic-based cell sorting can be employed when a magnetic label is chosen; microscopy can also be employed. The number of cells in the sample is know ab initio and thus the fraction of cells present in a binding complex can be easily determined.

Continuing, the concentration of cells in the initial sample expressing a molecule comprising the selected amino acid sequence (i.e., SEQ ID NO: 1, 2, 3, 499 or 500) is determined; the determination is based on the fraction of cells determined to be present in the binding complex, and thus expressing the therapeutic protein bearing a detectable label.

The fraction of cells presenting the therapeutic protein is known, and the volume of the aliquot is known; thus a simple comparison of the number of cells in the sample from which the aliquot was taken that are expressing the therapeutic molecule to the volume of the larger sample provides the fraction of the cells in the sample bearing the therapeutic molecule on a therapeutic molecule/volume basis (i.e., the concentration of cells bearing the therapeutic molecule in the larger sample).

The volume of the sample that comprises the selected number of cells is determined, by extrapolation based on the concentration of cells bearing therapeutic molecule present in the sample.

Finally, the volume of sample comprising the desired number of cells is administered to the subject. The administration can comprise an aspect of a therapeutic regimen based on the therapeutic molecule present in the sample and expressed by the cells in the sample.

Although the administration can be performed one time or more than one time, an advantage of the method is that by administering a dose comprising the preselected number of cells, which number of cells will be determined based on a known or expected efficacy, unnecessary administration of cells presenting the therapeutic molecule is avoided; i.e., the subject receives the correct number of cells to provide a desired therapeutic benefit and is not too many or too few cells.

Vb. Method of Activating Cells

The disclosed methods of activating an immune cell can be employed in connection with any immune cell presenting a molecule comprising a sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500). In the context of the disclosed methods, T cells (including T cytotoxic, T helper and Treg cells) presenting such molecules are preferred and will be used to exemplify the disclosed methods, however other immune cells presenting such molecules (e.g., lymphocytes such as tumor infiltrating lymphocytes (TILs), cytotoxic T lymphocytes, tumor infiltrating lymphocytes, neutrophils, basophils, or T helper cells, Treg cells, dendritic cells, B cells, hematopoietic stem cells, macrophages, monocytes, Langerhans cells, keratinocytes, endothelial cells, astrocytes, fibroblasts, and oligodendrocytes and NK cells) can also be employed in the disclosed methods.

Activation (which term is used interchangeably with the term "stimulation") of T cells is dependent upon signals transferred through antigen-specific T cells receptor recognition and accessory receptors on the T cell. For example, clustering of CD3gamma, CD3delta, CD3epsilon and CD3zeta proteins, further associate with other components of the T cell Receptor (TCR), induces activation of the T cell and makes it immunocompetent. Thus, "activation" or "stimulation" as used herein, refers to a primary response induced by binding of a molecule with a ligand (which may be another copy of the same molecule, e.g., CD3zeta associating with another copy of CD3zeta), wherein the binding mediates a signal transduction event.

In one embodiment, T cells are activated in vitro by means of an antigen binding molecule provided herein, and the T cells activated in accordance with the methods of the instant disclosure can be subsequently expanded ex vivo and used in a variety of applications, including those disclosed herein.

In another embodiment, activation occurs in vivo, by means of an antigen binding molecule provided herein, and the T cells activated in accordance with the methods of the instant disclosure; expansion occurs within the organism in which the activated cells are disposed. In vivo activation can form a component of a therapeutic regime, examples of which are described herein.

Prior to activation, immune cells, such as T cells, are obtained from a subject (e.g., a mammal such as a human, dog, cat, mouse, rat, rabbit or transgenic species thereof; cells derived from an artificial system such as an artificial thymic organoid (ATO; see, e.g., Seet et al., Nature Methods 14(5):521 (2017), incorporated by reference herein) can also be employed in the disclosed in vivo and in vitro activation methods). Immune cells, including T cells, can be obtained from a number of sources, as described herein, including PBMCs, bone marrow, lymph node tissue, cord blood, thymus tissue, tissue from a site of infection, spleen tissue, tumors or T cell lines. T cells can also be obtained from a volume of blood collected from a subject using any number of techniques known to the skilled artisan, such as FICOLL separation. Gradient purification, cell culture selection and/or cell sorting can also be employed.

In view thereof, a method of activating an immune cell, such as a T cell, presenting a molecule comprising an amino acid sequence selected from the group consisting of GST-SGSGKPGSGEGSTKG (SEQ ID NO: 1), GSGKPGSGEG (SEQ ID NO: 2), GKPGSGEG (SEQ ID NO: 3), SGK-PGSGE (SEQ ID NO: 499) and KPGSG (SEQ ID NO: 500), is provided.

Initially, a sample comprising an immune cell known or suspected to be presenting a molecule comprising an amino acid sequence selected from the group consisting of GST-SGSGKPGSGEGSTKG (SEQ ID NO: 1), GSGKPGSGEG (SEQ ID NO: 2), GKPGSGEG (SEQ ID NO: 3), SGK-PGSGE (SEQ ID NO: 499) and KPGSG (SEQ ID NO: 500) is provided. In specific embodiments the selected amino acid sequence is GSTSGSGKPGSGEGSTKG (SEQ ID NO: 1); in other embodiments the selected amino acid sequence is GSGKPGSGEG (SEQ ID NO: 2); in other embodiments the selected amino acid sequence is GKPGSGEG (SEQ ID NO: 3); in other embodiments the selected amino acid sequence is SGKPGSGE (SEQ ID NO: 499); and in other embodiments the selected amino acid sequence is KPGSG (SEQ ID NO: 500).

In specific embodiments, the cells are T cells, which can be obtained as described herein and by methods known in the art. The cell can be a human or non-human cell. The T cells can be autologous, allogeneic, or heterologous. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc.

In specific embodiments, the molecule comprising the selected amino acid sequence (i.e., SEQ ID NO: 1, 2, 3, 499 or 500) is a CAR. When the molecule is a CAR it can comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule is then contacted with the sample, under conditions that permit the formation of a binding complex comprising the antigen binding molecule and two molecules comprising the selected amino acid sequence (i.e., SEQ ID NO: 1, 2, 3, 499 or 500), wherein the molecules comprising the selected amino acid sequence are disposed on two different immune cells. The binding event has the effect of bringing both immune cells into closer proximity to one another, with multiple cells being clustered together following multiple binding events.

The antigen binding molecule is preferably an antigen binding molecule (or fragment thereof) disclosed herein, e.g., in the Figures, Sequence Listing or the instant section of the disclosure. Any antigen binding molecule that specifically binds the selected amino acid sequence (i.e., SEQ ID NO: 1, 2, 3, 499 or 500) can be employed. Multiple examples of suitable antigen binding molecules are provided herein, e.g., those having one or more of the CDRs shown in FIGS. 6 and 8. The molecules comprising the selected sequences that are present on each immune cell of a binding complex can be the same or they can be different, so long as they are specifically recognized by the antigen binding molecule.

In specific embodiments of the disclosed method, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27. In other specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

The antigen binding molecule can be disposed on any surface, or no surface at all. For example, in in vivo applications the antigen binding molecule can be present in a buffer and the contacting can be achieved by injecting the antigen binding molecule into the body of a subject, whereupon activation will occur when the antigen binding molecule contacts a cell presenting the molecule comprising the amino acid sequence selected from the group consisting of GSTSGSGKPGSGEGSTKG (SEQ ID NO: 1), GSGKPGS-GEG (SEQ ID NO: 2), GKPGSGEG (SEQ ID NO: 3), SGKPGSGE (SEQ ID NO: 499) and KPGSG (SEQ ID NO: 500).

The precise amount of antigen binding molecule that will achieve a desired level of activation can be determined empirically, and will depend on various subject-specific criteria. For in vivo activation, the amount of antigen binding molecule can be, for example, 25 µg/kg/day, 20 µg/kg/day, 15 µg/kg/day, 10 µg/kg/day or 5 µg/kg/day. The antigen binding molecule can administered to a subject for a desired number days, for example 5, 4, 3, 2 or 1 day. Other activating antibodies can be used as a guide when determining how much antigen binding molecule to administer to a subject. For example, the clinical experiences with anti-CD3 activating antibody OKT3 may be illustrative and beneficial when performing the disclosed method.

Those of skill in the art will recognize that a specific therapeutic regime can be tailored to a given subject, and dosing amounts and conditions can depend on a variety of factors normally considered by clinicians. Examples that can be considered when determining a suitable dose of antigen binding molecule for an in vivo activation include the overall health and strength of a subject, the subject's weigh, a desired overall degree of activation, the efficacy and in vivo efficacy of the cells presenting the molecule having the selected sequence, In an in vitro activation, the antigen binding molecule can be present in a buffer and the buffer-antigen binding molecule can be contacted with the sample. Alternatively, in some embodiments, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

In practice, when the binding of the antigen binding molecule specifically binds to the molecules comprising the selected amino acid sequence (i.e., SEQ ID NO: 1, 2, 3, 499 or 500), one molecule on each of two different immune cells, the two cells are drawn closer to one another. This close proximity, or clustering, has the effect of activating the immune cells.

Vc. Method of Determining a Number of Cells Presenting a Molecule of Interest

There are situations in which it may be desirable to determine the number of cells present in a sample that are expressing a molecule of interest. For example, it may be desirable to determine the number of immune cells present a sample obtained from a subject that are expressing a molecule of interest. Or it may be desirable to determine the number of cells transfected and expressing a molecule of interest, which can be used as a measure of the level of efficiency of the transfection. The disclosed method can be employed in these and other applications in which it is desirable to determine the number of cells present in a sample that are expressing a molecule of interest.

Thus, a method of determining a number of cells presenting a molecule in a sample wherein the molecule comprises an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499), and/or KPGSG (SEQ ID NO: 500) is provided.

In on embodiment, a sample comprising cells known or suspected to be expressing a molecule of interest comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided.

In specific embodiments the selected amino acid sequence is GSTSGSGKPGSGEGSTKG (SEQ ID NO: 1); in other embodiments the selected amino acid sequence is GSGKPGSGEG (SEQ ID NO: 2); in other embodiments the selected amino acid sequence is GKPGSGEG (SEQ ID NO: 3); in other embodiments the selected amino acid sequence is SGKPGSGE (SEQ ID NO: 499); in other embodiments the selected amino acid sequence is KPGSG (SEQ ID NO: 500).

The cell can be of any type, and can be human or non-human (e.g., mouse, rate, rabbit, hamster, etc). In a preferred embodiment, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed in this embodiment of the disclosed method. Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc.

In specific embodiments, the molecule of interest is a CAR. When the molecule is a CAR it can comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

The sample is then contacted with an antigen binding molecule that specifically binds the molecule of interest and comprises a detectable label, under conditions that permit the formation of a binding complex comprising a cell present in the sample and the antigen binding molecule. The antigen binding molecule is preferably an antigen binding molecule (or fragment thereof) disclosed herein, e.g., in the Figures, Sequence Listing or the instant section of the disclosure. Any antigen binding molecule that specifically binds the selected amino acid sequence (i.e., SEQ ID NO: 1, 2, 3, 499 or 500) can be employed in the disclosed method. Multiple examples of suitable antigen binding molecules are provided herein, e.g., those having one or more of the CDRs shown in FIGS. 6 and 8.

Any detectable label can be employed in the method, and suitable labels can be selected using a desired set of criteria. Examples of types of detectable labels include a fluorescent dye, which can be selected from the group consisting of an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. Other types of detectable labels include optical dyes, which are described in Johnson, *Molecular Probes Handbook: A Guide to Fluorescent Probes and Labeling Techniques,* 11$^{th}$ Edition, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$I, $^{124}$I, $^{125}$I, $^{131}$I), photochromic compounds, magnetic labels (e.g., DYNABEADS), etc. Strategies for the labeling of proteins are known in the art and can be employed in the disclosed method.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule or fragment thereof that specifically binds the molecule of interest comprising the selected amino acid sequence (i.e., SEQ ID NO: 1, 2, 3, 499 or 500) can be employed in the disclosed method.

In specific embodiments of the disclosed method, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27. In other specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

Continuing, the number of cells present in a binding complex in the sample is determined. The specific method employed to determine the number of cells present in a binding complex will be dependent on the nature of the label selected. For example, FACS can be employed when a fluorescent label is selected; when an isotope label is selected mass spectrometry, NMR or other technique can be employed; magnetic-based cell sorting can be employed when a magnetic label is chosen; microscopy can also be employed. The output of these detection methods can be in the form of a number of cells or the output can be of a form that allows the calculation of the number of cells based on the output.

Vd. Method of Isolating a Molecule

It is of tremendous value to have the ability to separate populations of different molecules, and particularly biologically-relevant molecules, from one another. Using the antigen binding molecules provided herein, such separation can be achieved and employed in a range of biotechnological, biopharmaceutical and therapeutic applications.

In one aspect of the instant disclosure, a method of isolating a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500) is provided.

In one embodiment, the method comprises providing a sample known or suspected to comprise a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500).

In specific embodiments the selected amino acid sequence is GSTSGSGKPGSGEGSTKG (SEQ ID NO: 1); in other embodiments the selected amino acid sequence is GSGKPGSGEG (SEQ ID NO: 2); in other embodiments the selected amino acid sequence is GKPGSGEG (SEQ ID NO: 3); in other embodiments the selected amino acid sequence is SGKPGSGE (SEQ ID NO: 499); in other embodiments the selected amino acid sequence is KPGSG (SEQ ID NO: 500).

In specific embodiments, the molecule of interest is a CAR. When the molecule is a CAR it can comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule that specifically binds the selected amino acid sequence (i.e., SEQ ID NO: 1, 2 or 3) and optionally comprises a detectable label is provided. When it is decided to employ a detectable label, any detectable label can be employed in the method, as described herein, and suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I). Photochromic compounds, a Halo-tag, Atto dyes, Tracy dyes, proteinaceous fluorescent labels (e.g., proteinaceous fluorescent labels also include, but are not limited to, green fluorescent protein, including a *Renilla*, *Ptilosarcus*, or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNABEADS), etc can also be employed. Strategies for the labeling of proteins are well known in the art and can be employed in the disclosed method.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule, or fragment thereof, that specifically binds the selected amino acid sequence (i.e., SEQ ID NO: 1, 2, 3, 499 or 500) can be employed, such as those disclosed herein, e.g., those having one or more of the CDRs shown in FIGS. 6 and 8.

In specific embodiments of the disclosed method, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27. In other specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

The sample is contacted with the antigen binding molecule, under conditions that permit the formation of a binding complex comprising a molecule comprising the selected amino acid sequence and the antigen binding molecule. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

At this stage, no binding complexes may have formed, or a plurality of binding complexes comprising one or more antigen binding molecules bound to a molecule comprising the selected amino acid sequence (i.e., SEQ ID NO: 1, 2, 3, 499 or 500) may have formed. Unbound molecules comprising the selected amino acid sequence and/or unbound antigen binding molecules may also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture can be washed away using a solution that leaves formed binding complexes intact. If a binding complex is disposed on a bead, the bead itself may be situated in a column or other structure and the same approach can be used.

The solution used to induce the formation of binding complexes can be used, for example, as a wash solution to remove unbound components. Any suitable buffer or solution that does not disrupt formed binding complexes can be used. Typically, buffers having high salt concentrations, non-physiological pH, containing chaotropes or denaturants, are preferably avoided when performing this step of the method.

A formed binding complex is then separated into (a) a molecule comprising the selected amino acid sequence (i.e., SEQ ID NO: 1, 2, 3, 499 or 500), and (b) an antigen binding molecule. The separation can be achieved using standard methodologies known to those of skill in the art. For example, a solution of suitable pH and composition can be washed over the complexes. A solution that is commonly employed for this purpose is 0.1 M glycine HCl, pH 2.5-3.0, and this solution can be employed to achieve the separation. Other solutions that can be employed include 100 mM citric acid, pH 3.0, 50-100 mM triethylamine or triethanolamine, pH 11.5; 150 mM ammonium hydroxide, pH 10.5; 0.1 M glycine.NaOH, pH 10.0; 5 M lithium chloride, 3.5 M magnesium or potassium chloride, 3.0 M potassium chloride, 2.5 M sodium or potassium iodide, 0.2-3.0 M sodium thiocyanate, 0.1 M Tris-acetate with 2.0 M NaCl, pH 7.7; 2-6 M guanidine HCl, 2-8 M urea, 1.0 M ammonium thiocyanate, 1% sodium deoxycholate 1% SDS; and 10% dioxane 50% ethylene glycol, pH 8-11.5.

Following the separation, if the molecule comprising the selected amino acid sequence (i.e., SEQ ID NO: 1, 2, 499 or 500) is of primary interest it can be collected; alternatively, if the antigen binding molecule is of primary interest it can be collected.

Ve. Method of Determining the Presence or Absence of a Molecule

As disclosed herein, it may sometimes be desirable to isolate a molecule comprising an amino acid sequence selected from the group consisting of SEQ ID NO: 1, 2, 499 or 500. In other cases, simply knowing whether a molecule comprising an amino acid sequence selected from the group consisting of SEQ ID NO: 1, 2, 499 or 500, is present or absent from a sample is enough information. For example, it may be beneficial to know that such a molecule is being expressed, regardless of the level of expression. In other cases it may be desirable to know if a purification process or step designed to remove such a molecule has been effectively. Thus, the qualitative determination of the presence or absence of a molecule comprising an amino acid sequence selected from the group consisting of SEQ ID NO: 1, 2, 499 or 500, can be useful in multiple applications.

In view thereof, a method of determining the presence or absence in a sample of a molecule comprising an amino acid selected from the Group consisting of GSTSGSGKPGS-GEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500), in a sample is provided.

In one embodiment, the method comprises providing a sample known or suspected to comprise a molecule comprising an amino acid sequence selected from the Group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500).

In specific embodiments the selected amino acid sequence is GSTSGSGKPGSGEGSTKG (SEQ ID NO: 1); in other embodiments the selected amino acid sequence is GSGKPGSGEG (SEQ ID NO: 2); in other embodiments the selected amino sequence is GKPGSGEG (SEQ ID NO: 3); in other embodiments the selected amino acid sequence is SGKPGSGE (SEQ ID NO: 499); and in other embodiments the selected amino acid sequence is KPGSG (SEQ ID NO: 500).

In specific embodiments, the molecule comprising the selected amino acid sequence (i.e., SEQ ID NO: 1, 2, 499 or 500) is a CAR. When the molecule is a CAR it can comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule comprising a detectable label, which antigen binding molecule specifically binds the selected amino acid sequence (i.e., SEQ ID NO: 1, 2, 499 or 500) is provided. Suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling*

Techniques, 11th Edition, Life Technologies, (2010), hereby expressly incorporated by reference, radiolabels (e.g., isotope markers such as $^3H$, $^{11}C$, $^{14}C$, $^{15}N$, $^{18}F$, $^{35}S$, $^{64}CU$, $^{90}Y$, $^{99}Tc$, $^{111}In$, $^{124}I$, $^{125}I$, $^{131}I$ Photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus*, or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNABEADS), etc can also be employed. Strategies for the labeling of proteins are well known in the art and can be employed in the disclosed method.

In specific embodiments of the disclosed method, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27. In other specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds the a molecule comprising the selected amino acid sequence (i.e., SEQ ID NO: 1, 2, 3, 499 or 500) can be employed, such as those disclosed herein, e.g., those having one or more of the CDRs shown in FIGS. 6 and 8.

Continuing, the sample is contacted with the antigen binding molecule under conditions that permit the formation of a binding complex comprising a cell present in the sample and the antigen binding molecule. The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

The sample is contacted with the antigen binding molecule, under conditions that permit the formation of a binding complex comprising a molecule comprising the molecule comprising the selected amino acid sequence (i.e., SEQ ID NO: 1, 2, 3, 499 or 500) and the antigen binding molecule. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

At this stage, no binding complexes may have formed, or a plurality of binding complexes comprising one or more antigen binding molecules bound to a molecule comprising the selected amino acid sequence (i.e., SEQ ID NO: 1, 2, 499 or 500) (or one or more molecules comprising the selected amino acid sequence bound to an antigen binding molecule) may have formed. Unbound molecules comprising the selected amino acid sequence (i.e., SEQ ID NO: 1, 2, 499 or 500) and/or unbound antigen binding molecules may also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture can be washed away using a solution that leaves formed binding complexes intact. If a binding complex is disposed on a bead, the bead itself may be situated in a column or other structure and the same approach can be used.

The solution used to induce the formation of binding complexes can be used, for example, as a wash solution to remove unbound components. Any suitable buffer or solution that does not disrupt formed binding complexes can also be used. Typically, buffers having high salt concentrations, non-physiological pH, containing chaotropes or denaturants, should be avoided when performing this step of the method.

Lastly, the presence or absence of a binding complex—which will comprise a molecule comprising the selected amino acid sequence (i.e., SEQ ID NO: 1, 2, 499 or 500) and an antigen binding molecule—is detected. The specific method employed to detect the presence or absence of a binding complex will be dependent on the nature of the label selected. For example, FACS can be employed when a fluorescent label is selected; when an isotope label is selected mass spectrometry, NMR or other technique can be employed; magnetic-based cell sorting can be employed when a magnetic label is chosen; microscopy can also be employed. The end result of the method is a qualitative assessment of the presence or absence of the antigen binding molecule comprising the detectable label, and thus, the presence or absence of its binding partner, the molecule comprising the selected amino acid sequence (i.e., SEQ ID NO: 1, 2, 499 or 500).

As is the case with all of the disclosed methods, the molecule comprising the selected amino acid sequence (i.e., SEQ ID NO: 1, 2, 499 or 500) can be disposed in any environment. In preferred embodiments, the molecule comprising the selected amino acid sequence (i.e., SEQ ID NO: 1, 2, 499 or 500) is expressed on the surface of a cell. In this embodiment, the cell can be of any type, and can be human or non-human (e.g., mouse, rate, rabbit, hamster, etc). In a preferred embodiment, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed in this embodiment of the disclosed method, and the cell can be a human or non-human cell. Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell.

In additional embodiment, the cell can be disposed in, or isolated from, any environment capable of maintaining the cell in a viable form, such as blood, tissue or any other sample obtained from a subject, cell culture media, tissue grown ex vivo, a suitable buffer, etc.

Vf. Method of Increasing the Concentration of a Molecule

Very often a molecule of interest is present in a sample in lower-than-desired levels. For example, when a cell is transfected with a foreign gene expression levels of the protein(s) encoded by the foreign gene are low. The same can be true for molecules secreted from a cell; such molecules are often present in low quantities (but can still be detected using the methods provided herein, if the molecule comprises one of the disclosed amino acid sequences of SEQ ID NO: 1, 2 or 3). One solution to the problem of low expression levels is to increase the concentration of the molecule of interest, which can be free in solution, or expressed on the surface of a cell. The concentration of intracellularly-expressed molecules of interest can also be enhanced, however the cells must first be lysed to release the molecule.

To address this problem, a method of increasing the concentration of cells presenting a molecule comprising an amino acid sequence selected from the group consisting of GSTSGSGKPGSGEGSTKG (SEQ ID NO: 1), GSGKPGS-GEG (SEQ ID NO: 2), GKPGSGEG (SEQ ID NO: 3), SGKPGSGE (SEQ ID NO: 499) and KPGSG (SEQ ID NO: 500) is provided.

In one embodiment, the method comprises providing a sample comprising cells known or suspected to comprise a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500).

In specific embodiments, the selected amino acid sequence is GSTSGSGKPGSGEGSTKG (SEQ ID NO: 1); in other embodiments the selected amino acid sequence is GSGKPGSGEG (SEQ ID NO: 2); in other embodiments the selected amino acid sequence is GKPGSGEG (SEQ ID NO: 3); in other embodiments the selected amino acid sequence is SGKPGSGE (SEQ ID NO: 499); in other embodiments the selected amino acid sequence is KPGSG (SEQ ID NO: 500).

In specific embodiments, the molecule comprising the selected amino acid sequence (i.e., SEQ ID NO: 1, 2, 3, 499 or 500) is a CAR. When the molecule is a CAR it can comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule that specifically binds the selected amino acid sequence (i.e., SEQ ID NO: 1, 2, 3, 499 or 500) and optionally comprises a detectable label is provided. When it is preferable to employ a detectable label, any detectable label can be employed in the method, as described herein, and suitable labels can be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling Techniques*, 11$^{th}$ *Edition*, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I Photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNA-BEADS), etc can also be employed. Strategies for the labeling of proteins are well known in the art and can be employed in the disclosed method.

The label can be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds the molecule comprising the selected amino acid sequence (i.e., SEQ ID NO: 1, 2, 3, 499 or 500; or one or more molecules comprising the selected amino acid sequence bound to an antigen binding molecule or fragment thereof) can be employed, such as those disclosed herein, e.g., those having one or more of the CDRs shown in FIGS. 6 and 8.

In specific embodiments of the disclosed methods, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27. In other specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

The antigen binding molecule can be disposed on any surface, or no surface at all. For example, the antigen binding molecule can be present in a buffer and the buffer-antigen binding molecule can be contacted with the sample. Alternatively, the antigen binding molecule can be associated with a surface. Suitable surfaces include agarose beads, magnetic beads such as DYNABEADS, or a plastic, glass or ceramic plate such as a welled plate, a bag such as a cell culture bag, etc. The surface can itself be disposed in another structure, such as a column.

A cell expressing a molecule comprising the selected amino acid sequence (i.e., SEQ ID NO: 1, 2, 3, 499 or 500) can be of any type, and can be human or non-human (e.g., mouse, rate, rabbit, hamster, etc). In a preferred embodiment, the cell is an immune cell. An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed, and the cell can be a human or non-human cell. Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc.

The sample comprising cells is contacted with the antigen binding molecule, under conditions that permit the formation of a binding complex comprising a molecule comprising the selected amino acid sequence (i.e., SEQ ID NO: 1, 2, 3, 499 or 500) and the antigen binding molecule. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

At this stage, no binding complexes may have formed, or a plurality of binding complexes comprising one or more antigen binding molecules bound to a molecule comprising the selected amino acid sequence (i.e., SEQ ID NO: 1, 2, 3, 499 or 500) may have formed. Unbound molecules comprising the selected amino acid sequence (i.e., SEQ ID NO: 1, 2, 3, 499 or 500) and/or unbound antigen binding molecules may also be present in the local environment of any formed binding complexes.

Any molecules or cells not part of a binding complex are then separated from any formed binding complexes. The method of the removal will depend on the structure and/or local environment of the binding complexes. For example, if the antigen binding molecule is disposed on a bead, plate or bag the unbound components of the reaction mixture can be washed away using a solution that leaves formed binding complexes intact. If a binding complex is disposed on a bead, the bead itself may be situated in a column or other structure and the same approach can be used.

The solution used to induce the formation of binding complexes can be used, for example, as a wash solution to remove unbound components. Any suitable buffer or solution that does not disrupt formed binding complexes can also be used. Typically, buffers having high salt concentrations, non-physiological pH, containing chaotropes or denaturants, should be avoided when performing this step of the method.

At this stage of the method, a population of cells presenting a molecule comprising the selected amino acid sequence (i.e., SEQ ID NO: 1, 2, 3, 499 or 500) will be present. If a detectable label was employed, the concentration of the cells can be easily determined, consistent with the nature of the label. Cells not expressing the molecule comprising the selected amino acid sequence (i.e., SEQ ID NO: 1, 2, 3, 499 or 500) will be absent, and thus the population (or concentration) of cells presenting a molecule comprising the selected amino acid sequence (i.e., SEQ ID NO: 1, 2, 3, 499 or 500) will be increased compared to the levels prior to performing the method.

If the concentration of the molecule comprising the selected amino acid sequence (i.e., SEQ ID NO: 1, 2, 3, 499 or 500) is not at a desired level, the above steps can be repeated a desired number of times. In the context of this step of the method, a desired number of times can also be zero, if the desired concentration of cells is already present.

Vg. Method of Depleting a Population of Immune Cells

When a subject has an immune cell-mediated condition, it can be of significant importance that the condition be controlled in a timely fashion so as to prevent harm to the subject. For example, when a subject has an autoimmune reaction it may be desirable to suppress an immune cell-mediated response by depleting a population of immune cells, in an effort to prevent harm. In another example, a subject receiving immunotherapy may react too strongly to the therapy and be at risk of harm; depleting the population of immune cells administered to the subject may be an effective approach to mitigating the subject's reaction to the immunotherapy. In view of the need for a method of controlling a subject's immune cell-mediated response, a method of depleting a population of immune cells presenting a molecule comprising an amino acid sequence selected from the group consisting of GSTSGSGKPGSGEGSTKG (SEQ ID NO: 1), GSGKPGSGEG (SEQ ID NO: 2) and GKPGSGEG (SEQ ID NO: 3), SGKPGSGE (SEQ ID NO: 499), KPGSG (SEQ ID NO: 500) is provided. An antigen binding molecule that specifically recognizes GSTSGSGK-PGSGEGSTKG (SEQ ID NO: 1) and more specifically the subsequence GSGKPGSGEG (SEQ ID NO: 2), the subsequence GKPGSGEG (SEQ ID NO: 3), the subsequence SGKPGSGE (SEQ ID NO: 499), or the subsequence KPGSG (SEQ ID NO: 500) such as those provided herein, e.g., those having one or more of the CDRs shown in FIGS. 6 and 8, can be employed in the disclosed method.

In specific embodiments of the disclosed method, the antigen binding molecule comprises a heavy chain CDR1 comprising the amino acid sequence SEQ ID NO: 19, a heavy chain CDR2 comprising the amino acid sequence SEQ ID NO: 20, a heavy chain CDR3 comprising the amino acid sequence SEQ ID NO: 21, a light chain CDR1 comprising the amino acid sequence SEQ ID NO: 25, a light chain CDR2 comprising the amino acid sequence SEQ ID NO: 26, and a light chain CDR3 comprising the amino acid sequence SEQ ID NO: 27. In other specific embodiments of the disclosed methods, the antigen binding molecule comprises a heavy chain CDR1 comprising the amino acid sequence SEQ ID NO: 7, a heavy chain CDR2 comprising the amino acid sequence SEQ ID NO: 8, a heavy chain CDR3 comprising the amino acid sequence SEQ ID NO: 9, a light chain CDR1 comprising the amino acid sequence SEQ ID NO: 13, a light chain CDR2 comprising the amino acid sequence SEQ ID NO: 14, and a light chain CDR3 comprising the amino acid sequence SEQ ID NO: 15.

In one embodiment, the method comprises providing a population of immune cells to be depleted, wherein the cells are known or suspected to be presenting a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499) and KPGSG (SEQ ID NO: 500).

In specific embodiments the selected amino acid sequence is GSTSGSGKPGSGEGSTKG (SEQ ID NO: 1); in other embodiments the selected amino acid sequence is GSGK-PGSGEG (SEQ ID NO: 2); in other embodiments the selected amino acid sequence is GKPGSGEG (SEQ ID NO: 3), in other embodiments the selected amino acid sequence is SGKPGSGE (SEQ ID NO: 499), in other embodiments the selected amino acid sequence is KPGSG (SEQ ID NO: 500).

In specific embodiments, the molecule comprising the selected amino acid sequence (i.e., SEQ ID NO: 1, 2, 3, 499 or 500) is a CAR. When the molecule is a CAR it can comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

In some embodiments, it may be beneficial to kill cells expressing a molecule, such as a CAR. As described above, in some embodiments, a therapeutic cell, such as a CAR T-cell may be used therapeutically and, subsequently, need to be depleted in a patient. In one embodiment, the present invention provides a method of removing these T-cells comprising using T-cells to kill other T-cells that express a CAR. A cell presenting a molecule comprising a specific epitope recognized by a specific antigen binding molecule, such as those disclosed herein (i.e. anti-linker Clone 8 and/or 16, and fragments thereof) can be killed using a diabody, a bispecific molecule comprising a human CD3-binding scFv linked to a specific antigen-binding scFv, such as those composed of fragments of Clone 8 and/or 16, as described herein). In certain embodiments, the diabody binds to a cell expressing a molecule comprising GSTSGSGKPGSGEG-STKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) and to a human T-cell to form an immunological synapse and facilitate cell death.

An immune cell presenting a molecule comprising the selected amino acid sequence (i.e., SEQ ID NO: 1, 2, 3, 499 or 500) can be of any type, and can be human or non-human (e.g., mouse, rate, rabbit, hamster, etc). An immune cell of the method can be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which can be obtained as described herein and by methods known in the art. Any type of immune cell can be employed in this embodiment of the disclosed method, and the cell can be a human or non-human cell. Exemplary cells include, but are not limited to immune cells such as T cells, tumor infiltrating lymphocytes (TILs), NK cells, TCR-expressing cells, dendritic cells, and NK-T cells. The T cells can be autologous, allogeneic, or heterologous. In additional embodiments, the cells are T cells presenting a CAR. The T cells can be CD4+ T cells or CD8+ T cells. When a T cell is employed in the disclosed methods, the T cell can be an in vivo T cell or an in vitro T cell. Moreover, the cells can be disposed in, or isolated from, any environment capable of maintaining the cells in a viable form, such as blood, tissue or any other sample obtained from a subject, cell culture media, tissue grown ex vivo, a suitable buffer, etc. As the disclosed method can be employed in therapeutic settings, in preferred embodiments the population of immune cells are disposed in a subject, and more preferably a human subject.

Continuing, immune cells are contacted with an antigen binding molecule that specifically binds to (a) the molecule comprising the selected amino acid sequence (i.e., SEQ ID NO: 1, 2 or 3), and (b) an activating molecule expressed on the surface of the an immune cell not expressing the molecule comprising the selected amino acid sequence, under conditions that permit the formation of a ternary binding complex comprising the molecule comprising the selected amino acid sequence (i.e., SEQ ID NO: 1, 2, 3, 499 or 500), the activating molecule and the antigen binding molecule. The antigen binding molecule can be disposed on any surface, or no surface at all. For example, the antigen binding molecule (which can also comprise the population of immune cells to be depleted and/or can be present in a buffer) and the buffer-antigen binding molecule can be contacted with the sample. Alternatively, the antigen binding molecule can be associated with a surface. Suitable surfaces include agarose beads, magnetic beads such as DYNA-BEADS, or a plastic, glass or ceramic plate such as a welled plate, a bag such as a cell culture bag, etc. The surface can itself be disposed in another structure, such as a column.

The immune cells are contacted with the antigen binding molecule, under conditions that permit the formation of a ternary binding complex comprising a molecule comprising the selected amino acid sequence (i.e., SEQ ID NO: 1, 2, 3, 499 or 500), the antigen binding molecule and an activating molecule expressed on the surface of an immune cell not expressing the molecule comprising the selected amino acid sequence (i.e., SEQ ID NO: 1, 2, 3, 499 or 500). Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex can be disposed on surfaces as described herein, formed binding complexes can also be disposed on surfaces.

In preferred embodiments, the contacting is performed by administering the antigen binding molecule directly to a subject. In this embodiment, the subject will already have a population of cells to be depleted, wherein the cells express a molecule comprising the selected amino acid sequence (i.e., SEQ ID NO: 1, 2, 3, 499 or 500). Thus, these cells, as well as cells presenting an activating molecule, will be present in the subject prior to the administration of the antigen binding molecule to the subject. The human blood, lymph and tissue environment will permit the formation of ternary binding complexes. The binding of the antigen binding molecule with the molecule comprising the selected amino acid sequence (i.e., SEQ ID NO: 1, 2, 3, 499 or 500) serves to "tag" those cells presenting the molecule comprising the selected amino acid sequence (i.e., SEQ ID NO: 1, 2, 3, 499 or 500) (i.e., the cells to be depleted). This binding event may or may not lead to depletion on its own. When the antigen binding molecule binds the activating molecule to form the ternary binding complex, however, this binding event brings both cells (i.e., the cell expressing the molecule comprising the selected amino acid sequence (i.e., SEQ ID NO: 1, 2, 3, 499 or 500), and the cell expressing the activating molecule) together into proximity. The physiological result of the binding event is the killing of the cell expressing the molecule comprising the selected amino acid sequence (i.e., SEQ ID NO: 1, 2, 3, 499 or 500). Thus, with multiple binding events occurring throughout the subject the population of immune cells bearing the molecule comprising the selected amino acid sequence (i.e., SEQ ID NO: 1, 2, 3, 499 or 500) are depleted and the risk of harm to the subject decreases.

Vh. Method of Monitoring a Molecule In Vivo

Positron emission tomography (PET) imaging is often used in oncology research and patient care. For space-occupying lesions in the head, chest, abdomen and pelvis, one of the best documented applications of PET is in the discrimination of benign from malignant causes. Particularly, $^{18}$F-fluorodeoxyglucose (FDG) has been used to image the distribution of glucose uptake in all of these applications. In addition, the development of other radiotracers which image different aspects of tumor metabolism and growth add a further dimension of capabilities. These tracers include $^{11}$C-methionine to measure amino acid incorporation, $^{18}$F-thymidine to measure nucleotide incorporation (a measure of cell proliferation), and $^{18}$F-fluoromisonidazole to measure tissue hypoxia.

The present invention provides the use of antigen binding molecules in PET analysis to increase specificity of FDG uptake. In particular, the methods provided herein may be used to assess changes early after treatment with CAR cells, in addition to monitoring, detection, stimulation, activation, or depletion of CAR T-cells. Specifically, the methods provided herein may facilitate the use of PET for whole-body scans. Using this technique to stage cancer, occult metastatic disease in almost any region of the body can potentially be detected by increased FDG accumulation.

In some embodiments, the present invention provides an in vivo method of detecting a molecule comprising an amino acid sequence selected from the group consisting of SEQ ID NO: 1, 2, 499 or 500. For example, in particular embodiments the antigen binding molecules can be used to follow or monitor the presence or absence of a molecule comprising an amino acid sequence selected from the group consisting of SEQ ID NO: 1, 2, 499 or 500 in a living subject. In some embodiments, the living subject is a human. In some embodiments, the molecule comprising an amino acid sequence selected from the group consisting of SEQ ID NO: 1, 2, 499 or 500 is provided to a living subject and the presence or absence of said molecule is determined using an antigen binding molecule provided herein and a positron emission tomography (PET) scan.

In some embodiments, antigen binding molecules provided herein can be used to control CAR T-cells in vivo. In some embodiments, the antigen binding molecules provided herein can be used to activate or stimulate CAR T-cells in vivo. In some embodiments, the antigen binding molecules provided herein can be used to deplete CAR T-cells in vivo. In some embodiments, the antigen binding molecules provided herein can be used to monitor CAR T-cells in vivo. Specifically, when combined with PET, antigen binding molecules provided herein (e.g., anti-linker antibodies) can be used to monitor or follow the distribution of cells expressing a molecule comprising a selected amino acid sequence (e.g., SEQ ID NO: 1, 2, 499 or 500) in vivo.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control. The foregoing written specification is considered to be sufficient to enable one skilled in the art to practice the invention. The foregoing description and Examples that follow detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

EXAMPLES

The present invention is further illustrated by the following examples which should not be construed as further limiting. The contents of all references cited throughout this application are expressly incorporated herein by reference.

Example 1: Generation of Antigen Binding Molecules

Figure 2:
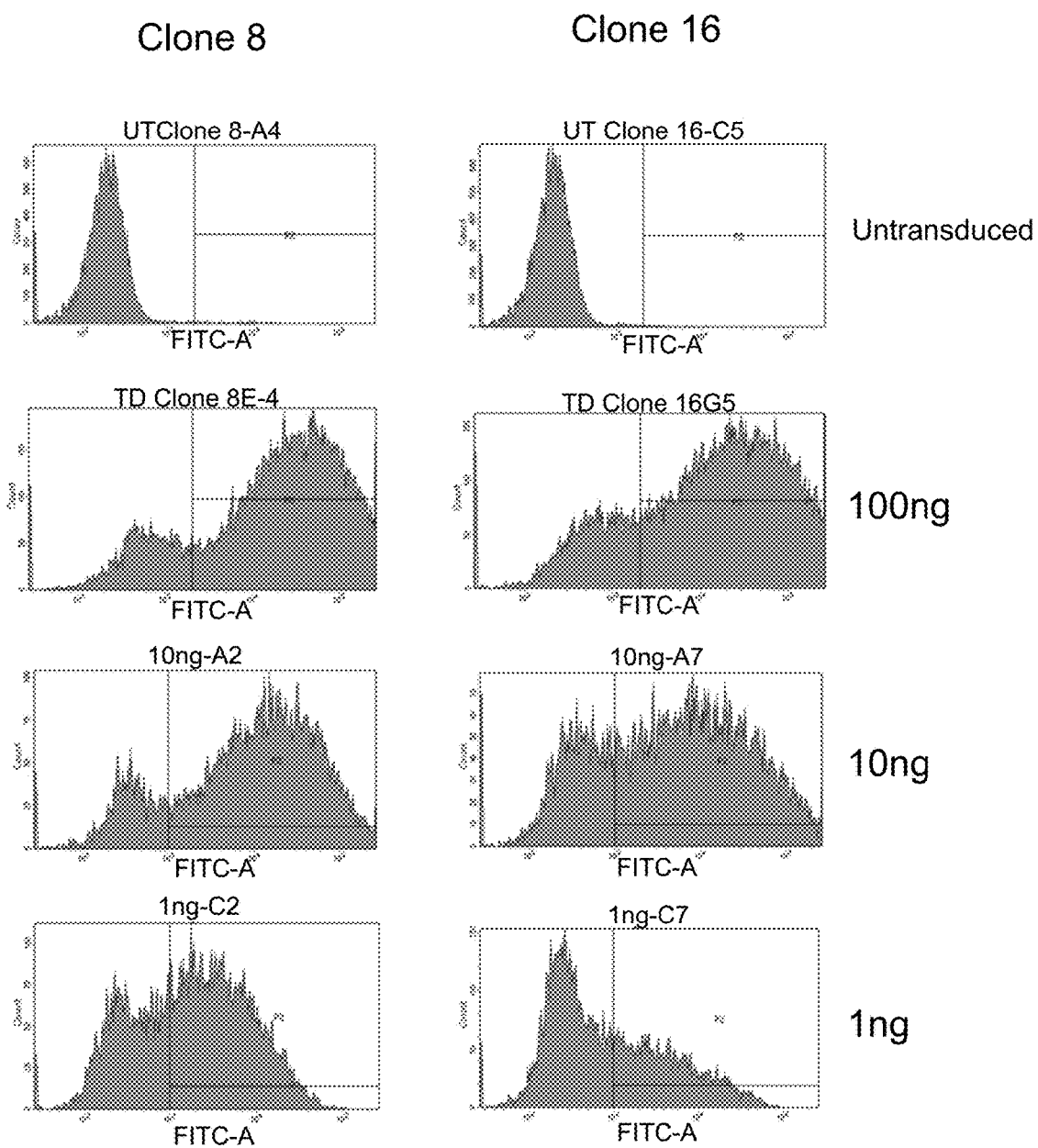
FIG. 2 is series of plots showing the results of flow cytometry experiments performed using cells presenting a chimeric antigen receptor (CAR) comprising the linker sequence of SEQ ID NO: 1; results were generated using 1, 10 or 100 ng of an antibody generated from two different clones (clone 8, left; and clone 16, right), and demonstrate specific binding of the antibodies to the expressed CAR at all three amounts.
Figure 3:
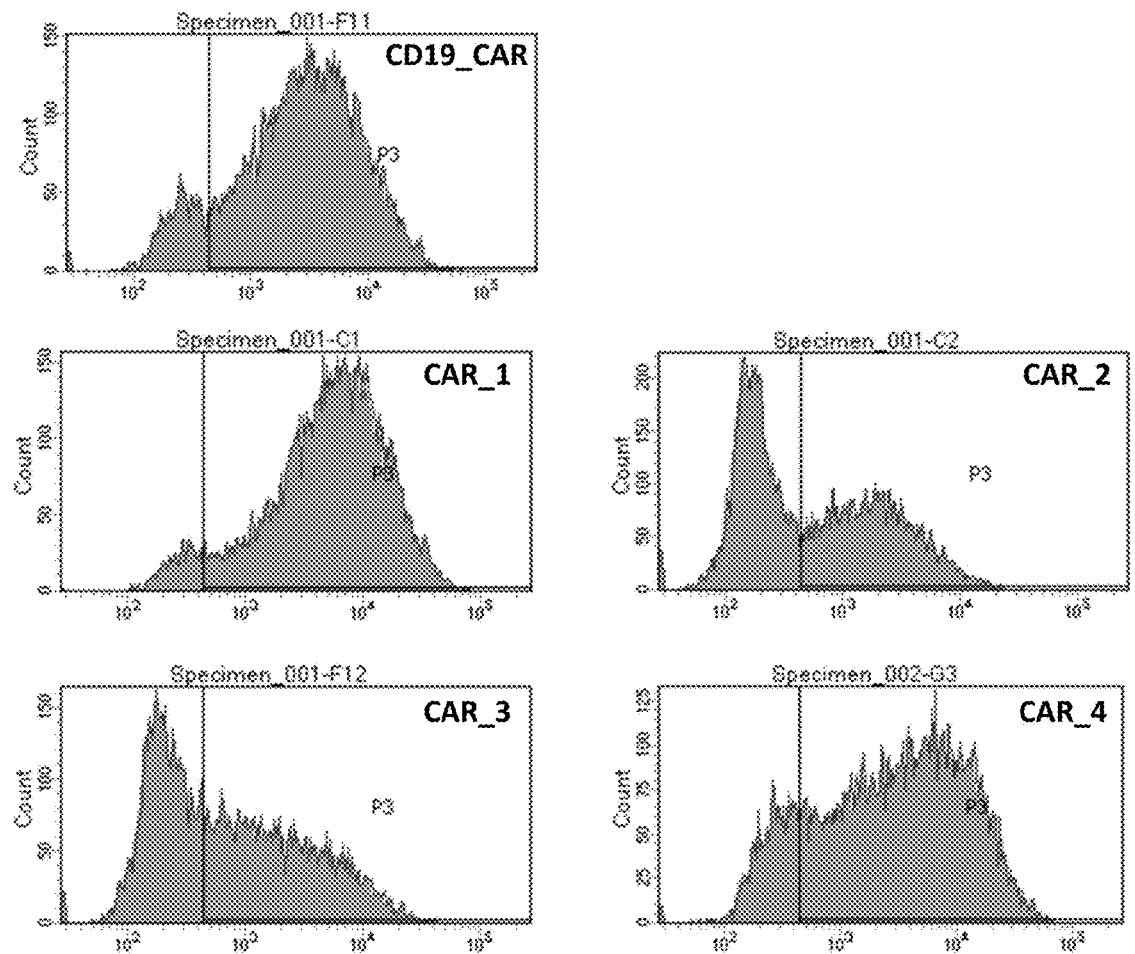
FIG. 3 is series of plots showing the results of flow cytometry experiments performed using cells presenting 5 different CARs comprising the linker sequence of SEQ ID NO: 1; and demonstrate specific binding of the antibodies to the expressed CARs.

Monoclonal antibodies were generated through immunization of rabbits using the 18 mer peptide, GSTSGSGKPGSGEGSTKG (SEQ ID NO: 1), conjugated to the carrier protein KLH as immunogen. Titer was determined via screening polyclonal sera by ELISA using the full-length linker peptide, GSTSGSGKPGSGEGSTKG (SEQ ID NO: 1), conjugated to ovalbumin. A secondary screen was performed using CAR T cells assayed via flow cytometry (FIGS. 2 and 3). Once titer was achieved, the immunized rabbits were sacrificed and monoclonals were derived using standard hybridoma generation and subcloning techniques. The final screening of the hybridoma subclones was accomplished via additional rounds of flow cytometry and immunohistochemistry (IHC) of proliferating CAR T cells or fixed cell pellets derived from CAR T cells, respectively. The sequences of the final two subclones selected were determined by standard Sanger sequencing of the hybridomas subclones.

Example 2: Immunohistochemistry (IHC)

Figure 4:
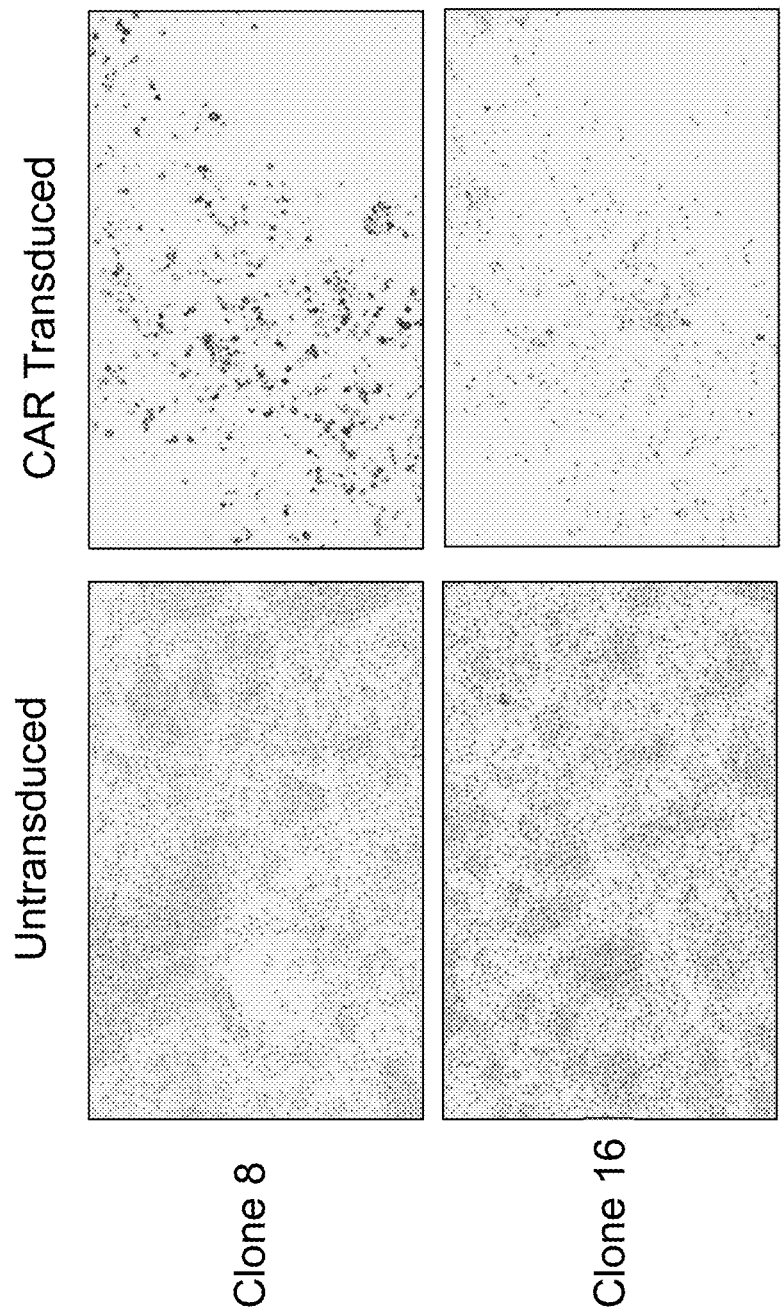
FIG. 4 is a series of photographs depicting the results of immunohistochemistry (IHC) studies performed using cells presenting a CAR; the upper figures demonstrate the specific binding of antibody Clone 8 and directed against a CAR comprising the linker sequence of SEQ ID NO: 1 to cells presenting the CAR, while the lower figures demonstrate the specific binding of antibody Clone 16 and directed against a CAR comprising the linker sequence of SEQ ID NO: 1 to cells presenting the CAR.

The candidate antibodies were screened for their utility in immunohistochemistry (IHC; FIG. 4). To create the fixed cell pellets for IHC staining, ~2e6 CAR T cells were centrifuged and washed with PBS. The cells were resuspended in PBS containing 0.45% paraformaldehyde (PFA) and incubated on a shaking platform for 2 hours at room temperature. After the incubation the cells were washed once more with PBS and resuspended in PBS with 5% BSA. As shown in FIG. 4, CAR transduced cells were positively recognized by exemplary anti-linker antibodies provided herein.

Example 3: Epitope Mapping

Figure 5:
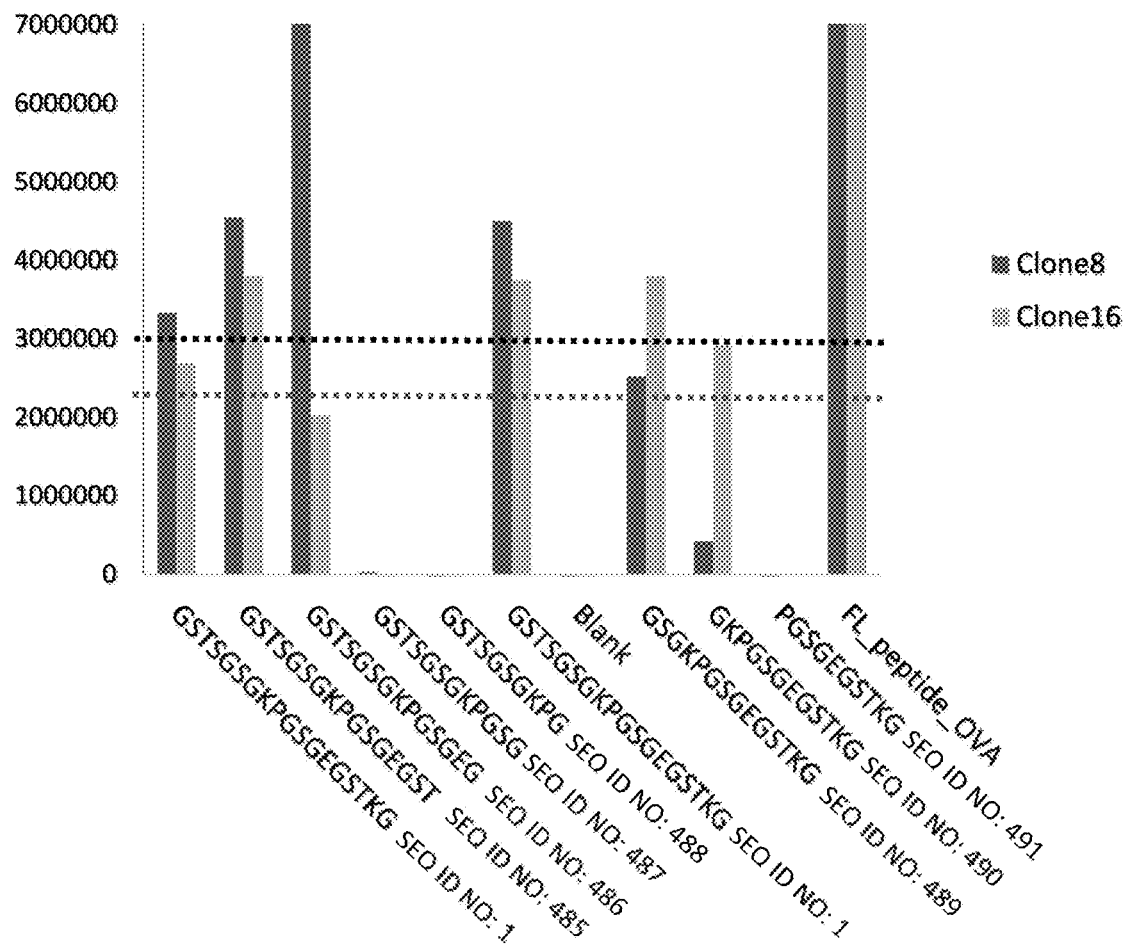
FIG. 5 is a histogram depicting the results of epitope mapping ELISA experiments performed on the antibodies Clone 8 and Clone 16; the results demonstrate that although all antibodies bind to the full length 18 mer (SEQ ID NO: 1), Clone 8 specifically binds to the 10 mer subsequence GSGKPGSGEG (SEQ ID NO: 2) and Clone 16 specifically binds to the 8 mer subsequence GKPGSGEG (SEQ ID NO: 3). Figure discloses SEQ ID NOS 1, 485-488, 1, and 489-491, respectively, in order of appearance.
Figure 9:
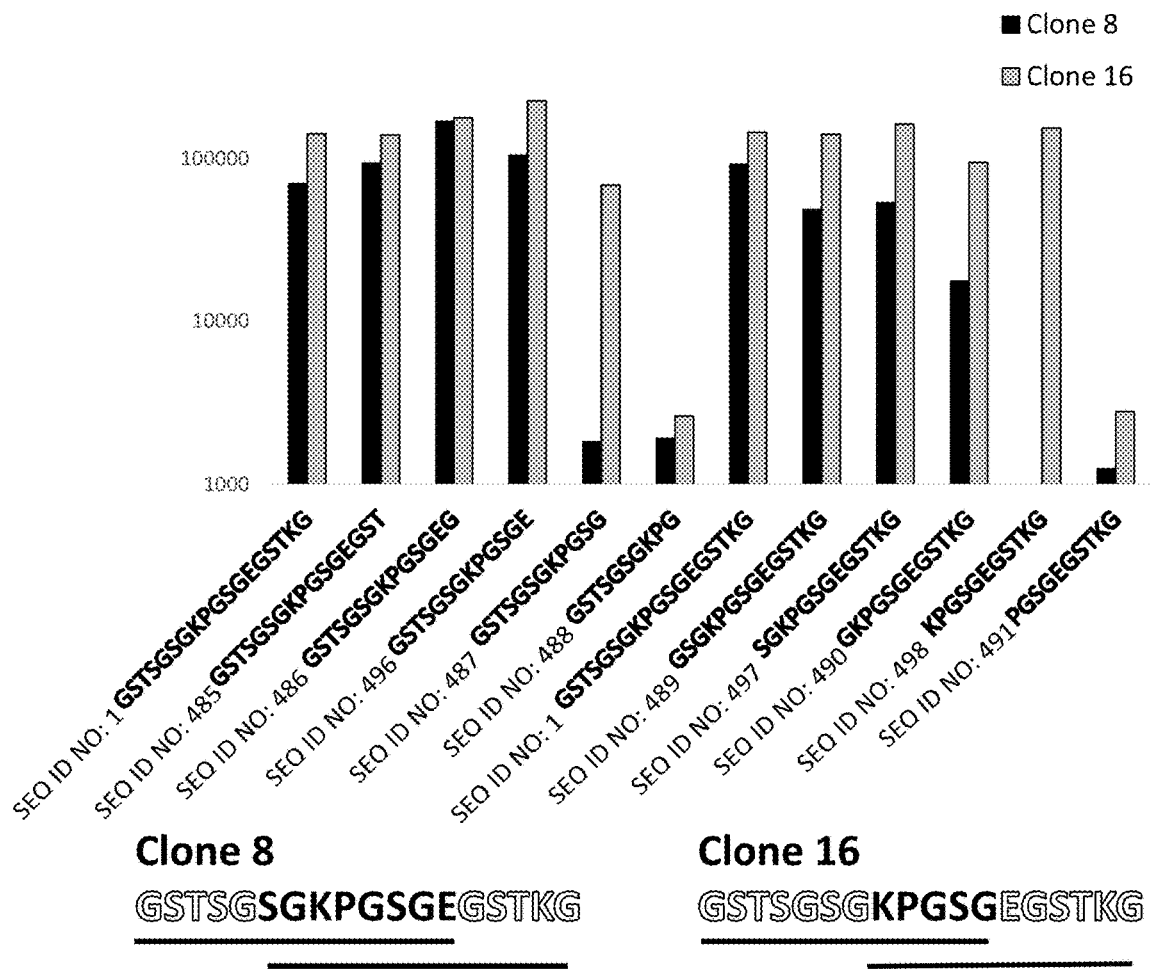
FIG. 9 is a bar chart indicating regions of SEQ ID NO: 1 where the antigen binding molecules disclosed herein were found to bind via epitope mapping by ELISA. This assay further narrows the linker antibody epitopes from the ELISA shown in FIG. 5 using a more narrow range of peptide sequences focusing on the region identified in the previous experiment.

The antibodies (i.e., antigen binding molecules) were epitope mapped via ELISA using the full length peptide, GSTSGSGKPGSGEGSTKG (SEQ ID NO:1), and variants truncated on either the N- or C-terminus and containing either a biotin moiety on the N-terminus, or a lysine residue with a biotin moiety on the C-terminus. The antibodies were captured in 96-well plate format using plates pre-coated with Protein G (Pierce). The plates were washed 6× in PBST buffer followed by incubation with target peptides. An additional 6× wash was performed with PBST and the antibodies were further incubated with streptavidin-HRP. Upon a final 6× wash in PBST, signal was detected and quantified via enhanced chemiluminescense kit (ECL, from GE Healthcare) and a Varioskan Flash plate reader (Thermo Fisher). The results of the epitope mapping work are shown in FIGS. 5, 7 and 9.

Example 4: Generation of Humanized Sequences from Rabbit Antibodies Clone 8-4 and Clone 16-6

The Molecular Operating Environment (MOE) software developed by Chemical Computing Group (CCG) was used to generate alignments between the rabbit antibody Clones 8-4 and 16-6 and pairs of variable light and heavy chains, VL and VH, respectively from two databases:
(1) The Abysis human database: a database of about 2000 known human VL/VH sequence pairs from IMGT-LigM DB; and
(2) A human germline database: a database of germline sequences.

Humanized models show the best sequence alignments (highest identity to both the VL and VH domains) with fewest gaps. The top 100 antibody pairs from each human database was exported and clustered using kClust (Hauser, Mayer, & Soding, (2013) *BMC Bioinformatics,* 248). Presented below are tables for VL and VH sequences for each of the two antibodies, 8-4 (Tables 1-8) and 8-16 (Tables 9-16), with sequences from each of the two databases clustered at 90% (Tables 1, 2, 5, 6, 9, 10, 13, 14) and 95% (Tables 3, 4, 7, 8, 11, 12, 15, 16). Results are presented herein and in FIG. 8.

Table 1. 8-4 VH humanized sequences—IMGT-LigM DB (Abysis) clustered at 90% (18 sequences)
Table 2. 8-4 VL humanized sequences—IMGT-LigM DB (Abysis) clustered at 90% (39 sequences)
Table 3. 8-4 VH humanized sequences—IMGT-LigM DB (Abysis) clustered at 95% (47 sequences)
Table 4. 8-4 LC humanized sequences—IMGT-LigM DB (Abysis) clustered at 95% (99 sequences).
Table 5. 8-4 VH humanized sequences—germline database clustered at 90% (2 sequences).
Table 6. 8-4 VL humanized sequences—germline database clustered at 90% (5 sequences).
Table 7. 8-4 VH humanized sequences—germline database clustered at 95% (7 sequences)
Table 8. 8-4 VL humanized sequences—germline database clustered at 95% (12 sequences)
Table 9. 16-6 VH humanized sequences—IMGT-LigM DB (Abysis) clustered at 90% (41 sequences).
Table 10. 16-6 VL humanized sequences—IMGT-LigM DB (Abysis) clustered at 90% (21 sequences).
Table 11. 16-6 VH humanized sequences—IMGT-Light DB (Abysis) clustered at 95% (81 sequences).
Table 12. 16-6 VL humanized sequences—IMGT-LigM DB (Abysis) clustered at 95% (64 sequences).
Table 13. 16-6 VH humanized sequences—germline database clustered at 90% (3 sequences).
Table 14. 16-6 VL humanized sequences—germline database clustered at 90% (1 sequences).
Table 15. 16-6 VH humanized sequences—germline database clustered at 95% (10 sequences).
Table 16. 16-6 VL humanized sequences—germline database clustered at 95% (7 sequences).

TABLE 1

8-4 VH humanized sequences-IMGT-LigM DB (Abysis)
clustered at 90% (18 sequences)

>8_4_HC_humanized 866
VQLQESGGGVVQPGRSLRLSCAASGFTISNLAIIWVRQAPGKGLEWVADIDGRGDI
YCATWAKGRFTISRDNSTLYLQMNSLRADDTAVYYCARDGDGSGWGDFNFWGQ
GTLVTVSS (SEQ ID NO: 28)

>8_4_HC_humanized 673
QSVVESGGVVVQPGGSLRLSCAASGFTISNLAIIWVRQAPGKGPEWVSDIDGRGDIY
CATWAKGRFTISRDNSSLYLQMNSLRTEDTAVYYCAKDGDGSGWGDFNFWGQGT
MVTVSS (SEQ ID NO: 29)

>8_4_HC_humanized 631
QSVEESGGRLVTPGATVKISCKVSGFTISNLAIIWVQQAPGKGLEWMGDIDGRGDIY
CATWAQGRVTITADSSTAYMELNGLRYADTAVYYCATDGDGSGWGDFNFWGQG
TLVTVSS (SEQ ID NO: 30)

>8_4_HC_humanized 1002
QSLEESGGGVVQPGKSLRLSCTASGFTISNLAIIWVRQAPGKGLESVADIDGRGDIY
CATWATGRFAISRDNSKLYLHMDNLRAEDTAVYYCARDGDGSGWGDFNFWGQG
TTVIVSS (SEQ ID NO: 31)

>8_4_HC_humanized 771
QSLEQSGGGLVQPGGSLRLSCAASGFTISNLAIIWVRQAPGKGLEWVSDIDGRGDIY
CATWAKGRFTISKSKNTLYLQMNSLRAEDTAVYYCAVDGDGSGWGDFNFWGQG
TLVTVSS (SEQ ID NO: 32)

>8_4_HC_humanized 849
QSVEESGGDLVKPGGSLRLSCAASGFTISNLAIIWIRQAPGKGLEWLSDIDGRGDIYC
ATWAKGRFTISRDNASLNLQMNSLRAEDTAVYYCAVDGDGSGWGDFNFWGQGT
LVTVSS (SEQ ID NO: 33)

>8_4_HC_humanized 706
VLLLESGGGLAQPGGTLRLSCSASGFTISNLAIIWVRQAPGKGLEWVSDIDGRGDIY
CATWARGRFIISRDNSTLYLQMNSLRAEDTAVYYCAKDGDGSGWGDFNFWGQGIL
VTVSS (SEQ ID NO: 34)

>8_4_HC_humanized 703
VQLVESGGTLVQPGGSLRLSCSASGFTISNLAIIWVRQAPGKGLEYVSDIDGRGDIY
CATWAKGRITISRDNSTLSLQMSTLRTEDTAVYYCVRDGDGSGWGDFNFWGQGTL
VTVSS (SEQ ID NO: 35)

>8_4_HC_humanized 278
VQLVQSGGGLVKPGGSLRLSCEASGFTISNLAIIWIRQAPGKGLEWVGDIDGRGDIY
CATWAKGRFTISRDDSTLYLQVNSLKTEDSAVYYCTTDGDGSGWGDFNFWGQGT
LVTVSS (SEQ ID NO: 36)

>8_4_HC_humanized 800
QSVLESGPGLVKPSETLSLTCTVSGFTISNLAIIWIRQPPGKGLEWIGDIDGRGDIYCA
TWAKSRLTISTSKNQFSLRLTSVTAADTAMYYCAVDGDGSGWGDFNFWGQGTLV
SVSS (SEQ ID NO: 37)

>8_4_HC_humanized 809
VQLVESGGGLVQPGGSLRLSCAASGFTISNLAIIWVRQAPGKGLEWLSDIDGRGDIY
CATWARGRFAISNARNSLYLQMNSLRDEDTAVYFCARDGDGSGWGDFNFWGQGT
LVTVSS (SEQ ID NO: 38)

>8_4_HC_humanized 273
VQLVQSGGGLVQPGGSLRLSCAASGFTISNLAIIWVRQASGKGLEWIGDIDGRGDIY
CATWAKGRFTVSRSQNSVFLQMNSLETEDTAVYYCARDGDGSGWGDFNFWGQG
TLVTVSS (SEQ ID NO: 39)

>8_4_HC_humanized 716
QSVLESGGGWVQPGRSLRLSCSASGFTISNLAIIWVRQAPGKGLEWVSDIDGRGDIY
CATWAKGRFTISRDNNSLYLQMNSLRPEDTALYYCAKDGDGSGWGDFNFWGQGV
LVTVSS (SEQ ID NO: 40)

>8_4_HC_humanized 202
VQLQESGEGLVQPGGSLRLSCAASGFTISNLAIIWVRQAPGKGLEYVSDIDGRGDIY
CATWAKGRFTISRDNSTLYLQMGSLRAEDMAVYYCAVDGDGSGWGDFNFWGQG
TMVTVSS (SEQ ID NO: 41)

>8_4_HC_humanized 21
VQLVESGGGLVQPGGSLRLSCAASGFTISNLAIIWVRQAPGKGLEFVSDIDGRGDIY
CATWAKDRFTISRDNSTVYLQMDSLRTEDTAMYFCARDGDGSGWGDFNFWGQGT
LVTVSS (SEQ ID NO: 42)

TABLE 1 -continued 8-4 VH humanized sequences-IMGT-LigM DB (Abysis) clustered at 90% (18 sequences)

>8_4_HC_humanized 173
QSVEESGGRLVTPGGSLRLSCTATGFTISNLAIIWFRQAPGKGLEWVGDIDGRGDIY
CATWAKGRFTISRDDNSLYLQMNSLKTEDTAVYYCARDGDGSGWGDFNFWGQGT
LVTVSS (SEQ ID NO: 43)

>8_4_HC_humanized 23
QSVLESGGDLVQPGGSLRLSCEASGFTISNLAIIWVRQAPGKGLEWVSDIDGRGDIY
CATWAKGRFTISKSKHTLFLQMHSLRVEDTAVYYCAKDGDGSGWGDFNFWGQGT
TVTVSS (SEQ ID NO: 44)

>8_4_HC_humanized 879
QSVEESGGGLVQPGGSLRLSCTASGFTISNLAIIWVRQAPGKGLEWVSDIDGRGDIY
CATWAKGRFTISRDSSTLYLQMNNLRVEDTALYYCAHDGDGSGWGDFNFWGRGT
QVTVSS (SEQ ID NO: 45)

TABLE 2

8-4 VL humanized sequences-IMGT-LigM DB (Abysis) clustered at 90% (39 sequences)

>8_4_LC_humanized 866
DIQMTQSPSSLSASVGDRVTITCQASQSISTALAWYQQKPGKAPKRLIYRASTLASG
VPSRFSGSGSGTEFTLTISSLQPEDFATYYCQQGWSTVNVDNVFGQGTKVEIK (SEQ ID NO: 46)

>8_4_LC_humanized 340
DIQMTQSPFSLSASVGDRVTITCQASQSISTALAWYQQKPGKAPKLLIYRASTLASG
VPSRFSGSGSGTDFTLTISSLQPEDFATYFCQQGWSTVNVDNVFGGGTKLEIK (SEQ ID NO: 47)

>8_4_LC_humanized 322
DIQLTQSPSFLSASVGDTVSITCQASQSISTALAWYQQKPGKAPKHLIYRASTLASGV
PSRFSGGGSGTDFTLTISSLQPEDFATYYCQQGWSTVNVDNVFGGGTKVEIK (SEQ ID NO: 48)

>8_4_LC_humanized 305
DIQLTQSPSSLSASVGDRVTITCQASQSISTALAWFQQKPGKAPKSLIYRASTLASGV
PSRFSGSGSGTDFTLTISSLQPEDSATYYCQQGWSTVNVDNVFGGGTKVEIK (SEQ ID NO: 49)

>8_4_LC_humanized 303
DIQMTQSPSSLSASVGDRVTITCQASQSISTALAWYQQKPGKAPKLLIYRASTLASG
VPSRFSGSGSGTDFTFTISSLQPEDIATYYCQQGWSTVNVDNVFGPGTKVDIK (SEQ ID NO: 50)

>8_4_LC_humanized 291
DIQLTQSPSSLSASVGDRVTITCQASQSISTALAWYQQKPGKGPKLLIYRASTLASGV
PSRFSGSGSGTDFSLTISSLQPEDLATYYCQQGWSTVNVDNVFGGGTKVEIK (SEQ ID NO: 51)

>8_4_LC_humanized 217
DIVMTQSPDSLAVSLGERATINCQASQSISTALAWYQQKPGQPPKLLIYRASTLASG
VPDRFSGSGSGTDFTLTISSLQAEDVAVYYCQQGWSTVNVDNVFGQGTKVEIK
(SEQ ID NO: 52)

>8_4_LC_humanized 197
AYDMTQTPATLSLSPGERATLSCQASQSISTALAWYQQKPGQAPRLLIYRASTLASG
IPARFSGSGSGTDFTLTISSLEPEDFAVYYCQQGWSTVNVDNVFGQGTEVVVR (SEQ ID NO: 53)

>8_4_LC_humanized 169
EIVLTQSPSFLSAFVGDRITITCQASQSISTALAWYQQKPGKAPKLLIYRASTLASGV
PSRFSGSGSGTEFTLTISGLQPEDFASYYCQQGWSTVNVDNVFGGGTKLEIK (SEQ ID NO: 54)

>8_4_LC_humanized 17
DIQLTQSPSSLSAAVGDRVTIACQASQSISTALAWYQQKPGKAPKLLIYRASTLASG
VPSRFSGSGSGTDFTLSISSLQPGDFATYYCQQGWSTVNVDNVFGGGTKVQMK
(SEQ ID NO: 55)

>8_4_LC_humanized 13
DIQMTQSPSSLSASVGDSVTITCQASQSISTALAWYQQKPGKAPKLLIYRASTLASG
VPSRFSGSGSGTEFTLTINGLQPEDFATYYCQQGWSTVNVDNVFGGGTKLEIK (SEQ ID NO: 56)

>8_4_LC_humanized 791
AYELTQTPLSSPVTLGQPASISCQASQSISTALAWLHQRPGQPPRLLIYRASTLASGV
PDRFSGSGAGTAFTLKISRVEVEDVGIYYCQQGWSTVNVDNVFGQGTKVEIK (SEQ ID NO: 57)

>8_4_LC_humanized 673
AYDMTQTPASVEVSPGERATLSCQASQSISTALAWYQHKPGQAPRLLIYRASTLAS
GIPARFSGSGSGTEFTLTISSVQSDDFAVYYCQQGWSTVNVDNVFGPGTKVDIK
(SEQ ID NO: 58)

TABLE 2 -continued 8-4 VL humanized sequences-IMGT-LigM DB (Abysis) clustered at 90%
(39 sequences)

>8_4_LC_humanized 678
AYELTQSPSSLSASVGDRVTITCQASQSISTALAWFQQKPGKAPKLLIYRASTLASG
VPSRFSGSGSGTDFTLTISSLLPTDFATYFCQQGWSTVNVDNVFGQGTQVEVK (SEQ ID NO: 59)

>8_4_LC_humanized 631
AYDMTQTPASVEVSVGDRVTITCQASQSISTALAWYQQKPGKAPKLLIYRASTLAS
GVPSRFGGSGSGTDFTLTISSLQPEDFATYYCQQGWSTVNVDNVFGGGTKVEIK
(SEQ ID NO: 60)

>8_4_LC_humanized 1002
AYELTQSPSSLSASVGDRVTITCQASQSISTALAWYQQKPGKAPKLLIYRASTLASG
VSSRFSGSGSGTDFTLTISSLQPEDFATYYCQQGWSTVNVDNVFGQGTKLEIK (SEQ ID NO: 61)

>8_4_LC_humanized 775
AYELTQTPLSSPVTLGQPASISCQASQSISTALAWLQQRPGQPPRLLIYRASTLASGV
PDRFSGSGARTDFTLNISRVEAEDAGVYYCQQGWSTVNVDNVFGQGTKLEIK (SEQ ID NO: 62)

>8_4_LC_humanized 771
AYELTQSPATLSLSPGERATLSCQASQSISTALAWYQQKPGQAPRLLIHRASTLASGI
PARFSGSGSGTDFTLTISSLEPEDFAVYYCQQGWSTVNVDNVFGGGTRVEIK (SEQ ID NO: 63)

>8_4_LC_humanized 188
DIQLTQSPSTLSASVGDRITITCQASQSISTALAWYQQKPGKAPKLLIYRASTLASGV
PPRFSGSGSGTEFTLTISSLQPDDFATYYCQQGWSTVNVDNVFGQGTKVVVR (SEQ ID NO: 64)

>8_4_LC_humanized 717
ELVMTQSPSSLSASVGDRVTITCQASQSISTALAWYQQKPGKAPNLLIYRASTLASG
IPSRFSGSGSGTYFTLTINGLQPEDFATYYCQQGWSTVNVDNVFGGGTKVDIK (SEQ ID NO: 65)

>8_4_LC_humanized 1048
SYELTQTPPSVSVSPGQTARITCQASQSISTALAWYQQKPGQAPKVLIYRASTLASGI
PERFSGSSSGTTVTLTISGVQAEDEADYYCQQGWSTVNVDNVFGGGTKLTVL (SEQ ID NO: 66)

>8_4_LC_humanized 849
AYELTQSPLSLSVTPGQPASISCQASQSISTALAWYLQKPGQPPQLLIYRASTLASGV
PDRFSGSGSGTDFTLKISRVEAEDVGVYYCQQGWSTVNVDNVFGQGTKVEIK (SEQ ID NO: 67)

>8_4_LC_humanized 1016
DIELTQSPSSLSASIGDRVSITCQASQSISTALAWYQQKPGKAPKWYRASTLASGVP
SRFSGSGSGTDFTLTISSLQPEDFATFYCQQGWSTVNVDNVFGGGTRVEIK (SEQ ID NO: 68)

>8_4_LC_humanized 978
EIVLTQSPSSLSASVGDRVTITCQASQSISTALAWYQQKPGKAPKLLIYRASTLASGV
PSRFSGSGSGTDFTLTISNLQPEDFATYYCQQGWSTVNVDNVFGGGTKVEIK (SEQ ID NO: 69)

>8_4_LC_humanized 706
DIQMTQYPSSLSASVGDRVTIACQASQSISTALAWYQQKPGKPPKLLIYRASTLASG
VPSRFSGSGSGTDFTLTISCLQPEDVATYYCQQGWSTVNVDNVFGQGTRVEFK
(SEQ ID NO: 70)

>8_4_LC_humanized 278
ELVLTQSPSSLSASVGDRVTITCQASQSISTALAWCQQKPGKSPTLLIYRASTLASGV
PSRFSGSGSGTGFTLTISGLQPEDFATYYCQQGWSTVNVDNVFGGGTKVEIR (SEQ ID NO: 71)

>8_4_LC_humanized 129
EIVNITQSPSSLSASVGDRVTITCQASQSISTALAWYQHKPGKAPRLLIYRASTLASG
VPSRFSGSGSGTDFTLTISSLQPDDFATYYCQQGWSTVNVDNVFGQGTKVEVK
(SEQ ID NO: 72)

>8_4_LC_humanized 1133
AYDMTQPPSVSVSPGQTASITCQASQSISTALAWYQQKPGQSPVLIYRASTLASG
IPERF SGSNSGNTATLTISGTQAMDEADYYCQQGWSTVNVDNVFGTGTEVVVR
(SEQ ID NO: 73)

>8_4_LC_humanized 881
AYDMTQSPSSLSASVGDRVTITCQASQSISTALAWYQQKPGKAPNLLIYRASTLASG
VPSRFSGSGSGTDFTLTISSLQPEDFATYYCQQGWSTVNVDNVFGGGTKVQIK (SEQ ID NO: 74)

>8_4_LC_humanized 882
AYDMTQSPSSLSASVGDRVTITCQASQSISTALAWYQQKPGKAPKLLIYRASTLASG
VPSRFSGSGFGTDFTFTISSLQPEDSATYYCQQGWSTVNVDNVFGQGTKLEIK (SEQ ID NO: 75)

>8_4_LC_humanized 273
ELVMTQSPSSLSASVGDRVTITCQASQSISTALAWYQQKPGEAPKLLIYRASTLASG
VPSRFSGSGSGTDFTLTISGLQSEDFATYYCQQGWSTVNVDNVFGQGTKVEIK (SEQ ID NO: 76)

TABLE 2 -continued 8-4 VL humanized sequences-IMGT-LigM DB (Abysis) clustered at 90%
(39 sequences)

>8_4_LC_humanized 716
ELVMTQSPSSLSASEGDRVTITCQASQSISTALAWYQQKPGRAPKLLIHRASTLASG
VPSRFSGSGSGTEFTLTISGLQSEDFATYYCQQGWSTVNVDNVFGGGTTVDVK
(SEQ ID NO: 77)

>8_4_LC_humanized 677
AYDMTQSPSFLSASVGDRVTITCQASQSISTALAWYQQKPGKAPKLLIYRASTLASG
VPSRFSGSGSGTEFTLTISSLQPEDFATYYCQQGWSTVNVDNVFGQGTRLEIK (SEQ ID NO: 78)

>8_4_LC_humanized 192
AYDMTQSPSSLSASVGDRVTITCQASQSISTALAWYQQKPGKAPKLLIYRASTLASG
VPSRFSGSGSGTDFTLTISSLQAEDFTTYYCQQGWSTVNVDNVFGQGTKVEFK
(SEQ ID NO: 79)

>8_4_LC_humanized 802
AIRMTQSPSSF SASTGDRVTITCQASQSISTALAWYQQKPGKAPKLLIYRASTLASG
VPSRFSGSGSGTDFTLTISCLQSEDFATYYCQQGWSTVNVDNVFGGGTKVEIK (SEQ ID NO: 80)

>8_4_LC_humanized 54
AYGMTQSPDSLAVSLGERASINCQASQSISTALAWYQQKPGQPPKWYRASTLASG
VPDRFSGGGSGTDFTLTISSLQAEDVAVYYCQQGWSTVNVDNVFGGGTKVEIK
(SEQ ID NO: 81)

>8_4_LC_humanized 173
AIQMTQSPFSLSASVGDRVTITCQASQSISTALAWFQQKPGKAPKSLIYRASTLASG
VSSKFSGSGSGTDFTLTISSLQPEDFATYYCQQGWSTVNVDNVFGQGTRLVVR
(SEQ ID NO: 82)

>8_4_LC_humanized 224
AYDMTQTPASVSLSPGERATLSCQASQSISTALAWYQQKPGQAPRLLIYRASTLAS
GIPDRFRGSGSATDFTLTISRLEPEDFAVYYCQQGWSTVNVDNVFGGGTEVVVR
(SEQ ID NO: 83)

>8_4_LC_humanized 657
AYDMTQTPASVEVSVGDRVSITCQASQSISTALAWYQQKPGKAPKLLIYRASTLAS
GVPSRFSGSGSGTDFTLTITSLQPVDFATYYCQQGWSTVNVDNVFGPGTTVDAK
(SEQ ID NO: 84)

TABLE 3

8-4 VH humanized sequences-IMGT-LigM DB (Abysis) clustered at 95%
(47 sequences)

>cl|CABBABABA|10|117 >8_4_HC_humanized 866 >8_4_HC_humanized 340
>8_4_HC_humanized 336 >8_4_HC_humanized 332 >8_4_HC_humanized 322
VQLVESGGGVVQPGRSLRLSCAASGFTISNLAIIWVRQAPGKGLEWVADIDGRGDI
YCATWAKGRFTISRDNSTLYLQMNSLRAEDTAVYYCAVDGDGSGWGDFNFWGQ
GTLVTVSS (SEQ ID NO: 85)

>cl|KABBABABA|13|117 >8_4_HC_humanized 315 >8_4_HC_humanized 314
>8_4_HC_humanized 305 >8_4_HC_humanized 303 >8_4_HC_humanized 296
VQLVQSGGGVVQPGRSLRLSCAASGFTISNLAIIWVRQAPGKGLEWVADIDGRGDI
YCATWAKGRFTISRDNSTLYLQMNSLRAEDTAVYYCAVDGDGSGWGDFNFWGQ
GTLVTVSS (SEQ ID NO: 86)

>cl|TABBABABA|8|117 >8_4_HC_humanized 217 >8_4_HC_humanized 197
>8_4_HC_humanized 678 >8_4_HC_humanized 978 >8_4_HC_humanized 635
VQLVESGGGLVKPGGSLRLSCAASGFTISNLAIIWVRQAPGKGLEWVSDIDGRGDIY
CATWAKGRFTISRDNASLYLQMNSLRAEDTAVYYCARDGDGSGWGDFNFWGQG
TLVTVSS (SEQ ID NO: 87)

>cl|WABBABABA|7|117 >8_4_HC_humanized 169 >8_4_HC_humanized 122
>8_4_HC_humanized 676 >8_4_HC_humanized 893 >8_4_HC_humanized 57
VQLVESGGGLVQPGGSLRLSCAASGFTISNLAIIWVRQAPGKGLEWVSDIDGRGDIY
CATWAKGRFTISRDNSTLYLQMNSLRAEDTAVYYCAKDGDGSGWGDFNFWGQGT
LVTVSS (SEQ ID NO: 88)

>cl|ZABBABABA|1|117 >8_4_HC_humanized 17
VQLVESGGGLVQPGGSLRLSCAASGFTISNLAIIWVRQAPGRGLVWVSDIDGRGDIY
CATWAKGRFTISRDNATLYLQMNNLRAEDTAVYYCARDGDGSGWGDFNFWGQG
TLVTVSS (SEQ ID NO: 89)

TABLE 3 -continued 8-4 VH humanized sequences-IMGT-LigM DB (Abysis) clustered at 95%
(47 sequences)

>cl|CEBBABABA|1|117 >8_4_HC_humanized 791
QSVLESGGGLVQPGGSLRLSCAASGFTISNLAIIWVRQAPGKGLEWVSDIDGRGDIY
CATWARGRFTISRDNSTLYLQMNSLRAEDTAIYYCAKDGDGSGWGDFNFWGRGT
HVTVSS (SEQ ID NO: 90)

>cl|DEBBABABA|1|117 >8_4_HC_humanized 673
QSVVESGGVVVQPGGSLRLSCAASGFTISNLAIIWVRQAPGKGPEWVSDIDGRGDIY
CATWAKGRFTISRDNSSLYLQMNSLRTEDTAVYYCAKDGDGSGWGDFNFWGQGT
MVTVSS (SEQ ID NO: 91)

>cl|GEBBABABA|1|117 >8_4_HC_humanized 631
QSVEESGGRLVTPGATVKISCKVSGFTISNLAIIWVQQAPGKGLEWMGDIDGRGDIY
CATWAQGRVTITADSSTAYMELNGLRYADTAVYYCATDGDGSGWGDFNF WGQG
TLVTVSS (SEQ ID NO: 92)

>cl|BEBBABABA|1|117 >8_4_HC_humanized 1002
QSLEESGGGVVQPGKSLRLSCTASGFTISNLAIIWVRQAPGKGLESVADIDGRGDIY
CATWATGRFAISRDNSKLYLHMDNLRAEDTAVYYCARDGDGSGWGDFNFWGQG
TTVIVSS (SEQ ID NO: 93)

>cl|KEBBABABA|1|117 >8_4_HC_humanized 775
QSLEESGGGLVQPGGSLRLSCAASGFTISNLAIIWVRQASGKGLEWVSDIDGRGDIY
CATWAKGRFTISRDNSTLYLQMNSLRAEDTAVYSCAVDGDGSGWGDFNFWGQGT
LVTVSS (SEQ ID NO: 94)

>cl|LEBBABABA|2|117 >8_4_HC_humanized 771 >8_4_HC_humanized 772
QSLEQSGGGLVQPGGSLRLSCAASGFTISNLAIIWVRQAPGKGLEWVSDIDGRGDIY
CATWAKGRFTISKSKNTLYLQMNSLRAEDTAVYYCAVDGDGSGWGDFNFWGQG
TLVTVSS (SEQ ID NO: 95)

>cl|NEBBABABA|1|117 >8_4_HC_humanized 188
VQLVESGGGLVQPGGSLRLSCAASGFTISNLAIIWVRQAPGKGLEWASDIDGRGDIY
CATWAKGRFTISRDSSTLYLQMNSLRTDDTAVYYCAADGDGSGWGDFNFWGQGT
LVTVSS (SEQ ID NO: 96)

>cl|PEBBABABA|9|117 >8_4_HC_humanized 186 >8_4_HC_humanized 292
>8_4_HC_humanized 283 >8_4_HC_humanized 204 >8_4_HC_humanized 201
VQLVESGGGVVQPGRSLRLSCAASGFTISNLAIIWVRQAPGKGLEWVADIDGRGDI
YCATWAKGRFTISRDNSTLYLQMNSLRAEDTAVYYCAKDGDGSGWGDFNFWGQ
GTLVTVSS (SEQ ID NO: 97)

>cl|QEBBABABA|1|117 >8_4_HC_humanized 717
QSVLESGGGWVQPGRSLRLSCAASGFTISNLAIIWVRQAPGKGLEWVADIDGRGDI
YCATWAKGRFTISRDNASLYLEMKSLRAEDTAIYYCARDGDGSGWGDFNFWGQG
VLVTVSS (SEQ ID NO: 98)

>cl|REBBABABA|2|117 >8_4_HC_humanized 1048 >8_4_HC_humanized 675
QSVEESGGGLVQPGGSLRLSCAASGFTISNLAIIWVRQAPGKGLEWVSDIDGRGDIY
CATWAKGRFTISRDNASLYLQMNSLRAEDTAVYYCARDGDGSGWGDFNFWGQG
TLVTVSS (SEQ ID NO: 99)
>cl|SEBBABABA|1|117 >8_4_HC_humanized 849
QSVEESGGDLVKPGGSLRLSCAASGFTISNLAIIWIRQAPGKGLEWLSDIDGRGDIYC
ATWAKGRFTISRDNASLNLQMNSLRAEDTAVYYCAVDGDGSGWGDFNFWGQGT
LVTVSS (SEQ ID NO: 100)

>cl|TEBBABABA|3|117 >8_4_HC_humanized 1016 >8_4_HC_humanized 295
>8_4_HC_humanized 319
VQLVQSGGGLVKPGGSLRLSCAASGFTISNLAIIWVRQAPGKGLEWVADIDGRGDI
YCATWAKGRFTISRDNSTLYLQMNSLRAEDTAVYYCAVDGDGSGWGDFNFWGQ
GTLVTVSS (SEQ ID NO: 101)

>cl|XEBBABABA|2|117 >8_4_HC_humanized 868 >8_4_HC_humanized 55
QQLQESGGGLVQPGGSLRLSCSASGFTISNLAIIWVRQAPGKGLEYVSDIDGRGDIY
CATWAKGRFTISRDNSTLYLQMSSLRAEDTAVYYCVKDGDGSGWGDFNFWGQGT
LVTVSS (SEQ ID NO: 102)

>cl1YEBBABABA|1|117 >8_4_HC_humanized 862
VRLVESGGGVVQPGRSLRLSCAASGFTISNLAIIWVRQAPGKGLEWVADIDGRGDI
YCATWAKGRFTISRDNSTLHLQMNSLRAEDTAVYYCAKDGDGSGWGDFNFWGK
GTTVTVSS (SEQ ID NO: 103)

>cl|ZEBBABABA|1|117 >8_4_HC_humanized 715
VQLVESGGGLVQPGGSLRLSCAASGFTISNLAIIWVRQAPGKGLEWVSDIDGRGDIY
CATWAKGRFTISRSKNTLYLQMNSLRAEDTAVYYCARDGDGSGWGDFNFWGQGT
TVTVSS (SEQ ID NO: 104)

TABLE 3 -continued 8-4 VH humanized sequences-IMGT-LigM DB (Abysis) clustered at 95%
(47 sequences)

>cl|BIBBABABA|1|117 >8_4_HC_humanized 706
VLLLESGGGLAQPGGTLRLSCSASGFTISNLAIIWVRQAPGKGLEWVSDIDGRGDIY
CATWARGRFIISRDNSTLYLQMNSLRAEDTAVYYCAKDGDGSGWGDFNFWGQGIL
VTVSS (SEQ ID NO: 105)

>cl|CIBBABABA|1|117 >8_4_HC_humanized 703
VQLVESGGTLVQPGGSLRLSCSASGFTISNLAIIWVRQAPGKGLEYVSDIDGRGDIY
CATWAKGRITISRDNSTLSLQMSTLRTEDTAVYYCVRDGDGSGWGDFNFWGQGTL
VTVSS (SEQ ID NO: 106)

>cl|FIBBABABA|1|117 >8_4_HC_humanized 341
VQLVQSGGSLVQPGRSLRLSCAASGFTISNLAIIWVRQAPGKGLEWVADIDGRGDIY
CATWAKGRFTTSRDNSTLYLQMNSLRADDTAVYFCAVDGDGSGWGDFNFWGQG
TLVTVSS (SEQ ID NO: 107)

>cl|KIBBABABA|1|117 >8_4_HC_humanized 301
VQLVESGGDLVQPGESLRLSCAASGFTISNLAIIWVRQAPGKGLEWVSDIDGRGDIY
CATWAKGRFTISRDNSTLYLQMNSLRAEDTAVYYCARDGDGSGWGDFNFWGQGT
LVTVSS (SEQ ID NO: 108)

>cl|QIBBABABA|1|117 >8_4_HC_humanized 278
VQLVQSGGGLVKPGGSLRLSCEASGFTISNLAIIWIRQAPGKGLEWVGDIDGRGDIY
CATWAKGRFTISRDDSTLYLQVNSLKTEDSAVYYCTTDGDGSGWGDFNFWGQGT
LVTVSS (SEQ ID NO: 109)

>cl|TIBBABABA|1|117 >8_4_HC_humanized 129
MQLVESGGGLVQPGRSLRLSCVTSGFTISNLAIIWVRQVPGKGLEWVSDIDGRGDIY
CATWAKGRFTISRDNTSLYLQMNSLRPEDTAVYYCAKDGDGSGWGDFNFWGQGT
LVTVSS (SEQ ID NO: 110)

>cl|XIBBABABA|1|117 >8_4_HC_humanized 800
QSVLESGPGLVKPSETLSLTCTVSGFTISNLAIIWIRQPPGKGLEWIGDIDGRGDIYCA
TWAKSRLTISTSKNQFSLRLTSVTAADTAMYYCAVDGDGSGWGDFNFWGQGTLV
SVSS (SEQ ID NO: 111)

>cl|YIBBABABA|7|117 >8_4_HC_humanized 1133 >8_4_HC_humanized 881
>8_4_HC_humanized 677 >8_4_HC_humanized 192 >8_4_HC_humanized 65
QSVEESGGGVVQPGRSLRLSCAASGFTISNLAIIWVRQAPGKGLEWVADIDGRGDIY
CATWAKGRFTISRDNSTLYLQMNSLRAEDTAVYYCARDGDGSGWGDFNFWGQGT
TVTVSS (SEQ ID NO: 112)

>cl|FOBBABABA|1|117 >8_4_HC_humanized 882
QSVEESGGGLVQPGGSLRLSCAASGFTISNLAIIWVRQPPGKGLEWVGDIDGRGDIY
CATWAKGRFTISRSKSTVYLQMNSLKTEDTAVYYCTADGDGSGWGDFNFWGQG
MLVTVSS (SEQ ID NO: 113)

>cl|GOBBABABA|1|117 >8_4_HC_humanized 660
QSVEESGGGLIQPGGSLRLSCAASGFTISNLAIIWVRQAPGKGLECVSDIDGRGDIYC
ATWAKGRFTISRDNSTLYLQMTSLRAEDTAVYYCALDGDGSGWGDFNFWGQGTL
VTVSS (SEQ ID NO: 114)

>cl1HOBBABABA|2|117 >8_4_HC_humanized 1051 >8_4_HC_humanized 1050
VQLVESGGGLVKPGGSLRLSCAASGFTISNLAIIWVRQAPGKGLEWVGDIDGRGDI
YCATWAKGRFTISRSKNTLYLQMNSLKTEDTAVYYCTVDGDGSGWGDFNFWGQG
TLVTVSS (SEQ ID NO: 115)

>cl|MOBBABABA|1|117 >8_4_HC_humanized 809
VQLVESGGGLVQPGGSLRLSCAASGFTISNLAIIWVRQAPGKGLEWLSDIDGRGDIY
CATWARGRFAISNARNSLYLQMNSLRDEDTAVYFCARDGDGSGWGDFNFWGQGT
LVTVSS (SEQ ID NO: 116)

>cl|VOBBABABA|1|117 >8_4_HC_humanized 273
VQLVQSGGGLVQPGGSLRLSC AASGFTISNLAIIWVRQASGKGLEWIGDIDGRGDIY
CATWAKGRFTVSRSQNSVFLQMNSLETEDTAVYYCARDGDGSGWGDFNFWGQG
TLVTVSS (SEQ ID NO: 117)

>cl|WOBBABABA|1|117 >8_4_HC_humanized 716
QSVLESGGGWVQPGRSLRLSCSASGFTISNLAIIWVRQAPGKGLEWVSDIDGRGDIY
CATWAKGRFTISRDNNSLYLQMNSLRPEDTALYYCAKDGDGSGWGDFNFWGQGV
LVTVSS (SEQ ID NO: 118)

>cl|ZOBBABABA|1|117 >8_4_HC_humanized 202
VQLQESGEGLVQPGGSLRLSCAASGFTISNLAIIWVRQAPGKGLEYVSDIDGRGDIY
CATWAKGRFTISRDNSTLYLQMGSLRAEDMAVYYCAVDGDGSGWGDFNFWGQG
TMVTVSS (SEQ ID NO: 119)

TABLE 3 -continued 8-4 VH humanized sequences-IMGT-LigM DB (Abysis) clustered at 95%
(47 sequences)

>cl|GUBBABABA|1|117 >8_4_HC_humanized 54
VQLVESGGGLVQPGGSLRLSCATSGFTISNLAIIWVRQPPGKGLEWVSDIDGRGDIY
CATWAKGRFTISRENATLYLQMNSLRAEDTAVYYCAVDGDGSGWGDFNFWGQG
TLVTVSS (SEQ ID NO: 120)

>cl|HUBBABABA|1|117 >8_4_HC_humanized 21
VQLVESGGGLVQPGGSLRLSCAASGFTISNLAIIWVRQAPGKGLEFVSDIDGRGDIY
CATWAKDRFTISRDNSTVYLQMDSLRTEDTAMYFCARDGDGSGWGDFNFWGQGT
LVTVSS (SEQ ID NO: 121)

>cl|KUBBABABA|1|117 >8_4_HC_humanized 788
QSVLESGGGLVQPGGSLRLSCAASGFTISNLAIIWVRQAPGKGLEWVSDIDGRGDIY
CATWAKGRFTISRDNSTLFLQISSLRAEDTAVYYCAKDGDGSGWGDFNFWGPGTL
VTVSS (SEQ ID NO: 122)

>cl|MUBBABABA|1|117 >8_4_HC_humanized 762
VKLLESGGGLVQPGGSLRLSCAASGFTISNLAIIWVRQAPGKGLEWVADIDGRGDIY
CATWAKGRFTISRDNSTLYLQMNSLGAEDTAVYYCARDGDGSGWGDFNFWGQGT
LVTVSS (SEQ ID NO: 123)

>cl|PUBBABABA|1|117 >8_4_HC_humanized 173
QSVEESGGRLVTPGGSLRLSCTATGFTISNLAIIWFRQAPGKGLEWVGDIDGRGDIY
CATWAKGRFTISRDDNSLYLQMNSLKTEDTAVYYCARDGDGSGWGDFNFWGQGT
LVTVSS (SEQ ID NO: 124)

>cl1RUBBABABA|1|117 >8_4_HC_humanized 224
QSVEESGGGLVKPGGSLRLSCAASGFTISNLAIIWVRQAPGKGLEWVGDIDGRGDIY
CATWAKGRFTISRSKNTLYLQMNSLKTEDTAVYYCATDGDGSGWGDFNFWGQGT
LVTVSS (SEQ ID NO: 125)

>cl|VUBBABABA|1|117 >8_4_HC_humanized 672
QSVVESGGGLIQPGGSLRLSCAASGFTISNLAIIWVRQAPGKGLEWVSDIDGRGDIY
CATWAKGRFTISRDNSTLYLQMNSLRAEDTAVYYCALDGDGSGWGDFNFWGQGT
LVTVSS (SEQ ID NO: 126)

>cl|XUBBABABA|1|117 >8_4_HC_humanized 267
QSVEQSGGGLVQPGESLRLSCAGSGFTISNLAIIWVRQAPGKGLEWVADIDGRGDIY
CATWAKGRFTISRDNASLFLQMNSLRVEDTAVYYCARDGDGSGWGDFNFWGQGT
LVTVSS (SEQ ID NO: 127)

>cl|YUBBABABA|1|117 >8_4_HC_humanized 23
QSVLESGGDLVQPGGSLRLSCEASGFTISNLAIIWVRQAPGKGLEWVSDIDGRGDIY
CATWAKGRFTISKSKHTLFLQMHSLRVEDTAVYYCAKDGDGSGWGDFNFWGQGT
TVTVSS (SEQ ID NO: 128)

>cl|ZUBBABABA|1|117 >8_4_HC_humanized 657
QSVEESGGRLVTPGGSLRLSCAASGFTISNLAIIWVRQAPGKGLEWVSDIDGRGDIY
CATWAKGRFTISRDNSSLYLQMNSLRTEDSALYYCAIDGDGSGWGDFNFWGQGSL
VTVSS (SEQ ID NO: 129)

>cl|BACBABABA|1|117 >8_4_HC_humanized 879
QSVEESGGGLVQPGGSLRLSCTASGFTISNLAIIWVRQAPGKGLEWVSDIDGRGDIY
CATWAKGRFTISRDSSTLYLQMNNLRVEDTALYYCAHDGDGSGWGDFNFWGRGT
QVTVSS (SEQ ID NO: 130)

8-4 LC humanized sequences-IMGT-LigM DB (Abysis) clustered at 95%
(99 sequences).

>cl|CACBABABA|1|110 >8_4_LC_humanized 866
DIQMTQSPSSLSASVGDRVTITCQASQSISTALAWYQQKPGKAPKRLIYRASTLASG
VPSRFSGSGSGTEFTLTISSLQPEDFATYYCQQGWSTVNVDNVFGQGTKVEIK (SEQ
ID NO: 131)

>cl|DACBABABA|1|110 >8_4_LC_humanized 340
DIQMTQSPFSLSASVGDRVTITCQASQSISTALAWYQQKPGKAPKLLIYRASTLASG
VPSRFSGSGSGTDFTLTISSLQPEDFATYFCQQGWSTVNVDNVFGGGTKLEIK (SEQ
ID NO: 132)

>cl1FACBABABA|1|110 >8_4_LC_humanized 336
DIQLTQSPSSLSASVGDRVTITCQASQSISTALAWYQQKPGKAPKLLIYRASTLASGV
PSRFSGSGSGTDFTLTISSLQPEDFATYYCQQGWSTVNVDNVFGQGTKLEIK (SEQ
ID NO: 133)

8-4 LC humanized sequences-IMGT-LigM DB (Abysis) clustered at 95%
(99 sequences).

```
>cl|GACBABABA|1|110 >8_4_LC_humanized 332
DIQMTQSPSSLSASVGDRVTITCQASQSISTALAWYQQKPGKAPKLLVYRASTLASG
VPSRFSGSGSGTDFTLTISSLQPEDFATYYCQQGWSTVNVDNVFGQGTKVEIK (SEQ
ID NO: 134)

>cl|HACBABABA|1|110 >8_4_LC_humanized 322
DIQLTQSPSFLSASVGDTVSITCQASQSISTALAWYQQKPGKAPKHLIYRASTLASGV
PSRFSGGGSGTDFTLTISSLQPEDFATYYCQQGWSTVNVDNVFGGGTKVEIK (SEQ
ID NO: 135)

>cl|KACBABABA|1|110 >8_4_LC_humanized 315
DIQLTQSPSSLSASVGDRVTITCQASQSISTALAWYQQKPGKAPKLLIYRASTLASGV
PSRFSGSGSGTGFTLTISSLQPEDFATYYCQQGWSTVNVDNVFGGGTKVEIK (SEQ
ID NO: 136)

>cl|LACBABABA|1|110 >8_4_LC_humanized 314
DIQMTQSPSSLSASVGDRVTITCQASQSISTALAWYQQKPGKAPNLLIYRASTLASG
VPSRFSGSGSGTDFTLTISSLQPEDFATYYCQQGWSTVNVDNVFGQGTKVEIK (SEQ
ID NO: 137)

>cl|MACBABABA|1|110 >8_4_LC_humanized 305
DIQLTQSPSSLSASVGDRVTITCQASQSISTALAWFQQKPGKAPKSLIYRASTLASGV
PSRFSGSGSGTDFTLTISSLQPEDSATYYCQQGWSTVNVDNVFGGGTKVEIK (SEQ
ID NO: 138)

>cl|NACBABABA|1|110 >8_4_LC_humanized 303
DIQMTQSPSSLSASVGDRVTITCQASQSISTALAWYQQKPGKAPKLLIYRASTLASG
VPSRFSGSGSGTDFTFTISSLQPEDIATYYCQQGWSTVNVDNVFGPGTKVDIK (SEQ
ID NO: 139)

>cl|PACBABABA|1|110 >8_4_LC_humanized 296
DIQMTQSPSSLSASVGDRVTITCQASQSISTALAWYQQKPGKAPKLLIYRASTLASG
VPSTFSGSGSGTDFTLTISSLQPEDFATYYCQQGWSTVNVDNVFGQGTKVEIK (SEQ
ID NO: 140)

>cl|QACBABABA|1|110 >8_4_LC_humanized 294
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGGGTKVEIK (SEQ
ID NO: 141)

>cl|RACBABABA|1|110 >8_4_LC_humanized 291
DIQLTQSPSSLSASVGDRVTITCQASQSISTALAWYQQKPGKGPKLLIYRASTLASGV
PSRFSGSGSGTDFSLTISSLQPEDLATYYCQQGWSTVNVDNVFGGGTKVEIK (SEQ
ID NO: 142)

>cl|SACBABABA|1|110 >8_4_LC_humanized 284
DIQMTQSPSSLSASVGDRVTITCQASQSISTALAWYQQKPGKAPKSLIYRASTLASG
VPSKFSGSGSGTEFTLTISSLQPDDFATYYCQQGWSTVNVDNVFGQGTRLEIK (SEQ
ID NO: 143)

>cl|TACBABABA|1|110 >8_4_LC_humanized 217
DIVMTQSPDSLAVSLGERATINCQASQSISTALAWYQQKPGQPPKWYRASTLASG
VPDRFSGSGSGTDFTLTISSLQAEDVAVYYCQQGWSTVNVDNVFGQGTKVEIK
(SEQ ID NO: 144)

>cl|VACBABABA|1|110 >8_4_LC_humanized 197
AYDMTQTPATLSLSPGERATLSCQASQSISTALAWYQQKPGQAPRLLIYRASTLASG
IPARFSGSGSGTDFTLTISSLEPEDFAVYYCQQGWSTVNVDNVFGQGTEVVVR (SEQ
ID NO: 145)

>cl|WACBABABA|1|110 >8_4_LC_humanized 169
EIVLTQSPSFLSAFVGDRITITCQASQSISTALAWYQQKPGKAPKLLIYRASTLASGV
PSRFSGSGSGTEFTLTISGLQPEDFASYYCQQGWSTVNVDNVFGGGTKLEIK (SEQ
ID NO: 146)

>cl|XACBABABA|1|110 >8_4_LC_humanized 122
DVVMTQSPASLSASVGDRVTIICQASQSISTALAWYQQKPGKAPKWYRASTLASG
VPSRFSGSGSRTDFTFTISSLQPEDIATYYCQQGWSTVNVDNVFGPGTKVDIK (SEQ
ID NO: 147)

>cl|YACBABABA|1|110 >8_4_LC_humanized 44
DIQMTQSPSSLSASVGDRVTITCQASQSISTALAWYQQKPGKAPKRLIYRASTLASG
VPSRFSGSGSGTEFTLTISSLQPEDFATYYCQQGWSTVNVDNVFGQGTKVEIK (SEQ
ID NO: 148)
```

8-4 LC humanized sequences-IMGT-LigM DB (Abysis) clustered at 95% (99 sequences).

>cl|ZACBABABA|1|110 >8_4_LC_humanized 17
DIQLTQSPSSLSAAVGDRVTIACQASQSISTALAWYQQKPGKAPKLLIYRASTLASG
VPSRFSGSGSGTDFTLSISSLQPGDFATYYCQQGWSTVNVDNVFGGGTKVQMK
(SEQ ID NO: 149)

>cl|BECBABABA|1|110 >8_4_LC_humanized 13
DIQMTQSPSSLSASVGDSVTITCQASQSISTALAWYQQKPGKAPKLLIYRASTLASG
VPSRFSGSGSGTEFTLTINGLQPEDFATYYCQQGWSTVNVDNVFGGGTKLEIK (SEQ
ID NO: 150)

>cl|CECBABABA|1|110 >8_4_LC_humanized 791
AYELTQTPLSSPVTLGQPASISCQASQSISTALAWLHQRPGQPPRLLIYRASTLASGV
PDRFSGSGAGTAFTLKISRVEVEDVGIYYCQQGWSTVNVDNVFGQGTKVEIK (SEQ
ID NO: 151)

>cl|DECBABABA|1|110 >8_4_LC_humanized 673
AYDMTQTPASVEVSPGERATLSCQASQSISTALAWYQHKPGQAPRLLIYRASTLAS
GIPARFSGSGSGTEFTLTISSVQSDDFAVYYCQQGWSTVNVDNVFGPGTKVDIK
(SEQ ID NO: 152)

>cl|FECBABABA|1|110 >8_4_LC_humanized 678
AYELTQSPSSLSASVGDRVTITCQASQSISTALAWFQQKPGKAPKLLIYRASTLASG
VPSRFSGSGSGTDFTLTISSLLPTDFATYFCQQGWSTVNVDNVFGQGTQVEVK (SEQ
ID NO: 153)

>cl|GECBABABA|1|110 >8_4_LC_humanized 631
AYDMTQTPASVEVSVGDRVTITCQASQSISTALAWYQQKPGKAPKLLIYRASTLAS
GVPSRFGGSGSGTDFTLTISSLQPEDFATYYCQQGWSTVNVDNVFGGGTKVEIK
(SEQ ID NO: 154)

>cl|HECBABABA|1|110 >8_4_LC_humanized 1002
AYELTQSPSSLSASVGDRVTITCQASQSISTALAWYQQKPGKAPKLLIYRASTLASG
VSSRFSGSGSGTDFTLTISSLQPEDFATYYCQQGWSTVNVDNVFGQGTKLEIK (SEQ
ID NO: 155)

>cl|KECBABABA|1|110 >8_4_LC_humanized 775
AYELTQTPLSSPVTLGQPASISCQASQSISTALAWLQQRPGQPPRLLIYRASTLASGV
PDRFSGSGARTDFTLNISRVEAEDAGVYYCQQGWSTVNVDNVFGQGTKLEIK (SEQ
ID NO: 156)

>cl|LECBABABA|21110 >8_4_LC_humanized 771 >8_4_LC_humanized 772
AYELTQSPATLSLSPGERATLSCQASQSISTALAWYQQKPGQAPRLLIHRASTLASGI
PARFSGSGSGTDFTLTISSLEPEDFAVYYCQQGWSTVNVDNVFGGGTRVEIK (SEQ
ID NO: 157)

>cl|MECBABABA|1|110 >8_4_LC_humanized 676
AYDMTQSPATLSLSPGERATLSCQASQSISTALAWYQQKPGQAPRLLIYRASTLASG
IPARFSGSGSGTDFTLTISSLEPEDFAVYYCQQGWSTVNVDNVFGGGTKVEIK (SEQ
ID NO: 158)

>cl|NECBABABA|1|110 >8_4_LC_humanized 188
DIQLTQSPSTLSASVGDRITITCQASQSISTALAWYQQKPGKAPKLLIYRASTLASGV
PPRFSGSGSGTEFTLTISSLQPDDFATYYCQQGWSTVNVDNVFGQGTKVVVR (SEQ
ID NO: 159)

>cl|PECBABABA|1|110 >8_4_LC_humanized 186
DIQLTQSPSTLSASVGDRVTITCQASQSISTALAWYQQKPGKAPKLLIYRASTLASG
VP SRF SGSGSGTEFTLTISSLQPDDFATYYCQQGWSTVNVDNVFGQGTKVVVR
(SEQ ID NO: 160)

>cl|QECBABABA|1|110 >8_4_LC_humanized 717
ELVMTQSPSSLSASVGDRVTITCQASQSISTALAWYQQKPGKAPNLLIYRASTLASG
IPSRFSGSGSGTYFTLTINGLQPEDFATYYCQQGWSTVNVDNVEGGGTKVDIK (SEQ
ID NO: 161)

>cl|RECBABABA|1|110 >8_4_LC_humanized 1048
SYELTQTPPSVSVSPGQTARITCQASQSISTALAWYQQKPGQAPKVLIYRASTLASGI
PERFSGSSSGTTVTLTISGVQAEDEADYYCQQGWSTVNVDNVFGGGTKLTVL (SEQ
ID NO: 162)

>cl|SECBABABA|1|110 >8_4_LC_humanized 849
AYELTQSPLSLSVTPGQPASISCQASQSISTALAWYLQKPGQPPQLLIYRASTLASGV
PDRFSGSGSGTDFTLKISRVEAEDVGVYYCQQGWSTVNVDNVEGQGTKVEIK (SEQ
ID NO: 163)

8-4 LC humanized sequences-IMGT-LigM DB (Abysis) clustered at 95% (99 sequences).

>cl|TECBABABA|1|110 >8_4_LC_humanized 1016
DIELTQSPSSLSASIGDRVSITCQASQSISTALAWYQQKPGKAPKLLIYRASTLASGVP
SRFSGSGSGTDFTLTISSLQPEDFATFYCQQGWSTVNVDNVEGGGTRVEIK (SEQ ID
NO: 164)

>cl|VECBABABA|1|110 >8_4_LC_humanized 978
EIVLTQSPSSLSASVGDRVTITCQASQSISTALAWYQQKPGKAPKLLIYRASTLASGV
PSRFSGSGSGTDFTLTISNLQPEDFATYYCQQGWSTVNVDNVEGGGTKVEIK (SEQ
ID NO: 165)

>cl|WECBABABA|1|110 >8_4_LC_humanized 893
DIEMTQSPSSLSASVGDRVTITCQASQSISTALAWYQQKPGKAPKRLIQRASTLASG
VPSRFSGSGSGTEFTLTISSLQPEDFATYHCQQGWSTVNVDNVEGGGTKVEIK (SEQ
ID NO: 166)

>cl|XECBABABA|1|110 >8_4_LC_humanized 868
DIVMTQSPDSLAVSLGERATINCQASQSISTALAWYQQKPGQPPKLLIYRASTLASG
VPDRFSGSGSGTDFTLTISSLQAEDVAVYYCQQGWSTVNVDNVFGQGTKLEIK
(SEQ ID NO: 167)

>cl|YECBABABA|1|110 >8_4_LC_humanized 862
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVEGQGTKVEIK (SEQ
ID NO: 168)

>cl|ZECBABABA|1|110 >8_4_LC_humanized 715
DIQMTQSPSSLSASVGDRVTITCQASQSISTALAWYQQKPGKAPKFLIYRASTLASG
VPSRFSGSGSGTDFTLTISSLQPEDFATYYCQQGWSTVNVDNVFGQGTKVEIK (SEQ
ID NO: 169)

>cl|BICBABABA|1|110 >8_4_LC_humanized 706
DIQMTQYPSSLSASVGDRVTIACQASQSISTALAWYQQKPGKPPKLLIYRASTLASG
VPSRFSGSGSGTDFTLTISCLQPEDVATYYCQQGWSTVNVDNVFGQGTRVEFK
(SEQ ID NO: 170)

>cl|CICBABABA|1|110 >8_4_LC_humanized 703
DIVMTQSPDSLAVSLGERATINCQASQSISTALAWYQQKAGQPPKWYRASTLASG
VPDRFSGSGSGTDFTLTISSLQAEDVAVYYCQQGWSTVNVDNVFGGGTKVEIK
(SEQ ID NO: 171)

>cl|DICBABABA|1|110 >8_4_LC_humanized 635
DIQMTQSPSSLSASVGDRVTITCQASQSISTALAWYQQKPGKVPKLLIYRASTLASG
VPSRFSGSGSGTDFTLTISSLQPEDVATYYCQQGWSTVNVDNVFGQGTKLEIK (SEQ
ID NO: 172)

>cl|FICBABABA|1|110 >8_4_LC_humanized 341
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGGGTKLEIK (SEQ
ID NO: 173)

>cl|GICBABABA|1|110 >8_4_LC_humanized 328
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGRGTKVEIK (SEQ
ID NO: 174)

>cl|HICBABABA|1|110 >8_4_LC_humanized 324
DIQMTQSPSSLSASVGDRVTITCQASQSISTALAWYQQKPGNAPKSLIYRASTLASG
VPSKFSGSGSGTDFTLTISSLQPEDFATYYCQQGWSTVNVDNVFGGGTKVEIK (SEQ
ID NO: 175)

>cl|KICBABABA|1|110 >8_4_LC_humanized 301
DIQMTQSPDSLAVSLGERATINCQASQSISTALAWYQQKPGQPPKLLIYRASTLASG
VPDRFSGSGSGTDFTLTISSLQAEDVAVYYCQQGWSTVNVDNVFGQGTKLEIK
(SEQ ID NO: 176)

>cl|LICBABABA|1|110 >8_4_LC_humanized 295
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGQGTRLEIK (SEQ
ID NO: 177)

>cl|MICBABABA|1|110 >8_4_LC_humanized 292
DIQMTQSPSSLSASVGDRVTITCQASQSISTALAWYQQKPGKAPNLLIYRASTLASG
VPSRFSGSVSGTDFTLTISSLQPEDFATYYCQQGWSTVNVDNVFGGGTKVEIK (SEQ
ID NO: 178)

8-4 LC humanized sequences-IMGT-LigM DB (Abysis) clustered at 95% (99 sequences).

>cl|NICBABABA|1|110 >8_4_LC_humanized 283
DIQLTQSPSSVSASVGDRVTITCQASQSISTALAWYQQKPGKAPKLLIYRASTLASG
VPSRFSGSGSGTDFTLTISSLQPEDFATYYCQQGWSTVNVDNVFGQGTRLEIK (SEQ
ID NO: 179)

>cl|PICBABABA|1|110 >8_4_LC_humanized 282
DIQMTQSPSSVSASVGDRVTITCQASQSISTALAWYQQKLGKAPKLLIYRASTLASG
VPSRFSGSGSGTDFTLTISSLQPEDFATYYCQQGWSTVNVDNVFGGGTKVEIK (SEQ
ID NO: 180)

>cl|QICBABABA|1|110 >8_4_LC_humanized 278
ELVLTQSPSSLSASVGDRVTITCQASQSISTALAWCQQKPGKSPTLLIYRASTLASGV
PSRFSGSGSGTGFTLTISGLQPEDFATYYCQQGWSTVNVDNVFGGGTKVEIR (SEQ
ID NO: 181)

>cl|RICBABABA|1|110 >8_4_LC_humanized 204
DIQLTQSPSSLSASVGDRVTITCQASQSISTALAWYQQKPGKAPKLLIYRASTLASGV
PSRFSGSGSGTDFTLTISSLQPEDFATYYCQQGWSTVNVDNVFGQGTKVEIK (SEQ
ID NO: 182)

>cl|SICBABABA|1|110 >8_4_LC_humanized 201
DIRVTQSPSSLSASVGDRVTITCQASQSISTALAWYQQKPGKAPKWYRASTLASG
VPSRFSGSGSGTDFTFTISSLQPEDIATYYCQQGWSTVNVDNVFGGGTKVDIK (SEQ
ID NO: 183)

>cl|TICBABABA|1|110 >8_4_LC_humanized 129
EIVMTQSPSSLSASVGDRVTITCQASQSISTALAWYQHKPGKAPRLLIYRASTLASG
VPSRFSGSGSGTDFTLTISSLQPDDFATYYCQQGWSTVNVDNVFGQGTKVEVK
(SEQ ID NO: 184)

>cl|VICBABABA|1|110 >8_4_LC_humanized 108
DVVMTQSPSSVSASVGDRVTITCQASQSISTALAWYQQKPGKAPKLLIYRASTLAS
GVPSRFSGSGSGTDFTLTITSLQPEDFATYYCQQGWSTVNVDNVFGGGTKVEIK
(SEQ ID NO: 185)

>cl|WICBABABA|1|110 >8_4_LC_humanized 57
DIQMTQSPSSLSASVGDRVTITCQASQSISTALAWYQQKPGKAPKRLIYRASTLASG
VPSRFSGSGSGTEFTLTISSLQPEDFATYYCQQGWSTVNVDNVFGQGTRLEIK (SEQ
ID NO: 186)

>cl|XICBABABA|1|110 >8_4_LC_humanized 800
AYELTQPPSLSVTPGQPASISCQASQSISTALAWYLQKPGQPPQLLIYRASTLASGV
PDRFSGSGSGTDFTLKISRVEAEDVGVYYCQQGWSTVNVDNVFGQGTKVEIK (SEQ
ID NO: 187)

>cl|YICBABABA|1|110 >8_4_LC_humanized 1133
AYDMTQPPSVSVSPGQTASITCQASQSISTALAWYQQKPGQSPVLVIYRASTLASG
IPERF SGSNSGNTATL TISGT QAMDEAD YYCQQGWSTVNVDNVFGTGTEVVVR
(SEQ ID NO: 188)

>cl|ZICBABABA|1|110 >8_4_LC_humanized 621
AYELTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGQGTKVEIK (SEQ
ID NO: 189)

>cl|COCBABABA|1|110 >8_4_LC_humanized 881
AYDMTQSPSSLSASVGDRVTITCQASQSISTALAWYQQKPGKAPNLLIYRASTLASG
VPSRFSGSGSGTDFTLTISSLQPEDFATYYCQQGWSTVNVDNVFGGGTKVQIK (SEQ
ID NO: 190)

>cl|DOCBABABA|1|110 >8_4_LC_humanized 55
AYDMTQTPASVEVSPGERATLSCQASQSISTALAWYQQKPGQAPRLLIYRASTLAS
GIPARFSGSGSGTEFTLTISSLQSEDFAVYYCQQGWSTVNVDNVFGQGTEVVVR
(SEQ ID NO: 191)

>cl|FOCBABABA|1|110 >8_4_LC_humanized 882
AYDMTQSPSSLSASVGDRVTITCQASQSISTALAWYQQKPGKAPKLLIYRASTLASG
VPSRFSGSGFGTDFTFTISSLQPEDSATYYCQQGWSTVNVDNVFGQGTKLEIK (SEQ
ID NO: 192)

>cl|GOCBABABA|1|110 >8_4_LC_humanized 660
AYVMTQSPATLSLSPGERATLSCQASQSISTALAWYQQRPGQAPRLLIYRASTLASG
IPARFSGSGSGTDFTLTISSLEPEDFAVYYCQQGWSTVNVDNVFGGGTKVEIK (SEQ
ID NO: 193)

8-4 LC humanized sequences-IMGT-LigM DB (Abysis) clustered at 95%
(99 sequences).

>cl|HOCBABABA|1|110 >8_4_LC_humanized 1051
SYELTQTPPSVSVSPGQTARITCQASQSISTALAWYQQKPGQAPVLVIYRASTLASGI
PERF SGSSSGT TVTLTISGVQAEDEAD YYCQQGWSTVNVDNVFGTGTKVTVL (SEQ
ID NO: 194)

>cl|KOCBABABA|1|110 >8_4_LC_humanized 1050
SYELTQTPPSVSVSPGQTARITCQASQSISTALAWYQQKPGQAPVLVIYRASTLASGI
PERFSGSSSGTTVTLTISGVQAEDEADYYCQQGWSTVNVDNVFGTGTKVTVL (SEQ
ID NO: 195)

>cl|LOCBABABA|1|110 >8_4_LC_humanized 860
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGGGTKVEIK (SEQ
ID NO: 196)

>cl|MOCBABABA|1|110 >8_4_LC_humanized 809
DIQMTQSPSSVSASVRDRVTITCQASQSISTALAWYQQKPGKAPKLLIYRASTLASG
VPSRFSGSGSGTDFTLTISSLQPEDFATYYCQQGWSTVNVDNVFGPGTKVDIK (SEQ
ID NO: 197)

>cl|NOCBABABA|1|110 >8_4_LC_humanized 346
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGQGTKVEIK (SEQ
ID NO: 198)

>cl|POCBABABA|1|110 >8_4_LC_humanized 345
DIQMTQSPSSLSASVGDRVTITCQASQSISTALAWYQQKPGKAPKLLIYRASTLASG
VP SRF SGSGSGTDF TF TIS SLQPDDFATYYCQQGWSTVNVDNVFGGGTKVEIK (SEQ
ID NO: 199)

>cl|QOCBABABA|1|110 >8_4_LC_humanized 334
DIQMTQSPSFVSASVGDRVTITCQASQSISTALAWYQQKPGKAPKLLIYRASTLASG
VPSRFSGSGSGTDFTLTISSLQPEDFATYYCQQGWSTVNVDNVFGGGTKVEIK (SEQ
ID NO: 200)

>cl|ROCBABABA|1|110 >8_4_LC_humanized 319
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGQGTKVEIK (SEQ
ID NO: 201)

>cl|SOCBABABA|1|110 >8_4_LC_humanized 308
DIQMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGGGTKVEIK (SEQ
ID NO: 202)

>cl|TOCBABABA|1|110 >8_4_LC_humanized 281
DIQLTQSPSSVSASVGDRVTITCQASQSISTALAWYQQKPGKAPKLLIYRASTLASG
VPSRFSGSGSGTDFTLTISSLQPEDFATYYCQQGWSTVNVDNVFGGGTKVDIK (SEQ
ID NO: 203)

>cl|VOCBABABA|1|110 >8_4_LC_humanized 273
ELVMTQSPSSLSASVGDRVTITCQASQSISTALAWYQQKPGEAPKLLIYRASTLASG
VPSRFSGSGSGTDFTLTISGLQSEDFATYYCQQGWSTVNVDNVFGQGTKVEIK (SEQ
ID NO: 204)

>cl|WOCBABABA|1|110 >8_4_LC_humanized 716
ELVMTQSPSSLSASEGDRVTITCQASQSISTALAWYQQKPGRAPKLLIHRASTLASG
VPSRFSGSGSGTEFTLTISGLQSEDFATYYCQQGWSTVNVDNVFGGGTTVDVK
(SEQ ID NO: 205)

>cl|XOCBABABA|1|110 >8_4_LC_humanized 677
AYDMTQSPSFLSASVGDRVTITCQASQSISTALAWYQQKPGKAPKLLIYRASTLASG
VPSRFSGSGSGTEFTLTISSLQPEDFATYYCQQGWSTVNVDNVFGQGTRLEIK (SEQ
ID NO: 206)

>cl|YOCBABABA|1|110 >8_4_LC_humanized 192
AYDMTQSPSSLSASVGDRVTITCQASQSISTALAWYQQKPGKAPKLLIYRASTLASG
VPSRFSGSGSGTDFTLTISSLQAEDFTTYYCQQGWSTVNVDNVFGQGTKVEFK
(SEQ ID NO: 207)

>cl|ZOCBABABA|1|110 >8_4_LC_humanized 202
DIRMTQSPSSLSASVGDRVTITCQASQSISTALAWYQQKPGKVPKWYRASTLASG
VPSRFSGSGSGTDFTLTISSLQPEDVATYYCQQGWSTVNVDNVFGPGTKVVVR
(SEQ ID NO: 208)

| 8-4 LC humanized sequences-IMGT-LigM DB (Abysis) clustered at 95% (99 sequences). |
|---|

>cl|BUCBABABA|1|110 >8_4_LC_humanized 802
AIRMTQSPSSFSASTGDRVTITCQASQSISTALAWYQQKPGKAPKLLIYRASTLASG
VPSRFSGSGSGTDFTLTISCLQSEDFATYYCQQGWSTVNVDNVFGGGTKVEIK (SEQ
ID NO: 209)

>cl|CUCBABABA|1|110 >8_4_LC_humanized 347
DIQMTQSPSSLSASVGDRVSITCQASQSISTALAWYQQKPGKAPKRLIYRASTLASG
VPSRFSGSGSGTEFTLTISSLQPDDFATYYCQQGWSTVNVDNVFGGGTKVEIK (SEQ
ID NO: 210)

>cl|DUCBABABA|1|110 >8_4_LC_humanized 339
DIQLTQSPSSLSASVGDRVTITCQASQSISTALAWYQQKPGKAPKLLIYRASTLASGV
PSRFSGSGSGTEFTLTISSLQPDDFATYYCQQGWSTVNVDNVFGGGTKVEIK (SEQ
ID NO: 211)

>cl|FUCBABABA|1|110 >8_4_LC_humanized 168
DIVMTQSPSTLSASVGDRVTITCQASQSISTALAWYQQKPGKAPKLLIYRASTLASG
VPSRFSGSGSGTEFTLTISGLQPEDFATYYCQQGWSTVNVDNVFGGGTKLEIK (SEQ
ID NO: 212)

>cl|GUCBABABA|1|110 >8_4_LC_humanized 54
AYGMTQSPDSLAVSLGERASINCQASQSISTALAWYQQKPGQPPKWYRASTLASG
VPDRFSGGGSGTDFTLTISSLQAEDVAVYYCQQGWSTVNVDNVFGGGTKVEIK
(SEQ ID NO: 213)

>cl|flUCBABABA|1|110 >8_4_LC_humanized 21
DIQMTQSPSSLSASVGDRVTITCQASQSISTALAWYQQKPGKAPKVLIYRASTLASG
VPSRFSGSGSGTDFTLTISSLQPEDFATYYCQQGWSTVNVDNVFGPGTKVEVR (SEQ
ID NO: 214)

>cl|KUCBABABA|1|110 >8_4_LC_humanized 788
AYELTQTPLSSPVTLGQPASISCQASQSISTALAWLQQRPGQPPRLLIYRASTLASGV
PDRFSGSGAGTDFTLKISRVEAEDVGIYYCQQGWSTVNVDNVFGQGTKVEIK (SEQ
ID NO: 215)

>cl|LUCBABABA|1|110 >8_4_LC_humanized 675
AYDMTQSPSSLSASVGDRVTITCQASQSISTALAWYQQKPGKAPKLLIYRASTLASG
VPSRFSGSGSGTEFTLTITSLQPEDFATYYCQQGWSTVNVDNVFGPGTKLEIK (SEQ
ID NO: 216)

>cl|MUCBABABA|1|110 >8_4_LC_humanized 762
AYELTQSPDSLAVSLGERATINCQASQSISTALAWYQQKPGQPPKWYRASTLASG
VPDRFSGSGSGTDFTLTISSLQAEDVAVYYCQQGWSTVNVDNVFGGGTKVEIK
(SEQ ID NO: 217)

>cl|NUCBABABA|1|110 >8_4_LC_humanized 818
AYDMTQTPSSVSASVGDRVTITCQASQSISTALAWYQQKPGKAPKLLIYRASTLAS
GVPSRFSGSGSGTDFTLTISSLQPEDFATYYCQQGWSTVNVDNVFGQGTKVEIK
(SEQ ID NO: 218)

>cl|PUCBABABA|1|110 >8_4_LC_humanized 173
AIQMTQSPFSLSASVGDRVTITCQASQSISTALAWFQQKPGKAPKSLIYRASTLASG
VSSKFSGSGSGTDFTLTISSLQPEDFATYYCQQGWSTVNVDNVFGQGTRLVVR
(SEQ ID NO: 219)

>cl|QUCBABABA|1|110 >8_4_LC_humanized 65
DIQMTQSPSTLSASVGDRVTITCQASQSISTALAWYQQKPGKAPKLLIYRASTLASG
VPSRFSGSGSGTEFTLTISSLQPDDFATYYCQQGWSTVNVDNVFGQGTKVEIK (SEQ
ID NO: 220)

>cl|RUCBABABA|1|110 >8_4_LC_humanized 224
AYDMTQTPASVSLSPGERATLSCQASQSISTALAWYQQKPGQAPRLLIYRASTLAS
GIPDRFRGSGSATDFTLTISRLEPEDFAVYYCQQGWSTVNVDNVFGGGTEVVVR
(SEQ ID NO: 221)

>cl|SUCBABABA|1|110 >8_4_LC_humanized 230
AYDMTQTPASVSASVGDRVTITCQASQSISTALAWYQQKPGKAPKVLIYRASTLAS
GVPSRFSGSGSGTDFTLTISTLQPEDFATYYCQQGWSTVNVDNVFGQGTKLEIK
(SEQ ID NO: 222)

>cl|TUCBABABA|1|110 >8_4_LC_humanized 880
AYDMTQSPSSLSASVGDRVNITCQASQSISTALAWYQQKPGKAPKLLIYRASTLAS
GVPSRFSGSGSGTDFTLTISSLQPEDFATYYCQQGWSTVNVDNVFGPGTKVDIK
(SEQ ID NO: 223)

| 8-4 LC humanized sequences-IMGT-LigM DB (Abysis) clustered at 95% (99 sequences). |
|---|

>cl|VUCBABABA|1|110 >8_4_LC_humanized 672
AYDMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGQGTKLEIK (SEQ
ID NO: 224)

>cl|WUCBABABA|1|110 >8_4_LC_humanized 299
DIQMTQSPSSVSASVGDRVTITCQASQSISTALAWYQQKPGKAPKLLIYRASTLASG
VPSRFSGSGSGTEFTLTISSLQPDDFATYYCQQGWSTVNVDNVFGGGTKVEIK (SEQ
ID NO: 225)

>cl|XUCBABABA|1|110 >8_4_LC_humanized 267
AYDMTQSPSTLAASVGDRVTITCQASQSISTALAWYQQKPGKAPKLLIYRASTLAS
GVPSRFSGSGSGTEFTLTISSLQPDDFATYYCQQGWSTVNVDNVFGQGTKVEVK
(SEQ ID NO: 226)

>cl|YUCBABABA|1|110 >8_4_LC_humanized 23
AYELTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGPGTKVDIK (SEQ
ID NO: 227)

>cl|ZUCBABABA|1|110 >8_4_LC_humanized 657
AYDMTQTPASVEVSVGDRVSITCQASQSISTALAWYQQKPGKAPKLLIYRASTLAS
GVPSRFSGSGSGTDFTLTITSLQPVDFATYYCQQGWSTVNVDNVFGPGTTVDAK
(SEQ ID NO: 228)

>cl|BADBABABA|1|110 >8_4_LC_humanized 879
AYDMTQSPSSLSASVGDRVTITCQASQSISTALAWYQQKPGKAPKLLIYRASTLASG
VPSRFSGSGSGTDFTLTISSLQPEDFATYFCQQGWSTVNVDNVFGGGTKVEIK (SEQ
ID NO: 229)

TABLE 5

| 8-4 VH humanized sequences-germline database clustered at 90% (2 sequences) |
|---|

>cl|CABBABABA|15|117 >8_4_HC_humanized_356 >8_4_HC_humanized_340
>8_4_HC_humanized_335 >8_4_HC_humanized_303 >8_4_HC_humanized_287
VQLVESGGGVVQPGGSLRLSCAASGFTISNLAIIWVRQAPGKGLEWVSDIDGRGDI
YCATWAKGRFTISRDNSSLYLQMNSLRAEDTAVYYCARDGDGSGWGDFNFWGPG
TLVTVSS (SEQ ID NO: 230)

>cl|LABBABABA|85|117 >8_4_HC_humanized_2049 >8_4_HC_human-
ized_2033
>8_4_HC_humanized_1360 >8_4_HC_humanized_1344 >8_4_HC_human-
ized_777
VQLVESGGGLVQPGGSLRLSCAASGFTISNLAIIWVRQAPGKGLEWVSDIDGRGDIY
CATWAKGRFTISRDNSTLYLQMNSLRAEDTAVYYCARDGDGSGWGDFNFWGPGT
LVTVSS (SEQ ID NO: 231)

TABLE 6

| 8-4 VL humanized sequences-germline database clustered at 90% (5 sequences). |
|---|

>cl|CACBABABA|76|110 >8_4_LC_humanized_356 >8_4_LC_humanized_340
>8_4_LC_humanized_335 >8_4_LC_humanized_303 >8_4_LC_humanized_287
AYDMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGGGTEVVR
(SEQ ID NO: 232)

>cl|LACBABABA|2|110 >8_4_LC_humanized_2049 >8_4_LC_humanized_2033
AYDMTQSPDSLAVSLGERATINCQASQSISTALAWYQQKPGQPPKWYRASTLASG
VPDRFSGSGSGTDFTLTISSLQAEDVAVYYCQQGWSTVNVDNVFGGGTEVVR
(SEQ ID NO: 233)

>cl|NACBABABA|2|110 >8_4_LC_humanized_1360 >8_4_LC_humanized_1344
AYDMTQTPLSLSVTPGQPASISCQASQSISTALAWYLQKPGQPPQLLIYRASTLASG
VPDRFSGSGSGTDFTLKISRVEAEDVGVYYCQQGWSTVNVDNVFGGGTEVVR
(SEQ ID NO: 234)

TABLE 6 -continued 8-4 VL humanized sequences-germline database clustered at 90%
(5 sequences).

>cl|CECBABABA|5|110 >8_4_LC_humanized_2207 >8_4_LC_humanized_2206
>8_4_LC_humanized_2197 >8_4_LC_humanized_2208 >8_4_LC_humanized_2192
AYDMTQSPAFLSVTPGEKVTITCQASQSISTALAWYQQKPDQAPKLLIKRASTLASG
VPSRFSGSGSGTDFTFTISSLEAEDAATYYCQQGWSTVNVDNVFGGGTEVVVR
(SEQ ID NO: 235)

>cl|DICBABABA|15|110 >8_4_LC_humanized_2263 >8_4_LC_humanized_2262
>8_4_LC_humanized_2258 >8_4_LC_humanized_2257 >8_4_LC_humanized_2256
AYDMTQSPASLAVSPGQRATITCQASQSISTALAWYQQKPGQPPKLLIYRASTLASG
VPARFSGSGSGTDFTLTINPVEANDTANYYCQQGWSTVNVDNVFGGGTEVVVR
(SEQ ID NO: 236)

TABLE 7

8-4 VH humanized sequences-germline database clustered at 95%
(7 sequences)

>cl|CABBABABAI2|117 >8_4_HC_humanized_356 >8_4_HC_humanized_303
VQLVESRGVLVQPGGSLRLSCAASGFTISNLAIIWVRQAPGKGLEWVSDIDGRGDIY
CATWAKGRFTISRDNSTLHLQMNSLRAEDTAVYYCKKDGDGSGWGDFNFWGPGT
LVTVSS (SEQ ID NO: 237)

>cl|DABBABABA|17|117 >8_4_HC_humanized_340 >8_4_HC_humanized_335
>8_4_HC_humanized_287 >8_4_HC_humanized_282 >8_4_HC_humanized_2207
VQLVESGGGLVQPGGSLRLSCAASGFTISNLAIIWVRQAPGKGLEWVSDIDGRGDIY
CATWAKGRFTISRDNASLYLQMNSLRAEDTAVYYCARDGDGSGWGDFNFWGPGT
LVTVSS (SEQ ID NO: 238)

>cl|LABBABABA|37|117 >8_4_HC_humanized_2049 >8_4_HC_humanized_2033
>8_4_HC_humanized_1360 >8_4_HC_humanized_1344 >8_4_HC_humanized_777
VQLVESGGGLVQPGGSLRLSCAASGFTISNLAIIWVRQAPGKGLEWVGDIDGRGDI
YCATWAKGRFTISRSKNTLYLQMNSLKTEDTAVYYCTRDGDGSGWGDFNFWGPG
TLVTVSS (SEQ ID NO: 239)

>cl|DEBBABABA|22|117 >8_4_HC_humanized_2206 >8_4_HC_humanized_988
>8_4_HC_humanized_987 >8_4_HC_humanized_935 >8_4_HC_humanized_934
VQLVESGGGLVQPGGSLRLSCAASGFTISNLAIIWVRQAPGKGLEWVSDIDGRGDIY
CATWAKGRFTISRDNSTLYLQMNSLRAEDTAVYYCARDGDGSGWGDFNFWGPGT
LVTVSS (SEQ ID NO: 240)

>cl|FEBBABABA|16|117 >8_4_HC_humanized_2197 >8_4_HC_humanized_978
>8_4_HC_humanized_925 >8_4_HC_humanized_660 >8_4_HC_humanized_395
VQLLESGGGLVQPGGSLRLSCAASGFTISNLAIIWVRQAPGKGLEWVSDIDGRGDIY
CATWAKGRFTISRDNSTLYLQMNSLRAEDTAVYYCAKDGDGSGWGDFNFWGPGT
LVTVSS (SEQ ID NO: 241)

>cl|HIBBABABA|3|117 >8_4_HC_humanized_2257 >8_4_HC_humanized_349
>8_4_HC_humanized_296
VQLVESGGGLVQPGRSLRLSCTASGFTISNLAIIWFRQAPGKGLEWVGDIDGRGDIY
CATWAKGRFTISRSKSIAYLQMNSLKTEDTAVYYCTRDGDGSGWGDFNFWGPGTL
VTVSS (SEQ ID NO: 242)

>cl|LIBBABABA|3|117 >8_4_HC_humanized_2254 >8_4_HC_humanized_346
>8_4_HC_humanized_293
VQLVESGGVVVQPGGSLRLSCAASGFTISNLAIIWVRQAPGKGLEWVSDIDGRGDI
YCATWAKGRFTISRDNSSLYLQMNSLRTEDTALYYCAKDGDGSGWGDFNFWGPG
TLVTVSS (SEQ ID NO: 243)

TABLE 8

8-4 VL humanized sequences-germline database clustered at 95%
(12 sequences)

>cl|CACBABABA|1|110 >8_4_LC_humanized_356
AYDMTQSPSSVSASVGDRVTITCQASQSISTALAWYQQKPGKAPKLLIYRASTLAS
GVPSRFSGSGSGTDFTLTISSLQPEDFATYYCQQGWSTVNVDNVFGGGTEVVVR
(SEQ ID NO: 244)

>cl|LACBABABA|2|110 >8_4_LC_humanized_2049 >8_4_LC_humanized_2033
AYDMTQSPDSLAVSLGERATINCQASQSISTALAWYQQKPGQPPKWYRASTLASG

TABLE 8 -continued

8-4 VL humanized sequences-germline database clustered at 95% (12 sequences)

VPDRFSGSGSGTDFTLTISSLQAEDVAVYYCQQGWSTVNVDNVFGGGTEVVVR
(SEQ ID NO: 245)

>cl|NACBABABA|2|110 >8_4_LC_humanized_1360 >8_4_LC_humanized_1344
AYDMTQTPLSLSVTPGQPASISCQASQSISTALAWYLQKPGQPPQLLIYRASTLASG
VPDRFSGSGSGTDFTLKISRVEAEDVGVYYCQQGWSTVNVDNVFGGGTEVVVR
(SEQ ID NO: 246)

>cl|QACBABABA|1|110 >8_4_LC_humanized_777
AYDMTQSPSSLSASVGDRVTITCQASQSISTALAWYQQKPGKAPKLLIYRASTLASG
VPSRFSGSGSGTDFTFTISSLQPEDIATYYCQQGWSTVNVDNVFGGGTEVVVR (SEQ
ID NO: 247)

>cl|VACBABABA|1|110 >8_4_LC_humanized_565
AYDMTQSPSSLSASVGDRVTITCQASQSISTALAWYQQKPGKAPKRLIYRASTLASG
VPSRFSGSGSGTEFTLTISSLQPEDFATYYCQQGWSTVNVDNVFGGGTEVVVR
(SEQ ID NO: 248)

>cl|XACBABABA|2|110 >8_4_LC_humanized_247 >8_4_LC_humanized_231
AYDMTQSPSFLSASVGDRVTITCQASQSISTALAWYQQKPGKAPKLLIYRASTLASG
VPSRFSGSGSGTEFTLTISSLQPEDFATYYCQQGWSTVNVDNVFGGGTEVVVR
(SEQ ID NO: 249)

>cl|ZACBABABA|2|110 >8_4_LC_humanized_141 >8_4_LC_humanized_125
AYDMTQSPSSFSASTGDRVTITCQASQSISTALAWYQQKPGKAPKLLIYRASTLASG
VPSRFSGSGSGTDFTLTISCLQSEDFATYYCQQGWSTVNVDNVFGGGTEVVVR
(SEQ ID NO: 250)

>cl|CECBABABA|1|110 >8_4_LC_humanized_2207
AYDMTQSPAFLSVTPGEKVTITCQASQSISTALAWYQQKPDQAPKLLIKRASTLASG
VPSRFSGSGSGTDFTFTISSLEAEDAATYYCQQGWSTVNVDNVFGGGTEVVVR
(SEQ ID NO: 251)

>cl|GECBABABA|1|110 >8_4_LC_humanized_988
AYDMTQSPSSLSASVGDRVTITCQASQSISTALAWYQQKPGKAPKLLIYRASTLASG
VPSRFSGSGSGTDFTLTISSLQPEDFATYYCQQGWSTVNVDNVFGGGTEVVVR
(SEQ ID NO: 252)

>cl|PECBABABA|1|110 >8_4_LC_humanized_670
AYDMTQSPSSLSASVGDRVTITCQASQSISTALAWYQQKPGKVPKLLIYRASTLASG
VPSRFSGSGSGTDFTLTISSLQPEDVATYYCQQGWSTVNVDNVFGGGTEVVVR
(SEQ ID NO: 253)

>cl|ZECBABABA|1|110 >8_4_LC_humanized_34
AYDMTQSPSTLSASVGDRVTITCQASQSISTALAWYQQKPGKAPKLLIYRASTLASG
VPSRFSGSGSGTEFTLTISSLQPDDFATYYCQQGWSTVNVDNVFGGGTEVVVR
(SEQ ID NO: 254)

>cl|DICBABABA|15|110 >8_4_LC_humanized_2263 >8_4_LC_humanized_2262
>8_4_LC_humanized_2258 >8_4_LC_humanized_2257 >8_4_LC_humanized_2256
AYDMTQSPASLAVSPGQRATITCQASQSISTALAWYQQKPGQPPKLLIYRASTLASG
VPARFSGSGSGTDFTLTINPVEANDTANYYCQQGWSTVNVDNVFGGGTEVVVR
(SEQ ID NO: 255)

TABLE 9

16-6 VH humanized sequences-IMGT-LigM DB (Abysis) clustered at 90% (41 sequences)

>cl|CABBABABA|1|115 >16_6_HC_humanized_586
VQLQESGGGVVQPGTSLRLSCVVSGSDISSYHMGWVRQAPGKGLEWLAIIVSSGSA
YYATWAKGRFTVSRSKSTLFLKMNSLRADDTAVYYCARNQYSGYGFSFWGQGTL
VTVSS (SEQ ID NO: 256)

>cl|DABBABABA|2|115 >16_6_HC_humanized_411 >16_6_HC_humanized_213
LQLQESGPRLVKPSETLSLTCTVSGSDISSYHMGWIRQPPGKGLEWIGIIVSSGSAYY
ATWAKSRLTISTSKNQFSLRLSSVTAADSAVYYCARNQYSGYGFSFWGQGTLVTVS
S (SEQ ID NO: 257)

>cl|FABBABABA|1|115 >16_6_HC_humanized_372
VQLVESGGGLVQPGGSLRLSCAASGSDISSYHMGWVRQAPGKGLEAVAIIVSSGSA
YYATWAKGRFTISRDSSTLFLQLNSLRVEDSGIYYCAKNQYSGYGFSFWGQGTLVT
VSS (SEQ ID NO: 258)

TABLE 9 -continued 16-6 VH humanized sequences-IMGT-LigM DB (Abysis)
clustered at 90% (41 sequences)

>cl|GABBABABA|7|115 >16_6_HC_humanized_1996 >16_6_HC_humanized_230
>16_6_HC_humanized_2056 >16_6_HC_humanized_672
>16_6_HC_humanized_657
QSLEESGGRLVTPGGSLRLSCAASGSDISSYHMGWVRQAPGKGLEWVSIIVSSGSA
YYATWAKGRFTISRDNSTLYLQMNSLRAEDTAVYYCARNQYSGYGFSFWGQGTL
VTVSS (SEQ ID NO: 259)

>cl|HABBABABA|2|115 >16_6_HC_humanized_1907 >16_6_HC_humanized_716
QSLLESGGGWVQPGRSLRLSCSASGSDISSYHMGWVRQAPGKGLEWVGIIVSSGSA
YYATWAKGRFTISRDNNSLYLQMNSLRPEDTALYYCAKNQYSGYGFSFWGQGVL
VTVSS (SEQ ID NO: 260)

>cl|LABBABABA|3|115 >16_6_HC_humanized_1945 >16_6_HC_humanized_1451
>16_6_HC_humanized_65
QSLEESGGGLVKPGESLRLSCAASGSDISSYHMGWVRQAPGKGLEWVGIIVSSGSA
YYATWAKGRFTISRDDSTVYLEMNSLKTEDTAVYYCATNQYSGYGFSFWGQGTL
VTVSS (SEQ ID NO: 261)

>cl|NABBABABA|1|115 >16_6_HC_humanized_1004
QSLLESGPRLVKPSETLSLTCSVSGSDISSYHMGWVRQPPGQGLEWIGIIVSSGSAYY
ATWARSRVSISTSQNQVSLKLTSVTAADTAVYYCARNQYSGYGFSFWGQGILVTV
SS (SEQ ID NO: 262)

>cl|PABBABABA|13|115 >16_6_HC_humanized_1971 >16_6_HC_humanized_305
>16_6_HC_humanized_1877 >16_6_HC_humanized_860
>16_6_HC_humanized_283
VQLVESGGGVVQPGRSLRLSCAASGSDISSYHMGWVRQAPGKGLEWVAIIVSSGSA
YYATWAKGRFTISRDNSTLYLQMNSLRAEDTAVYYCAKNQYSGYGFSFWGQGTL
VTVSS (SEQ ID NO: 263)

>cl|QABBABABA|22|115 >16_6_HC_humanized_802 >16_6_HC_humanized_587
>16_6_HC_humanized_1012 >16_6_HC_humanized_988
>16_6_HC_humanized_129
VQLVESGGGLVQPGGSLRLSCAASGSDISSYHMGWVRQAPGKGLEWVSIIVSSGSA
YYATWAKGRFTISRDNSTLYLQMNSLRAEDTAVYYCARNQYSGYGFSFWGQGTL
VTVSS (SEQ ID NO: 264)

>cl|RABBABABA|1|115 >16_6_HC_humanized_609
VQLVESGGGLVQPGGSLRLSCTTSGSDISSYHMGWVRQVPGKGLEWVSIIVSSGSA
YYATWAKGRFTISRDNSTSYLQMTSLTPEDTAVYYCAKNQYSGYGFSFWGQGTVV
SVSS (SEQ ID NO: 265)

>cl|YABBABABA|4|115 >16_6_HC_humanized_910 >16_6_HC_humanized_218
>16_6_HC_humanized_912 >16_6_HC_humanized_917
VQLQESGPGLVKPSQTLSLTCTVSGSDISSYHMGWIRQPPGKGLEWIGIIVSSGSAYY
ATWAKSRVTISTSKNQLSLKLTSVTAADTAVYYCARNQYSGYGFSFWGQGTTVTV
SS (SEQ ID NO: 266)

>cl|GEBBABABA|1|115 >16_6_HC_humanized_136
VQLQQSGPGLVKTSETLPLTCTVSGSDISSYHMGWIRQPPGKGLEYIGIIVSSGSAYY
ATWAKNRVTISTSKNQFSLKLSSVTAADTALYYCARNQYSGYGFSFWGQGTLVTV
SS (SEQ ID NO: 267)

>cl|KEBBABABA|1|115 >16_6_HC_humanized_109
VQLVESGPGLVKPSQTLSLTCTVSGSDISSYHMGWIRQPPGKGLEYIGIIVSSGSAYY
ATWAKSRLTMSVDTSNYQLKLSSVTAADTAVYYCARNQYSGYGFSFWGQGTTVT
VSS (SEQ ID NO: 268)

>cl|LEBBABABA|1|115 >16_6_HC_humanized_103
VQLQQSGPGLVKPSGTLSLTCDVSGSDIS SYHMGWVRQPPGKGLEWIGIIVSSGSAY
YATWAKSRVTISKSKNQFSLRLTSVTAADTAVYYCARNQYSGYGFSFWGQGTLVT
VSS (SEQ ID NO: 269)

>cl|NEBBABABA|6|115 >16_6_HC_humanized_902 >16_6_HC_humanized_1982
>16_6_HC_humanized_734 >16_6_HC_humanized_920
>16_6_HC_humanized_149
VQLVESGPGLVKPSQTLSLTCTVSGSDISSYHMGWIRQPPGKGLEWIGIIVSSGSAYY
ATWAKSRVTISTSKNQFSLKLSSVTAADTAVYYCARNQYSGYGFSFWGQGTLVTV
SS (SEQ ID NO: 270)

>cl|PEBBABABA|1|115 >16_6_HC_humanized_851
VQLVQSGGGVVQPGGSLRVSCAASGSDISSYHMGWVRQAPGKGLEWMAIIVSSGS
AYYATWAKGRFTISRDNSTVSLQMSSLRAEDTAVYYCAKNQYSGYGFSFWGRGTL
VTVSS (SEQ ID NO: 271)

TABLE 9 -continued 16-6 VH humanized sequences-IMGT-LigM DB (Abysis)
clustered at 90% (41 sequences)

>cl|SEBBABABA|1|115 >16_6_HC_humanized_926
VQLVESGPGLVKPSQTLSLTCTVSGSDISSYHMGWIRQHSGKTLEWIGIIVSSGSAY
YATWAESRVTISADTSKISLKLSSVTAADTAVYYCARNQYSGYGFSFWGQGTTVT
VSS (SEQ ID NO: 272)

>cl|VEBBABABA|1|115 >16_6_HC_humanized_904
VQLVESGPGLVKPSQTLSLTCNVSGSDISSYHMGWIRQSPGKGLEWIGIIVSSGSAY
YATWARSRVTISADTSKVSLELSPMTAADTAVYYCARNQYSGYGFSFWGQGTTVT
VSS (SEQ ID NO: 273)

>cl|WEBBABABA|1|115 >16_6_HC_humanized_903
VQLQESGPGLVKPSQTLSLTCTVSGSDISSYHMGWIRQPPGTGLEWIGIIVSSGSAYY
ATWAKSRVTISGDTSKFSLMLRSVTAADTAVYYCARNQYSGYGFSFWGQGTMVT
VSS (SEQ ID NO: 274)

>cl|YEBBABABA|1|115 >16_6_HC_humanized_946
VQLVESGGGLIKPGGSLRLSCEVPGSDISSYHMGWVRQGPGRGLEWVGIIVSSGSA
YYATWARGRFTISRSKSTVYLEMNALKTEDTGIYYCVTNQYSGYGFSFWGQGTMV
TVSS (SEQ ID NO: 275)

>cl|ZEBBABABA|1|115 >16_6_HC_humanized_882
QSLEESGGGLVQPGGSLRLSCAASGSDISSYHMGWVRQPPGKGLEWVGIIVSSGSA
YYATWAKGRFTISRSKSTVYLQMNSLKTEDTAVYYCTANQYSGYGFSFWGQGML
VTVSS (SEQ ID NO: 276)

>cl|CIBBABABA|1|115 >16_6_HC_humanized_2041
QSLVQSGTEVRKPGASVKVSCKASGSDISSYHMGWVRQAPGQGLEWMGIIVSSGS
AYYATWAQGRVTMSDTSTTVYMELSSLTSEDTAIYYCARNQYSGYGFSFWGPGTL
VTVSS (SEQ ID NO: 277)

>cl|KIBBABABA|1|115 >16_6_HC_humanized_1944
QSLEESGGRLVTPGTPLTLTCTVSGSDISSYHMGWVRQPPGKGLEWIGIIVSSGSAY
YATWAKNRVTISTSKNQFSLRLNSVTAADTAVYYCARNQYSGYGFSFWGQGTLVT
VSS (SEQ ID NO: 278)

>cl|LIBBABABA|4|115 >16_6_HC_humanized_1895 >16_6_HC_humanized_1992
>16_6_HC_humanized_1995 >16_6_HC_humanized_1949
QSLEESGGRLVTPGTPLTLTCTVSGSDISSYHMGWVRQAPGKGLVWVSIIVSSGSAY
YATWAKGRFTISRDNATLYLQMNSLRAEDTAVYYCARNQYSGYGFSFWGPGTLV
TVSS (SEQ ID NO: 279)

>cl|SIBBABABA|2|115 >16_6_HC_humanized_993 >16_6_HC_humanized_994
VQLVESGGGLIQPGRPLRLSCSGSGSDISSYHMGWVRQAPGKGLEWVGIIVSSGSA
YYATWAKGRFTISRDDSVVHLQMNSLRSEDTAVYYCTRNQYSGYGFSFWGQGTM
VTVSS (SEQ ID NO: 280)

>cl|TIBBABABA|2|115 >16_6_HC_humanized_956 >16_6_HC_humanized_965
VQLQESGPGLVKPSQTLSLTCTVSGSDISSYHMGWIRQHPGKGLEWIGIIVSSGSAY
YATWAESRLTISADTSNIQLRLSSVTAADTAVYFCARNQYSGYGFSFWGQGTTVTV
SS (SEQ ID NO: 281)

>cl|WIBBABABA|1|115 >16_6_HC_humanized_278
VQLVQSGGGLVKPGGSLRLSCEASGSDISSYHMGWIRQAPGKGLEWVGIIVSSGSA
YYATWAKGRFTISRDDSTLYLQVNSLKTEDSAVYYCTTNQYSGYGFSFWGQGTLV
TVSS (SEQ ID NO: 282)

>cl|GOBBABABA|1|115 >16_6_HC_humanized_1894
QSLEESGGRLVTPGTPLTLTCTVSGSDISSYHMGWVRQAPGKGLEWVSIIVSSGSAY
YATWAKGRFTISRDNASLYLQMNSLRAEDTAVYYCARNQYSGYGFSFFSDYWLVT
VSS (SEQ ID NO: 283)

>cl|MOBBABABA|3|115 >16_6_HC_humanized_1917 >16_6_HC_humanized_677
>16_6_HC_humanized_267
QSLEESGGGVVQPGRSLRLSCAASGSDISSYHMGWVRQAPGKGLEWVAIIVSSGSA
YYATWAKRRFTISRDNSTLYLQMNSLRAEDTAVYYCARNQYSGYGFSFWGQGTL
VTVSS (SEQ ID NO: 284)

>cl|POBBABABA|1|115 >16_6_HC_humanized_2038
QSLEESGGRLVTPGTPLTLTCTVSGSDISSYHMGWVRQAPGKGLEWVAIIVSSGSAY
YATWAKGRFTISRDNASLYLQMNSLRAEDTAVYYCARNQYSGYGFSFPTSGYYY
MDVS (SEQ ID NO: 285)

>cl|QOBBABABA|1|115 >16_6_HC_humanized_23
QSLLESGGDLVQPGGSLRLSCEASGSDISSYHMGWVRQAPGKGLEWVSIIVSSGSA
YYATWAKGRFTISRDKSTLFLQMHSLRVEDTAVYYCAKNQYSGYGFSFWGQGTT
VTVSS (SEQ ID NO: 286)

TABLE 9 -continued 16-6 VH humanized sequences-IMGT-LigM DB (Abysis)
clustered at 90% (41 sequences)

>cl|VOBBABABA|1|115 >16_6_HC_humanized_1013
VQLVQSGGGVVQPGRSLRLSCEVSGSDISSYHMGWVRQAPGKGLEWVAIIVSSGSA
YYATWAKGRFTISRSNNTLYLQMNSLTAEDTALYFCARNQYSGYGFSFWGKGTTV
TVSS (SEQ ID NO: 287)

>cl|YOBBABABA|1|115 >16_6_HC_humanized_113
LQLQESGPGLVKPSQTLSLTCSVSGSDISSYHMGWIRQHPGKGLEWIGIIVSSGSAYY
ATWAKSRITISTSKNQFSLKLTSVTAADTALYYCARNQYSGYGFSFWGRGTLVTVS
S (SEQ ID NO: 288)

>cl|HUBBABABA|1|115 >16_6_HC_humanized_12
VQLVQSGGGVVQPGGSLRLSCAASGSDISSYHMGWVRQAPGKGLEWVAIIVSSGS
AYYATWAQGRVTISRDNSTVHLQITSLKSEDTAVYYCAKNQYSGYGFSFWGQGTL
VTVSS (SEQ ID NO: 289)

>cl|LUBBABABA|1|115 >16_6_HC_humanized_273
VQLVQSGGGLVQPGGSLRLSCAASGSDISSYHMGWVRQASGKGLEWIGIIVSSGSA
YYATWAKGRFTVSRSQNSVFLQMNSLETEDTAVYYCARNQYSGYGFSFWGQGTL
VTVSS (SEQ ID NO: 290)

>cl|NUBBABABA|1|115 >16_6_HC_humanized_879
QSLEESGGGLVQPGGSLRLSCTASGSDISSYHMGWVRQAPGKGLEWVSIIVSSGSA
YYATWAKGRFTISRDSSTLYLQMNNLRVEDTALYYCAHNQYSGYGFSFWGRGTQ
VTVSS (SEQ ID NO: 291)

>cl|TUBBABABA|1|115 >16_6_HC_humanized_1934
QSLEESGGRLVTPGTPLTLTCTVSGSDISSYHMGWVRQAPGKGLEWVSIIVSSGSAY
YATWAKGRFTISRDNASLYLQMNSLRAEDTAVYYCARNQYSGYGFSFGIFDYWVT
VSS (SEQ ID NO: 292)

>cl|VUBBABABA|1|115 >16_6_HC_humanized_200
VQLQESGPGLVKPSETLSLTC SVSGSDISSYHMGWIRQPAGKGLEWIGIIVSSGSAYY
ATWARSRVTMSMSKNHFSLKLRSVTAADTAVYFCARNQYSGYGFSFWGQGTLVT
VSS (SEQ ID NO: 293)

>cl|WUBBABABA|1|115 >16_6_HC_humanized_1977
QSLEESGGRLVTPGTPLTLTCTVSGSDISSYHMGWVRQAPGKGLEWVAIIVSSGSAY
YATWAKGRFTISRSKNTLYLQMNSLRAEDTAVYYCARNQYSGYGFSFTCPYFDYW
VSS (SEQ ID NO: 294)

>cl|XUBBABABA|1|115 >16_6_HC_humanized_2027
QSLEESGGRLVTPGTPLTLTCTVSGSDISSYHMGWVRQAPGKGLEWVAIIVSSGSAY
YATWAEGRFTISRDNSTLYLQMYSLRTEDTAVYYCARNQYSGYGFSFYYYGMGV
WVSS (SEQ ID NO: 295)

>cl|YUBBABABA|1|115 >16_6_HC_humanized_1958
VHLVESGGGVVQPGRSLRLSCAASGSDISSYHMGWVRQAPGKGLEWVAIIVSSGSA
YYATWAEGRFTISRDNSKLYLQMNSLRAED SATYYCARNQYSGYGFSFFGPPYYY
YYMS (SEQ ID NO: 296)

>cl|BACBABABA|1|115 >16_6_HC_humanized_1905
QSLEESGGRLVTPGTPLTLTCTVSGSDISSYHMGWVRQAPGKGLEWVSIIVSSGSAY
YATWAKGRFTISRDNSTLYLQMNSLRAEDTALYYCARNQYSGYGFSFVRGGYFYH
MDS (SEQ ID NO: 297)

TABLE 10

16-6 VL humanized sequences-IMGT-LigM DB (Abysis) clustered at 90%
(21 sequences)

>cl|CACBABABA|1|110 >16_6_LC_humanized_586
IVLTQTPSSLSASVGDRITITCQSSHSVYYGDWLAWYQQKPGKAPKLLIYRASNLAS
GVPSRFSGSRSGTDFTFTISSLRPEDIATYYCLGGYDDDGETAFGGGTKVEIK (SEQ
ID NO: 298)

>cl|DACBABABA|27|110 >16_6_LC_humanized_411 >16_6_LC_humanized_1004
>16_6_LC_humanized_587 >16_6_LC_humanized_305 >16_6_LC_humanized_988
IVLTQSPSSLSASVGDRVTITCQSSHSVYYGDWLAWYQQKPGKAPKLLIYRASNLA
SGVPSRFSGSGSGTDFTLTISSLQPEDFATYYCLGGYDDDGETAFGGGTKVEIK
(SEQ ID NO: 299)

TABLE 10 -continued 16-6 VL humanized sequences-IMGT-LigM DB (Abysis) clustered at 90%
(21 sequences)

>cl|FACBABABA|15|110 >16_6_LC_humanized_372 >16_6_LC_humanized_1877
>16_6_LC_humanized_1012 >16_6_LC_humanized_860 >16_6_LC_humanized_283
IQLTQSPSSLSASVGDRVTITCQSSHSVYYGDWLAWYQQKPGKAPKLLIYRASNLA
SGVPSRFSGSGSGTEFTLTISSLQPDDFATYYCLGGYDDDGETAFGQGTKVEIK
(SEQ ID NO: 300)

>cl|GACBABABA|1|110 >16_6_LC_humanized_1996
VVLTQTPSPVSTAVGGTVTLSCQSSHSVYYGDWLAWYQQKPGQAPRLLIYRASNL
ASGIPDRFSGSGSGTDFTLTISRLEPEDFAVYYCLGGYDDDGETAKGPGTEVVVK
(SEQ ID NO: 301)

>cl|HACBABABA|2|110 >16_6_LC_humanized_1907 >16_6_LC_humanized_716
LVIVITQSPSSLSASEGDRVTITCQSSHSVYYGDWLAWYQQKPGRAPKLLIHRASNLA
SGVPSRFSGSGSGTEFTLTISGLQSEDFATYYCLGGYDDDGETAFGGGTTVDVK
(SEQ ID NO: 302)

>cl|LACBABABA|2|110 >16_6_LC_humanized_1945 >16_6_LC_humanized_1451
VELTQPPSPVSAAPGQKVTISCQSSHSVYYGDWLAWYQQLPGTAPKLLIYRASNLA
SGIPDRFSGSKSGTSATLGITGLQTGDEADYYCLGGYDDDGETAFGGGTRLTVL
(SEQ ID NO: 303)

>cl|PACBABABA|10|110 >16_6_LC_humanized_1971 >16_6_LC_humanized_2041
>16_6_LC_humanized_2038 >16_6_LC_humanized_2008 >16_6_LC_human-
ized_1992
VVLTQTPSPVSTAVGGTVTITCQSSHSVYYGDWLAWYQQKPGKAPKLLIYRASNL
ASGVPSRFSGSGSGTDFTLTISSLQPEDFATYYCLGGYDDDGETAFGGGTEVVVK
(SEQ ID NO: 304)

>cl|QACBABABA|5|110 >16_6_LC_humanized_802 >16_6_LC_humanized_609
>16_6_LC_humanized_851 >16_6_LC_humanized_908 >16_6_LC_humanized_108
VVMTQSPSSLSASVGDRVTITCQSSHSVYYGDWLAWYQQKPGKAPKLLIYRASNL
ASGVPSRFSGSGSGTDFTLTISSLQPEDFATYYCLGGYDDDGETAFGGGTKVEIK
(SEQ ID NO: 305)

>cl|CECBABABA|7|110 >16_6_LC_humanized_253 >16_6_LC_humanized_103
>16_6_LC_humanized_882 >16_6_LC_humanized_1982 >16_6_LC_humanized_734
IVLTQSPSSLSASVGDRVTITCQSSHSVYYGDWLAWYQQKPGKAPKLLIYRASNLA
SGVPSRFSGSGSGTEFTLTISSLQPEDSATYYCLGGYDDDGETAFGQGTKVEIK (SEQ
ID NO: 306)

>cl|KECBABABA|2|110 >16_6_LC_humanized_109 >16_6_LC_humanized_334
IQLTQSPSFVSASVGDRITITCQSSHSVYYGDWLAWYQQKPGKAPKLLIYRASNLAS
GVPSRFSGSRSGTDFTLTISSLQPEDFATYYCLGGYDDDGETAFGQGTKVEIK (SEQ
ID NO: 307)

>cl|RECBABABA|2|110 >16_6_LC_humanized_17 >16_6_LC_humanized_21
IQLTQSPSSLSAAVGDRVTIACQSSHSVYYGDWLAWYQQKPGKAPKLLIYRASNLA
SGVPSRFSGSGSGTDFTLSISSLQPEDFATYYCLGGYDDDGETAFGGGTKVQMK
(SEQ ID NO: 308)

>cl|DICBABABA|1|110 >16_6_LC_humanized_202
IRMTQSPSSLSASVGDRVTITCQSSHSVYYGDWLAWYQQKPGKVPKLLIYRASNLA
SGVPSRFSGSGSGTDFTLTISSLQPEDVATYYCLGGYDDDGETAFGPGTKVVVK
(SEQ ID NO: 309)

>cl|FICBABABA|14|110 >16_6_LC_humanized_192 >16_6_LC_humanized_956
>16_6_LC_humanized_230 >16_6_LC_humanized_880 >16_6_LC_humanized_2056
VVLTQSPSSLSASVGDRVTITCQSSHSVYYGDWLAWYQQKPGKAPKLLIYRASNLA
SGVPSRFSGSGSGTDFTLTISSLQPEDFATYYCLGGYDDDGETAFGQGTKVEIK
(SEQ ID NO: 310)

>cl|NICBABABA|2|110 >16_6_LC_humanized_1938 >16_6_LC_humanized_762
VELTQSPDSLAVSLGERATINCQSSHSVYYGDWLAWYQQKPGQPPKLLIYRASNLA
SGVPDRFSGSGSGTDFTLTISSLQAEDVAVYYCLGGYDDDGETAFGGGTKVEIK
(SEQ ID NO: 311)

>cl|WICBABABA|1|110 >16_6_LC_humanized_278
LVLTQSPSSLSASVGDRVTITCQSSHSVYYGDWLAWCQQKPGKSPTLLIYRASNLA
SGVPSRFSGSGSGTGFTLTISGLQPEDFATYYCLGGYDDDGETAFGGGTKVEIR
(SEQ ID NO: 312)

>cl|YICBABABA|1|110 >16_6_LC_humanized_169
IVLTQSPSFLSAFVGDRITITCQSSHSVYYGDWLAWYQQKPGKAPKLLIYRASNLAS
GVPSRFSGSGSGTEFTLTISGLQPEDFASYYCLGGYDDDGETAFGGGTKLEIK (SEQ
ID NO: 313)

TABLE 10 -continued 16-6 VL humanized sequences-IMGT-LigM DB (Abysis) clustered at 90%
(21 sequences)

>cl|GOCBABABA|1|110 >16_6_LC_humanized_1894
VVLTQTPSPVSTAVGDRVTITCQSSHSVYYGDWLAWYRQKPGKVPKLLIYRASNL
ASGVPSRFSGSGSGTDFTLTISSLQPEDVATYYGLGGYDDDGETAFGGGTEVVVK
(SEQ ID NO: 314)

>cl|LOCBABABA|1|110 >16_6_LC_humanized_657
VVLTQTPSPVSTSVGDRVSITCQSSHSVYYGDWLAWYQQKPGKAPKLLIYRASNLA
SGVPSRFSGSGSGTDFTLTITSLQPVDFATYYCLGGYDDDGETAFGPGTTVDAK
(SEQ ID NO: 315)

>cl|YOCBABABA|1|110 >16_6_LC_humanized_113
IVLTQSPSSVSASVGDRVTITCQSSHSVYYGDWLAWYQLKPGKAPKLLINRASNLA
SGVPSRFSGSGSGTDFTLTISGLQPEDFATYYCLGGYDDDGETAFGPGTTVDIK
(SEQ ID NO: 316)

>cl|MUCBABABA|3|110 >16_6_LC_humanized_2032 >16_6_LC_humanized_200
>16_6_LC_humanized_1905
VVLTQTPSPVSTAVGGTGTINCQSSHSVYYGDWLAWYQQKPGQPPKLLIYRASNL
ASGVPDRFSGSGSGTDFTLTISSLQAEDVAVYYCLGGYDDDGETAFGGGTKVVVK
(SEQ ID NO: 317)

>cl|RUCBABABA|1|110 >16_6_LC_humanized_1995
VVLTQTPSPVSTAVGGTVTINCQSSHSVYYGDWLAWYQQKPGQPXKLLIYRASNL
ASGVPDRFSGSGSGTDFTLTISSLQAEDVAVYYCLGGYDDDGETAFGQGTEVVVK
(SEQ ID NO: 318)

TABLE 11

16-6VH humanized sequences-IMGT-LigM DB (Abysis) clustered at 95%
(81 sequences)

>cl|CABBABABA|1|115 >16_6_HC_humanized_586
VQLQESGGGVVQPGTSLRLSCVVSGSDISSYHMGWVRQAPGKGLEWLAIIVSSGSA
YYATWAKGRFTVSRSKSTLFLKMNSLRADDTAVYYCARNQYSGYGFSFWGQGTL
VTVSS (SEQ ID NO: 319)

>cl|DABBABABA|1|115 >16_6_HC_humanized_411
LQLQESGPRLVKPSETLSLTCTVSGSDISSYHMGWIRQSPGKGLEWIGIIVSSGSAYY
ATWAKSRLTMSTSKNQFSLRLSSVTAADSAVYYCARNQYSGYGFSFWGQGTLVTV
SS (SEQ ID NO: 320)

>cl1FABBABABA|1|115 >16_6_HC_humanized_372
VQLVESGGGLVQPGGSLRLSCAASGSDISSYHMGWVRQAPGKGLEAVAIIVSSGSA
YYATWAKGRFTISRDSSTLFLQLNSLRVEDSGIYYCAKNQYSGYGFSFWGQGTLVT
VSS (SEQ ID NO: 321)

>cl|GABBABABA|1|115 >16_6_HC_humanized_1996
QSLEESGGRLVTPGGSLRLSCAASGSDISSYHMGWVRQAPGKGLEWVGIIVSSGSA
YYATWAKGRFTISRDNSTLYLQMNSLRVEDTARYYCARNQYSGYGFSFWGQGTL
VTVSS (SEQ ID NO: 322)

>cl|HABBABABA|2|115 >16_6_HC_humanized_1907 >16_6_HC_humanized_716
QSLLESGGGWVQPGRSLRLSCSASGSDISSYHMGWVRQAPGKGLEWVGIIVSSGSA
YYATWAKGRFTISRDNNSLYLQMN SLRPEDTALYYCAKNQ YSGYGFSFWGQGVL
VTVSS (SEQ ID NO: 323)

>cl|LABBABABA|2|115 >16_6_HC_humanized_1945 >16_6_HC_humanized_1451
QSLEESGGGLVKPGESLRLSCAASGSDISSYHMGWVRQAPGKGLEWVGIIVSSGSA
YYATWAKGRFTISRDDSTVYLEMNSLKTEDTAVYYCATNQYSGYGFSFWGQGTL
VTVSS (SEQ ID NO: 324)

>cl|NABBABABA|1|115 >16_6_HC_humanized_1004
QSLLESGPRLVKPSETLSLTCSVSGSDISSYHMGWVRQPPGQGLEWIGIIVSSGSAYY
ATWARSRVSISTSQNQVSLKLTSVTAADTAVYYCARNQYSGYGFSFWGQGILVTV
SS (SEQ ID NO: 325)

>cl|PABBABABA|1|115 >16_6_HC_humanized_1971
VQLVESGGGVVQPGRSLRLSCAASGSDISSYHMGWVRQAPGKGLEWLAIIVSSGSA
YYATWAKGRFTISRDNSSLYLQLSSLRNEDTAVYYCAKNQYSGYGFSFWGPGTLV
TVSS (SEQ ID NO: 326)

TABLE 11 -continued 16-6VH humanized sequences-IMGT-LigM DB (Abysis) clustered at 95%
(81 sequences)

>cl|QABBABABA|2|115 >16_6_HC_humanized_802 >16_6_HC_humanized_988
VQLVESGGGLIQPGGSLRLSCAASGSDISSYHMGWVRQAPGKGLEWVSIIVSSGSA
YYATWAKGRFTISRDNASLYLQMNSLRAEDTAVYYCARNQYSGYGFSFWGQGTL
VTVSS (SEQ ID NO: 327)

>cl|RABBABABA|1|115 >16_6_HC_humanized_609
VQLVESGGGLVQPGGSLRLSCTTSGSDISSYHMGWVRQVPGKGLEWVSIIVSSGSA
YYATWAKGRFTISRDNSTSYLQMTSLTPEDTAVYYCAKNQYSGYGFSFWGQGTVV
SVSS (SEQ ID NO: 328)

>cl|SABBABABA|1|115 >16_6_HC_humanized_587
VQLVESGGGLVKPGGSLRLSCVVSGSDISSYHMGWVRQAPGKGLEWLSIIVSSGSA
YYATWAKGRFTISRDNASLFLQMNSLRADDTALYFCARNQYSGYGFSFWGQGTLV
TVSS (SEQ ID NO: 329)

>cl|TABBABABA|6|115 >16_6_HC_humanized_305 >16_6_HC_humanized_283
>16_6_HC_humanized_334 >16_6_HC_humanized_281 >16_6_HC_human-
ized_339
VQLVESGGGVVQPGRSLRLSCAASGSDISSYHMGWVRQAPGKGLEWVAIIVSSGSA
YYATWAKGRFTISRDNSTLYLQMNSLRAEDTAVYYCAKNQYSGYGFSFWGQGTL
VTVSS (SEQ ID NO: 330)

>cl|VABBABABA|4|115 >16_6_HC_humanized_1877 >16_6_HC_humanized_860
>16_6_HC_humanized_204 >16_6_HC_humanized_818
VQLVESGGGVVQPGRSLRLSCAASGSDISSYHMGWVRQAPGKGLEWVAIIVSSGSA
YYATWAKGRFTISRDNSTLYLQMNSLRAEDTAVYYCARNQYSGYGFSFWGQGTL
VTVSS (SEQ ID NO: 331)

>cl|WABBABABA|1|115 >16_6_HC_humanized_1012
VQLQEWGGGVVQPGRSLRLSCAASGSDISSYHMGWVRQAPGKGLEWVAIIVSSGS
AYYATWAKGRFTISRDNSTLYLQMNSLRAEDTAVYYCARNQYSGYGFSFWGQGT
LVTVSS (SEQ ID NO: 332)

>cl|YABBABABA|1|115 >16_6_HC_humanized_910
VQLQESGPGLVKPSQTLSLTCTVSGSDISSYHMGWIRQPPGKGLEWIGIIVSSGSAYY
ATWAQSRVLISTSKSQLSLKLTSVTAADTAVYYCARNQYSGYGFSFWGQGTTVTV
SS (SEQ ID NO: 333)

>cl|CEBBABABA|1|115 >16_6_HC_humanized_253
VQLVESGGGLVQPGRSLRLSCATSGSDISSYHMGWVRQAPGKGLEWVGIIVSSGSA
YYATWAKGRFTISRDNASLYLQMSSLRAEDTALYYCAKNQYSGYGFSFWGQGTL
VTVSS (SEQ ID NO: 334)

>cl|DEBBABABA|1|115 >16_6_HC_humanized_218
VQLQESGPGLVKPSETLSLTCTVSGSDISSYHMGWIRQPPGKGLEWIGIIVSSGSAYY
ATWAKSRVTISTSKNQFSLKLSSVTAADTAVYYCARNQYSGYGFSFWGQGTTVTV
SS (SEQ ID NO: 335)

>cl|FEBBABABA|1|115 >16_6_HC_humanized_213
LQLQESGPGLVKPSETLSLTCTVSGSDISSYHMGWIRQPPGKGLEWIGIIVSSGSAYY
ATWAKSRVTISTSKNQFSLKLSSVTAADTAVYYCASNQYSGYGFSFWGQGTLVTV
SS (SEQ ID NO: 336)

>cl|GEBBABABA|1|115 >16_6_HC_humanized_136
VQLQQSGPGLVKTSETLPLTCTVSGSDISSYHMGWIRQPPGKGLEYIGIIVSSGSAYY
ATWAKNRVTISTSKNQFSLKLSSVTAADTALYYCARNQYSGYGFSFWGQGTLVTV
SS (SEQ ID NO: 337)

>cl|BEBBABABA|1|115 >16_6_HC_humanized_129
MQLVESGGGLVQPGRSLRLSCVTSGSDISSYHMGWVRQVPGKGLEWVGIIVSSGSA
YYATWAKGRFTISRDNTSLYLQMNSLRPEDTAVYYCAKNQYSGYGFSFWGQGTL
VTVSS (SEQ ID NO: 338)

>cl|KEBBABABA|1|115 >16_6_HC_humanized_109
VQLVESGPGLVKPSQTLSLTCTVSGSDISSYHMGWIRQPPGKGLEYIGIIVSSGSAYY
ATWAKSRLTMSVDTSNYQLKLSSVTAADTAVYYCARNQYSGYGFSFWGQGTTVT
VSS (SEQ ID NO: 339)

>cl|LEBBABABA|1|115 >16_6_HC_humanized_103
VQLQQSGPGLVKPSGTLSLTCDVSGSDISSYHMGWVRQPPGKGLEWIGIIVSSGSAY
YATWAKSRVTISKSKNQFSLRLTSVTAADTAVYYCARNQYSGYGFSFWGQGTLVT
VSS (SEQ ID NO: 340)

>cl|MEBBABABA|1|115 >16_6_HC_humanized_954
VQLVESGGGVVQPGRSLRLSCAASGSDISSYHMGWVRQAPGKGLEWVAIIVSSGSA
YYATWAKGRFTISRDNSTLYLQMNSLRAEDTAVYYCAKNQYSGYGFSFWGQGTT
VTVSS (SEQ ID NO: 341)

TABLE 11 -continued 16-6VH humanized sequences-IMGT-LigM DB (Abysis) clustered at 95%
(81 sequences)

>cl|NEBBABABA|1|115 >16_6_HC_humanized_902
VQLVESGPGLVKPSQTLSLTCTVSGSDISSYHMGWLRQPPGRGLEWIGIIVSSGSAY
YATWAKSRVTLSTSKNQFSLKLNSVTAADTAVYYCARNQYSGYGFSFWGQGTLV
TVSS (SEQ ID NO: 342)

>cl|PEBBABABA|1|115 >16_6_HC_humanized_851
VQLVQSGGGVVQPGGSLRVSCAASGSDISSYHMGWVRQAPGKGLEWMAIIVSSGS
AYYATWAKGRFTISRDNSTVSLQMSSLRAEDTAVYYCAKNQYSGYGFSFWGRGTL
VTVSS (SEQ ID NO: 343)

>cl|REBBABABA|1|115 >16_6_HC_humanized_17
VQLVESGGGLVQPGGSLRLSCAASGSDISSYHMGWVRQAPGRGLVWVSIIVSSGSA
YYATWAKGRFTISRDNATLYLQMNNLRAEDTAVYYCARNQYSGYGFSFWGQGTL
VTVSS (SEQ ID NO: 344)

>cl|SEBBABABA|1|115 >16_6_HC_humanized_926
VQLVESGPGLVKPSQTLSLTCTVSGSDISSYHMGWIRQHSGKTLEWIGIIVSSGSAY
YATWAESRVTISADTSKISLKLSSVTAADTAVYYCARNQYSGYGFSFWGQGTTVT
VSS (SEQ ID NO: 345)

>cl|TEBBABABA|1|115 >16_6_HC_humanized_908
VQLVESGGGLVEPGGSLRLSCAASGSDISSYHMGWIRQAPGKGLEWLSIIVSSGSAY
YATWAKGRFTISRDNASLYLQMNSLRAEDTAVYYCVRNQYSGYGFSFWGQGTMV
TVSS (SEQ ID NO: 346)

>cl|VEBBABABA|1|115 >16_6_HC_humanized_904
VQLVESGPGLVKPSQTLSLTCNVSGSDISSYHMGWIRQSPGKGLEWIGIIVSSGSAY
YATWARSRVTISADTSKVSLELSPMTAADTAVYYCARNQYSGYGFSFWGQGTTVT
VSS (SEQ ID NO: 347)

>cl|WEBBABABA|1|115 >16_6_HC_humanized_903
VQLQESGPGLVKPSQTLSLTCTVSGSDISSYHMGWIRQPPGTGLEWIGIIVSSGSAYY
ATWAKSRVTISGDTSKFSLMLRSVTAADTAVYYCARNQYSGYGFSFWGQGTMVT
VSS (SEQ ID NO: 348)

>cl|XEBBABABA|1|115 >16_6_HC_humanized_108
VQLVESGGGLVKPGGSLRLSCAASGSDISSYHMGWIRQAPGKGLEWVSIIVSSGSA
YYATWAKGRFTISRDNASLFLQMNSLRAEDTAVYYCAKNQYSGYGFSFWGQGTLI
TVSS (SEQ ID NO: 349)

>cl|YEBBABABA|1|115 >16_6_HC_humanized_946
VQLVESGGGLIKPGGSLRLSCEVPGSDISSYHMGWVRQGPGRGLEWVGIIVSSGSA
YYATWARGRFTISRSKSTVYLEMNALKTEDTGIYYCVTNQYSGYGFSFWGQGTMV
TVSS (SEQ ID NO: 350)

>cl|ZEBBABABA|1|115 >16_6_HC_humanized_882
QSLEESGGGLVQPGGSLRLSCAASGSDISSYHMGWVRQPPGKGLEWVGIIVSSGSA
YYATWAKGRFTISRSKSTVYLQMNSLKTEDTAVYYCTANQYSGYGFSFWGQGML
VTVSS (SEQ ID NO: 351)

>cl|BIBBABABA|1|115 >16_6_HC_humanized_186
VQLVESGGGVVQPGRSLRLSCAASGSDISSYHMGWVRQAPGKGLESVAIIVSSGSA
YYATWAKGRFTISRDNSTLYLQMNSLRAEDTAVYYCARNQYSGYGFSFWGQGTL
VTVSS (SEQ ID NO: 352)

>cl|CIBBABABA|1|115 >16_6_HC_humanized_2041
QSLVQSGTEVRKPGASVKVSCKASGSDISSYHMGWVRQAPGQGLEWMGIIVSSGS
AYYATWAQGRVTMSDTSTTVYMELSSLTSEDTAIYYCARNQYSGYGFPGPGTL
VTVSS (SEQ ID NO: 353)

>cl|DIBBABABA|1|115 >16_6_HC_humanized_202
VQLQESGEGLVQPGGSLRLSCAASGSDISSYHMGWVRQAPGKGLEYVSIIVSSGSA
YYATWAKGRFTISRDNSTLYLQMGSLRAEDMAVYYCARNQYSGYGFSFWGQGT
MVTVSS (SEQ ID NO: 354)

>cl|FIBBABABA|2|115 >16_6_HC_humanized_192 >16_6_HC_humanized_880
QHLEESGGGVVQPGRSLRLSCAASGSDISSYHMGWVRQAPGKGLEWVAIIVSSGSA
YYATWAKGRFTISRDNSTLYLQMNSLRAEDTAVYYCARNQYSGYGFSFWGQGTT
VTVSS (SEQ ID NO: 355)

>cl|GIBBABABA|2|115 >16_6_HC_humanized_1982 >16_6_HC_humanized_734
QSLLESGPGLVKPSQTLSLTCTVSGSDISSYHMGWIRQPPGKGLEWIGIIVSSGSAYY
ATWAKSRVTMSTSKNHFSLRLSSVTAADTAVYYCARNQYSGYGFSFWGQGTLVT
VSS (SEQ ID NO: 356)

TABLE 11 -continued 16-6VH humanized sequences-IMGT-LigM DB (Abysis) clustered at 95%
(81 sequences)

>cl|KIBBABABA|1|115 >16_6_HC_humanized_1944
QSLEESGGRLVTPGTPLTLTCTVSGSDISSYHMGWVRQPPGKGLEWIGIIVSSGSAY
YATWAKNRVTISTSKNQFSLRLNSVTAADTAVYYCARNQYSGYGFSFWGQGTLVT
VSS (SEQ ID NO: 357)

>cl|LIBBABABA|1|115 >16_6_HC_humanized_1895
QSLEESGGRLVTPGTPLTLTCTVSGSDISSYHMGWVRQAPGKGLVWVSIIVSSGSAY
YATWAKGRFTISRDNATLYLQMNSLRAEDTAVYYCARNQYSGYGFSFWGKGTTV
TVSS (SEQ ID NO: 358)

>cl|MIBBABABA|1|115 >16_6_HC_humanized_65
QSLEESGGGLVQPGRSLRLSCAASGSDISSYHMGWVRQAPGKGLEWVGIIVSSGSA
YYATWAKGRFTISRDNASLYLQMNSLRAEDTALYYCAKNQYSGYGFSFWGQGTL
VTVSS (SEQ ID NO: 359)

>cl|NIBBABABA|2|115 >16_6_HC_humanized_1938 >16_6_HC_humanized_762
VKLLESGGGLVQPGGSLRLSCAASGSDISSYHMGWVRQAPGKGLEWVAIIVSSGSA
YYATWAKGRFTISRDNSTLYLQMNSLGAEDTAVYYCARNQYSGYGFSFWGQGTL
VTVSS (SEQ ID NO: 360)

>cl|QIBBABABA|2|115 >16_6_HC_humanized_2031 >16_6_HC_humanized_621
VQLVESGGGLVKPGGSLRLSCAASGSDISSYHMGWVRQAPGKGLEWVSIIVSSGSA
YYATWAKGRFTISRDNSTLYLQMNNLRAEDTAVYYCARNQYSGYGFSFWGQGTL
VTVLS (SEQ ID NO: 361)

>cl|SIBBABABA|1|115 >16_6_HC_humanized_993
VQLVESGGGLIQPGRPLRLSCSGSGSDISSYHMGWVRQAPGKGLEWVGIIVSSGSA
YYATWAKGRFTISRDDSVVHLQMNSLKSEDTAVYYCTRNQYSGYGFSFWGQGTT
VTVSS (SEQ ID NO: 362)

>cl|TIBBABABA|1|115 >16_6_HC_humanized_956
VQLQESGPGLVKPSQTLSLTCTVSGSDISSYHMGWFRQHPGKGLEWIGIIVSSGSAY
YATWAESRLTISEDTSNIQLRLTSVTAADTAVYFCARNQYSGYGFSFWGQGTTVTV
SS (SEQ ID NO: 363)

>cl|VIBBABABA|1|115 >16_6_HC_humanized_920
VQLVESGPGLVKPSQTLSLTCTVSGSDISSYHMGWIRQFPGKGLEWIGIIVSSGSAYY
ATWAKSRFTISTSKNQFSLKVDSVTAADTAVYYCARNQYSGYGFSFWGQGTTVTV
SS (SEQ ID NO: 364)

>cl|WIBBABABA|1|115 >16_6_HC_humanized_278
VQLVQSGGGLVKPGGSLRLSCEASGSDISSYHMGWIRQAPGKGLEWVGIIVSSGSA
YYATWAKGRFTISRDDSTLYLQVNSLKTEDSAVYYCTTNQYSGYGFSFWGQGTLV
TVSS (SEQ ID NO: 365)

>cl|YIBBABABA|2|115 >16_6_HC_humanized_169 >16_6_HC_humanized_168
VQLVESGGGLVQPGGSLRLSCAASGSDISSYHMGWVRQAPGKGLEWVSIIVSSGSA
YYATWAKGRFTISRDNSTLYLQMDSLRAEDTAIYYCAKNQYSGYGFSFWGQGTLV
TVSS (SEQ ID NO: 366)

>cl|ZIBBABABA|1|115 >16_6_HC_humanized_994
VQLVESGGGLIQPGRSLRLSCSGSGSDISSYHMGWVRQAPGKGLEWVGIIVSSGSA
YYATWAKGRFTISRDDSVVYLQMNSLRSEDTAVYYCTRNQYSGYGFSFWGQGTM
VTVSS (SEQ ID NO: 367)

>cl|BOBBABABA|2|115 >16_6_HC_humanized_975 >16_6_HC_humanized_978
VQLVESGGGVVRPGGSLRLSCAASGSDISSYHMGWVRQAPGKGLEWVGIIVSSGSA
YYATWAKGRFTISRDNASLYLEMNSLRAEDTALYFCARNQYSGYGFSFWGQGTM
VTVSS (SEQ ID NO: 368)

>cl|DOBBABABA|1|115 >16_6_HC_humanized_230
QSLEESGGGLVQPGGSLRLSCAASGSDISSYHMGWVRQAPGKGLEWVSIIVSSGSA
YYATWAKGRFTISRDNSTLYLQMNSLRAEDTAVYYCAKNQYSGYGFSFWGQGTT
VTVSS (SEQ ID NO: 369)

>cl|GOBBABABA|1|115 >16_6_HC_humanized_1894
QSLEESGGRLVTPGTPLTLTCTVSGSDISSYHMGWVRQAPGKGLEWVSIIVSSGSAY
YATWAKGRFTISRDNASLYLQMNSLRAEDTAVYYCARNQYSGYGFSFFSDYWLVT
VSS (SEQ ID NO: 370)

>cl|HOBBABABA|2|115 >16_6_HC_humanized_2056 >16_6_HC_humanized_672
QSLVESGGGLIQPGGSLRLSCAASGSDISSYHMGWVRQAPGKGLEWVSIIVSSGSAY
YATWAKGRFTISRDNSTLYLQMNSLRAEDTAVYYCARNQYSGYGFSFWGQGTLV
TVSS (SEQ ID NO: 371)

>cl|LOBBABABA|1|115 >16_6_HC_humanized_657
QSLEESGGRLVTPGGSLRLSCAASGSDISSYHMGWVRQAPGKGLEWVSIIVSSGSA TABLE 11 -continued 16-6VH humanized sequences-IMGT-LigM DB (Abysis) clustered at 95%
(81 sequences)

YYATWAKGRFTISRDNSSLYLQMNSLRTEDSALYYCALNQYSGYGFSFWGQGS LV
TVSS (SEQ ID NO: 372)

>cl|MOBBABABA|2|115 >16_6_HC_humanized_1917 >16_6_HC_humanized_677
QSLEESGGGVVQPGRSLRLSCAASGSDISSYHMGWVRQAPGKGLEWVAIIVSSGSA
YYATWAKRRFTISRDNSTLYLQMNSLRAEDTAVYYCARNQYSGYGFSFWGQGTL
VTVSS (SEQ ID NO: 373)

>cl|POBBABABA|1|115 >16_6_HC_humanized_2038
QSLEESGGRLVTPGTPLTLTCTVSGSDISSYHMGWVRQAPGKGLEWVAIIVSSGSAY
YATWAKGRFTISRDNASLYLQMNSLRAEDTAVYYCARNQYSGYGFSFPTSGYYY
MDVS (SEQ ID NO: 374)

>cl|QOBBABABA|1|115 >16_6_HC_humanized_23
QSLLESGGDLVQPGGSLRLSCEASGSDISSYHMGWVRQAPGKGLEWVSIIVSSGSA
YYATWAKGRFTISRDKSTLFLQMHSLRVEDTAVYYCAKNQYSGYGFSFWGQGTT
VTVSS (SEQ ID NO: 375)

>cl|ROBBABABA|1|115 >16_6_HC_humanized_21
VQLVESGGGLVQPGGSLRLSCAASGSDISSYHMGWVRQAPGKGLEFVSIIVSSGSA
YYATWAKDRFTISRDNSTVYLQMDSLRTEDTAMYFCARNQYSGYGFSFWGQGTL
VTVSS (SEQ ID NO: 376)

>cl|SOBBABABA|1|115 >16_6_HC_humanized_469
VQLVESGGGLVQPGGSLRLSCAASGSDISSYHMGWVRQAPGKGLEWVAIIVSSGSA
YYATWAKGRFTISRDNTSLFLHMSSLRGEDTAIYYCARNQYSGYGFSFWGQGTLV
TVSS (SEQ ID NO: 377)

>cl|TOBBABABA|1|115 >16_6_HC_humanized_2008
QSLEESGGRLVTPGTSLRLSCAVSGSDISSYHMGWVRQAPGKGLEWVSIIVSSGSAY
YATWAKGRFTISRDNSTVYLQMNSLRAEDTAVFYCARNQYSGYGFSFWGQGTLV
TVSS (SEQ ID NO: 378)

>cl|VOBBABABA|1|115 >16_6_HC_humanized_1013
VQLVQSGGGVVQPGRSLRLSCEVSGSDISSYHMGWVRQAPGKGLEWVAIIVSSGSA
YYATWAKGRFTISRSNNTLYLQMNSLTAEDTALYFCARNQYSGYGFSFWGKGTTV
TVSS (SEQ ID NO: 379)

>cl|XOBBABABA|1|115 >16_6_HC_humanized_149
VQLVQSGPGLVKPSRTLSLTCTVSGSDISSYHMGWIRQPPGKGLEWIGIIVSSGSAY
YATWAQNRLTISTSKNQFSLKLASVTAADTAVYFCARNQYSGYGFSFWGQGTLVT
VSS (SEQ ID NO: 380)

>cl|YOBBABABA|1|115 >16_6_HC_humanized_113
LQLQESGPGLVKPSQTLSLTCSVSGSDISSYHMGWIRQHPGKGLEWIGIIVSSGSAYY
ATWAKSRITISTSKNQFSLKLTSVTAADTALYYCARNQYSGYGFSFWGRGTLVTVS
S (SEQ ID NO: 381)

>cl|BUBBABABA|1|115 >16_6_HC_humanized_965
VQLQESGPGLVKPSQTLSLTCTVSGSDISSYHMGWIRQHPGKGLEWIGIIVSSGSAY
YATWAKSRVTISADTSKISLKLSSVTAADTAVYYCARNQYSGYGFSFWGQGTTVT
VSS (SEQ ID NO: 382)

>cl|CUBBABABA|1|115 >16_6_HC_humanized_912
VQLQESGPGLVKPSQTLSLTCTVSGSDISSYHMGWIRQPPGKGLEWIGIIVSSGSAYY
ATWAKSRVLISTSKNQVSLKLSSVTAADTAVYYCARNQYSGYGFSFWGQGTTVTV
SS (SEQ ID NO: 383)

>cl|HUBBABABA|1|115 >16_6_HC_humanized_12
VQLVQSGGGVVQPGGSLRLSCAASGSDISSYHMGWVRQAPGKGLEWVAIIVSSGS
AYYATWAQGRVTISRDNSTVHLQITSLKSEDTAVYYCAKNQYSGYGFSFWGQGTL
VTVSS (SEQ ID NO: 384)

>cl|KUBBABABA|1|115 >16_6_HC_humanized_924
VQLVESGPGLVKPSQTLSLTCTVSGSDISSYHMGWFRQPPGKGLEWIGIIVSSGSAY
YATWAKSRVTISTSKNQVSLKLSPVTGADTAVYFCARNQYSGYGFSFWGQGTLVT
VSS (SEQ ID NO: 385)

>cl|LUBBABABA|1|115 >16_6_HC_humanized_273
VQLVQSGGGLVQPGGSLRLSCAASGSDISSYHMGWVRQASGKGLEWIGIIVSSGSA
YYATWAKGRFTVSRSQNSVFLQMNSLETEDTAVYYCARNQYSGYGFSFWGQGTL
VTVSS (SEQ ID NO: 386)

>cl|MUBBABABA|1|115 >16_6_HC_humanized_2032
QSLEESGGRLVTPGGSLRLSCAGSGSDISSYHMGWVRQAPGKGLEWVSIIVSSGSA
YYATWAEGRFTISRDNATLYLQMNSLRVEDTAVYYCATNQYSGYGFSFWGQGTL
VTVSS (SEQ ID NO: 387)

TABLE 11 -continued 16-6VH humanized sequences-IMGT-LigM DB (Abysis) clustered at 95%
(81 sequences)

>cl|NUBBABABA|1|115 >16_6_HC_humanized_879
QSLEESGGGLVQPGGSLRLSCTASGSDISSYHMGWVRQAPGKGLEWVSIIVSSGSA
YYATWAKGRFTISRDSSTLYLQMNNLRVEDTALYYCAHNQYSGYGFSFWGRGTQ
VTVSS (SEQ ID NO: 388)

>cl|PUBBABABA|1|115 >16_6_HC_humanized_267
QSLEQSGGGLVQPGESLRLSCAGSGSDISSYHMGWVRQAPGKGLEWVAIIVSSGSA
YYATWAKGRFTISRDNASLFLQMNSLRVEDTAVYYCARNQYSGYGFSFWGQGTL
VTVSS (SEQ ID NO: 389)

>cl|QUBBABABA|1|115 >16_6_HC_humanized_1992
QSLEESGGRLVTPGTPLTLTCTVSGSDISSYHMGWVRQAPGKGLVWVSIIVSSGSAY
YATWAKGRFTISRDNATLYLQMNSLRVEDTAVYYCARNQYSGYGFSFWGPGTLV
TVSS (SEQ ID NO: 390)

>cl|RUBBABABA|1|115 >16_6_HC_humanized_1995
QSLEESGGRLVTPGTPLTLTCTVSGSDISSYHMGWVRQAPGKGLEWVSIIVSSGSAY
YATWAKGRFTISRDNSTLYLQMNSLRAEDTAVYYCAKNQYSGYGFSFWGPGTLVT
VSS (SEQ ID NO: 391)

>cl|SUBBABABA|1|115 >16_6_HC_humanized_917
VQLQESGPGLVKPSQTLSLTCTVSGSDISSYHMGWIRQPPGKGLEWIGIIVSSGSAYY
ATWARSRITISETSKNLSLKLTSVTAADTAVYYCARNQYSGYGFSFWGQGTTVTVS
S (SEQ ID NO: 392)

>cl|TUBBABABA|1|115 >16_6_HC_humanized_1934
QSLEESGGRLVTPGTPLTLTCTVSGSDISSYHMGWVRQAPGKGLEWVSIIVSSGSAY
YATWAKGRFTISRDNASLYLQMNSLRAEDTAVYYCARNQYSGYGFSFGIFDYWVT
VSS (SEQ ID NO: 393)

>cl|VUBBABABA|1|115 >16_6_HC_humanized_200
VQLQESGPGLVKPSETLSLTCSVSGSDISSYHMGWIRQPAGKGLEWIGIIVSSGSAYY
ATWARSRVTMSMSKNHFSLKLRSVTAADTAVYFCARNQYSGYGFSFWGQGTLVT
VSS (SEQ ID NO: 394)

>cl|WUBBABABA|1|115 >16_6_HC_humanized_1977
QSLEESGGRLVTPGTPLTLTCTVSGSDISSYHMGWVRQAPGKGLEWVAIIVSSGSAY
YATWAKGRFTISRSKNTLYLQMNSLRAEDTAVYYCARNQYSGYGFSFTCPYFDYW
VSS (SEQ ID NO: 395)

>cl|XUBBABABA|1|115 >16_6_HC_humanized_2027
QSLEESGGRLVTPGTPLTLTCTVSGSDISSYHMGWVRQAPGKGLEWVAIIVSSGSAY
YATWAEGRFTISRDNSTLYLQMYSLRTEDTAVYYCARNQYSGYGFSFYYYGMGV
WVSS (SEQ ID NO: 396)

>cl|YUBBABABA|1|115 >16_6_HC_humanized_1958
VHLVESGGGVVQPGRSLRLSCAASGSDISSYHMGWVRQAPGKGLEWVAIIVSSGSA
YYATWAEGRFTISRDNSKLYLQMNSLRAEDSATYYCARNQYSGYGFSFFGPPYYY
YYMS (SEQ ID NO: 397)

>cl|ZUBBABABA|1|115 >16_6_HC_humanized_1949
QSLEESGGRLVTPGTPLTLTCTVSGSDISSYHMGWVRQAPGKGLEYVSIIVSSGSAY
YATWAKGRFTISRDNSTLYLQMSSLRAEDTAVYYCVKNQYSGYGFSFWGPGTLVT
VSS (SEQ ID NO: 398)

>cl|BACBABABA|1|115 >16_6_HC_humanized_1905
QSLEESGGRLVTPGTPLTLTCTVSGSDISSYHMGWVRQAPGKGLEWVSIIVSSGSAY
YATWAKGRFTISRDNSTLYLQMNSLRAEDTALYYCARNQYSGYGFSFVRGGYFYH
MDS (SEQ ID NO: 399)

TABLE 12

16-6 VL humanized sequences-IMGT-LigM DB (Abysis) clustered at 95%
(64 sequences)

>cl|CACBABABA|1|110 >16_6_LC_humanized_586
IVLTQTPSSLSASVGDRITITCQSSHSVYYGDWLAWYQQKPGKAPKLLIYRASNLAS
GVPSRFSGSRSGTDFTFTISSLRPEDIATYYCLGGYDDDGETAFGGGTKVEIK (SEQ
ID NO: 400)

>cl|DACBABABA|1|110 >16_6_LC_humanized_411
IVLTQSPSSLSASVGDRVTITCQSSHSVYYGDWLAWYQQKPGKAPNLLIYRASNLA
SGVPSRFSGSGSATDFTLTISSLQPEDFATYYCLGGYDDDGETAFGGGTRVEIK
(SEQ ID NO: 401)

TABLE 12 -continued 16-6 VL humanized sequences-IMGT-LigM DB (Abysis) clustered at 95% (64 sequences)

>c11FACBABABA|1|110 >16_6_LC_humanized_372
IQLTQSPSTLSASVGDRVTITCQSSHSVYYGDWLAWYQQKAGKAPTLLIYRASNLA
SGVPSRFSGSGSGTEFTLTISSLQPDDFATYYCLGGYDDDGETAFGQGTKVDIK
(SEQ ID NO: 402)

>cl|GACBABABA|1|110 >16_6_LC_humanized_1996
VVLTQTPSPVSTAVGGTVTLSCQSSHSVYYGDWLAWYQQKPGQAPRLLIYRASNL
ASGIPDRFSGSGSGTDFTLTISRLEPEDFAVYYCLGGYDDDGETAKGPGTEVVVK
(SEQ ID NO: 403)

>cl|HACBABABA|2|110 >16_6_LC_humanized_1907 >16_6_LC_humanized_716
LVMTQSPSSLSASEGDRVTITCQSSHSVYYGDWLAWYQQKPGRAPKLLIHRASNLA
SGVPSRFSGSGSGTEFTLTISGLQSEDFATYYCLGGYDDDGETAFGGGTTVDVK
(SEQ ID NO: 404)

>cl|LACBABABA|2|110 >16_6_LC_humanized_1945 >16_6_LC_humanized_1451
VELTQPPSPVSAAPGQKVTISCQSSHSVYYGDWLAWYQQLPGTAPKLLIYRASNLA
SGIPDRFSGSKSGTSATLGITGLQTGDEADYYCLGGYDDDGETAFGGGTRLTVL
(SEQ ID NO: 405)

>cl|NACBABABA|2|110 >16_6_LC_humanized_1004 >16_6_LC_humanized_283
IQLTQSPSSVSASVGDRVTITCQSSHSVYYGDWLAWYQQKPGKAPKLLIYRASNLA
SGVPSRFSGSGSGTDFALTISSLQPEDFATYYCLGGYDDDGETAFGQGTRLEIK
(SEQ ID NO: 406)

>cl|PACBABABA|1|110 >16_6_LC_humanized_1971
VVLTQTPSPVSTAVGGTVTITCQSSHSVYYGDWLAWYQQKSGKAPKLLIYRASNL
ASGVPSRFSGSGSGTDFTLTISSLQPEDFATYYCLGGYDDDGETAFGGGTEVVVK
(SEQ ID NO: 407)

>cl|QACBABABA|1|110 >16_6_LC_humanized_802
IRMTQSPSSFSASTGDRVTITCQSSHSVYYGDWLAWYQQKPGKAPKLLIYRASNLA
SGVPSRFSGSGSGTDFTLTISCLQSEDFATYYCLGGYDDDGETAFGGGTKVEIK
(SEQ ID NO: 408)

>cl|RACBABABA|1|110 >16_6_LC_humanized_609
IRLTQSPSFLSASVGDRVTITCQSSHSVYYGDWLAWYQQKPGKAPKLLIYRASNLA
SGVPSRFSGSGSGTDFTLTISTLQPEDFATYYCLGGYDDDGETAFGQGTKLEIK
(SEQ ID NO: 409)

>cl|SACBABABA|1|110 >16_6_LC_humanized_587
VVMTQSPSSLSASVGDRVTITCQSSHSVYYGDWLAWFQQKPGKAPNLLIYRASNL
ASGVPSRFSGSGSGTEFTLTISSLQPEDFATYYCLGGYDDDGETAFGQGTKVEIK
(SEQ ID NO: 410)

>cl|TACBABABA|1|110 >16_6_LC_humanized_305
IQLTQSPSSLSASVGDRVTITCQSSHSVYYGDWLAWFQQKPGKAPKSLIYRASNLAS
GVPSRFSGSGSGTDFTLTISSLQPEDSATYYCLGGYDDDGETAFGGGTKVEIK (SEQ
ID NO: 411)

>cl|VACBABABA|12|110 >16_6_LC_humanized_1877 >16_6_LC_humanized_860
>16_6_LC_humanized_213 >16_6_LC_humanized_902 >16_6_LC_human-
ized_334
IQLTQSPSSLSASVGDRVTITCQSSHSVYYGDWLAWYQQKPGKAPKLLIYRASNLA
SGVPSRFSGSGSGTDFTLTISSLQPEDFATYYCLGGYDDDGETAFGGGTKVEIK
(SEQ ID NO: 412)

>cl|WACBABABA|2|110 >16_6_LC_humanized_1012 >16_6_LC_humanized_65
IQLTQSPSTLSASVGDRVTITCQSSHSVYYGDWLAWYQQKPGKAPKLLIYRASNLA
SGVPSRFSGSGSGTEFTLTISSLQPDDFATYYCLGGYDDDGETAFGQGTKLEIK (SEQ
ID NO: 413)

>cl|XACBABABA|6|110 >16_6_LC_humanized_988 >16_6_LC_humanized_910
>16_6_LC_humanized_956 >16_6_LC_humanized_2056 >16_6_LC_human-
ized_672
IVLTQSPSSLSASVGDRVTITCQSSHSVYYGDWLAWYQQKPGKAPKLLIYRASNLA
SGVPSRFSGSGSGTDFTLTISSLQPEDFATYYCLGGYDDDGETAFGQGTRLEIK (SEQ
ID NO: 414)

>cl|CECBABABA|1|110 >16_6_LC_humanized_253
IVLTQSPSAMSASVGDRVTITCQSSHSVYYGDWLAWFQQKPGKAPKLLIYRASNLA
SGVPSRFSGSGSGTEFTLTISSLQPEDSATYYCLGGYDDDGETAFGQGTKVDIK
(SEQ ID NO: 415)

>cl|DECBABABA|1|110 >16_6_LC_humanized_218
IVMTQSPSSLSASVGDRVTITCQSSHSVYYGDWLAWYQQKPGKVPKLLIYRASNLA

TABLE 12 -continued 16-6 VL humanized sequences-IMGT-LigM DB (Abysis) clustered at 95%
(64 sequences)

SGVPSRFSGSGSGTDFTLTISSLQPEDVATYYCLGGYDDDGETAFGPGTKVEIK
(SEQ ID NO: 416)

>cl|GECBABABAI1|110 >16_6_LC_humanized_136
VVMTQSPSTLSASVGDRVTITCQSSHSVYYGDWLAWYQQKPGKAPKVLIYRASNL
ASGVPSRFSGSGSGTEFTLTISSLQPDDFASYYCLGGYDDDGETAFGPGTKVDIK
(SEQ ID NO: 417)

>cl|HECBABABA|1|110 >16_6_LC_humanized_129
IVMTQSPSSLSASVGDRVTITCQSSHSVYYGDWLAWYQHKPGKAPRLLTYRASNLA
SGVPSRFSGSGSGTDFTLTISSLQPDDFATYYCLGGYDDDGETAFGQGTKVEVK
(SEQ ID NO: 418)

>cl|KECBABABAI1|110 >16_6_LC_humanized_109
IQLTQSPSSVSASVGDTITITCQSSHSVYYGDWLAWYQQKPGKAPKLLIYRASNLAS
GVPSRFSGSRSGTDFTLTISSLQPEDFATYYCLGGYDDDGETAFGQGTKVEIK (SEQ
ID NO: 419)

>cl|LECBABABA|1|110 >16_6_LC_humanized_103
IVLTQSPSTLSASVGDRVTITCQSSHSVYYGDWLAWYQQKPGQAPKLLIYRASNLA
SGVPSRFSGSGSGTEFTLSINSLQPDDSATYFCLGGYDDDGETAFGQGTKVEIK
(SEQ ID NO: 420)

>cl|MECBABABA|1|110 >16_6_LC_humanized_954
IVLTQSPSTLSASVGDRVTITCQSSHSVYYGDWLAWYQQKPGKAPKLLIYRASNLA
SGVPSRFSGSGSGTEFTLTISSLQPDDFATYYCLGGYDDDGETAFGQGTKAEIK
(SEQ ID NO: 421)

>cl|PECBABABA|3|110 >16_6_LC_humanized_851 >16_6_LC_humanized_908
>16_6_LC_humanized_912
VVMTQSPSSLSASVGDRVTITCQSSHSVYYGDWLAWYQQKPGKAPKLLIYRASNL
ASGVPSRFSGSGSGTDFTLTISSLQPEDFATYYCLGGYDDDGETAFGGGTKVEIK
(SEQ ID NO: 422)

>cl|RECBABABA|1|110 >16_6_LC_humanized_17
IQLTQSPSSLSAAVGDRVTIACQSSHSVYYGDWLAWYQQKPGKAPKLLIYRASNLA
SGVPSRFSGSGSGTDFTLSISSLQPGDFATYYCLGGYDDDGETAFGGGTKVQMK
(SEQ ID NO: 423)

>cl|XECBABABA|2|110 >16_6_LC_humanized_108 >16_6_LC_humanized_946
IVLTQSPSSVSASVGDRVTITCQSSHSVYYGDWLAWYQQKPGKAPKLLIYRASNLA
SGVPSRFSGSGSGTDFTLTISSLQPEDFATYYCLGGYDDDGETAFGGGTKVEIK
(SEQ ID NO: 424)

>cl|ZECBABABA|1|110 >16_6_LC_humanized_882
VVLTQSPSSLSASVGDRVTITCQSSHSVYYGDWLAWYQQKPGKAPKLLIYRASNLA
SGVPSRFSGSGFGTDFTFTISSLQPEDSATYYCLGGYDDDGETAFGQGTKLEIK (SEQ
ID NO: 425)

>cl|BICBABABA|1|110 >16_6_LC_humanized_186
IQLTQSPSTLSASVGDRVTITCQSSHSVYYGDWLAWYQQKPGKAPKLLIYRASNLA
SGVPSRFSGSGSGTEFTLTISSLQPDDFATYYCLGGYDDDGETAFGQGTKVVVK
(SEQ ID NO: 426)

>cl|CICBABABA|1|110 >16_6_LC_humanized_2041
VVLTQTPSPVSTAVGGTVTITCQSSHSVYYGDWLAWYQQKPGKAPKLLIYRASNL
ASGVPSRFSGSGSGTDFTLTISCLQSEDFATYYCLGGYDDDGETAFGGGTEVVVK
(SEQ ID NO: 427)

>cl|DICBABABA|1|110 >16_6_LC_humanized_202
IRMTQSPSSLSASVGDRVTITCQSSHSVYYGDWLAWYQQKPGKVPKLLIYRASNLA
SGVPSRFSGSGSGTDFTLTISSLQPEDVATYYCLGGYDDDGETAFGPGTKVVVK
(SEQ ID NO: 428)

>cl|FICBABABA|1|110 >16_6_LC_humanized_192
VVMTQSPSSLSASVGDRVTITCQSSHSVYYGDWLAWYQQKPGKAPKLLIYRASNL
ASGVPSRFSGSGSGTDFTLTISSLQAEDFTTYYCLGGYDDDGETAFGQGTKVEFK
(SEQ ID NO: 429)

>cl|GICBABABA|2|110 >16_6_LC_humanized_1982 >16_6_LC_humanized_734
VELTQSPSSVSASVGDRVTITCQSSHSVYYGDWLAWYQQKPGKAPKLLIYRASNLA
SGVPSRFSGSGSGTDFSLTISSLQPEDSATYYCLGGYDDDGETAFGQGTKVEIK
(SEQ ID NO: 430)

TABLE 12 -continued 16-6 VL humanized sequences-IMGT-LigM DB (Abysis) clustered at 95%
(64 sequences)

>cl|KICBABABA|2|110 >16_6_LC_humanized_1944 >16_6_LC_humanized_1895
IELTQSPSTLSASVGDRVIISCQSSHSVYYGDWLAWYQQKPGKAPKLLIYRASNLAS
GVPSRFSGSGSGTEFSLTINSLQPDDFATYYCLGGYDDDGETAFGPGTKVDIK (SEQ
ID NO: 431)

>cl|NICBABABA|2|110 >16_6_LC_humanized_1938 >16_6_LC_humanized_762
VELTQSPDSLAVSLGERATINCQSSHSVYYGDWLAWYQQKPGQPPKLLIYRASNLA
SGVPDRFSGSGSGTDFTLTISSLQAEDVAVYYCLGGYDDDGETAFGGGTKVEIK
(SEQ ID NO: 432)

>cl|QICBABABA|2|110 >16_6_LC_humanized_2031 >16_6_LC_humanized_621
VELTQSPSSLSASVGDRVTITCQSSHSVYYGDWLAWYQQKPGKAPKLLIYRASNLA
SGVPSRFSGSGSGTDFTLTISSLQPEDFATYYCLGGYDDDGETAFGQGTKVEIK
(SEQ ID NO: 433)

>cl|SICBABABA|4|110 >16_6_LC_humanized_993 >16_6_LC_humanized_880
>16_6_LC_humanized_23 >16_6_LC_humanized_917
VVLTQSPSSLSASVGDRVTITCQSSHSVYYGDWLAWYQQKPGKAPKLLIYRASNLA
SGVPSRFSGSGSGTDFTLTISSLQPEDFATYYCLGGYDDDGETAFGPGTKVDIK
(SEQ ID NO: 434)

>cl|VICBABABA|1|110 >16_6_LC_humanized_920
IVMTQSPSSLSASVGDRVTITCQSSHSVYYGDWLAWYQQKPGKAPKLLIYRASNLA
SGVPSRFSGSGSGTDFTLTISSLQPEDIATYYCLGGYDDDGETAFGQGTKVEIK (SEQ
ID NO: 435)

>cl|WICBABABA|1|110 >16_6_LC_humanized_278
LVLTQSPSSLSASVGDRVTITCQSSHSVYYGDWLAWCQQKPGKSPTLLIYRASNLA
SGVPSRFSGSGSGTGFTLTISGLQPEDFATYYCLGGYDDDGETAFGGGTKVEIR
(SEQ ID NO: 436)

>cl|YICBABABA|1|110 >16_6_LC_humanized_169
IVLTQSPSFLSAFVGDRITITCQSSHSVYYGDWLAWYQQKPGKAPKLLIYRASNLAS
GVPSRFSGSGSGTEFTLTISGLQPEDFASYYCLGGYDDDGETAFGGGTKLEIK (SEQ
ID NO: 437)

>cl|ZICBABABA|1|110 >16_6_LC_humanized_994
IVLTQSPSSLSASVGDRVTITCQSSHSVYYGDWLAWYQQKPGKVPKLLIYRASNLA
SGVPSRFSGSGSGTDFTLTISSLQPEDVATYYCLGGYDDDGETAFGQGTKVEIK
(SEQ ID NO: 438)

>cl|BOCBABABA|1|110 >16_6_LC_humanized_975
IVLTQSPSTQSASVGDRVTITCQSSHSVYYGDWLAWYQQKPGKAPKLLIYRASNLA
SGVPSRFSGSGSGTEFTLTISSLQPDDFATYYCLGGYDDDGETAFGQGTKLEIK (SEQ
ID NO: 439)

>cl|DOCBABABA|1|110 >16_6_LC_humanized_230
VVLTQTPSPVSASVGDRVTITCQSSHSVYYGDWLAWYQQKPGKAPKVLIYRASNL
ASGVPSRFSGSGSGTDFTLTISTLQPEDFATYYCLGGYDDDGETAFGQGTKLEIK
(SEQ ID NO: 440)

>cl|GOCBABABA|1|110 >16_6_LC_humanized_1894
VVLTQTPSPVSTAVGDRVTITCQSSHSVYYGDWLAWYRQKPGKVPKLLIYRASNL
ASGVPSRFSGSGSGTDFTLTISSLQPEDVATYYGLGGYDDDGETAFGGGTEVVK
(SEQ ID NO: 441)

>cl|LOCBABABA|1|110 >16_6_LC_humanized_657
VVLTQTPSPVSTSVGDRVSITCQSSHSVYYGDWLAWYQQKPGKAPKLLIYRASNLA
SGVPSRFSGSGSGTDFTLTITSLQPVDFATYYCLGGYDDDGETAFGPGTTVDAK
(SEQ ID NO: 442)

>cl|MOCBABABA|2|110 >16_6_LC_humanized_1917 >16_6_LC_humanized_677
VVLTQSPSFLSASVGDRVTITCQSSHSVYYGDWLAWYQQKPGKAPKLLIYRASNLA
SGVPSRFSGSGSGTEFTLTISSLQ
PEDFATYYCLGGYDDDGETAFGQGTRLEIK (SEQ ID NO: 443)

>cl|POCBABABA|1|110 >16_6_LC_humanized_2038
VVLTQTPSPVSTAVGGRVTITCQSSHSVYYGDWLAWYQQKPGKAPKLLIYRASNL
ASGVPSRFSGSGSGTEFTLTISSLQDKPFATYYCLGGYDDDGETAFGGGTEVVK
(SEQ ID NO: 444)

>cl|ROCBABABA|1|110 >16_6_LC_humanized_21
IQMTQSPSSLSASVGDRVTITCQSSHSVYYGDWLAWYQQKPGKAPKVLIYRASNLA
SGVPSRFSGSGSGTDFTLTISSLQPEDFATYYCLGGYDDDGETAFGPGTKVEVK
(SEQ ID NO: 445)

TABLE 12 -continued 16-6 VL humanized sequences-IMGT-LigM DB (Abysis) clustered at 95%
(64 sequences)

>cl|SOCBABABA|1|110 >16_6_LC_humanized_469
IVLTQSPSLLSASIGDRVTIPCQSSHSVYYGDWLAWYQQKPGKAPKLLIYRASNLAS
GVPSRFSGSGSGTEFTLTISSLQPEDFATYYCLGGYDDDGETAFGGGTKVDIK (SEQ
ID NO: 446)

>cl|TOCBABABA|1|110 >16_6_LC_humanized_2008
VVLTQTPSPVSTAVGGRVTITCQSSHSVYYGDWLAWYQQKPGKAPKLLIYRASNL
ASGVPSRFSGSGSGTDFTLTIGSLQPEDFAAYFCLGGYDDDGETAFGGGTKVEIK
(SEQ ID NO: 447)

>cl|WOCBABABA|1|110 >16_6_LC_humanized_168
IVNITQSPSTLSASVGDRVTITCQSSHSVYYGDWLAWYQQKPGKAPKLLIYRASNLA
SGVPSRFSGSGSGTEFTLTISGLQPEDFATYYCLGGYDDDGETAFGGGTKLEIK
(SEQ ID NO: 448)

>cl|XOCBABABA|1|110 >16_6_LC_humanized_149
IVLTQSPSSLSASVGDRVTITCQSSHSVYYGDWLAWYQQKPGKAPKRLIYRASNLA
SGVPSRFSGSGSGTEFTLTISGLQPEDIATYYCLGGYDDDGETAFGQGTKVEIK (SEQ
ID NO: 449)

>cl|YOCBABABA|1|110 >16_6_LC_humanized_113
IVLTQSPSSVSASVGDRVTITCQSSHSVYYGDWLAWYQLKPGKAPKLLINRASNLA
SGVPSRFSGSGSGTDFTLTISGLQPEDFATYYCLGGYDDDGETAFGPGTTVDIK
(SEQ ID NO: 450)

>cl|ZOCBABABA|4|110 >16_6_LC_humanized_978 >16_6_LC_humanized_965
>16_6_LC_humanized_924 >16_6_LC_humanized_879
IVLTQSPSSLSASVGDRVTITCQSSHSVYYGDWLAWYQQKPGKAPKLLIYRASNLA
SGVPSRFSGSGSGTDFTLTISSLQPEDFATYYCLGGYDDDGETAFGGGTKVEIK
(SEQ ID NO: 451)

>cl|GUCBABABA|1|110 >16_6_LC_humanized_818
VVLTQTPSSVSASVGDRVTITCQSSHSVYYGDWLAWYQQKPGKAPKLLIYRASNL
ASGVPSRFSGSGSGTDFTLTISSLQPEDFATYYCLGGYDDDGETAFGQGTKVEIK
(SEQ ID NO: 452)

>cl|HUCBABABA|1|110 >16_6_LC_humanized_12
VVMTQSPSTVSASVGDRVTLTCQSSHSVYYGDWLAWYQQKPGQPPKLLIYRASNL
ASGVPDRFSGSGSGTDFTLTISSLQADDFATYYCLGGYDDDGETAFGQGTKVEIK
(SEQ ID NO: 453)

>cl|LUCBABABA|1|110 >16_6_LC_humanized_273
LVMTQSPSSLSASVGDRVTITCQSSHSVYYGDWLAWYQQKPGEAPKLLIYRASNLA
SGVPSRFSGSGSGTDFTLTISGLQSEDFATYYCLGGYDDDGETAFGQGTKVEIK
(SEQ ID NO: 454)

>cl|MUCBABABA|1|110 >16_6_LC_humanized_2032
VVLTQTPSPVSTAVGGTGPINCQSSHSVYYGDWLAWYQQKPGQPPKLLIYRASNLA
SGVPDRFSGSGSGTDFTLTISSLQAEDVAVYYCLGGYDDDGETAFGGGTKLEIK
(SEQ ID NO: 455)

>cl|PUCBABABA|1|110 >16_6_LC_humanized_267
VVLTQSPSTLAASVGDRVTITCQSSHSVYYGDWLAWYQQKPGKAPKLLIYRASNL
ASGVPSRFSGSGSGTEFTLTISSLQPDDFATYYCLGGYDDDGETAFGQGTKVEVK
(SEQ ID NO: 456)

>cl|QUCBABABA|1|110 >16_6_LC_humanized_1992
VVLTQTPSPVSTAVGDRVTITCQSSHSVYYGDWLAWYQQKPGKAPKLLIYRASNL
ASGVPSRFSGSGSGTDFTLTISSLQPEDFATYYCLGGYDDDGETAFGGGTEVVK
(SEQ ID NO: 457)

>cl|RUCBABABA|1|110 >16_6_LC_humanized_1995
VVLTQTPSPVSTAVGGTVTINCQSSHSVYYGDWLAWYQQKPGQPXKLLIYRASNL
ASGVPDRFSGSGSGTDFTLTISSLQAEDVAVYYCLGGYDDDGETAFGQGTEVVK
(SEQ ID NO: 458)

>cl|TUCBABABA|2|110 >16_6_LC_humanized_1934 >16_6_LC_humanized_1977
VVLTQTPSPVSTAVGGTVTITCQSSHSVYYGDWLAWYQQKPGKAPKLLIYRASNL
ASGVPSRFSGSGSGTDFTFTISSLQPEDIATYYCLGGYDDDGETAFGGGTEVVK
(SEQ ID NO: 459)

>cl|VUCBABABA|1|110 >16_6_LC_humanized_200
VVLTQTPSPVSTAVGERATINCQSSHSVYYGDWLAWYQQKPGQPPKLLIYRASNLA
SGVPDRFSGTGSGTDFTLTISSLQAEDVAVYYCLGGYDDDGETAFGGGTKVVVK
(SEQ ID NO: 460)

TABLE 12 -continued 16-6 VL humanized sequences-IMGT-LigM DB (Abysis) clustered at 95% (64 sequences)

>cl|XUCBABABA|1|110 >16_6_LC_humanized_2027
VVLTQTPSPVSTAVGGTVTITCQSSHSVYYGDWLAWYQQKPGKAPKRLIYRASNL
ASGVPSRFSGSGSGTEFTLTISSLQPEDFATYYXLGGYDDDGETAFGGGTEVVVK
(SEQ ID NO: 461)

>cl|YUCBABABA|2|110 >16_6_LC_humanized_1958 >16_6_LC_humanized_1949
VVLTQTPSPVSTAVGGTVTIPCQSSHSVYYGDWLAWYQQKPGKAPKLLIYRASNL
ASGVPSRFSGSGSGTEFTLTISSLQPDDFATYYCLGGYDDDGETAFGGGTEVVVK
(SEQ ID NO: 462)

>cl|BADBABABA|1|110 >16_6_LC_humanized_1905
VVLTQTPSPVSTAVGGTVTINCQSSHSVYYGDWLAWYQQKPGQPPKLLIYRASNL
ASGVPDRFSGSGSGTDFTLTISSLQAEDVAVYYCLGGYDDDGETAFGGGTEVVVK
(SEQ ID NO: 463)

TABLE 13

16-6 VH humanized sequences-germline database clustered at 90% (3 sequences)

>cl|CABBABABA|43|115 >16_6_HC_humanized_775
>16_6_HC_humanized_722 >16_6_HC_humanized_563
>16_6_HC_humanized_139 >16_6_HC_humanized_988
VQLVESGGGLVQPGGSLRLSCAASGSDISSYHMGWVRQAPGKGLEWVSI
IVSSGSAYYATWAKGRFTISRDNSTLYLQMNSLRAEDTAVYYCARNQYS
GYGFSFWGPGTLVTVSS (SEQ ID NO: 464)

>cl|DABBABABA|39|115 >16_6_HC_humanized_724
>16_6_HC_humanized_565 >16_6_HC_humanized_141
>16_6_HC_humanized_990 >16_6_HC_humanized_985
VQLVESGGGLVQPGGSLRLSCAASGSDISSYHMGWVRQAPGKGLEWVGI
IVSSGSAYYATWAKGRFTISRSKNTLYLQMNSLKTEDTAVYYCTRNQYS
GYGFSFWGPGTLVTVSS (SEQ ID NO: 465)

TABLE 13 -continued 16-6 VH humanized sequences-germline database clustered at 90% (3 sequences)

>cl|REBBABABA|18|115 >16_6_HC_humanized_365
>16_6_HC_humanized_364 >16_6_HC_humanized_363
>16_6_HC_humanized_360 >16_6_HC_humanized_359
VQLQESGPGLVKPSETLSLTCTVSGSDISSYHMGWIRQPPGKGLEWIGI
IVSSGSAYYATWAKSRVTISTSKNQFSLKLSSVTAADTAVYYCARNQYS
GYGFSFWGPGTLVTVSS (SEQ ID NO: 466)

TABLE 14

16-6 VL humanized sequences-germline database clustered at 90% (1 sequences)

>cl|CACBABABA|100|110 >16_6_LC_humanized_775
>16_6_LC_humanized_724 >16_6_LC_humanized_722
>16_6_LC_humanized_565 >16_6_LC_humanized_563
VVLTQSPSSLSASVGDRVTITCQSSHSVYYGDWLAWYQQKPGKAPKLL
IYRASNLASGVPSRFSGSGSGTDFTLTISSLQPEDFATYYCLGGYDDD
GETAFGGGTEVVVK (SEQ ID NO: 467)

TABLE 15

16-6 VH humanized sequences-germline database clustered at 95% (10 sequences)

>cl|CABBABABA|13|115 >16_6_HC_humanized_775 >16_6_HC_humanized_722
>16_6_HC_humanized_563 >16_6_HC_humanized_139 >16_6_HC_humanized_987
VQLVESGGGLVQPGGSLRLSCAASGSDISSYHMGWVRQAPGKGLEYVSIIVSSGSA
YYATWAKGRFTISRDNSTLYLQMGSLRAEDMAVYYCARNQYSGYGFSFWGPGTL
VTVSS (SEQ ID NO: 468)

>cl|DABBABABA|12|115 >16_6_HC_humanized_724 >16_6_HC_humanized_565
>16_6_HC_humanized_141 >16_6_HC_humanized_989 >16_6_HC_humanized_936
VQLVESGGGLVQPGGSLRLSCAASGSDISSYHMGWVRQAPGKGLEWVGIIVSSGSA
YYATWAKGRFTISRSKNSLYLQMNSLKTEDTAVYYCARNQYSGYGFSFWGPGTLV
TVSS (SEQ ID NO: 469)

>cl|MABBABABA|9|115 >16_6_HC_humanized_990 >16_6_HC_humanized_937
>16_6_HC_humanized_672 >16_6_HC_humanized_407 >16_6_HC_humanized_248
VQLVESGGGLVQPGGSLKLSCAASGSDISSYHMGWVRQASGKGLEWVGIIVSSGSA
YYATWAKGRFTISRSKNTAYLQMNSLKTEDTAVYYCTRNQYSGYGFSFWGPGTLV
TVSS (SEQ ID NO: 470)

>cl|NABBABABA|27|115 >16_6_HC_humanized_988 >16_6_HC_humanized_935
>16_6_HC_humanized_670 >16_6_HC_humanized_405 >16_6_HC_humanized_246
VQLVESGGGLVQPGGSLRLSCAASGSDISSYHMGWVRQAPGKGLEWVSIIVSSGSA
YYATWAKGRFTISRDNSTLYLQMNSLRAEDTAVYYCARNQYSGYGFSFWGPGTL
VTVSS (SEQ ID NO: 471)

TABLE 15 -continued 16-6 VH humanized sequences-germline database clustered at 95%
(10 sequences)

>cl|PABBABABA|9|115 >16_6_HC_humanized_985 >16_6_HC_humanized_932
>16_6_HC_humanized_667 >16_6_HC_humanized_402 >16_6_HC_humanized_243
VQLVESGGGLVQPGRSLRLSCTASGSDISSYHMGWFRQAPGKGLEWVGIIVSSGSA
YYATWAKGRFTISRSKSIAYLQMNSLKTEDTAVYYCTRNQYSGYGFSFWGPGTLV
TVSS (SEQ ID NO: 472)

>cl|QABBABABA|9|115 >16_6_HC_humanized_973 >16_6_HC_humanized_920
>16_6_HC_humanized_655 >16_6_HC_humanized_390 >16_6_HC_humanized_231
VQLVESGGGLVKPGGSLRLSCAASGSDISSYHMGWVRQAPGKGLEWVGIIVSSGSA
YYATWAKGRFTISRSKNTLYLQMNSLKTEDTAVYYCTTNQYSGYGFSFWGPGTLV
TVSS (SEQ ID NO: 473)

>cl|REBBABABA|12|115 >16_6_HC_humanized_365 >16_6_HC_humanized_364
>16_6_HC_humanized_363 >16_6_HC_humanized_360 >16_6_HC_humanized_312
VQLQESGPGLVKPSETLSLTCTVSGSDISSYHMGWIRQPPGKGLEWIGIIVSSGSAYY
ATWAKSRVTISTSKNQFSLKLSSVTAADTAVYYCARNQYSGYGFSFWGPGTLVTV
SS (SEQ ID NO: 474)

>cl|WEBBABABA|3|115 >16_6_HC_humanized_359 >16_6_HC_humanized_306
>16_6_HC_humanized_41
LQLQESGSGLVKPSQTLSLTCAVSGSDISSYHMGWIRQPPGKGLEWIGIIVSSGSAYY
ATWAKSRVTISRSKNQFSLKLSSVTAADTAVYYCARNQYSGYGFSFWGPGTLVTV
SS (SEQ ID NO: 475)

>cl|XEBBABABA|3|115 >16_6_HC_humanized_357 >16_6_HC_humanized_304
>16_6_HC_humanized_39
VQLQESGPGLVKPPGTLSLTCAVSGSDISSYHMGWVRQPPGKGLEWIGIIVSSGSAY
YATWAKSRVTISKSKNQFSLKLSSVTAADTAVYCCARNQYSGYGFSFWGPGTLVT
VSS (SEQ ID NO: 476)

>cl|CIBBABABA|3|115 >16_6_HC_humanized_343 >16_6_HC_humanized_290
>16_6_HC_humanized_25
VQLVESGGGVVQPGRSLRLSCAASGSDISSYHMGWVRQAPGKGLEWVAIIVSSGSA
YYATWAKGRFTISRDNSTLYLQMNSLRAEDTAVYYCARNQYSGYGFSFWGPGTL
VTVSS (SEQ ID NO: 477)

TABLE 16

16-6 VL humanized sequences-germline database clustered at 95%
(7 sequences)

>cl|CACBABABA|3|110 >16_6_LC_humanized_775 >16_6_LC_humanized_724
>16_6_LC_humanized_722
VVLTQSPSSLSASVGDRVTITCQSSHSVYYGDWLAWYQQKPGKAPKLLIYRASNLA
SGVPSRFSGSGSGTDFTFTISSLQPEDIATYYCLGGYDDDGETAFGGGTEVVVK
(SEQ ID NO: 478)

>cl|GACBABABA|2|110 >16_6_LC_humanized_565 >16_6_LC_humanized_563
VVLTQSPSSLSASVGDRVTITCQSSHSVYYGDWLAWYQQKPGKAPKRLIYRASNLA
SGVPSRFSGSGSGTEFTLTISSLQPEDFATYYCLGGYDDDGETAFGGGTEVVVK
(SEQ ID NO: 479)

>cl|KACBABABA|2|110 >16_6_LC_humanized_141 >16_6_LC_humanized_139
VVLTQSPSSFSASTGDRVTITCQSSHSVYYGDWLAWYQQKPGKAPKLLIYRASNLA
SGVPSRFSGSGSGTDFTLTISCLQSEDFATYYCLGGYDDDGETAFGGGTEVVVK
(SEQ ID NO: 480)

>cl|MACBABABA|62|110 >16_6_LC_humanized_990 >16_6_LC_humanized_988
>16_6_LC_humanized_985 >16_6_LC_humanized_973 >16_6_LC_humanized_937
VVLTQSPSSVSASVGDRVTITCQSSHSVYYGDWLAWYQQKPGKAPKLLIYRASNL
ASGVPSRFSGSGSGTDFTLTISSLQPEDFATYYCLGGYDDDGETAFGGGTEVVVK
(SEQ ID NO: 481)

>cl|WACBABABA|6|110 >16_6_LC_humanized_672 >16_6_LC_humanized_670
>16_6_LC_humanized_667 >16_6_LC_humanized_655 >16_6_LC_humanized_671
VVLTQSPSSLSASVGDRVTITCQSSHSVYYGDWLAWYQQKPGKVPKLLIYRASNLA
SGVPSRFSGSGSGTDFTLTISSLQPEDVATYYCLGGYDDDGETAFGGGTEVVVK
(SEQ ID NO: 482)

>cl|GECBABABA|6|110 >16_6_LC_humanized_248 >16_6_LC_humanized_246
>16_6_LC_humanized_243 >16_6_LC_humanized_231 >16_6_LC_humanized_247
VVLTQSPSFLSASVGDRVTITCQSSHSVYYGDWLAWYQQKPGKAPKLLIYRASNLA
SGVPSRFSGSGSGTEFTLTISSLQPEDFATYYCLGGYDDDGETAFGGGTEVVVK
(SEQ ID NO: 483)

TABLE 16 -continued 16-6 VL humanized sequences-germline database clustered at 95%
(7 sequences)

>c1|YICBABABA|19|110 >16_6_LC_humanized_47 >16_6_LC_humanized_46
>16_6_LC_humanized_45 >16_6_LC_humanized_42 >16_6_LC_humanized_41
VVLTQSPSTLSASVGDRVTITCQSSHSVYYGDWLAWYQQKPGKAPKLLIYRASNLA
SGVPSRFSGSGSGTEFTLTISSLQPDDFATYYCLGGYDDDGETAFGGGTEVVVK
(SEQ ID NO: 484)

Example 5: Use of an Anti-Linker Antibody for Purifying Macromolecules and Cells The antigen binding molecules disclosed herein are antigen binding molecules, such as antibodies, which specifically bind to the sequence GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), molecules comprising these sequences and cells presenting such molecules, polynucleotides encoding such antigen binding molecules, as well as humanized forms of the antigen binding molecules. An antigen binding molecule (e.g., an antibody) disclosed herein can thus be used to purify a molecule, such as, macromolecule, polymer, cell, material, etc., displaying an epitope that is recognized by the antigen binding molecules disclosed herein (e.g., GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500)).

In one embodiment, an antigen binding molecule disclosed herein (e.g., Clones 8 and/or 16 and fragments thereof) can be attached to beads, attached to or associated with a resin, which can be disposed in a column or other structure. A sample comprising a molecule comprising all or a fragment of GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) can then be contacted with the beads, resin, etc. to which the antigen binding molecule was attached or with which an antigen binding molecule was associated. This allows the formation of an association or binding complex comprising the antigen binding molecule and the molecule comprising all or a fragment of GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500). The beads or resin can then be washed with a suitable solution, such as a buffer solution (e.g., PBS, HEPES, MOPS, Tris, Tricine, etc) having a pH selected to maintain the stability of the molecule comprising all or a fragment of GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500). The washing can remove unwanted and unbound components of the sample. Following the washing step, the molecule comprising all or a fragment of the GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) can then be eluted from the antigen binding molecules using an elution buffer and conditions selected to disrupt any association or binding complexes formed. Examples of suitable elution buffers include incubation with peptide epitope in molar excess, 0.1M glycine, pH 2.5-3.0, and 0.1M citric acid, pH 3.0, 50-100 mM triethylamine or triethanolamine, pH 11.5, 3.5-4.0M magnesium chloride, pH 7.0 in 10 mM Tris, 2-6M guanidine, and 2-8M urea, or a buffer solution around pH 7-8, including, but not limited to, 10 mM Tris, HEPES, or 1×PBS, containing free peptide GSTSGSGKPGSGEGSTKG and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500). During the elution step, eluted molecules, cells and moieties of interest comprising all or a fragment of GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) is collected, and purity can be subsequently checked by running a sample on an SDS polyacrylamide gel.

In another embodiment, an antigen binding molecule can be disposed in solution with any molecular entity displaying the epitope, and purified from a mixed population of molecules, cells, etc. and eluted from the beads, resin, or free antibody by washing with 300-500 mM sodium chloride or lowering the pH and neutralizing with 1 M Tris, for proteins, or phosphate buffer, or with buffer containing free peptide, such as GSTSGSGKPGSGEGSTKG and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500). Subsequently, dialysis can be used to return materials to desired buffer conditions.

In a specific embodiment, cells displaying a molecule comprising all or a fragment of GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) can be incubated with magnetic beads (e.g., DYNABEADS) with which an antigen binding molecule disclosed herein has been associated. Preferably the incubation is performed under conditions that both allow for the formation of binding complexes/associations, such as under physiological conditions, in the presence of a media selected for this purpose (e.g., RPMI-1640).

Cells bound by the beads (which will be presenting molecules comprising GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500)) are then separated from cells not displaying a molecule comprising GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500). In one embodiment, the beads can be washed with media, such as RPMI-1640 supplemented with 10% FBS, in the presence of a magnet.

Selected cells, i.e., those presenting molecules that comprise GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) can then be separated from the beads: First, selected cells are grown out in media. After growing out cells for 48 hours, the magnetic beads can be separated from cells in solution and discarded, leaving a pure population of cells presenting desired molecule.

In an alternative embodiment, the beads are not magnetic, and in this embodiment, the above steps can also be followed and adapted to maintain cell integrity, but also to allow separation of bead-bound cells from non-bead bound cells.

In an alternative embodiment, an antigen binding molecule disclosed herein (e.g., Clones 8 and/or 16 and fragments thereof) can be His-tagged (i.e., labeled with a short polyhistidine sequence), thereby facilitating the separation of cells using a resin comprising a transition metal ion such as $Ni^{2+}$, $Co^{2+}$, $Cu^{2+}$ or $Zn^{2+}$, which are immobilized on the resin. The antigen binding molecules can then be incubated with cells known or suspected to be presenting a molecule comprising GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500) under conditions suitable for the formation of complexes comprising the cells and the antigen binding molecules. Following the incubation, the cells are contacted with the resin, which can be disposed in a solid structure such as a welled plate, column or other structure. The antigen binding molecule-cell complexes can then be separated from one another by washing with imidazole, which will be of a higher concentration than any imidazole included in any solutions used in the formation of the binding complexes. Eluted cells can then be spun down, washed in RPMI or other suitable media, and then resuspended in media.

Example 6: Sorting of CAR-Positive T-Cells

PBMCs were isolated from healthy donor leukopaks (Hemacare™) using Ficoll-Paque density centrifugation per manufacturer's instructions. PBMCs were stimulated using OKT3 (50 ng/ml, Miltenyi Biotec™) in R10 media+IL-2 (300 IU/ml, Proleukin®, Prometheus® Therapeutics and Diagnostics). Two days after stimulation, CAR T cells were generated through viral transduction of these activated primary human T cells. Transduction was performed using either a retro- (pMSVG vector) or lentivirus (pGAR vector) depending upon the origin of the CARs used in the screening. Confirmation of CAR construct expression and viral transduction efficiency was determined using Protein L conjugated to phycoerythrin (PE) or fluorescein isothiocyanate (FITC).

Figure 10:
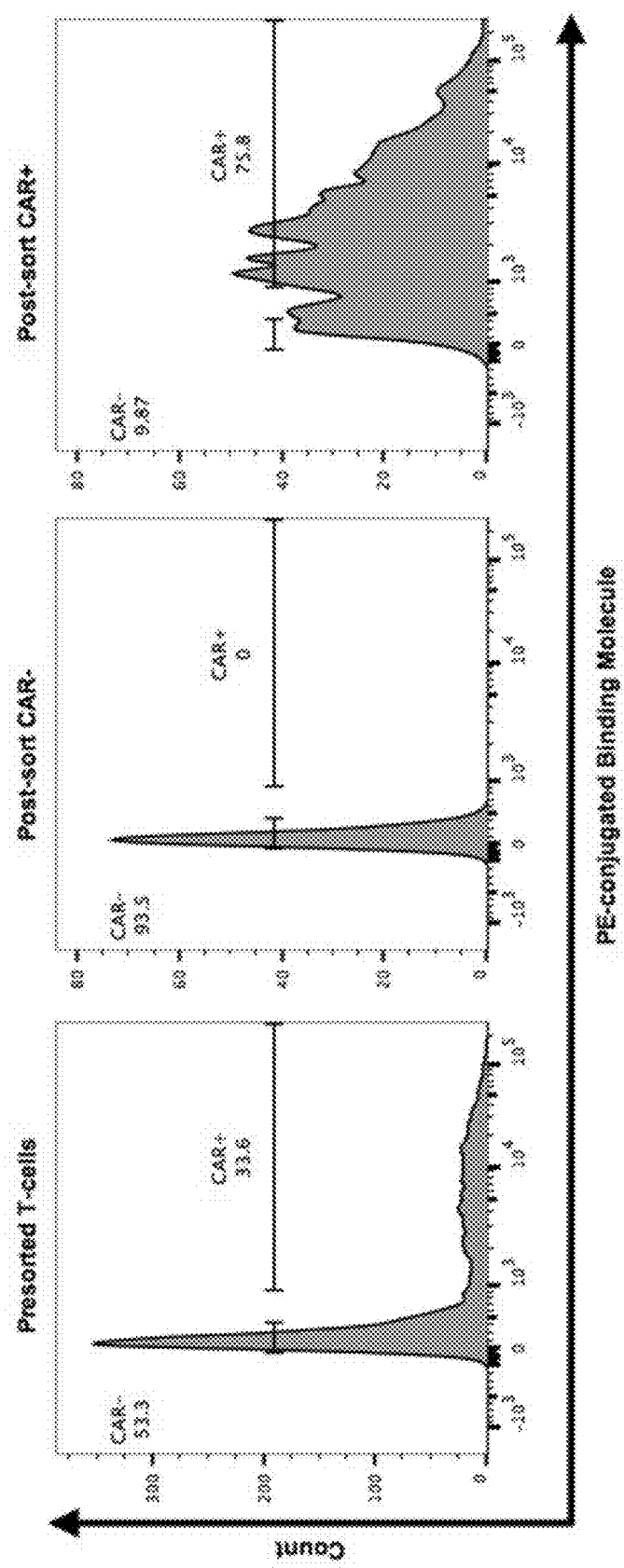
FIG. 10 is the result of Fluorescense activated cell sorting (FACS) plots showing CAR-T cells that were negatively- and positively-gated using the antigen binding molecules disclosed herein.

Cultured CAR T-cells were removed from culture, washed with PBS, and incubated with the anti-linker antibody conjugated to PE for 30 minutes in stain buffer comprising PBS pH 7.4, 0.2% (w/v) bovine serum albumin, and 0.09% sodium azide. Cells were washed two times in stain buffer, resuspended and sorted with a BD Aria cell sorter. Negatively- and positively-gated cells were analyzed post sort for composition (FIG. 10).

Example 7: Stimulating/Activating CAR-Positive T Cells Using an Antigen Binding Molecule T-cells are often stimulated through their T-cell receptors (TCR) using an anti-CD3 antibody, such as clone OKT3, a mouse anti-CD3 antibody, along with an anti-CD28 antibody to provide a second signal or costimulatory signal. CAR T-cells, upon interaction with cognate antigen can provide both signals through their intracellular CD3zeta and costimulatory domain, such as CD28.

Accordingly, also provided is a method of activating CAR-positive T cells presenting a molecule comprising a specific epitope recognized by a specific antigen binding molecule (e.g., an antigen binding molecule, such as an antibody that recognizes a molecule comprising GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500)), such as those disclosed herein: Clone 8 and/or 16, and fragments thereof). This method can be adapted for any antibody recognizing a protein of interest on a T cell containing an activation domain, such as a chimeric antigen receptor (CAR) comprising GSTSGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500). Activation can be achieved using plate-bound, bead-bound, polymer-bound, or other form of the antibody that specifically recognizes an extracellular component of the CAR or similar molecule.

In this Example, we show that CAR+ T-cells can be selectively stimulated in vitro with an anti-linker antibody, such as those provided herein. For purposes of comparison, OKT3 antibodies, which are commonly used to activate T cells in vitro (see, e.g., Landegren et al., (1984) *Eur. J. Immunol.* 14(4):325-28) were used to stimulate all T-cells. Bags, flasks, plates, or other vessels for growing T-cells can be used for the stimulation or, as described herein, welled plates can also be used for the stimulation.

In one instance, CAR-T cells were sorted, as described in EXAMPLE 4 (FIG. 10), and mixed to form populations of cells at fixed percentages of CAR-positive cells; these cells were then allowed to recover from sort for 24 hours at 37° C. in OpTmizer media. 12-well tissue culture treated plates were incubated with either OKT3 or anti-linker antibody at 1.5 µg/mL in HBSS for 2 hours at 37° C., and washed three times with HBSS. 0.5e6 T-cells of defined populations were added in 2 mL of OpTmizer media with IL-2 to the plates pre-coated with antibody and cells were incubated for up to 1 week at 37° C. and sampled at various time points.

Figure 11:
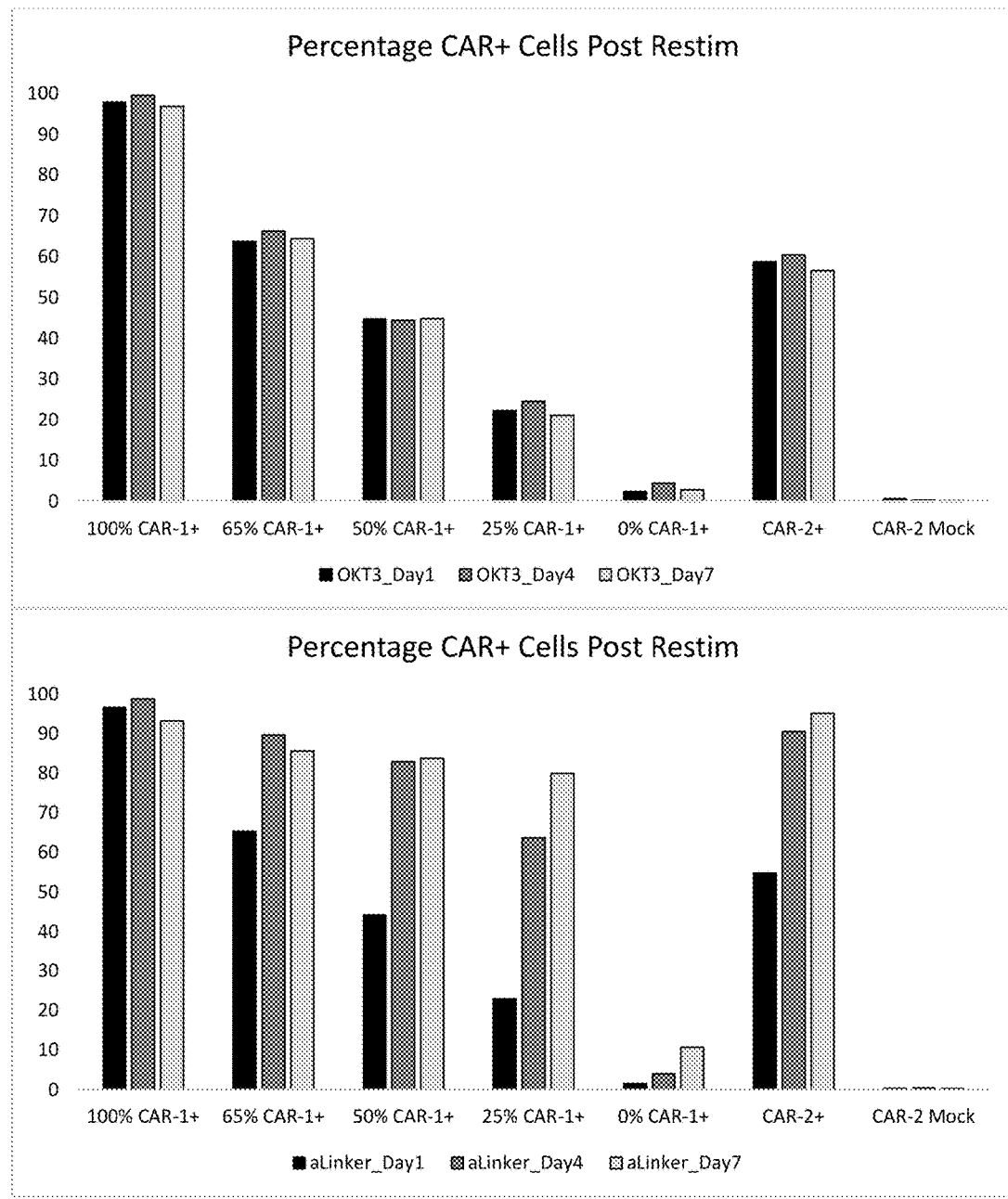
FIG. 11 is a series of bar charts showing the results of in vitro stimulation of CAR-T cells using OKT3 antibodies and the anti-linker antibody disclosed herein. Whereas OKT3 activates all T cells in a given population, the anti-linker MAb preferentially activates and thereby enriches the population of CAR-T cells over time as shown by using a gradient of CAR+ to CAR− population ratios.
Figure 12A:
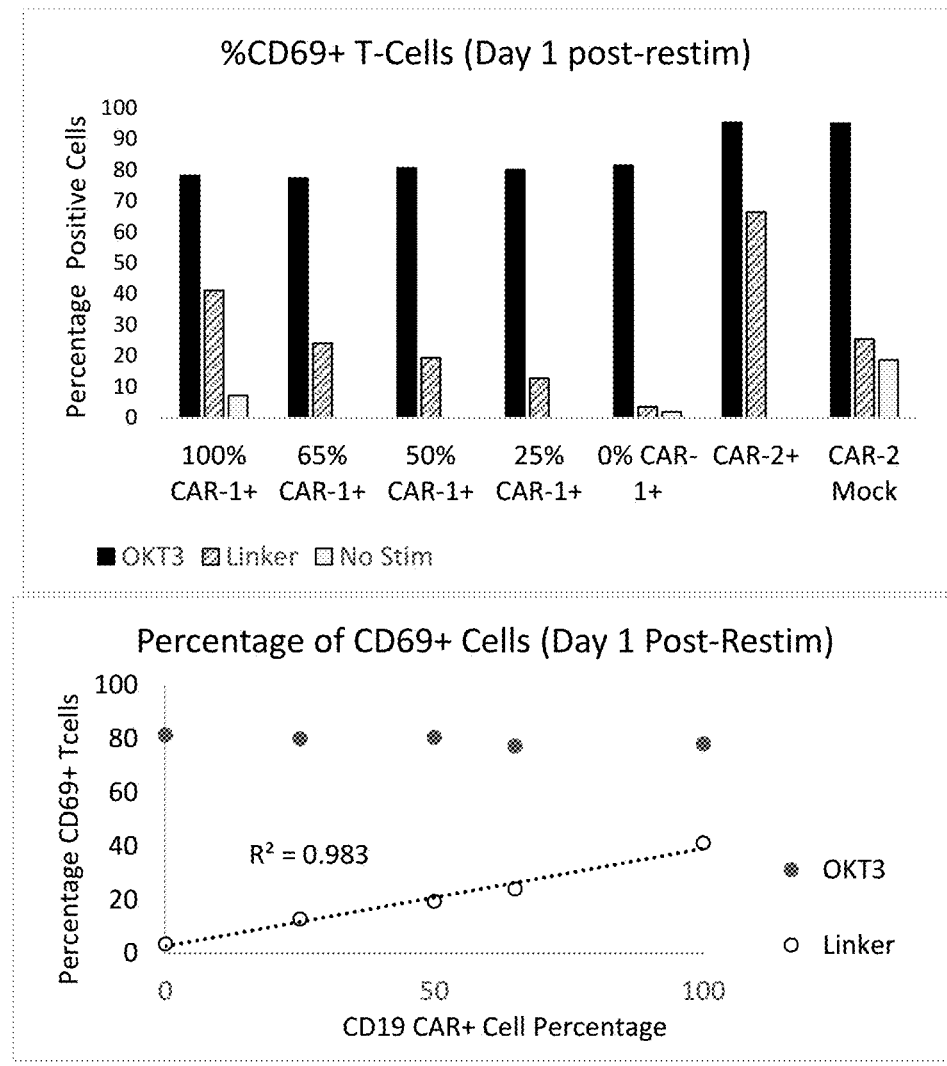
FIGS. 12A and 12B are a series of bar charts and plots showing the effects of in vitro stimulation of CAR-T positive cells; the figures show that that OKT3 antibodies stimulated all T-cells, while the antigen binding molecules disclosed herein selectively stimulated only CAR-T positive cells.
Figure 12B:
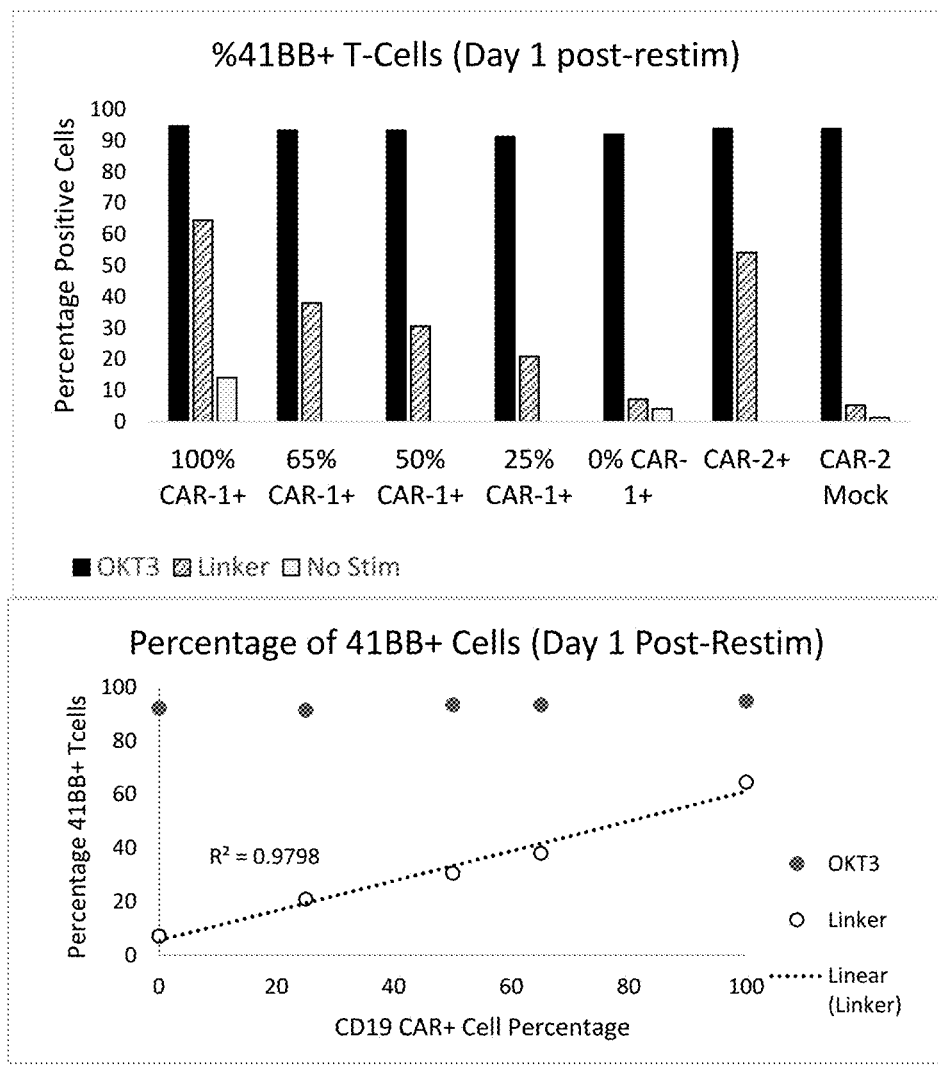

Samples were subject to analysis by flow cytometry to check for presence of CAR and various activation markers, including CD25, CD69, and 4-1BB. Over time, we observed that OKT3 antibodies stimulated all T-cells, and the percentage of CAR-positive cells was unchanged. In contrast, when incubated with the anti-linker antibody, T-cells that were CAR-positive received stimulation and proliferated, becoming a larger percentage of the population (FIG. 11). Additionally, we observed that OKT3 stimulated all T-cells as observed by levels of CD69 and 4-1BB on the surface of T-cells. In contrast, stimulation with the anti-linker antibody selectively stimulated CAR-positive cells (FIGS. 12A and 12B).

Thus, cells presenting a molecule comprising GSTSGS-GKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), can be selectively stimulated in vitro.

Figure 13:
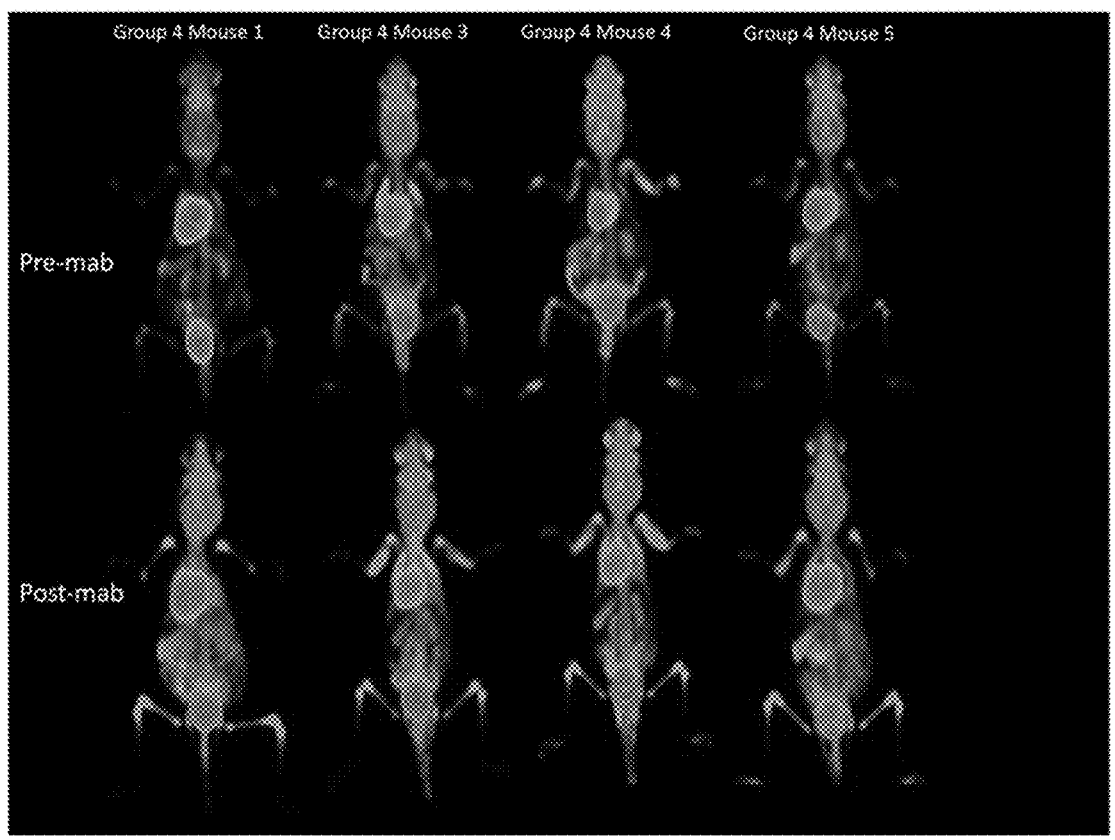
FIG. 13 shows FDG-PET imaging of female NSG mice previously injected with CAR T cells before and after stimulation with anti-linker Clone 8 Mab.

Example 8: Stimulating/Activating CAR-Positive T Cells Using an Antigen Binding Molecule In Vivo In this example, CAR+ T-cells were selectively stimulated in vivo with an anti-linker antibody, provided herein. MM1S cells were implanted into female NSG mice. To clear the MM1S cells, CAR-T cells comprising the peptide GSTSGS-GKPGSGEGSTKG (SEQ ID NO: 1) were injected on Day 6. On Day 13, fludeoxyglucose positron emission tomography (FDG-PET) experiments were performed to assess baseline metabolism. Clone 8 anti-linker antibody was injected into each mouse and the FDG-PET experiment was repeated after 24 hours. As shown in FIG. 13, an increase in FDG-PET signal post antibody treatment was best observed in the hind limbs suggesting stimulation of CAR+ T cells in vivo responsive to anti-linker injection.

Figure 14A:
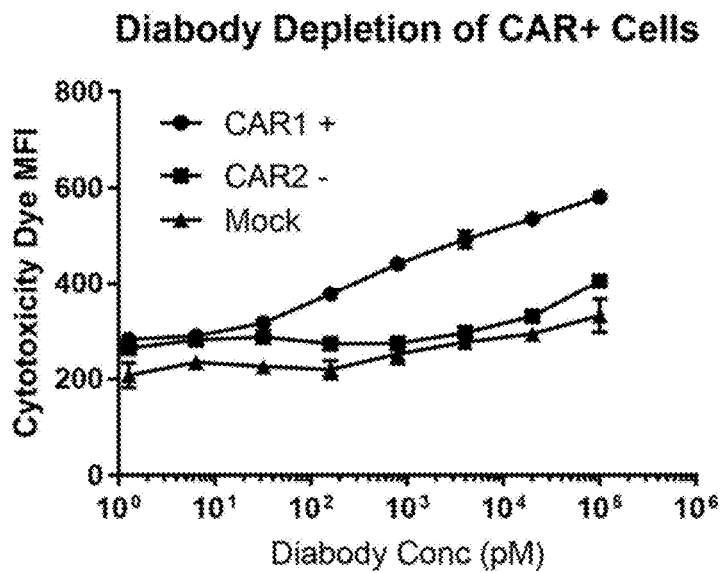
FIGS. 14A and 14B demonstrates the diabody incubated with CAR constructs comprising the peptide GSTSGSGKPGSGEGSTKG leads to increased cell death.
Figure 14B:
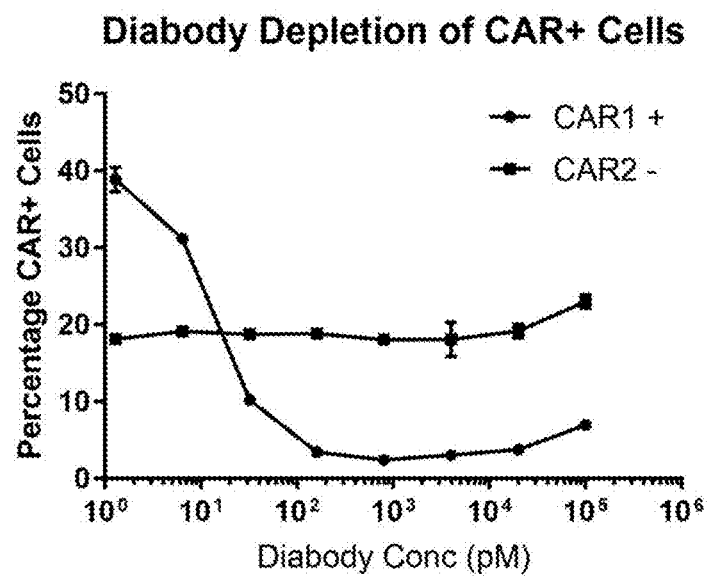

Example 9: Depletion of Cells Expressing Molecules Containing Specific Peptides Using a Diabody In this Example, CAR+ T-cells can be selectively killed in vitro with an anti-linker/anti-human CD3 diabody, comprising an anti-linker binding moiety, such as in Clone and 16. T-cells transduced with a CAR containing the specific epitope GSTSGSGKPGSGEGSTKG (SEQ ID NO: 1) (CAR1), a CAR not containing the epitope (CAR2), or not transduced (Mock) were grown in 96-well U-bottom in OpTmizer media with T-cell supplements, penicillin, streptomycin, glutamine, and IL-2. Each well contained 20,000 T-cells. The diabody was added to each CAR- and Mock-transduced T-cell samples at concentrations from 1.28 pM to 100 nM. After 16 hours, cells were stained with Live/Dead Violet (Molecular Probes) and recombinant protein L/streptavidin-PE to assess the number of dead cells and percentage of CAR+ T-cells as a function of the concentration of the diabody. As shown in FIG. 14A, the amount of dye that binds to cells with ruptured membranes is increased in the CAR1 samples, whereas the expression of a control CAR or no CAR does not lead to a significant increase in dye fluorescence (see CAR2 and Mock, respectively). This can be further observed by a decrease in the percentage of CAR1 T-cells compared to CAR2 T-cells (FIG. 14B). CAR1 cells start at approximately 40% positive, but are depleted to about 10% of total T-cells at the highest concentration of the diabody, whereas CAR2 T-cells stay at a constant 20% CAR+. Thus, cells presenting a molecule comprising GST-SGSGKPGSGEGSTKG (SEQ ID NO: 1) and subsequences thereof, particularly GSGKPGSGEG (SEQ ID NO: 2), GKPGSGEG (SEQ ID NO: 3), SGKPGSGE (SEQ ID NO: 499), and/or KPGSG (SEQ ID NO: 500), can be selectively depleted in vitro with a diabody specific for T-cells and the specific peptide.

---

What is claimed is:

1. An isolated antigen binding molecule that specifically binds to a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499), and KPGSG (SEQ ID NO: 500), wherein the antigen binding molecule comprises
   (a) a VH CDR1 region comprising the amino acid sequence of SEQ ID NO: 7;
   (b) a VH CDR2 region comprising the amino acid sequence of SEQ ID NO: 8;
   (c) a VH CDR3 region comprising the amino acid sequence of SEQ ID NO: 9;
   (d) a VL CDR1 region comprising the amino acid sequence of SEQ ID NO: 13;
   (e) a VL CDR2 region comprising the amino acid sequence of SEQ ID NO: 14; and
   (f) a VL CDR3 region comprising the amino acid sequence of SEQ ID NO: 15.

2. The isolated antigen binding molecule of claim 1, wherein the antigen binding molecule is selected from the group consisting of an antibody, an scFv, a Fab, a Fab', a Fv, a F(ab')2, a dAb, a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody, an IgG2 antibody having at least one mutation in the hinge region, an IgG3 antibody, an IgG3 antibody having at least one mutation in the hinge region, an IgG4 antibody, and an IgG4 and antibody having at least one mutation in the hinge region.

3. The isolated antigen binding molecule of claim 2, wherein the antigen binding molecule is a humanized antibody.

4. The isolated antigen binding molecule of claim 1, comprising
   (a) a heavy chain variable region (VH) amino acid sequence that is at least about 95% identical to the amino acid sequence of SEQ ID NO: 5; and
   (b) a light chain variable region (VL) amino acid sequence that is at least about 95% identical to the amino acid sequence of SEQ ID NO: 11.

5. The isolated antigen binding molecule of claim 4, comprising
   (a) a heavy chain variable region (VH) comprising the amino acid sequence of SEQ ID NO: 5; and
   (b) a light chain variable region (VL) comprising the amino acid sequence of SEQ ID NO: 11.

6. The isolated antigen binding molecule of claim 1 comprising
   (a) a heavy chain comprising an amino acid sequence that is at least 95%, 96%, 97%, 98% or 99% identical to the amino acid sequence of SEQ ID NO: 6; and
   (b) a light chain comprising an amino acid sequence that is 95%, 96%, 97%, 98% or 99% identical to the amino acid sequence of SEQ ID NO: 12.

7. The isolated antigen binding molecule of claim 6 comprising at least one of
   (a) a heavy chain comprising the amino acid sequence of SEQ ID NO: 6; and
   (b) a light chain comprising the amino acid sequence of SEQ ID NO: 12.

8. The isolated antigen binding molecule of claim 6 comprising
   (a) a heavy chain comprising the amino acid sequence of SEQ ID NO: 6; and
   (b) a light chain comprising the amino acid sequence of SEQ ID NO: 12.

9. An isolated antigen binding molecule that specifically binds to a molecule comprising an amino acid sequence selected from the group consisting of GSTSGSGKPGSGEGSTKG (SEQ ID NO: 1), GSGKPGSGEG (SEQ ID NO: 2), GKPGSGEG (SEQ ID NO: 3), SGKPGSGE (SEQ ID NO: 499), and KPGSG (SEQ ID NO: 500), wherein the antigen binding molecule comprises:
   (a) a VH CDR1 region comprising the amino acid sequence of SEQ ID NO: 19;
   (b) a VH CDR2 region comprising the amino acid sequence of SEQ ID NO: 20;
   (c) a VH CDR3 region comprising the amino acid sequence of SEQ ID NO: 21;
   (d) a VL CDR1 region comprising the amino acid sequence of SEQ ID NO: 25;
   (e) a VL CDR2 region comprising the amino acid sequence of SEQ ID NO: 26; and
   (f) a VL CDR3 region comprising the amino acid sequence of SEQ ID NO: 27.

10. The isolated antigen binding molecule of claim 9, wherein the antigen binding molecule is selected from the group consisting of an antibody, an scFv, a Fab, a Fab', a Fv, a F(ab')2, a dAb, a human antibody, a humanized antibody, a chimeric antibody, a monoclonal antibody, a polyclonal antibody, a recombinant antibody, an IgE antibody, an IgD antibody, an IgM antibody, an IgG1 antibody, an IgG1 antibody having at least one mutation in the hinge region, an IgG2 antibody, an IgG2 antibody having at least one mutation in the hinge region, an IgG3 antibody, an IgG3 antibody having at least one mutation in the hinge region, an IgG4 antibody, and an IgG4 and antibody having at least one mutation in the hinge region.

11. The isolated antigen binding molecule of claim 10, wherein the antigen binding molecule is a humanized antibody.

12. The isolated antigen binding molecule of claim 9, comprising
   (a) a heavy chain variable region (VH) amino acid sequence that is at least about 95% identical to the amino acid sequence of SEQ ID NO: 17; and
   (b) a light chain variable region (VL) amino acid sequence that is at least about 95% identical to the amino acid sequence of SEQ ID NO: 23.

13. The isolated antigen binding molecule of claim 10, comprising
   (a) a heavy chain variable region (VH) comprising the amino acid sequence of SEQ ID NO: 17; and
   (b) a light chain variable region (VL) comprising the amino acid sequence of SEQ ID NO: 23.

14. The isolated antigen binding molecule of claim 13 comprising
   (a) a heavy chain comprising an amino acid sequence that is at least 95%, 96%, 97%, 98% or 99% identical to the amino acid sequence of SEQ ID NO: 18; and
   (b) a light chain comprising an amino acid sequence that is at least 95%, 96%, 97%, 98% or 99% identical to the amino acid sequence of SEQ ID NO: 24.

15. The isolated antigen binding molecule of claim 14 comprising at least one of
   (a) a heavy chain comprising the amino acid sequence of SEQ ID NO: 18; and
   (b) a light chain comprising the amino acid sequence of SEQ ID NO: 24.

16. The isolated antigen binding molecule of claim 14 comprising
   (a) a heavy chain comprising the amino acid sequence of SEQ ID NO: 18; and
   (b) a light chain comprising the amino acid sequence of SEQ ID NO: 24.

17. The antigen binding molecule of any of claims 1-16, wherein the antigen binding molecule further comprises a detectable label.

18. The antigen binding molecule of claim 17, wherein the detectable label is selected from the group consisting of a fluorescent label, a photochromic compound, a proteinaceous fluorescent label, a magnetic label, a radiolabel, and a hapten.

19. The antigen binding molecule of claim 18, comprising a fluorescent label selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry.

20. A composition comprising the antigen binding molecule of any one of claims 1-19.

* * * * *